US008512986B2

(12) United States Patent
Fukuyama et al.

(10) Patent No.: US 8,512,986 B2
(45) Date of Patent: Aug. 20, 2013

(54) ENZYMES FOR STARCH PROCESSING

(75) Inventors: Shiro Fukuyama, Chiba (JP); Tomoko Matsui, Chiba (JP); Chee Leong Soong, Raleigh, NC (US); Eric Allain, Wake Forest, NC (US); Anders Vikso Nielsen, Slangerup (DK); Hiroaki Udagawa, Yokohama (JP); Ye Liu, Beijing (CN); Junxin Duan, Beijing (CN); Wenping Wu, Beijing (CN); Lene Nonboe Andersen, Alleroed (DK); Sara Landvik, Vedbaek (DK)

(73) Assignees: Novozymes A/S, Bagsvaerd (DK); Novozymes North America, Inc., Franklinton, NC (US)

( * ) Notice: Subject to any disclaimer, the term of this patent is extended or adjusted under 35 U.S.C. 154(b) by 0 days.

(21) Appl. No.: 12/973,113

(22) Filed: Dec. 20, 2010

(65) Prior Publication Data
US 2011/0104759 A1    May 5, 2011

Related U.S. Application Data

(63) Continuation of application No. 11/316,535, filed on Dec. 22, 2005, now abandoned.

(60) Provisional application No. 60/638,614, filed on Dec. 22, 2004, provisional application No. 60/650,612, filed on Feb. 7, 2005.

(51) Int. Cl.
| C12P 19/00 | (2006.01) |
| C12P 7/08 | (2006.01) |
| C12P 19/04 | (2006.01) |
| C12P 19/02 | (2006.01) |
| C12N 9/26 | (2006.01) |
| C12N 9/34 | (2006.01) |
| C07H 21/04 | (2006.01) |
| C07K 1/00 | (2006.01) |

(52) U.S. Cl.
USPC .......... 435/72; 435/163; 435/101; 435/105; 435/201; 435/205; 536/23.2; 536/23.4; 530/350

(58) Field of Classification Search
USPC ............... 435/72, 163, 101, 105, 201, 205; 536/23.2, 234; 530/350
See application file for complete search history.

(56) References Cited

U.S. PATENT DOCUMENTS

| 4,009,074 | A | 2/1977 | Walon |
| 4,591,560 | A | 5/1986 | Kainuma et al. |
| 4,727,026 | A | 2/1988 | Sawada et al. |
| 6,537,792 | B1 | 3/2003 | Allen et al. |
| 7,129,069 | B2 | 10/2006 | Borchert et al. |
| 7,189,552 | B2 * | 3/2007 | Lan et al. ............ 435/203 |
| 2005/0054071 | A1 | 3/2005 | Udagawa et al. |
| 2005/0158839 | A1 | 7/2005 | Borchert et al. |
| 2006/0147581 | A1 | 7/2006 | Svendsen et al. |
| 2006/0257984 | A1 | 11/2006 | Borchert et al. |

FOREIGN PATENT DOCUMENTS

| EP | 0126206 A2 | 1/1984 |
| EP | 0 171 218 A2 | 2/1986 |
| WO | WO 98/14601 A1 | 4/1998 |
| WO | WO 98/16633 A1 | 4/1998 |
| WO | WO 00/77165 A2 | 12/2000 |
| WO | 03/056002 A1 | 7/2003 |
| WO | 2004/055178 A1 | 7/2004 |
| WO | WO 2004/055178 A1 | 7/2004 |
| WO | WO 2005/003311 A2 | 1/2005 |
| WO | 2006/066579 A1 | 6/2006 |
| WO | 2006/066582 A1 | 6/2006 |
| WO | WO 2006/065579 A2 | 6/2006 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Guo et al., PNAs, vol. 101, No. 25, pp. 9205-9210 (2004).
Kaneko et al., Journal of Fermentation and Bioengineering, vol. 81, No. 4, pp. 292-298 (1996).
Machovic et al., FEBS Journal, vol. 272, No. 21, pp. 5497-5513 (2005).
Somkuti et al., Developments in Industrial Microbiology, vol. 21, pp. 327-337 (1979).
Nagasaka et al., Appl. Micobiol. Biotechnol., vol. 50, No. 3, pp. 323-330 (1998).
Cornett et al., Protein Engineering, vol. 16, No. 7, pp. 521-529 (2003).
Finnie et al., Journal of Applied Glycoscience, vol. 50, pp. 277-282 (2003).
Nagasaka et al., Journal of Applied Glycoscience, vol. 46, No. 2, pp. 169-178 (1999).
Ohdan et al., Appled and Environmental Microbiology, vol. 66, No. 7, pp. 3058-3064 (2000).
Paldi et al., Biochem. J., vol. 372, pp. 905-910 (2003).

* cited by examiner

*Primary Examiner* — Ganapathirama Raghu
(74) *Attorney, Agent, or Firm* — Michael W. Krenicky

(57) ABSTRACT

The present invention relates to polypeptides comprising a carbohydrate-binding module amino acid sequence and an alpha-amylase amino acid sequence as well as to the application of such polypeptides.

20 Claims, No Drawings

SEQUENCE LISTING

```
<160> NUMBER OF SEQ ID NOS: 179

<210> SEQ ID NO 1
<211> LENGTH: 1533
<212> TYPE: DNA
<213> ORGANISM: Aspergillus niger
<220> FEATURE:
<221> NAME/KEY: CDS
<222> LOCATION: (1)..(1533)

<400> SEQUENCE: 1 atg aga tta tcg act tcg agt ctc ttc ctt tcc gtg tct ctg ctg ggg      48
Met Arg Leu Ser Thr Ser Ser Leu Phe Leu Ser Val Ser Leu Leu Gly
1               5                   10                  15 aag ctg gcc ctc ggg ctg tcg gct gca gaa tgg cgc act cag tcg att      96
Lys Leu Ala Leu Gly Leu Ser Ala Ala Glu Trp Arg Thr Gln Ser Ile
            20                  25                  30 tac ttc cta ttg acg gat cgg ttc ggt agg acg gac aat tcg acg aca     144
Tyr Phe Leu Leu Thr Asp Arg Phe Gly Arg Thr Asp Asn Ser Thr Thr
        35                  40                  45 gct aca tgc gat acg ggt gac caa atc tat tgt ggt ggc agt tgg caa     192
Ala Thr Cys Asp Thr Gly Asp Gln Ile Tyr Cys Gly Gly Ser Trp Gln
    50                  55                  60 gga atc atc aac cat ctg gat tat atc cag ggc atg gga ttc acg gcc     240
Gly Ile Ile Asn His Leu Asp Tyr Ile Gln Gly Met Gly Phe Thr Ala
65                  70                  75                  80 atc tgg atc tcg cct atc act gaa cag ctg ccc cag gat act gct gat     288
Ile Trp Ile Ser Pro Ile Thr Glu Gln Leu Pro Gln Asp Thr Ala Asp
                85                  90                  95 ggt gaa gct tac cat gga tat tgg cag cag aag ata tac gac gtg aac     336
```

```
Gly Glu Ala Tyr His Gly Tyr Trp Gln Gln Lys Ile Tyr Asp Val Asn
            100                 105                 110 tcc aac ttc ggc act gca gat gac ctc aag tcc ctc tca gat gcg ctt        384
Ser Asn Phe Gly Thr Ala Asp Asp Leu Lys Ser Leu Ser Asp Ala Leu
        115                 120                 125 cat gcc cgc gga atg tac ctc atg gtg gac gtc gtc cct aac cac atg        432
His Ala Arg Gly Met Tyr Leu Met Val Asp Val Val Pro Asn His Met
    130                 135                 140 ggc tac gcc ggc aac ggc aac gat gta gac tac agc gtc ttc gac ccc        480
Gly Tyr Ala Gly Asn Gly Asn Asp Val Asp Tyr Ser Val Phe Asp Pro
145                 150                 155                 160 ttc gat tcc tcc tcc tac ttc cac cca tac tgc ctg atc aca gat tgg        528
Phe Asp Ser Ser Ser Tyr Phe His Pro Tyr Cys Leu Ile Thr Asp Trp
                165                 170                 175 gac aac ttg acc atg gtc caa gat tgt tgg gag ggt gac acc atc gta        576
Asp Asn Leu Thr Met Val Gln Asp Cys Trp Glu Gly Asp Thr Ile Val
            180                 185                 190 tct ctg cca gac cta aac acc acc gaa act gcc gtg aga aca atc tgg        624
Ser Leu Pro Asp Leu Asn Thr Thr Glu Thr Ala Val Arg Thr Ile Trp
        195                 200                 205 tat gac tgg gta gcc gac ctg gta tcc aat tat tca gtc gac gga ctc        672
Tyr Asp Trp Val Ala Asp Leu Val Ser Asn Tyr Ser Val Asp Gly Leu
    210                 215                 220 cgc atc gac agt gtc ctc gaa gtc gaa cca gac ttc ttc ccg ggc tac        720
Arg Ile Asp Ser Val Leu Glu Val Glu Pro Asp Phe Phe Pro Gly Tyr
225                 230                 235                 240 cag gaa gca gca ggt gtc tac tgc gtc ggc gaa gtc gac aac ggc aac        768
Gln Glu Ala Ala Gly Val Tyr Cys Val Gly Glu Val Asp Asn Gly Asn
                245                 250                 255 cct gcc ctc gac tgc cca tac cag aag gtc ctg gac ggc gtc ctc aac        816
Pro Ala Leu Asp Cys Pro Tyr Gln Lys Val Leu Asp Gly Val Leu Asn
            260                 265                 270 tat ccg atc tac tgg caa ctc ctc tac gcc ttc gaa tcc tcc agc ggc        864
Tyr Pro Ile Tyr Trp Gln Leu Leu Tyr Ala Phe Glu Ser Ser Ser Gly
        275                 280                 285 agc atc agc aat ctc tac aac atg atc aaa tcc gtc gca agc gac tgc        912
Ser Ile Ser Asn Leu Tyr Asn Met Ile Lys Ser Val Ala Ser Asp Cys
    290                 295                 300 tcc gat ccg aca cta ctc ggc aac ttc atc gaa aac cac gac aat ccc        960
Ser Asp Pro Thr Leu Leu Gly Asn Phe Ile Glu Asn His Asp Asn Pro
305                 310                 315                 320 cgt ttc gcc tcc tac acc tcc gac tac tcg caa gcc aaa aac gtc ctc       1008
Arg Phe Ala Ser Tyr Thr Ser Asp Tyr Ser Gln Ala Lys Asn Val Leu
                325                 330                 335 agc tac atc ttc ctc tcc gac ggc atc ccc atc gtc tac gcc ggc gaa       1056
Ser Tyr Ile Phe Leu Ser Asp Gly Ile Pro Ile Val Tyr Ala Gly Glu
            340                 345                 350 gaa cag cac tac tcc ggc ggc aag gtg ccc tac aac cgc gaa gcg acc       1104
Glu Gln His Tyr Ser Gly Gly Lys Val Pro Tyr Asn Arg Glu Ala Thr
        355                 360                 365 tgg ctt tca ggc tac gac acc tcc gca gag ctg tac acc tgg ata gcc       1152
Trp Leu Ser Gly Tyr Asp Thr Ser Ala Glu Leu Tyr Thr Trp Ile Ala
    370                 375                 380 acc acg aac gcg atc cgc aaa cta gcc atc tca gct gac tcg gcc tac       1200
Thr Thr Asn Ala Ile Arg Lys Leu Ala Ile Ser Ala Asp Ser Ala Tyr
385                 390                 395                 400 att acc tac gcg aat gat gca ttc tac act gac agc aac acc atc gca       1248
Ile Thr Tyr Ala Asn Asp Ala Phe Tyr Thr Asp Ser Asn Thr Ile Ala
                405                 410                 415 atg cgc aaa ggc acc tca ggg agc caa gtc atc acc gtc ctc tcc aac       1296
```

```
                Met Arg Lys Gly Thr Ser Gly Ser Gln Val Ile Thr Val Leu Ser Asn
                                420                 425                 430 aaa ggc tcc tca gga agc agc tac acc ctg acc ctc agc gga agc ggc           1344
Lys Gly Ser Ser Gly Ser Ser Tyr Thr Leu Thr Leu Ser Gly Ser Gly
            435                 440                 445 tac aca tcc ggc acg aag ctg atc gaa gcg tac aca tgc aca tcc gtg           1392
Tyr Thr Ser Gly Thr Lys Leu Ile Glu Ala Tyr Thr Cys Thr Ser Val
        450                 455                 460 acc gtg gac tcg agc ggc gat att ccc gtg ccg atg gcg tcg gga tta           1440
Thr Val Asp Ser Ser Gly Asp Ile Pro Val Pro Met Ala Ser Gly Leu
465                 470                 475                 480 ccg aga gtt ctt ctg ccc gcg tcc gtc gtc gat agc tct tcg ctc tgt           1488
Pro Arg Val Leu Leu Pro Ala Ser Val Val Asp Ser Ser Ser Leu Cys
                485                 490                 495 ggc ggg agc gga aga aca acc acg acc aca act gct gct act agt               1533
Gly Gly Ser Gly Arg Thr Thr Thr Thr Thr Thr Ala Ala Thr Ser
            500                 505                 510

<210> SEQ ID NO 2
<211> LENGTH: 511
<212> TYPE: PRT
<213> ORGANISM: Aspergillus niger

<400> SEQUENCE: 2

Met Arg Leu Ser Thr Ser Ser Leu Phe Leu Ser Val Ser Leu Leu Gly
1               5                   10                  15

Lys Leu Ala Leu Gly Leu Ser Ala Ala Glu Trp Arg Thr Gln Ser Ile
            20                  25                  30

Tyr Phe Leu Leu Thr Asp Arg Phe Gly Arg Thr Asp Asn Ser Thr Thr
        35                  40                  45

Ala Thr Cys Asp Thr Gly Asp Gln Ile Tyr Cys Gly Gly Ser Trp Gln
    50                  55                  60

Gly Ile Ile Asn His Leu Asp Tyr Ile Gln Gly Met Gly Phe Thr Ala
65                  70                  75                  80

Ile Trp Ile Ser Pro Ile Thr Glu Gln Leu Pro Gln Asp Thr Ala Asp
                85                  90                  95

Gly Glu Ala Tyr His Gly Tyr Trp Gln Gln Lys Ile Tyr Asp Val Asn
            100                 105                 110

Ser Asn Phe Gly Thr Ala Asp Asp Leu Lys Ser Leu Ser Asp Ala Leu
        115                 120                 125

His Ala Arg Gly Met Tyr Leu Met Val Asp Val Val Pro Asn His Met
    130                 135                 140

Gly Tyr Ala Gly Asn Gly Asn Asp Val Asp Tyr Ser Val Phe Asp Pro
145                 150                 155                 160

Phe Asp Ser Ser Ser Tyr Phe His Pro Tyr Cys Leu Ile Thr Asp Trp
                165                 170                 175

Asp Asn Leu Thr Met Val Gln Asp Cys Trp Glu Gly Asp Thr Ile Val
            180                 185                 190

Ser Leu Pro Asp Leu Asn Thr Thr Glu Thr Ala Val Arg Thr Ile Trp
        195                 200                 205

Tyr Asp Trp Val Ala Asp Leu Val Ser Asn Tyr Ser Val Asp Gly Leu
    210                 215                 220

Arg Ile Asp Ser Val Leu Glu Val Glu Pro Asp Phe Phe Pro Gly Tyr
225                 230                 235                 240

Gln Glu Ala Ala Gly Val Tyr Cys Val Gly Glu Val Asp Asn Gly Asn
                245                 250                 255

Pro Ala Leu Asp Cys Pro Tyr Gln Lys Val Leu Asp Gly Val Leu Asn
```

```
                    260                265                270
Tyr Pro Ile Tyr Trp Gln Leu Leu Tyr Ala Phe Glu Ser Ser Ser Gly
        275                280                285

Ser Ile Ser Asn Leu Tyr Asn Met Ile Lys Ser Val Ala Ser Asp Cys
        290                295                300

Ser Asp Pro Thr Leu Leu Gly Asn Phe Ile Glu Asn His Asp Asn Pro
305                310                315                320

Arg Phe Ala Ser Tyr Thr Ser Asp Tyr Ser Gln Ala Lys Asn Val Leu
                325                330                335

Ser Tyr Ile Phe Leu Ser Asp Gly Ile Pro Ile Val Tyr Ala Gly Glu
        340                345                350

Glu Gln His Tyr Ser Gly Gly Lys Val Pro Tyr Asn Arg Glu Ala Thr
        355                360                365

Trp Leu Ser Gly Tyr Asp Thr Ser Ala Glu Leu Tyr Thr Trp Ile Ala
        370                375                380

Thr Thr Asn Ala Ile Arg Lys Leu Ala Ile Ser Ala Asp Ser Ala Tyr
385                390                395                400

Ile Thr Tyr Ala Asn Asp Ala Phe Tyr Thr Asp Ser Asn Thr Ile Ala
                405                410                415

Met Arg Lys Gly Thr Gly Ser Gln Val Ile Thr Val Leu Ser Asn
        420                425                430

Lys Gly Ser Ser Gly Ser Ser Tyr Thr Leu Thr Leu Ser Gly Ser Gly
        435                440                445

Tyr Thr Ser Gly Thr Lys Leu Ile Glu Ala Tyr Thr Cys Thr Ser Val
        450                455                460

Thr Val Asp Ser Ser Gly Asp Ile Pro Val Pro Met Ala Ser Gly Leu
465                470                475                480

Pro Arg Val Leu Leu Pro Ala Ser Val Val Asp Ser Ser Leu Cys
                485                490                495

Gly Gly Ser Gly Arg Thr Thr Thr Thr Thr Ala Ala Thr Ser
                500                505                510

<210> SEQ ID NO 3
<211> LENGTH: 1440
<212> TYPE: DNA
<213> ORGANISM: Aspergillus oryzae
<220> FEATURE:
<221> NAME/KEY: CDS
<222> LOCATION: (1)..(1440)

<400> SEQUENCE: 3 gca acg cct gcg gac tgg cga tcg caa tcc att tat ttc ctt ctc acg      48
Ala Thr Pro Ala Asp Trp Arg Ser Gln Ser Ile Tyr Phe Leu Leu Thr
1               5                  10                  15 gat cga ttt gca agg acg gat ggg tcg acg act gcg act tgt aat act      96
Asp Arg Phe Ala Arg Thr Asp Gly Ser Thr Thr Ala Thr Cys Asn Thr
            20                  25                  30 gcg gat cag aaa tac tgt ggt gga aca tgg cag ggc atc atc gac aag     144
Ala Asp Gln Lys Tyr Cys Gly Gly Thr Trp Gln Gly Ile Ile Asp Lys
        35                  40                  45 ttg gac tat atc cag gga atg ggc ttc aca gcc atc tgg atc acc ccc     192
Leu Asp Tyr Ile Gln Gly Met Gly Phe Thr Ala Ile Trp Ile Thr Pro
    50                  55                  60 gtt aca gcc cag ctg ccc cag acc acc gca tat gga gat gcc tac cat     240
Val Thr Ala Gln Leu Pro Gln Thr Thr Ala Tyr Gly Asp Ala Tyr His
65                  70                  75                  80 ggc tac tgg cag cag gat ata tac tct ctg aac gaa aac tac ggc act     288
Gly Tyr Trp Gln Gln Asp Ile Tyr Ser Leu Asn Glu Asn Tyr Gly Thr
```

-continued

|     |     |     | 85  |     |     |     |     | 90  |     |     |     |     | 95  |     |     |      |
|-----|-----|-----|-----|-----|-----|-----|-----|-----|-----|-----|-----|-----|-----|-----|-----|------|
| gca | gat | gac | ttg | aag | gcg | ctc | tct | tcg | gcc | ctt | cat | gag | agg | ggg | atg | 336  |
| Ala | Asp | Asp | Leu | Lys | Ala | Leu | Ser | Ser | Ala | Leu | His | Glu | Arg | Gly | Met |      |
|     |     | 100 |     |     |     |     | 105 |     |     |     |     | 110 |     |     |     |      |

| tat | ctt | atg | gtc | gat | gtg | gtt | gct | aac | cat | atg | ggc | tat | gat | gga | gcg | 384 |
|-----|-----|-----|-----|-----|-----|-----|-----|-----|-----|-----|-----|-----|-----|-----|-----|-----|
| Tyr | Leu | Met | Val | Asp | Val | Val | Ala | Asn | His | Met | Gly | Tyr | Asp | Gly | Ala |     |
|     | 115 |     |     |     |     | 120 |     |     |     |     | 125 |     |     |     |     |     |

| ggt | agc | tca | gtc | gat | tac | agt | gtg | ttt | aaa | ccg | ttc | agt | tcc | caa | gac | 432 |
|-----|-----|-----|-----|-----|-----|-----|-----|-----|-----|-----|-----|-----|-----|-----|-----|-----|
| Gly | Ser | Ser | Val | Asp | Tyr | Ser | Val | Phe | Lys | Pro | Phe | Ser | Ser | Gln | Asp |     |
| 130 |     |     |     |     | 135 |     |     |     |     | 140 |     |     |     |     |     |     |

| tac | ttc | cac | ccg | ttc | tgt | ttc | att | caa | aac | tat | gaa | gat | cag | act | cag | 480 |
|-----|-----|-----|-----|-----|-----|-----|-----|-----|-----|-----|-----|-----|-----|-----|-----|-----|
| Tyr | Phe | His | Pro | Phe | Cys | Phe | Ile | Gln | Asn | Tyr | Glu | Asp | Gln | Thr | Gln |     |
| 145 |     |     |     | 150 |     |     |     |     | 155 |     |     |     |     | 160 |     |     |

| gtt | gag | gat | tgc | tgg | cta | gga | gat | aac | act | gtc | tcc | ttg | cct | gat | ctc | 528 |
|-----|-----|-----|-----|-----|-----|-----|-----|-----|-----|-----|-----|-----|-----|-----|-----|-----|
| Val | Glu | Asp | Cys | Trp | Leu | Gly | Asp | Asn | Thr | Val | Ser | Leu | Pro | Asp | Leu |     |
|     |     |     |     | 165 |     |     |     |     | 170 |     |     |     |     | 175 |     |     |

| gat | acc | acc | aag | gat | gtg | gtc | aag | aat | gaa | tgg | tac | gac | tgg | gtg | gga | 576 |
|-----|-----|-----|-----|-----|-----|-----|-----|-----|-----|-----|-----|-----|-----|-----|-----|-----|
| Asp | Thr | Thr | Lys | Asp | Val | Val | Lys | Asn | Glu | Trp | Tyr | Asp | Trp | Val | Gly |     |
|     |     |     | 180 |     |     |     |     | 185 |     |     |     |     | 190 |     |     |     |

| tca | ttg | gta | tcg | aac | tac | tcc | att | gac | ggc | ctc | cgt | atc | gac | aca | gta | 624 |
|-----|-----|-----|-----|-----|-----|-----|-----|-----|-----|-----|-----|-----|-----|-----|-----|-----|
| Ser | Leu | Val | Ser | Asn | Tyr | Ser | Ile | Asp | Gly | Leu | Arg | Ile | Asp | Thr | Val |     |
|     |     | 195 |     |     |     |     | 200 |     |     |     |     | 205 |     |     |     |     |

| aaa | cac | gtc | cag | aag | gac | ttc | tgg | ccc | ggg | tac | aac | aaa | gcc | gca | ggc | 672 |
|-----|-----|-----|-----|-----|-----|-----|-----|-----|-----|-----|-----|-----|-----|-----|-----|-----|
| Lys | His | Val | Gln | Lys | Asp | Phe | Trp | Pro | Gly | Tyr | Asn | Lys | Ala | Ala | Gly |     |
| 210 |     |     |     |     | 215 |     |     |     |     | 220 |     |     |     |     |     |     |

| gtg | tac | tgt | atc | ggc | gag | gtg | ctc | gac | ggt | gat | ccg | gcc | tac | act | tgt | 720 |
|-----|-----|-----|-----|-----|-----|-----|-----|-----|-----|-----|-----|-----|-----|-----|-----|-----|
| Val | Tyr | Cys | Ile | Gly | Glu | Val | Leu | Asp | Gly | Asp | Pro | Ala | Tyr | Thr | Cys |     |
| 225 |     |     |     |     | 230 |     |     |     |     | 235 |     |     |     |     | 240 |     |

| ccc | tac | cag | aac | gtc | atg | gac | ggc | gta | ctg | aac | tat | ccc | att | tac | tat | 768 |
|-----|-----|-----|-----|-----|-----|-----|-----|-----|-----|-----|-----|-----|-----|-----|-----|-----|
| Pro | Tyr | Gln | Asn | Val | Met | Asp | Gly | Val | Leu | Asn | Tyr | Pro | Ile | Tyr | Tyr |     |
|     |     |     |     | 245 |     |     |     |     | 250 |     |     |     |     | 255 |     |     |

| cca | ctc | ctc | aac | gcc | ttc | aag | tca | acc | tcc | ggc | agc | atg | gac | gac | ctc | 816 |
|-----|-----|-----|-----|-----|-----|-----|-----|-----|-----|-----|-----|-----|-----|-----|-----|-----|
| Pro | Leu | Leu | Asn | Ala | Phe | Lys | Ser | Thr | Ser | Gly | Ser | Met | Asp | Asp | Leu |     |
|     |     |     | 260 |     |     |     |     | 265 |     |     |     |     | 270 |     |     |     |

| tac | aac | atg | atc | aac | acc | gtc | aaa | tcc | gac | tgt | cca | gac | tca | aca | ctc | 864 |
|-----|-----|-----|-----|-----|-----|-----|-----|-----|-----|-----|-----|-----|-----|-----|-----|-----|
| Tyr | Asn | Met | Ile | Asn | Thr | Val | Lys | Ser | Asp | Cys | Pro | Asp | Ser | Thr | Leu |     |
|     |     | 275 |     |     |     |     | 280 |     |     |     |     | 285 |     |     |     |     |

| ctg | ggc | aca | ttc | gtc | gag | aac | cac | gac | aac | cca | cgg | ttc | gct | tct | tac | 912 |
|-----|-----|-----|-----|-----|-----|-----|-----|-----|-----|-----|-----|-----|-----|-----|-----|-----|
| Leu | Gly | Thr | Phe | Val | Glu | Asn | His | Asp | Asn | Pro | Arg | Phe | Ala | Ser | Tyr |     |
|     | 290 |     |     |     |     | 295 |     |     |     |     | 300 |     |     |     |     |     |

| acc | aac | gac | ata | gcc | ctc | gcc | aag | aac | gtc | gca | gca | ttc | atc | atc | ctc | 960 |
|-----|-----|-----|-----|-----|-----|-----|-----|-----|-----|-----|-----|-----|-----|-----|-----|-----|
| Thr | Asn | Asp | Ile | Ala | Leu | Ala | Lys | Asn | Val | Ala | Ala | Phe | Ile | Ile | Leu |     |
| 305 |     |     |     | 310 |     |     |     |     | 315 |     |     |     |     | 320 |     |     |

| aac | gac | gga | atc | ccc | atc | atc | tac | gcc | ggc | caa | gaa | cag | cac | tac | gcc | 1008 |
|-----|-----|-----|-----|-----|-----|-----|-----|-----|-----|-----|-----|-----|-----|-----|-----|------|
| Asn | Asp | Gly | Ile | Pro | Ile | Ile | Tyr | Ala | Gly | Gln | Glu | Gln | His | Tyr | Ala |      |
|     |     |     | 325 |     |     |     |     | 330 |     |     |     |     | 335 |     |     |      |

| ggc | gga | aac | gac | ccc | gcg | aac | cgc | gaa | gca | acc | tgg | ctc | tcg | ggc | tac | 1056 |
|-----|-----|-----|-----|-----|-----|-----|-----|-----|-----|-----|-----|-----|-----|-----|-----|------|
| Gly | Gly | Asn | Asp | Pro | Ala | Asn | Arg | Glu | Ala | Thr | Trp | Leu | Ser | Gly | Tyr |      |
|     |     |     | 340 |     |     |     |     | 345 |     |     |     |     | 350 |     |     |      |

| ccg | acc | gac | agc | gag | ctg | tac | aag | tta | att | gcc | tcc | gcg | aac | gca | atc | 1104 |
|-----|-----|-----|-----|-----|-----|-----|-----|-----|-----|-----|-----|-----|-----|-----|-----|------|
| Pro | Thr | Asp | Ser | Glu | Leu | Tyr | Lys | Leu | Ile | Ala | Ser | Ala | Asn | Ala | Ile |      |
|     |     | 355 |     |     |     |     | 360 |     |     |     |     | 365 |     |     |     |      |

| cgg | aac | tat | gcc | att | agc | aaa | gat | aca | gga | ttc | gtg | acc | tac | aag | aac | 1152 |
|-----|-----|-----|-----|-----|-----|-----|-----|-----|-----|-----|-----|-----|-----|-----|-----|------|
| Arg | Asn | Tyr | Ala | Ile | Ser | Lys | Asp | Thr | Gly | Phe | Val | Thr | Tyr | Lys | Asn |      |
|     | 370 |     |     |     |     | 375 |     |     |     |     | 380 |     |     |     |     |      |

| tgg | ccc | atc | tac | aaa | gac | gac | aca | acg | atc | gcc | atg | cgc | aag | ggc | aca | 1200 |
|-----|-----|-----|-----|-----|-----|-----|-----|-----|-----|-----|-----|-----|-----|-----|-----|------|
| Trp | Pro | Ile | Tyr | Lys | Asp | Asp | Thr | Thr | Ile | Ala | Met | Arg | Lys | Gly | Thr |      |
| 385 |     |     |     | 390 |     |     |     |     | 395 |     |     |     |     | 400 |     |      |

| gat | ggg | tcg | cag | atc | gtg | act | atc | ttg | tcc | aac | aag | ggt | gct | tcg | ggt | 1248 |
|-----|-----|-----|-----|-----|-----|-----|-----|-----|-----|-----|-----|-----|-----|-----|-----|------|
| Asp | Gly | Ser | Gln | Ile | Val | Thr | Ile | Leu | Ser | Asn | Lys | Gly | Ala | Ser | Gly |      |

```
                    405                 410                 415
gat tcg tat acc ctc tcc ttg agt ggt gcg ggt tac aca gcc ggc cag     1296
Asp Ser Tyr Thr Leu Ser Leu Ser Gly Ala Gly Tyr Thr Ala Gly Gln
                420                 425                 430 caa ttg acg gag gtc att ggc tgc acg acc gtg acg gtt ggt tcg gat     1344
Gln Leu Thr Glu Val Ile Gly Cys Thr Thr Val Thr Val Gly Ser Asp
            435                 440                 445 gga aat gtg cct gtt cct atg gca ggt ggg cta cct agg gta ttg tat     1392
Gly Asn Val Pro Val Pro Met Ala Gly Gly Leu Pro Arg Val Leu Tyr
450                 455                 460 ccg act gag aag ttg gca ggt agc aag atc tgt agt agc tcg gga aga     1440
Pro Thr Glu Lys Leu Ala Gly Ser Lys Ile Cys Ser Ser Ser Gly Arg
465                 470                 475                 480

<210> SEQ ID NO 4
<211> LENGTH: 480
<212> TYPE: PRT
<213> ORGANISM: Aspergillus oryzae

<400> SEQUENCE: 4

Ala Thr Pro Ala Asp Trp Arg Ser Gln Ser Ile Tyr Phe Leu Leu Thr
1               5                   10                  15

Asp Arg Phe Ala Arg Thr Asp Gly Ser Thr Thr Ala Thr Cys Asn Thr
            20                  25                  30

Ala Asp Gln Lys Tyr Cys Gly Gly Thr Trp Gln Gly Ile Ile Asp Lys
        35                  40                  45

Leu Asp Tyr Ile Gln Gly Met Gly Phe Thr Ala Ile Trp Ile Thr Pro
    50                  55                  60

Val Thr Ala Gln Leu Pro Gln Thr Thr Ala Tyr Gly Asp Ala Tyr His
65                  70                  75                  80

Gly Tyr Trp Gln Gln Asp Ile Tyr Ser Leu Asn Glu Asn Tyr Gly Thr
                85                  90                  95

Ala Asp Asp Leu Lys Ala Leu Ser Ala Leu His Glu Arg Gly Met
            100                 105                 110

Tyr Leu Met Val Asp Val Val Ala Asn His Met Gly Tyr Asp Gly Ala
        115                 120                 125

Gly Ser Ser Val Asp Tyr Ser Val Phe Lys Pro Phe Ser Ser Gln Asp
    130                 135                 140

Tyr Phe His Pro Phe Cys Phe Ile Gln Asn Tyr Glu Asp Gln Thr Gln
145                 150                 155                 160

Val Glu Asp Cys Trp Leu Gly Asp Asn Thr Val Ser Leu Pro Asp Leu
                165                 170                 175

Asp Thr Thr Lys Asp Val Val Lys Asn Glu Trp Tyr Asp Trp Val Gly
            180                 185                 190

Ser Leu Val Ser Asn Tyr Ser Ile Asp Gly Leu Arg Ile Asp Thr Val
        195                 200                 205

Lys His Val Gln Lys Asp Phe Trp Pro Gly Tyr Asn Lys Ala Ala Gly
    210                 215                 220

Val Tyr Cys Ile Gly Glu Val Leu Asp Gly Asp Pro Ala Tyr Thr Cys
225                 230                 235                 240

Pro Tyr Gln Asn Val Met Asp Gly Val Leu Asn Tyr Pro Ile Tyr Tyr
                245                 250                 255

Pro Leu Leu Asn Ala Phe Lys Ser Thr Ser Gly Ser Met Asp Asp Leu
            260                 265                 270

Tyr Asn Met Ile Asn Thr Val Lys Ser Asp Cys Pro Asp Ser Thr Leu
        275                 280                 285
```

```
Leu Gly Thr Phe Val Glu Asn His Asp Asn Pro Arg Phe Ala Ser Tyr
            290                 295                 300

Thr Asn Asp Ile Ala Leu Ala Lys Asn Val Ala Ala Phe Ile Ile Leu
305                 310                 315                 320

Asn Asp Gly Ile Pro Ile Ile Tyr Ala Gly Gln Glu Gln His Tyr Ala
                325                 330                 335

Gly Gly Asn Asp Pro Ala Asn Arg Glu Ala Thr Trp Leu Ser Gly Tyr
            340                 345                 350

Pro Thr Asp Ser Glu Leu Tyr Lys Leu Ile Ala Ser Ala Asn Ala Ile
        355                 360                 365

Arg Asn Tyr Ala Ile Ser Lys Asp Thr Gly Phe Val Thr Tyr Lys Asn
370                 375                 380

Trp Pro Ile Tyr Lys Asp Asp Thr Thr Ile Ala Met Arg Lys Gly Thr
385                 390                 395                 400

Asp Gly Ser Gln Ile Val Thr Ile Leu Ser Asn Lys Gly Ala Ser Gly
                405                 410                 415

Asp Ser Tyr Thr Leu Ser Leu Ser Gly Ala Gly Tyr Thr Ala Gly Gln
            420                 425                 430

Gln Leu Thr Glu Val Ile Gly Cys Thr Thr Val Thr Val Gly Ser Asp
        435                 440                 445

Gly Asn Val Pro Val Pro Met Ala Gly Gly Leu Pro Arg Val Leu Tyr
450                 455                 460

Pro Thr Glu Lys Leu Ala Gly Ser Lys Ile Cys Ser Ser Ser Gly Arg
465                 470                 475                 480

<210> SEQ ID NO 5
<211> LENGTH: 1434
<212> TYPE: DNA
<213> ORGANISM: Aspergillus oryzae
<220> FEATURE:
<221> NAME/KEY: CDS
<222> LOCATION: (1)..(1434)

<400> SEQUENCE: 5 gca acg cct gcg gac tgg cga tcg caa tcc att tat ttc ctt ctc acg    48
Ala Thr Pro Ala Asp Trp Arg Ser Gln Ser Ile Tyr Phe Leu Leu Thr
1               5                   10                  15 gat cga ttt gca agg acg gat ggg tcg acg act gcg act tgt aat act    96
Asp Arg Phe Ala Arg Thr Asp Gly Ser Thr Thr Ala Thr Cys Asn Thr
            20                  25                  30 gcg gat cag aaa tac tgt ggt gga aca tgg cag ggc atc atc gac aag   144
Ala Asp Gln Lys Tyr Cys Gly Gly Thr Trp Gln Gly Ile Ile Asp Lys
        35                  40                  45 ttg gac tat atc cag gga atg ggc ttc aca gcc atc tgg atc acc ccc   192
Leu Asp Tyr Ile Gln Gly Met Gly Phe Thr Ala Ile Trp Ile Thr Pro
    50                  55                  60 gtt aca gcc cag ctg ccc cag acc acc gca tat gga gat gcc tac cat   240
Val Thr Ala Gln Leu Pro Gln Thr Thr Ala Tyr Gly Asp Ala Tyr His
65                  70                  75                  80 ggc tac tgg cag cag gat ata tac tct ctg aac gaa aac tac ggc act   288
Gly Tyr Trp Gln Gln Asp Ile Tyr Ser Leu Asn Glu Asn Tyr Gly Thr
                85                  90                  95 gca gat gac ttg aag gcg ctc tct tcg gcc ctt cat gag agg ggg atg   336
Ala Asp Asp Leu Lys Ala Leu Ser Ser Ala Leu His Glu Arg Gly Met
            100                 105                 110 tat ctt atg gtc gat gtg gtt gct aac cat atg ggc tat gat gga ccg   384
Tyr Leu Met Val Asp Val Val Ala Asn His Met Gly Tyr Asp Gly Pro
        115                 120                 125 ggt agc tca gtc gat tac agt gtg ttt gtt ccg ttc aat tcc gct agc   432
```

```
Gly Ser Ser Val Asp Tyr Ser Val Phe Val Pro Phe Asn Ser Ala Ser
        130                 135                 140 tac ttc cac ccg ttc tgt ttc att caa aac tgg aat gat cag act cag      480
Tyr Phe His Pro Phe Cys Phe Ile Gln Asn Trp Asn Asp Gln Thr Gln
145                 150                 155                 160 gtt gag gat tgc tgg cta gga gat aac act gtc tcc ttg cct gat ctc      528
Val Glu Asp Cys Trp Leu Gly Asp Asn Thr Val Ser Leu Pro Asp Leu
                165                 170                 175 gat acc acc aag gat gtg gtc aag aat gaa tgg tac gac tgg gtg gga      576
Asp Thr Thr Lys Asp Val Val Lys Asn Glu Trp Tyr Asp Trp Val Gly
            180                 185                 190 tca ttg gta tcg aac tac tcc att gac ggc ctc cgt atc gac aca gta      624
Ser Leu Val Ser Asn Tyr Ser Ile Asp Gly Leu Arg Ile Asp Thr Val
        195                 200                 205 aaa cac gtc cag aag gac ttc tgg ccc ggg tac aac aaa gcc gca ggc      672
Lys His Val Gln Lys Asp Phe Trp Pro Gly Tyr Asn Lys Ala Ala Gly
210                 215                 220 gtg tac tgt atc ggc gag gtg ctc gac ggt gat ccg gcc tac act tgt      720
Val Tyr Cys Ile Gly Glu Val Leu Asp Gly Asp Pro Ala Tyr Thr Cys
225                 230                 235                 240 ccc tac cag gaa gtc ctg gac ggc gta ctg aac tac ccc att tac tat      768
Pro Tyr Gln Glu Val Leu Asp Gly Val Leu Asn Tyr Pro Ile Tyr Tyr
                245                 250                 255 cca ctc ctc aac gcc ttc aag tca acc tcc ggc agc atg gac gac ctc      816
Pro Leu Leu Asn Ala Phe Lys Ser Thr Ser Gly Ser Met Asp Asp Leu
            260                 265                 270 tac aac atg atc aac acc gtc aaa tcc gac tgt cca gac tca aca ctc      864
Tyr Asn Met Ile Asn Thr Val Lys Ser Asp Cys Pro Asp Ser Thr Leu
        275                 280                 285 ctg ggc aca ttc gtc gag aac cac gac aac cca cgg ttc gct tct tac      912
Leu Gly Thr Phe Val Glu Asn His Asp Asn Pro Arg Phe Ala Ser Tyr
290                 295                 300 acc aac gac ata gcc ctc gcc aag aac gtc gca gca ttc atc atc ctc      960
Thr Asn Asp Ile Ala Leu Ala Lys Asn Val Ala Ala Phe Ile Ile Leu
305                 310                 315                 320 aac gac gga atc ccc atc atc tac gcc ggc caa gaa cag cac tac gcc     1008
Asn Asp Gly Ile Pro Ile Ile Tyr Ala Gly Gln Glu Gln His Tyr Ala
                325                 330                 335 ggc gga aac gac ccc gcg aac cgc gaa gca acc tgg ctc tcg ggc tac     1056
Gly Gly Asn Asp Pro Ala Asn Arg Glu Ala Thr Trp Leu Ser Gly Tyr
            340                 345                 350 ccg acc gac agc gag ctg tac aag tta att gcc tcc gcg aac gca atc     1104
Pro Thr Asp Ser Glu Leu Tyr Lys Leu Ile Ala Ser Ala Asn Ala Ile
        355                 360                 365 cgg aac tat gcc att agc aaa gat aca gga ttc gtg acc tac aag aac     1152
Arg Asn Tyr Ala Ile Ser Lys Asp Thr Gly Phe Val Thr Tyr Lys Asn
370                 375                 380 tgg ccc atc tac aaa gac gac aca acg atc gcc atg cgc aag ggc aca     1200
Trp Pro Ile Tyr Lys Asp Asp Thr Thr Ile Ala Met Arg Lys Gly Thr
385                 390                 395                 400 gat ggg tcg cag atc gtg act atc ttg tcc aac aag ggt gct tcg ggt     1248
Asp Gly Ser Gln Ile Val Thr Ile Leu Ser Asn Lys Gly Ala Ser Gly
                405                 410                 415 gat tcg tat acc ctc tcc ttg agt ggt gcg ggt tac aca gcc ggc cag     1296
Asp Ser Tyr Thr Leu Ser Leu Ser Gly Ala Gly Tyr Thr Ala Gly Gln
            420                 425                 430 caa ttg acg gag gtc att ggc tgc acg acc gtg acg gtt gat tcg tcg     1344
Gln Leu Thr Glu Val Ile Gly Cys Thr Thr Val Thr Val Asp Ser Ser
        435                 440                 445 gga gat gtg cct gtt cct atg gcg ggt ggg cta cct agg gta ttg tat     1392
```

```
Gly Asp Val Pro Val Pro Met Ala Gly Gly Leu Pro Arg Val Leu Tyr
            450                 455                 460 ccg act gag aag ttg gca ggt agc aag atc tgt agt agc tcg              1434
Pro Thr Glu Lys Leu Ala Gly Ser Lys Ile Cys Ser Ser Ser
465                 470                 475
```

<210> SEQ ID NO 6
<211> LENGTH: 478
<212> TYPE: PRT
<213> ORGANISM: Aspergillus oryzae

<400> SEQUENCE: 6

```
Ala Thr Pro Ala Asp Trp Arg Ser Gln Ser Ile Tyr Phe Leu Leu Thr
1               5                   10                  15

Asp Arg Phe Ala Arg Thr Asp Gly Ser Thr Thr Ala Thr Cys Asn Thr
            20                  25                  30

Ala Asp Gln Lys Tyr Cys Gly Gly Thr Trp Gln Gly Ile Ile Asp Lys
        35                  40                  45

Leu Asp Tyr Ile Gln Gly Met Gly Phe Thr Ala Ile Trp Ile Thr Pro
    50                  55                  60

Val Thr Ala Gln Leu Pro Gln Thr Thr Ala Tyr Gly Asp Ala Tyr His
65                  70                  75                  80

Gly Tyr Trp Gln Gln Asp Ile Tyr Ser Leu Asn Glu Asn Tyr Gly Thr
                85                  90                  95

Ala Asp Asp Leu Lys Ala Leu Ser Ser Ala Leu His Glu Arg Gly Met
            100                 105                 110

Tyr Leu Met Val Asp Val Val Ala Asn His Met Gly Tyr Asp Gly Pro
        115                 120                 125

Gly Ser Ser Val Asp Tyr Ser Val Phe Val Pro Phe Asn Ser Ala Ser
    130                 135                 140

Tyr Phe His Pro Phe Cys Phe Ile Gln Asn Trp Asn Asp Gln Thr Gln
145                 150                 155                 160

Val Glu Asp Cys Trp Leu Gly Asp Asn Thr Val Ser Leu Pro Asp Leu
                165                 170                 175

Asp Thr Thr Lys Asp Val Val Lys Asn Glu Trp Tyr Asp Trp Val Gly
            180                 185                 190

Ser Leu Val Ser Asn Tyr Ser Ile Asp Gly Leu Arg Ile Asp Thr Val
        195                 200                 205

Lys His Val Gln Lys Asp Phe Trp Pro Gly Tyr Asn Lys Ala Ala Gly
    210                 215                 220

Val Tyr Cys Ile Gly Glu Val Leu Asp Gly Asp Pro Ala Tyr Thr Cys
225                 230                 235                 240

Pro Tyr Gln Glu Val Leu Asp Gly Val Leu Asn Tyr Pro Ile Tyr Tyr
                245                 250                 255

Pro Leu Leu Asn Ala Phe Lys Ser Thr Ser Gly Ser Met Asp Asp Leu
            260                 265                 270

Tyr Asn Met Ile Asn Thr Val Lys Ser Asp Cys Pro Asp Ser Thr Leu
        275                 280                 285

Leu Gly Thr Phe Val Glu Asn His Asp Asn Pro Arg Phe Ala Ser Tyr
    290                 295                 300

Thr Asn Asp Ile Ala Leu Ala Lys Asn Val Ala Ala Phe Ile Ile Leu
305                 310                 315                 320

Asn Asp Gly Ile Pro Ile Ile Tyr Ala Gly Gln Glu Gln His Tyr Ala
                325                 330                 335

Gly Gly Asn Asp Pro Ala Asn Arg Glu Ala Thr Trp Leu Ser Gly Tyr
            340                 345                 350
```

```
Pro Thr Asp Ser Glu Leu Tyr Lys Leu Ile Ala Ser Ala Asn Ala Ile
        355                 360                 365

Arg Asn Tyr Ala Ile Ser Lys Asp Thr Gly Phe Val Thr Tyr Lys Asn
    370                 375                 380

Trp Pro Ile Tyr Lys Asp Thr Thr Ile Ala Met Arg Lys Gly Thr
385                 390                 395                 400

Asp Gly Ser Gln Ile Val Thr Ile Leu Ser Asn Lys Gly Ala Ser Gly
                405                 410                 415

Asp Ser Tyr Thr Leu Ser Leu Ser Gly Ala Gly Tyr Thr Ala Gly Gln
            420                 425                 430

Gln Leu Thr Glu Val Ile Gly Cys Thr Thr Val Thr Val Asp Ser Ser
        435                 440                 445

Gly Asp Val Pro Val Pro Met Ala Gly Gly Leu Pro Arg Val Leu Tyr
    450                 455                 460

Pro Thr Glu Lys Leu Ala Gly Ser Lys Ile Cys Ser Ser Ser
465                 470                 475

<210> SEQ ID NO 7
<211> LENGTH: 1461
<212> TYPE: DNA
<213> ORGANISM: Trichophaea saccata
<220> FEATURE:
<221> NAME/KEY: CDS
<222> LOCATION: (1)..(1461)

<400> SEQUENCE: 7 tca tcc ggc aag aaa tta gag ctg gag gcc ctc aac ttt gtt tgg cag      48
Ser Ser Gly Lys Lys Leu Glu Leu Glu Ala Leu Asn Phe Val Trp Gln
1               5                   10                  15 aat gca gtt ctt act ggc gct cag agc act ttc aac aat ggg cag aag      96
Asn Ala Val Leu Thr Gly Ala Gln Ser Thr Phe Asn Asn Gly Gln Lys
            20                  25                  30 ggc gct att gtg gag ctt ttt ggg tgg ccg tat gca gat att gca aag     144
Gly Ala Ile Val Glu Leu Phe Gly Trp Pro Tyr Ala Asp Ile Ala Lys
        35                  40                  45 gag tgc gct ttc ctt gga aaa gcc gga tac atg gga gtc aag gtt tgg     192
Glu Cys Ala Phe Leu Gly Lys Ala Gly Tyr Met Gly Val Lys Val Trp
    50                  55                  60 cct cca aac gag cac atc tgg gga tcg gac tac tac gaa acc gac aat     240
Pro Pro Asn Glu His Ile Trp Gly Ser Asp Tyr Tyr Glu Thr Asp Asn
65                  70                  75                  80 atg ttc cgt ccg tgg tat ctg gtg tac cag ccg gtc agt tac aag ctt     288
Met Phe Arg Pro Trp Tyr Leu Val Tyr Gln Pro Val Ser Tyr Lys Leu
                85                  90                  95 gtg agc cgt caa gga acc cgt gag gag ctt cga gct atg ata act gct     336
Val Ser Arg Gln Gly Thr Arg Glu Glu Leu Arg Ala Met Ile Thr Ala
            100                 105                 110 tgc cgg agt gct gga gtg cgc gtc tat gcc gac gcc gtc att aat cac     384
Cys Arg Ser Ala Gly Val Arg Val Tyr Ala Asp Ala Val Ile Asn His
        115                 120                 125 atg tct gga aac gga aac gat atc caa aac cat cgt aat acc gcc tgc     432
Met Ser Gly Asn Gly Asn Asp Ile Gln Asn His Arg Asn Thr Ala Cys
    130                 135                 140 gcc tac tgg aca ggc cac aac gca acc gcg aat tcg cct tac ttc acc     480
Ala Tyr Trp Thr Gly His Asn Ala Thr Ala Asn Ser Pro Tyr Phe Thr
145                 150                 155                 160 tcc ggt tac acc tat ctt att aat ccc ttc acg aac aca cgc ccc acc     528
Ser Gly Tyr Thr Tyr Leu Ile Asn Pro Phe Thr Asn Thr Arg Pro Thr
                165                 170                 175
```

```
ttc gag tac cca gcg gta cca tgg ggc cca act gat ttc cat tgc gtt      576
Phe Glu Tyr Pro Ala Val Pro Trp Gly Pro Thr Asp Phe His Cys Val
            180                 185                 190 tcc tct atc aca gat tgg acc aac ggc caa atc gtc aca aag ggc tat      624
Ser Ser Ile Thr Asp Trp Thr Asn Gly Gln Ile Val Thr Lys Gly Tyr
        195                 200                 205 ctc gtg gga ctc tcc gat ctc aac aca gag aag gat tac gtc cag gac      672
Leu Val Gly Leu Ser Asp Leu Asn Thr Glu Lys Asp Tyr Val Gln Asp
    210                 215                 220 cgc atc gcc act tat ctt gtg gat ctc ttg tca atc ggc ttc tcc ggc      720
Arg Ile Ala Thr Tyr Leu Val Asp Leu Leu Ser Ile Gly Phe Ser Gly
225                 230                 235                 240 ttc cgt gtt gat gcg gca aaa cat att ggc ccc acc tcc atg gca cag      768
Phe Arg Val Asp Ala Ala Lys His Ile Gly Pro Thr Ser Met Ala Gln
                245                 250                 255 atc ttc gga agg gtt gca aag aag atg ggc gga agt ctt cca gat gat      816
Ile Phe Gly Arg Val Ala Lys Lys Met Gly Gly Ser Leu Pro Asp Asp
            260                 265                 270 ttt atc act tgg ctt gaa gtg ttg atg ggt ggt gag aag gag cag tat      864
Phe Ile Thr Trp Leu Glu Val Leu Met Gly Gly Glu Lys Glu Gln Tyr
        275                 280                 285 gct tgc ggc ggc ggt gaa tgg agt tgg tac acc aac ttc aat acc cag      912
Ala Cys Gly Gly Gly Glu Trp Ser Trp Tyr Thr Asn Phe Asn Thr Gln
    290                 295                 300 ctt tcc aat gcg gga att agt gac act gat atc aat aag atc aag att      960
Leu Ser Asn Ala Gly Ile Ser Asp Thr Asp Ile Asn Lys Ile Lys Ile
305                 310                 315                 320 tgg agc tcc gac tat ccc aag gag ttc ccg atc tgc ggt tct tgg atc     1008
Trp Ser Ser Asp Tyr Pro Lys Glu Phe Pro Ile Cys Gly Ser Trp Ile
                325                 330                 335 atc cca tcc act cgc ttt gtc atc caa aat gac gac cat gac cag cag     1056
Ile Pro Ser Thr Arg Phe Val Ile Gln Asn Asp Asp His Asp Gln Gln
            340                 345                 350 aac ccg ggc tct tcc tcc aga gat atg ggt gac caa ggc tcc gta ctc     1104
Asn Pro Gly Ser Ser Ser Arg Asp Met Gly Asp Gln Gly Ser Val Leu
        355                 360                 365 atc aaa gat caa gat gta gcc aag cac cgg gca ttt gag gtc aag ctc     1152
Ile Lys Asp Gln Asp Val Ala Lys His Arg Ala Phe Glu Val Lys Leu
    370                 375                 380 ttc acc cgt acc gac ggt gac tgg caa atc agg aat atc ctc tcc tct     1200
Phe Thr Arg Thr Asp Gly Asp Trp Gln Ile Arg Asn Ile Leu Ser Ser
385                 390                 395                 400 tat atg ttt gcc tcc aac gga gca aat ggc ttc ccc gat ggt ctt tcg     1248
Tyr Met Phe Ala Ser Asn Gly Ala Asn Gly Phe Pro Asp Gly Leu Ser
                405                 410                 415 gat tgt tcc ctt tat act ggc tca cag agt gcg agt ggt tgt ttg ggt     1296
Asp Cys Ser Leu Tyr Thr Gly Ser Gln Ser Ala Ser Gly Cys Leu Gly
            420                 425                 430 atc gcg aag gat acc gct tat gta gaa ggt atc tgt ggg tat act atg     1344
Ile Ala Lys Asp Thr Ala Tyr Val Glu Gly Ile Cys Gly Tyr Thr Met
        435                 440                 445 gtt gct gga agg tac acc agg ccg cat agg gat ctg agc atc att aat     1392
Val Ala Gly Arg Tyr Thr Arg Pro His Arg Asp Leu Ser Ile Ile Asn
    450                 455                 460 gct atg agg agt tgg gtc ggg ttg tcg agt acc aca gcg gat gct ctt     1440
Ala Met Arg Ser Trp Val Gly Leu Ser Ser Thr Thr Ala Asp Ala Leu
465                 470                 475                 480 gga atc ccc ggt tgt agc tga                                         1461
Gly Ile Pro Gly Cys Ser
                485
```

<210> SEQ ID NO 8
<211> LENGTH: 486
<212> TYPE: PRT
<213> ORGANISM: Trichophaea saccata

<400> SEQUENCE: 8

```
Ser Ser Gly Lys Lys Leu Glu Leu Glu Ala Leu Asn Phe Val Trp Gln
1               5                   10                  15

Asn Ala Val Leu Thr Gly Ala Gln Ser Thr Phe Asn Asn Gly Gln Lys
            20                  25                  30

Gly Ala Ile Val Glu Leu Phe Gly Trp Pro Tyr Ala Asp Ile Ala Lys
        35                  40                  45

Glu Cys Ala Phe Leu Gly Lys Ala Gly Tyr Met Gly Val Lys Val Trp
    50                  55                  60

Pro Pro Asn Glu His Ile Trp Gly Ser Asp Tyr Tyr Glu Thr Asp Asn
65                  70                  75                  80

Met Phe Arg Pro Trp Tyr Leu Val Tyr Gln Pro Val Ser Tyr Lys Leu
                85                  90                  95

Val Ser Arg Gln Gly Thr Arg Glu Glu Leu Arg Ala Met Ile Thr Ala
            100                 105                 110

Cys Arg Ser Ala Gly Val Arg Val Tyr Ala Asp Ala Val Ile Asn His
        115                 120                 125

Met Ser Gly Asn Gly Asn Asp Ile Gln Asn His Arg Asn Thr Ala Cys
    130                 135                 140

Ala Tyr Trp Thr Gly His Asn Ala Thr Ala Asn Ser Pro Tyr Phe Thr
145                 150                 155                 160

Ser Gly Tyr Thr Tyr Leu Ile Asn Pro Phe Thr Asn Thr Arg Pro Thr
                165                 170                 175

Phe Glu Tyr Pro Ala Val Pro Trp Gly Pro Thr Asp Phe His Cys Val
            180                 185                 190

Ser Ser Ile Thr Asp Trp Thr Asn Gly Gln Ile Val Thr Lys Gly Tyr
        195                 200                 205

Leu Val Gly Leu Ser Asp Leu Asn Thr Glu Lys Asp Tyr Val Gln Asp
    210                 215                 220

Arg Ile Ala Thr Tyr Leu Val Asp Leu Leu Ser Ile Gly Phe Ser Gly
225                 230                 235                 240

Phe Arg Val Asp Ala Ala Lys His Ile Gly Pro Thr Ser Met Ala Gln
                245                 250                 255

Ile Phe Gly Arg Val Ala Lys Lys Met Gly Gly Ser Leu Pro Asp Asp
            260                 265                 270

Phe Ile Thr Trp Leu Glu Val Leu Met Gly Gly Glu Lys Glu Gln Tyr
        275                 280                 285

Ala Cys Gly Gly Gly Glu Trp Ser Trp Tyr Thr Asn Phe Asn Thr Gln
    290                 295                 300

Leu Ser Asn Ala Gly Ile Ser Asp Thr Asp Ile Asn Lys Ile Lys Ile
305                 310                 315                 320

Trp Ser Ser Asp Tyr Pro Lys Glu Phe Pro Ile Cys Gly Ser Trp Ile
                325                 330                 335

Ile Pro Ser Thr Arg Phe Val Ile Gln Asn Asp Asp His Asp Gln Gln
            340                 345                 350

Asn Pro Gly Ser Ser Ser Arg Asp Met Gly Asp Gln Gly Ser Val Leu
        355                 360                 365

Ile Lys Asp Gln Asp Val Ala Lys His Arg Ala Phe Glu Val Lys Leu
    370                 375                 380
```

```
Phe Thr Arg Thr Asp Gly Asp Trp Gln Ile Arg Asn Ile Leu Ser Ser
385                 390                 395                 400

Tyr Met Phe Ala Ser Asn Gly Ala Asn Gly Phe Pro Asp Gly Leu Ser
                405                 410                 415

Asp Cys Ser Leu Tyr Thr Gly Ser Gln Ser Ala Ser Gly Cys Leu Gly
            420                 425                 430

Ile Ala Lys Asp Thr Ala Tyr Val Glu Gly Ile Cys Gly Tyr Thr Met
        435                 440                 445

Val Ala Gly Arg Tyr Thr Arg Pro His Arg Asp Leu Ser Ile Ile Asn
    450                 455                 460

Ala Met Arg Ser Trp Val Gly Leu Ser Ser Thr Thr Ala Asp Ala Leu
465                 470                 475                 480

Gly Ile Pro Gly Cys Ser
                485

<210> SEQ ID NO 9
<211> LENGTH: 1398
<212> TYPE: DNA
<213> ORGANISM: Subulispora provurvata
<220> FEATURE:
<221> NAME/KEY: CDS
<222> LOCATION: (1)..(1398)

<400> SEQUENCE: 9 acc gaa tgg ggg agt cag tcc atc tac cag gta ttg acg gat cgc ttt      48
Thr Glu Trp Gly Ser Gln Ser Ile Tyr Gln Val Leu Thr Asp Arg Phe
1               5                   10                  15 gcc cgc act gat ggg tct act acc gcc tcc tgt gat gtg aac aag tac      96
Ala Arg Thr Asp Gly Ser Thr Thr Ala Ser Cys Asp Val Asn Lys Tyr
            20                  25                  30 tgc ggc ggc acc tgg cag ggc ata atc gac aag ctg gac tac atc cag     144
Cys Gly Gly Thr Trp Gln Gly Ile Ile Asp Lys Leu Asp Tyr Ile Gln
        35                  40                  45 ggc atg ggt ttc act gcg atc tgg att tcg cct atc gtc gac aac atc     192
Gly Met Gly Phe Thr Ala Ile Trp Ile Ser Pro Ile Val Asp Asn Ile
    50                  55                  60 gac gcc gat act gtt gat ggc acc tct tat cac ggt tac tgg gcc cag     240
Asp Ala Asp Thr Val Asp Gly Thr Ser Tyr His Gly Tyr Trp Ala Gln
65                  70                  75                  80 gac atc acc tca gtg aac tcg gcg ttc ggc acg gag cag gac ctc atc     288
Asp Ile Thr Ser Val Asn Ser Ala Phe Gly Thr Glu Gln Asp Leu Ile
                85                  90                  95 aac ctc tca gca gct ctg cac gac agg ggc atg tat ctg atg gta gac     336
Asn Leu Ser Ala Ala Leu His Asp Arg Gly Met Tyr Leu Met Val Asp
            100                 105                 110 gtg gta aac aac cac atg gga tac aac ggc tgc ggc gat tgt gtt gac     384
Val Val Asn Asn His Met Gly Tyr Asn Gly Cys Gly Asp Cys Val Asp
        115                 120                 125 tac agc ata tac acg cca ttc aac cag cag tcc tac tac cac ccg tac     432
Tyr Ser Ile Tyr Thr Pro Phe Asn Gln Gln Ser Tyr Tyr His Pro Tyr
    130                 135                 140 tgc gcc act gat tac agc aac ctg acc tcc atc cag gtg tgc tgg gag     480
Cys Ala Thr Asp Tyr Ser Asn Leu Thr Ser Ile Gln Val Cys Trp Glu
145                 150                 155                 160 ggt gac aac att gtc agt ctc ccc gac ctg agg aca gag gat gac gat     528
Gly Asp Asn Ile Val Ser Leu Pro Asp Leu Arg Thr Glu Asp Asp Asp
                165                 170                 175 gtc cgc acc atg tgg tac gac tgg atc acg ccg ttg gta acc aag tac     576
Val Arg Thr Met Trp Tyr Asp Trp Ile Thr Pro Leu Val Thr Lys Tyr
            180                 185                 190
```

| | | |
|---|---|---|
| tcg atc gat gga ctg cgc atg gac agc gcc gag cat gtc gag aag agc<br>Ser Ile Asp Gly Leu Arg Met Asp Ser Ala Glu His Val Glu Lys Ser<br>195 200 205 | | 624 |
| ttc tgg cct ggt tgg gta tcc gcc tcg gga gta tac aac ata gga gag<br>Phe Trp Pro Gly Trp Val Ser Ala Ser Gly Val Tyr Asn Ile Gly Glu<br>210 215 220 | | 672 |
| gtt gat gag ggc gac ccc acc atc ttc cca gac tgg ctg aac tac atc<br>Val Asp Glu Gly Asp Pro Thr Ile Phe Pro Asp Trp Leu Asn Tyr Ile<br>225 230 235 240 | | 720 |
| gac gga acc ttg aac tat cca gct tac tac tgg atc act caa gct ttc<br>Asp Gly Thr Leu Asn Tyr Pro Ala Tyr Tyr Trp Ile Thr Gln Ala Phe<br>245 250 255 | | 768 |
| cag tca act tct ggt tct atc agc aac ctg gtt aat gga atc aac caa<br>Gln Ser Thr Ser Gly Ser Ile Ser Asn Leu Val Asn Gly Ile Asn Gln<br>260 265 270 | | 816 |
| atg aag ggc tca atg aaa acc agc acc ctc ggg tcg ttc ctt gag aat<br>Met Lys Gly Ser Met Lys Thr Ser Thr Leu Gly Ser Phe Leu Glu Asn<br>275 280 285 | | 864 |
| cac gac cag cca cga ttc cct tct ctg act agt gat gcg gat ttg gcg<br>His Asp Gln Pro Arg Phe Pro Ser Leu Thr Ser Asp Ala Asp Leu Ala<br>290 295 300 | | 912 |
| aag aac gct atc gct ttt gct atg ctt gct gat ggc gtc cca atc gtc<br>Lys Asn Ala Ile Ala Phe Ala Met Leu Ala Asp Gly Val Pro Ile Val<br>305 310 315 320 | | 960 |
| tac tat ggt caa gag cag gcc tac tcg ggt ggt gcg cct aat gac<br>Tyr Tyr Gly Gln Glu Gln Ala Tyr Ser Gly Gly Val Pro Asn Asp<br>325 330 335 | | 1008 |
| cgt gag cca ctg tgg aca tcg gga tac agc acc aca tcg gca ggt tac<br>Arg Glu Pro Leu Trp Thr Ser Gly Tyr Ser Thr Thr Ser Ala Gly Tyr<br>340 345 350 | | 1056 |
| acg ttc atc acg acc atc aac aaa atc cgc cgc ctg gct ctc acc cag<br>Thr Phe Ile Thr Thr Ile Asn Lys Ile Arg Arg Leu Ala Leu Thr Gln<br>355 360 365 | | 1104 |
| gac agt gcc tac gta gca tac cag acc tac ccg atc tat tcg gat tct<br>Asp Ser Ala Tyr Val Ala Tyr Gln Thr Tyr Pro Ile Tyr Ser Asp Ser<br>370 375 380 | | 1152 |
| cac gtc atc gcc atg aag aag agc agc gtc gtc tcc gtc tat agc aac<br>His Val Ile Ala Met Lys Lys Ser Ser Val Val Ser Val Tyr Ser Asn<br>385 390 395 400 | | 1200 |
| att ggc tcc agc ggc agc acc tat tcg atc acc cta cct gcc ggc aca<br>Ile Gly Ser Ser Gly Ser Thr Tyr Ser Ile Thr Leu Pro Ala Gly Thr<br>405 410 415 | | 1248 |
| ttc act ggg agt gta gcg ctc aca gac gtg gtg agc tgc cag acg tac<br>Phe Thr Gly Ser Val Ala Leu Thr Asp Val Val Ser Cys Gln Thr Tyr<br>420 425 430 | | 1296 |
| acg gcg agc tct act ggc agc ctc acc ttc acc ttc gga caa gtt ccc<br>Thr Ala Ser Ser Thr Gly Ser Leu Thr Phe Thr Phe Gly Gln Val Pro<br>435 440 445 | | 1344 |
| tcc gtc ttc tac ccg acg gca agc ctg tcc ggc agc ggg ctc tgc tct<br>Ser Val Phe Tyr Pro Thr Ala Ser Leu Ser Gly Ser Gly Leu Cys Ser<br>450 455 460 | | 1392 |
| agc tcc<br>Ser Ser<br>465 | | 1398 |

<210> SEQ ID NO 10
<211> LENGTH: 466
<212> TYPE: PRT
<213> ORGANISM: Subulispora provurvata

<400> SEQUENCE: 10

-continued

```
Thr Glu Trp Gly Ser Gln Ser Ile Tyr Gln Val Leu Thr Asp Arg Phe
 1               5                  10                  15

Ala Arg Thr Asp Gly Ser Thr Ala Ser Cys Asp Val Asn Lys Tyr
            20                  25                  30

Cys Gly Gly Thr Trp Gln Gly Ile Ile Asp Lys Leu Asp Tyr Ile Gln
            35                  40                  45

Gly Met Gly Phe Thr Ala Ile Trp Ile Ser Pro Ile Val Asp Asn Ile
 50                  55                  60

Asp Ala Asp Thr Val Asp Gly Thr Ser Tyr His Gly Tyr Trp Ala Gln
 65                  70                  75                  80

Asp Ile Thr Ser Val Asn Ser Ala Phe Gly Thr Glu Gln Asp Leu Ile
            85                  90                  95

Asn Leu Ser Ala Ala Leu His Asp Arg Gly Met Tyr Leu Met Val Asp
            100                 105                 110

Val Val Asn Asn His Met Gly Tyr Asn Gly Cys Gly Asp Cys Val Asp
            115                 120                 125

Tyr Ser Ile Tyr Thr Pro Phe Asn Gln Gln Ser Tyr Tyr His Pro Tyr
            130                 135                 140

Cys Ala Thr Asp Tyr Ser Asn Leu Thr Ser Ile Gln Val Cys Trp Glu
145                 150                 155                 160

Gly Asp Asn Ile Val Ser Leu Pro Asp Leu Arg Thr Glu Asp Asp
            165                 170                 175

Val Arg Thr Met Trp Tyr Asp Trp Ile Thr Pro Leu Val Thr Lys Tyr
            180                 185                 190

Ser Ile Asp Gly Leu Arg Met Asp Ser Ala Glu His Val Glu Lys Ser
            195                 200                 205

Phe Trp Pro Gly Trp Val Ser Ala Ser Gly Val Tyr Asn Ile Gly Glu
            210                 215                 220

Val Asp Glu Gly Asp Pro Thr Ile Phe Pro Asp Trp Leu Asn Tyr Ile
225                 230                 235                 240

Asp Gly Thr Leu Asn Tyr Pro Ala Tyr Tyr Trp Ile Thr Gln Ala Phe
            245                 250                 255

Gln Ser Thr Ser Gly Ser Ile Ser Asn Leu Val Asn Gly Ile Asn Gln
            260                 265                 270

Met Lys Gly Ser Met Lys Thr Ser Thr Leu Gly Ser Phe Leu Glu Asn
            275                 280                 285

His Asp Gln Pro Arg Phe Pro Ser Leu Thr Ser Asp Ala Asp Leu Ala
            290                 295                 300

Lys Asn Ala Ile Ala Phe Ala Met Leu Ala Asp Gly Val Pro Ile Val
305                 310                 315                 320

Tyr Tyr Gly Gln Glu Gln Ala Tyr Ser Gly Gly Val Pro Asn Asp
            325                 330                 335

Arg Glu Pro Leu Trp Thr Ser Gly Tyr Ser Thr Thr Ser Ala Gly Tyr
            340                 345                 350

Thr Phe Ile Thr Thr Ile Asn Lys Ile Arg Arg Leu Ala Leu Thr Gln
            355                 360                 365

Asp Ser Ala Tyr Val Ala Tyr Gln Thr Tyr Pro Ile Tyr Ser Asp Ser
            370                 375                 380

His Val Ile Ala Met Lys Lys Ser Ser Val Ser Val Tyr Ser Asn
385                 390                 395                 400

Ile Gly Ser Ser Gly Ser Thr Tyr Ser Ile Thr Leu Pro Ala Gly Thr
            405                 410                 415

Phe Thr Gly Ser Val Ala Leu Thr Asp Val Val Ser Cys Gln Thr Tyr
            420                 425                 430
```

```
Thr Ala Ser Ser Thr Gly Ser Leu Thr Phe Thr Phe Gly Gln Val Pro
            435                 440                 445

Ser Val Phe Tyr Pro Thr Ala Ser Leu Ser Gly Ser Gly Leu Cys Ser
    450                 455                 460

Ser Ser
465

<210> SEQ ID NO 11
<211> LENGTH: 1350
<212> TYPE: DNA
<213> ORGANISM: Valsaria rubricosa
<220> FEATURE:
<221> NAME/KEY: CDS
<222> LOCATION: (1)..(1350)

<400> SEQUENCE: 11 agc aac tcc gac tgg agg tcc cgc aat atc tac ttt gcc ttg acc gac      48
Ser Asn Ser Asp Trp Arg Ser Arg Asn Ile Tyr Phe Ala Leu Thr Asp
1               5                   10                  15 cgc gtc gcc aat ccg tcc acc acg acc gca tgt agt gac ctg agc aac      96
Arg Val Ala Asn Pro Ser Thr Thr Thr Ala Cys Ser Asp Leu Ser Asn
            20                  25                  30 tac tgc ggc ggc acg tgg agc ggc ctg tcg agc aag ctg gac tac atc     144
Tyr Cys Gly Gly Thr Trp Ser Gly Leu Ser Ser Lys Leu Asp Tyr Ile
        35                  40                  45 caa ggg atg ggc ttc gat tcc atc tgg att acc ccc gtg gtc gag aac     192
Gln Gly Met Gly Phe Asp Ser Ile Trp Ile Thr Pro Val Val Glu Asn
    50                  55                  60 tgc gac ggt ggc tac cac ggc tac tgg gcc aag gcg ctc tac aac gtc     240
Cys Asp Gly Gly Tyr His Gly Tyr Trp Ala Lys Ala Leu Tyr Asn Val
65                  70                  75                  80 aac acg aac tac ggc agt gcg gat gat ctg aag aac ttc gtt gcg gcc     288
Asn Thr Asn Tyr Gly Ser Ala Asp Asp Leu Lys Asn Phe Val Ala Ala
                85                  90                  95 gcc cat gcg aag ggc atg tac gtg atg gtg gac gtc gtc gcg aat cac     336
Ala His Ala Lys Gly Met Tyr Val Met Val Asp Val Val Ala Asn His
            100                 105                 110 atg ggt tcc tgc ggc atc gcc aac ctc tcc cca cct ccc ctg aac gag     384
Met Gly Ser Cys Gly Ile Ala Asn Leu Ser Pro Pro Pro Leu Asn Glu
        115                 120                 125 cag agc tct tat cac acc cag tgc gac att gac tac agc agt cag tcc     432
Gln Ser Ser Tyr His Thr Gln Cys Asp Ile Asp Tyr Ser Ser Gln Ser
    130                 135                 140 agc att gag acg tgc tgg ata tcc ggc ctc cct gac ctg gac acc acc     480
Ser Ile Glu Thr Cys Trp Ile Ser Gly Leu Pro Asp Leu Asp Thr Thr
145                 150                 155                 160 gat agc act atc cga tcc ctc ttc cag acc tgg gtc cac ggc ctg gtc     528
Asp Ser Thr Ile Arg Ser Leu Phe Gln Thr Trp Val His Gly Leu Val
                165                 170                 175 agc aac tac agc ttc gac ggt ctc cgc gtc gac acc gtc aag cac gtg     576
Ser Asn Tyr Ser Phe Asp Gly Leu Arg Val Asp Thr Val Lys His Val
            180                 185                 190 gag aag gat tac tgg ccc ggc ttc gtg tcg gcg gcg ggc acc tac gcc     624
Glu Lys Asp Tyr Trp Pro Gly Phe Val Ser Ala Ala Gly Thr Tyr Ala
        195                 200                 205 atc ggc gaa gtc ttc tcc ggc gac acc tcc tac gtg gcc ggc tat caa     672
Ile Gly Glu Val Phe Ser Gly Asp Thr Ser Tyr Val Ala Gly Tyr Gln
    210                 215                 220 tcg gtg atg ccg ggc ttg ctc aac tat ccc atc tac tat ccg ctc atc     720
Ser Val Met Pro Gly Leu Leu Asn Tyr Pro Ile Tyr Tyr Pro Leu Ile
225                 230                 235                 240
```

-continued

```
cgc gtc ttc gcg cag ggt gcg tcc ttc acc gat ctc gtc aac aac cac      768
Arg Val Phe Ala Gln Gly Ala Ser Phe Thr Asp Leu Val Asn Asn His
            245                 250                 255 gat acc gtc ggc tcg acc ttc tcc gac ccg acg ctg ctg ggt aac ttt      816
Asp Thr Val Gly Ser Thr Phe Ser Asp Pro Thr Leu Leu Gly Asn Phe
        260                 265                 270 atc gac aac cac gac aac cca cgt ttc ctg agc tac acc agc gac cac      864
Ile Asp Asn His Asp Asn Pro Arg Phe Leu Ser Tyr Thr Ser Asp His
    275                 280                 285 gcc ctc ctc aag aac gct ctg gcc tac gtc atc ctg gcc aga ggc atc      912
Ala Leu Leu Lys Asn Ala Leu Ala Tyr Val Ile Leu Ala Arg Gly Ile
290                 295                 300 ccc atc gtc tac tac ggc acc gag caa ggc tac tcg ggt tcg tcc gac      960
Pro Ile Val Tyr Tyr Gly Thr Glu Gln Gly Tyr Ser Gly Ser Ser Asp
305                 310                 315                 320 ccg gcg aac cgc gag gat ctc tgg cgt agc gga tac agc act acg gga     1008
Pro Ala Asn Arg Glu Asp Leu Trp Arg Ser Gly Tyr Ser Thr Thr Gly
                325                 330                 335 gac atc tac acc acc atc gcc gcg ctc tcc gcc gcg cgc acc gcg gcc     1056
Asp Ile Tyr Thr Thr Ile Ala Ala Leu Ser Ala Ala Arg Thr Ala Ala
            340                 345                 350 ggt ggc ctc gcc ggt aac gac cac gtc cac ctg tac acg acc gac aac     1104
Gly Gly Leu Ala Gly Asn Asp His Val His Leu Tyr Thr Thr Asp Asn
        355                 360                 365 gcg tac gcc tgg tcc cgg gcg agc ggc aag ctc atc gtc gtc acg tcc     1152
Ala Tyr Ala Trp Ser Arg Ala Ser Gly Lys Leu Ile Val Val Thr Ser
    370                 375                 380 aac cgc ggc agc tcc gac agc agc acc atc tgc ttc agc acc cag cag     1200
Asn Arg Gly Ser Ser Asp Ser Ser Thr Ile Cys Phe Ser Thr Gln Gln
385                 390                 395                 400 gcc agc ggc acc acc tgg acc agc acg atc acc ggc aac tcg tac acc     1248
Ala Ser Gly Thr Thr Trp Thr Ser Thr Ile Thr Gly Asn Ser Tyr Thr
                405                 410                 415 gcc gac agc aac ggc cag atc tgc gtg cag ctg tcc agc ggc gga ccc     1296
Ala Asp Ser Asn Gly Gln Ile Cys Val Gln Leu Ser Ser Gly Gly Pro
            420                 425                 430 gag gcg ctc gtc gtc tcc acc gcg acc ggc acc gcc acc gcg acg act     1344
Glu Ala Leu Val Val Ser Thr Ala Thr Gly Thr Ala Thr Ala Thr Thr
        435                 440                 445 ctg tcc                                                             1350
Leu Ser
    450

<210> SEQ ID NO 12
<211> LENGTH: 450
<212> TYPE: PRT
<213> ORGANISM: Valsaria rubricosa

<400> SEQUENCE: 12

Ser Asn Ser Asp Trp Arg Ser Arg Asn Ile Tyr Phe Ala Leu Thr Asp
1               5                   10                  15

Arg Val Ala Asn Pro Ser Thr Thr Ala Cys Ser Asp Leu Ser Asn
            20                  25                  30

Tyr Cys Gly Gly Thr Trp Ser Gly Leu Ser Ser Lys Leu Asp Tyr Ile
        35                  40                  45

Gln Gly Met Gly Phe Asp Ser Ile Trp Ile Thr Pro Val Val Glu Asn
    50                  55                  60

Cys Asp Gly Gly Tyr His Gly Tyr Trp Ala Lys Ala Leu Tyr Asn Val
65                  70                  75                  80
```

```
Asn Thr Asn Tyr Gly Ser Ala Asp Asp Leu Lys Asn Phe Val Ala Ala
                 85                  90                  95

Ala His Ala Lys Gly Met Tyr Val Met Val Asp Val Val Ala Asn His
            100                 105                 110

Met Gly Ser Cys Gly Ile Ala Asn Leu Ser Pro Pro Pro Leu Asn Glu
        115                 120                 125

Gln Ser Ser Tyr His Thr Gln Cys Asp Ile Asp Tyr Ser Ser Gln Ser
    130                 135                 140

Ser Ile Glu Thr Cys Trp Ile Ser Gly Leu Pro Asp Leu Asp Thr Thr
145                 150                 155                 160

Asp Ser Thr Ile Arg Ser Leu Phe Gln Thr Trp Val His Gly Leu Val
                165                 170                 175

Ser Asn Tyr Ser Phe Asp Gly Leu Arg Val Asp Thr Val Lys His Val
            180                 185                 190

Glu Lys Asp Tyr Trp Pro Gly Phe Val Ser Ala Ala Gly Thr Tyr Ala
        195                 200                 205

Ile Gly Glu Val Phe Ser Gly Asp Thr Ser Tyr Val Ala Gly Tyr Gln
    210                 215                 220

Ser Val Met Pro Gly Leu Leu Asn Tyr Pro Ile Tyr Tyr Pro Leu Ile
225                 230                 235                 240

Arg Val Phe Ala Gln Gly Ala Ser Phe Thr Asp Leu Val Asn Asn His
                245                 250                 255

Asp Thr Val Gly Ser Thr Phe Ser Asp Pro Thr Leu Leu Gly Asn Phe
            260                 265                 270

Ile Asp Asn His Asp Asn Pro Arg Phe Leu Ser Tyr Thr Ser Asp His
        275                 280                 285

Ala Leu Leu Lys Asn Ala Leu Ala Tyr Val Ile Leu Ala Arg Gly Ile
    290                 295                 300

Pro Ile Val Tyr Tyr Gly Thr Glu Gln Gly Tyr Ser Gly Ser Ser Asp
305                 310                 315                 320

Pro Ala Asn Arg Glu Asp Leu Trp Arg Ser Gly Tyr Ser Thr Thr Gly
                325                 330                 335

Asp Ile Tyr Thr Thr Ile Ala Ala Leu Ser Ala Ala Arg Thr Ala Ala
            340                 345                 350

Gly Gly Leu Ala Gly Asn Asp His Val His Leu Tyr Thr Thr Asp Asn
        355                 360                 365

Ala Tyr Ala Trp Ser Arg Ala Ser Gly Lys Leu Ile Val Val Thr Ser
    370                 375                 380

Asn Arg Gly Ser Ser Asp Ser Ser Thr Ile Cys Phe Ser Thr Gln Gln
385                 390                 395                 400

Ala Ser Gly Thr Thr Trp Thr Ser Thr Ile Thr Gly Asn Ser Tyr Thr
                405                 410                 415

Ala Asp Ser Asn Gly Gln Ile Cys Val Gln Leu Ser Ser Gly Gly Pro
            420                 425                 430

Glu Ala Leu Val Val Ser Thr Ala Thr Gly Thr Ala Thr Ala Thr Thr
        435                 440                 445

Leu Ser
    450

<210> SEQ ID NO 13
<211> LENGTH: 1326
<212> TYPE: DNA
<213> ORGANISM: Thermomyces lanuginosus
<220> FEATURE:
<221> NAME/KEY: CDS
<222> LOCATION: (1)..(1326)
```

<400> SEQUENCE: 13

| | | | | | | | | | | | | | | | | |
|---|---|---|---|---|---|---|---|---|---|---|---|---|---|---|---|---|
| aaa | tat | tgc | ggg | gga | aca | tgg | cga | ggt | atc | atc | aac | aac | ctg | gat | tac | 48 |
| Lys | Tyr | Cys | Gly | Gly | Thr | Trp | Arg | Gly | Ile | Ile | Asn | Asn | Leu | Asp | Tyr | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| atc | cag | gat | atg | ggc | ttc | aca | gct | atc | tgg | att | act | cca | gtg | aca | gcc | 96 |
| Ile | Gln | Asp | Met | Gly | Phe | Thr | Ala | Ile | Trp | Ile | Thr | Pro | Val | Thr | Ala | |
| | | | 20 | | | | | 25 | | | | | 30 | | | |

| | | | | | | | | | | | | | | | | |
|---|---|---|---|---|---|---|---|---|---|---|---|---|---|---|---|---|
| cag | tgg | gac | gac | gat | gtg | gat | gcg | gca | gat | gca | acg | tcg | tat | cac | ggt | 144 |
| Gln | Trp | Asp | Asp | Asp | Val | Asp | Ala | Ala | Asp | Ala | Thr | Ser | Tyr | His | Gly | |
| | | 35 | | | | | 40 | | | | | 45 | | | | |

| | | | | | | | | | | | | | | | | |
|---|---|---|---|---|---|---|---|---|---|---|---|---|---|---|---|---|
| tat | tgg | cag | aaa | gac | cta | tac | tct | ctg | aat | tcg | aaa | ttc | ggc | act | gcc | 192 |
| Tyr | Trp | Gln | Lys | Asp | Leu | Tyr | Ser | Leu | Asn | Ser | Lys | Phe | Gly | Thr | Ala | |
| 50 | | | | | 55 | | | | | 60 | | | | | | |

| | | | | | | | | | | | | | | | | |
|---|---|---|---|---|---|---|---|---|---|---|---|---|---|---|---|---|
| gat | gac | ttg | aaa | gcc | ctg | gct | gat | acc | ctt | cac | gcc | cgt | ggg | atg | ctt | 240 |
| Asp | Asp | Leu | Lys | Ala | Leu | Ala | Asp | Thr | Leu | His | Ala | Arg | Gly | Met | Leu | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| ctc | atg | gtc | gac | gtc | gtg | gct | aat | cac | ttt | ggc | tac | ggc | ggt | tct | cat | 288 |
| Leu | Met | Val | Asp | Val | Val | Ala | Asn | His | Phe | Gly | Tyr | Gly | Gly | Ser | His | |
| | | | | 85 | | | | | 90 | | | | | 95 | | |

| | | | | | | | | | | | | | | | | |
|---|---|---|---|---|---|---|---|---|---|---|---|---|---|---|---|---|
| agc | gag | gtg | gat | tac | tcg | atc | ttc | aat | cct | ctg | aac | agc | cag | gat | tac | 336 |
| Ser | Glu | Val | Asp | Tyr | Ser | Ile | Phe | Asn | Pro | Leu | Asn | Ser | Gln | Asp | Tyr | |
| | | | 100 | | | | | 105 | | | | | 110 | | | |

| | | | | | | | | | | | | | | | | |
|---|---|---|---|---|---|---|---|---|---|---|---|---|---|---|---|---|
| ttc | cac | ccg | ttc | tgt | ctc | att | gag | gac | tac | gac | aac | cag | gaa | gaa | gtc | 384 |
| Phe | His | Pro | Phe | Cys | Leu | Ile | Glu | Asp | Tyr | Asp | Asn | Gln | Glu | Glu | Val | |
| | | 115 | | | | | 120 | | | | | 125 | | | | |

| | | | | | | | | | | | | | | | | |
|---|---|---|---|---|---|---|---|---|---|---|---|---|---|---|---|---|
| gaa | caa | tgc | tgg | ctg | gcc | gat | act | ccg | acg | aca | ttg | ccc | gac | gtg | gac | 432 |
| Glu | Gln | Cys | Trp | Leu | Ala | Asp | Thr | Pro | Thr | Thr | Leu | Pro | Asp | Val | Asp | |
| 130 | | | | | 135 | | | | | 140 | | | | | | |

| | | | | | | | | | | | | | | | | |
|---|---|---|---|---|---|---|---|---|---|---|---|---|---|---|---|---|
| acc | acc | aat | cct | cag | gtt | cgg | acg | ttt | ttc | aac | gac | tgg | atc | aag | agc | 480 |
| Thr | Thr | Asn | Pro | Gln | Val | Arg | Thr | Phe | Phe | Asn | Asp | Trp | Ile | Lys | Ser | |
| 145 | | | | 150 | | | | | 155 | | | | | 160 | | |

| | | | | | | | | | | | | | | | | |
|---|---|---|---|---|---|---|---|---|---|---|---|---|---|---|---|---|
| ctg | gtg | gcg | aac | tac | tcc | atc | gat | ggt | ctg | cgc | gtc | gac | acc | gtt | aag | 528 |
| Leu | Val | Ala | Asn | Tyr | Ser | Ile | Asp | Gly | Leu | Arg | Val | Asp | Thr | Val | Lys | |
| | | | | 165 | | | | | 170 | | | | | 175 | | |

| | | | | | | | | | | | | | | | | |
|---|---|---|---|---|---|---|---|---|---|---|---|---|---|---|---|---|
| cac | gtg | gag | aaa | gat | ttc | tgg | ccc | gac | ttc | aac | gaa | gct | gct | ggc | gtg | 576 |
| His | Val | Glu | Lys | Asp | Phe | Trp | Pro | Asp | Phe | Asn | Glu | Ala | Ala | Gly | Val | |
| | | | 180 | | | | | 185 | | | | | 190 | | | |

| | | | | | | | | | | | | | | | | |
|---|---|---|---|---|---|---|---|---|---|---|---|---|---|---|---|---|
| tac | gcc | gtc | ggc | gag | gtg | ttc | aac | ggt | gac | cca | gcg | tac | acc | tgc | cca | 624 |
| Tyr | Ala | Val | Gly | Glu | Val | Phe | Asn | Gly | Asp | Pro | Ala | Tyr | Thr | Cys | Pro | |
| | | 195 | | | | | 200 | | | | | 205 | | | | |

| | | | | | | | | | | | | | | | | |
|---|---|---|---|---|---|---|---|---|---|---|---|---|---|---|---|---|
| tac | cag | gaa | gtg | ctg | gat | ggc | gtt | ctg | aac | tat | ccg | atc | tac | tat | cct | 672 |
| Tyr | Gln | Glu | Val | Leu | Asp | Gly | Val | Leu | Asn | Tyr | Pro | Ile | Tyr | Tyr | Pro | |
| 210 | | | | | 215 | | | | | 220 | | | | | | |

| | | | | | | | | | | | | | | | | |
|---|---|---|---|---|---|---|---|---|---|---|---|---|---|---|---|---|
| gcg | ctt | gat | gca | ttc | aag | tct | gtc | ggc | ggc | aat | ctc | ggc | ggc | ttg | gct | 720 |
| Ala | Leu | Asp | Ala | Phe | Lys | Ser | Val | Gly | Gly | Asn | Leu | Gly | Gly | Leu | Ala | |
| 225 | | | | 230 | | | | | 235 | | | | | 240 | | |

| | | | | | | | | | | | | | | | | |
|---|---|---|---|---|---|---|---|---|---|---|---|---|---|---|---|---|
| cag | gcc | atc | acc | acc | gtg | cag | gag | agc | tgc | aag | gat | tcc | aat | ctg | ctc | 768 |
| Gln | Ala | Ile | Thr | Thr | Val | Gln | Glu | Ser | Cys | Lys | Asp | Ser | Asn | Leu | Leu | |
| | | | | 245 | | | | | 250 | | | | | 255 | | |

| | | | | | | | | | | | | | | | | |
|---|---|---|---|---|---|---|---|---|---|---|---|---|---|---|---|---|
| ggc | aat | ttc | ctt | gag | aat | cac | gac | att | gct | cgc | ttt | gct | tcg | tac | acg | 816 |
| Gly | Asn | Phe | Leu | Glu | Asn | His | Asp | Ile | Ala | Arg | Phe | Ala | Ser | Tyr | Thr | |
| | | | 260 | | | | | 265 | | | | | 270 | | | |

| | | | | | | | | | | | | | | | | |
|---|---|---|---|---|---|---|---|---|---|---|---|---|---|---|---|---|
| gat | gac | ctt | gct | ctc | gcc | aag | aat | ggt | ctc | gct | ttc | atc | atc | ctc | tcg | 864 |
| Asp | Asp | Leu | Ala | Leu | Ala | Lys | Asn | Gly | Leu | Ala | Phe | Ile | Ile | Leu | Ser | |
| | | 275 | | | | | 280 | | | | | 285 | | | | |

| | | | | | | | | | | | | | | | | |
|---|---|---|---|---|---|---|---|---|---|---|---|---|---|---|---|---|
| gat | ggt | att | ccg | atc | atc | tac | gcg | ggc | cag | gag | cag | cac | tac | gcc | ggt | 912 |
| Asp | Gly | Ile | Pro | Ile | Ile | Tyr | Ala | Gly | Gln | Glu | Gln | His | Tyr | Ala | Gly | |
| 290 | | | | | 295 | | | | | 300 | | | | | | |

| | | | | | | | | | | | | | | | | |
|---|---|---|---|---|---|---|---|---|---|---|---|---|---|---|---|---|
| gat | cac | gat | ccc | aca | aat | cgt | gag | gcc | gtc | tgg | ctg | tct | ggc | tac | aat | 960 |

```
Asp His Asp Pro Thr Asn Arg Glu Ala Val Trp Leu Ser Gly Tyr Asn
305                 310                 315                 320 acc gac gcc gag ctg tac cag ttc atc aag aag gcc aat ggc atc cgc    1008
Thr Asp Ala Glu Leu Tyr Gln Phe Ile Lys Lys Ala Asn Gly Ile Arg
                325                 330                 335 aac ttg gct atc agc cag aac ccg gaa ttc acc tcc tcc aag acc aag    1056
Asn Leu Ala Ile Ser Gln Asn Pro Glu Phe Thr Ser Ser Lys Thr Lys
                340                 345                 350 gtc atc tac caa gac gat tcg acc ctt gcc att aac cgg ggc ggc gtc    1104
Val Ile Tyr Gln Asp Asp Ser Thr Leu Ala Ile Asn Arg Gly Gly Val
                355                 360                 365 gtt act gtc ctg agc aat gaa ggc gcc tcc gga gga gac cgg act gtc    1152
Val Thr Val Leu Ser Asn Glu Gly Ala Ser Gly Gly Asp Arg Thr Val
        370                 375                 380 tcc att ccg gga act ggc ttc gag gcc ggc acg gaa ttg act gat gtc    1200
Ser Ile Pro Gly Thr Gly Phe Glu Ala Gly Thr Glu Leu Thr Asp Val
385                 390                 395                 400 atc tcc tgc aag acc gtg act gcg ggg gac agc ggg gcg gtc gac gtg    1248
Ile Ser Cys Lys Thr Val Thr Ala Gly Asp Ser Gly Ala Val Asp Val
                405                 410                 415 ccc ttg tcg ggc gga ctg cca agc gtg ctc tat ccc agc tcc cag ctg    1296
Pro Leu Ser Gly Gly Leu Pro Ser Val Leu Tyr Pro Ser Ser Gln Leu
                420                 425                 430 gcc aag agt ggt ctg tgt gcg tcg gcg tga                            1326
Ala Lys Ser Gly Leu Cys Ala Ser Ala
        435                 440

<210> SEQ ID NO 14
<211> LENGTH: 441
<212> TYPE: PRT
<213> ORGANISM: Thermomyces lanuginosus

<400> SEQUENCE: 14

Lys Tyr Cys Gly Gly Thr Trp Arg Gly Ile Ile Asn Asn Leu Asp Tyr
1               5                   10                  15

Ile Gln Asp Met Gly Phe Thr Ala Ile Trp Ile Thr Pro Val Thr Ala
                20                  25                  30

Gln Trp Asp Asp Val Asp Ala Ala Asp Ala Thr Ser Tyr His Gly
            35                  40                  45

Tyr Trp Gln Lys Asp Leu Tyr Ser Leu Asn Ser Lys Phe Gly Thr Ala
    50                  55                  60

Asp Asp Leu Lys Ala Leu Ala Asp Thr Leu His Ala Arg Gly Met Leu
65                  70                  75                  80

Leu Met Val Asp Val Val Ala Asn His Phe Gly Tyr Gly Gly Ser His
                85                  90                  95

Ser Glu Val Asp Tyr Ser Ile Phe Asn Pro Leu Asn Ser Gln Asp Tyr
                100                 105                 110

Phe His Pro Phe Cys Leu Ile Glu Asp Tyr Asp Asn Gln Glu Glu Val
            115                 120                 125

Glu Gln Cys Trp Leu Ala Asp Thr Pro Thr Thr Leu Pro Asp Val Asp
    130                 135                 140

Thr Thr Asn Pro Gln Val Arg Thr Phe Phe Asn Asp Trp Ile Lys Ser
145                 150                 155                 160

Leu Val Ala Asn Tyr Ser Ile Asp Gly Leu Arg Val Asp Thr Val Lys
                165                 170                 175

His Val Glu Lys Asp Phe Trp Pro Asp Phe Asn Glu Ala Ala Gly Val
                180                 185                 190

Tyr Ala Val Gly Glu Val Phe Asn Gly Asp Pro Ala Tyr Thr Cys Pro
```

```
              195                 200                 205
Tyr Gln Glu Val Leu Asp Gly Val Leu Asn Tyr Pro Ile Tyr Tyr Pro
    210                 215                 220

Ala Leu Asp Ala Phe Lys Ser Val Gly Gly Asn Leu Gly Gly Leu Ala
225                 230                 235                 240

Gln Ala Ile Thr Thr Val Gln Glu Ser Cys Lys Asp Ser Asn Leu Leu
                245                 250                 255

Gly Asn Phe Leu Glu Asn His Asp Ile Ala Arg Phe Ala Ser Tyr Thr
            260                 265                 270

Asp Asp Leu Ala Leu Ala Lys Asn Gly Leu Ala Phe Ile Ile Leu Ser
        275                 280                 285

Asp Gly Ile Pro Ile Ile Tyr Ala Gly Gln Glu Gln His Tyr Ala Gly
    290                 295                 300

Asp His Asp Pro Thr Asn Arg Glu Ala Val Trp Leu Ser Gly Tyr Asn
305                 310                 315                 320

Thr Asp Ala Glu Leu Tyr Gln Phe Ile Lys Lys Ala Asn Gly Ile Arg
                325                 330                 335

Asn Leu Ala Ile Ser Gln Asn Pro Glu Phe Thr Ser Ser Lys Thr Lys
            340                 345                 350

Val Ile Tyr Gln Asp Asp Ser Thr Leu Ala Ile Asn Arg Gly Gly Val
        355                 360                 365

Val Thr Val Leu Ser Asn Glu Gly Ala Ser Gly Gly Asp Arg Thr Val
    370                 375                 380

Ser Ile Pro Gly Thr Gly Phe Glu Ala Gly Thr Glu Leu Thr Asp Val
385                 390                 395                 400

Ile Ser Cys Lys Thr Val Thr Ala Gly Asp Ser Gly Ala Val Asp Val
                405                 410                 415

Pro Leu Ser Gly Gly Leu Pro Ser Val Leu Tyr Pro Ser Ser Gln Leu
            420                 425                 430

Ala Lys Ser Gly Leu Cys Ala Ser Ala
        435                 440

<210> SEQ ID NO 15
<211> LENGTH: 1443
<212> TYPE: DNA
<213> ORGANISM: Acremonium sp.
<220> FEATURE:
<221> NAME/KEY: CDS
<222> LOCATION: (1)..(1443)

<400> SEQUENCE: 15 gct gcc ggg ctc tcg gct gcc gag tgg cgg agc cag tcc atc tac cag      48
Ala Ala Gly Leu Ser Ala Ala Glu Trp Arg Ser Gln Ser Ile Tyr Gln
1               5                  10                  15 gtt gtc acc gac agg ttc gcc cgg acc gac ctg tcg acc acg gcg tcg      96
Val Val Thr Asp Arg Phe Ala Arg Thr Asp Leu Ser Thr Thr Ala Ser
                20                  25                  30 tgc aac acg gca gac caa gtc tac tgc gga ggg aca tgg cag ggg ctc     144
Cys Asn Thr Ala Asp Gln Val Tyr Cys Gly Gly Thr Trp Gln Gly Leu
            35                  40                  45 atc tcc aag ctg gac tac atc cag ggc atg ggt ttc acc gcc gta tgg     192
Ile Ser Lys Leu Asp Tyr Ile Gln Gly Met Gly Phe Thr Ala Val Trp
        50                  55                  60 atc tca cca gtg gtc aag cag gtg gaa ggc aat tcc cag gac ggg tcg     240
Ile Ser Pro Val Val Lys Gln Val Glu Gly Asn Ser Gln Asp Gly Ser
65                  70                  75                  80 gcc tat cac gga tac tgg gcg cag gat atc tgg gcc ttg aat ccg gct     288
Ala Tyr His Gly Tyr Trp Ala Gln Asp Ile Trp Ala Leu Asn Pro Ala
```

|     |     |     |     |     |     |     |     |     |     |     |     |     |     |     |     |     |
|---|---|---|---|---|---|---|---|---|---|---|---|---|---|---|---|---|
| ttt | ggg | acc | gag | gag | gat | ctc | gct | gcg | ctt | gcc | gcg | gcg | ctg | cat | gcc | 336 |
| Phe | Gly | Thr | Glu | Glu | Asp | Leu | Ala | Ala | Leu | Ala | Ala | Ala | Leu | His | Ala | |
| | | | 100 | | | | | 105 | | | | | 110 | | | |
| cga | ggc | atg | tac | ctc | atg | gtt | gac | att | gtc | acc | aac | cac | atg | gca | tac | 384 |
| Arg | Gly | Met | Tyr | Leu | Met | Val | Asp | Ile | Val | Thr | Asn | His | Met | Ala | Tyr | |
| | | | 115 | | | | | 120 | | | | | 125 | | | |
| atg | ggc | tgc | ggc | acc | tgt | gta | gac | tac | agc | ctg | ttc | aac | ccc | ttc | tca | 432 |
| Met | Gly | Cys | Gly | Thr | Cys | Val | Asp | Tyr | Ser | Leu | Phe | Asn | Pro | Phe | Ser | |
| | 130 | | | | | 135 | | | | | 140 | | | | | |
| tcg | tca | tcg | tac | ttc | cac | cca | tat | tgc | gcc | atc | gac | tac | agc | aac | cag | 480 |
| Ser | Ser | Ser | Tyr | Phe | His | Pro | Tyr | Cys | Ala | Ile | Asp | Tyr | Ser | Asn | Gln | |
| 145 | | | | | 150 | | | | | 155 | | | | | 160 | |
| acg | tcg | gtc | gag | gtt | tgc | tgg | caa | ggg | gat | aac | att | gtc | agt | ctg | cct | 528 |
| Thr | Ser | Val | Glu | Val | Cys | Trp | Gln | Gly | Asp | Asn | Ile | Val | Ser | Leu | Pro | |
| | | | | 165 | | | | | 170 | | | | | 175 | | |
| gac | ctg | cgc | acc | gag | gat | gac | acg | gtg | cgc | agc | atc | tgg | aac | cgc | tgg | 576 |
| Asp | Leu | Arg | Thr | Glu | Asp | Asp | Thr | Val | Arg | Ser | Ile | Trp | Asn | Arg | Trp | |
| | | | 180 | | | | | 185 | | | | | 190 | | | |
| gtt | agc | cag | ctc | gtg | tcc | aac | tac | tcc | atc | gac | ggc | ttc | cga | gtc | gac | 624 |
| Val | Ser | Gln | Leu | Val | Ser | Asn | Tyr | Ser | Ile | Asp | Gly | Phe | Arg | Val | Asp | |
| | | | 195 | | | | | 200 | | | | | 205 | | | |
| agc | gca | aaa | cac | gtc | gag | acg | tcc | ttt | tgg | caa | gac | ttc | tcg | aca | gcg | 672 |
| Ser | Ala | Lys | His | Val | Glu | Thr | Ser | Phe | Trp | Gln | Asp | Phe | Ser | Thr | Ala | |
| | 210 | | | | | 215 | | | | | 220 | | | | | |
| gcg | ggc | gtg | tac | ctg | ctg | ggc | gag | gtc | ttt | gac | ggg | gac | ccg | tcg | tac | 720 |
| Ala | Gly | Val | Tyr | Leu | Leu | Gly | Glu | Val | Phe | Asp | Gly | Asp | Pro | Ser | Tyr | |
| 225 | | | | | 230 | | | | | 235 | | | | | 240 | |
| gtg | gcg | cct | tac | cag | aac | tac | ctc | aac | ggg | gtt | ctg | gat | tat | ccc | agc | 768 |
| Val | Ala | Pro | Tyr | Gln | Asn | Tyr | Leu | Asn | Gly | Val | Leu | Asp | Tyr | Pro | Ser | |
| | | | | 245 | | | | | 250 | | | | | 255 | | |
| tac | tac | tgg | atc | ctc | cgg | gct | ttc | cag | tca | tcc | agc | ggc | agc | atc | agc | 816 |
| Tyr | Tyr | Trp | Ile | Leu | Arg | Ala | Phe | Gln | Ser | Ser | Ser | Gly | Ser | Ile | Ser | |
| | | | 260 | | | | | 265 | | | | | 270 | | | |
| gac | ctc | gtc | tcc | ggg | ctc | aac | acg | ctc | cat | ggc | gtt | gct | ctg | gac | ctg | 864 |
| Asp | Leu | Val | Ser | Gly | Leu | Asn | Thr | Leu | His | Gly | Val | Ala | Leu | Asp | Leu | |
| | | | 275 | | | | | 280 | | | | | 285 | | | |
| agt | cta | tat | ggg | tcc | ttc | ctc | gag | aac | cac | gat | gtg | gcg | cgg | ttt | gcg | 912 |
| Ser | Leu | Tyr | Gly | Ser | Phe | Leu | Glu | Asn | His | Asp | Val | Ala | Arg | Phe | Ala | |
| | | | 290 | | | | | 295 | | | | | 300 | | | |
| tcc | ttc | acg | cag | gac | atg | tcc | cta | gcg | aag | aat | gcc | atc | gca | ttc | aca | 960 |
| Ser | Phe | Thr | Gln | Asp | Met | Ser | Leu | Ala | Lys | Asn | Ala | Ile | Ala | Phe | Thr | |
| 305 | | | | | 310 | | | | | 315 | | | | | 320 | |
| atg | ctg | aaa | gac | ggc | atc | ccc | atc | ata | tac | cag | gga | caa | gag | caa | cat | 1008 |
| Met | Leu | Lys | Asp | Gly | Ile | Pro | Ile | Ile | Tyr | Gln | Gly | Gln | Glu | Gln | His | |
| | | | | 325 | | | | | 330 | | | | | 335 | | |
| tac | gct | ggc | gga | acg | acg | ccc | aac | aac | cgc | gag | gcg | ctc | tgg | ctc | tcg | 1056 |
| Tyr | Ala | Gly | Gly | Thr | Thr | Pro | Asn | Asn | Arg | Glu | Ala | Leu | Trp | Leu | Ser | |
| | | | 340 | | | | | 345 | | | | | 350 | | | |
| ggc | tac | tcg | act | agc | tcc | gag | ctc | tac | aag | tgg | att | gcc | gcc | ttg | aac | 1104 |
| Gly | Tyr | Ser | Thr | Ser | Ser | Glu | Leu | Tyr | Lys | Trp | Ile | Ala | Ala | Leu | Asn | |
| | | | | 355 | | | | | 360 | | | | | 365 | | |
| cag | atc | cgg | gcc | cga | gct | att | gct | caa | gat | agc | ggc | tac | ctc | tcc | tac | 1152 |
| Gln | Ile | Arg | Ala | Arg | Ala | Ile | Ala | Gln | Asp | Ser | Gly | Tyr | Leu | Ser | Tyr | |
| | | | 370 | | | | | 375 | | | | | 380 | | | |
| agc | agc | caa | gcc | atc | tac | tcg | gac | agc | cat | acc | att | gcc | atg | cgc | aaa | 1200 |
| Ser | Ser | Gln | Ala | Ile | Tyr | Ser | Asp | Ser | His | Thr | Ile | Ala | Met | Arg | Lys | |
| 385 | | | | | 390 | | | | | 395 | | | | | 400 | |
| ggt | acc | tcg | gga | tac | cag | atc | gtg | ggc | gtg | ttc | acc | aat | gtc | ggg | gcc | 1248 |
| Gly | Thr | Ser | Gly | Tyr | Gln | Ile | Val | Gly | Val | Phe | Thr | Asn | Val | Gly | Ala | |

```
                      405                 410                 415
tcg tcg tcg gct acg gtc acc cta acc tct tcc gca acg ggc ttc ggg      1296
Ser Ser Ser Ala Thr Val Thr Leu Thr Ser Ser Ala Thr Gly Phe Gly
            420                 425                 430 gcg aac caa gca ctc gtc gac gtg atg agc tgc acc gct tac acc aca      1344
Ala Asn Gln Ala Leu Val Asp Val Met Ser Cys Thr Ala Tyr Thr Thr
            435                 440                 445 gat tcg acg gga gcc ctc acg gta acc ctg aac gac ggc ctg ccc aag      1392
Asp Ser Thr Gly Ala Leu Thr Val Thr Leu Asn Asp Gly Leu Pro Lys
            450                 455                 460 gtg ctt tat ccg att gcg cgg ctc tcg ggc agc ggt atc tgc cca ggg      1440
Val Leu Tyr Pro Ile Ala Arg Leu Ser Gly Ser Gly Ile Cys Pro Gly
465                 470                 475                 480 cag                                                                   1443
Gln
```

<210> SEQ ID NO 16
<211> LENGTH: 481
<212> TYPE: PRT
<213> ORGANISM: Acremonium sp.

<400> SEQUENCE: 16

```
Ala Ala Gly Leu Ser Ala Ala Glu Trp Arg Ser Gln Ser Ile Tyr Gln
1               5                   10                  15

Val Val Thr Asp Arg Phe Ala Arg Thr Asp Leu Ser Thr Thr Ala Ser
            20                  25                  30

Cys Asn Thr Ala Asp Gln Val Tyr Cys Gly Gly Thr Trp Gln Gly Leu
        35                  40                  45

Ile Ser Lys Leu Asp Tyr Ile Gln Gly Met Gly Phe Thr Ala Val Trp
50                  55                  60

Ile Ser Pro Val Val Lys Gln Val Glu Gly Asn Ser Gln Asp Gly Ser
65                  70                  75                  80

Ala Tyr His Gly Tyr Trp Ala Gln Asp Ile Trp Ala Leu Asn Pro Ala
                85                  90                  95

Phe Gly Thr Glu Glu Asp Leu Ala Ala Leu Ala Ala Leu His Ala
            100                 105                 110

Arg Gly Met Tyr Leu Met Val Asp Ile Val Thr Asn His Met Ala Tyr
        115                 120                 125

Met Gly Cys Gly Thr Cys Val Asp Tyr Ser Leu Phe Asn Pro Phe Ser
130                 135                 140

Ser Ser Ser Tyr Phe His Pro Tyr Cys Ala Ile Asp Tyr Ser Asn Gln
145                 150                 155                 160

Thr Ser Val Glu Val Cys Trp Gln Gly Asp Asn Ile Val Ser Leu Pro
                165                 170                 175

Asp Leu Arg Thr Glu Asp Thr Val Arg Ser Ile Trp Asn Arg Trp
            180                 185                 190

Val Ser Gln Leu Val Ser Asn Tyr Ser Ile Asp Gly Phe Arg Val Asp
        195                 200                 205

Ser Ala Lys His Val Glu Thr Ser Phe Trp Gln Asp Phe Ser Thr Ala
210                 215                 220

Ala Gly Val Tyr Leu Leu Gly Glu Val Phe Asp Gly Asp Pro Ser Tyr
225                 230                 235                 240

Val Ala Pro Tyr Gln Asn Tyr Leu Asn Gly Val Leu Asp Tyr Pro Ser
                245                 250                 255

Tyr Tyr Trp Ile Leu Arg Ala Phe Gln Ser Ser Gly Ser Ile Ser
            260                 265                 270
```

```
Asp Leu Val Ser Gly Leu Asn Thr Leu His Gly Val Ala Leu Asp Leu
            275                 280                 285

Ser Leu Tyr Gly Ser Phe Leu Glu Asn His Asp Val Ala Arg Phe Ala
        290                 295                 300

Ser Phe Thr Gln Asp Met Ser Leu Ala Lys Asn Ala Ile Ala Phe Thr
305                 310                 315                 320

Met Leu Lys Asp Gly Ile Pro Ile Ile Tyr Gln Gly Gln Glu Gln His
                325                 330                 335

Tyr Ala Gly Gly Thr Thr Pro Asn Asn Arg Glu Ala Leu Trp Leu Ser
            340                 345                 350

Gly Tyr Ser Thr Ser Ser Glu Leu Tyr Lys Trp Ile Ala Ala Leu Asn
        355                 360                 365

Gln Ile Arg Ala Arg Ala Ile Ala Gln Asp Ser Gly Tyr Leu Ser Tyr
370                 375                 380

Ser Ser Gln Ala Ile Tyr Ser Asp Ser His Thr Ile Ala Met Arg Lys
385                 390                 395                 400

Gly Thr Ser Gly Tyr Gln Ile Val Gly Val Phe Thr Asn Val Gly Ala
                405                 410                 415

Ser Ser Ser Ala Thr Val Thr Leu Thr Ser Ser Ala Thr Gly Phe Gly
            420                 425                 430

Ala Asn Gln Ala Leu Val Asp Val Met Ser Cys Thr Ala Tyr Thr Thr
        435                 440                 445

Asp Ser Thr Gly Ala Leu Thr Val Thr Leu Asn Asp Gly Leu Pro Lys
450                 455                 460

Val Leu Tyr Pro Ile Ala Arg Leu Ser Gly Ser Gly Ile Cys Pro Gly
465                 470                 475                 480

Gln

<210> SEQ ID NO 17
<211> LENGTH: 1413
<212> TYPE: DNA
<213> ORGANISM: Malbranchea sp.
<220> FEATURE:
<221> NAME/KEY: CDS
<222> LOCATION: (1)..(1413)

<400> SEQUENCE: 17 gcc acg cct gat gag tgg cgc tca agg tcc atc tat cag gtc ctg acc      48
Ala Thr Pro Asp Glu Trp Arg Ser Arg Ser Ile Tyr Gln Val Leu Thr
1               5                   10                  15 gac cgg ttc gcc cgc ggg gat ggc tcg acc gat gcc ccg tgc gat acg      96
Asp Arg Phe Ala Arg Gly Asp Gly Ser Thr Asp Ala Pro Cys Asp Thr
                20                  25                  30 ggt gcc agg aag tat tgc gga gga aac tat cgg gga ctc atc agc cag     144
Gly Ala Arg Lys Tyr Cys Gly Gly Asn Tyr Arg Gly Leu Ile Ser Gln
            35                  40                  45 ctc gac tat atc cag ggc atg gga ttc gac agc gtc tgg ata tcc ccc     192
Leu Asp Tyr Ile Gln Gly Met Gly Phe Asp Ser Val Trp Ile Ser Pro
        50                  55                  60 atc acc aag cag ttt gag gat gac tgg aac ggt gcc ccg tac cac ggg     240
Ile Thr Lys Gln Phe Glu Asp Asp Trp Asn Gly Ala Pro Tyr His Gly
65                  70                  75                  80 tac tgg cag acg gac ctc tat gcg ctg aac gag cac ttt ggt acc gag     288
Tyr Trp Gln Thr Asp Leu Tyr Ala Leu Asn Glu His Phe Gly Thr Glu
                85                  90                  95 gag gat ctc cga gct ctc gcc gat gag ctc cac gcc cgt ggc atg ttc     336
Glu Asp Leu Arg Ala Leu Ala Asp Glu Leu His Ala Arg Gly Met Phe
            100                 105                 110
```

-continued

| | |
|---|---|
| ctc atg gtc gac gtc gtc atc aac cac aac ggc tgg ccc ggc gac gca<br>Leu Met Val Asp Val Val Ile Asn His Asn Gly Trp Pro Gly Asp Ala<br>     115                      120                     125 | 384 |
| gcg tcc atc gac tac tcg cag ttc aac ccg ttc aac agc tcc gac tat<br>Ala Ser Ile Asp Tyr Ser Gln Phe Asn Pro Phe Asn Ser Ser Asp Tyr<br>130                     135                     140 | 432 |
| tac cat cca ccc tgt gag atc aac tat gac gac cag act tcg gtc gag<br>Tyr His Pro Pro Cys Glu Ile Asn Tyr Asp Asp Gln Thr Ser Val Glu<br>145               150               155             160 | 480 |
| cag tgc tgg ctc tac acc ggg gcc aat gcg ctg cct gat ctc aag acg<br>Gln Cys Trp Leu Tyr Thr Gly Ala Asn Ala Leu Pro Asp Leu Lys Thr<br>                 165               170             175 | 528 |
| gag gac ccc cat gtc tcg cag gtg cac aac gac tgg atc gcc gac ctc<br>Glu Asp Pro His Val Ser Gln Val His Asn Asp Trp Ile Ala Asp Leu<br>           180               185               190 | 576 |
| gtc tcc aag tat tcc atc gac ggc ttg cgc att gac acc aca aag cat<br>Val Ser Lys Tyr Ser Ile Asp Gly Leu Arg Ile Asp Thr Thr Lys His<br>                 195               200             205 | 624 |
| gtg gac aaa ccc gct atc ggt tcc ttc aat gac gcc gct ggc gtg tac<br>Val Asp Lys Pro Ala Ile Gly Ser Phe Asn Asp Ala Ala Gly Val Tyr<br>210                     215                     220 | 672 |
| gcc gtc gga gag gtt tac cac ggt gat cct gca tac act tgt ccc tac<br>Ala Val Gly Glu Val Tyr His Gly Asp Pro Ala Tyr Thr Cys Pro Tyr<br>225                     230               235             240 | 720 |
| cag gac tgg gtc gac ggg gtc ctc aac ttc cct gtc tac tac ccg cta<br>Gln Asp Trp Val Asp Gly Val Leu Asn Phe Pro Val Tyr Tyr Pro Leu<br>                     245               250             255 | 768 |
| atc gac gcg ttc aag tcg cct tcg ggc acc atg tgg tct ctt gtc gac<br>Ile Asp Ala Phe Lys Ser Pro Ser Gly Thr Met Trp Ser Leu Val Asp<br>               260               265               270 | 816 |
| aac atc aac aaa gtc ttc caa acc tgc aat gac ccg cgg ctc ctg ggg<br>Asn Ile Asn Lys Val Phe Gln Thr Cys Asn Asp Pro Arg Leu Leu Gly<br>         275                   280               285 | 864 |
| acc ttc tcg gag aac cat gac atc ccc cgc ttc gcc tcg tac acg caa<br>Thr Phe Ser Glu Asn His Asp Ile Pro Arg Phe Ala Ser Tyr Thr Gln<br>         290                   295               300 | 912 |
| gac ctc gcc ctc gcg aag aac gtg ctg gcc ttc acg atc ctg ttc gac<br>Asp Leu Ala Leu Ala Lys Asn Val Leu Ala Phe Thr Ile Leu Phe Asp<br>305                     310               315             320 | 960 |
| ggc atc cca atc gtc tac gcg ggc cag gag caa cag tac tct gga gac<br>Gly Ile Pro Ile Val Tyr Ala Gly Gln Glu Gln Gln Tyr Ser Gly Asp<br>                     325               330             335 | 1008 |
| tcg gac ccg tat aat cga gag gcc ctc tgg ctc tcc gga ttc aac acc<br>Ser Asp Pro Tyr Asn Arg Glu Ala Leu Trp Leu Ser Gly Phe Asn Thr<br>               340               345               350 | 1056 |
| gac gct cct cta tac aag cac att gca gct tgc aac aga ata cgg tcg<br>Asp Ala Pro Leu Tyr Lys His Ile Ala Ala Cys Asn Arg Ile Arg Ser<br>         355                   360               365 | 1104 |
| cac gca gtg tcc aac gac gac gcg tac atc acc act ccg acg gac atc<br>His Ala Val Ser Asn Asp Asp Ala Tyr Ile Thr Thr Pro Thr Asp Ile<br>         370                   375               380 | 1152 |
| aag tac agc gat gac cac acc ctg gcg ctg gtc aag ggt gcg gtg acg<br>Lys Tyr Ser Asp Asp His Thr Leu Ala Leu Val Lys Gly Ala Val Thr<br>385                     390               395             400 | 1200 |
| acc gtg ctg acc aac gcc ggc gcc aac gcc ggc gag acc acc gta acg<br>Thr Val Leu Thr Asn Ala Gly Ala Asn Ala Gly Glu Thr Thr Val Thr<br>                 405                   410             415 | 1248 |
| gtg gaa gca acc ggc tat gcc agt gga gag cag gtt act gat gtg ctg<br>Val Glu Ala Thr Gly Tyr Ala Ser Gly Glu Gln Val Thr Asp Val Leu<br>420                     425               430 | 1296 |

```
agc tgc gag tcg atc gct gcg tcg gat ggc gga cgt ctc agt gta aca     1344
Ser Cys Glu Ser Ile Ala Ala Ser Asp Gly Gly Arg Leu Ser Val Thr
        435                 440                 445 ctg aac cag ggc ctt cca cgt gtg ttc ttc ccg act gat gcc ctt gcg     1392
Leu Asn Gln Gly Leu Pro Arg Val Phe Phe Pro Thr Asp Ala Leu Ala
450                 455                 460 ggc tcc ggg ctc tgc gag aac                                         1413
Gly Ser Gly Leu Cys Glu Asn
465                 470
```

<210> SEQ ID NO 18
<211> LENGTH: 471
<212> TYPE: PRT
<213> ORGANISM: Malbranchea sp.

<400> SEQUENCE: 18

```
Ala Thr Pro Asp Glu Trp Arg Ser Arg Ser Ile Tyr Gln Val Leu Thr
1               5                   10                  15

Asp Arg Phe Ala Arg Gly Asp Gly Ser Thr Asp Ala Pro Cys Asp Thr
            20                  25                  30

Gly Ala Arg Lys Tyr Cys Gly Gly Asn Tyr Arg Gly Leu Ile Ser Gln
        35                  40                  45

Leu Asp Tyr Ile Gln Gly Met Gly Phe Asp Ser Val Trp Ile Ser Pro
50                  55                  60

Ile Thr Lys Gln Phe Glu Asp Trp Asn Gly Ala Pro Tyr His Gly
65                  70                  75                  80

Tyr Trp Gln Thr Asp Leu Tyr Ala Leu Asn Glu His Phe Gly Thr Glu
                85                  90                  95

Glu Asp Leu Arg Ala Leu Ala Asp Glu Leu His Ala Arg Gly Met Phe
            100                 105                 110

Leu Met Val Asp Val Val Ile Asn His Asn Gly Trp Pro Gly Asp Ala
        115                 120                 125

Ala Ser Ile Asp Tyr Ser Gln Phe Asn Pro Phe Asn Ser Ser Asp Tyr
130                 135                 140

Tyr His Pro Pro Cys Glu Ile Asn Tyr Asp Asp Gln Thr Ser Val Glu
145                 150                 155                 160

Gln Cys Trp Leu Tyr Thr Gly Ala Asn Ala Leu Pro Asp Leu Lys Thr
                165                 170                 175

Glu Asp Pro His Val Ser Gln Val His Asn Asp Trp Ile Ala Asp Leu
            180                 185                 190

Val Ser Lys Tyr Ser Ile Asp Gly Leu Arg Ile Asp Thr Thr Lys His
        195                 200                 205

Val Asp Lys Pro Ala Ile Gly Ser Phe Asn Asp Ala Ala Gly Val Tyr
210                 215                 220

Ala Val Gly Glu Val Tyr His Gly Asp Pro Ala Tyr Thr Cys Pro Tyr
225                 230                 235                 240

Gln Asp Trp Val Asp Gly Val Leu Asn Phe Pro Val Tyr Tyr Pro Leu
                245                 250                 255

Ile Asp Ala Phe Lys Ser Pro Ser Gly Thr Met Trp Ser Leu Val Asp
            260                 265                 270

Asn Ile Asn Lys Val Phe Gln Thr Cys Asn Asp Pro Arg Leu Leu Gly
        275                 280                 285

Thr Phe Ser Glu Asn His Asp Ile Pro Arg Phe Ala Ser Tyr Thr Gln
290                 295                 300

Asp Leu Ala Leu Ala Lys Asn Val Leu Ala Phe Thr Ile Leu Phe Asp
305                 310                 315                 320
```

```
Gly Ile Pro Ile Val Tyr Ala Gly Gln Glu Gln Tyr Ser Gly Asp
            325                 330                 335

Ser Asp Pro Tyr Asn Arg Glu Ala Leu Trp Leu Ser Gly Phe Asn Thr
            340                 345                 350

Asp Ala Pro Leu Tyr Lys His Ile Ala Ala Cys Asn Arg Ile Arg Ser
            355                 360                 365

His Ala Val Ser Asn Asp Asp Ala Tyr Ile Thr Thr Pro Thr Asp Ile
        370                 375                 380

Lys Tyr Ser Asp Asp His Thr Leu Ala Leu Val Lys Gly Ala Val Thr
385                 390                 395                 400

Thr Val Leu Thr Asn Ala Gly Ala Asn Ala Gly Glu Thr Thr Val Thr
                405                 410                 415

Val Glu Ala Thr Gly Tyr Ala Ser Gly Glu Gln Val Thr Asp Val Leu
                420                 425                 430

Ser Cys Glu Ser Ile Ala Ala Ser Asp Gly Gly Arg Leu Ser Val Thr
                435                 440                 445

Leu Asn Gln Gly Leu Pro Arg Val Phe Phe Pro Thr Asp Ala Leu Ala
            450                 455                 460

Gly Ser Gly Leu Cys Glu Asn
465                 470

<210> SEQ ID NO 19
<211> LENGTH: 1350
<212> TYPE: DNA
<213> ORGANISM: Rhizomucor pusillus
<220> FEATURE:
<221> NAME/KEY: CDS
<222> LOCATION: (1)..(1350)

<400> SEQUENCE: 19 agc cct ttg ccc caa cag cag cga tat ggc aaa aga gca act tcg gat      48
Ser Pro Leu Pro Gln Gln Gln Arg Tyr Gly Lys Arg Ala Thr Ser Asp
1               5                   10                  15 gac tgg aaa ggc aag gcc att tat cag ctg ctt aca gat cga ttt ggc      96
Asp Trp Lys Gly Lys Ala Ile Tyr Gln Leu Leu Thr Asp Arg Phe Gly
                20                  25                  30 cgc gcc gat gac tca aca agc aac tgc tct aat tta tcc aac tac tgt     144
Arg Ala Asp Asp Ser Thr Ser Asn Cys Ser Asn Leu Ser Asn Tyr Cys
            35                  40                  45 ggt ggt acc tac gaa ggc att acg aag cat ctt gac tac att tcc ggt     192
Gly Gly Thr Tyr Glu Gly Ile Thr Lys His Leu Asp Tyr Ile Ser Gly
    50                  55                  60 atg ggc ttt gat gct atc tgg ata tcg cca att ccc aag aac tcg gat     240
Met Gly Phe Asp Ala Ile Trp Ile Ser Pro Ile Pro Lys Asn Ser Asp
65              70                  75                  80 gga ggc tac cac ggc tac tgg gct aca gat ttc tac caa cta aac agc     288
Gly Gly Tyr His Gly Tyr Trp Ala Thr Asp Phe Tyr Gln Leu Asn Ser
                85                  90                  95 aac ttt ggt gat gaa tcc cag ctc aaa gcg ctc atc cag gct gcc cat     336
Asn Phe Gly Asp Glu Ser Gln Leu Lys Ala Leu Ile Gln Ala Ala His
            100                 105                 110 gaa cgt gac atg tat gtt atg ctt gat gtc gta gcc aat cat gca ggt     384
Glu Arg Asp Met Tyr Val Met Leu Asp Val Val Ala Asn His Ala Gly
        115                 120                 125 ccc acc agc aat ggc tac tcg ggt tac aca ttc ggc gat gca agt tta     432
Pro Thr Ser Asn Gly Tyr Ser Gly Tyr Thr Phe Gly Asp Ala Ser Leu
    130                 135                 140 tat cat cct aaa tgc acc ata gat tac aat gat cag acg tct att gag     480
Tyr His Pro Lys Cys Thr Ile Asp Tyr Asn Asp Gln Thr Ser Ile Glu
145                 150                 155                 160
```

| | | |
|---|---|---|
| caa tgc tgg gtt gct gac gag ttg cct gat att gac act gaa aat tct<br>Gln Cys Trp Val Ala Asp Glu Leu Pro Asp Ile Asp Thr Glu Asn Ser<br>                    165                  170                175 | 528 |
| gac aac gtg gcc att ctc aac gac atc gtc tcc ggc tgg gtg ggt aac<br>Asp Asn Val Ala Ile Leu Asn Asp Ile Val Ser Gly Trp Val Gly Asn<br>            180                    185                    190 | 576 |
| tat agc ttt gac ggc atc cgc att gat act gtc aag cat att cgc aag<br>Tyr Ser Phe Asp Gly Ile Arg Ile Asp Thr Val Lys His Ile Arg Lys<br>        195                    200                  205 | 624 |
| gac ttt tgg aca ggc tac gca gaa gct gcc ggc gta ttc gca act gga<br>Asp Phe Trp Thr Gly Tyr Ala Glu Ala Ala Gly Val Phe Ala Thr Gly<br>      210                  215                    220 | 672 |
| gag gtc ttc aat ggt gat ccg gcc tac gtt gga cct tat caa aag tac<br>Glu Val Phe Asn Gly Asp Pro Ala Tyr Val Gly Pro Tyr Gln Lys Tyr<br>225                    230                  235                  240 | 720 |
| ctg cca tct ctc atc aat tac cca atg tat tac gct ttg aac gac gtc<br>Leu Pro Ser Leu Ile Asn Tyr Pro Met Tyr Tyr Ala Leu Asn Asp Val<br>                245                  250                  255 | 768 |
| ttt gta tcc aaa agc aaa gga ttc agc cgc atc agc gaa atg cta gga<br>Phe Val Ser Lys Ser Lys Gly Phe Ser Arg Ile Ser Glu Met Leu Gly<br>            260                    265                  270 | 816 |
| tca aat cgc aat gcg ttt gag gat acc agc gta ctt aca acg ttt gta<br>Ser Asn Arg Asn Ala Phe Glu Asp Thr Ser Val Leu Thr Thr Phe Val<br>        275                    280                  285 | 864 |
| gac aac cat gac aat ccg cgc ttc ttg aac agt caa agc gac aag gct<br>Asp Asn His Asp Asn Pro Arg Phe Leu Asn Ser Gln Ser Asp Lys Ala<br>      290                  295                    300 | 912 |
| ctc ttc aag aac gct ctc aca tac gta ctg cta ggt gaa ggc atc cca<br>Leu Phe Lys Asn Ala Leu Thr Tyr Val Leu Leu Gly Glu Gly Ile Pro<br>305                    310                  315                  320 | 960 |
| att gtg tat tat ggt tct gag caa ggt ttc agc gga gga gcg gat cct<br>Ile Val Tyr Tyr Gly Ser Glu Gln Gly Phe Ser Gly Gly Ala Asp Pro<br>                325                  330                  335 | 1008 |
| gct aac cgt gaa gtg ctg tgg acc acc aat tat gat aca tcc agc gat<br>Ala Asn Arg Glu Val Leu Trp Thr Thr Asn Tyr Asp Thr Ser Ser Asp<br>            340                    345                  350 | 1056 |
| ctc tac caa ttt atc aag aca gtc aac agt gtc cgc atg aaa agc aac<br>Leu Tyr Gln Phe Ile Lys Thr Val Asn Ser Val Arg Met Lys Ser Asn<br>        355                    360                  365 | 1104 |
| aag gcc gtc tac atg gat att tat gtt ggc gac aat gct tac gcc ttc<br>Lys Ala Val Tyr Met Asp Ile Tyr Val Gly Asp Asn Ala Tyr Ala Phe<br>      370                  375                    380 | 1152 |
| aag cac ggc gat gct ttg gtt gtt ctc aat aac tat gga tca ggt tcc<br>Lys His Gly Asp Ala Leu Val Val Leu Asn Asn Tyr Gly Ser Gly Ser<br>385                    390                  395                  400 | 1200 |
| aca aac caa gtc agc ttc agc gtt agt ggc aag ttc gat agc ggc gca<br>Thr Asn Gln Val Ser Phe Ser Val Ser Gly Lys Phe Asp Ser Gly Ala<br>                405                  410                  415 | 1248 |
| agc ctc atg gat att gtc agt aac att acc acc acg gtg tcc tcg gat<br>Ser Leu Met Asp Ile Val Ser Asn Ile Thr Thr Thr Val Ser Ser Asp<br>            420                    425                  430 | 1296 |
| gga aca gtc act ttc aac ctt aaa gat gga ctt ccg gct atc ttc acc<br>Gly Thr Val Thr Phe Asn Leu Lys Asp Gly Leu Pro Ala Ile Phe Thr<br>        435                    440                  445 | 1344 |
| tct gct<br>Ser Ala<br>      450 | 1350 |

<210> SEQ ID NO 20
<211> LENGTH: 450

<212> TYPE: PRT
<213> ORGANISM: Rhizomucor pusillus

<400> SEQUENCE: 20

```
Ser Pro Leu Pro Gln Gln Arg Tyr Gly Lys Arg Ala Thr Ser Asp
1               5                   10                  15

Asp Trp Lys Gly Lys Ala Ile Tyr Gln Leu Leu Thr Asp Arg Phe Gly
            20                  25                  30

Arg Ala Asp Asp Ser Thr Ser Asn Cys Ser Asn Leu Ser Asn Tyr Cys
        35                  40                  45

Gly Gly Thr Tyr Glu Gly Ile Thr Lys His Leu Asp Tyr Ile Ser Gly
        50                  55                  60

Met Gly Phe Asp Ala Ile Trp Ile Ser Pro Ile Pro Lys Asn Ser Asp
65                  70                  75                  80

Gly Gly Tyr His Gly Tyr Trp Ala Thr Asp Phe Tyr Gln Leu Asn Ser
                85                  90                  95

Asn Phe Gly Asp Glu Ser Gln Leu Lys Ala Leu Ile Gln Ala Ala His
            100                 105                 110

Glu Arg Asp Met Tyr Val Met Leu Asp Val Val Ala Asn His Ala Gly
        115                 120                 125

Pro Thr Ser Asn Gly Tyr Ser Gly Tyr Thr Phe Gly Asp Ala Ser Leu
130                 135                 140

Tyr His Pro Lys Cys Thr Ile Asp Tyr Asn Asp Gln Thr Ser Ile Glu
145                 150                 155                 160

Gln Cys Trp Val Ala Asp Glu Leu Pro Asp Ile Asp Thr Glu Asn Ser
                165                 170                 175

Asp Asn Val Ala Ile Leu Asn Asp Ile Val Ser Gly Trp Val Gly Asn
            180                 185                 190

Tyr Ser Phe Asp Gly Ile Arg Ile Asp Thr Val Lys His Ile Arg Lys
        195                 200                 205

Asp Phe Trp Thr Gly Tyr Ala Glu Ala Ala Gly Val Phe Ala Thr Gly
210                 215                 220

Glu Val Phe Asn Gly Asp Pro Ala Tyr Val Gly Pro Tyr Gln Lys Tyr
225                 230                 235                 240

Leu Pro Ser Leu Ile Asn Tyr Pro Met Tyr Tyr Ala Leu Asn Asp Val
                245                 250                 255

Phe Val Ser Lys Ser Lys Gly Phe Ser Arg Ile Ser Glu Met Leu Gly
            260                 265                 270

Ser Asn Arg Asn Ala Phe Glu Asp Thr Ser Val Leu Thr Thr Phe Val
        275                 280                 285

Asp Asn His Asp Asn Pro Arg Phe Leu Asn Ser Gln Ser Asp Lys Ala
290                 295                 300

Leu Phe Lys Asn Ala Leu Thr Tyr Val Leu Leu Gly Glu Gly Ile Pro
305                 310                 315                 320

Ile Val Tyr Tyr Gly Ser Glu Gln Gly Phe Ser Gly Gly Ala Asp Pro
                325                 330                 335

Ala Asn Arg Glu Val Leu Trp Thr Thr Asn Tyr Asp Thr Ser Ser Asp
            340                 345                 350

Leu Tyr Gln Phe Ile Lys Thr Val Asn Ser Val Arg Met Lys Ser Asn
        355                 360                 365

Lys Ala Val Tyr Met Asp Ile Tyr Val Gly Asp Asn Ala Tyr Ala Phe
370                 375                 380

Lys His Gly Asp Ala Leu Val Val Leu Asn Asn Tyr Gly Ser Gly Ser
385                 390                 395                 400
```

```
Thr Asn Gln Val Ser Phe Ser Val Ser Gly Lys Phe Asp Ser Gly Ala
            405                 410                 415

Ser Leu Met Asp Ile Val Ser Asn Ile Thr Thr Val Ser Ser Asp
        420                 425                 430

Gly Thr Val Thr Phe Asn Leu Lys Asp Gly Leu Pro Ala Ile Phe Thr
            435                 440                 445

Ser Ala
    450

<210> SEQ ID NO 21
<211> LENGTH: 1338
<212> TYPE: DNA
<213> ORGANISM: Dichotomocladium hesseltinei
<220> FEATURE:
<221> NAME/KEY: CDS
<222> LOCATION: (1)..(1338)

<400> SEQUENCE: 21 caa ccg gtg aac atc acg aag cga gct tct gct gct gac tgg cgc tcg      48
Gln Pro Val Asn Ile Thr Lys Arg Ala Ser Ala Ala Asp Trp Arg Ser
1                   5                   10                  15 cgt gcc atc tac caa gtc ctg acc gac cgc ttt gcg cgt acc gat ggg      96
Arg Ala Ile Tyr Gln Val Leu Thr Asp Arg Phe Ala Arg Thr Asp Gly
            20                  25                  30 tcc aca agc gga tgc tca aac ttg tca aat tat tgc ggt ggc acg ttc     144
Ser Thr Ser Gly Cys Ser Asn Leu Ser Asn Tyr Cys Gly Gly Thr Phe
        35                  40                  45 aaa ggc att acc aac aag ctt gac tac att gcc aac ctg ggc ttt gac     192
Lys Gly Ile Thr Asn Lys Leu Asp Tyr Ile Ala Asn Leu Gly Phe Asp
50                  55                  60 gct atc tgg atc tca ccc atc cca aca aac tcg ccc ggc ggc tac cat     240
Ala Ile Trp Ile Ser Pro Ile Pro Thr Asn Ser Pro Gly Gly Tyr His
65                  70                  75                  80 ggc tac tgg gcc acc gac ttt tat ggt atc aat agc aac ttt gga tcc     288
Gly Tyr Trp Ala Thr Asp Phe Tyr Gly Ile Asn Ser Asn Phe Gly Ser
                85                  90                  95 tcg aac gat ctc aag gag ctt gtc aat gct gct cac gcc aag ggt atg     336
Ser Asn Asp Leu Lys Glu Leu Val Asn Ala Ala His Ala Lys Gly Met
            100                 105                 110 tac gtc atg ctc gat gtc gtg gca aac cac gct ggt cca acc tcg aac     384
Tyr Val Met Leu Asp Val Val Ala Asn His Ala Gly Pro Thr Ser Asn
        115                 120                 125 ggc gac tac tct ggc tac acg ttc ggt tcc tct ggc ctc tac cat aac     432
Gly Asp Tyr Ser Gly Tyr Thr Phe Gly Ser Ser Gly Leu Tyr His Asn
    130                 135                 140 cgg tgc tcg atc aac tac aac gac cag aga tcc att gag cag tgc tgg     480
Arg Cys Ser Ile Asn Tyr Asn Asp Gln Arg Ser Ile Glu Gln Cys Trp
145                 150                 155                 160 gtg gcc gac gat ctc cct gat att aac acc gag aac aac gac aac gtc     528
Val Ala Asp Asp Leu Pro Asp Ile Asn Thr Glu Asn Asn Asp Asn Val
                165                 170                 175 aac aag ccc aat aac att gtg tcc acc tgg gtc aag aca tat ggc ttt     576
Asn Lys Pro Asn Asn Ile Val Ser Thr Trp Val Lys Thr Tyr Gly Phe
            180                 185                 190 gat gct atc cgc att gac acc gtc aag cat gtc cgc aag gat ttc tgg     624
Asp Ala Ile Arg Ile Asp Thr Val Lys His Val Arg Lys Asp Phe Trp
        195                 200                 205 cct ggt tat aca tct gct gca ggc gtg ttc gcc act ggc gag gtc ttt     672
Pro Gly Tyr Thr Ser Ala Ala Gly Val Phe Ala Thr Gly Glu Val Phe
    210                 215                 220 gat ggt aac ccg agt tat gtg gcc gat tat caa aac tac atg gag tcg     720
```

```
Asp Gly Asn Pro Ser Tyr Val Ala Asp Tyr Gln Asn Tyr Met Glu Ser
225                 230                 235                 240 ctc atc aac tac ccg ctc tac tac gcg ctc aat gac gtc ttt gcg tcg      768
Leu Ile Asn Tyr Pro Leu Tyr Tyr Ala Leu Asn Asp Val Phe Ala Ser
                245                 250                 255 ggt tat agc ttc agc cgg ctg agc aac cag cgt gtc gca aac tac cac      816
Gly Tyr Ser Phe Ser Arg Leu Ser Asn Gln Arg Val Ala Asn Tyr His
                260                 265                 270 gcc ttc aaa gac gtg agc gtc ctt ccc att ttt atc gac aac cac gac      864
Ala Phe Lys Asp Val Ser Val Leu Pro Ile Phe Ile Asp Asn His Asp
            275                 280                 285 aac ccc cgc ttc ctc aac aaa aag aat gac atc gcc cag ttc aag aac      912
Asn Pro Arg Phe Leu Asn Lys Lys Asn Asp Ile Ala Gln Phe Lys Asn
        290                 295                 300 gct ctg acc tac gtg ctt ctc ggt gag ggc atc cct gtc gtc tac tac      960
Ala Leu Thr Tyr Val Leu Leu Gly Glu Gly Ile Pro Val Val Tyr Tyr
305                 310                 315                 320 ggc tcc gag caa gct tac gcg ggt ggt gcc gac ccg gcc aac cgc gag     1008
Gly Ser Glu Gln Ala Tyr Ala Gly Gly Ala Asp Pro Ala Asn Arg Glu
                325                 330                 335 gcc ctc tgg tcg agc ggg ttc tcg acc aac tcg gac atg tac cag ttc     1056
Ala Leu Trp Ser Ser Gly Phe Ser Thr Asn Ser Asp Met Tyr Gln Phe
                340                 345                 350 att gcc aaa ctc aat cgc gtc cgt caa aag agc aac aag agc gtg tac     1104
Ile Ala Lys Leu Asn Arg Val Arg Gln Lys Ser Asn Lys Ser Val Tyr
            355                 360                 365 atg gac ctg gac gtc cag aac aat gtg tac gcc ttc atg cac ggc aaa     1152
Met Asp Leu Asp Val Gln Asn Asn Val Tyr Ala Phe Met His Gly Lys
        370                 375                 380 tcg ctc gtt gtg ctc aac aac ttt ggt aac ggt gcc tcg aga cag gtt     1200
Ser Leu Val Val Leu Asn Asn Phe Gly Asn Gly Ala Ser Arg Gln Val
385                 390                 395                 400 act gtc aat gtc gga gct cag gtg gcc agc aac acc cga ttg acg gat     1248
Thr Val Asn Val Gly Ala Gln Val Ala Ser Asn Thr Arg Leu Thr Asp
                405                 410                 415 gtt gtc agc ggc aca tcg gtc acg gtt tcg ggc agc tct gtc acc ttc     1296
Val Val Ser Gly Thr Ser Val Thr Val Ser Gly Ser Ser Val Thr Phe
                420                 425                 430 act atc aac aac ggt ttg ccc gca gtc ttc act gtt tct tag              1338
Thr Ile Asn Asn Gly Leu Pro Ala Val Phe Thr Val Ser
            435                 440                 445

<210> SEQ ID NO 22
<211> LENGTH: 445
<212> TYPE: PRT
<213> ORGANISM: Dichotomocladium hesseltinei

<400> SEQUENCE: 22

Gln Pro Val Asn Ile Thr Lys Arg Ala Ser Ala Ala Asp Trp Arg Ser
1               5                   10                  15

Arg Ala Ile Tyr Gln Val Leu Thr Asp Arg Phe Ala Arg Thr Asp Gly
                20                  25                  30

Ser Thr Ser Gly Cys Ser Asn Leu Ser Asn Tyr Cys Gly Gly Thr Phe
            35                  40                  45

Lys Gly Ile Thr Asn Lys Leu Asp Tyr Ile Ala Asn Leu Gly Phe Asp
        50                  55                  60

Ala Ile Trp Ile Ser Pro Ile Pro Thr Asn Ser Pro Gly Gly Tyr His
65                  70                  75                  80

Gly Tyr Trp Ala Thr Asp Phe Tyr Gly Ile Asn Ser Asn Phe Gly Ser
                85                  90                  95
```

```
Ser Asn Asp Leu Lys Glu Leu Val Asn Ala Ala His Ala Lys Gly Met
                100                 105                 110

Tyr Val Met Leu Asp Val Val Ala Asn His Ala Gly Pro Thr Ser Asn
            115                 120                 125

Gly Asp Tyr Ser Gly Tyr Thr Phe Gly Ser Ser Gly Leu Tyr His Asn
130                 135                 140

Arg Cys Ser Ile Asn Tyr Asn Asp Gln Arg Ser Ile Glu Gln Cys Trp
145                 150                 155                 160

Val Ala Asp Asp Leu Pro Asp Ile Asn Thr Glu Asn Asn Asp Asn Val
                165                 170                 175

Asn Lys Pro Asn Asn Ile Val Ser Thr Trp Val Lys Thr Tyr Gly Phe
            180                 185                 190

Asp Ala Ile Arg Ile Asp Thr Val Lys His Val Arg Lys Asp Phe Trp
        195                 200                 205

Pro Gly Tyr Thr Ser Ala Ala Gly Val Phe Ala Thr Gly Glu Val Phe
    210                 215                 220

Asp Gly Asn Pro Ser Tyr Val Ala Asp Tyr Gln Asn Tyr Met Glu Ser
225                 230                 235                 240

Leu Ile Asn Tyr Pro Leu Tyr Tyr Ala Leu Asn Asp Val Phe Ala Ser
                245                 250                 255

Gly Tyr Ser Phe Ser Arg Leu Ser Asn Gln Arg Val Ala Asn Tyr His
            260                 265                 270

Ala Phe Lys Asp Val Ser Val Leu Pro Ile Phe Ile Asp Asn His Asp
        275                 280                 285

Asn Pro Arg Phe Leu Asn Lys Lys Asn Asp Ile Ala Gln Phe Lys Asn
    290                 295                 300

Ala Leu Thr Tyr Val Leu Leu Gly Glu Gly Ile Pro Val Val Tyr Tyr
305                 310                 315                 320

Gly Ser Glu Gln Ala Tyr Ala Gly Gly Ala Asp Pro Ala Asn Arg Glu
                325                 330                 335

Ala Leu Trp Ser Ser Gly Phe Ser Thr Asn Ser Asp Met Tyr Gln Phe
            340                 345                 350

Ile Ala Lys Leu Asn Arg Val Arg Gln Lys Ser Asn Lys Ser Val Tyr
        355                 360                 365

Met Asp Leu Asp Val Gln Asn Asn Val Tyr Ala Phe Met His Gly Lys
    370                 375                 380

Ser Leu Val Val Leu Asn Asn Phe Gly Asn Gly Ala Ser Arg Gln Val
385                 390                 395                 400

Thr Val Asn Val Gly Ala Gln Val Ala Ser Asn Thr Arg Leu Thr Asp
                405                 410                 415

Val Val Ser Gly Thr Ser Val Thr Val Ser Gly Ser Ser Val Thr Phe
            420                 425                 430

Thr Ile Asn Asn Gly Leu Pro Ala Val Phe Thr Val Ser
        435                 440                 445

<210> SEQ ID NO 23
<211> LENGTH: 1398
<212> TYPE: DNA
<213> ORGANISM: Meripilus giganteus
<220> FEATURE:
<221> NAME/KEY: CDS
<222> LOCATION: (1)..(1398)

<400> SEQUENCE: 23 cgc cct act gtc ttt gac gcc ggc gcg gac gca cac tcg ctg cat gcc      48
Arg Pro Thr Val Phe Asp Ala Gly Ala Asp Ala His Ser Leu His Ala
```

|   |   |
|---|---|
| cgg gcc ccc tcc ggc agc aag gat gtc atc atc cag atg ttt gag tgg<br>Arg Ala Pro Ser Gly Ser Lys Asp Val Ile Ile Gln Met Phe Glu Trp<br>                  20                  25                  30 | 96 |
| aac tgg gac agc gtc gct gcc gag tgc act aac ttc atc ggc ccc gcc<br>Asn Trp Asp Ser Val Ala Ala Glu Cys Thr Asn Phe Ile Gly Pro Ala<br>      35                  40                  45 | 144 |
| ggg tac ggc ttc gtg caa gtg agc ccg ccc cag gag acc atc cag ggc<br>Gly Tyr Gly Phe Val Gln Val Ser Pro Pro Gln Glu Thr Ile Gln Gly<br>    50                  55                  60 | 192 |
| gcg cag tgg tgg acc gac tac cag ccg gtg tcg tac acg ctc act ggg<br>Ala Gln Trp Trp Thr Asp Tyr Gln Pro Val Ser Tyr Thr Leu Thr Gly<br>65                  70                  75                  80 | 240 |
| aag cgg ggc gac cgc tcc cag ttt gcg aac atg att act acg tgc cac<br>Lys Arg Gly Asp Arg Ser Gln Phe Ala Asn Met Ile Thr Thr Cys His<br>                  85                  90                  95 | 288 |
| gcc gcg ggc gtc ggc gtg atc gtt gac acc atc tgg aac cac atg gcg<br>Ala Ala Gly Val Gly Val Ile Val Asp Thr Ile Trp Asn His Met Ala<br>                100                105                110 | 336 |
| ggc gtc gac tcc ggc acg ggt acc gcc ggc tcg tcc ttc acg cac tac<br>Gly Val Asp Ser Gly Thr Gly Thr Ala Gly Ser Ser Phe Thr His Tyr<br>            115                120                125 | 384 |
| aac tac ccc ggc atc tac caa aac cag gac ttt cac cac tgc ggc ctc<br>Asn Tyr Pro Gly Ile Tyr Gln Asn Gln Asp Phe His His Cys Gly Leu<br>      130                135                140 | 432 |
| gag ccg ggc gat gac atc gtc aac tac gac aac gcg gtt gag gtc cag<br>Glu Pro Gly Asp Asp Ile Val Asn Tyr Asp Asn Ala Val Glu Val Gln<br>145                  150                155                160 | 480 |
| acc tgc gag ctt gtc aac ctc gct gac ctc gcc acc gac acg gag tat<br>Thr Cys Glu Leu Val Asn Leu Ala Asp Leu Ala Thr Asp Thr Glu Tyr<br>                165                170                175 | 528 |
| gtg cgc ggt cgc ctt gcc cag tac gga aac gac ctg ctc tcg ctc ggt<br>Val Arg Gly Arg Leu Ala Gln Tyr Gly Asn Asp Leu Leu Ser Leu Gly<br>            180                185                190 | 576 |
| gcc gat ggc ctg cgt ctt gac gct tcc aaa cac att cct gtg ggc gac<br>Ala Asp Gly Leu Arg Leu Asp Ala Ser Lys His Ile Pro Val Gly Asp<br>                195                200                205 | 624 |
| atc gcg aac atc ctg tct cgc ctc agt cgc tct gtc tac atc acc cag<br>Ile Ala Asn Ile Leu Ser Arg Leu Ser Arg Ser Val Tyr Ile Thr Gln<br>      210                215                220 | 672 |
| gaa gtc atc ttt ggg gcc ggc gag ccc atc acg ccg aac cag tac acc<br>Glu Val Ile Phe Gly Ala Gly Glu Pro Ile Thr Pro Asn Gln Tyr Thr<br>225                  230                235                240 | 720 |
| ggg aac ggc gac gtt cag gag ttc cgc tac acc tct gcg cta aag gac<br>Gly Asn Gly Asp Val Gln Glu Phe Arg Tyr Thr Ser Ala Leu Lys Asp<br>                245                250                255 | 768 |
| gcc ttc ttg agc tcg ggc ata tcc aac ctg cag gac ttc gaa aac cgt<br>Ala Phe Leu Ser Ser Gly Ile Ser Asn Leu Gln Asp Phe Glu Asn Arg<br>      260                265                270 | 816 |
| gga tgg gta cct ggc tcg ggc gcc aac gtg ttc gtc gtc aac cat gac<br>Gly Trp Val Pro Gly Ser Gly Ala Asn Val Phe Val Val Asn His Asp<br>            275                280                285 | 864 |
| acc gag cgg aac ggc gcg tcg ctg aac aac aac tcg cct tcg aac acc<br>Thr Glu Arg Asn Gly Ala Ser Leu Asn Asn Asn Ser Pro Ser Asn Thr<br>290                  295                300 | 912 |
| tac gtc acc gcg acg atc ttc tcg ctc gca cac ccg tac ggc acg ccc<br>Tyr Val Thr Ala Thr Ile Phe Ser Leu Ala His Pro Tyr Gly Thr Pro<br>305                  310                315                320 | 960 |
| acg atc ctc tcc tcg tat gat ggc ttc acg aac acc gac gcc ggt gcg<br>Thr Ile Leu Ser Ser Tyr Asp Gly Phe Thr Asn Thr Asp Ala Gly Ala | 1008 |

```
                325                 330                 335
ccg aac aac aac gtc ggc aca tgc tcg acc agc ggt ggt gcg aac ggg    1056
Pro Asn Asn Asn Val Gly Thr Cys Ser Thr Ser Gly Gly Ala Asn Gly
        340                 345                 350 tgg ctc tgc cag cac cgc tgg acc gcg atc gcc ggc atg gtc ggc ttc    1104
Trp Leu Cys Gln His Arg Trp Thr Ala Ile Ala Gly Met Val Gly Phe
    355                 360                 365 cgc aac aac gtc ggc agc gct gca ctc aac aac tgg cag gcc ccg cag    1152
Arg Asn Asn Val Gly Ser Ala Ala Leu Asn Asn Trp Gln Ala Pro Gln
370                 375                 380 tcg cag cag att gcg ttc ggt cgc ggc gca ctt ggc ttc gtc gcg atc    1200
Ser Gln Gln Ile Ala Phe Gly Arg Gly Ala Leu Gly Phe Val Ala Ile
385                 390                 395                 400 aac aac gcc gac tcg gcc tgg tct acg acg ttc acc act tcc ctc ccc    1248
Asn Asn Ala Asp Ser Ala Trp Ser Thr Thr Phe Thr Thr Ser Leu Pro
                405                 410                 415 gat ggt tcc tac tgc gat gtc atc agc ggc aag gcc tcc ggc agt agc    1296
Asp Gly Ser Tyr Cys Asp Val Ile Ser Gly Lys Ala Ser Gly Ser Ser
            420                 425                 430 tgc acc ggt tct tcg ttc acc gtc tcc ggc ggg aag ctg acc gcc acg    1344
Cys Thr Gly Ser Ser Phe Thr Val Ser Gly Gly Lys Leu Thr Ala Thr
        435                 440                 445 gtg ccg gcg cgt agc gcc atc gcc gtg cac acc ggt cag aaa ggt tct    1392
Val Pro Ala Arg Ser Ala Ile Ala Val His Thr Gly Gln Lys Gly Ser
450                 455                 460 ggt ggt                                                            1398
Gly Gly
465

<210> SEQ ID NO 24
<211> LENGTH: 466
<212> TYPE: PRT
<213> ORGANISM: Meripilus giganteus

<400> SEQUENCE: 24

Arg Pro Thr Val Phe Asp Ala Gly Ala Asp Ala His Ser Leu His Ala
1               5                   10                  15

Arg Ala Pro Ser Gly Ser Lys Asp Val Ile Ile Gln Met Phe Glu Trp
            20                  25                  30

Asn Trp Asp Ser Val Ala Ala Glu Cys Thr Asn Phe Ile Gly Pro Ala
        35                  40                  45

Gly Tyr Gly Phe Val Gln Val Ser Pro Pro Gln Glu Thr Ile Gln Gly
    50                  55                  60

Ala Gln Trp Trp Thr Asp Tyr Gln Pro Val Ser Tyr Thr Leu Thr Gly
65                  70                  75                  80

Lys Arg Gly Asp Arg Ser Gln Phe Ala Asn Met Ile Thr Thr Cys His
                85                  90                  95

Ala Ala Gly Val Gly Val Ile Val Asp Thr Ile Trp Asn His Met Ala
            100                 105                 110

Gly Val Asp Ser Gly Thr Gly Thr Ala Gly Ser Ser Phe Thr His Tyr
        115                 120                 125

Asn Tyr Pro Gly Ile Tyr Gln Asn Gln Asp Phe His His Cys Gly Leu
    130                 135                 140

Glu Pro Gly Asp Asp Ile Val Asn Tyr Asp Asn Ala Val Glu Val Gln
145                 150                 155                 160

Thr Cys Glu Leu Val Asn Leu Ala Asp Leu Ala Thr Asp Thr Glu Tyr
                165                 170                 175

Val Arg Gly Arg Leu Ala Gln Tyr Gly Asn Asp Leu Leu Ser Leu Gly
```

```
                    180                 185                 190
Ala Asp Gly Leu Arg Leu Asp Ala Ser Lys His Ile Pro Val Gly Asp
        195                 200                 205

Ile Ala Asn Ile Leu Ser Arg Leu Ser Arg Ser Val Tyr Ile Thr Gln
    210                 215                 220

Glu Val Ile Phe Gly Ala Gly Glu Pro Ile Thr Pro Asn Gln Tyr Thr
225                 230                 235                 240

Gly Asn Gly Asp Val Gln Glu Phe Arg Tyr Thr Ser Ala Leu Lys Asp
                245                 250                 255

Ala Phe Leu Ser Ser Gly Ile Ser Asn Leu Gln Asp Phe Glu Asn Arg
            260                 265                 270

Gly Trp Val Pro Gly Ser Gly Ala Asn Val Phe Val Asn His Asp
        275                 280                 285

Thr Glu Arg Asn Gly Ala Ser Leu Asn Asn Asn Ser Pro Ser Asn Thr
    290                 295                 300

Tyr Val Thr Ala Thr Ile Phe Ser Leu Ala His Pro Tyr Gly Thr Pro
305                 310                 315                 320

Thr Ile Leu Ser Ser Tyr Asp Gly Phe Thr Asn Thr Asp Ala Gly Ala
                325                 330                 335

Pro Asn Asn Asn Val Gly Thr Cys Ser Thr Ser Gly Gly Ala Asn Gly
            340                 345                 350

Trp Leu Cys Gln His Arg Trp Thr Ala Ile Ala Gly Met Val Gly Phe
        355                 360                 365

Arg Asn Asn Val Gly Ser Ala Ala Leu Asn Asn Trp Gln Ala Pro Gln
    370                 375                 380

Ser Gln Gln Ile Ala Phe Gly Arg Gly Ala Leu Gly Phe Val Ala Ile
385                 390                 395                 400

Asn Asn Ala Asp Ser Ala Trp Ser Thr Thr Phe Thr Thr Ser Leu Pro
                405                 410                 415

Asp Gly Ser Tyr Cys Asp Val Ile Ser Gly Lys Ala Ser Gly Ser Ser
            420                 425                 430

Cys Thr Gly Ser Ser Phe Thr Val Ser Gly Gly Lys Leu Thr Ala Thr
        435                 440                 445

Val Pro Ala Arg Ser Ala Ile Ala Val His Thr Gly Gln Lys Gly Ser
    450                 455                 460

Gly Gly
465

<210> SEQ ID NO 25
<211> LENGTH: 1494
<212> TYPE: DNA
<213> ORGANISM: Stereum sp.
<220> FEATURE:
<221> NAME/KEY: CDS
<222> LOCATION: (1)..(1494)

<400> SEQUENCE: 25 gat gat tgg aag aac cgt act atc tat cag ctc gtg acg gac cgc ttc      48
Asp Asp Trp Lys Asn Arg Thr Ile Tyr Gln Leu Val Thr Asp Arg Phe
1               5                   10                  15 gcg cta gcc aat gat tcc agc ggt tca tgc gac act tca gac cgt gtt      96
Ala Leu Ala Asn Asp Ser Ser Gly Ser Cys Asp Thr Ser Asp Arg Val
            20                  25                  30 tac tgt gga gga tca tgg caa ggt gtt atc aac cac ctc gat tac atc     144
Tyr Cys Gly Gly Ser Trp Gln Gly Val Ile Asn His Leu Asp Tyr Ile
        35                  40                  45 caa aac atg ggc ttc gac gcc gtc tgg att tct ccc gtc agc acc aac     192
```

-continued

| | | |
|---|---|---|
| Gln Asn Met Gly Phe Asp Ala Val Trp Ile Ser Pro Val Ser Thr Asn<br>50              55              60 | | |
| ttt gaa ggc tcg agt gct tat ggc gag gcc ttc cat ggt tac tgg ccc<br>Phe Glu Gly Ser Ser Ala Tyr Gly Glu Ala Phe His Gly Tyr Trp Pro<br>65              70              75              80 | | 240 |
| tct gac ctt tca tct gtc aac tct cac ttc ggt tct gat gac gac ctc<br>Ser Asp Leu Ser Ser Val Asn Ser His Phe Gly Ser Asp Asp Asp Leu<br>85              90              95 | | 288 |
| aag agc ctt gca tca gcc ctt cat gat cgc tca atg tac ctc atg att<br>Lys Ser Leu Ala Ser Ala Leu His Asp Arg Ser Met Tyr Leu Met Ile<br>100             105             110 | | 336 |
| gat gtc gtc gtc aat cac ctc gtc tac ccc tcc aac cct ccc acc ttc<br>Asp Val Val Val Asn His Leu Val Tyr Pro Ser Asn Pro Pro Thr Phe<br>115             120             125 | | 384 |
| agt gac ttc aac cct ttc aac acc gag tcc gac ttc cat ccc gag tgc<br>Ser Asp Phe Asn Pro Phe Asn Thr Glu Ser Asp Phe His Pro Glu Cys<br>130             135             140 | | 432 |
| ttc atc acc gac tat aat aac caa act gat gtt gag cag tgc tgg ctc<br>Phe Ile Thr Asp Tyr Asn Asn Gln Thr Asp Val Glu Gln Cys Trp Leu<br>145             150             155             160 | | 480 |
| ggt gat tca aac ttg cct ctg gca gat acc aac acg gag gat gat gat<br>Gly Asp Ser Asn Leu Pro Leu Ala Asp Thr Asn Thr Glu Asp Asp Asp<br>165             170             175 | | 528 |
| aac gtc tcg agc ttg tac agc tgg att aag aac ctt gtc agc acg tac<br>Asn Val Ser Ser Leu Tyr Ser Trp Ile Lys Asn Leu Val Ser Thr Tyr<br>180             185             190 | | 576 |
| agc gct gac ggt atc cgt atc gac acc gtg aag cac atc cgt cag gac<br>Ser Ala Asp Gly Ile Arg Ile Asp Thr Val Lys His Ile Arg Gln Asp<br>195             200             205 | | 624 |
| ttc tgg ccc gac ttt gct agc tct gct gga gtc tac acc att gga gag<br>Phe Trp Pro Asp Phe Ala Ser Ser Ala Gly Val Tyr Thr Ile Gly Glu<br>210             215             220 | | 672 |
| gtt ctg agc aac gac acc gcc tac atc gcc aac tac acg caa gtc ctt<br>Val Leu Ser Asn Asp Thr Ala Tyr Ile Ala Asn Tyr Thr Gln Val Leu<br>225             230             235             240 | | 720 |
| gac ggt gtt ctc gat tac tct acc tgg tat cct ctc gtg gct ggc ttc<br>Asp Gly Val Leu Asp Tyr Ser Thr Trp Tyr Pro Leu Val Ala Gly Phe<br>245             250             255 | | 768 |
| cag tcg acc tcc gga aac ctt tcc gct atc aag gcc acc tat agc caa<br>Gln Ser Thr Ser Gly Asn Leu Ser Ala Ile Lys Ala Thr Tyr Ser Gln<br>260             265             270 | | 816 |
| gtc tcc agc tcg ttc aag aac ggc ggg ttc caa tca ggc tct ttc ctc<br>Val Ser Ser Ser Phe Lys Asn Gly Gly Phe Gln Ser Gly Ser Phe Leu<br>275             280             285 | | 864 |
| gaa aac cat gac cag ccc cgt ttc cag agc atg acc acg gat cag tct<br>Glu Asn His Asp Gln Pro Arg Phe Gln Ser Met Thr Thr Asp Gln Ser<br>290             295             300 | | 912 |
| ctc gtc aag aac gcg atg acc tgg ccc ttc atc aac gat ggt att ccc<br>Leu Val Lys Asn Ala Met Thr Trp Pro Phe Ile Asn Asp Gly Ile Pro<br>305             310             315             320 | | 960 |
| att ctg tac tac gga caa gag caa ggc tac tct ggt ggc gct gac ccc<br>Ile Leu Tyr Tyr Gly Gln Glu Gln Gly Tyr Ser Gly Gly Ala Asp Pro<br>325             330             335 | | 1008 |
| gct aac cgt gag gcc ctt tgg tcg tcc ggc tac gaa gag gat aag gat<br>Ala Asn Arg Glu Ala Leu Trp Ser Ser Gly Tyr Glu Glu Asp Lys Asp<br>340             345             350 | | 1056 |
| ctc gtt acc cac gtg aag acg ctc gtt gcc gcc cgc aag ctc gct gct<br>Leu Val Thr His Val Lys Thr Leu Val Ala Ala Arg Lys Leu Ala Ala<br>355             360             365 | | 1104 |
| gcc gct aac agc aac ttc cac agt acc gct gcc acg ttc ccc acg act | | 1152 |

```
                                                          -continued

Ala Ala Asn Ser Asn Phe His Ser Thr Ala Thr Phe Pro Thr Thr
    370                 375                 380 agc gac gaa tcc acc ctg gcc gtc ctc aaa acc cca atg ctt gcc ctc       1200
Ser Asp Glu Ser Thr Leu Ala Val Leu Lys Thr Pro Met Leu Ala Leu
385                 390                 395                 400 ctc act aac acc ggc tca tcc ggc tct gca tcc ttc tcg act tca ggc       1248
Leu Thr Asn Thr Gly Ser Ser Gly Ser Ala Ser Phe Ser Thr Ser Gly
                405                 410                 415 gcc ggc ttt tcc gct aac gag gcg ctc gtt gat gtc ctc act tgc aac       1296
Ala Gly Phe Ser Ala Asn Glu Ala Leu Val Asp Val Leu Thr Cys Asn
            420                 425                 430 acc gtc acc gct gac tcg tcc ggt gag gtc ggg ctc gcg tct aag tcg       1344
Thr Val Thr Ala Asp Ser Ser Gly Glu Val Gly Leu Ala Ser Lys Ser
        435                 440                 445 ggc ctg ccg cag gtg tta ttg ccc gtc agt gcg ctg acg tcg gcc ggt       1392
Gly Leu Pro Gln Val Leu Leu Pro Val Ser Ala Leu Thr Ser Ala Gly
    450                 455                 460 ggc gtg tgc acg aac ttg gtg agc gcg gcg cat gtc agc gcg aga gtg       1440
Gly Val Cys Thr Asn Leu Val Ser Ala Ala His Val Ser Ala Arg Val
465                 470                 475                 480 ccg agt gcg atg gtg gcg acg acg gtg ttg ttt gcg ctc ttc cga ttc       1488
Pro Ser Ala Met Val Ala Thr Thr Val Leu Phe Ala Leu Phe Arg Phe
                485                 490                 495 ctg gcg                                                               1494
Leu Ala <210> SEQ ID NO 26
<211> LENGTH: 498
<212> TYPE: PRT
<213> ORGANISM: Stereum sp.

<400> SEQUENCE: 26

Asp Asp Trp Lys Asn Arg Thr Ile Tyr Gln Leu Val Thr Asp Arg Phe
1               5                   10                  15

Ala Leu Ala Asn Asp Ser Ser Gly Ser Cys Asp Thr Ser Asp Arg Val
            20                  25                  30

Tyr Cys Gly Gly Ser Trp Gln Gly Val Ile Asn His Leu Asp Tyr Ile
        35                  40                  45

Gln Asn Met Gly Phe Asp Ala Val Trp Ile Ser Pro Val Ser Thr Asn
    50                  55                  60

Phe Glu Gly Ser Ser Ala Tyr Gly Glu Ala Phe His Gly Tyr Trp Pro
65                  70                  75                  80

Ser Asp Leu Ser Ser Val Asn Ser His Phe Gly Ser Asp Asp Asp Leu
                85                  90                  95

Lys Ser Leu Ala Ser Ala Leu His Asp Arg Ser Met Tyr Leu Met Ile
            100                 105                 110

Asp Val Val Val Asn His Leu Val Tyr Pro Ser Asn Pro Thr Phe
        115                 120                 125

Ser Asp Phe Asn Pro Phe Asn Thr Glu Ser Asp Phe His Pro Glu Cys
    130                 135                 140

Phe Ile Thr Asp Tyr Asn Asn Gln Thr Asp Val Glu Gln Cys Trp Leu
145                 150                 155                 160

Gly Asp Ser Asn Leu Pro Leu Ala Asp Thr Asn Thr Glu Asp Asp
                165                 170                 175

Asn Val Ser Ser Leu Tyr Ser Trp Ile Lys Asn Leu Val Ser Thr Tyr
            180                 185                 190

Ser Ala Asp Gly Ile Arg Ile Asp Thr Val Lys His Ile Arg Gln Asp
        195                 200                 205
```

```
Phe Trp Pro Asp Phe Ala Ser Ser Ala Gly Val Tyr Thr Ile Gly Glu
    210                 215                 220

Val Leu Ser Asn Asp Thr Ala Tyr Ile Ala Asn Tyr Thr Gln Val Leu
225                 230                 235                 240

Asp Gly Val Leu Asp Tyr Ser Thr Trp Tyr Pro Leu Val Ala Gly Phe
                245                 250                 255

Gln Ser Thr Ser Gly Asn Leu Ser Ala Ile Lys Ala Thr Tyr Ser Gln
            260                 265                 270

Val Ser Ser Ser Phe Lys Asn Gly Gly Phe Gln Ser Gly Ser Phe Leu
        275                 280                 285

Glu Asn His Asp Gln Pro Arg Phe Gln Ser Met Thr Thr Asp Gln Ser
290                 295                 300

Leu Val Lys Asn Ala Met Thr Trp Pro Phe Ile Asn Asp Gly Ile Pro
305                 310                 315                 320

Ile Leu Tyr Tyr Gly Gln Glu Gln Gly Tyr Ser Gly Gly Ala Asp Pro
                325                 330                 335

Ala Asn Arg Glu Ala Leu Trp Ser Ser Gly Tyr Glu Glu Asp Lys Asp
            340                 345                 350

Leu Val Thr His Val Lys Thr Leu Val Ala Ala Arg Lys Leu Ala Ala
        355                 360                 365

Ala Ala Asn Ser Asn Phe His Ser Thr Ala Ala Thr Phe Pro Thr Thr
370                 375                 380

Ser Asp Glu Ser Thr Leu Ala Val Leu Lys Thr Pro Met Leu Ala Leu
385                 390                 395                 400

Leu Thr Asn Thr Gly Ser Ser Gly Ser Ala Ser Phe Ser Thr Ser Gly
                405                 410                 415

Ala Gly Phe Ser Ala Asn Glu Ala Leu Val Asp Val Leu Thr Cys Asn
            420                 425                 430

Thr Val Thr Ala Asp Ser Ser Gly Glu Val Gly Leu Ala Ser Lys Ser
        435                 440                 445

Gly Leu Pro Gln Val Leu Leu Pro Val Ser Ala Leu Thr Ser Ala Gly
    450                 455                 460

Gly Val Cys Thr Asn Leu Val Ser Ala Ala His Val Ser Ala Arg Val
465                 470                 475                 480

Pro Ser Ala Met Val Ala Thr Val Leu Phe Ala Leu Phe Arg Phe
                485                 490                 495

Leu Ala
```

<210> SEQ ID NO 27
<211> LENGTH: 1539
<212> TYPE: DNA
<213> ORGANISM: Trametes sp.
<220> FEATURE:
<221> NAME/KEY: CDS
<222> LOCATION: (1)..(1539)

<400> SEQUENCE: 27

```
gcg agc gca gac cag tgg cag aac cgg tct atc tac cag ttg gta aca      48
Ala Ser Ala Asp Gln Trp Gln Asn Arg Ser Ile Tyr Gln Leu Val Thr
1               5                   10                  15 gat cgt ttt gca acc cct gac ggc tct agc ccg tca tgc gac act tcg      96
Asp Arg Phe Ala Thr Pro Asp Gly Ser Ser Pro Ser Cys Asp Thr Ser
                20                  25                  30 caa cgc cag tat tgt ggt ggc acc tgg aaa ggc gtg gca aac aaa ctc     144
Gln Arg Gln Tyr Cys Gly Gly Thr Trp Lys Gly Val Ala Asn Lys Leu
            35                  40                  45
```

```
gac tac att cag aac atg ggc ttt gac gcg atc tgg atc tcc ccg atc      192
Asp Tyr Ile Gln Asn Met Gly Phe Asp Ala Ile Trp Ile Ser Pro Ile
 50              55                  60 gtc gca aac gtc gag ggg aac acc tca tat ggc gaa gca ttc cat gga      240
Val Ala Asn Val Glu Gly Asn Thr Ser Tyr Gly Glu Ala Phe His Gly
65              70                  75                  80 tac tgg aca caa gac atc aac tcg ctc aac tct cat ttc ggt tcc gcc      288
Tyr Trp Thr Gln Asp Ile Asn Ser Leu Asn Ser His Phe Gly Ser Ala
                 85                  90                  95 gac gat ctc aaa gcc ctc agc tca gcc ttg cat gat cga ggc atg tac      336
Asp Asp Leu Lys Ala Leu Ser Ser Ala Leu His Asp Arg Gly Met Tyr
            100                 105                 110 ctc atg gtc gac gtc gtt gta aac cac atg gtt ggc acc tcc gac ccg      384
Leu Met Val Asp Val Val Val Asn His Met Val Gly Thr Ser Asp Pro
        115                 120                 125 ccc aac ttc tct tcc ttc cag ccg ttc tcg tca cag tcc gac ttc cac      432
Pro Asn Phe Ser Ser Phe Gln Pro Phe Ser Ser Gln Ser Asp Phe His
    130                 135                 140 tcc gag tgc ttt gtg tcg aac tac gac aac cag acc gaa gtc gaa cag      480
Ser Glu Cys Phe Val Ser Asn Tyr Asp Asn Gln Thr Glu Val Glu Gln
145                 150                 155                 160 tgc tgg cta ggc gac aag aac gtc ccc ttg gta gac ttg aac acc gag      528
Cys Trp Leu Gly Asp Lys Asn Val Pro Leu Val Asp Leu Asn Thr Glu
                165                 170                 175 gat gcg gac atc gta aag acc atg aac aca tgg atc tct acg ctc gtt      576
Asp Ala Asp Ile Val Lys Thr Met Asn Thr Trp Ile Ser Thr Leu Val
            180                 185                 190 ggt aac tac agc gtc gac ggt gtc cgt atc gac act gtc aag cac gtc      624
Gly Asn Tyr Ser Val Asp Gly Val Arg Ile Asp Thr Val Lys His Val
        195                 200                 205 cgg aaa gac ttc tgg ccc gac ttc gcc aag tct gct ggc gtc ttc acc      672
Arg Lys Asp Phe Trp Pro Asp Phe Ala Lys Ser Ala Gly Val Phe Thr
210                 215                 220 att ggc gag gtc ctc cac aat gag acg gat tac gtc tcg gca tac act      720
Ile Gly Glu Val Leu His Asn Glu Thr Asp Tyr Val Ser Ala Tyr Thr
225                 230                 235                 240 cag gtc ctc gac agc gtc ctc gac tac ccc acc tgg ttc ccg ctt gtg      768
Gln Val Leu Asp Ser Val Leu Asp Tyr Pro Thr Trp Phe Pro Leu Val
                245                 250                 255 gct gct ttc cag act acg ggt ggc aat ctg tca gct ctt gct gcg acc      816
Ala Ala Phe Gln Thr Thr Gly Gly Asn Leu Ser Ala Leu Ala Ala Thr
            260                 265                 270 gtt caa cag gcg caa ggc tct tat aag aag ggc gag ttc atg acg ggt      864
Val Gln Gln Ala Gln Gly Ser Tyr Lys Lys Gly Glu Phe Met Thr Gly
        275                 280                 285 tcc ttc ctt gag aac cac gat cag cct cga ttc caa tcc ctc acg caa      912
Ser Phe Leu Glu Asn His Asp Gln Pro Arg Phe Gln Ser Leu Thr Gln
290                 295                 300 gat cag gcg ttg gta aag aac gcc atg act tgg cca ttc gtt caa gat      960
Asp Gln Ala Leu Val Lys Asn Ala Met Thr Trp Pro Phe Val Gln Asp
305                 310                 315                 320 ggt gtc ccg att atg tac tac ggc caa gaa cag tcc tac gct gga gga     1008
Gly Val Pro Ile Met Tyr Tyr Gly Gln Glu Gln Ser Tyr Ala Gly Gly
                325                 330                 335 cct gac ccg gcc aac cgt gaa gct ttg tgg ctc tcc ggc tat gtc gaa     1056
Pro Asp Pro Ala Asn Arg Glu Ala Leu Trp Leu Ser Gly Tyr Val Glu
            340                 345                 350 gat aag ccc ctg gtc aag cat gtt agg gca cta aac gca gcc cgc aaa     1104
Asp Lys Pro Leu Val Lys His Val Arg Ala Leu Asn Ala Ala Arg Lys
        355                 360                 365
```

```
gct gcg atc tcg gcg aac agt aac tat ctg aac acc ggc gtc aaa ttt    1152
Ala Ala Ile Ser Ala Asn Ser Asn Tyr Leu Asn Thr Gly Val Lys Phe
370             375                 380 ttg tcc acc gga tcc gaa tcc tcc atg gcc gtg tct aag ccg ccc atg    1200
Leu Ser Thr Gly Ser Glu Ser Ser Met Ala Val Ser Lys Pro Pro Met
385             390                 395                 400 ctg gct ctc ctc acg aac ggc ggc agc tcg tca acg cct tcg tgg acc    1248
Leu Ala Leu Leu Thr Asn Gly Gly Ser Ser Ser Thr Pro Ser Trp Thr
                405                 410                 415 gtc tca gat gct ggg tac caa gcc aac gag gag ctg atc gac gtg ctc    1296
Val Ser Asp Ala Gly Tyr Gln Ala Asn Glu Glu Leu Ile Asp Val Leu
            420                 425                 430 agt tgc cag aag gtc acc gcc gac gga aac ggc ggg gtg agc gtg cag    1344
Ser Cys Gln Lys Val Thr Ala Asp Gly Asn Gly Gly Val Ser Val Gln
        435                 440                 445 gga tcc agc ggc agc cct caa gtc ctc atg ccg acg tct gcg ctc aac    1392
Gly Ser Ser Gly Ser Pro Gln Val Leu Met Pro Thr Ser Ala Leu Asn
    450                 455                 460 aag tct gga agc atc tgt gca gaa gac gcg acg gga ggc caa gcc tcg    1440
Lys Ser Gly Ser Ile Cys Ala Glu Asp Ala Thr Gly Gly Gln Ala Ser
465                 470                 475                 480 gct gcg caa ggc tgg atc gaa cgt gcg gca gag tct ctg cca atc gct    1488
Ala Ala Gln Gly Trp Ile Glu Arg Ala Ala Glu Ser Leu Pro Ile Ala
                485                 490                 495 gct gcg ctg ttg ctc gcg gga tgg gct gcg cag tcc agc ctt gtt atc    1536
Ala Ala Leu Leu Leu Ala Gly Trp Ala Ala Gln Ser Ser Leu Val Ile
            500                 505                 510 ctg                                                                1539
Leu

<210> SEQ ID NO 28
<211> LENGTH: 513
<212> TYPE: PRT
<213> ORGANISM: Trametes sp.

<400> SEQUENCE: 28

Ala Ser Ala Asp Gln Trp Gln Asn Arg Ser Ile Tyr Gln Leu Val Thr
1               5                   10                  15

Asp Arg Phe Ala Thr Pro Asp Gly Ser Ser Pro Ser Cys Asp Thr Ser
                20                  25                  30

Gln Arg Gln Tyr Cys Gly Gly Thr Trp Lys Gly Val Ala Asn Lys Leu
            35                  40                  45

Asp Tyr Ile Gln Asn Met Gly Phe Asp Ala Ile Trp Ile Ser Pro Ile
        50                  55                  60

Val Ala Asn Val Glu Gly Asn Thr Ser Tyr Gly Glu Ala Phe His Gly
65                  70                  75                  80

Tyr Trp Thr Gln Asp Ile Asn Ser Leu Asn Ser His Phe Gly Ser Ala
                85                  90                  95

Asp Asp Leu Lys Ala Leu Ser Ser Ala Leu His Asp Arg Gly Met Tyr
            100                 105                 110

Leu Met Val Asp Val Val Val Asn His Met Val Gly Thr Ser Asp Pro
        115                 120                 125

Pro Asn Phe Ser Ser Phe Gln Pro Phe Ser Ser Gln Ser Asp Phe His
    130                 135                 140

Ser Glu Cys Phe Val Ser Asn Tyr Asp Asn Gln Thr Glu Val Glu Gln
145                 150                 155                 160

Cys Trp Leu Gly Asp Lys Asn Val Pro Leu Val Asp Leu Asn Thr Glu
                165                 170                 175
```

```
Asp Ala Asp Ile Val Lys Thr Met Asn Thr Trp Ile Ser Thr Leu Val
            180                 185                 190
Gly Asn Tyr Ser Val Asp Gly Val Arg Ile Asp Thr Val Lys His Val
        195                 200                 205
Arg Lys Asp Phe Trp Pro Asp Phe Ala Lys Ser Ala Gly Val Phe Thr
    210                 215                 220
Ile Gly Glu Val Leu His Asn Glu Thr Asp Tyr Val Ser Ala Tyr Thr
225                 230                 235                 240
Gln Val Leu Asp Ser Val Leu Asp Tyr Pro Thr Trp Phe Pro Leu Val
                245                 250                 255
Ala Ala Phe Gln Thr Thr Gly Gly Asn Leu Ser Ala Leu Ala Ala Thr
            260                 265                 270
Val Gln Gln Ala Gln Gly Ser Tyr Lys Lys Gly Glu Phe Met Thr Gly
        275                 280                 285
Ser Phe Leu Glu Asn His Asp Gln Pro Arg Phe Gln Ser Leu Thr Gln
    290                 295                 300
Asp Gln Ala Leu Val Lys Asn Ala Met Thr Trp Pro Phe Val Gln Asp
305                 310                 315                 320
Gly Val Pro Ile Met Tyr Tyr Gly Gln Glu Gln Ser Tyr Ala Gly Gly
                325                 330                 335
Pro Asp Pro Ala Asn Arg Glu Ala Leu Trp Leu Ser Gly Tyr Val Glu
            340                 345                 350
Asp Lys Pro Leu Val Lys His Val Arg Ala Leu Asn Ala Ala Arg Lys
        355                 360                 365
Ala Ala Ile Ser Ala Asn Ser Asn Tyr Leu Asn Thr Gly Val Lys Phe
    370                 375                 380
Leu Ser Thr Gly Ser Glu Ser Ser Met Ala Val Ser Lys Pro Pro Met
385                 390                 395                 400
Leu Ala Leu Leu Thr Asn Gly Gly Ser Ser Thr Pro Ser Trp Thr
                405                 410                 415
Val Ser Asp Ala Gly Tyr Gln Ala Asn Glu Glu Leu Ile Asp Val Leu
            420                 425                 430
Ser Cys Gln Lys Val Thr Ala Asp Gly Asn Gly Val Ser Val Gln
        435                 440                 445
Gly Ser Ser Gly Ser Pro Gln Val Leu Met Pro Thr Ser Ala Leu Asn
    450                 455                 460
Lys Ser Gly Ser Ile Cys Ala Glu Asp Ala Thr Gly Gly Gln Ala Ser
465                 470                 475                 480
Ala Ala Gln Gly Trp Ile Glu Arg Ala Ala Glu Ser Leu Pro Ile Ala
                485                 490                 495
Ala Ala Leu Leu Leu Ala Gly Trp Ala Ala Gln Ser Ser Leu Val Ile
            500                 505                 510
Leu

<210> SEQ ID NO 29
<211> LENGTH: 1521
<212> TYPE: DNA
<213> ORGANISM: Coriolus censor
<220> FEATURE:
<221> NAME/KEY: CDS
<222> LOCATION: (1)..(1521)

<400> SEQUENCE: 29 gcc tct cct gac gac tgg cgt act agg tcg atc tac cag ctt gtg acc    48
Ala Ser Pro Asp Asp Trp Arg Thr Arg Ser Ile Tyr Gln Leu Val Thr
1               5                   10                  15
```

```
gac aga ttt gca acc cct gat ggc tca agc cca aca tgt aac acc gag      96
Asp Arg Phe Ala Thr Pro Asp Gly Ser Ser Pro Thr Cys Asn Thr Glu
         20                  25                  30 gac cga agg tac tgc ggt ggt aac tac aag ggt atc atc aac aag ctc     144
Asp Arg Arg Tyr Cys Gly Gly Asn Tyr Lys Gly Ile Ile Asn Lys Leu
             35                  40                  45 gac tac att caa aac atg ggg ttt gac gcc atc tgg atc tca cct gtg     192
Asp Tyr Ile Gln Asn Met Gly Phe Asp Ala Ile Trp Ile Ser Pro Val
     50                  55                  60 gtc gcg aat gta gag gga aat acc agt ctc ggt gaa gcc ttc cat ggc     240
Val Ala Asn Val Glu Gly Asn Thr Ser Leu Gly Glu Ala Phe His Gly
 65                  70                  75                  80 tac tgg act caa gat atc aac aaa ttg aac gat cat ttc ggg tct act     288
Tyr Trp Thr Gln Asp Ile Asn Lys Leu Asn Asp His Phe Gly Ser Thr
                     85                  90                  95 gac gat ttg aag tcg ctt tcg gat gcc ctg cac aag cgt aac atg tat     336
Asp Asp Leu Lys Ser Leu Ser Asp Ala Leu His Lys Arg Asn Met Tyr
                100                 105                 110 ctg atg gtc gat gtg gtt gtc aac cat atg gcg gca acg tca aac cca     384
Leu Met Val Asp Val Val Val Asn His Met Ala Ala Thr Ser Asn Pro
            115                 120                 125 ccg aac ttt ggc agt ttc gcg ccc ttc aat caa cag tcc aac ttc cac     432
Pro Asn Phe Gly Ser Phe Ala Pro Phe Asn Gln Gln Ser Asn Phe His
        130                 135                 140 ccg gaa tgt ttt atc caa gcc tcg gac tac gac aac aat cag acc gct     480
Pro Glu Cys Phe Ile Gln Ala Ser Asp Tyr Asp Asn Asn Gln Thr Ala
145                 150                 155                 160 gtc gaa caa tgc tgg ctt ggc gac gaa aat ctc cca ctc gcg gat atg     528
Val Glu Gln Cys Trp Leu Gly Asp Glu Asn Leu Pro Leu Ala Asp Met
                165                 170                 175 aat acc gag gac caa aac gtg atc agc aca tgg aac aca tgg atc ggc     576
Asn Thr Glu Asp Gln Asn Val Ile Ser Thr Trp Asn Thr Trp Ile Gly
            180                 185                 190 gac ttg gtc aag aac tat act atc gat ggt gtc cgc att gat act gtc     624
Asp Leu Val Lys Asn Tyr Thr Ile Asp Gly Val Arg Ile Asp Thr Val
        195                 200                 205 aag cat gtg cga aag gac ttc tgg ccc gac ttt gcc aag gcc gct ggc     672
Lys His Val Arg Lys Asp Phe Trp Pro Asp Phe Ala Lys Ala Ala Gly
210                 215                 220 gta tac act att ggt gaa gtt ttg cac aac gat acc aac tat gtt gca     720
Val Tyr Thr Ile Gly Glu Val Leu His Asn Asp Thr Asn Tyr Val Ala
225                 230                 235                 240 ccc tac acg cag gcg ctt tct gct gca cta gac tat cct gcc tac ttc     768
Pro Tyr Thr Gln Ala Leu Ser Ala Ala Leu Asp Tyr Pro Ala Tyr Phe
                245                 250                 255 ttc ttg act gct ggt ttc caa acc tcc aac ggc aac tta tcg aat ttt     816
Phe Leu Thr Ala Gly Phe Gln Thr Ser Asn Gly Asn Leu Ser Asn Phe
            260                 265                 270 gct tcg gtt atc cag gcc ggg cag ggt gca tac aac aat ggc gag cac     864
Ala Ser Val Ile Gln Ala Gly Gln Gly Ala Tyr Asn Asn Gly Glu His
        275                 280                 285 tac atg ggc tcc ttc ctt gag aat cac gac aac cct cgt ttc caa tcc     912
Tyr Met Gly Ser Phe Leu Glu Asn His Asp Asn Pro Arg Phe Gln Ser
    290                 295                 300 ctc act caa gat caa gca ttg gta aag aat gcg atg act tgg cca ttt     960
Leu Thr Gln Asp Gln Ala Leu Val Lys Asn Ala Met Thr Trp Pro Phe
305                 310                 315                 320 atc caa gac ggt atc ccg atc ctt tac tac ggt cag gaa caa ggc tac    1008
Ile Gln Asp Gly Ile Pro Ile Leu Tyr Tyr Gly Gln Glu Gln Gly Tyr
                325                 330                 335
```

```
gcc ggt gga aat gat cct gct aac cgt gaa gca ctc tgg ctg tcc ggg     1056
Ala Gly Gly Asn Asp Pro Ala Asn Arg Glu Ala Leu Trp Leu Ser Gly
            340                 345                 350 tac ggc gaa gac aaa ccc ctg gtt cag cat gtc aag acg ttg aac gcc     1104
Tyr Gly Glu Asp Lys Pro Leu Val Gln His Val Lys Thr Leu Asn Ala
        355                 360                 365 gcg cgt aag gcc gct gcc gct gcc aaa agc gac ttc cac acc agc agc     1152
Ala Arg Lys Ala Ala Ala Ala Ala Lys Ser Asp Phe His Thr Ser Ser
    370                 375                 380 ctc caa ttc ctt gtc agc aca cag aac aat ctg gcc att tcg aag ccc     1200
Leu Gln Phe Leu Val Ser Thr Gln Asn Asn Leu Ala Ile Ser Lys Pro
385                 390                 395                 400 cct atg ctt acg ctg ctc act aat gaa ggt agc act tct acg cca caa     1248
Pro Met Leu Thr Leu Leu Thr Asn Glu Gly Ser Thr Ser Thr Pro Gln
                405                 410                 415 tgg agc gtc cca aac gct ggg ttc agc gca aac gag gaa gtc gtc gat     1296
Trp Ser Val Pro Asn Ala Gly Phe Ser Ala Asn Glu Glu Val Val Asp
            420                 425                 430 gtg ttg act tgc acg aag ata aac gct gac gct aac gga ggt gtc act     1344
Val Leu Thr Cys Thr Lys Ile Asn Ala Asp Ala Asn Gly Gly Val Thr
        435                 440                 445 gtc aaa ggc tcg gga ggt aat ccc caa gtc ctg atg cct act tct gcc     1392
Val Lys Gly Ser Gly Gly Asn Pro Gln Val Leu Met Pro Thr Ser Ala
    450                 455                 460 ctt cca aaa ggc ggg acc gta tgt ccc gac tta gca acg gga gca cag     1440
Leu Pro Lys Gly Gly Thr Val Cys Pro Asp Leu Ala Thr Gly Ala Gln
465                 470                 475                 480 tct tcc tct gct cgt tca ctc gcg gtg cag gtg ctt ggg act tct ctc     1488
Ser Ser Ser Ala Arg Ser Leu Ala Val Gln Val Leu Gly Thr Ser Leu
                485                 490                 495 gct gcc gtt ctc act ctc gcc att gca ttc tcg                         1521
Ala Ala Val Leu Thr Leu Ala Ile Ala Phe Ser
            500                 505

<210> SEQ ID NO 30
<211> LENGTH: 507
<212> TYPE: PRT
<213> ORGANISM: Coriolus censor

<400> SEQUENCE: 30

Ala Ser Pro Asp Asp Trp Arg Thr Arg Ser Ile Tyr Gln Leu Val Thr
1               5                   10                  15

Asp Arg Phe Ala Thr Pro Asp Gly Ser Ser Pro Thr Cys Asn Thr Glu
            20                  25                  30

Asp Arg Arg Tyr Cys Gly Gly Asn Tyr Lys Gly Ile Ile Asn Lys Leu
        35                  40                  45

Asp Tyr Ile Gln Asn Met Gly Phe Asp Ala Ile Trp Ile Ser Pro Val
    50                  55                  60

Val Ala Asn Val Glu Gly Asn Thr Ser Leu Gly Glu Ala Phe His Gly
65                  70                  75                  80

Tyr Trp Thr Gln Asp Ile Asn Lys Leu Asn Asp His Phe Gly Ser Thr
            85                  90                  95

Asp Asp Leu Lys Ser Leu Ser Asp Ala Leu His Lys Arg Asn Met Tyr
        100                 105                 110

Leu Met Val Asp Val Val Val Asn His Met Ala Ala Thr Ser Asn Pro
    115                 120                 125

Pro Asn Phe Gly Ser Phe Ala Pro Phe Asn Gln Gln Ser Asn Phe His
    130                 135                 140

Pro Glu Cys Phe Ile Gln Ala Ser Asp Tyr Asp Asn Asn Gln Thr Ala
```

```
                145                 150                 155                 160
Val Glu Gln Cys Trp Leu Gly Asp Glu Asn Leu Pro Leu Ala Asp Met
                    165                 170                 175

Asn Thr Glu Asp Gln Asn Val Ile Ser Thr Trp Asn Thr Trp Ile Gly
                180                 185                 190

Asp Leu Val Lys Asn Tyr Thr Ile Asp Gly Val Arg Ile Asp Thr Val
            195                 200                 205

Lys His Val Arg Lys Asp Phe Trp Pro Asp Phe Ala Lys Ala Ala Gly
        210                 215                 220

Val Tyr Thr Ile Gly Glu Val Leu His Asn Asp Thr Asn Tyr Val Ala
225                 230                 235                 240

Pro Tyr Thr Gln Ala Leu Ser Ala Ala Leu Asp Tyr Pro Ala Tyr Phe
                245                 250                 255

Phe Leu Thr Ala Gly Phe Gln Thr Ser Asn Gly Asn Leu Ser Asn Phe
                260                 265                 270

Ala Ser Val Ile Gln Ala Gly Gln Gly Ala Tyr Asn Asn Gly Glu His
            275                 280                 285

Tyr Met Gly Ser Phe Leu Glu Asn His Asp Asn Pro Arg Phe Gln Ser
        290                 295                 300

Leu Thr Gln Asp Gln Ala Leu Val Lys Asn Ala Met Thr Trp Pro Phe
305                 310                 315                 320

Ile Gln Asp Gly Ile Pro Ile Leu Tyr Tyr Gly Gln Glu Gln Gly Tyr
                325                 330                 335

Ala Gly Gly Asn Asp Pro Ala Asn Arg Glu Ala Leu Trp Leu Ser Gly
                340                 345                 350

Tyr Gly Glu Asp Lys Pro Leu Val Gln His Val Lys Thr Leu Asn Ala
            355                 360                 365

Ala Arg Lys Ala Ala Ala Ala Lys Ser Asp Phe His Thr Ser Ser
        370                 375                 380

Leu Gln Phe Leu Val Ser Thr Gln Asn Asn Leu Ala Ile Ser Lys Pro
385                 390                 395                 400

Pro Met Leu Thr Leu Leu Thr Asn Glu Gly Ser Thr Ser Thr Pro Gln
                405                 410                 415

Trp Ser Val Pro Asn Ala Gly Phe Ser Ala Asn Glu Glu Val Val Asp
                420                 425                 430

Val Leu Thr Cys Thr Lys Ile Asn Ala Asp Ala Asn Gly Val Thr
            435                 440                 445

Val Lys Gly Ser Gly Asn Pro Gln Val Leu Met Pro Thr Ser Ala
        450                 455                 460

Leu Pro Lys Gly Gly Thr Val Cys Pro Asp Leu Ala Thr Gly Ala Gln
465                 470                 475                 480

Ser Ser Ser Ala Arg Ser Leu Ala Val Gln Val Leu Gly Thr Ser Leu
                485                 490                 495

Ala Ala Val Leu Thr Leu Ala Ile Ala Phe Ser
            500                 505

<210> SEQ ID NO 31
<211> LENGTH: 1443
<212> TYPE: DNA
<213> ORGANISM: Dinemasporium sp.
<220> FEATURE:
<221> NAME/KEY: CDS
<222> LOCATION: (1)..(1443)

<400> SEQUENCE: 31 gcc acg gca gag caa tgg agg tcg cgg gcg ata tat cag ctt ctc act        48
```

-continued

| | | | | | | | | | | | | | | | |
|---|---|---|---|---|---|---|---|---|---|---|---|---|---|---|---|
| Ala | Thr | Ala | Glu | Gln | Trp | Arg | Ser | Arg | Ala | Ile | Tyr | Gln | Leu | Leu | Thr |
| 1 | | | | 5 | | | | | 10 | | | | | 15 | |

| gat | cga | ttc | gca | aga | cca | gat | aat | agc | acg | aca | gca | aca | tgt | tat | aca | 96 |
|---|---|---|---|---|---|---|---|---|---|---|---|---|---|---|---|---|
| Asp | Arg | Phe | Ala | Arg | Pro | Asp | Asn | Ser | Thr | Thr | Ala | Thr | Cys | Tyr | Thr | |
| | | | 20 | | | | | 25 | | | | | 30 | | | |

| cca | gat | aga | aac | tac | tgt | gga | gga | act | tgg | agt | ggc | atc | atc | agc | caa | 144 |
|---|---|---|---|---|---|---|---|---|---|---|---|---|---|---|---|---|
| Pro | Asp | Arg | Asn | Tyr | Cys | Gly | Gly | Thr | Trp | Ser | Gly | Ile | Ile | Ser | Gln | |
| | | 35 | | | | | 40 | | | | | 45 | | | | |

| tta | gat | tac | atc | cag | gac | atg | ggc | ttc | acc | gcg | ata | tgg | ata | tct | ccc | 192 |
|---|---|---|---|---|---|---|---|---|---|---|---|---|---|---|---|---|
| Leu | Asp | Tyr | Ile | Gln | Asp | Met | Gly | Phe | Thr | Ala | Ile | Trp | Ile | Ser | Pro | |
| 50 | | | | | 55 | | | | | 60 | | | | | | |

| gta | act | tcg | aac | att | cct | aat | ata | act | tct | tac | ggc | tac | gct | tat | cac | 240 |
|---|---|---|---|---|---|---|---|---|---|---|---|---|---|---|---|---|
| Val | Thr | Ser | Asn | Ile | Pro | Asn | Ile | Thr | Ser | Tyr | Gly | Tyr | Ala | Tyr | His | |
| 65 | | | | | 70 | | | | | 75 | | | | | 80 | |

| gga | tac | tgg | caa | caa | gac | ctt | tat | aag | ttg | aat | gat | cat | ttt | ggc | act | 288 |
|---|---|---|---|---|---|---|---|---|---|---|---|---|---|---|---|---|
| Gly | Tyr | Trp | Gln | Gln | Asp | Leu | Tyr | Lys | Leu | Asn | Asp | His | Phe | Gly | Thr | |
| | | | | 85 | | | | | 90 | | | | | 95 | | |

| gcc | gaa | gat | ttg | aaa | gca | ctc | agc | cag | gca | ttg | cat | gac | aga | gac | atg | 336 |
|---|---|---|---|---|---|---|---|---|---|---|---|---|---|---|---|---|
| Ala | Glu | Asp | Leu | Lys | Ala | Leu | Ser | Gln | Ala | Leu | His | Asp | Arg | Asp | Met | |
| | | | | 100 | | | | | 105 | | | | | 110 | | |

| tat | ctg | atg | gta | gat | gta | gtc | gca | aac | cat | aac | ggc | tgg | ccc | ggc | gat | 384 |
|---|---|---|---|---|---|---|---|---|---|---|---|---|---|---|---|---|
| Tyr | Leu | Met | Val | Asp | Val | Val | Ala | Asn | His | Asn | Gly | Trp | Pro | Gly | Asp | |
| | | | 115 | | | | | 120 | | | | | 125 | | | |

| tct | gcc | tca | gta | aat | tac | tcc | gcg | ttc | tac | ccg | ttc | gac | aat | gca | tca | 432 |
|---|---|---|---|---|---|---|---|---|---|---|---|---|---|---|---|---|
| Ser | Ala | Ser | Val | Asn | Tyr | Ser | Ala | Phe | Tyr | Pro | Phe | Asp | Asn | Ala | Ser | |
| | 130 | | | | | 135 | | | | | 140 | | | | | |

| cac | tat | cat | ttg | ttc | tgc | gtc | gtc | gac | gat | tat | agc | aat | cag | acc | gac | 480 |
|---|---|---|---|---|---|---|---|---|---|---|---|---|---|---|---|---|
| His | Tyr | His | Leu | Phe | Cys | Val | Val | Asp | Asp | Tyr | Ser | Asn | Gln | Thr | Asp | |
| 145 | | | | | 150 | | | | | 155 | | | | | 160 | |

| gtc | gag | gac | tgt | tgg | ctc | ggg | gat | acg | aat | gtc | gag | ctg | gtg | gat | tta | 528 |
|---|---|---|---|---|---|---|---|---|---|---|---|---|---|---|---|---|
| Val | Glu | Asp | Cys | Trp | Leu | Gly | Asp | Thr | Asn | Val | Glu | Leu | Val | Asp | Leu | |
| | | | | 165 | | | | | 170 | | | | | 175 | | |

| gac | acg | aac | agt | caa | gat | gtt | gtt | gat | ggg | tac | tct | aaa | tgg | att | ggt | 576 |
|---|---|---|---|---|---|---|---|---|---|---|---|---|---|---|---|---|
| Asp | Thr | Asn | Ser | Gln | Asp | Val | Val | Asp | Gly | Tyr | Ser | Lys | Trp | Ile | Gly | |
| | | | 180 | | | | | 185 | | | | | 190 | | | |

| gaa | ttg | gtc | tcg | aac | tac | tcc | atc | gac | ggt | ctc | cgc | atc | gac | acg | gta | 624 |
|---|---|---|---|---|---|---|---|---|---|---|---|---|---|---|---|---|
| Glu | Leu | Val | Ser | Asn | Tyr | Ser | Ile | Asp | Gly | Leu | Arg | Ile | Asp | Thr | Val | |
| | | 195 | | | | | 200 | | | | | 205 | | | | |

| aag | cac | gtc | gac | aag | ccc | ttc | tgg | act | tct | ttc | caa | caa | gca | gcc | ggc | 672 |
|---|---|---|---|---|---|---|---|---|---|---|---|---|---|---|---|---|
| Lys | His | Val | Asp | Lys | Pro | Phe | Trp | Thr | Ser | Phe | Gln | Gln | Ala | Ala | Gly | |
| | 210 | | | | | 215 | | | | | 220 | | | | | |

| gtc | ttc | acg | aca | ggg | gaa | ata | ctc | tcg | ggt | gat | cct | tcc | tat | act | tgc | 720 |
|---|---|---|---|---|---|---|---|---|---|---|---|---|---|---|---|---|
| Val | Phe | Thr | Thr | Gly | Glu | Ile | Leu | Ser | Gly | Asp | Pro | Ser | Tyr | Thr | Cys | |
| 225 | | | | 230 | | | | | 235 | | | | | 240 | | |

| gac | tac | cag | aat | tat | ctt | gat | agt | aca | ttg | aac | tac | ccg | tta | tgg | tgg | 768 |
|---|---|---|---|---|---|---|---|---|---|---|---|---|---|---|---|---|
| Asp | Tyr | Gln | Asn | Tyr | Leu | Asp | Ser | Thr | Leu | Asn | Tyr | Pro | Leu | Trp | Trp | |
| | | | | 245 | | | | | 250 | | | | | 255 | | |

| cca | gca | atg | gcg | ttc | ctc | aac | tca | aca | tct | ggc | tcc | tcc | gcc | aac | ctc | 816 |
|---|---|---|---|---|---|---|---|---|---|---|---|---|---|---|---|---|
| Pro | Ala | Met | Ala | Phe | Leu | Asn | Ser | Thr | Ser | Gly | Ser | Ser | Ala | Asn | Leu | |
| | | | 260 | | | | | 265 | | | | | 270 | | | |

| ctc | aac | cta | ctg | agc | tcc | cta | cgg | tct | act | tgc | aaa | gac | gtc | tcc | gtc | 864 |
|---|---|---|---|---|---|---|---|---|---|---|---|---|---|---|---|---|
| Leu | Asn | Leu | Leu | Ser | Ser | Leu | Arg | Ser | Thr | Cys | Lys | Asp | Val | Ser | Val | |
| | | 275 | | | | | 280 | | | | | 285 | | | | |

| ctc | ggt | gta | ttc | acc | gag | aac | cac | gac | ctc | cct | cgc | ttc | gcc | tcg | caa | 912 |
|---|---|---|---|---|---|---|---|---|---|---|---|---|---|---|---|---|
| Leu | Gly | Val | Phe | Thr | Glu | Asn | His | Asp | Leu | Pro | Arg | Phe | Ala | Ser | Gln | |
| | 290 | | | | | 295 | | | | | 300 | | | | | |

| act | caa | gac | atg | gct | tta | gcc | aag | aac | gct | ctc | gcc | ctc | acg | atc | ttg | 960 |
|---|---|---|---|---|---|---|---|---|---|---|---|---|---|---|---|---|
| Thr | Gln | Asp | Met | Ala | Leu | Ala | Lys | Asn | Ala | Leu | Ala | Leu | Thr | Ile | Leu | |
| 305 | | | | 310 | | | | | 315 | | | | | 320 | | |

| tct | gac | ggc | ata | ccc | ata | gtc | tac | gca | gga | caa | gaa | caa | cac | tac | gac | 1008 |

```
Ser Asp Gly Ile Pro Ile Val Tyr Ala Gly Gln Gln His Tyr Asp
                325                 330                 335 gga tcg ggc gat ccc tac aac aga gag gca aat tgg ctc tcg ggc tac    1056
Gly Ser Gly Asp Pro Tyr Asn Arg Glu Ala Asn Trp Leu Ser Gly Tyr
                340                 345                 350 tcg cgc tcg aac gaa ctg tac ctc ctc gtc gcc gcc gtc aac caa gtc    1104
Ser Arg Ser Asn Glu Leu Tyr Leu Leu Val Ala Ala Val Asn Gln Val
            355                 360                 365 cgc aac aga gcc ttg tat cga gat gca aac tac gcg act tat aat gct    1152
Arg Asn Arg Ala Leu Tyr Arg Asp Ala Asn Tyr Ala Thr Tyr Asn Ala
        370                 375                 380 acc tct atc tat agt gat caa cat act gtt gcg ttc cgc aaa ggg tac    1200
Thr Ser Ile Tyr Ser Asp Gln His Thr Val Ala Phe Arg Lys Gly Tyr
385                 390                 395                 400 gat gga cac cag atc atc tcc gtc atc acc aat acc ggg acc tct act    1248
Asp Gly His Gln Ile Ile Ser Val Ile Thr Asn Thr Gly Thr Ser Thr
                405                 410                 415 cct cta tgg aac ctc acg gtg ccg gac aca ggt ctg gca tct ggc act    1296
Pro Leu Trp Asn Leu Thr Val Pro Asp Thr Gly Leu Ala Ser Gly Thr
                420                 425                 430 gct gtt gta gag att ata acg tgc gat cag tct gtc att gcg agt gat    1344
Ala Val Val Glu Ile Ile Thr Cys Asp Gln Ser Val Ile Ala Ser Asp
            435                 440                 445 ggg agt cta gct gtg ccg atg gaa gga ggg atg ccg agg ata tat tat    1392
Gly Ser Leu Ala Val Pro Met Glu Gly Gly Met Pro Arg Ile Tyr Tyr
        450                 455                 460 ccg gtg gat gag gcg gtt ggt agt ggg att tgt aat ctt acg agt agc    1440
Pro Val Asp Glu Ala Val Gly Ser Gly Ile Cys Asn Leu Thr Ser Ser
465                 470                 475                 480 tat                                                                1443
Tyr

<210> SEQ ID NO 32
<211> LENGTH: 481
<212> TYPE: PRT
<213> ORGANISM: Dinemasporium sp.

<400> SEQUENCE: 32

Ala Thr Ala Glu Gln Trp Arg Ser Arg Ala Ile Tyr Gln Leu Leu Thr
1               5                   10                  15

Asp Arg Phe Ala Arg Pro Asp Asn Ser Thr Thr Ala Thr Cys Tyr Thr
                20                  25                  30

Pro Asp Arg Asn Tyr Cys Gly Gly Thr Trp Ser Gly Ile Ile Ser Gln
            35                  40                  45

Leu Asp Tyr Ile Gln Asp Met Gly Phe Thr Ala Ile Trp Ile Ser Pro
        50                  55                  60

Val Thr Ser Asn Ile Pro Asn Ile Thr Ser Tyr Gly Tyr Ala Tyr His
65                  70                  75                  80

Gly Tyr Trp Gln Gln Asp Leu Tyr Lys Leu Asn Asp His Phe Gly Thr
                85                  90                  95

Ala Glu Asp Leu Lys Ala Leu Ser Gln Ala Leu His Asp Arg Asp Met
                100                 105                 110

Tyr Leu Met Val Asp Val Val Ala Asn His Asn Gly Trp Pro Gly Asp
            115                 120                 125

Ser Ala Ser Val Asn Tyr Ser Ala Phe Tyr Pro Phe Asp Asn Ala Ser
        130                 135                 140

His Tyr His Leu Phe Cys Val Val Asp Asp Tyr Ser Asn Gln Thr Asp
145                 150                 155                 160
```

-continued

```
Val Glu Asp Cys Trp Leu Gly Asp Thr Asn Val Glu Leu Val Asp Leu
                165                 170                 175

Asp Thr Asn Ser Gln Asp Val Val Asp Gly Tyr Ser Lys Trp Ile Gly
            180                 185                 190

Glu Leu Val Ser Asn Tyr Ser Ile Asp Gly Leu Arg Ile Asp Thr Val
            195                 200                 205

Lys His Val Asp Lys Pro Phe Trp Thr Ser Phe Gln Gln Ala Ala Gly
210                 215                 220

Val Phe Thr Thr Gly Glu Ile Leu Ser Gly Asp Pro Ser Tyr Thr Cys
225                 230                 235                 240

Asp Tyr Gln Asn Tyr Leu Asp Ser Thr Leu Asn Tyr Pro Leu Trp Trp
                245                 250                 255

Pro Ala Met Ala Phe Leu Asn Ser Thr Ser Gly Ser Ser Ala Asn Leu
            260                 265                 270

Leu Asn Leu Leu Ser Ser Leu Arg Ser Thr Cys Lys Asp Val Ser Val
            275                 280                 285

Leu Gly Val Phe Thr Glu Asn His Asp Leu Pro Arg Phe Ala Ser Gln
290                 295                 300

Thr Gln Asp Met Ala Leu Ala Lys Asn Ala Leu Ala Leu Thr Ile Leu
305                 310                 315                 320

Ser Asp Gly Ile Pro Ile Val Tyr Ala Gly Gln Glu Gln His Tyr Asp
                325                 330                 335

Gly Ser Gly Asp Pro Tyr Asn Arg Glu Ala Asn Trp Leu Ser Gly Tyr
            340                 345                 350

Ser Arg Ser Asn Glu Leu Tyr Leu Leu Val Ala Ala Val Asn Gln Val
            355                 360                 365

Arg Asn Arg Ala Leu Tyr Arg Asp Ala Asn Tyr Ala Thr Tyr Asn Ala
370                 375                 380

Thr Ser Ile Tyr Ser Asp Gln His Thr Val Ala Phe Arg Lys Gly Tyr
385                 390                 395                 400

Asp Gly His Gln Ile Ile Ser Val Ile Thr Asn Thr Gly Thr Ser Thr
                405                 410                 415

Pro Leu Trp Asn Leu Thr Val Pro Asp Thr Gly Leu Ala Ser Gly Thr
            420                 425                 430

Ala Val Val Glu Ile Ile Thr Cys Asp Gln Ser Val Ile Ala Ser Asp
            435                 440                 445

Gly Ser Leu Ala Val Pro Met Glu Gly Gly Met Pro Arg Ile Tyr Tyr
450                 455                 460

Pro Val Asp Glu Ala Val Gly Ser Gly Ile Cys Asn Leu Thr Ser Ser
465                 470                 475                 480

Tyr
```

```
<210> SEQ ID NO 33
<211> LENGTH: 1485
<212> TYPE: DNA
<213> ORGANISM: Cryptosporiopsis sp.
<220> FEATURE:
<221> NAME/KEY: CDS
<222> LOCATION: (1)..(1485)

<400> SEQUENCE: 33
```

```
ttg gac gca gca gga tgg cga aac cag agc atc tac cag gtc ctg acg      48
Leu Asp Ala Ala Gly Trp Arg Asn Gln Ser Ile Tyr Gln Val Leu Thr
1                   5                   10                  15 gac cgc ttc gcc atg gcc gac ggc tcg aca ccc gca tgc gac gca tcc      96
Asp Arg Phe Ala Met Ala Asp Gly Ser Thr Pro Ala Cys Asp Ala Ser
                20                  25                  30
```

-continued

| | | | | | | | | | | | | | | | |
|---|---|---|---|---|---|---|---|---|---|---|---|---|---|---|---|
| caa | ggc | ctc | tac | tgc | ggt | ggc | acc | tgg | cag | ggc | atc | acc | aac | cag | ttg | 144 |
| Gln | Gly | Leu | Tyr | Cys | Gly | Gly | Thr | Trp | Gln | Gly | Ile | Thr | Asn | Gln | Leu | |
| | | 35 | | | | 40 | | | | | 45 | | | | | |

| gat | tac | atc | cag | aac | ctg | ggt | gcc | acc | gcc | gtc | tgg | atc | tcc | cct | gtc | 192 |
| Asp | Tyr | Ile | Gln | Asn | Leu | Gly | Ala | Thr | Ala | Val | Trp | Ile | Ser | Pro | Val | |
| 50 | | | | | 55 | | | | | 60 | | | | | | |

| atc | aag | aac | gtc | gag | ggc | aac | ttt | gcc | gat | tcc | ggc | gag | gcc | tac | cac | 240 |
| Ile | Lys | Asn | Val | Glu | Gly | Asn | Phe | Ala | Asp | Ser | Gly | Glu | Ala | Tyr | His | |
| 65 | | | | | 70 | | | | | 75 | | | | | 80 | |

| ggc | ttc | tgg | gcg | caa | gac | ctc | tac | tcg | ctc | aac | tcg | cat | ttc | ggt | acc | 288 |
| Gly | Phe | Trp | Ala | Gln | Asp | Leu | Tyr | Ser | Leu | Asn | Ser | His | Phe | Gly | Thr | |
| | | | | 85 | | | | | 90 | | | | | 95 | | |

| gag | gcc | gac | ctc | aag | gcc | ctc | gcc | gac | gcg | ctc | cac | gcc | cgg | ggc | atg | 336 |
| Glu | Ala | Asp | Leu | Lys | Ala | Leu | Ala | Asp | Ala | Leu | His | Ala | Arg | Gly | Met | |
| | | | 100 | | | | | 105 | | | | | 110 | | | |

| tac | ctg | atg | gtc | gac | atc | gcc | ccg | aac | cac | gtg | ggc | ctg | aat | acg | gat | 384 |
| Tyr | Leu | Met | Val | Asp | Ile | Ala | Pro | Asn | His | Val | Gly | Leu | Asn | Thr | Asp | |
| | | 115 | | | | | 120 | | | | | 125 | | | | |

| gcc | aac | aac | tat | acc | ggt | tac | act | ccc | ttc | aac | gag | acc | gaa | tac | tac | 432 |
| Ala | Asn | Asn | Tyr | Thr | Gly | Tyr | Thr | Pro | Phe | Asn | Glu | Thr | Glu | Tyr | Tyr | |
| 130 | | | | | 135 | | | | | 140 | | | | | | |

| cac | gac | gag | tgc | agc | atc | gtc | tgg | aac | gtc | cct | acg | tcc | gag | agg | ctc | 480 |
| His | Asp | Glu | Cys | Ser | Ile | Val | Trp | Asn | Val | Pro | Thr | Ser | Glu | Arg | Leu | |
| 145 | | | | | 150 | | | | | 155 | | | | | 160 | |

| tgc | tgg | ctc | gag | ggt | ctg | ccc | gac | ctg | cgt | acc | gaa | gat | gcc | ggc | gta | 528 |
| Cys | Trp | Leu | Glu | Gly | Leu | Pro | Asp | Leu | Arg | Thr | Glu | Asp | Ala | Gly | Val | |
| | | | | 165 | | | | | 170 | | | | | 175 | | |

| cgc | cag | gtg | tat | gcg | gaa | tgg | atc | aag | gac | ctg | gtt | gcc | aat | tac | tcc | 576 |
| Arg | Gln | Val | Tyr | Ala | Glu | Trp | Ile | Lys | Asp | Leu | Val | Ala | Asn | Tyr | Ser | |
| | | | 180 | | | | | 185 | | | | | 190 | | | |

| atc | gac | ggt | ctc | cgt | atc | gat | acc | gcc | ctg | gag | atc | gag | ccg | gag | ttc | 624 |
| Ile | Asp | Gly | Leu | Arg | Ile | Asp | Thr | Ala | Leu | Glu | Ile | Glu | Pro | Glu | Phe | |
| | | 195 | | | | | 200 | | | | | 205 | | | | |

| tgg | acc | gac | ggt | ggt | gtc | cgc | gag | gcc | gcc | ggc | gtc | ttc | ctc | ctg | gcc | 672 |
| Trp | Thr | Asp | Gly | Gly | Val | Arg | Glu | Ala | Ala | Gly | Val | Phe | Leu | Leu | Ala | |
| | 210 | | | | | 215 | | | | | 220 | | | | | |

| gag | att | aac | cac | agc | aac | ccg | gag | acc | ctg | gcg | ccc | tac | cag | cag | tac | 720 |
| Glu | Ile | Asn | His | Ser | Asn | Pro | Glu | Thr | Leu | Ala | Pro | Tyr | Gln | Gln | Tyr | |
| 225 | | | | | 230 | | | | | 235 | | | | | 240 | |

| ctc | gac | ggg | tac | atg | gac | tac | agc | agc | tgg | aac | tgg | atc | acg | gat | tcg | 768 |
| Leu | Asp | Gly | Tyr | Met | Asp | Tyr | Ser | Ser | Trp | Asn | Trp | Ile | Thr | Asp | Ser | |
| | | | | 245 | | | | | 250 | | | | | 255 | | |

| ttc | cag | gcc | gtc | gac | gcc | agc | atg | acc | gac | ctc | tac | gag | ggg | acc | aac | 816 |
| Phe | Gln | Ala | Val | Asp | Ala | Ser | Met | Thr | Asp | Leu | Tyr | Glu | Gly | Thr | Asn | |
| | | | 260 | | | | | 265 | | | | | 270 | | | |

| cag | ctg | gcg | gcc | atg | acc | gac | atc | gac | ccg | tcg | ctc | ttc | ggc | tcc | ttt | 864 |
| Gln | Leu | Ala | Ala | Met | Thr | Asp | Ile | Asp | Pro | Ser | Leu | Phe | Gly | Ser | Phe | |
| | | 275 | | | | | 280 | | | | | 285 | | | | |

| gtc | gag | aac | cac | gac | cag | gtc | cgg | ttc | ccc | tac | cgc | aac | gcc | gac | atg | 912 |
| Val | Glu | Asn | His | Asp | Gln | Val | Arg | Phe | Pro | Tyr | Arg | Asn | Ala | Asp | Met | |
| | 290 | | | | | 295 | | | | | 300 | | | | | |

| gcc | ctg | gcc | aag | aac | ctg | tac | acc | ctc | gcc | ctg | ctc | cgg | gac | ggg | atc | 960 |
| Ala | Leu | Ala | Lys | Asn | Leu | Tyr | Thr | Leu | Ala | Leu | Leu | Arg | Asp | Gly | Ile | |
| 305 | | | | | 310 | | | | | 315 | | | | | 320 | |

| ccc | atc | gtc | tac | tac | gga | cag | gag | cag | cac | ttt | gac | ggc | ggc | atc | gtg | 1008 |
| Pro | Ile | Val | Tyr | Tyr | Gly | Gln | Glu | Gln | His | Phe | Asp | Gly | Gly | Ile | Val | |
| | | | | 325 | | | | | 330 | | | | | 335 | | |

| ccc | agc | aac | cgg | gag | gcg | ctc | tgg | ctc | ggc | acc | tac | gac | atc | tac | gcc | 1056 |
| Pro | Ser | Asn | Arg | Glu | Ala | Leu | Trp | Leu | Gly | Thr | Tyr | Asp | Ile | Tyr | Ala | |
| | | | 340 | | | | | 345 | | | | | 350 | | | |

-continued

```
gag ctg tac ggc tgg atc cag cag acc atc aag gcg cgc gcg cac gcc      1104
Glu Leu Tyr Gly Trp Ile Gln Gln Thr Ile Lys Ala Arg Ala His Ala
    355                 360                 365 gcg gcg gcg gac gcc acc ttc ctc acg acg cag agg aca cag gcc atc      1152
Ala Ala Ala Asp Ala Thr Phe Leu Thr Thr Gln Arg Thr Gln Ala Ile
370                 375                 380 ttc tac cag aac gcc acc gac atc aac agc agc gtc atc ggc ttc cgc      1200
Phe Tyr Gln Asn Ala Thr Asp Ile Asn Ser Ser Val Ile Gly Phe Arg
385                 390                 395                 400 aag ggc cag atg ctc acc atg tac acc aac ggt ggc gcc gat gcc ctc      1248
Lys Gly Gln Met Leu Thr Met Tyr Thr Asn Gly Gly Ala Asp Ala Leu
            405                 410                 415 aac ggt gcc tac ttt gcc att gcc cgc aac gtg cac ggc tac gcc atc      1296
Asn Gly Ala Tyr Phe Ala Ile Ala Arg Asn Val His Gly Tyr Ala Ile
        420                 425                 430 ggt gag gac ctg gtc gac gtg gtg aac tgc gaa tcg ttc cag gtc gcc      1344
Gly Glu Asp Leu Val Asp Val Val Asn Cys Glu Ser Phe Gln Val Ala
    435                 440                 445 ccc cac gga cgg ctc tgg gtc cag atg ccc aac ggt ggt ctg ccg cgt      1392
Pro His Gly Arg Leu Trp Val Gln Met Pro Asn Gly Gly Leu Pro Arg
450                 455                 460 gtg ttt tta ccg gtg aat cag acc gag ggg ctc tgc aac aac gtc ggc      1440
Val Phe Leu Pro Val Asn Gln Thr Glu Gly Leu Cys Asn Asn Val Gly
465                 470                 475                 480 acg cct ttg tct aac tct acc atc act gtt gcg att gac aag gca          1485
Thr Pro Leu Ser Asn Ser Thr Ile Thr Val Ala Ile Asp Lys Ala
            485                 490                 495

<210> SEQ ID NO 34
<211> LENGTH: 495
<212> TYPE: PRT
<213> ORGANISM: Cryptosporiopsis sp.

<400> SEQUENCE: 34

Leu Asp Ala Ala Gly Trp Arg Asn Gln Ser Ile Tyr Gln Val Leu Thr
1               5                   10                  15

Asp Arg Phe Ala Met Ala Asp Gly Ser Thr Pro Ala Cys Asp Ala Ser
            20                  25                  30

Gln Gly Leu Tyr Cys Gly Gly Thr Trp Gln Gly Ile Thr Asn Gln Leu
        35                  40                  45

Asp Tyr Ile Gln Asn Leu Gly Ala Thr Ala Val Trp Ile Ser Pro Val
    50                  55                  60

Ile Lys Asn Val Glu Gly Asn Phe Ala Asp Gly Glu Ala Tyr His
65                  70                  75                  80

Gly Phe Trp Ala Gln Asp Leu Tyr Ser Leu Asn Ser His Phe Gly Thr
                85                  90                  95

Glu Ala Asp Leu Lys Ala Leu Ala Asp Ala Leu His Ala Arg Gly Met
            100                 105                 110

Tyr Leu Met Val Asp Ile Ala Pro Asn His Val Gly Leu Asn Thr Asp
        115                 120                 125

Ala Asn Asn Tyr Thr Gly Tyr Thr Pro Phe Asn Glu Thr Glu Tyr Tyr
    130                 135                 140

His Asp Glu Cys Ser Ile Val Trp Asn Val Pro Thr Ser Glu Arg Leu
145                 150                 155                 160

Cys Trp Leu Glu Gly Leu Pro Asp Leu Arg Thr Glu Asp Ala Gly Val
                165                 170                 175

Arg Gln Val Tyr Ala Glu Trp Ile Lys Asp Leu Val Ala Asn Tyr Ser
            180                 185                 190
```

```
Ile Asp Gly Leu Arg Ile Asp Thr Ala Leu Glu Ile Glu Pro Glu Phe
            195                 200                 205

Trp Thr Asp Gly Gly Val Arg Glu Ala Ala Gly Val Phe Leu Leu Ala
    210                 215                 220

Glu Ile Asn His Ser Asn Pro Glu Thr Leu Ala Pro Tyr Gln Gln Tyr
225                 230                 235                 240

Leu Asp Gly Tyr Met Asp Tyr Ser Ser Trp Asn Trp Ile Thr Asp Ser
                245                 250                 255

Phe Gln Ala Val Asp Ala Ser Met Thr Asp Leu Tyr Glu Gly Thr Asn
                260                 265                 270

Gln Leu Ala Ala Met Thr Asp Ile Asp Pro Ser Leu Phe Gly Ser Phe
            275                 280                 285

Val Glu Asn His Asp Gln Val Arg Phe Pro Tyr Arg Asn Ala Asp Met
        290                 295                 300

Ala Leu Ala Lys Asn Leu Tyr Thr Leu Ala Leu Leu Arg Asp Gly Ile
305                 310                 315                 320

Pro Ile Val Tyr Tyr Gly Gln Glu Gln His Phe Asp Gly Gly Ile Val
                325                 330                 335

Pro Ser Asn Arg Glu Ala Leu Trp Leu Gly Thr Tyr Asp Ile Tyr Ala
            340                 345                 350

Glu Leu Tyr Gly Trp Ile Gln Gln Thr Ile Lys Ala Arg Ala His Ala
        355                 360                 365

Ala Ala Ala Asp Ala Thr Phe Leu Thr Gln Arg Thr Gln Ala Ile
        370                 375                 380

Phe Tyr Gln Asn Ala Thr Asp Ile Asn Ser Ser Val Ile Gly Phe Arg
385                 390                 395                 400

Lys Gly Gln Met Leu Thr Met Tyr Thr Asn Gly Gly Ala Asp Ala Leu
                405                 410                 415

Asn Gly Ala Tyr Phe Ala Ile Ala Arg Asn Val His Gly Tyr Ala Ile
                420                 425                 430

Gly Glu Asp Leu Val Asp Val Val Asn Cys Glu Ser Phe Gln Val Ala
            435                 440                 445

Pro His Gly Arg Leu Trp Val Gln Met Pro Asn Gly Gly Leu Pro Arg
        450                 455                 460

Val Phe Leu Pro Val Asn Gln Thr Glu Gly Leu Cys Asn Asn Val Gly
465                 470                 475                 480

Thr Pro Leu Ser Asn Ser Thr Ile Thr Val Ala Ile Asp Lys Ala
                485                 490                 495

<210> SEQ ID NO 35
<211> LENGTH: 1428
<212> TYPE: DNA
<213> ORGANISM: Coniochaeta sp.
<220> FEATURE:
<221> NAME/KEY: CDS
<222> LOCATION: (1)..(1428)

<400> SEQUENCE: 35 gca gac tgg cgt gag cag tcc atc tac cag gtc gtg acg gac cgc ttc      48
Ala Asp Trp Arg Glu Gln Ser Ile Tyr Gln Val Val Thr Asp Arg Phe
1               5                   10                  15 gcg cgg acg gac ctg tcc acc acg gcc acg tgc gac acc tcg gcg cag      96
Ala Arg Thr Asp Leu Ser Thr Thr Ala Thr Cys Asp Thr Ser Ala Gln
            20                  25                  30 gtg tat tgc ggc ggc acg tac aag ggt ctg atc tcc aag ctg gat tac     144
Val Tyr Cys Gly Gly Thr Tyr Lys Gly Leu Ile Ser Lys Leu Asp Tyr
        35                  40                  45
```

```
att cag ggc atg ggc ttc act gcc atc tgg ata tcg ccc atc gtc gag      192
Ile Gln Gly Met Gly Phe Thr Ala Ile Trp Ile Ser Pro Ile Val Glu
    50              55                  60 cag atg gac ggt aat act gcc gac ggc tcc tcg tat cac ggt tac tgg      240
Gln Met Asp Gly Asn Thr Ala Asp Gly Ser Ser Tyr His Gly Tyr Trp
65              70                  75                  80 gcg cag gat att tgg agt ctg aac ccg tcg ttc gga tcg gct ggc gac      288
Ala Gln Asp Ile Trp Ser Leu Asn Pro Ser Phe Gly Ser Ala Gly Asp
                85                  90                  95 ctg atc gcg ctc tcc aac gcg ctg cac gcc cgg ggc atg tac ctc atg      336
Leu Ile Ala Leu Ser Asn Ala Leu His Ala Arg Gly Met Tyr Leu Met
            100                 105                 110 ctg gac gtg gtg acc aac cac ttt gct tac aac ggc tgc ggc aac tgc      384
Leu Asp Val Val Thr Asn His Phe Ala Tyr Asn Gly Cys Gly Asn Cys
        115                 120                 125 gtc gac tac agc atc ttc acc ccg ttc aac tcg tcg tcg tac ttc cac      432
Val Asp Tyr Ser Ile Phe Thr Pro Phe Asn Ser Ser Ser Tyr Phe His
    130                 135                 140 ccc ttc tgc ttg atc gac tac aac aac cag acg tcg atc gag cag tgc      480
Pro Phe Cys Leu Ile Asp Tyr Asn Asn Gln Thr Ser Ile Glu Gln Cys
145                 150                 155                 160 tgg gag gga gac aac acc gtc agc ctg ccg gac ctg cgg acg gag aac      528
Trp Glu Gly Asp Asn Thr Val Ser Leu Pro Asp Leu Arg Thr Glu Asn
                165                 170                 175 tcc aac gta cgc gcg ata tgg aac gac tgg atc acg cag att gtg gcg      576
Ser Asn Val Arg Ala Ile Trp Asn Asp Trp Ile Thr Gln Ile Val Ala
            180                 185                 190 gcg tac ggc atc gac ggt ctg cgc atc gac agc gtc aag cac cag gag      624
Ala Tyr Gly Ile Asp Gly Leu Arg Ile Asp Ser Val Lys His Gln Glu
        195                 200                 205 acg tcg ttc tgg tcc ggt ttc ggg tcg gcc gcc ggc gtg ttc atg ctg      672
Thr Ser Phe Trp Ser Gly Phe Gly Ser Ala Ala Gly Val Phe Met Leu
    210                 215                 220 ggc gag gtg tac aac ggc gat ccg acg cag ctg gcg ccg tac cag gat      720
Gly Glu Val Tyr Asn Gly Asp Pro Thr Gln Leu Ala Pro Tyr Gln Asp
225                 230                 235                 240 tac atg ccc gga ctg ctg gac tac gcg agc tac tac tgg atc acg agg      768
Tyr Met Pro Gly Leu Leu Asp Tyr Ala Ser Tyr Tyr Trp Ile Thr Arg
                245                 250                 255 gcg ttc cag tcg agc agc ggg agt atg agc gat ctg gcg tct ggt gtc      816
Ala Phe Gln Ser Ser Ser Gly Ser Met Ser Asp Leu Ala Ser Gly Val
            260                 265                 270 aac aca ctc aag agc att gcc agg aac aca agc ctg tac gga tct ttc      864
Asn Thr Leu Lys Ser Ile Ala Arg Asn Thr Ser Leu Tyr Gly Ser Phe
        275                 280                 285 ctg gag aac cac gac cag ccg cgg ttc gcg tcg ctt acc tcg gac gtc      912
Leu Glu Asn His Asp Gln Pro Arg Phe Ala Ser Leu Thr Ser Asp Val
    290                 295                 300 gcc ttg gcg aag aat gcg ata gcg ttt act atg ctg aag gac ggt atc      960
Ala Leu Ala Lys Asn Ala Ile Ala Phe Thr Met Leu Lys Asp Gly Ile
305                 310                 315                 320 ccg gtc gtt tac cag ggc caa gag cag cac tat gcg ggc gga aat gtc     1008
Pro Val Val Tyr Gln Gly Gln Glu Gln His Tyr Ala Gly Gly Asn Val
                325                 330                 335 cca gct gac cgc gaa gcg atc tgg ttg tcg ggg tac tcc acg tct gcg     1056
Pro Ala Asp Arg Glu Ala Ile Trp Leu Ser Gly Tyr Ser Thr Ser Ala
            340                 345                 350 acg ctg tac acc tgg atc gcc gcg ctg aac aag gtc cgt tcg agg gct     1104
Thr Leu Tyr Thr Trp Ile Ala Ala Leu Asn Lys Val Arg Ser Arg Ala
        355                 360                 365
```

```
atc gcg caa gac agc agc tac ctg agc tat cag gcg tat cct gtc tat    1152
Ile Ala Gln Asp Ser Ser Tyr Leu Ser Tyr Gln Ala Tyr Pro Val Tyr
    370                 375                 380 acg gac agc aac acc att gcc atg cgc aag gga cgg gac gga tac cag    1200
Thr Asp Ser Asn Thr Ile Ala Met Arg Lys Gly Arg Asp Gly Tyr Gln
385                 390                 395                 400 gtc atc ggg gtg ttc acc aac aag gga tcg agc ggg ttg tcc agt ctc    1248
Val Ile Gly Val Phe Thr Asn Lys Gly Ser Ser Gly Leu Ser Ser Leu
                405                 410                 415 acc ctc acg acg tcg atg acc gga ttc acg gcg ggc cag gcg gtc gtg    1296
Thr Leu Thr Thr Ser Met Thr Gly Phe Thr Ala Gly Gln Ala Val Val
            420                 425                 430 gat gtc atg agc tgc acc act ttc acg acg gac tac agc ggt agc ctc    1344
Asp Val Met Ser Cys Thr Thr Phe Thr Thr Asp Tyr Ser Gly Ser Leu
435                 440                 445 gct gtc acc ctt tcg gga ggc att ccg cgg gtg ttc tat cca agc gcg    1392
Ala Val Thr Leu Ser Gly Gly Ile Pro Arg Val Phe Tyr Pro Ser Ala
    450                 455                 460 agg ttg agt ggc tca gga ata tgt ggc tcc aat ggg                    1428
Arg Leu Ser Gly Ser Gly Ile Cys Gly Ser Asn Gly
465                 470                 475

<210> SEQ ID NO 36
<211> LENGTH: 476
<212> TYPE: PRT
<213> ORGANISM: Coniochaeta sp.

<400> SEQUENCE: 36

Ala Asp Trp Arg Glu Gln Ser Ile Tyr Gln Val Val Thr Asp Arg Phe
1               5                   10                  15

Ala Arg Thr Asp Leu Ser Thr Thr Ala Thr Cys Asp Thr Ser Ala Gln
            20                  25                  30

Val Tyr Cys Gly Gly Thr Tyr Lys Gly Leu Ile Ser Lys Leu Asp Tyr
        35                  40                  45

Ile Gln Gly Met Gly Phe Thr Ala Ile Trp Ile Ser Pro Ile Val Glu
    50                  55                  60

Gln Met Asp Gly Asn Thr Ala Asp Gly Ser Ser Tyr His Gly Tyr Trp
65                  70                  75                  80

Ala Gln Asp Ile Trp Ser Leu Asn Pro Ser Phe Gly Ser Ala Gly Asp
                85                  90                  95

Leu Ile Ala Leu Ser Asn Ala Leu His Ala Arg Gly Met Tyr Leu Met
            100                 105                 110

Leu Asp Val Val Thr Asn His Phe Ala Tyr Asn Gly Cys Gly Asn Cys
        115                 120                 125

Val Asp Tyr Ser Ile Phe Thr Pro Phe Asn Ser Ser Tyr Phe His
    130                 135                 140

Pro Phe Cys Leu Ile Asp Tyr Asn Asn Gln Thr Ser Ile Glu Gln Cys
145                 150                 155                 160

Trp Glu Gly Asp Asn Thr Val Ser Leu Pro Asp Leu Arg Thr Glu Asn
                165                 170                 175

Ser Asn Val Arg Ala Ile Trp Asn Asp Trp Ile Thr Gln Ile Val Ala
            180                 185                 190

Ala Tyr Gly Ile Asp Gly Leu Arg Ile Asp Ser Val Lys His Gln Glu
        195                 200                 205

Thr Ser Phe Trp Ser Gly Phe Gly Ser Ala Ala Gly Val Phe Met Leu
    210                 215                 220

Gly Glu Val Tyr Asn Gly Asp Pro Thr Gln Leu Ala Pro Tyr Gln Asp
```

```
                225                 230                 235                 240
Tyr Met Pro Gly Leu Leu Asp Tyr Ala Ser Tyr Tyr Trp Ile Thr Arg
                    245                 250                 255
Ala Phe Gln Ser Ser Ser Gly Ser Met Ser Asp Leu Ala Ser Gly Val
                260                 265                 270
Asn Thr Leu Lys Ser Ile Ala Arg Asn Thr Ser Leu Tyr Gly Ser Phe
            275                 280                 285
Leu Glu Asn His Asp Gln Pro Arg Phe Ala Ser Leu Thr Ser Asp Val
        290                 295                 300
Ala Leu Ala Lys Asn Ala Ile Ala Phe Thr Met Leu Lys Asp Gly Ile
305                 310                 315                 320
Pro Val Val Tyr Gln Gly Gln Glu Gln His Tyr Ala Gly Gly Asn Val
                325                 330                 335
Pro Ala Asp Arg Glu Ala Ile Trp Leu Ser Gly Tyr Ser Thr Ser Ala
                340                 345                 350
Thr Leu Tyr Thr Trp Ile Ala Ala Leu Asn Lys Val Arg Ser Arg Ala
                355                 360                 365
Ile Ala Gln Asp Ser Ser Tyr Leu Ser Tyr Gln Ala Tyr Pro Val Tyr
        370                 375                 380
Thr Asp Ser Asn Thr Ile Ala Met Arg Lys Gly Arg Asp Gly Tyr Gln
385                 390                 395                 400
Val Ile Gly Val Phe Thr Asn Lys Gly Ser Gly Leu Ser Ser Leu
                405                 410                 415
Thr Leu Thr Thr Ser Met Thr Gly Phe Thr Ala Gly Gln Ala Val Val
                420                 425                 430
Asp Val Met Ser Cys Thr Thr Phe Thr Thr Asp Tyr Ser Gly Ser Leu
                435                 440                 445
Ala Val Thr Leu Ser Gly Gly Ile Pro Arg Val Phe Tyr Pro Ser Ala
        450                 455                 460
Arg Leu Ser Gly Ser Gly Ile Cys Gly Ser Asn Gly
465                 470                 475

<210> SEQ ID NO 37
<211> LENGTH: 1431
<212> TYPE: DNA
<213> ORGANISM: Diplodia sp.
<220> FEATURE:
<221> NAME/KEY: CDS
<222> LOCATION: (1)..(1431)

<400> SEQUENCE: 37 gct act ccc gcc caa tgg cgc tcc aag tcc atc tac cag gtc ctc act       48
Ala Thr Pro Ala Gln Trp Arg Ser Lys Ser Ile Tyr Gln Val Leu Thr
1               5                   10                  15 gat agg ttt gcc cgc acc gat ggc agc acc agc gca acg tgc aac acg       96
Asp Arg Phe Ala Arg Thr Asp Gly Ser Thr Ser Ala Thr Cys Asn Thr
                20                  25                  30 cag gac aga aag tac tgc ggc gga acg tac cag gga atc atc aac caa      144
Gln Asp Arg Lys Tyr Cys Gly Gly Thr Tyr Gln Gly Ile Ile Asn Gln
            35                  40                  45 ctg gac tac ata cag ggc atg ggc ttc act gcc att tgg atc tcc ccc      192
Leu Asp Tyr Ile Gln Gly Met Gly Phe Thr Ala Ile Trp Ile Ser Pro
        50                  55                  60 gtc gtc aag aat ctg ccc gag acc act ggc tat gga gag gcc tac cac      240
Val Val Lys Asn Leu Pro Glu Thr Thr Gly Tyr Gly Glu Ala Tyr His
65                  70                  75                  80 ggc tac tgg cag cag gac ctg tac agc ctc aat gag aac ttt gga tct      288
Gly Tyr Trp Gln Gln Asp Leu Tyr Ser Leu Asn Glu Asn Phe Gly Ser
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 85  |     |     |     |     | 90  |     |     |     |     | 95  |     |      |
| gca | gct | gat | ctc | cag | gct | ctc | gct | gcc | gag | ctg | cat | gac | cgc | gac | atg | 336  |
| Ala | Ala | Asp | Leu | Gln | Ala | Leu | Ala | Ala | Glu | Leu | His | Asp | Arg | Asp | Met |      |
|     |     |     | 100 |     |     |     |     | 105 |     |     |     |     | 110 |     |     |      |
| tac | ttg | atg | gtg | gat | att | gtc | gtc | aac | cac | aat | ggc | tgg | gct | ggc | tcg | 384  |
| Tyr | Leu | Met | Val | Asp | Ile | Val | Val | Asn | His | Asn | Gly | Trp | Ala | Gly | Ser |      |
|     |     |     | 115 |     |     |     |     | 120 |     |     |     |     | 125 |     |     |      |
| tca | agc | tct | gtg | gac | tac | agc | agg | ttc | aac | ccg | ttc | aac | tcg | cag | gac | 432  |
| Ser | Ser | Ser | Val | Asp | Tyr | Ser | Arg | Phe | Asn | Pro | Phe | Asn | Ser | Gln | Asp |      |
|     | 130 |     |     |     |     | 135 |     |     |     |     | 140 |     |     |     |     |      |
| tac | tat | cat | tcg | tac | tgc | acc | gtc | tcc | gac | tac | aac | aac | cag | gac | ctc | 480  |
| Tyr | Tyr | His | Ser | Tyr | Cys | Thr | Val | Ser | Asp | Tyr | Asn | Asn | Gln | Asp | Leu |      |
| 145 |     |     |     |     | 150 |     |     |     |     | 155 |     |     |     |     | 160 |      |
| gtc | gag | gat | tgc | tgg | ctt | ggt | gac | aac | act | gtc | cag | ctc | gtc | gac | ctc | 528  |
| Val | Glu | Asp | Cys | Trp | Leu | Gly | Asp | Asn | Thr | Val | Gln | Leu | Val | Asp | Leu |      |
|     |     |     |     | 165 |     |     |     |     | 170 |     |     |     |     | 175 |     |      |
| aag | acc | gaa | gac | tcg | gcc | gtt | gcc | gat | ggc | tac | aac | acc | tgg | atc | tcc | 576  |
| Lys | Thr | Glu | Asp | Ser | Ala | Val | Ala | Asp | Gly | Tyr | Asn | Thr | Trp | Ile | Ser |      |
|     |     |     | 180 |     |     |     |     | 185 |     |     |     |     | 190 |     |     |      |
| caa | ctt | gtt | gca | aac | tac | tcc | att | gac | ggt | ctg | cgg | atc | gac | acg | gcc | 624  |
| Gln | Leu | Val | Ala | Asn | Tyr | Ser | Ile | Asp | Gly | Leu | Arg | Ile | Asp | Thr | Ala |      |
|     |     |     | 195 |     |     |     |     | 200 |     |     |     |     | 205 |     |     |      |
| aag | cac | gtg | gac | aag | gca | ttc | tac | cct | ccc | ttt | gag | gct | gcg | gct | ggt | 672  |
| Lys | His | Val | Asp | Lys | Ala | Phe | Tyr | Pro | Pro | Phe | Glu | Ala | Ala | Ala | Gly |      |
|     | 210 |     |     |     |     | 215 |     |     |     |     | 220 |     |     |     |     |      |
| gtc | ttc | tcc | acc | ggc | gaa | gtc | tac | gat | ggc | aac | cca | tcc | tac | act | tgt | 720  |
| Val | Phe | Ser | Thr | Gly | Glu | Val | Tyr | Asp | Gly | Asn | Pro | Ser | Tyr | Thr | Cys |      |
| 225 |     |     |     |     | 230 |     |     |     |     | 235 |     |     |     |     | 240 |      |
| gac | tac | cag | aac | tat | atg | gac | agc | gtg | ctc | aac | tat | ccc | gta | tac | tac | 768  |
| Asp | Tyr | Gln | Asn | Tyr | Met | Asp | Ser | Val | Leu | Asn | Tyr | Pro | Val | Tyr | Tyr |      |
|     |     |     |     | 245 |     |     |     |     | 250 |     |     |     |     | 255 |     |      |
| ccg | cta | gtc | cgg | gcc | ttc | act | tcg | acc | agt | ggc | tcc | atc | tcc | gat | ctt | 816  |
| Pro | Leu | Val | Arg | Ala | Phe | Thr | Ser | Thr | Ser | Gly | Ser | Ile | Ser | Asp | Leu |      |
|     |     |     | 260 |     |     |     |     | 265 |     |     |     |     | 270 |     |     |      |
| gtg | aac | atg | gtc | agc | acg | ctc | aag | agc | ggc | tgc | aag | gac | acc | acg | ctt | 864  |
| Val | Asn | Met | Val | Ser | Thr | Leu | Lys | Ser | Gly | Cys | Lys | Asp | Thr | Thr | Leu |      |
|     |     | 275 |     |     |     |     | 280 |     |     |     |     | 285 |     |     |     |      |
| ctc | ggc | acc | ttc | tcc | gag | aac | cac | gac | atc | acg | cgc | ttc | gcc | gcc | atc | 912  |
| Leu | Gly | Thr | Phe | Ser | Glu | Asn | His | Asp | Ile | Thr | Arg | Phe | Ala | Ala | Ile |      |
|     | 290 |     |     |     |     | 295 |     |     |     |     | 300 |     |     |     |     |      |
| acg | tcc | gac | ttc | tcg | cag | gcc | aag | aac | gtc | atc | gcc | ttc | aac | atc | ctc | 960  |
| Thr | Ser | Asp | Phe | Ser | Gln | Ala | Lys | Asn | Val | Ile | Ala | Phe | Asn | Ile | Leu |      |
| 305 |     |     |     | 310 |     |     |     |     | 315 |     |     |     |     | 320 |     |      |
| gcc | gac | ggc | atc | cct | atc | atc | tac | cag | ggc | cag | gag | caa | cac | tac | tcg | 1008 |
| Ala | Asp | Gly | Ile | Pro | Ile | Ile | Tyr | Gln | Gly | Gln | Glu | Gln | His | Tyr | Ser |      |
|     |     |     |     | 325 |     |     |     |     | 330 |     |     |     |     | 335 |     |      |
| ggc | gcc | gag | gac | ccg | gac | aac | cgc | gag | gcc | gtc | tgg | ctc | tcg | ggc | tac | 1056 |
| Gly | Ala | Glu | Asp | Pro | Asp | Asn | Arg | Glu | Ala | Val | Trp | Leu | Ser | Gly | Tyr |      |
|     |     |     | 340 |     |     |     |     | 345 |     |     |     |     | 350 |     |     |      |
| aac | acg | ggc | gcc | gag | ctg | tac | acc | ttc | acc | gcc | gcc | gtc | aac | gcc | atc | 1104 |
| Asn | Thr | Gly | Ala | Glu | Leu | Tyr | Thr | Phe | Thr | Ala | Ala | Val | Asn | Ala | Ile |      |
|     |     | 355 |     |     |     |     | 360 |     |     |     |     | 365 |     |     |     |      |
| cgc | aac | cgc | gcc | atc | gcc | gac | gac | gcc | gac | tac | ctg | acg | tac | cag | aac | 1152 |
| Arg | Asn | Arg | Ala | Ile | Ala | Asp | Asp | Ala | Asp | Tyr | Leu | Thr | Tyr | Gln | Asn |      |
|     | 370 |     |     |     |     | 375 |     |     |     |     | 380 |     |     |     |     |      |
| tgg | gtc | atc | tac | agc | gac | acg | acc | atc | gct | atg | cgc | aag | ggc | ttc | | 1200 |
| Trp | Val | Ile | Tyr | Ser | Asp | Thr | Thr | Ile | Ala | Met | Arg | Lys | Gly | Phe | |      |
| 385 |     |     |     | 390 |     |     |     |     | 395 |     |     |     |     | 400 | |      |
| gac | ggc | tac | cag | atc | atc | acc | gtc | ttg | agc | aac | aag | ggc | gcc | aat | ggc | 1248 |
| Asp | Gly | Tyr | Gln | Ile | Ile | Thr | Val | Leu | Ser | Asn | Lys | Gly | Ala | Asn | Gly |      |

```
                              405                 410                 415
gat gcg tac acg ctc aat ctg tcc aac acg ggc tgg acg agt gga acc       1296
Asp Ala Tyr Thr Leu Asn Leu Ser Asn Thr Gly Trp Thr Ser Gly Thr
        420                 425                 430 gag gtc gtc gag gtg ctg acg tgc agc aga gtc acg gtg acg agc agc       1344
Glu Val Val Glu Val Leu Thr Cys Ser Arg Val Thr Val Thr Ser Ser
    435                 440                 445 ggg acg gtg acg gta ccc atg tcg aat ggt ctg ccg agg gtc tac tac       1392
Gly Thr Val Thr Val Pro Met Ser Asn Gly Leu Pro Arg Val Tyr Tyr
450                 455                 460 ccg gct gcc cgg ctg agc ggg tcg ggc atc tgt gat cta                   1431
Pro Ala Ala Arg Leu Ser Gly Ser Gly Ile Cys Asp Leu
465                 470                 475

<210> SEQ ID NO 38
<211> LENGTH: 477
<212> TYPE: PRT
<213> ORGANISM: Diplodia sp.

<400> SEQUENCE: 38

Ala Thr Pro Ala Gln Trp Arg Ser Lys Ser Ile Tyr Gln Val Leu Thr
1               5                   10                  15

Asp Arg Phe Ala Arg Thr Asp Gly Ser Thr Ser Ala Thr Cys Asn Thr
            20                  25                  30

Gln Asp Arg Lys Tyr Cys Gly Gly Thr Tyr Gln Gly Ile Ile Asn Gln
        35                  40                  45

Leu Asp Tyr Ile Gln Gly Met Gly Phe Thr Ala Ile Trp Ile Ser Pro
    50                  55                  60

Val Val Lys Asn Leu Pro Glu Thr Thr Gly Tyr Gly Glu Ala Tyr His
65                  70                  75                  80

Gly Tyr Trp Gln Gln Asp Leu Tyr Ser Leu Asn Glu Asn Phe Gly Ser
                85                  90                  95

Ala Ala Asp Leu Gln Ala Leu Ala Ala Glu Leu His Arg Asp Met
            100                 105                 110

Tyr Leu Met Val Asp Ile Val Val Asn His Asn Gly Trp Ala Gly Ser
        115                 120                 125

Ser Ser Ser Val Asp Tyr Ser Arg Phe Asn Pro Phe Asn Ser Gln Asp
    130                 135                 140

Tyr Tyr His Ser Tyr Cys Thr Val Ser Asp Tyr Asn Asn Gln Asp Leu
145                 150                 155                 160

Val Glu Asp Cys Trp Leu Gly Asp Asn Thr Val Gln Leu Val Asp Leu
                165                 170                 175

Lys Thr Glu Asp Ser Ala Val Ala Asp Gly Tyr Asn Thr Trp Ile Ser
            180                 185                 190

Gln Leu Val Ala Asn Tyr Ser Ile Asp Gly Leu Arg Ile Asp Thr Ala
        195                 200                 205

Lys His Val Asp Lys Ala Phe Tyr Pro Pro Phe Glu Ala Ala Ala Gly
    210                 215                 220

Val Phe Ser Thr Gly Glu Val Tyr Asp Gly Asn Pro Ser Tyr Thr Cys
225                 230                 235                 240

Asp Tyr Gln Asn Tyr Met Asp Ser Val Leu Asn Tyr Pro Val Tyr Tyr
                245                 250                 255

Pro Leu Val Arg Ala Phe Thr Ser Ser Gly Ser Ile Ser Asp Leu
            260                 265                 270

Val Asn Met Val Ser Thr Leu Lys Ser Gly Cys Lys Asp Thr Thr Leu
        275                 280                 285
```

```
Leu Gly Thr Phe Ser Glu Asn His Asp Ile Thr Arg Phe Ala Ala Ile
            290                 295                 300

Thr Ser Asp Phe Ser Gln Ala Lys Asn Val Ile Ala Phe Asn Ile Leu
305                 310                 315                 320

Ala Asp Gly Ile Pro Ile Ile Tyr Gln Gly Gln Glu Gln His Tyr Ser
                325                 330                 335

Gly Ala Glu Asp Pro Asp Asn Arg Glu Ala Val Trp Leu Ser Gly Tyr
            340                 345                 350

Asn Thr Gly Ala Glu Leu Tyr Thr Phe Thr Ala Ala Val Asn Ala Ile
        355                 360                 365

Arg Asn Arg Ala Ile Ala Asp Asp Ala Asp Tyr Leu Thr Tyr Gln Asn
370                 375                 380

Trp Val Ile Tyr Ser Asp Thr Thr Thr Ile Ala Met Arg Lys Gly Phe
385                 390                 395                 400

Asp Gly Tyr Gln Ile Ile Thr Val Leu Ser Asn Lys Gly Ala Asn Gly
                405                 410                 415

Asp Ala Tyr Thr Leu Asn Leu Ser Asn Thr Gly Trp Thr Ser Gly Thr
            420                 425                 430

Glu Val Val Glu Val Leu Thr Cys Ser Arg Val Thr Val Thr Ser Ser
        435                 440                 445

Gly Thr Val Thr Val Pro Met Ser Asn Gly Leu Pro Arg Val Tyr Tyr
450                 455                 460

Pro Ala Ala Arg Leu Ser Gly Ser Gly Ile Cys Asp Leu
465                 470                 475

<210> SEQ ID NO 39
<211> LENGTH: 1323
<212> TYPE: DNA
<213> ORGANISM: Nectria sp.
<220> FEATURE:
<221> NAME/KEY: CDS
<222> LOCATION: (1)..(1323)

<400> SEQUENCE: 39 gcc gac acc cag tca tgg aag tct cgc aac atc tat ttt gcc ctg aca      48
Ala Asp Thr Gln Ser Trp Lys Ser Arg Asn Ile Tyr Phe Ala Leu Thr
1               5                   10                  15 gac cgc atc gcc aag agc agc tcg gac act ggc ggc agt gcc tgt ggc      96
Asp Arg Ile Ala Lys Ser Ser Ser Asp Thr Gly Gly Ser Ala Cys Gly
            20                  25                  30 aat ctt gga aac tac tgt ggt ggc acg ttc cag ggt ctg cag tcc aag     144
Asn Leu Gly Asn Tyr Cys Gly Gly Thr Phe Gln Gly Leu Gln Ser Lys
        35                  40                  45 ctt gac tac atc aag ggc atg ggc ttt gac gcc atc tgg ata aca ccc     192
Leu Asp Tyr Ile Lys Gly Met Gly Phe Asp Ala Ile Trp Ile Thr Pro
    50                  55                  60 gtc gtg gag aac act gat ggt ggc tac cat gga tac tgg gcc aag gac     240
Val Val Glu Asn Thr Asp Gly Gly Tyr His Gly Tyr Trp Ala Lys Asp
65                  70                  75                  80 ctg tac tct gtc aat tcc aag tac gga act gcg gat gac ttg aag agc     288
Leu Tyr Ser Val Asn Ser Lys Tyr Gly Thr Ala Asp Asp Leu Lys Ser
                85                  90                  95 ttg gtc agc gca gcg cat ggc aag ggc atc tac atg atg gtt gac gtt     336
Leu Val Ser Ala Ala His Gly Lys Gly Ile Tyr Met Met Val Asp Val
            100                 105                 110 gtt gcc aac cac atg ggt agt ggc gac atc agc aca tac aac ccc ccg     384
Val Ala Asn His Met Gly Ser Gly Asp Ile Ser Thr Tyr Asn Pro Pro
        115                 120                 125 ccg ctc aac caa gcg agc gcc tac cac ggc tcg tgt gat atc aac tac     432
```

```
         Pro Leu Asn Gln Ala Ser Ala Tyr His Gly Ser Cys Asp Ile Asn Tyr
             130                 135                 140 gac gac cag aac agc att gag cag tgc agg att tcc ggt ctt ccg gat        480
Asp Asp Gln Asn Ser Ile Glu Gln Cys Arg Ile Ser Gly Leu Pro Asp
145                 150                 155                 160 atc aac acg gag gat aac tca gtg aaa gcg gcc ctg cac gaa tgg gtc        528
Ile Asn Thr Glu Asp Asn Ser Val Lys Ala Ala Leu His Glu Trp Val
                165                 170                 175 gga tgg ctt gtc aag gag tac aac ttt gac ggt gtc cgc atc gac aca        576
Gly Trp Leu Val Lys Glu Tyr Asn Phe Asp Gly Val Arg Ile Asp Thr
            180                 185                 190 gtc aag cat gtg tcg aag agt ttc tgg cct gat ttt gcc tgg tcc tct        624
Val Lys His Val Ser Lys Ser Phe Trp Pro Asp Phe Ala Trp Ser Ser
        195                 200                 205 gga gta tac acc att ggc gag gtc ttc aat ggc gac ccc gat tac cta        672
Gly Val Tyr Thr Ile Gly Glu Val Phe Asn Gly Asp Pro Asp Tyr Leu
    210                 215                 220 gcc gaa tat gac aac ctc atg gga ggt ctc ctc aac tat gcc gtc tac        720
Ala Glu Tyr Asp Asn Leu Met Gly Gly Leu Leu Asn Tyr Ala Val Tyr
225                 230                 235                 240 tac ccc atg aac cgg ttc tac cag cag gag gga tcc tcg aag gac ctt        768
Tyr Pro Met Asn Arg Phe Tyr Gln Gln Glu Gly Ser Ser Lys Asp Leu
                245                 250                 255 gcc agc atg atc gac acg gtt agt gcc aaa ttc tcc gat ccg acg acc        816
Ala Ser Met Ile Asp Thr Val Ser Ala Lys Phe Ser Asp Pro Thr Thr
            260                 265                 270 ctg gga aca ttc ctc gac aac cat gac aac cct cga tgg ctc aac aag        864
Leu Gly Thr Phe Leu Asp Asn His Asp Asn Pro Arg Trp Leu Asn Lys
        275                 280                 285 aag aac gac gtc act ctg ttc aag aac gcc ctg gct ttc gtc atc ctc        912
Lys Asn Asp Val Thr Leu Phe Lys Asn Ala Leu Ala Phe Val Ile Leu
    290                 295                 300 gct cgt ggc att ccc atc gtc tac tac ggt agt gag cag ggc tac ggc        960
Ala Arg Gly Ile Pro Ile Val Tyr Tyr Gly Ser Glu Gln Gly Tyr Gly
305                 310                 315                 320 ggt ggt gct gat ccg cag aac cgg gag gac ctt tgg cga agc ggc ttc       1008
Gly Gly Ala Asp Pro Gln Asn Arg Glu Asp Leu Trp Arg Ser Gly Phe
                325                 330                 335 aac acc aac tct gac ctg tac ggt gcc atc tcg cgc ctc tct gct gcg       1056
Asn Thr Asn Ser Asp Leu Tyr Gly Ala Ile Ser Arg Leu Ser Ala Ala
            340                 345                 350 cga tca gca cat ggt ggc ctc ccc aac aac gac cac gtc cac ctc aac       1104
Arg Ser Ala His Gly Gly Leu Pro Asn Asn Asp His Val His Leu Asn
        355                 360                 365 acc gaa gac gga ata tac gcc tgg agc cga gcg ggc ggc gat ctc gtc       1152
Thr Glu Asp Gly Ile Tyr Ala Trp Ser Arg Ala Gly Gly Asp Leu Val
    370                 375                 380 gtc ttc act tcc aac cgc ggc tcc agc ctc aac ggc gag tac tgc ttc       1200
Val Phe Thr Ser Asn Arg Gly Ser Ser Leu Asn Gly Glu Tyr Cys Phe
385                 390                 395                 400 act act gat cgt tca aat gga tcg tgg aac gat gtt ttt ggc agc ggg       1248
Thr Thr Asp Arg Ser Asn Gly Ser Trp Asn Asp Val Phe Gly Ser Gly
                405                 410                 415 tcc tat act tcg gat ggt aac ggc agg gtc tgt gtc aat gtg aac aat       1296
Ser Tyr Thr Ser Asp Gly Asn Gly Arg Val Cys Val Asn Val Asn Asn
            420                 425                 430 ggc cag ccg gtg gtc ctg agt gct aaa                                   1323
Gly Gln Pro Val Val Leu Ser Ala Lys
        435                 440
```

```
<210> SEQ ID NO 40
<211> LENGTH: 441
<212> TYPE: PRT
<213> ORGANISM: Nectria sp.

<400> SEQUENCE: 40

Ala Asp Thr Gln Ser Trp Lys Ser Arg Asn Ile Tyr Phe Ala Leu Thr
1               5                   10                  15

Asp Arg Ile Ala Lys Ser Ser Asp Thr Gly Gly Ser Ala Cys Gly
            20                  25                  30

Asn Leu Gly Asn Tyr Cys Gly Gly Thr Phe Gln Gly Leu Gln Ser Lys
        35                  40                  45

Leu Asp Tyr Ile Lys Gly Met Gly Phe Asp Ala Ile Trp Ile Thr Pro
    50                  55                  60

Val Val Glu Asn Thr Asp Gly Gly Tyr His Gly Tyr Trp Ala Lys Asp
65                  70                  75                  80

Leu Tyr Ser Val Asn Ser Lys Tyr Gly Thr Ala Asp Asp Leu Lys Ser
                85                  90                  95

Leu Val Ser Ala Ala His Gly Lys Gly Ile Tyr Met Met Val Asp Val
            100                 105                 110

Val Ala Asn His Met Gly Ser Gly Asp Ile Ser Thr Tyr Asn Pro Pro
        115                 120                 125

Pro Leu Asn Gln Ala Ser Ala Tyr His Gly Ser Cys Asp Ile Asn Tyr
    130                 135                 140

Asp Asp Gln Asn Ser Ile Glu Gln Cys Arg Ile Ser Gly Leu Pro Asp
145                 150                 155                 160

Ile Asn Thr Glu Asp Asn Ser Val Lys Ala Ala Leu His Glu Trp Val
                165                 170                 175

Gly Trp Leu Val Lys Glu Tyr Asn Phe Asp Gly Val Arg Ile Asp Thr
            180                 185                 190

Val Lys His Val Ser Lys Ser Phe Trp Pro Asp Phe Ala Trp Ser Ser
        195                 200                 205

Gly Val Tyr Thr Ile Gly Glu Val Phe Asn Gly Asp Pro Asp Tyr Leu
    210                 215                 220

Ala Glu Tyr Asp Asn Leu Met Gly Gly Leu Leu Asn Tyr Ala Val Tyr
225                 230                 235                 240

Tyr Pro Met Asn Arg Phe Tyr Gln Gln Glu Gly Ser Ser Lys Asp Leu
                245                 250                 255

Ala Ser Met Ile Asp Thr Val Ser Ala Lys Phe Ser Asp Pro Thr Thr
            260                 265                 270

Leu Gly Thr Phe Leu Asp Asn His Asp Asn Pro Arg Trp Leu Asn Lys
        275                 280                 285

Lys Asn Asp Val Thr Leu Phe Lys Asn Ala Leu Ala Phe Val Ile Leu
    290                 295                 300

Ala Arg Gly Ile Pro Ile Val Tyr Tyr Gly Ser Glu Gln Gly Tyr Gly
305                 310                 315                 320

Gly Gly Ala Asp Pro Gln Asn Arg Glu Asp Leu Trp Arg Ser Gly Phe
                325                 330                 335

Asn Thr Asn Ser Asp Leu Tyr Gly Ala Ile Ser Arg Leu Ser Ala Ala
            340                 345                 350

Arg Ser Ala His Gly Gly Leu Pro Asn Asn Asp His Val His Leu Asn
        355                 360                 365

Thr Glu Asp Gly Ile Tyr Ala Trp Ser Arg Ala Gly Gly Asp Leu Val
    370                 375                 380

Val Phe Thr Ser Asn Arg Gly Ser Ser Leu Asn Gly Glu Tyr Cys Phe
```

```
                385                 390                 395                 400
Thr Thr Asp Arg Ser Asn Gly Ser Trp Asn Asp Val Phe Gly Ser Gly
                    405                 410                 415
Ser Tyr Thr Ser Asp Gly Asn Gly Arg Val Cys Val Asn Val Asn Asn
                    420                 425                 430
Gly Gln Pro Val Val Leu Ser Ala Lys
                    435                 440

<210> SEQ ID NO 41
<211> LENGTH: 1347
<212> TYPE: DNA
<213> ORGANISM: Gliocladium sp.
<220> FEATURE:
<221> NAME/KEY: CDS
<222> LOCATION: (1)..(1347)

<400> SEQUENCE: 41 gcc act act gcc aca tgg aag tcc cgc aga att tac ttt gcg ctg acg      48
Ala Asp Thr Ala Thr Trp Lys Ser Arg Arg Ile Tyr Phe Ala Leu Thr
1               5                   10                  15 gac cgc att gcc cgg agc agc acc gac gcc ggt gga ggc tcg tgc agc      96
Asp Arg Ile Ala Arg Ser Ser Thr Asp Ala Gly Gly Gly Ser Cys Ser
            20                  25                  30 gac ctt ggt agc tac tgc ggt ggc acg ttc cag ggc ctg cag gcc aag     144
Asp Leu Gly Ser Tyr Cys Gly Gly Thr Phe Gln Gly Leu Gln Ala Lys
        35                  40                  45 ctc gac tac atc cag ggt ctg ggt ttt gac gct gtc tgg atc acg cca     192
Leu Asp Tyr Ile Gln Gly Leu Gly Phe Asp Ala Val Trp Ile Thr Pro
    50                  55                  60 gtc gtc gcg aac agc gat ggc ggc tac cac ggc tac tgg gcc gag gac     240
Val Val Ala Asn Ser Asp Gly Gly Tyr His Gly Tyr Trp Ala Glu Asp
65                  70                  75                  80 ctc ttc gcc att aac ccc aag tac gga tct gcc gac gac ctg aag agc     288
Leu Phe Ala Ile Asn Pro Lys Tyr Gly Ser Ala Asp Asp Leu Lys Ser
                85                  90                  95 ctc gtc aat gcg agc cac gaa aaa ggc atg ttt gtt atg gtc gac gtc     336
Leu Val Asn Ala Ser His Glu Lys Gly Met Phe Val Met Val Asp Val
            100                 105                 110 gtc gcc aac cat atg ggc cgc gcc aac atc gcc gac gac aag ccc tcg     384
Val Ala Asn His Met Gly Arg Ala Asn Ile Ala Asp Asp Lys Pro Ser
        115                 120                 125 ccc ctc gat cag gag acg tcc tac cac gcg cca tgc acc atc gac tac     432
Pro Leu Asp Gln Glu Thr Ser Tyr His Ala Pro Cys Thr Ile Asp Tyr
    130                 135                 140 tcc aac cag acg agt gtc gag aac tgc cgc atc gcc gcc gat ttg ccc     480
Ser Asn Gln Thr Ser Val Glu Asn Cys Arg Ile Ala Ala Asp Leu Pro
145                 150                 155                 160 gat gtg gac acg cat gac ccg gcc att cgg cag ctc tat cag tcg tgg     528
Asp Val Asp Thr His Asp Pro Ala Ile Arg Gln Leu Tyr Gln Ser Trp
                165                 170                 175 gtg cac tgg ctc gtg tct gag ttc agc ttc gac ggc gtg cgc att gac     576
Val His Trp Leu Val Ser Glu Phe Ser Phe Asp Gly Val Arg Ile Asp
            180                 185                 190 acg gtc aag cac gtc gaa aag gac ttc tgg ccg ccg ttt gct acc gcc     624
Thr Val Lys His Val Glu Lys Asp Phe Trp Pro Pro Phe Ala Thr Ala
        195                 200                 205 gcc ggt gtc tac acc atc ggc gag gtc ttc cat ggc gat ccg gcc tac     672
Ala Gly Val Tyr Thr Ile Gly Glu Val Phe His Gly Asp Pro Ala Tyr
    210                 215                 220 gtc gct agc tac gcg gga ctc atg tcg ggg ctg ctc aac tat gct gtc     720
Val Ala Ser Tyr Ala Gly Leu Met Ser Gly Leu Leu Asn Tyr Ala Val
```

```
                     225                 230                 235                 240 tac ttc ccg ctc acc cgt ttt tac cag cag cgc ggt tcg tct cag gat        768
Tyr Phe Pro Leu Thr Arg Phe Tyr Gln Gln Arg Gly Ser Ser Gln Asp
                245                 250                 255 ctc gtc gat atg cac gat gca gtc agc tcc aag ttc ccc gac ccg gcc        816
Leu Val Asp Met His Asp Ala Val Ser Ser Lys Phe Pro Asp Pro Ala
                260                 265                 270 gcc ctg ggc acc ttt ctc gac aac cac gac aat ccg cgg tgg cta ggc        864
Ala Leu Gly Thr Phe Leu Asp Asn His Asp Asn Pro Arg Trp Leu Gly
            275                 280                 285 cag aac ggc gac acc gtc ctg cta cgc aac gct ttg acg tac gta ctg        912
Gln Asn Gly Asp Thr Val Leu Leu Arg Asn Ala Leu Thr Tyr Val Leu
        290                 295                 300 ctt gcg cgg ggg gtc ccc atc ctg tac tac ggc acc gag cag ggg ttc        960
Leu Ala Arg Gly Val Pro Ile Leu Tyr Tyr Gly Thr Glu Gln Gly Phe
305                 310                 315                 320 tca ggt ggt gcc gac ccg gcc aac cgg gag gac ctc tgg cgc agc ggc       1008
Ser Gly Gly Ala Asp Pro Ala Asn Arg Glu Asp Leu Trp Arg Ser Gly
                325                 330                 335 ttc gcc act gac ggg cct ctc tac aag ttc ata gcc acc atg gcg ggt       1056
Phe Ala Thr Asp Gly Pro Leu Tyr Lys Phe Ile Ala Thr Met Ala Gly
                340                 345                 350 gta cgc agg tct gct ggt ggg ctg ccg gat aac gac cat gtg cat ctt       1104
Val Arg Arg Ser Ala Gly Gly Leu Pro Asp Asn Asp His Val His Leu
            355                 360                 365 tac gtt gcg ggt gat gcg tac gcg tgg agc cgc gcc ggc ggt aag gtc       1152
Tyr Val Ala Gly Asp Ala Tyr Ala Trp Ser Arg Ala Gly Gly Lys Val
        370                 375                 380 atc gca ctg acg agc aac ggc ggg agc ggc aag tcg cag cgc tac tgc       1200
Ile Ala Leu Thr Ser Asn Gly Gly Ser Gly Lys Ser Gln Arg Tyr Cys
385                 390                 395                 400 ttc aac tca cag agg cag aac gga gcg tgg aag ggg gcc tta gac ggc       1248
Phe Asn Ser Gln Arg Gln Asn Gly Ala Trp Lys Gly Ala Leu Asp Gly
                405                 410                 415 aag acg tac gcg tcg gat gga aga ggg cag ctt tgt gcg gac gtg acc       1296
Lys Thr Tyr Ala Ser Asp Gly Arg Gly Gln Leu Cys Ala Asp Val Thr
                420                 425                 430 aag ggg gag ccc gtc gtc ctt gtc gct tcc acc gcc atg cca ggg gaa       1344
Lys Gly Glu Pro Val Val Leu Val Ala Ser Thr Ala Met Pro Gly Glu
            435                 440                 445 ttg                                                                   1347
Leu

<210> SEQ ID NO 42
<211> LENGTH: 449
<212> TYPE: PRT
<213> ORGANISM: Gliocladium sp.

<400> SEQUENCE: 42

Ala Asp Thr Ala Thr Trp Lys Ser Arg Arg Ile Tyr Phe Ala Leu Thr
1               5                   10                  15

Asp Arg Ile Ala Arg Ser Ser Thr Asp Ala Gly Gly Gly Ser Cys Ser
            20                  25                  30

Asp Leu Gly Ser Tyr Cys Gly Gly Thr Phe Gln Gly Leu Gln Ala Lys
        35                  40                  45

Leu Asp Tyr Ile Gln Gly Leu Gly Phe Asp Ala Val Trp Ile Thr Pro
    50                  55                  60

Val Val Ala Asn Ser Asp Gly Gly Tyr His Gly Tyr Trp Ala Glu Asp
65                  70                  75                  80
```

```
Leu Phe Ala Ile Asn Pro Lys Tyr Gly Ser Ala Asp Leu Lys Ser
                85                  90                  95

Leu Val Asn Ala Ser His Glu Lys Gly Met Phe Val Met Val Asp Val
            100                 105                 110

Val Ala Asn His Met Gly Arg Ala Asn Ile Ala Asp Asp Lys Pro Ser
            115                 120                 125

Pro Leu Asp Gln Glu Thr Ser Tyr His Ala Pro Cys Thr Ile Asp Tyr
        130                 135                 140

Ser Asn Gln Thr Ser Val Glu Asn Cys Arg Ile Ala Ala Asp Leu Pro
145                 150                 155                 160

Asp Val Asp Thr His Asp Pro Ala Ile Arg Gln Leu Tyr Gln Ser Trp
                165                 170                 175

Val His Trp Leu Val Ser Glu Phe Ser Phe Asp Gly Val Arg Ile Asp
                180                 185                 190

Thr Val Lys His Val Glu Lys Asp Phe Trp Pro Pro Phe Ala Thr Ala
            195                 200                 205

Ala Gly Val Tyr Thr Ile Gly Glu Val Phe His Gly Asp Pro Ala Tyr
        210                 215                 220

Val Ala Ser Tyr Ala Gly Leu Met Ser Gly Leu Leu Asn Tyr Ala Val
225                 230                 235                 240

Tyr Phe Pro Leu Thr Arg Phe Tyr Gln Gln Arg Gly Ser Ser Gln Asp
                245                 250                 255

Leu Val Asp Met His Asp Ala Val Ser Ser Lys Phe Pro Asp Pro Ala
                260                 265                 270

Ala Leu Gly Thr Phe Leu Asp Asn His Asp Asn Pro Arg Trp Leu Gly
            275                 280                 285

Gln Asn Gly Asp Thr Val Leu Leu Arg Asn Ala Leu Thr Tyr Val Leu
        290                 295                 300

Leu Ala Arg Gly Val Pro Ile Leu Tyr Tyr Gly Thr Glu Gln Gly Phe
305                 310                 315                 320

Ser Gly Gly Ala Asp Pro Ala Asn Arg Glu Asp Leu Trp Arg Ser Gly
                325                 330                 335

Phe Ala Thr Asp Gly Pro Leu Tyr Lys Phe Ile Ala Thr Met Ala Gly
                340                 345                 350

Val Arg Arg Ser Ala Gly Gly Leu Pro Asp Asn Asp His Val His Leu
            355                 360                 365

Tyr Val Ala Gly Asp Ala Tyr Ala Trp Ser Arg Ala Gly Gly Lys Val
        370                 375                 380

Ile Ala Leu Thr Ser Asn Gly Ser Gly Lys Ser Gln Arg Tyr Cys
385                 390                 395                 400

Phe Asn Ser Gln Arg Gln Asn Gly Ala Trp Lys Gly Ala Leu Asp Gly
                405                 410                 415

Lys Thr Tyr Ala Ser Asp Gly Arg Gly Gln Leu Cys Ala Asp Val Thr
                420                 425                 430

Lys Gly Glu Pro Val Val Leu Val Ala Ser Thr Ala Met Pro Gly Glu
            435                 440                 445

Leu

<210> SEQ ID NO 43
<211> LENGTH: 1317
<212> TYPE: DNA
<213> ORGANISM: Streptomyces thermocyaneoviolaceus
<220> FEATURE:
<221> NAME/KEY: CDS
<222> LOCATION: (1)..(1317)
```

<400> SEQUENCE: 43

```
gct ccc gcc acc gtc gcc cac gcc tcc ccg ccc ggc acc aag gac gtc       48
Ala Pro Ala Thr Val Ala His Ala Ser Pro Pro Gly Thr Lys Asp Val
1               5                   10                  15 acc gcc gtc ctc ttc gag tgg gac tac gcc tcc gtg gcc aag gag tgc       96
Thr Ala Val Leu Phe Glu Trp Asp Tyr Ala Ser Val Ala Lys Glu Cys
            20                  25                  30 acc agc acc ctc ggc ccg gcc ggc tac ggc tac gtg cag gtc tcc ccg      144
Thr Ser Thr Leu Gly Pro Ala Gly Tyr Gly Tyr Val Gln Val Ser Pro
        35                  40                  45 ccc gcc gag cac atc cag ggc tcc cag tgg tgg acg tcg tac cag ccg      192
Pro Ala Glu His Ile Gln Gly Ser Gln Trp Trp Thr Ser Tyr Gln Pro
    50                  55                  60 gtg agc tac aag atc gcc ggc cgg ctc ggc gac cgt gcc gcc ttc cga      240
Val Ser Tyr Lys Ile Ala Gly Arg Leu Gly Asp Arg Ala Ala Phe Arg
65                  70                  75                  80 tcc atg gtg aac acc tgc cac gcc gcc ggg gtg aag gtg gtc gtc gac      288
Ser Met Val Asn Thr Cys His Ala Ala Gly Val Lys Val Val Val Asp
                85                  90                  95 acg gtg atc aac cac atg tcg gcc ggc agc ggc acc ggc acc gga ggc      336
Thr Val Ile Asn His Met Ser Ala Gly Ser Gly Thr Gly Thr Gly Gly
            100                 105                 110 tcg tcg tac acg aag tac gac tac ccg ggg ctg tac tcg gcc ccg gac      384
Ser Ser Tyr Thr Lys Tyr Asp Tyr Pro Gly Leu Tyr Ser Ala Pro Asp
        115                 120                 125 ttc gac gac tgc acc gcg gag atc acc gac tac cag gac cgc tgg aac      432
Phe Asp Asp Cys Thr Ala Glu Ile Thr Asp Tyr Gln Asp Arg Trp Asn
    130                 135                 140 gtc cag cac tgc gaa ctg gtg ggc ctc gcc gac ctc gac acc ggt gag      480
Val Gln His Cys Glu Leu Val Gly Leu Ala Asp Leu Asp Thr Gly Glu
145                 150                 155                 160 gag tac gtg cga cag acg atc gcc ggc tac atg aac gac ctg ctc tcc      528
Glu Tyr Val Arg Gln Thr Ile Ala Gly Tyr Met Asn Asp Leu Leu Ser
                165                 170                 175 ctc ggc gtc gac ggc ttc cgc atc gac gcg gcc aag cac atc ccc gcc      576
Leu Gly Val Asp Gly Phe Arg Ile Asp Ala Ala Lys His Ile Pro Ala
            180                 185                 190 gag gac ctc gcg aac atc aag tcc cgc ctg agc aac ccg aac gcc tac      624
Glu Asp Leu Ala Asn Ile Lys Ser Arg Leu Ser Asn Pro Asn Ala Tyr
        195                 200                 205 tgg aag cag gag gtc atc tac ggc gcc ggc gaa gcc gtc cag ccc ggc      672
Trp Lys Gln Glu Val Ile Tyr Gly Ala Gly Glu Ala Val Gln Pro Gly
    210                 215                 220 gag tac acc ggc acc ggc gac gtc cag gag ttc cgc tac gcc tac gac      720
Glu Tyr Thr Gly Thr Gly Asp Val Gln Glu Phe Arg Tyr Ala Tyr Asp
225                 230                 235                 240 ctc aag cgg gtc ttc acc cag gag cac ctc gcc tac ctg aag aac tac      768
Leu Lys Arg Val Phe Thr Gln Glu His Leu Ala Tyr Leu Lys Asn Tyr
                245                 250                 255 ggc gag gac tgg ggc tac ctg agc agc acg acg gcc ggg gtc ttc gtc      816
Gly Glu Asp Trp Gly Tyr Leu Ser Ser Thr Thr Ala Gly Val Phe Val
            260                 265                 270 gac aac cac gac acc gag cgc aac ggc tcc acg ctg aac tac aag aac      864
Asp Asn His Asp Thr Glu Arg Asn Gly Ser Thr Leu Asn Tyr Lys Asn
        275                 280                 285 gac gcc acc tac acc ctg gcc aac gtc ttc atg ctg gcc tgg ccc tac      912
Asp Ala Thr Tyr Thr Leu Ala Asn Val Phe Met Leu Ala Trp Pro Tyr
    290                 295                 300 ggc gcc ccc gac atc aat tcc ggc tac gag tgg tcc gac ccg gac gcc      960
Gly Ala Pro Asp Ile Asn Ser Gly Tyr Glu Trp Ser Asp Pro Asp Ala
```

```
                305                 310                 315                 320
ggc ccg ccc gac ggc ggc cac gtc gac gcc tgc tgg cag aac ggc tgg         1008
Gly Pro Pro Asp Gly Gly His Val Asp Ala Cys Trp Gln Asn Gly Trp
                325                 330                 335 aag tgc cag cac aag tgg ccc gag atc gcc tcc atg gtc gcc ttc cgc         1056
Lys Cys Gln His Lys Trp Pro Glu Ile Ala Ser Met Val Ala Phe Arg
            340                 345                 350 aac gcc acc cgc ggc gag ccg gtc acc gac tgg tgg gac gac ggc gcg         1104
Asn Ala Thr Arg Gly Glu Pro Val Thr Asp Trp Trp Asp Asp Gly Ala
        355                 360                 365 gac gcc atc gcc ttc ggc cgg ggc agc aag ggc ttc gtg gcc atc aac         1152
Asp Ala Ile Ala Phe Gly Arg Gly Ser Lys Gly Phe Val Ala Ile Asn
    370                 375                 380 cac gag tcc gcc acc gtc cag cgc acc tac cag acc tcc ctg ccc gcc         1200
His Glu Ser Ala Thr Val Gln Arg Thr Tyr Gln Thr Ser Leu Pro Ala
385                 390                 395                 400 ggc acc tac tgc gac gtg cag agc aac acc acg gtg acg gtg gac tcc         1248
Gly Thr Tyr Cys Asp Val Gln Ser Asn Thr Thr Val Thr Val Asp Ser
                405                 410                 415 gcc gga cgg ttc acc gcc gcg ctc ggc ccg gac acg gca ctg gcc ctg         1296
Ala Gly Arg Phe Thr Ala Ala Leu Gly Pro Asp Thr Ala Leu Ala Leu
            420                 425                 430 cac acc ggc agg acg agc tgc                                             1317
His Thr Gly Arg Thr Ser Cys
        435

<210> SEQ ID NO 44
<211> LENGTH: 439
<212> TYPE: PRT
<213> ORGANISM: Streptomyces thermocyaneoviolaceus

<400> SEQUENCE: 44

Ala Pro Ala Thr Val Ala His Ala Ser Pro Gly Thr Lys Asp Val
1               5                   10                  15

Thr Ala Val Leu Phe Glu Trp Asp Tyr Ala Ser Val Ala Lys Glu Cys
            20                  25                  30

Thr Ser Thr Leu Gly Pro Ala Gly Tyr Gly Tyr Val Gln Val Ser Pro
        35                  40                  45

Pro Ala Glu His Ile Gln Gly Ser Gln Trp Trp Thr Ser Tyr Gln Pro
    50                  55                  60

Val Ser Tyr Lys Ile Ala Gly Arg Leu Gly Asp Arg Ala Ala Phe Arg
65                  70                  75                  80

Ser Met Val Asn Thr Cys His Ala Ala Gly Val Lys Val Val Val Asp
                85                  90                  95

Thr Val Ile Asn His Met Ser Ala Gly Ser Gly Thr Gly Thr Gly Gly
            100                 105                 110

Ser Ser Tyr Thr Lys Tyr Asp Tyr Pro Gly Leu Tyr Ser Ala Pro Asp
        115                 120                 125

Phe Asp Asp Cys Thr Ala Glu Ile Thr Asp Tyr Gln Asp Arg Trp Asn
    130                 135                 140

Val Gln His Cys Glu Leu Val Gly Leu Ala Asp Leu Asp Thr Gly Glu
145                 150                 155                 160

Glu Tyr Val Arg Gln Thr Ile Ala Gly Tyr Met Asn Asp Leu Leu Ser
                165                 170                 175

Leu Gly Val Asp Gly Phe Arg Ile Asp Ala Ala Lys His Ile Pro Ala
            180                 185                 190

Glu Asp Leu Ala Asn Ile Lys Ser Arg Leu Ser Asn Pro Asn Ala Tyr
        195                 200                 205
```

```
Trp Lys Gln Glu Val Ile Tyr Gly Ala Gly Glu Ala Val Gln Pro Gly
    210                 215                 220
Glu Tyr Thr Gly Thr Gly Asp Val Gln Glu Phe Arg Tyr Ala Tyr Asp
225                 230                 235                 240
Leu Lys Arg Val Phe Thr Gln Glu His Leu Ala Tyr Leu Lys Asn Tyr
                245                 250                 255
Gly Glu Asp Trp Gly Tyr Leu Ser Ser Thr Thr Ala Gly Val Phe Val
            260                 265                 270
Asp Asn His Asp Thr Glu Arg Asn Gly Ser Thr Leu Asn Tyr Lys Asn
        275                 280                 285
Asp Ala Thr Tyr Thr Leu Ala Asn Val Phe Met Leu Ala Trp Pro Tyr
    290                 295                 300
Gly Ala Pro Asp Ile Asn Ser Gly Tyr Glu Trp Ser Asp Pro Asp Ala
305                 310                 315                 320
Gly Pro Pro Asp Gly Gly His Val Asp Ala Cys Trp Gln Asn Gly Trp
                325                 330                 335
Lys Cys Gln His Lys Trp Pro Glu Ile Ala Ser Met Val Ala Phe Arg
            340                 345                 350
Asn Ala Thr Arg Gly Glu Pro Val Thr Asp Trp Trp Asp Asp Gly Ala
        355                 360                 365
Asp Ala Ile Ala Phe Gly Arg Gly Ser Lys Gly Phe Val Ala Ile Asn
    370                 375                 380
His Glu Ser Ala Thr Val Gln Arg Thr Tyr Gln Thr Ser Leu Pro Ala
385                 390                 395                 400
Gly Thr Tyr Cys Asp Val Gln Ser Asn Thr Thr Val Thr Val Asp Ser
                405                 410                 415
Ala Gly Arg Phe Thr Ala Ala Leu Gly Pro Asp Thr Ala Leu Ala Leu
            420                 425                 430
His Thr Gly Arg Thr Ser Cys
            435

<210> SEQ ID NO 45
<211> LENGTH: 18
<212> TYPE: DNA
<213> ORGANISM: Pachykytospora papayracea
<220> FEATURE:
<221> NAME/KEY: CDS
<222> LOCATION: (1)..(18)

<400> SEQUENCE: 45 ggt aac gcg ggc ccc agc                                            18
Gly Asn Ala Gly Pro Ser
1               5

<210> SEQ ID NO 46
<211> LENGTH: 6
<212> TYPE: PRT
<213> ORGANISM: Pachykytospora papayracea

<400> SEQUENCE: 46

Gly Asn Ala Gly Pro Ser
1               5

<210> SEQ ID NO 47
<211> LENGTH: 21
<212> TYPE: DNA
<213> ORGANISM: Trametes cingulata
<220> FEATURE:
<221> NAME/KEY: CDS
<222> LOCATION: (1)..(21)
```

```
<400> SEQUENCE: 47 ggg agt ggc ggt gct ggg act                                          21
Gly Ser Gly Gly Ala Gly Thr
1               5

<210> SEQ ID NO 48
<211> LENGTH: 7
<212> TYPE: PRT
<213> ORGANISM: Trametes cingulata

<400> SEQUENCE: 48

Gly Ser Gly Gly Ala Gly Thr
1               5

<210> SEQ ID NO 49
<211> LENGTH: 33
<212> TYPE: DNA
<213> ORGANISM: Leucopaxillus gigantus
<220> FEATURE:
<221> NAME/KEY: CDS
<222> LOCATION: (1)..(33)

<400> SEQUENCE: 49 ggg ggt ggt tca aac cca ggt ggt gga ggg tcg                          33
Gly Gly Gly Ser Asn Pro Gly Gly Gly Gly Ser
1               5                   10

<210> SEQ ID NO 50
<211> LENGTH: 11
<212> TYPE: PRT
<213> ORGANISM: Leucopaxillus gigantus

<400> SEQUENCE: 50

Gly Gly Gly Ser Asn Pro Gly Gly Gly Gly Ser
1               5                   10

<210> SEQ ID NO 51
<211> LENGTH: 801
<212> TYPE: DNA
<213> ORGANISM: Trichophaea saccata
<220> FEATURE:
<221> NAME/KEY: CDS
<222> LOCATION: (1)..(801)

<400> SEQUENCE: 51 tcg cca gtt cat cag aac acc aaa cga tct acc caa gtg tcg ttg atc     48
Ser Pro Val His Gln Asn Thr Lys Arg Ser Thr Gln Val Ser Leu Ile
1               5                   10                  15 agc tat acg ttt tct aac aat att ctc tct gga tcc atc agc att caa     96
Ser Tyr Thr Phe Ser Asn Asn Ile Leu Ser Gly Ser Ile Ser Ile Gln
            20                  25                  30 aac att gct tac gcc aaa acg gtc agc gtt acc tat gcc att ggg agc    144
Asn Ile Ala Tyr Ala Lys Thr Val Ser Val Thr Tyr Ala Ile Gly Ser
        35                  40                  45 tct tgg agc tcc tct cag gtg ata agc gct gcc tac tcc aca ggt cct    192
Ser Trp Ser Ser Ser Gln Val Ile Ser Ala Ala Tyr Ser Thr Gly Pro
    50                  55                  60 gat agc acc ggt tat gaa gtc tgg acg ttt agc ggc aca gca acg ggg    240
Asp Ser Thr Gly Tyr Glu Val Trp Thr Phe Ser Gly Thr Ala Thr Gly
65                  70                  75                  80 gca act cag ttc tac att gcg tat act gtc tca ggg acc acc tac tac    288
Ala Thr Gln Phe Tyr Ile Ala Tyr Thr Val Ser Gly Thr Thr Tyr Tyr
                85                  90                  95 gat cct gga aat ggc atc aat tac acg atc ggc acg ggt tcg tcc act    336
```

```
Asp Pro Gly Asn Gly Ile Asn Tyr Thr Ile Gly Thr Gly Ser Ser Thr
                100                 105                 110 act tcc agc aca tct gcc act tcg aca acc aaa agt tcc acc act tcc      384
Thr Ser Ser Thr Ser Ala Thr Ser Thr Thr Lys Ser Ser Thr Thr Ser
            115                 120                 125 acg agc act gcg act agc aca agc gtg gcg acc agc agt ctc cct gct      432
Thr Ser Thr Ala Thr Ser Thr Ser Val Ala Thr Ser Ser Leu Pro Ala
        130                 135                 140 atc att tca tcc agt att cct tct gag gcg gca gcc acc gcg ctt tct      480
Ile Ile Ser Ser Ser Ile Pro Ser Glu Ala Ala Ala Thr Ala Leu Ser
145                 150                 155                 160 gga tgc aat act tgg gat ggt ttt gac aac tgc caa act agt ggc gtg      528
Gly Cys Asn Thr Trp Asp Gly Phe Asp Asn Cys Gln Thr Ser Gly Val
                165                 170                 175 tac gac ttt gtg gcc agt gcc gaa aac cgc aga tgg cag acg ccc ccg      576
Tyr Asp Phe Val Ala Ser Ala Glu Asn Arg Arg Trp Gln Thr Pro Pro
            180                 185                 190 gac ggc gat cct gcc tat gtc aat acg ttc caa gac tac cga gat ctc      624
Asp Gly Asp Pro Ala Tyr Val Asn Thr Phe Gln Asp Tyr Arg Asp Leu
        195                 200                 205 att ggc tac gcc gat atc cag tac agc cct tca cga acc tcc gcc gtt      672
Ile Gly Tyr Ala Asp Ile Gln Tyr Ser Pro Ser Arg Thr Ser Ala Val
210                 215                 220 gtg act gtc aat gct gct tcg cgg acc ggc gag act ttg acc tac aaa      720
Val Thr Val Asn Ala Ala Ser Arg Thr Gly Glu Thr Leu Thr Tyr Lys
225                 230                 235                 240 ttt ggg gga att act cag acg tct aac gcg tac acc gtg agc agc tcg      768
Phe Gly Gly Ile Thr Gln Thr Ser Asn Ala Tyr Thr Val Ser Ser Ser
                245                 250                 255 ttt atc gga acc ctg gca atc aca gtc acc agt                          801
Phe Ile Gly Thr Leu Ala Ile Thr Val Thr Ser
            260                 265

<210> SEQ ID NO 52
<211> LENGTH: 267
<212> TYPE: PRT
<213> ORGANISM: Trichophaea saccata

<400> SEQUENCE: 52

Ser Pro Val His Gln Asn Thr Lys Arg Ser Thr Gln Val Ser Leu Ile
1               5                   10                  15

Ser Tyr Thr Phe Ser Asn Asn Ile Leu Ser Gly Ser Ile Ser Ile Gln
                20                  25                  30

Asn Ile Ala Tyr Ala Lys Thr Val Ser Val Thr Tyr Ala Ile Gly Ser
            35                  40                  45

Ser Trp Ser Ser Ser Gln Val Ile Ser Ala Ala Tyr Ser Thr Gly Pro
        50                  55                  60

Asp Ser Thr Gly Tyr Glu Val Trp Thr Phe Ser Gly Thr Ala Thr Gly
65                  70                  75                  80

Ala Thr Gln Phe Tyr Ile Ala Tyr Thr Val Ser Gly Thr Thr Tyr Tyr
                85                  90                  95

Asp Pro Gly Asn Gly Ile Asn Tyr Thr Ile Gly Thr Gly Ser Ser Thr
            100                 105                 110

Thr Ser Ser Thr Ser Ala Thr Ser Thr Thr Lys Ser Ser Thr Thr Ser
        115                 120                 125

Thr Ser Thr Ala Thr Ser Thr Ser Val Ala Thr Ser Ser Leu Pro Ala
    130                 135                 140

Ile Ile Ser Ser Ser Ile Pro Ser Glu Ala Ala Ala Thr Ala Leu Ser
145                 150                 155                 160
```

```
Gly Cys Asn Thr Trp Asp Gly Phe Asp Asn Cys Gln Thr Ser Gly Val
            165                 170                 175

Tyr Asp Phe Val Ala Ser Ala Glu Asn Arg Arg Trp Gln Thr Pro Pro
            180                 185                 190

Asp Gly Asp Pro Ala Tyr Val Asn Thr Phe Gln Asp Tyr Arg Asp Leu
            195                 200                 205

Ile Gly Tyr Ala Asp Ile Gln Tyr Ser Pro Ser Arg Thr Ser Ala Val
            210                 215                 220

Val Thr Val Asn Ala Ala Ser Arg Thr Gly Glu Thr Leu Thr Tyr Lys
225                 230                 235                 240

Phe Gly Gly Ile Thr Gln Thr Ser Asn Ala Tyr Thr Val Ser Ser Ser
            245                 250                 255

Phe Ile Gly Thr Leu Ala Ile Thr Val Thr Ser
            260                 265
```

<210> SEQ ID NO 53
<211> LENGTH: 75
<212> TYPE: DNA
<213> ORGANISM: Subulispora provurvata
<220> FEATURE:
<221> NAME/KEY: CDS
<222> LOCATION: (1)..(75)

<400> SEQUENCE: 53

```
gga ggc agc ggt acc act acc acg acc act acc agc act gca ggc aca    48
Gly Gly Ser Gly Thr Thr Thr Thr Thr Thr Ser Thr Ala Gly Thr
1               5                   10                  15 tcg cca act tcg aca gcg tgc tcc tcg                                 75
Ser Pro Thr Ser Thr Ala Cys Ser Ser
            20                  25
```

<210> SEQ ID NO 54
<211> LENGTH: 25
<212> TYPE: PRT
<213> ORGANISM: Subulispora provurvata

<400> SEQUENCE: 54

```
Gly Gly Ser Gly Thr Thr Thr Thr Thr Thr Ser Thr Ala Gly Thr
1               5                   10                  15

Ser Pro Thr Ser Thr Ala Cys Ser Ser
            20                  25
```

<210> SEQ ID NO 55
<211> LENGTH: 45
<212> TYPE: DNA
<213> ORGANISM: Valsaria rubricosa
<220> FEATURE:
<221> NAME/KEY: CDS
<222> LOCATION: (1)..(45)

<400> SEQUENCE: 55

```
acg acc acc aag acg tcc acc tcg acc gcc tcc tgc gcc gcc acc         45
Thr Thr Thr Lys Thr Ser Thr Ser Thr Ala Ser Cys Ala Ala Thr
1               5                   10                  15
```

<210> SEQ ID NO 56
<211> LENGTH: 15
<212> TYPE: PRT
<213> ORGANISM: Valsaria rubricosa

<400> SEQUENCE: 56

```
Thr Thr Thr Lys Thr Ser Thr Ser Thr Ala Ser Cys Ala Ala Thr
1               5                   10                  15
```

<210> SEQ ID NO 57
<211> LENGTH: 78
<212> TYPE: DNA
<213> ORGANISM: Acremonium sp.
<220> FEATURE:
<221> NAME/KEY: CDS
<222> LOCATION: (1)..(78)

<400> SEQUENCE: 57

```
acc agc aca gcg ctg ccg acg tca agc ttg act gca gca tca gcc acg      48
Thr Ser Thr Ala Leu Pro Thr Ser Ser Leu Thr Ala Ala Ser Ala Thr
1               5                   10                  15 acg act gcc tca gcc tgc tcc ttg tcg gcg                              78
Thr Thr Ala Ser Ala Cys Ser Leu Ser Ala
            20                  25
```

<210> SEQ ID NO 58
<211> LENGTH: 26
<212> TYPE: PRT
<213> ORGANISM: Acremonium sp.

<400> SEQUENCE: 58

```
Thr Ser Thr Ala Leu Pro Thr Ser Ser Leu Thr Ala Ala Ser Ala Thr
1               5                   10                  15

Thr Thr Ala Ser Ala Cys Ser Leu Ser Ala
            20                  25
```

<210> SEQ ID NO 59
<211> LENGTH: 45
<212> TYPE: DNA
<213> ORGANISM: Meripilus giganteus
<220> FEATURE:
<221> NAME/KEY: CDS
<222> LOCATION: (1)..(45)

<400> SEQUENCE: 59

```
gcc acg ccc acc tcc gcc cct agt act aca cca acc agc ggc act         45
Ala Thr Pro Thr Ser Ala Pro Ser Thr Thr Pro Thr Ser Gly Thr
1               5                   10                  15
```

<210> SEQ ID NO 60
<211> LENGTH: 15
<212> TYPE: PRT
<213> ORGANISM: Meripilus giganteus

<400> SEQUENCE: 60

```
Ala Thr Pro Thr Ser Ala Pro Ser Thr Thr Pro Thr Ser Gly Thr
1               5                   10                  15
```

<210> SEQ ID NO 61
<211> LENGTH: 9
<212> TYPE: DNA
<213> ORGANISM: Bacillus flavothermus
<220> FEATURE:
<221> NAME/KEY: CDS
<222> LOCATION: (1)..(9)

<400> SEQUENCE: 61

```
aac gcc aca                                                          9
Asn Ala Thr
1
```

<210> SEQ ID NO 62
<211> LENGTH: 3
<212> TYPE: PRT
<213> ORGANISM: Bacillus flavothermus

```
<220> FEATURE:
<221> NAME/KEY: PEPTIDE
<222> LOCATION: (1)..(3)

<400> SEQUENCE: 62

Asn Ala Thr
1

<210> SEQ ID NO 63
<211> LENGTH: 186
<212> TYPE: DNA
<213> ORGANISM: Bacillus flavothermus
<220> FEATURE:
<221> NAME/KEY: CDS
<222> LOCATION: (1)..(186)

<400> SEQUENCE: 63 act gag aag ttg gca ggt agc aag atc tgt agt ggc agt gga aat acc      48
Thr Glu Lys Leu Ala Gly Ser Lys Ile Cys Ser Gly Ser Gly Asn Thr
1               5                   10                  15 aca aca acg act acc gcg gct act agc acc agt aaa gcc act aca tca      96
Thr Thr Thr Thr Thr Ala Ala Thr Ser Thr Ser Lys Ala Thr Thr Ser
            20                  25                  30 agt tcc agc tct tcg gcg gct gca aca act agt tca tct tgt act gct     144
Ser Ser Ser Ser Ser Ala Ala Ala Thr Thr Ser Ser Ser Cys Thr Ala
        35                  40                  45 aca tct act acg ctg cct ata aca ttt gaa gag ctc gta acg             186
Thr Ser Thr Thr Leu Pro Ile Thr Phe Glu Glu Leu Val Thr
    50                  55                  60

<210> SEQ ID NO 64
<211> LENGTH: 62
<212> TYPE: PRT
<213> ORGANISM: Bacillus flavothermus

<400> SEQUENCE: 64

Thr Glu Lys Leu Ala Gly Ser Lys Ile Cys Ser Gly Ser Gly Asn Thr
1               5                   10                  15

Thr Thr Thr Thr Thr Ala Ala Thr Ser Thr Ser Lys Ala Thr Thr Ser
            20                  25                  30

Ser Ser Ser Ser Ser Ala Ala Ala Thr Thr Ser Ser Ser Cys Thr Ala
        35                  40                  45

Thr Ser Thr Thr Leu Pro Ile Thr Phe Glu Glu Leu Val Thr
    50                  55                  60

<210> SEQ ID NO 65
<211> LENGTH: 105
<212> TYPE: DNA
<213> ORGANISM: Bacillus flavothermus
<220> FEATURE:
<221> NAME/KEY: CDS
<222> LOCATION: (1)..(105)

<400> SEQUENCE: 65 act gag aag ttg gca ggt agc aag atc tgt agt aca tac act acg gcc      48
Thr Glu Lys Leu Ala Gly Ser Lys Ile Cys Ser Thr Tyr Thr Thr Ala
1               5                   10                  15 tca cca cct ccg gga ggt tgt tct gcg gga act gta gtt ttc gat gtg     96
Ser Pro Pro Pro Gly Gly Cys Ser Ala Gly Thr Val Val Phe Asp Val
            20                  25                  30 tat gtc caa                                                         105
Tyr Val Gln
        35
```

```
<210> SEQ ID NO 66
<211> LENGTH: 35
<212> TYPE: PRT
<213> ORGANISM: Bacillus flavothermus

<400> SEQUENCE: 66

Thr Glu Lys Leu Ala Gly Ser Lys Ile Cys Ser Thr Tyr Thr Thr Ala
1               5                   10                  15

Ser Pro Pro Gly Gly Cys Ser Ala Gly Thr Val Val Phe Asp Val
            20                  25                  30

Tyr Val Gln
        35

<210> SEQ ID NO 67
<211> LENGTH: 33
<212> TYPE: DNA
<213> ORGANISM: Athelia rolfsii
<220> FEATURE:
<221> NAME/KEY: CDS
<222> LOCATION: (1)..(33)

<400> SEQUENCE: 67 ggt gct aca agc ccg ggt ggc tcc tcg ggt agt                     33
Gly Ala Thr Ser Pro Gly Gly Ser Ser Gly Ser
1               5                   10

<210> SEQ ID NO 68
<211> LENGTH: 11
<212> TYPE: PRT
<213> ORGANISM: Athelia rolfsii

<400> SEQUENCE: 68

Gly Ala Thr Ser Pro Gly Gly Ser Ser Gly Ser
1               5                   10

<210> SEQ ID NO 69
<211> LENGTH: 93
<212> TYPE: DNA
<213> ORGANISM: Aspergillus kawachii
<220> FEATURE:
<221> NAME/KEY: CDS
<222> LOCATION: (1)..(93)

<400> SEQUENCE: 69 aca acc acg acc aca act gct gct gct act agt aca tcc aaa gcc acc  48
Thr Thr Thr Thr Thr Thr Ala Ala Ala Thr Ser Thr Ser Lys Ala Thr
1               5                   10                  15 acc tcc tct tct tct tct tct gct gct gct act act tct tca tca       93
Thr Ser Ser Ser Ser Ser Ser Ala Ala Ala Thr Thr Ser Ser Ser
            20                  25                  30

<210> SEQ ID NO 70
<211> LENGTH: 31
<212> TYPE: PRT
<213> ORGANISM: Aspergillus kawachii

<400> SEQUENCE: 70

Thr Thr Thr Thr Thr Thr Ala Ala Ala Thr Ser Thr Ser Lys Ala Thr
1               5                   10                  15

Thr Ser Ser Ser Ser Ser Ser Ala Ala Ala Thr Thr Ser Ser Ser
            20                  25                  30

<210> SEQ ID NO 71
<211> LENGTH: 111
<212> TYPE: DNA
<213> ORGANISM: Aspergillus niger
```

```
<220> FEATURE:
<221> NAME/KEY: CDS
<222> LOCATION: (1)..(111)

<400> SEQUENCE: 71 act ggc ggc acc act acg acg gct acc ccc act gga tcc ggc agc gtg      48
Thr Gly Gly Thr Thr Thr Thr Ala Thr Pro Thr Gly Ser Gly Ser Val
1               5                   10                  15 acc tcg acc agc aag acc acc gcg act gct agc aag acc agc acc agt      96
Thr Ser Thr Ser Lys Thr Thr Ala Thr Ala Ser Lys Thr Ser Thr Ser
            20                  25                  30 acg tca tca acc tcc                                                  111
Thr Ser Ser Thr Ser
        35

<210> SEQ ID NO 72
<211> LENGTH: 37
<212> TYPE: PRT
<213> ORGANISM: Aspergillus niger

<400> SEQUENCE: 72

Thr Gly Gly Thr Thr Thr Thr Ala Thr Pro Thr Gly Ser Gly Ser Val
1               5                   10                  15

Thr Ser Thr Ser Lys Thr Thr Ala Thr Ala Ser Lys Thr Ser Thr Ser
            20                  25                  30

Thr Ser Ser Thr Ser
        35

<210> SEQ ID NO 73
<211> LENGTH: 96
<212> TYPE: DNA
<213> ORGANISM: Coniochaeta sp.
<220> FEATURE:
<221> NAME/KEY: CDS
<222> LOCATION: (1)..(96)

<400> SEQUENCE: 73 acc acg aca aca gct acg acg aag acg agc acg acg ctg acc acg tcg      48
Thr Thr Thr Thr Ala Thr Thr Lys Thr Ser Thr Thr Leu Thr Thr Ser
1               5                   10                  15 acg aca aca acc tcc aca aag aca agt agt tct tgc acc gcc acc gcg      96
Thr Thr Thr Thr Ser Thr Lys Thr Ser Ser Ser Cys Thr Ala Thr Ala
            20                  25                  30

<210> SEQ ID NO 74
<211> LENGTH: 32
<212> TYPE: PRT
<213> ORGANISM: Coniochaeta sp.

<400> SEQUENCE: 74

Thr Thr Thr Thr Ala Thr Thr Lys Thr Ser Thr Thr Leu Thr Thr Ser
1               5                   10                  15

Thr Thr Thr Thr Ser Thr Lys Thr Ser Ser Ser Cys Thr Ala Thr Ala
            20                  25                  30

<210> SEQ ID NO 75
<211> LENGTH: 285
<212> TYPE: DNA
<213> ORGANISM: Pachykytospora papayracea
<220> FEATURE:
<221> NAME/KEY: CDS
<222> LOCATION: (1)..(285)

<400> SEQUENCE: 75 gtg aag gtg acg ttc aac gtc cag gct acg act acc ttc ggc gag aac      48
```

```
Val Lys Val Thr Phe Asn Val Gln Ala Thr Thr Thr Phe Gly Glu Asn
1               5                   10                  15 atc tac atc acc ggt aac acc gct gcg ctc cag aac tgg tcg ccc gat    96
Ile Tyr Ile Thr Gly Asn Thr Ala Ala Leu Gln Asn Trp Ser Pro Asp
            20                  25                  30 aac gcg ctc ctc ctc tct gct gac aag tac ccc acc tgg agc atc acg   144
Asn Ala Leu Leu Leu Ser Ala Asp Lys Tyr Pro Thr Trp Ser Ile Thr
        35                  40                  45 ctc gac ctc ccc gcg aac acc gtc gtc gag tac aaa tac atc cgc aag   192
Leu Asp Leu Pro Ala Asn Thr Val Val Glu Tyr Lys Tyr Ile Arg Lys
    50                  55                  60 ttc aac ggc cag gtc acc tgg gaa tcg gac ccc aac aac tcg atc acg   240
Phe Asn Gly Gln Val Thr Trp Glu Ser Asp Pro Asn Asn Ser Ile Thr
65                  70                  75                  80 acg ccc gcc gac ggt acc ttc acc cag aac gac acc tgg cgg tga       285
Thr Pro Ala Asp Gly Thr Phe Thr Gln Asn Asp Thr Trp Arg
                85                  90

<210> SEQ ID NO 76
<211> LENGTH: 94
<212> TYPE: PRT
<213> ORGANISM: Pachykytospora papayracea

<400> SEQUENCE: 76

Val Lys Val Thr Phe Asn Val Gln Ala Thr Thr Thr Phe Gly Glu Asn
1               5                   10                  15

Ile Tyr Ile Thr Gly Asn Thr Ala Ala Leu Gln Asn Trp Ser Pro Asp
            20                  25                  30

Asn Ala Leu Leu Leu Ser Ala Asp Lys Tyr Pro Thr Trp Ser Ile Thr
        35                  40                  45

Leu Asp Leu Pro Ala Asn Thr Val Val Glu Tyr Lys Tyr Ile Arg Lys
    50                  55                  60

Phe Asn Gly Gln Val Thr Trp Glu Ser Asp Pro Asn Asn Ser Ile Thr
65                  70                  75                  80

Thr Pro Ala Asp Gly Thr Phe Thr Gln Asn Asp Thr Trp Arg
                85                  90

<210> SEQ ID NO 77
<211> LENGTH: 285
<212> TYPE: DNA
<213> ORGANISM: Trametes cingulata
<220> FEATURE:
<221> NAME/KEY: CDS
<222> LOCATION: (1)..(285)

<400> SEQUENCE: 77 gtg gcc gtc acc ttc aac gtg cag gcg acc acc gtg ttc ggc gag aac    48
Val Ala Val Thr Phe Asn Val Gln Ala Thr Thr Val Phe Gly Glu Asn
1               5                   10                  15 att tac atc aca ggc tcg gtc ccc gct ctc cag aac tgg tcg ccc gac    96
Ile Tyr Ile Thr Gly Ser Val Pro Ala Leu Gln Asn Trp Ser Pro Asp
            20                  25                  30 aac gcg ctc atc ctc tca gcg gcc aac tac ccc act tgg agc atc acc   144
Asn Ala Leu Ile Leu Ser Ala Ala Asn Tyr Pro Thr Trp Ser Ile Thr
        35                  40                  45 gtg aac ctg ccg gcg agc acg acg atc gag tac aag tac att cgc aag   192
Val Asn Leu Pro Ala Ser Thr Thr Ile Glu Tyr Lys Tyr Ile Arg Lys
    50                  55                  60 ttc aac ggc gcg gtc acc tgg gag tcc gac ccg aac aac tcg atc acg   240
Phe Asn Gly Ala Val Thr Trp Glu Ser Asp Pro Asn Asn Ser Ile Thr
65                  70                  75                  80
```

```
acg ccc gcg agc ggc acg ttc acc cag aac gac acc tgg cgg tag        285
Thr Pro Ala Ser Gly Thr Phe Thr Gln Asn Asp Thr Trp Arg
                85                  90

<210> SEQ ID NO 78
<211> LENGTH: 94
<212> TYPE: PRT
<213> ORGANISM: Trametes cingulata

<400> SEQUENCE: 78

Val Ala Val Thr Phe Asn Val Gln Ala Thr Thr Val Phe Gly Glu Asn
1               5                   10                  15

Ile Tyr Ile Thr Gly Ser Val Pro Ala Leu Gln Asn Trp Ser Pro Asp
            20                  25                  30

Asn Ala Leu Ile Leu Ser Ala Ala Asn Tyr Pro Thr Trp Ser Ile Thr
        35                  40                  45

Val Asn Leu Pro Ala Ser Thr Thr Ile Glu Tyr Lys Tyr Ile Arg Lys
    50                  55                  60

Phe Asn Gly Ala Val Thr Trp Glu Ser Asp Pro Asn Asn Ser Ile Thr
65                  70                  75                  80

Thr Pro Ala Ser Gly Thr Phe Thr Gln Asn Asp Thr Trp Arg
                85                  90

<210> SEQ ID NO 79
<211> LENGTH: 285
<212> TYPE: DNA
<213> ORGANISM: Leucopaxillus gigantus
<220> FEATURE:
<221> NAME/KEY: CDS
<222> LOCATION: (1)..(285)

<400> SEQUENCE: 79 gtc tct gtt acg ttc aat gtt caa gct aca acc acc ttt ggt gaa aac     48
Val Ser Val Thr Phe Asn Val Gln Ala Thr Thr Thr Phe Gly Glu Asn
1               5                   10                  15 att ttt ttg acc ggc tcg atc aac gag tta gct aac tgg tct cct gat    96
Ile Phe Leu Thr Gly Ser Ile Asn Glu Leu Ala Asn Trp Ser Pro Asp
            20                  25                  30 aat gct ctc gcc ctc tct gcg gcc aat tat ccc acc tgg agc agt acc   144
Asn Ala Leu Ala Leu Ser Ala Ala Asn Tyr Pro Thr Trp Ser Ser Thr
        35                  40                  45 gtc aac gtt ccc gca agc act acg atc caa tac aag ttt atc cgt aaa   192
Val Asn Val Pro Ala Ser Thr Thr Ile Gln Tyr Lys Phe Ile Arg Lys
    50                  55                  60 ttc aac gga gcc atc acc tgg gag tcc gac ccg aat agg cag atc aca   240
Phe Asn Gly Ala Ile Thr Trp Glu Ser Asp Pro Asn Arg Gln Ile Thr
65                  70                  75                  80 acg ccg tct tcg gga agt ttt gtc cag aat gac tcg tgg aag tag       285
Thr Pro Ser Ser Gly Ser Phe Val Gln Asn Asp Ser Trp Lys
                85                  90

<210> SEQ ID NO 80
<211> LENGTH: 94
<212> TYPE: PRT
<213> ORGANISM: Leucopaxillus gigantus

<400> SEQUENCE: 80

Val Ser Val Thr Phe Asn Val Gln Ala Thr Thr Thr Phe Gly Glu Asn
1               5                   10                  15

Ile Phe Leu Thr Gly Ser Ile Asn Glu Leu Ala Asn Trp Ser Pro Asp
            20                  25                  30

Asn Ala Leu Ala Leu Ser Ala Ala Asn Tyr Pro Thr Trp Ser Ser Thr
```

```
                35                  40                  45
Val Asn Val Pro Ala Ser Thr Thr Ile Gln Tyr Lys Phe Ile Arg Lys
 50                  55                  60

Phe Asn Gly Ala Ile Thr Trp Glu Ser Asp Pro Asn Arg Gln Ile Thr
 65                  70                  75                  80

Thr Pro Ser Ser Gly Ser Phe Val Gln Asn Asp Ser Trp Lys
                 85                  90

<210> SEQ ID NO 81
<211> LENGTH: 306
<212> TYPE: DNA
<213> ORGANISM: Subulispora provurvata
<220> FEATURE:
<221> NAME/KEY: CDS
<222> LOCATION: (1)..(306)

<400> SEQUENCE: 81 gtc ccc gta acg ttc cgc gaa acg gtc aca act acg gta gga cag aca      48
Val Pro Val Thr Phe Arg Glu Thr Val Thr Thr Thr Val Gly Gln Thr
 1               5                  10                  15 atc aag ata tct ggc gac gtc tcc gcc ctt gga aac tgg gat acg gac      96
Ile Lys Ile Ser Gly Asp Val Ser Ala Leu Gly Asn Trp Asp Thr Asp
                20                  25                  30 gac gcg gtg gcc ctg agc gcc gcg agc tac acg tcc agc aac ccc gtg     144
Asp Ala Val Ala Leu Ser Ala Ala Ser Tyr Thr Ser Ser Asn Pro Val
            35                  40                  45 tgg gac gtg acc gtc agc ttc gcc ccc ggc acc gtc atc gag tac aag     192
Trp Asp Val Thr Val Ser Phe Ala Pro Gly Thr Val Ile Glu Tyr Lys
         50                  55                  60 tac atc aac gtg gcg agc ggc ggc gcc gtg acc tgg gag gcc gac ccg     240
Tyr Ile Asn Val Ala Ser Gly Gly Ala Val Thr Trp Glu Ala Asp Pro
 65                  70                  75                  80 aac cac acc tac acg gtg cct tcg tcc tgc gcc acc gcc gtg gtc tcc     288
Asn His Thr Tyr Thr Val Pro Ser Ser Cys Ala Thr Ala Val Val Ser
                 85                  90                  95 aac acc tgg cag acg tga                                             306
Asn Thr Trp Gln Thr
            100

<210> SEQ ID NO 82
<211> LENGTH: 101
<212> TYPE: PRT
<213> ORGANISM: Subulispora provurvata

<400> SEQUENCE: 82

Val Pro Val Thr Phe Arg Glu Thr Val Thr Thr Thr Val Gly Gln Thr
 1               5                  10                  15

Ile Lys Ile Ser Gly Asp Val Ser Ala Leu Gly Asn Trp Asp Thr Asp
                20                  25                  30

Asp Ala Val Ala Leu Ser Ala Ala Ser Tyr Thr Ser Ser Asn Pro Val
            35                  40                  45

Trp Asp Val Thr Val Ser Phe Ala Pro Gly Thr Val Ile Glu Tyr Lys
         50                  55                  60

Tyr Ile Asn Val Ala Ser Gly Gly Ala Val Thr Trp Glu Ala Asp Pro
 65                  70                  75                  80

Asn His Thr Tyr Thr Val Pro Ser Ser Cys Ala Thr Ala Val Val Ser
                 85                  90                  95

Asn Thr Trp Gln Thr
            100
```

```
<210> SEQ ID NO 83
<211> LENGTH: 303
<212> TYPE: DNA
<213> ORGANISM: Valsaria rubricosa
<220> FEATURE:
<221> NAME/KEY: CDS
<222> LOCATION: (1)..(303)

<400> SEQUENCE: 83 gtc gcc gtc acc ttc aac gag ctc gtc acc acg aac tac ggc gac acc        48
Val Ala Val Thr Phe Asn Glu Leu Val Thr Thr Asn Tyr Gly Asp Thr
1               5                   10                  15 atc cgc ctg acg ggc tcc atc tcc cag ctc agc agc tgg agc gca acc        96
Ile Arg Leu Thr Gly Ser Ile Ser Gln Leu Ser Ser Trp Ser Ala Thr
            20                  25                  30 tcc ggg ctg gcc ctg agc gcg tcc gcg tac acg tcc agc aac ccg ctc       144
Ser Gly Leu Ala Leu Ser Ala Ser Ala Tyr Thr Ser Ser Asn Pro Leu
        35                  40                  45 tgg agc gtg acg gtc agc ctg ccg gcc ggc acg tcg ttc gag tac aag       192
Trp Ser Val Thr Val Ser Leu Pro Ala Gly Thr Ser Phe Glu Tyr Lys
    50                  55                  60 ttc gtc cgc atc acg agc gac ggc acc gtg acc tgg gaa tcg gac ccg       240
Phe Val Arg Ile Thr Ser Asp Gly Thr Val Thr Trp Glu Ser Asp Pro
65                  70                  75                  80 aac cgc agc tac acc gtc ccg acg tgc gcg agc acc gcg acg atc agc       288
Asn Arg Ser Tyr Thr Val Pro Thr Cys Ala Ser Thr Ala Thr Ile Ser
                85                  90                  95 aat acc tgg cgg tga                                                    303
Asn Thr Trp Arg
            100

<210> SEQ ID NO 84
<211> LENGTH: 100
<212> TYPE: PRT
<213> ORGANISM: Valsaria rubricosa

<400> SEQUENCE: 84

Val Ala Val Thr Phe Asn Glu Leu Val Thr Thr Asn Tyr Gly Asp Thr
1               5                   10                  15

Ile Arg Leu Thr Gly Ser Ile Ser Gln Leu Ser Ser Trp Ser Ala Thr
            20                  25                  30

Ser Gly Leu Ala Leu Ser Ala Ser Ala Tyr Thr Ser Ser Asn Pro Leu
        35                  40                  45

Trp Ser Val Thr Val Ser Leu Pro Ala Gly Thr Ser Phe Glu Tyr Lys
    50                  55                  60

Phe Val Arg Ile Thr Ser Asp Gly Thr Val Thr Trp Glu Ser Asp Pro
65                  70                  75                  80

Asn Arg Ser Tyr Thr Val Pro Thr Cys Ala Ser Thr Ala Thr Ile Ser
                85                  90                  95

Asn Thr Trp Arg
            100

<210> SEQ ID NO 85
<211> LENGTH: 294
<212> TYPE: DNA
<213> ORGANISM: Acremonium sp.
<220> FEATURE:
<221> NAME/KEY: CDS
<222> LOCATION: (1)..(294)

<400> SEQUENCE: 85 gtg aac atc acc ttc aac gag ctc gtc acc acg gtg tgg ggg gac acg        48
Val Asn Ile Thr Phe Asn Glu Leu Val Thr Thr Val Trp Gly Asp Thr
```

```
                1               5                   10                  15
atc aag ctg gcc ggc aac ata tcc gct ctc ggc agc tgg agc cca agc        96
Ile Lys Leu Ala Gly Asn Ile Ser Ala Leu Gly Ser Trp Ser Pro Ser
            20                  25                  30 agc gcc ttg aca ctg agc gca tcg cag tat tca caa agc aat ccg ctc       144
Ser Ala Leu Thr Leu Ser Ala Ser Gln Tyr Ser Gln Ser Asn Pro Leu
        35                  40                  45 tgg tcg gtc tca acc ctg ctc ggt cca gga acg gtg atc gag tac aag       192
Trp Ser Val Ser Thr Leu Leu Gly Pro Gly Thr Val Ile Glu Tyr Lys
    50                  55                  60 ttt atc aag gtc agc gcc tcc ggg act gta acg tgg gag tca gac ccg       240
Phe Ile Lys Val Ser Ala Ser Gly Thr Val Thr Trp Glu Ser Asp Pro
65                  70                  75                  80 aac cgc gtc tac act gtg ccc tgc gca act gcg acg gtc agt agc act       288
Asn Arg Val Tyr Thr Val Pro Cys Ala Thr Ala Thr Val Ser Ser Thr
                85                  90                  95 tgg cga                                                               294
Trp Arg
```

<210> SEQ ID NO 86
<211> LENGTH: 98
<212> TYPE: PRT
<213> ORGANISM: Acremonium sp.

<400> SEQUENCE: 86

```
Val Asn Ile Thr Phe Asn Glu Leu Val Thr Thr Val Trp Gly Asp Thr
1               5                   10                  15

Ile Lys Leu Ala Gly Asn Ile Ser Ala Leu Gly Ser Trp Ser Pro Ser
            20                  25                  30

Ser Ala Leu Thr Leu Ser Ala Ser Gln Tyr Ser Gln Ser Asn Pro Leu
        35                  40                  45

Trp Ser Val Ser Thr Leu Leu Gly Pro Gly Thr Val Ile Glu Tyr Lys
    50                  55                  60

Phe Ile Lys Val Ser Ala Ser Gly Thr Val Thr Trp Glu Ser Asp Pro
65                  70                  75                  80

Asn Arg Val Tyr Thr Val Pro Cys Ala Thr Ala Thr Val Ser Ser Thr
                85                  90                  95

Trp Arg
```

<210> SEQ ID NO 87
<211> LENGTH: 285
<212> TYPE: DNA
<213> ORGANISM: Meripilus giganteus
<220> FEATURE:
<221> NAME/KEY: CDS
<222> LOCATION: (1)..(285)

<400> SEQUENCE: 87

```
gtc agc atg acc ttc gct gag cag gcg acg acc acc ttc ggc gag aac        48
Val Ser Met Thr Phe Ala Glu Gln Ala Thr Thr Thr Phe Gly Glu Asn
1               5                   10                  15 atc ttc ctc gtc ggc agt att tcg cag ctc ggg aac tgg aac cca gcc        96
Ile Phe Leu Val Gly Ser Ile Ser Gln Leu Gly Asn Trp Asn Pro Ala
            20                  25                  30 agc gcg atc gcc ctg tcc tct gcg gcg tac cct acg tgg tct gtg tct       144
Ser Ala Ile Ala Leu Ser Ser Ala Ala Tyr Pro Thr Trp Ser Val Ser
        35                  40                  45 gtg aac att ccc gct gga acg acc ttc cag tac aag ttc atc cgc aag       192
Val Asn Ile Pro Ala Gly Thr Thr Phe Gln Tyr Lys Phe Ile Arg Lys
    50                  55                  60
```

```
gag acg gac ggt agc gtc gtc tgg gag tcg gac ccc aac cgc cag gct    240
Glu Thr Asp Gly Ser Val Val Trp Glu Ser Asp Pro Asn Arg Gln Ala
 65                  70                  75                  80 acc gcg ccc gcg tcc ggt acc acc acg ctc acg tcc agc tgg cgg        285
Thr Ala Pro Ala Ser Gly Thr Thr Thr Leu Thr Ser Ser Trp Arg
                 85                  90                  95
```

<210> SEQ ID NO 88
<211> LENGTH: 95
<212> TYPE: PRT
<213> ORGANISM: Meripilus giganteus

<400> SEQUENCE: 88

```
Val Ser Met Thr Phe Ala Glu Gln Ala Thr Thr Thr Phe Gly Glu Asn
 1               5                  10                  15

Ile Phe Leu Val Gly Ser Ile Ser Gln Leu Gly Asn Trp Asn Pro Ala
                20                  25                  30

Ser Ala Ile Ala Leu Ser Ser Ala Ala Tyr Pro Thr Trp Ser Val Ser
                35                  40                  45

Val Asn Ile Pro Ala Gly Thr Thr Phe Gln Tyr Lys Phe Ile Arg Lys
 50                  55                  60

Glu Thr Asp Gly Ser Val Val Trp Glu Ser Asp Pro Asn Arg Gln Ala
 65                  70                  75                  80

Thr Ala Pro Ala Ser Gly Thr Thr Thr Leu Thr Ser Ser Trp Arg
                 85                  90                  95
```

<210> SEQ ID NO 89
<211> LENGTH: 261
<212> TYPE: DNA
<213> ORGANISM: Bacillus flavothermus
<220> FEATURE:
<221> NAME/KEY: CDS
<222> LOCATION: (1)..(261)

<400> SEQUENCE: 89

```
acc gtt tgg gga caa aat gta tac gtt gtc ggg aat att tcg cag ctg    48
Thr Val Trp Gly Gln Asn Val Tyr Val Val Gly Asn Ile Ser Gln Leu
 1               5                  10                  15 ggg aac tgg gat cca gtc cac gca gtt caa atg acg ccg tct tct tat    96
Gly Asn Trp Asp Pro Val His Ala Val Gln Met Thr Pro Ser Ser Tyr
                20                  25                  30 cca aca tgg act gta aca atc cct ctt ctt caa ggg caa aac ata caa    144
Pro Thr Trp Thr Val Thr Ile Pro Leu Leu Gln Gly Gln Asn Ile Gln
             35                  40                  45 ttt aaa ttt atc aaa aaa gat tca gct gga aat gtc att tgg gaa gat    192
Phe Lys Phe Ile Lys Lys Asp Ser Ala Gly Asn Val Ile Trp Glu Asp
 50                  55                  60 ata tcg aat cga aca tac acc gtc cca act gct gca tcc gga gca tat    240
Ile Ser Asn Arg Thr Tyr Thr Val Pro Thr Ala Ala Ser Gly Ala Tyr
 65                  70                  75                  80 aca gcc agc tgg aac gtg ccc                                        261
Thr Ala Ser Trp Asn Val Pro
                 85
```

<210> SEQ ID NO 90
<211> LENGTH: 87
<212> TYPE: PRT
<213> ORGANISM: Bacillus flavothermus

<400> SEQUENCE: 90

```
Thr Val Trp Gly Gln Asn Val Tyr Val Val Gly Asn Ile Ser Gln Leu
 1               5                  10                  15
```

```
Gly Asn Trp Asp Pro Val His Ala Val Gln Met Thr Pro Ser Ser Tyr
            20                  25                  30

Pro Thr Trp Thr Val Thr Ile Pro Leu Leu Gln Gly Gln Asn Ile Gln
                35                  40                  45

Phe Lys Phe Ile Lys Lys Asp Ser Ala Gly Asn Val Ile Trp Glu Asp
 50                  55                  60

Ile Ser Asn Arg Thr Tyr Thr Val Pro Thr Ala Ala Ser Gly Ala Tyr
 65                  70                  75                  80

Thr Ala Ser Trp Asn Val Pro
                85

<210> SEQ ID NO 91
<211> LENGTH: 294
<212> TYPE: DNA
<213> ORGANISM: Athelia rolfsii
<220> FEATURE:
<221> NAME/KEY: CDS
<222> LOCATION: (1)..(294)

<400> SEQUENCE: 91 gtc gag gtc act ttc gac gtt tac gct acc aca gta tat ggc cag aac      48
Val Glu Val Thr Phe Asp Val Tyr Ala Thr Thr Val Tyr Gly Gln Asn
 1               5                  10                  15 atc tat atc acc ggt gat gtg agt gag ctc ggc aac tgg aca ccc gcc      96
Ile Tyr Ile Thr Gly Asp Val Ser Glu Leu Gly Asn Trp Thr Pro Ala
                20                  25                  30 aat ggt gtt gca ctc tct tct gct aac tac ccc acc tgg agt gcc acg     144
Asn Gly Val Ala Leu Ser Ser Ala Asn Tyr Pro Thr Trp Ser Ala Thr
             35                  40                  45 atc gct ctc ccc gct gac acg aca atc cag tac aag tat gtc aac att     192
Ile Ala Leu Pro Ala Asp Thr Thr Ile Gln Tyr Lys Tyr Val Asn Ile
 50                  55                  60 gac ggc agc acc gtc atc tgg gag gat gct atc agc aat cgc gag atc     240
Asp Gly Ser Thr Val Ile Trp Glu Asp Ala Ile Ser Asn Arg Glu Ile
 65                  70                  75                  80 acg acg ccc gcc agc ggc aca tac acc gaa aaa gac act tgg gat gaa     288
Thr Thr Pro Ala Ser Gly Thr Tyr Thr Glu Lys Asp Thr Trp Asp Glu
                 85                  90                  95 tct tag                                                             294
Ser

<210> SEQ ID NO 92
<211> LENGTH: 97
<212> TYPE: PRT
<213> ORGANISM: Athelia rolfsii

<400> SEQUENCE: 92

Val Glu Val Thr Phe Asp Val Tyr Ala Thr Thr Val Tyr Gly Gln Asn
 1               5                  10                  15

Ile Tyr Ile Thr Gly Asp Val Ser Glu Leu Gly Asn Trp Thr Pro Ala
                20                  25                  30

Asn Gly Val Ala Leu Ser Ser Ala Asn Tyr Pro Thr Trp Ser Ala Thr
             35                  40                  45

Ile Ala Leu Pro Ala Asp Thr Thr Ile Gln Tyr Lys Tyr Val Asn Ile
 50                  55                  60

Asp Gly Ser Thr Val Ile Trp Glu Asp Ala Ile Ser Asn Arg Glu Ile
 65                  70                  75                  80

Thr Thr Pro Ala Ser Gly Thr Tyr Thr Glu Lys Asp Thr Trp Asp Glu
                 85                  90                  95

Ser
```

-continued

```
<210> SEQ ID NO 93
<211> LENGTH: 327
<212> TYPE: DNA
<213> ORGANISM: Aspergillus kawachii
<220> FEATURE:
<221> NAME/KEY: CDS
<222> LOCATION: (1)..(327)

<400> SEQUENCE: 93 tgc acc gca aca agc acc acc ctc ccc atc acc ttc gaa gaa ctc gtc    48
Cys Thr Ala Thr Ser Thr Thr Leu Pro Ile Thr Phe Glu Glu Leu Val
1               5                   10                  15 acc act acc tac ggg gaa gaa gtc tac ctc agc gga tct atc tcc cag    96
Thr Thr Thr Tyr Gly Glu Glu Val Tyr Leu Ser Gly Ser Ile Ser Gln
            20                  25                  30 ctc gga gag tgg gat acg agt gac gcg gtg aag ttg tcc gcg gat gat   144
Leu Gly Glu Trp Asp Thr Ser Asp Ala Val Lys Leu Ser Ala Asp Asp
        35                  40                  45 tat acc tcg agt aac ccc gag tgg tct gtt act gtg tcg ttg ccg gtg   192
Tyr Thr Ser Ser Asn Pro Glu Trp Ser Val Thr Val Ser Leu Pro Val
    50                  55                  60 ggg acg acc ttc gag tat aag ttt att aag gtc gat gag ggt gga agt   240
Gly Thr Thr Phe Glu Tyr Lys Phe Ile Lys Val Asp Glu Gly Gly Ser
65                  70                  75                  80 gtg act tgg gaa agt gat ccg aat agg gag tat act gtg cct gaa tgt   288
Val Thr Trp Glu Ser Asp Pro Asn Arg Glu Tyr Thr Val Pro Glu Cys
                85                  90                  95 ggg aat ggg agt ggg gag acg gtg gtt gat acg tgg agg               327
Gly Asn Gly Ser Gly Glu Thr Val Val Asp Thr Trp Arg
            100                 105

<210> SEQ ID NO 94
<211> LENGTH: 109
<212> TYPE: PRT
<213> ORGANISM: Aspergillus kawachii

<400> SEQUENCE: 94

Cys Thr Ala Thr Ser Thr Thr Leu Pro Ile Thr Phe Glu Glu Leu Val
1               5                   10                  15

Thr Thr Thr Tyr Gly Glu Glu Val Tyr Leu Ser Gly Ser Ile Ser Gln
            20                  25                  30

Leu Gly Glu Trp Asp Thr Ser Asp Ala Val Lys Leu Ser Ala Asp Asp
        35                  40                  45

Tyr Thr Ser Ser Asn Pro Glu Trp Ser Val Thr Val Ser Leu Pro Val
    50                  55                  60

Gly Thr Thr Phe Glu Tyr Lys Phe Ile Lys Val Asp Glu Gly Gly Ser
65                  70                  75                  80

Val Thr Trp Glu Ser Asp Pro Asn Arg Glu Tyr Thr Val Pro Glu Cys
                85                  90                  95

Gly Asn Gly Ser Gly Glu Thr Val Val Asp Thr Trp Arg
            100                 105

<210> SEQ ID NO 95
<211> LENGTH: 324
<212> TYPE: DNA
<213> ORGANISM: Aspergillus niger
<220> FEATURE:
<221> NAME/KEY: CDS
<222> LOCATION: (1)..(324)

<400> SEQUENCE: 95
```

```
tgt acc act ccc acc gcc gtg gct gtg act ttc gat ctg aca gct acc      48
Cys Thr Thr Pro Thr Ala Val Ala Val Thr Phe Asp Leu Thr Ala Thr
1               5                   10                  15 acc acc tac ggc gag aac atc tac ctg gtc gga tcg atc tct cag ctg      96
Thr Thr Tyr Gly Glu Asn Ile Tyr Leu Val Gly Ser Ile Ser Gln Leu
            20                  25                  30 ggt gac tgg gaa acc agc gac ggc ata gct ctg agt gct gac aag tac     144
Gly Asp Trp Glu Thr Ser Asp Gly Ile Ala Leu Ser Ala Asp Lys Tyr
        35                  40                  45 act tcc agc gac ccg ctc tgg tat gtc act gtg act ctg ccg gct ggt     192
Thr Ser Ser Asp Pro Leu Trp Tyr Val Thr Val Thr Leu Pro Ala Gly
    50                  55                  60 gag tcg ttt gag tac aag ttt atc cgc att gag agc gat gac tcc gtg     240
Glu Ser Phe Glu Tyr Lys Phe Ile Arg Ile Glu Ser Asp Asp Ser Val
65                  70                  75                  80 gag tgg gag agt gat ccc aac cga gaa tac acc gtt cct cag gcg tgc     288
Glu Trp Glu Ser Asp Pro Asn Arg Glu Tyr Thr Val Pro Gln Ala Cys
                85                  90                  95 gga acg tcg acc gcg acg gtg act gac acc tgg cgg                     324
Gly Thr Ser Thr Ala Thr Val Thr Asp Thr Trp Arg
            100                 105

<210> SEQ ID NO 96
<211> LENGTH: 108
<212> TYPE: PRT
<213> ORGANISM: Aspergillus niger

<400> SEQUENCE: 96

Cys Thr Thr Pro Thr Ala Val Ala Val Thr Phe Asp Leu Thr Ala Thr
1               5                   10                  15

Thr Thr Tyr Gly Glu Asn Ile Tyr Leu Val Gly Ser Ile Ser Gln Leu
            20                  25                  30

Gly Asp Trp Glu Thr Ser Asp Gly Ile Ala Leu Ser Ala Asp Lys Tyr
        35                  40                  45

Thr Ser Ser Asp Pro Leu Trp Tyr Val Thr Val Thr Leu Pro Ala Gly
    50                  55                  60

Glu Ser Phe Glu Tyr Lys Phe Ile Arg Ile Glu Ser Asp Asp Ser Val
65                  70                  75                  80

Glu Trp Glu Ser Asp Pro Asn Arg Glu Tyr Thr Val Pro Gln Ala Cys
                85                  90                  95

Gly Thr Ser Thr Ala Thr Val Thr Asp Thr Trp Arg
            100                 105

<210> SEQ ID NO 97
<211> LENGTH: 300
<212> TYPE: DNA
<213> ORGANISM: Coniochaeta sp.
<220> FEATURE:
<221> NAME/KEY: CDS
<222> LOCATION: (1)..(300)

<400> SEQUENCE: 97 gta gca atc acc ttc aac gag ctc gtg tcg acc tcc tac ggc gac aca      48
Val Ala Ile Thr Phe Asn Glu Leu Val Ser Thr Ser Tyr Gly Asp Thr
1               5                   10                  15 gtc aag ctc acg ggc aac ata aca gcc ctg ggc agc tgg aac acg gcc      96
Val Lys Leu Thr Gly Asn Ile Thr Ala Leu Gly Ser Trp Asn Thr Ala
            20                  25                  30 aac gcc gtc agc ctc agc gca tcg cag tac aca tct ggt agc ccg ctc     144
Asn Ala Val Ser Leu Ser Ala Ser Gln Tyr Thr Ser Gly Ser Pro Leu
        35                  40                  45
```

-continued

```
tgg tcg ggc acc gtg tct ctg cct ccg ggc gtc ggg gta cag tac aag      192
Trp Ser Gly Thr Val Ser Leu Pro Pro Gly Val Gly Val Gln Tyr Lys
 50                  55                  60 ttc gtc agg gtc ggc agc tcg ggg agc gtg acg tgg gag gcg gac ccg      240
Phe Val Arg Val Gly Ser Ser Gly Ser Val Thr Trp Glu Ala Asp Pro
 65                  70                  75                  80 aac cac act tat tct gtg ccg tgc gcg gct gct act gtc ggt ggg agt      288
Asn His Thr Tyr Ser Val Pro Cys Ala Ala Ala Thr Val Gly Gly Ser
                 85                  90                  95 tgg cag agc tga                                                      300
Trp Gln Ser
```

<210> SEQ ID NO 98
<211> LENGTH: 99
<212> TYPE: PRT
<213> ORGANISM: Coniochaeta sp.

<400> SEQUENCE: 98

```
Val Ala Ile Thr Phe Asn Glu Leu Val Ser Thr Ser Tyr Gly Asp Thr
 1               5                  10                  15

Val Lys Leu Thr Gly Asn Ile Thr Ala Leu Gly Ser Trp Asn Thr Ala
                 20                  25                  30

Asn Ala Val Ser Leu Ser Ala Ser Gln Tyr Thr Ser Gly Ser Pro Leu
             35                  40                  45

Trp Ser Gly Thr Val Ser Leu Pro Pro Gly Val Gly Val Gln Tyr Lys
 50                  55                  60

Phe Val Arg Val Gly Ser Ser Gly Ser Val Thr Trp Glu Ala Asp Pro
 65                  70                  75                  80

Asn His Thr Tyr Ser Val Pro Cys Ala Ala Ala Thr Val Gly Gly Ser
                 85                  90                  95

Trp Gln Ser
```

<210> SEQ ID NO 99
<211> LENGTH: 1761
<212> TYPE: DNA
<213> ORGANISM: Artificial
<220> FEATURE:
<223> OTHER INFORMATION: Hybrid comprising Fungamyl vatiant CD ans
      A.rolfsii CBM
<220> FEATURE:
<221> NAME/KEY: CDS
<222> LOCATION: (1)..(1761)

<400> SEQUENCE: 99

```
gca acg cct gcg gac tgg cga tcg caa tcc att tat ttc ctt ctc acg       48
Ala Thr Pro Ala Asp Trp Arg Ser Gln Ser Ile Tyr Phe Leu Leu Thr
 1               5                  10                  15 gat cga ttt gca agg acg gat ggg tcg acg act gcg act tgt aat act       96
Asp Arg Phe Ala Arg Thr Asp Gly Ser Thr Thr Ala Thr Cys Asn Thr
                 20                  25                  30 gcg gat cag aaa tac tgt ggt gga aca tgg cag ggc atc atc gac aag      144
Ala Asp Gln Lys Tyr Cys Gly Gly Thr Trp Gln Gly Ile Ile Asp Lys
             35                  40                  45 ttg gac tat atc cag gga atg ggc ttc aca gcc atc tgg atc acc ccc      192
Leu Asp Tyr Ile Gln Gly Met Gly Phe Thr Ala Ile Trp Ile Thr Pro
 50                  55                  60 gtt aca gcc cag ctg ccc cag acc acc gca tat gga gat gcc tac cat      240
Val Thr Ala Gln Leu Pro Gln Thr Thr Ala Tyr Gly Asp Ala Tyr His
 65                  70                  75                  80 ggc tac tgg cag cag gat ata tac tct ctg aac gaa aac tac ggc act      288
Gly Tyr Trp Gln Gln Asp Ile Tyr Ser Leu Asn Glu Asn Tyr Gly Thr
                 85                  90                  95
```

-continued

| | | |
|---|---|---|
| gca gat gac ttg aag gcg ctc tct tcg gcc ctt cat gag agg ggg atg<br>Ala Asp Asp Leu Lys Ala Leu Ser Ser Ala Leu His Glu Arg Gly Met<br>100                     105                    110 | | 336 |
| tat ctt atg gtc gat gtg gtt gct aac cat atg ggc tat gat gga ccg<br>Tyr Leu Met Val Asp Val Val Ala Asn His Met Gly Tyr Asp Gly Pro<br>             115                    120                    125 | | 384 |
| ggt agc tca gtc gat tac agt gtg ttt gtt ccg ttc aat tcc gct agc<br>Gly Ser Ser Val Asp Tyr Ser Val Phe Val Pro Phe Asn Ser Ala Ser<br>130                    135                    140 | | 432 |
| tac ttc cac ccg ttc tgt ttc att caa aac tgg aat gat cag act cag<br>Tyr Phe His Pro Phe Cys Phe Ile Gln Asn Trp Asn Asp Gln Thr Gln<br>145                    150                    155                    160 | | 480 |
| gtt gag gat tgc tgg cta gga gat aac act gtc tcc ttg cct gat ctc<br>Val Glu Asp Cys Trp Leu Gly Asp Asn Thr Val Ser Leu Pro Asp Leu<br>             165                    170                    175 | | 528 |
| gat acc acc aag gat gtg gtc aag aat gaa tgg tac gac tgg gtg gga<br>Asp Thr Thr Lys Asp Val Val Lys Asn Glu Trp Tyr Asp Trp Val Gly<br>                 180                    185                    190 | | 576 |
| tca ttg gta tcg aac tac tcc att gac ggc ctc cgt atc gac aca gta<br>Ser Leu Val Ser Asn Tyr Ser Ile Asp Gly Leu Arg Ile Asp Thr Val<br>             195                    200                    205 | | 624 |
| aaa cac gtc cag aag gac ttc tgg ccc ggg tac aac aaa gcc gca ggc<br>Lys His Val Gln Lys Asp Phe Trp Pro Gly Tyr Asn Lys Ala Ala Gly<br>210                    215                    220 | | 672 |
| gtg tac tgt atc ggc gag gtg ctc gac ggt gat ccg gcc tac act tgt<br>Val Tyr Cys Ile Gly Glu Val Leu Asp Gly Asp Pro Ala Tyr Thr Cys<br>225                    230                    235                    240 | | 720 |
| ccc tac cag gaa gtc ctg gac ggc gta ctg aac tac ccc att tac tat<br>Pro Tyr Gln Glu Val Leu Asp Gly Val Leu Asn Tyr Pro Ile Tyr Tyr<br>             245                    250                    255 | | 768 |
| cca ctc ctc aac gcc ttc aag tca acc tcc ggc agc atg gac gac ctc<br>Pro Leu Leu Asn Ala Phe Lys Ser Thr Ser Gly Ser Met Asp Asp Leu<br>             260                    265                    270 | | 816 |
| tac aac atg atc aac acc gtc aaa tcc gac tgt cca gac tca aca ctc<br>Tyr Asn Met Ile Asn Thr Val Lys Ser Asp Cys Pro Asp Ser Thr Leu<br>             275                    280                    285 | | 864 |
| ctg ggc aca ttc gtc gag aac cac gac aac cca cgg ttc gct tct tac<br>Leu Gly Thr Phe Val Glu Asn His Asp Asn Pro Arg Phe Ala Ser Tyr<br>290                    295                    300 | | 912 |
| acc aac gac ata gcc ctc gcc aag aac gtc gca gca ttc atc atc ctc<br>Thr Asn Asp Ile Ala Leu Ala Lys Asn Val Ala Ala Phe Ile Ile Leu<br>305                    310                    315                    320 | | 960 |
| aac gac gga atc ccc atc atc tac gcc ggc caa gaa cag cac tac gcc<br>Asn Asp Gly Ile Pro Ile Ile Tyr Ala Gly Gln Glu Gln His Tyr Ala<br>             325                    330                    335 | | 1008 |
| ggc gga aac gac ccc gcg aac cgc gaa gca acc tgg ctc tcg ggc tac<br>Gly Gly Asn Asp Pro Ala Asn Arg Glu Ala Thr Trp Leu Ser Gly Tyr<br>             340                    345                    350 | | 1056 |
| ccg acc gac agc gag ctg tac aag tta att gcc tcc gcg aac gca atc<br>Pro Thr Asp Ser Glu Leu Tyr Lys Leu Ile Ala Ser Ala Asn Ala Ile<br>             355                    360                    365 | | 1104 |
| cgg aac tat gcc att agc aaa gat aca gga ttc gtg acc tac aag aac<br>Arg Asn Tyr Ala Ile Ser Lys Asp Thr Gly Phe Val Thr Tyr Lys Asn<br>370                    375                    380 | | 1152 |
| tgg ccc atc tac aaa gac gac aca acg atc gcc atg cgc aag ggc aca<br>Trp Pro Ile Tyr Lys Asp Asp Thr Thr Ile Ala Met Arg Lys Gly Thr<br>385                    390                    395                    400 | | 1200 |
| gat ggg tcg cag atc gtg act atc ttg tcc aac aag ggt gct tcg ggt<br>Asp Gly Ser Gln Ile Val Thr Ile Leu Ser Asn Lys Gly Ala Ser Gly<br>             405                    410                    415 | | 1248 |

```
gat tcg tat acc ctc tcc ttg agt ggt gcg ggt tac aca gcc ggc cag      1296
Asp Ser Tyr Thr Leu Ser Leu Ser Gly Ala Gly Tyr Thr Ala Gly Gln
            420                 425                 430 caa ttg acg gag gtc att ggc tgc acg acc gtg acg gtt gat tcg tcg      1344
Gln Leu Thr Glu Val Ile Gly Cys Thr Thr Val Thr Val Asp Ser Ser
        435                 440                 445 gga gat gtg cct gtt cct atg gcg ggt ggg cta cct agg gta ttg tat      1392
Gly Asp Val Pro Val Pro Met Ala Gly Gly Leu Pro Arg Val Leu Tyr
450                 455                 460 ccg act gag aag ttg gca ggt agc aag atc tgt agt agc tcg ggt gct      1440
Pro Thr Glu Lys Leu Ala Gly Ser Lys Ile Cys Ser Ser Ser Gly Ala
465                 470                 475                 480 aca agc ccg ggt ggc tcc tcg ggt agt gtc gag gtc act ttc gac gtt      1488
Thr Ser Pro Gly Gly Ser Ser Gly Ser Val Glu Val Thr Phe Asp Val
                485                 490                 495 tac gct acc aca gta tat ggc cag aac atc tat atc acc ggt gat gtg      1536
Tyr Ala Thr Thr Val Tyr Gly Gln Asn Ile Tyr Ile Thr Gly Asp Val
            500                 505                 510 agt gag ctc ggc aac tgg aca ccc gcc aat ggt gtt gca ctc tct tct      1584
Ser Glu Leu Gly Asn Trp Thr Pro Ala Asn Gly Val Ala Leu Ser Ser
        515                 520                 525 gct aac tac ccc acc tgg agt gcc acg atc gct ctc ccc gct gac acg      1632
Ala Asn Tyr Pro Thr Trp Ser Ala Thr Ile Ala Leu Pro Ala Asp Thr
530                 535                 540 aca atc cag tac aag tat gtc aac att gac ggc agc acc gtc atc tgg      1680
Thr Ile Gln Tyr Lys Tyr Val Asn Ile Asp Gly Ser Thr Val Ile Trp
545                 550                 555                 560 gag gat gct atc agc aat cgc gag atc acg acg ccc gcc agc ggc aca      1728
Glu Asp Ala Ile Ser Asn Arg Glu Ile Thr Thr Pro Ala Ser Gly Thr
                565                 570                 575 tac acc gaa aaa gac act tgg gat gaa tct tag                          1761
Tyr Thr Glu Lys Asp Thr Trp Asp Glu Ser
            580                 585

<210> SEQ ID NO 100
<211> LENGTH: 586
<212> TYPE: PRT
<213> ORGANISM: Artificial
<220> FEATURE:
<223> OTHER INFORMATION: Synthetic Construct

<400> SEQUENCE: 100

Ala Thr Pro Ala Asp Trp Arg Ser Gln Ser Ile Tyr Phe Leu Leu Thr
1               5                   10                  15

Asp Arg Phe Ala Arg Thr Asp Gly Ser Thr Thr Ala Thr Cys Asn Thr
            20                  25                  30

Ala Asp Gln Lys Tyr Cys Gly Gly Thr Trp Gln Gly Ile Ile Asp Lys
        35                  40                  45

Leu Asp Tyr Ile Gln Gly Met Gly Phe Thr Ala Ile Trp Ile Thr Pro
    50                  55                  60

Val Thr Ala Gln Leu Pro Gln Thr Thr Ala Tyr Gly Asp Ala Tyr His
65                  70                  75                  80

Gly Tyr Trp Gln Gln Asp Ile Tyr Ser Leu Asn Glu Asn Tyr Gly Thr
                85                  90                  95

Ala Asp Asp Leu Lys Ala Leu Ser Ala Leu His Glu Arg Gly Met
            100                 105                 110

Tyr Leu Met Val Asp Val Val Ala Asn His Met Gly Tyr Asp Gly Pro
        115                 120                 125

Gly Ser Ser Val Asp Tyr Ser Val Phe Val Pro Phe Asn Ser Ala Ser
```

-continued

```
            130                 135                 140
Tyr Phe His Pro Phe Cys Phe Ile Gln Asn Trp Asn Asp Gln Thr Gln
145                 150                 155                 160

Val Glu Asp Cys Trp Leu Gly Asp Asn Thr Val Ser Leu Pro Asp Leu
                165                 170                 175

Asp Thr Thr Lys Asp Val Val Lys Asn Glu Trp Tyr Asp Trp Val Gly
                180                 185                 190

Ser Leu Val Ser Asn Tyr Ser Ile Asp Gly Leu Arg Ile Asp Thr Val
                195                 200                 205

Lys His Val Gln Lys Asp Phe Trp Pro Gly Tyr Asn Lys Ala Ala Gly
210                 215                 220

Val Tyr Cys Ile Gly Glu Val Leu Asp Gly Asp Pro Ala Tyr Thr Cys
225                 230                 235                 240

Pro Tyr Gln Glu Val Leu Asp Gly Val Leu Asn Tyr Pro Ile Tyr Tyr
                245                 250                 255

Pro Leu Leu Asn Ala Phe Lys Ser Thr Ser Gly Ser Met Asp Asp Leu
                260                 265                 270

Tyr Asn Met Ile Asn Thr Val Lys Ser Asp Cys Pro Asp Ser Thr Leu
                275                 280                 285

Leu Gly Thr Phe Val Glu Asn His Asp Asn Pro Arg Phe Ala Ser Tyr
                290                 295                 300

Thr Asn Asp Ile Ala Leu Ala Lys Asn Val Ala Phe Ile Ile Leu
305                 310                 315                 320

Asn Asp Gly Ile Pro Ile Ile Tyr Ala Gly Gln Glu Gln His Tyr Ala
                325                 330                 335

Gly Gly Asn Asp Pro Ala Asn Arg Glu Ala Thr Trp Leu Ser Gly Tyr
                340                 345                 350

Pro Thr Asp Ser Glu Leu Tyr Lys Leu Ile Ala Ser Ala Asn Ala Ile
                355                 360                 365

Arg Asn Tyr Ala Ile Ser Lys Asp Thr Gly Phe Val Thr Tyr Lys Asn
370                 375                 380

Trp Pro Ile Tyr Lys Asp Asp Thr Thr Ile Ala Met Arg Lys Gly Thr
385                 390                 395                 400

Asp Gly Ser Gln Ile Val Thr Ile Leu Ser Asn Lys Gly Ala Ser Gly
                405                 410                 415

Asp Ser Tyr Thr Leu Ser Leu Ser Gly Ala Gly Tyr Thr Ala Gly Gln
                420                 425                 430

Gln Leu Thr Glu Val Ile Gly Cys Thr Thr Val Thr Val Asp Ser Ser
                435                 440                 445

Gly Asp Val Pro Val Pro Met Ala Gly Gly Leu Pro Arg Val Leu Tyr
450                 455                 460

Pro Thr Glu Lys Leu Ala Gly Ser Lys Ile Cys Ser Ser Ser Gly Ala
465                 470                 475                 480

Thr Ser Pro Gly Gly Ser Ser Gly Ser Val Glu Val Thr Phe Asp Val
                485                 490                 495

Tyr Ala Thr Thr Val Tyr Gly Gln Asn Ile Tyr Ile Thr Gly Asp Val
                500                 505                 510

Ser Glu Leu Gly Asn Trp Thr Pro Ala Asn Gly Val Ala Leu Ser Ser
                515                 520                 525

Ala Asn Tyr Pro Thr Trp Ser Ala Thr Ile Ala Leu Pro Ala Asp Thr
                530                 535                 540

Thr Ile Gln Tyr Lys Tyr Val Asn Ile Asp Gly Ser Thr Val Ile Trp
545                 550                 555                 560
```

-continued

Glu Asp Ala Ile Ser Asn Arg Glu Ile Thr Thr Pro Ala Ser Gly Thr
            565                 570                 575

Tyr Thr Glu Lys Asp Thr Trp Asp Glu Ser
            580                 585

<210> SEQ ID NO 101
<211> LENGTH: 558
<212> TYPE: PRT
<213> ORGANISM: Artificial
<220> FEATURE:
<223> OTHER INFORMATION: Rhizomucor pusillus amylase with linker and
      SBD from A. rolfsii

<400> SEQUENCE: 101

Ser Pro Leu Pro Gln Gln Arg Tyr Gly Lys Arg Ala Thr Ser Asp
1               5                   10                  15

Asp Trp Lys Ser Lys Ala Ile Tyr Gln Leu Leu Thr Asp Arg Phe Gly
            20                  25                  30

Arg Ala Asp Asp Ser Thr Ser Asn Cys Ser Asn Leu Ser Asn Tyr Cys
        35                  40                  45

Gly Gly Thr Tyr Glu Gly Ile Thr Lys His Leu Asp Tyr Ile Ser Gly
    50                  55                  60

Met Gly Phe Asp Ala Ile Trp Ile Ser Pro Ile Pro Lys Asn Ser Asp
65                  70                  75                  80

Gly Gly Tyr His Gly Tyr Trp Ala Thr Asp Phe Tyr Gln Leu Asn Ser
                85                  90                  95

Asn Phe Gly Asp Glu Ser Gln Leu Lys Ala Leu Ile Gln Ala Ala His
            100                 105                 110

Glu Arg Asp Met Tyr Val Met Leu Asp Val Val Ala Asn His Ala Gly
        115                 120                 125

Pro Thr Ser Asn Gly Tyr Ser Gly Tyr Thr Phe Gly Asp Ala Ser Leu
    130                 135                 140

Tyr His Pro Lys Cys Thr Ile Asp Tyr Asn Asp Gln Thr Ser Ile Glu
145                 150                 155                 160

Gln Cys Trp Val Ala Asp Glu Leu Pro Asp Ile Asp Thr Glu Asn Ser
                165                 170                 175

Asp Asn Val Ala Ile Leu Asn Asp Ile Val Ser Gly Trp Val Gly Asn
            180                 185                 190

Tyr Ser Phe Asp Gly Ile Arg Ile Asp Thr Val Lys His Ile Arg Lys
        195                 200                 205

Asp Phe Trp Thr Gly Tyr Ala Glu Ala Ala Gly Val Phe Ala Thr Gly
    210                 215                 220

Glu Val Phe Asn Gly Asp Pro Ala Tyr Val Gly Pro Tyr Gln Lys Tyr
225                 230                 235                 240

Leu Pro Ser Leu Ile Asn Tyr Pro Met Tyr Tyr Ala Leu Asn Asp Val
                245                 250                 255

Phe Val Ser Lys Ser Lys Gly Phe Ser Arg Ile Ser Glu Met Leu Gly
            260                 265                 270

Ser Asn Arg Asn Ala Phe Glu Asp Thr Ser Val Leu Thr Thr Phe Val
        275                 280                 285

Asp Asn His Asp Asn Pro Arg Phe Leu Asn Ser Gln Ser Asp Lys Ala
    290                 295                 300

Leu Phe Lys Asn Ala Leu Thr Tyr Val Leu Leu Gly Glu Gly Ile Pro
305                 310                 315                 320

Ile Val Tyr Tyr Gly Ser Glu Gln Gly Phe Ser Gly Gly Ala Asp Pro
                325                 330                 335

```
Ala Asn Arg Glu Val Leu Trp Thr Thr Asn Tyr Asp Thr Ser Ser Asp
            340                 345                 350

Leu Tyr Gln Phe Ile Lys Thr Val Asn Ser Val Arg Met Lys Ser Asn
            355                 360                 365

Lys Ala Val Tyr Met Asp Ile Tyr Val Gly Asp Asn Ala Tyr Ala Phe
            370                 375                 380

Lys His Gly Asp Ala Leu Val Val Leu Asn Asn Tyr Gly Ser Gly Ser
385                 390                 395                 400

Thr Asn Gln Val Ser Phe Ser Val Ser Gly Lys Phe Asp Ser Gly Ala
                405                 410                 415

Ser Leu Met Asp Ile Val Ser Asn Ile Thr Thr Thr Val Ser Ser Asp
            420                 425                 430

Gly Thr Val Thr Phe Asn Leu Lys Asp Gly Leu Pro Ala Ile Phe Thr
            435                 440                 445

Ser Ala Gly Ala Thr Ser Pro Gly Gly Ser Ser Gly Ser Val Glu Val
            450                 455                 460

Thr Phe Asp Val Tyr Ala Thr Thr Val Tyr Gly Gln Asn Ile Tyr Ile
465                 470                 475                 480

Thr Gly Asp Val Ser Glu Leu Gly Asn Trp Thr Pro Ala Asn Gly Val
                485                 490                 495

Ala Leu Ser Ser Ala Asn Tyr Pro Thr Trp Ser Ala Thr Ile Ala Leu
            500                 505                 510

Pro Ala Asp Thr Thr Ile Gln Tyr Lys Tyr Val Asn Ile Asp Gly Ser
            515                 520                 525

Thr Val Ile Trp Glu Asp Ala Ile Ser Asn Arg Glu Ile Thr Thr Pro
            530                 535                 540

Ala Ser Gly Thr Tyr Thr Glu Lys Asp Thr Trp Asp Glu Ser
545                 550                 555

<210> SEQ ID NO 102
<211> LENGTH: 574
<212> TYPE: PRT
<213> ORGANISM: Artificial
<220> FEATURE:
<223> OTHER INFORMATION: Hybrid of Meripilus giganteus amylase with
      A.rolfsii SBD

<400> SEQUENCE: 102

Arg Pro Thr Val Phe Asp Ala Gly Ala Asp Ala His Ser Leu His Ala
1               5                   10                  15

Arg Ala Pro Ser Gly Ser Lys Asp Val Ile Ile Gln Met Phe Glu Trp
            20                  25                  30

Asn Trp Asp Ser Val Ala Ala Glu Cys Thr Asn Phe Ile Gly Pro Ala
            35                  40                  45

Gly Tyr Gly Phe Val Gln Val Ser Pro Pro Gln Glu Thr Ile Gln Gly
        50                  55                  60

Ala Gln Trp Trp Thr Asp Tyr Gln Pro Val Ser Tyr Thr Leu Thr Gly
65              70                  75                  80

Lys Arg Gly Asp Arg Ser Gln Phe Ala Asn Met Ile Thr Thr Cys His
            85                  90                  95

Ala Ala Gly Val Gly Val Ile Val Asp Thr Ile Trp Asn His Met Ala
            100                 105                 110

Gly Val Asp Ser Gly Thr Gly Thr Ala Gly Ser Ser Phe Thr His Tyr
        115                 120                 125

Asn Tyr Pro Gly Ile Tyr Gln Asn Gln Asp Phe His His Cys Gly Leu
    130                 135                 140
```

-continued

Glu Pro Gly Asp Asp Ile Val Asn Tyr Asp Asn Ala Val Glu Val Gln
145                 150                 155                 160

Thr Cys Glu Leu Val Asn Leu Ala Asp Leu Ala Thr Asp Thr Glu Tyr
            165                 170                 175

Val Arg Gly Arg Leu Ala Gln Tyr Gly Asn Asp Leu Leu Ser Leu Gly
        180                 185                 190

Ala Asp Gly Leu Arg Leu Asp Ala Ser Lys His Ile Pro Val Gly Asp
    195                 200                 205

Ile Ala Asn Ile Leu Ser Arg Leu Ser Arg Ser Val Tyr Ile Thr Gln
210                 215                 220

Glu Val Ile Phe Gly Ala Gly Glu Pro Ile Thr Pro Asn Gln Tyr Thr
225                 230                 235                 240

Gly Asn Gly Asp Val Gln Glu Phe Arg Tyr Thr Ser Ala Leu Lys Asp
                245                 250                 255

Ala Phe Leu Ser Ser Gly Ile Ser Asn Leu Gln Asp Phe Glu Asn Arg
            260                 265                 270

Gly Trp Val Pro Gly Ser Gly Ala Asn Val Phe Val Asn His Asp
        275                 280                 285

Thr Glu Arg Asn Gly Ala Ser Leu Asn Asn Ser Pro Ser Asn Thr
    290                 295                 300

Tyr Val Thr Ala Thr Ile Phe Ser Leu Ala His Pro Tyr Gly Thr Pro
305                 310                 315                 320

Thr Ile Leu Ser Ser Tyr Asp Gly Phe Thr Asn Thr Asp Ala Gly Ala
                325                 330                 335

Pro Asn Asn Asn Val Gly Thr Cys Ser Thr Ser Gly Gly Ala Asn Gly
            340                 345                 350

Trp Leu Cys Gln His Arg Trp Thr Ala Ile Ala Gly Met Val Gly Phe
        355                 360                 365

Arg Asn Asn Val Gly Ser Ala Ala Leu Asn Asn Trp Gln Ala Pro Gln
    370                 375                 380

Ser Gln Gln Ile Ala Phe Gly Arg Gly Ala Leu Gly Phe Val Ala Ile
385                 390                 395                 400

Asn Asn Ala Asp Ser Ala Trp Ser Thr Thr Phe Thr Thr Ser Leu Pro
                405                 410                 415

Asp Gly Ser Tyr Cys Asp Val Ile Ser Gly Lys Ala Ser Gly Ser Ser
            420                 425                 430

Cys Thr Gly Ser Ser Phe Thr Val Ser Gly Gly Lys Leu Thr Ala Thr
        435                 440                 445

Val Pro Ala Arg Ser Ala Ile Ala Val His Thr Gly Gln Lys Gly Ser
    450                 455                 460

Gly Gly Gly Ala Thr Ser Pro Gly Gly Ser Gly Ser Val Glu Val
465                 470                 475                 480

Thr Phe Asp Val Tyr Ala Thr Thr Val Tyr Gly Gln Asn Ile Tyr Ile
                485                 490                 495

Thr Gly Asp Val Ser Glu Leu Gly Asn Trp Thr Pro Ala Asn Gly Val
            500                 505                 510

Ala Leu Ser Ser Ala Asn Tyr Pro Thr Trp Ser Ala Thr Ile Ala Leu
        515                 520                 525

Pro Ala Asp Thr Thr Ile Gln Tyr Lys Tyr Val Asn Ile Asp Gly Ser
    530                 535                 540

Thr Val Ile Trp Glu Asp Ala Ile Ser Asn Arg Glu Ile Thr Thr Pro
545                 550                 555                 560

Ala Ser Gly Thr Tyr Thr Glu Lys Asp Thr Trp Asp Glu Ser
                565                 570

<210> SEQ ID NO 103
<211> LENGTH: 7063
<212> TYPE: DNA
<213> ORGANISM: Artificial
<220> FEATURE:
<223> OTHER INFORMATION: Plasmid for contruction of hybrids
<220> FEATURE:
<221> NAME/KEY: misc_feature
<222> LOCATION: (1)..(7063)

<400> SEQUENCE: 103

| | | | | | |
|---|---|---|---|---|---|
| ctgcattaat | gaatcggcca | acgcgcgggg | agaggcggtt | tgcgtattgg | gcgctcttcc | 60 |
| gcttcctcgc | tcactgactc | gctgcgctcg | gtcgttcggc | tgcggcgagc | ggtatcagct | 120 |
| cactcaaagg | cggtaatacg | gttatccaca | gaatcagggg | ataacgcagg | aaagaacatg | 180 |
| tgagcaaaag | gccagcaaaa | ggccaggaac | cgtaaaaagg | ccgcgttgct | ggcgtttttc | 240 |
| cataggctcc | gcccccctga | cgagcatcac | aaaaatcgac | gctcaagtca | gaggtggcga | 300 |
| aacccgacag | gactataaag | ataccaggcg | tttccccctg | gaagctccct | cgtgcgctct | 360 |
| cctgttccga | ccctgccgct | taccggatac | ctgtccgcct | ttctcccttc | gggaagcgtg | 420 |
| gcgctttctc | atagctcacg | ctgtaggtat | ctcagttcgg | tgtaggtcgt | tcgctccaag | 480 |
| ctgggctgtg | tgcacgaacc | ccccgttcag | cccgaccgct | gcgccttatc | cggtaactat | 540 |
| cgtcttgagt | ccaacccggt | aagacacgac | ttatcgccac | tggcagcagc | cactggtaac | 600 |
| aggattagca | gagcgaggta | tgtaggcggt | gctacagagt | tcttgaagtg | gtggcctaac | 660 |
| tacggctaca | ctagaaggac | agtatttggt | atctgcgctc | tgctgaagcc | agttaccttc | 720 |
| ggaaaaagag | ttggtagctc | ttgatccggc | aaacaaacca | ccgctggtag | cggtggtttt | 780 |
| tttgtttgca | agcagcagat | tacgcgcaga | aaaaaggat | ctcaagaaga | tcctttgatc | 840 |
| ttttctacgg | ggtctgacgc | tcagtggaac | gaaaactcac | gttaagggat | tttggtcatg | 900 |
| agattatcaa | aaaggatctt | cacctagatc | cttttaaatt | aaaaatgaag | ttttaaatca | 960 |
| atctaaagta | tatatgagta | aacttggtct | gacagttacc | aatgcttaat | cagtgaggca | 1020 |
| cctatctcag | cgatctgtct | atttcgttca | tccatagttg | cctgactccc | cgtcgtgtag | 1080 |
| ataactacga | tacgggaggg | cttaccatct | ggccccagtg | ctgcaatgat | accgcgagac | 1140 |
| ccacgctcac | cggctccaga | tttatcagca | ataaaccagc | cagccggaag | ggccgagcgc | 1200 |
| agaagtggtc | ctgcaacttt | atccgcctcc | atccagtcta | ttaattgttg | ccgggaagct | 1260 |
| agagtaagta | gttcgccagt | taatagtttg | cgcaacgttg | ttgccattgc | tacaggcatc | 1320 |
| gtggtgtcac | gctcgtcgtt | tggtatggct | tcattcagct | ccggttccca | acgatcaagg | 1380 |
| cgagttacat | gatcccccat | gttgtgcaaa | aaagcggtta | gctccttcgg | tcctccgatc | 1440 |
| gttgtcagaa | gtaagttggc | cgcagtgtta | tcactcatgg | ttatggcagc | actgcataat | 1500 |
| tctcttactg | tcatgccatc | cgtaagatgc | ttttctgtga | ctggtgagta | ctcaaccaag | 1560 |
| tcattctgag | aatagtgtat | gcggcgaccg | agttgctctt | gcccggcgtc | aatacgggat | 1620 |
| aataccgcgc | cacatagcag | aactttaaaa | gtgctcatca | ttggaaaacg | ttcttcgggg | 1680 |
| cgaaaactct | caaggatctt | accgctgttg | agatccagtt | cgatgtaacc | cactcgtgca | 1740 |
| cccaactgat | cttcagcatc | ttttactttc | accagcgttt | ctgggtgagc | aaaaacagga | 1800 |
| aggcaaaatg | ccgcaaaaaa | gggaataagg | gcgacacgga | aatgttgaat | actcatactc | 1860 |
| ttcctttttc | aatgggtaat | aactgatata | attaaattga | agctctaatt | tgtgagttta | 1920 |
| gtatacatgc | atttacttat | aatacagttt | tttagttttg | ctggccgcat | cttctcaaat | 1980 |

```
atgcttccca gcctgctttt ctgtaacgtt caccctctac cttagcatcc cttcccttg     2040
caaatagtcc tcttccaaca ataataatgt cagatcctgt agagaccaca tcatccacgg     2100
ttctatactg ttgacccaat gcgtctccct tgtcatctaa acccacaccg ggtgtcataa     2160
tcaaccaatc gtaaccttca tctcttccac ccatgtctct tgagcaata aagccgataa      2220
caaaatcttt gtcgctcttc gcaatgtcaa cagtacccct agtatattct ccagtagata     2280
gggagccctt gcatgacaat tctgctaaca tcaaaaggcc tctaggttcc tttgttactt     2340
cttctgccgc ctgcttcaaa ccgctaacaa tacctgggcc caccacaccg tgtgcattcg     2400
taatgtctgc ccattctgct attctgtata cacccgcaga gtactgcaat ttgactgtat     2460
taccaatgtc agcaaatttt ctgtcttcga agagtaaaaa attgtacttg gcggataatg     2520
cctttagcgg cttaactgtg ccctccatgg aaaaatcagt caagatatcc acatgtgttt     2580
ttagtaaaca aattttggga cctaatgctt caactaactc cagtaattcg ttggtggtac     2640
gaacatccaa tgaagcacac aagtttgttt gcttttcgtg catgatatta aatagcttgg     2700
cagcaacagg actaggatga gtagcagcac gttccttata tgtagctttc gacatgattt     2760
atcttcgttt cctgcagctt ctcaatgata ttcgaatacg ctttgaggag atacagccta     2820
atatccgaca aactgtttta cagatttacg atcgtacttg ttacccatca ttgaattttg     2880
aacatccgaa cctgggagtt ttccctgaaa cagatagtat atttgaacct gtataataat     2940
atatagtcta gcgctttacg gaagacaatg tatgtatttc ggttcctgga gaaactattg     3000
catctattgc ataggtaatc ttgcacgtcg catcccggt tcatttctg cgtttccatc       3060
ttgcacttca atagcatatc tttgttaacg aagcatctgt gcttcatttt gtagaacaaa     3120
aatgcaacgc gagagcgcta atttttcaaa caaagaatct gagctgcatt tttacagaac     3180
agaaatgcaa cgcgaaagcg ctattttacc aacgaagaat ctgtgcttca tttttgtaaa     3240
acaaaaatgc aacgcgagag cgctaatttt tcaaacaaag aatctgagct gcattttac     3300
agaacagaaa tgcaacgcga gagcgctatt ttaccaacaa agaatctata cttcttttt     3360
gttctacaaa aatgcatccc gagagcgcta ttttctaac aaagcatctt agattacttt      3420
ttttctcctt tgtgcgctct ataatgcagt ctcttgataa cttttgcac tgtaggtccg       3480
ttaaggttag aagaaggcta ctttggtgtc tattttctct tccataaaaa aagcctgact     3540
ccacttcccg cgtttactga ttactagcga agctgcgggt gcattttttc aagataaagg     3600
catccccgat tatattctat accgatgtgg attgcgcata ctttgtgaag agaaagtgat     3660
agcgttgatg attcttcatt ggtcagaaaa ttatgaacgg tttcttctat tttgtctcta     3720
tatactacgt ataggaaatg tttacatttt cgtattgttt tcgattcact ctatgaatag     3780
ttcttactac aattttttg tctaaagagt aatactagag ataaacataa aaaatgtaga      3840
ggtcgagttt agatgcaagt tcaaggagcg aaaggtggat gggtaggtta tatagggata     3900
tagcacagag atatatagca aagagatact tttgagcaat gtttgtggaa gcggtattcg     3960
caatgggaag ctcccaggcc ggttgataat cagaaaagcc ccaaaaaaca ggaagattgt     4020
ataagcaaat atttaaattg taaacgttaa tattttgtta aaattcgcgt taaattttg      4080
ttaaatcagc tcatttttta acgaatagcc cgaaatcggc aaaatccctt ataaatcaaa     4140
agaatagacc gagataggt tgagtgtttgt tccagtttcc aacaagagtc cactattaaa     4200
gaacgtggac tccaacgtca aagggcgaaa aagggtctat cagggcgatg cccactacg      4260
tgaaccatca ccctaatgaa gttttttggg gtcgaggtgc cgtaaagcag taaatcggaa     4320
gggtaaacgg atgcccccat ttagagcttg acggggaaag ccggcgaacg tggcgagaaa     4380
```

```
ggaagggaag aaagcgaaac cagcgggggc tagggcggtg ggaagtgtag gggtcacgct   4440
gggcgtaacc accacacccg ccgcgcttaa tggggcgcta cagggcgcgt ggggatatcc   4500
actagcatgc ctcagcttcc tctattgatg ttacacctgg acacccctt tctggcatcc    4560 agtttttaat cttcagtggc atgtgagatt ctccgaaatt aattaaagca atcacacaat   4620
tctctcggat accacctcgg ttgaaactga caggtggttt gttacgctaa tgcaaaggag   4680
cctatatacc tttggctcgg ctgctgtaac agggaatata aagggcagca taatttagga   4740
gtttagtgaa cttgcaacat ttactatttt cccttcttac gtaaatattt ttcttttaa    4800 ttctaaatca atcttttca attttttgtt tgtattcttt tcttgcttaa atctataact    4860
acaaaaaaca catacagaaa ttcattcaag aatagttcaa acaagaagat tacaaactat   4920
caatttcata cacaatataa acgacgggac ccggggatcg aattcatgag attatcgact   4980
tcgagtctct tcctttccgt gtctctgctg gggaagctgg ccctcgggct gtcggctgca   5040
gaatggcgca ctcagtcgat ttacttccta ttgacggatc ggttcggtag gacggacaat   5100
tcgacgacag ctacatgcga tacgggtgac caaatctatt gtggtggcag ttggcaagga   5160
atcatcaacc atctggatta tatccagggc atgggattca cggccatctg gatctcgcct   5220
atcactgaac agctgcccca ggatactgct gatggtgaag cttaccatgg atattggcag   5280
cagaagatat acgacgtgaa ctccaacttc ggcactgcag atgacctcaa gtccctctca   5340
gatgcgcttc atgcccgcgg aatgtacctc atggtggacg tcgtccctaa ccacatgggc   5400
tacgccggca acggcaacga tgtagactac agcgtcttcg accccttcga ttcctcctcc   5460
tacttccacc catactgcct gatcacagat tgggacaact tgaccatggt ccaagattgt   5520
tgggagggtg acaccatcgt atctctgcca gacctaaaca ccaccgaaac tgccgtgaga   5580
acaatctggt atgactgggt agccgacctg gtatccaatt attcagtcga cggactccgc   5640
atcgacagtg tcctcgaagt cgaaccagac ttcttcccgg ctaccagga agcagcaggt    5700 gtctactgcg tcggcgaagt cgacaacggc aaccctgccc tcgactgccc ataccagaag   5760
gtcctggacg gcgtcctcaa ctatccgatc tactggcaac tcctctacgc cttcgaatcc   5820
tccagcggca gcatcagcaa tctctacaac atgatcaaat ccgtcgcaag cgactgctcc   5880
gatccgacac tactcggcaa cttcatcgaa aaccacgaca tccccgtttt cgcctcctac   5940
acctccgact actcgcaagc caaaaacgtc tcagctacaa tcttcctctc cgacggcatc   6000
cccatcgtct acgccggcga agaacagcac tactccggcg gcaaggtgcc ctacaaccgc   6060
gaagcgacct ggctttcagg ctacgacacc tccgcagagc tgtacacctg gataggccacc  6120 acgaacgcga tccgcaaact agccatctca gctgactcgg cctacattac ctacgcgaat   6180
gatgcattct acactgacag caacaccatc gcaatgcgca aaggcacctc agggagccaa   6240
gtcatcaccg tcctctccaa caaaggctcc tcaggaagca gctacaccct gaccctcagc   6300
ggaagcggct acacatccgg cacgaagctg atcgaagcgt acacatgcac atccgtgacc   6360
gtggactcga gcggcgatat tcccgtgccg atggcgtcgg gattaccgag agttcttctg   6420
cccgcgtccg tcgtcgatag ctcttcgctc tgtggcggga gcggaagagg tgctacaagc   6480
ccgggtggct cctcgggtag tgtcgaggtc actttcgacg tttacgctac cacagtatat   6540
ggccagaaca tctatatcac cggtgatgtg agtgagctcg gcaactggac acccgccaat   6600
ggtgttgcac tctcttctgc taactacccc acctggagtg ccacgatcgc tctccccgct   6660
gacacgacaa tccagtacaa gtatgtcaac attgacggca gcaccgtcat ctgggaggat   6720
gctatcagca atcgcgagat cacgacgccc gccagcggca catacaccga aaagacact   6780
```

```
tgggatgaat cttaggcggc cgcgggccgc atcatgtaat tagttatgtc acgcttacat    6840
tcacgccctc cccccacatc cgctctaacc gaaaaggaag gagttagaca acctgaagtc    6900
taggtcccta tttatttttt tatagttatg ttagtattaa gaacgttatt tatatttcaa    6960 attttttcttt tttttctgta cagacgcgtg tacgcatgta acattatact gaaaaccttg    7020
cttgagaagg ttttgggacg ctcgaaggct ttaatttgcg gcc                      7063

<210> SEQ ID NO 104
<211> LENGTH: 41
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(41)

<400> SEQUENCE: 104
gctggggaag ctggccctcg ggagcccttt gccccaacag c                        41

<210> SEQ ID NO 105
<211> LENGTH: 42
<212> TYPE: DNA
<213> ORGANISM: ja126r
<220> FEATURE:
<221> NAME/KEY: misc_feature
<222> LOCATION: (1)..(42)

<400> SEQUENCE: 105
agccacccgg gcttgtagca ccagcagagg tgaagatagc cg                       42

<210> SEQ ID NO 106
<211> LENGTH: 42
<212> TYPE: DNA
<213> ORGANISM: Artificial
<220> FEATURE:
<223> OTHER INFORMATION: Primer

<400> SEQUENCE: 106
gctggggaag ctggccctcg ggcgccctac tgtctttgac gc                       42

<210> SEQ ID NO 107
<211> LENGTH: 42
<212> TYPE: DNA
<213> ORGANISM: Artificial
<220> FEATURE:
<223> OTHER INFORMATION: Primer

<400> SEQUENCE: 107
agccacccgg gcttgtagca ccaccaccag aacctttctg ac                       42

<210> SEQ ID NO 108
<211> LENGTH: 387
<212> TYPE: DNA
<213> ORGANISM: Zea mays
<220> FEATURE:
<221> NAME/KEY: CDS
<222> LOCATION: (1)..(387)

<400> SEQUENCE: 108 gtg cgt gtt cga ttt gtg ctg aaa agg cag tgc acg ttc ggg cag agc      48
Val Arg Val Arg Phe Val Leu Lys Arg Gln Cys Thr Phe Gly Gln Ser
 1               5                  10                  15 gtc tgc ctt gtc ggc gac gac cct gcg ctc ggc ctc tgg gat ctg tcg      96
Val Cys Leu Val Gly Asp Asp Pro Ala Leu Gly Leu Trp Asp Leu Ser
             20                  25                  30
```

```
aac gcg ttt cct ttg aag tgg gcg gaa agc cac gac tgg acc tta gag    144
Asn Ala Phe Pro Leu Lys Trp Ala Glu Ser His Asp Trp Thr Leu Glu
         35                  40                  45 aaa gat ttg ccg gcc aac aag ctg att gag ttc aag ttc ttg ctc caa    192
Lys Asp Leu Pro Ala Asn Lys Leu Ile Glu Phe Lys Phe Leu Leu Gln
 50                  55                  60 gat tcc aca gga aag ttg cat tgg cag ggt ggg cca aac aga agc ttt    240
Asp Ser Thr Gly Lys Leu His Trp Gln Gly Gly Pro Asn Arg Ser Phe
 65                  70                  75                  80 cag aca ggt gaa acc gcc gca aac aca ttg gtt gtg ttt gaa gat tgg    288
Gln Thr Gly Glu Thr Ala Ala Asn Thr Leu Val Val Phe Glu Asp Trp
             85                  90                  95 ggt gat gtg aag aat cag aaa ata gta gaa gag ggg gga gtg gcg tct    336
Gly Asp Val Lys Asn Gln Lys Ile Val Glu Glu Gly Gly Val Ala Ser
        100                 105                 110 gct ggg ata gaa caa act gtt gtt tca aat gac agc gaa agc aga aag    384
Ala Gly Ile Glu Gln Thr Val Val Ser Asn Asp Ser Glu Ser Arg Lys
            115                 120                 125 tag                                                                387

<210> SEQ ID NO 109
<211> LENGTH: 128
<212> TYPE: PRT
<213> ORGANISM: Zea mays

<400> SEQUENCE: 109

Val Arg Val Arg Phe Val Leu Lys Arg Gln Cys Thr Phe Gly Gln Ser
 1               5                  10                  15

Val Cys Leu Val Gly Asp Asp Pro Ala Leu Gly Leu Trp Asp Leu Ser
             20                  25                  30

Asn Ala Phe Pro Leu Lys Trp Ala Glu Ser His Asp Trp Thr Leu Glu
         35                  40                  45

Lys Asp Leu Pro Ala Asn Lys Leu Ile Glu Phe Lys Phe Leu Leu Gln
 50                  55                  60

Asp Ser Thr Gly Lys Leu His Trp Gln Gly Gly Pro Asn Arg Ser Phe
 65                  70                  75                  80

Gln Thr Gly Glu Thr Ala Ala Asn Thr Leu Val Val Phe Glu Asp Trp
             85                  90                  95

Gly Asp Val Lys Asn Gln Lys Ile Val Glu Glu Gly Gly Val Ala Ser
        100                 105                 110

Ala Gly Ile Glu Gln Thr Val Val Ser Asn Asp Ser Glu Ser Arg Lys
            115                 120                 125

<210> SEQ ID NO 110
<211> LENGTH: 1428
<212> TYPE: DNA
<213> ORGANISM: Thermoascus sp.
<220> FEATURE:
<221> NAME/KEY: CDS
<222> LOCATION: (1)..(1428)

<400> SEQUENCE: 110 gcg acg cct gcc gaa tgg cgc tcg cag tca att tac ttt tta ctc acc     48
Ala Thr Pro Ala Glu Trp Arg Ser Gln Ser Ile Tyr Phe Leu Leu Thr
 1               5                  10                  15 gat cgc ttt gcc cgc acc gac aac tcg aca acc gcc gaa tgt gat act     96
Asp Arg Phe Ala Arg Thr Asp Asn Ser Thr Thr Ala Glu Cys Asp Thr
             20                  25                  30 agt gcg gtg aag tac tgt ggc ggg act tgg cag gga atc att aac cag    144
Ser Ala Val Lys Tyr Cys Gly Gly Thr Trp Gln Gly Ile Ile Asn Gln
```

```
                35                  40                  45
ctg gac tac atc cag ggg atg ggc ttc aca gca acc tgg atc acc cca      192
Leu Asp Tyr Ile Gln Gly Met Gly Phe Thr Ala Thr Trp Ile Thr Pro
 50                  55                  60 gtg acc gcc aat ctc gag gat ggg cag cat ggg gag gca tac cat ggg      240
Val Thr Ala Asn Leu Glu Asp Gly Gln His Gly Glu Ala Tyr His Gly
 65                  70                  75                  80 tac tgg cag cag gat ata tat gcg ttg aac ccg cac ttt ggc act caa      288
Tyr Trp Gln Gln Asp Ile Tyr Ala Leu Asn Pro His Phe Gly Thr Gln
                 85                  90                  95 gac gac ctc cga gca ctg tct gac gcg ctg cac gac cga gga atg tac      336
Asp Asp Leu Arg Ala Leu Ser Asp Ala Leu His Asp Arg Gly Met Tyr
            100                 105                 110 ctt atg gtc gac gtg gtt gcc aat cat ttt ggc tac gac gcc ccc gcc      384
Leu Met Val Asp Val Val Ala Asn His Phe Gly Tyr Asp Ala Pro Ala
        115                 120                 125 gcg tcg gtc gac tac agc gtc ttc aac ccg ttt aac tcg gca gac tac      432
Ala Ser Val Asp Tyr Ser Val Phe Asn Pro Phe Asn Ser Ala Asp Tyr
    130                 135                 140 ttc cac act ccc tgc gat atc acg gac tac gac aac cag acc cag gtc      480
Phe His Thr Pro Cys Asp Ile Thr Asp Tyr Asp Asn Gln Thr Gln Val
145                 150                 155                 160 gag gat tgc tgg ctg tac acc gac gcc gtc agt ctg cca gat gtc gat      528
Glu Asp Cys Trp Leu Tyr Thr Asp Ala Val Ser Leu Pro Asp Val Asp
                165                 170                 175 acc acc aac gag gag gtc aag gag att tgg tac gac tgg gtg ggt gac      576
Thr Thr Asn Glu Glu Val Lys Glu Ile Trp Tyr Asp Trp Val Gly Asp
            180                 185                 190 ctt gtg tct aac tac tct atc gac ggg ctt cgc atc gac acc gct cgg      624
Leu Val Ser Asn Tyr Ser Ile Asp Gly Leu Arg Ile Asp Thr Ala Arg
        195                 200                 205 cac gta cag aag gac ttc tgg cgc gac tac aac gat gcc gcg ggc gtg      672
His Val Gln Lys Asp Phe Trp Arg Asp Tyr Asn Asp Ala Ala Gly Val
    210                 215                 220 tac tgc gtc ggc gag gtc ttc cag ggc gat ccc gat tac aca tgc ggg      720
Tyr Cys Val Gly Glu Val Phe Gln Gly Asp Pro Asp Tyr Thr Cys Gly
225                 230                 235                 240 tac cag gag gtt atg gac ggg gtg ctg aac tat ccc atc tac tac ccc      768
Tyr Gln Glu Val Met Asp Gly Val Leu Asn Tyr Pro Ile Tyr Tyr Pro
                245                 250                 255 ctg ttg cgc gct ttc agc tcc aca tct ggc agt ctc agc gat cta gcc      816
Leu Leu Arg Ala Phe Ser Ser Thr Ser Gly Ser Leu Ser Asp Leu Ala
            260                 265                 270 aac atg atc gaa acg gtc aag tac acc tgc tca gac gct acc ttg ctg      864
Asn Met Ile Glu Thr Val Lys Tyr Thr Cys Ser Asp Ala Thr Leu Leu
        275                 280                 285 ggc aac ttc atc gag aac cac gat aac cca cgc ttt gcc tcg tac acc      912
Gly Asn Phe Ile Glu Asn His Asp Asn Pro Arg Phe Ala Ser Tyr Thr
    290                 295                 300 gac gac atc tcc ctc gcc aag aac gtc gcc gcc ttc gtg atc ctc tcc      960
Asp Asp Ile Ser Leu Ala Lys Asn Val Ala Ala Phe Val Ile Leu Ser
305                 310                 315                 320 gac ggg atc ccc ata atc tac gcc ggt caa gaa cag cac tac tcc ggc     1008
Asp Gly Ile Pro Ile Ile Tyr Ala Gly Gln Glu Gln His Tyr Ser Gly
                325                 330                 335 gca gga gac ccg gca aac cgc gag gca acc tgg cta tcc ggt tac gac     1056
Ala Gly Asp Pro Ala Asn Arg Glu Ala Thr Trp Leu Ser Gly Tyr Asp
            340                 345                 350 aca acg agc gag ctg tac cag ttc att gcg aag acg aac cag atc cgg     1104
Thr Thr Ser Glu Leu Tyr Gln Phe Ile Ala Lys Thr Asn Gln Ile Arg
```

```
                    355                 360                 365
aat cat gct atc tgg cag aat gag acc tac ctt tct tac aaa aac tat    1152
Asn His Ala Ile Trp Gln Asn Glu Thr Tyr Leu Ser Tyr Lys Asn Tyr
        370                 375                 380 gct atc tac aac gag aac aac gtc ctt gtc atg cgc aaa gga ttc gac    1200
Ala Ile Tyr Asn Glu Asn Asn Val Leu Val Met Arg Lys Gly Phe Asp
385                 390                 395                 400 ggg tcg cag atc att aca atc ctc acg aac gct ggc gct gac gct ggt    1248
Gly Ser Gln Ile Ile Thr Ile Leu Thr Asn Ala Gly Ala Asp Ala Gly
                405                 410                 415 tca tcg act gtc tcg gtt ccg aac acc ggg ttc acg gct ggt gcg gca    1296
Ser Ser Thr Val Ser Val Pro Asn Thr Gly Phe Thr Ala Gly Ala Ala
        420                 425                 430 gtc act gag atc tat acc tgt gag gac att acg gtc tcg gac agc ggt    1344
Val Thr Glu Ile Tyr Thr Cys Glu Asp Ile Thr Val Ser Asp Ser Gly
435                 440                 445 gaa gtg tca gtg cct atg gag agc ggc ttg ccg agg gtt ctg tat ccg    1392
Glu Val Ser Val Pro Met Glu Ser Gly Leu Pro Arg Val Leu Tyr Pro
    450                 455                 460 aag gcg aag ctg gaa ggg agc ggg att tgc gac ctg                    1428
Lys Ala Lys Leu Glu Gly Ser Gly Ile Cys Asp Leu
465                 470                 475

<210> SEQ ID NO 111
<211> LENGTH: 476
<212> TYPE: PRT
<213> ORGANISM: Thermoascus sp.

<400> SEQUENCE: 111

Ala Thr Pro Ala Glu Trp Arg Ser Gln Ser Ile Tyr Phe Leu Leu Thr
1               5                   10                  15

Asp Arg Phe Ala Arg Thr Asp Asn Ser Thr Thr Ala Glu Cys Asp Thr
            20                  25                  30

Ser Ala Val Lys Tyr Cys Gly Gly Thr Trp Gln Gly Ile Ile Asn Gln
        35                  40                  45

Leu Asp Tyr Ile Gln Gly Met Gly Phe Thr Ala Thr Trp Ile Thr Pro
50                  55                  60

Val Thr Ala Asn Leu Glu Asp Gly Gln His Gly Glu Ala Tyr His Gly
65                  70                  75                  80

Tyr Trp Gln Gln Asp Ile Tyr Ala Leu Asn Pro His Phe Gly Thr Gln
                85                  90                  95

Asp Asp Leu Arg Ala Leu Ser Asp Ala Leu His Asp Arg Gly Met Tyr
            100                 105                 110

Leu Met Val Asp Val Val Ala Asn His Phe Gly Tyr Asp Ala Pro Ala
        115                 120                 125

Ala Ser Val Asp Tyr Ser Val Phe Asn Pro Phe Asn Ser Ala Asp Tyr
    130                 135                 140

Phe His Thr Pro Cys Asp Ile Asp Tyr Asp Asn Gln Thr Gln Val
145                 150                 155                 160

Glu Asp Cys Trp Leu Tyr Thr Asp Ala Val Ser Leu Pro Asp Val Asp
                165                 170                 175

Thr Thr Asn Glu Glu Val Lys Glu Ile Trp Tyr Asp Trp Val Gly Asp
            180                 185                 190

Leu Val Ser Asn Tyr Ser Ile Asp Gly Leu Arg Ile Asp Thr Ala Arg
        195                 200                 205

His Val Gln Lys Asp Phe Trp Arg Asp Tyr Asn Asp Ala Ala Gly Val
    210                 215                 220
```

```
Tyr Cys Val Gly Glu Val Phe Gln Gly Asp Pro Asp Tyr Thr Cys Gly
225                 230                 235                 240

Tyr Gln Glu Val Met Asp Gly Val Leu Asn Tyr Pro Ile Tyr Tyr Pro
            245                 250                 255

Leu Leu Arg Ala Phe Ser Ser Thr Ser Gly Ser Leu Ser Asp Leu Ala
        260                 265                 270

Asn Met Ile Glu Thr Val Lys Tyr Thr Cys Ser Asp Ala Thr Leu Leu
    275                 280                 285

Gly Asn Phe Ile Glu Asn His Asp Asn Pro Arg Phe Ala Ser Tyr Thr
290                 295                 300

Asp Asp Ile Ser Leu Ala Lys Asn Val Ala Ala Phe Val Ile Leu Ser
305                 310                 315                 320

Asp Gly Ile Pro Ile Ile Tyr Ala Gly Gln Glu Gln His Tyr Ser Gly
                325                 330                 335

Ala Gly Asp Pro Ala Asn Arg Glu Ala Thr Trp Leu Ser Gly Tyr Asp
            340                 345                 350

Thr Thr Ser Glu Leu Tyr Gln Phe Ile Ala Lys Thr Asn Gln Ile Arg
        355                 360                 365

Asn His Ala Ile Trp Gln Asn Glu Thr Tyr Leu Ser Tyr Lys Asn Tyr
    370                 375                 380

Ala Ile Tyr Asn Glu Asn Asn Val Leu Val Met Arg Lys Gly Phe Asp
385                 390                 395                 400

Gly Ser Gln Ile Ile Thr Ile Leu Thr Asn Ala Gly Ala Asp Ala Gly
                405                 410                 415

Ser Ser Thr Val Ser Val Pro Asn Thr Gly Phe Thr Ala Gly Ala Ala
            420                 425                 430

Val Thr Glu Ile Tyr Thr Cys Glu Asp Ile Thr Val Ser Asp Ser Gly
        435                 440                 445

Glu Val Ser Val Pro Met Glu Ser Gly Leu Pro Arg Val Leu Tyr Pro
    450                 455                 460

Lys Ala Lys Leu Glu Gly Ser Gly Ile Cys Asp Leu
465                 470                 475
```

```
<210> SEQ ID NO 112
<211> LENGTH: 1440
<212> TYPE: DNA
<213> ORGANISM: Coniocheata sp.
<220> FEATURE:
<221> NAME/KEY: CDS
<222> LOCATION: (1)..(1440)

<400> SEQUENCE: 112 ctc agc gcg gcc ggc tgg cgc cag cag tcc att tac cag gtc atg acg      48
Leu Ser Ala Ala Gly Trp Arg Gln Gln Ser Ile Tyr Gln Val Met Thr
1               5                   10                  15 gac cgc ttc gcg ccg acc gac ctg tcc acc acc gcc gca tgc gac acc      96
Asp Arg Phe Ala Pro Thr Asp Leu Ser Thr Thr Ala Ala Cys Asp Thr
                20                  25                  30 tcg gcc cag gcg tac tgc ggc ggc acg tac cag ggc ctc atc tcc aag     144
Ser Ala Gln Ala Tyr Cys Gly Gly Thr Tyr Gln Gly Leu Ile Ser Lys
            35                  40                  45 ctg gac tac atc cag ggc atg ggc ttc acc gcc gtg tgg ata tcg ccc     192
Leu Asp Tyr Ile Gln Gly Met Gly Phe Thr Ala Val Trp Ile Ser Pro
        50                  55                  60 atc gtc aag cag atg gac ggc aac acc gcc gac ggg tcc tcg tac cac     240
Ile Val Lys Gln Met Asp Gly Asn Thr Ala Asp Gly Ser Ser Tyr His
65                  70                  75                  80 ggg tac tgg gcg cag gac atc tgg agt ctg aac ccc tcc ttc ggc acg     288
```

```
                        -continued

Gly Tyr Trp Ala Gln Asp Ile Trp Ser Leu Asn Pro Ser Phe Gly Thr
                85                  90                  95 gcg ggc gac ctg atc gcg ctc tcc aat gcg ctg cac gcc cgc ggg atg    336
Ala Gly Asp Leu Ile Ala Leu Ser Asn Ala Leu His Ala Arg Gly Met
            100                 105                 110 tac ctg atg cta gac gtg gtg acg aac cac gtc gcc tac aag ggc tgc    384
Tyr Leu Met Leu Asp Val Val Thr Asn His Val Ala Tyr Lys Gly Cys
        115                 120                 125 ggc gcc tgc gtc gac tac agc ctc ttc acg ccg ttc gac tcg gcg tcc    432
Gly Ala Cys Val Asp Tyr Ser Leu Phe Thr Pro Phe Asp Ser Ala Ser
    130                 135                 140 tac ttc cac ccc ttc tgt ctg atc gac tac agc aac cag acc tcc atc    480
Tyr Phe His Pro Phe Cys Leu Ile Asp Tyr Ser Asn Gln Thr Ser Ile
145                 150                 155                 160 gag cag tgc tgg gag ggc gac aac acc gtc agc ctg ccc gac ctg cgg    528
Glu Gln Cys Trp Glu Gly Asp Asn Thr Val Ser Leu Pro Asp Leu Arg
                165                 170                 175 acc gag gac tcc tcc gtg cgc gcc atc tgg aac gac tgg att gcg cag    576
Thr Glu Asp Ser Ser Val Arg Ala Ile Trp Asn Asp Trp Ile Ala Gln
            180                 185                 190 gtc gtg gag acg tac ggc atc gac ggc ctg cgc gtc gac agc gtc aag    624
Val Val Glu Thr Tyr Gly Ile Asp Gly Leu Arg Val Asp Ser Val Lys
        195                 200                 205 cac cag gag acg tcg ttc tgg tcc ggc ttc ggg gcc gcc gcc ggc gtc    672
His Gln Glu Thr Ser Phe Trp Ser Gly Phe Gly Ala Ala Ala Gly Val
    210                 215                 220 ttc atg ctg ggc gag gtg tac aac ggc gac ccg gcg cag ctg gcg ccc    720
Phe Met Leu Gly Glu Val Tyr Asn Gly Asp Pro Ala Gln Leu Ala Pro
225                 230                 235                 240 tac cag gac tac atg ccg ggc ctg ctg gac tac gcg agc tac tac tgg    768
Tyr Gln Asp Tyr Met Pro Gly Leu Leu Asp Tyr Ala Ser Tyr Tyr Trp
                245                 250                 255 atc acg cgc gcc ttc cag tcg agc tcg gga agc atc agc aac ctt gcc    816
Ile Thr Arg Ala Phe Gln Ser Ser Ser Gly Ser Ile Ser Asn Leu Ala
            260                 265                 270 tcc ggc atc aac acg ctc aag ggc gtc gcg agg aac acc agc ctg tac    864
Ser Gly Ile Asn Thr Leu Lys Gly Val Ala Arg Asn Thr Ser Leu Tyr
        275                 280                 285 ggg agc ttc ctc gag aac cac gac cag ccg cgg ttc gcg tcg ctg act    912
Gly Ser Phe Leu Glu Asn His Asp Gln Pro Arg Phe Ala Ser Leu Thr
    290                 295                 300 gcg gat ctc gcg ctg gcc aag aac gcg atc gcg ttc acg atg ctg aaa    960
Ala Asp Leu Ala Leu Ala Lys Asn Ala Ile Ala Phe Thr Met Leu Lys
305                 310                 315                 320 gac ggc atc ccg gtc gtg tac cag ggc cag gag cag cac ttc gcc gga    1008
Asp Gly Ile Pro Val Val Tyr Gln Gly Gln Glu Gln His Phe Ala Gly
                325                 330                 335 gga aac gtg ccg gcc gac cgc gag gcg ctc tgg tcg tcg ggg tac gac    1056
Gly Asn Val Pro Ala Asp Arg Glu Ala Leu Trp Ser Ser Gly Tyr Asp
            340                 345                 350 acg tcc gcg acg ctg tac gcg tgg atc gca gcg ctg aat aag atc cgc    1104
Thr Ser Ala Thr Leu Tyr Ala Trp Ile Ala Ala Leu Asn Lys Ile Arg
        355                 360                 365 gcg agg gcc atc gcg cag gac ggc gcg tac ctg agc tac cag gcg tat    1152
Ala Arg Ala Ile Ala Gln Asp Gly Ala Tyr Leu Ser Tyr Gln Ala Tyr
    370                 375                 380 ccg gtg tac acg gac agc aac acc atc gcc atg cgc aaa gga cga gac    1200
Pro Val Tyr Thr Asp Ser Asn Thr Ile Ala Met Arg Lys Gly Arg Asp
385                 390                 395                 400 ggg tac cag atc gtc ggg gtg ttc acc aac aag ggc tcc tcg gga ggg    1248
```

| | | | | | | | | | | | | | |
|---|---|---|---|---|---|---|---|---|---|---|---|---|---|
|Gly|Tyr|Gln|Ile|Val|Gly|Val|Phe|Thr|Asn|Lys|Gly|Ser|Ser|Gly|Gly|
| | | |405| | | |410| | | |415| | | |

```
acg tcg agc gtc acg ctc acg acg tcg atg acg ggg ttt act gcc ggc    1296
Thr Ser Ser Val Thr Leu Thr Thr Ser Met Thr Gly Phe Thr Ala Gly
            420                 425                 430 cag gcc gtg gtg gac gtc atg agc tgc acg acg ttc acg gcg gac tca    1344
Gln Ala Val Val Asp Val Met Ser Cys Thr Thr Phe Thr Ala Asp Ser
            435                 440                 445 agc ggc agc ctg ggc atc acg ctc tcg ggg ggg att cca agg gtg ttc    1392
Ser Gly Ser Leu Gly Ile Thr Leu Ser Gly Gly Ile Pro Arg Val Phe
    450                 455                 460 tac ccg agc gca agg ctg agc ggg tcc ggg ata tgc ggg tcc ggg agc    1440
Tyr Pro Ser Ala Arg Leu Ser Gly Ser Gly Ile Cys Gly Ser Gly Ser
465                 470                 475                 480
```

<210> SEQ ID NO 113
<211> LENGTH: 480
<212> TYPE: PRT
<213> ORGANISM: Coniocheata sp.

<400> SEQUENCE: 113

Leu Ser Ala Ala Gly Trp Arg Gln Gln Ser Ile Tyr Gln Val Met Thr
1               5                   10                  15

Asp Arg Phe Ala Pro Thr Asp Leu Ser Thr Thr Ala Ala Cys Asp Thr
            20                  25                  30

Ser Ala Gln Ala Tyr Cys Gly Gly Thr Tyr Gln Gly Leu Ile Ser Lys
        35                  40                  45

Leu Asp Tyr Ile Gln Gly Met Gly Phe Thr Ala Val Trp Ile Ser Pro
50                  55                  60

Ile Val Lys Gln Met Asp Gly Asn Thr Ala Asp Gly Ser Ser Tyr His
65                  70                  75                  80

Gly Tyr Trp Ala Gln Asp Ile Trp Ser Leu Asn Pro Ser Phe Gly Thr
                85                  90                  95

Ala Gly Asp Leu Ile Ala Leu Ser Asn Ala Leu His Ala Arg Gly Met
            100                 105                 110

Tyr Leu Met Leu Asp Val Val Thr Asn His Val Ala Tyr Lys Gly Cys
        115                 120                 125

Gly Ala Cys Val Asp Tyr Ser Leu Phe Thr Pro Phe Asp Ser Ala Ser
    130                 135                 140

Tyr Phe His Pro Phe Cys Leu Ile Asp Tyr Ser Asn Gln Thr Ser Ile
145                 150                 155                 160

Glu Gln Cys Trp Glu Gly Asp Asn Thr Val Ser Leu Pro Asp Leu Arg
                165                 170                 175

Thr Glu Asp Ser Ser Val Arg Ala Ile Trp Asn Asp Trp Ile Ala Gln
            180                 185                 190

Val Val Glu Thr Tyr Gly Ile Asp Gly Leu Arg Val Asp Ser Val Lys
        195                 200                 205

His Gln Glu Thr Ser Phe Trp Ser Gly Phe Gly Ala Ala Ala Gly Val
    210                 215                 220

Phe Met Leu Gly Glu Val Tyr Asn Gly Asp Pro Ala Gln Leu Ala Pro
225                 230                 235                 240

Tyr Gln Asp Tyr Met Pro Gly Leu Leu Asp Tyr Ala Ser Tyr Tyr Trp
                245                 250                 255

Ile Thr Arg Ala Phe Gln Ser Ser Gly Ser Ile Ser Asn Leu Ala
            260                 265                 270

Ser Gly Ile Asn Thr Leu Lys Gly Val Ala Arg Asn Thr Ser Leu Tyr
        275                 280                 285

```
Gly Ser Phe Leu Glu Asn His Asp Gln Pro Arg Phe Ala Ser Leu Thr
            290                 295                 300
Ala Asp Leu Ala Leu Ala Lys Asn Ala Ile Ala Phe Thr Met Leu Lys
305                 310                 315                 320
Asp Gly Ile Pro Val Val Tyr Gln Gly Gln Glu Gln His Phe Ala Gly
                    325                 330                 335
Gly Asn Val Pro Ala Asp Arg Glu Ala Leu Trp Ser Ser Gly Tyr Asp
                340                 345                 350
Thr Ser Ala Thr Leu Tyr Ala Trp Ile Ala Ala Leu Asn Lys Ile Arg
            355                 360                 365
Ala Arg Ala Ile Ala Gln Asp Gly Ala Tyr Leu Ser Tyr Gln Ala Tyr
370                 375                 380
Pro Val Tyr Thr Asp Ser Asn Thr Ile Ala Met Arg Lys Gly Arg Asp
385                 390                 395                 400
Gly Tyr Gln Ile Val Gly Val Phe Thr Asn Lys Gly Ser Ser Gly Gly
                    405                 410                 415
Thr Ser Ser Val Thr Leu Thr Thr Ser Met Thr Gly Phe Thr Ala Gly
                420                 425                 430
Gln Ala Val Asp Val Met Ser Cys Thr Thr Phe Thr Ala Asp Ser
            435                 440                 445
Ser Gly Ser Leu Gly Ile Thr Leu Ser Gly Gly Ile Pro Arg Val Phe
450                 455                 460
Tyr Pro Ser Ala Arg Leu Ser Gly Ser Gly Ile Cys Gly Ser Gly Ser
465                 470                 475                 480

<210> SEQ ID NO 114
<211> LENGTH: 1326
<212> TYPE: DNA
<213> ORGANISM: Nectria sp.
<220> FEATURE:
<221> NAME/KEY: CDS
<222> LOCATION: (1)..(1326)

<400> SEQUENCE: 114 gct gat acg gcg gcg tgg aag tcc cgc aac atc tac ttc gct ttg act      48
Ala Asp Thr Ala Ala Trp Lys Ser Arg Asn Ile Tyr Phe Ala Leu Thr
1               5                   10                  15 gac cgt att gcc cgc tct gct gat gac ggc ggc ggc gat gca tgc gga      96
Asp Arg Ile Ala Arg Ser Ala Asp Asp Gly Gly Gly Asp Ala Cys Gly
                20                  25                  30 aac ttg ggt cag tat tgt ggt ggc acc ttt aag ggc ctc gag ggc aag     144
Asn Leu Gly Gln Tyr Cys Gly Gly Thr Phe Lys Gly Leu Glu Gly Lys
            35                  40                  45 ctt gat tac atc aag gga atg ggg ttc gac gcc atc tgg att aca cca     192
Leu Asp Tyr Ile Lys Gly Met Gly Phe Asp Ala Ile Trp Ile Thr Pro
        50                  55                  60 gtt gtt caa aac agt cct ggt ggt tac cac ggc tac tgg gca aca gac     240
Val Val Gln Asn Ser Pro Gly Gly Tyr His Gly Tyr Trp Ala Thr Asp
65                  70                  75                  80 ctc tac tct gtc aac tcc gaa tat gga act gca gat gac ctg aag agc     288
Leu Tyr Ser Val Asn Ser Glu Tyr Gly Thr Ala Asp Asp Leu Lys Ser
                85                  90                  95 ctc gta gct act gct cat gac aag ggc att tat atc atg gcc gat gtg     336
Leu Val Ala Thr Ala His Asp Lys Gly Ile Tyr Ile Met Ala Asp Val
            100                 105                 110 gta gca aac cac atg ggc cct act gat att tca gca aac aag ccg gag     384
Val Ala Asn His Met Gly Pro Thr Asp Ile Ser Ala Asn Lys Pro Glu
        115                 120                 125
```

| | | | | | | | | | | | | | | | | |
|---|---|---|---|---|---|---|---|---|---|---|---|---|---|---|---|---|
| cct | ctc | aac | caa | ggt | tca | tcc | tat | cat | gac | aac | tgc | gac | atc | aac | tat | 432 |
| Pro | Leu | Asn | Gln | Gly | Ser | Ser | Tyr | His | Asp | Asn | Cys | Asp | Ile | Asn | Tyr | |
| | 130 | | | | 135 | | | | | 140 | | | | | | |

| | | | | | | | | | | | | | | | | |
|---|---|---|---|---|---|---|---|---|---|---|---|---|---|---|---|---|
| aat | gac | caa | aat | agt | atc | gag | acg | tgc | cgc | att | gcc | ggt | ctc | cca | gat | 480 |
| Asn | Asp | Gln | Asn | Ser | Ile | Glu | Thr | Cys | Arg | Ile | Ala | Gly | Leu | Pro | Asp | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gtc | aag | aca | gag | gat | gag | act | atc | cga | acc | ctc | tat | aaa | gat | tgg | atc | 528 |
| Val | Lys | Thr | Glu | Asp | Glu | Thr | Ile | Arg | Thr | Leu | Tyr | Lys | Asp | Trp | Ile | |
| | | | | | 165 | | | | | 170 | | | | | 175 | |

| | | | | | | | | | | | | | | | | |
|---|---|---|---|---|---|---|---|---|---|---|---|---|---|---|---|---|
| aag | tgg | ctt | gtt | gaa | gag | tac | tct | ttc | gac | ggc | att | cgc | att | gac | act | 576 |
| Lys | Trp | Leu | Val | Glu | Glu | Tyr | Ser | Phe | Asp | Gly | Ile | Arg | Ile | Asp | Thr | |
| | | | 180 | | | | | 185 | | | | | 190 | | | |

| | | | | | | | | | | | | | | | | |
|---|---|---|---|---|---|---|---|---|---|---|---|---|---|---|---|---|
| gtt | aag | cat | gtt | gaa | aag | agc | ttc | tgg | cct | gga | ttc | gcc | gag | gcc | gca | 624 |
| Val | Lys | His | Val | Glu | Lys | Ser | Phe | Trp | Pro | Gly | Phe | Ala | Glu | Ala | Ala | |
| | | 195 | | | | | 200 | | | | | 205 | | | | |

| | | | | | | | | | | | | | | | | |
|---|---|---|---|---|---|---|---|---|---|---|---|---|---|---|---|---|
| ggg | gtc | tac | tcc | atc | ggc | gaa | gtc | ttc | gac | gga | ggc | cca | gac | tac | ctc | 672 |
| Gly | Val | Tyr | Ser | Ile | Gly | Glu | Val | Phe | Asp | Gly | Gly | Pro | Asp | Tyr | Leu | |
| | 210 | | | | | 215 | | | | | 220 | | | | | |

| | | | | | | | | | | | | | | | | |
|---|---|---|---|---|---|---|---|---|---|---|---|---|---|---|---|---|
| gct | ggc | tac | gcg | agc | gtt | ttg | cct | ggt | ctt | ctt | aac | tat | gcc | atc | tat | 720 |
| Ala | Gly | Tyr | Ala | Ser | Val | Leu | Pro | Gly | Leu | Leu | Asn | Tyr | Ala | Ile | Tyr | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| tat | ccc | atg | aac | agg | ttc | tat | cag | cag | gcg | ggt | tca | tcg | caa | gac | ctg | 768 |
| Tyr | Pro | Met | Asn | Arg | Phe | Tyr | Gln | Gln | Ala | Gly | Ser | Ser | Gln | Asp | Leu | |
| | | | | 245 | | | | | 250 | | | | | 255 | | |

| | | | | | | | | | | | | | | | | |
|---|---|---|---|---|---|---|---|---|---|---|---|---|---|---|---|---|
| gct | aat | atg | gtt | gac | gag | gtc | tcg | tcc | aag | ttc | ccc | gac | cct | tcc | gct | 816 |
| Ala | Asn | Met | Val | Asp | Glu | Val | Ser | Ser | Lys | Phe | Pro | Asp | Pro | Ser | Ala | |
| | | | 260 | | | | | 265 | | | | | 270 | | | |

| | | | | | | | | | | | | | | | | |
|---|---|---|---|---|---|---|---|---|---|---|---|---|---|---|---|---|
| ctt | ggt | act | ttc | ctc | gat | aat | cac | gac | aac | gcg | cgt | tgg | ctc | aac | acc | 864 |
| Leu | Gly | Thr | Phe | Leu | Asp | Asn | His | Asp | Asn | Ala | Arg | Trp | Leu | Asn | Thr | |
| | | 275 | | | | | 280 | | | | | 285 | | | | |

| | | | | | | | | | | | | | | | | |
|---|---|---|---|---|---|---|---|---|---|---|---|---|---|---|---|---|
| aag | aac | gac | aag | act | ctg | ctc | aag | aac | gcc | ctg | gct | tat | gtg | atc | ctc | 912 |
| Lys | Asn | Asp | Lys | Thr | Leu | Leu | Lys | Asn | Ala | Leu | Ala | Tyr | Val | Ile | Leu | |
| | 290 | | | | | 295 | | | | | 300 | | | | | |

| | | | | | | | | | | | | | | | | |
|---|---|---|---|---|---|---|---|---|---|---|---|---|---|---|---|---|
| gcc | cga | ggt | atc | ccc | atc | gtc | tat | tat | gga | acc | gaa | cag | ggg | tac | gct | 960 |
| Ala | Arg | Gly | Ile | Pro | Ile | Val | Tyr | Tyr | Gly | Thr | Glu | Gln | Gly | Tyr | Ala | |
| 305 | | | | | 310 | | | | | 315 | | | | | 320 | |

| | | | | | | | | | | | | | | | | |
|---|---|---|---|---|---|---|---|---|---|---|---|---|---|---|---|---|
| ggc | ggt | aac | gac | cca | gcc | aac | cgc | gaa | gat | ctc | tgg | cgc | agc | agc | ttc | 1008 |
| Gly | Gly | Asn | Asp | Pro | Ala | Asn | Arg | Glu | Asp | Leu | Trp | Arg | Ser | Ser | Phe | |
| | | | 325 | | | | | 330 | | | | | 335 | | | |

| | | | | | | | | | | | | | | | | |
|---|---|---|---|---|---|---|---|---|---|---|---|---|---|---|---|---|
| agc | act | gat | gcg | gaa | ctt | tac | caa | gcc | att | aag | cgt | ctc | tct | gct | gct | 1056 |
| Ser | Thr | Asp | Ala | Glu | Leu | Tyr | Gln | Ala | Ile | Lys | Arg | Leu | Ser | Ala | Ala | |
| | | | 340 | | | | | 345 | | | | | 350 | | | |

| | | | | | | | | | | | | | | | | |
|---|---|---|---|---|---|---|---|---|---|---|---|---|---|---|---|---|
| aga | tct | gcc | gtc | ggt | ggc | cta | gct | gcg | gac | gat | cat | caa | cat | gtc | ctt | 1104 |
| Arg | Ser | Ala | Val | Gly | Gly | Leu | Ala | Ala | Asp | Asp | His | Gln | His | Val | Leu | |
| | 355 | | | | | 360 | | | | | 365 | | | | | |

| | | | | | | | | | | | | | | | | |
|---|---|---|---|---|---|---|---|---|---|---|---|---|---|---|---|---|
| gtg | tct | gac | ggt | gtt | tac | gct | tgg | aag | cgc | gct | ggt | gga | gac | ctc | gtt | 1152 |
| Val | Ser | Asp | Gly | Val | Tyr | Ala | Trp | Lys | Arg | Ala | Gly | Gly | Asp | Leu | Val | |
| | 370 | | | | | 375 | | | | | 380 | | | | | |

| | | | | | | | | | | | | | | | | |
|---|---|---|---|---|---|---|---|---|---|---|---|---|---|---|---|---|
| gtt | ctc | aca | acc | aac | agt | ggt | agc | agt | ggt | ggt | ggt | gag | cgt | tgc | ctg | 1200 |
| Val | Leu | Thr | Thr | Asn | Ser | Gly | Ser | Ser | Gly | Gly | Gly | Glu | Arg | Cys | Leu | |
| 385 | | | | | 390 | | | | | 395 | | | | | 400 | |

| | | | | | | | | | | | | | | | | |
|---|---|---|---|---|---|---|---|---|---|---|---|---|---|---|---|---|
| caa | act | gga | cgg | gct | aac | caa | aaa | tac | gat | gac | gca | ttc | ggt | gat | ggc | 1248 |
| Gln | Thr | Gly | Arg | Ala | Asn | Gln | Lys | Tyr | Asp | Asp | Ala | Phe | Gly | Asp | Gly | |
| | | | 405 | | | | | 410 | | | | | 415 | | | |

| | | | | | | | | | | | | | | | | |
|---|---|---|---|---|---|---|---|---|---|---|---|---|---|---|---|---|
| tct | tat | acc | gct | gat | gga | aat | ggg | cag | gtc | tgc | gtt | act | atc | tcc | ggc | 1296 |
| Ser | Tyr | Thr | Ala | Asp | Gly | Asn | Gly | Gln | Val | Cys | Val | Thr | Ile | Ser | Gly | |
| | | | 420 | | | | | 425 | | | | | 430 | | | |

| | | | | | | | | |
|---|---|---|---|---|---|---|---|---|
| ggt | aac | cct | gtg | gtg | ctg | gtg | gct | tcg | gga | 1326 |
| Gly | Asn | Pro | Val | Val | Leu | Val | Ala | Ser | Gly | |
| | 435 | | | | | 440 | | | | |

```
<210> SEQ ID NO 115
<211> LENGTH: 442
<212> TYPE: PRT
<213> ORGANISM: Nectria sp.

<400> SEQUENCE: 115
```

| | | | | | | | | | | | | | | |
|---|---|---|---|---|---|---|---|---|---|---|---|---|---|---|
| Ala | Asp | Thr | Ala | Ala | Trp | Lys | Ser | Arg | Asn | Ile | Tyr | Phe | Ala | Leu | Thr |
| 1 | | | | 5 | | | | | 10 | | | | | 15 | |
| Asp | Arg | Ile | Ala | Arg | Ser | Ala | Asp | Asp | Gly | Gly | Gly | Asp | Ala | Cys | Gly |
| | | | 20 | | | | | 25 | | | | | 30 | | |
| Asn | Leu | Gly | Gln | Tyr | Cys | Gly | Gly | Thr | Phe | Lys | Gly | Leu | Glu | Gly | Lys |
| | | | 35 | | | | | 40 | | | | | 45 | | |
| Leu | Asp | Tyr | Ile | Lys | Gly | Met | Gly | Phe | Asp | Ala | Ile | Trp | Ile | Thr | Pro |
| 50 | | | | | 55 | | | | | 60 | | | | | |
| Val | Val | Gln | Asn | Ser | Pro | Gly | Gly | Tyr | His | Gly | Tyr | Trp | Ala | Thr | Asp |
| 65 | | | | | 70 | | | | | 75 | | | | | 80 |
| Leu | Tyr | Ser | Val | Asn | Ser | Glu | Tyr | Gly | Thr | Ala | Asp | Asp | Leu | Lys | Ser |
| | | | | 85 | | | | | 90 | | | | | 95 | |
| Leu | Val | Ala | Thr | Ala | His | Asp | Lys | Gly | Ile | Tyr | Ile | Met | Ala | Asp | Val |
| | | | 100 | | | | | 105 | | | | | 110 | | |
| Val | Ala | Asn | His | Met | Gly | Pro | Thr | Asp | Ile | Ser | Ala | Asn | Lys | Pro | Glu |
| | | | 115 | | | | | 120 | | | | | 125 | | |
| Pro | Leu | Asn | Gln | Gly | Ser | Ser | Tyr | His | Asp | Asn | Cys | Asp | Ile | Asn | Tyr |
| | | 130 | | | | | 135 | | | | | 140 | | | |
| Asn | Asp | Gln | Asn | Ser | Ile | Glu | Thr | Cys | Arg | Ile | Ala | Gly | Leu | Pro | Asp |
| 145 | | | | | 150 | | | | | 155 | | | | | 160 |
| Val | Lys | Thr | Glu | Asp | Glu | Thr | Ile | Arg | Thr | Leu | Tyr | Lys | Asp | Trp | Ile |
| | | | | 165 | | | | | 170 | | | | | 175 | |
| Lys | Trp | Leu | Val | Glu | Glu | Tyr | Ser | Phe | Asp | Gly | Ile | Arg | Ile | Asp | Thr |
| | | | 180 | | | | | 185 | | | | | 190 | | |
| Val | Lys | His | Val | Glu | Lys | Ser | Phe | Trp | Pro | Gly | Phe | Ala | Glu | Ala | Ala |
| | | | 195 | | | | | 200 | | | | | 205 | | |
| Gly | Val | Tyr | Ser | Ile | Gly | Glu | Val | Phe | Asp | Gly | Pro | Asp | Tyr | Leu |
| | | 210 | | | | | 215 | | | | | 220 | | | |
| Ala | Gly | Tyr | Ala | Ser | Val | Leu | Pro | Gly | Leu | Leu | Asn | Tyr | Ala | Ile | Tyr |
| 225 | | | | | 230 | | | | | 235 | | | | | 240 |
| Tyr | Pro | Met | Asn | Arg | Phe | Tyr | Gln | Gln | Ala | Gly | Ser | Ser | Gln | Asp | Leu |
| | | | | 245 | | | | | 250 | | | | | 255 | |
| Ala | Asn | Met | Val | Asp | Glu | Val | Ser | Ser | Lys | Phe | Pro | Asp | Pro | Ser | Ala |
| | | | 260 | | | | | 265 | | | | | 270 | | |
| Leu | Gly | Thr | Phe | Leu | Asp | Asn | His | Asp | Asn | Ala | Arg | Trp | Leu | Asn | Thr |
| | | | 275 | | | | | 280 | | | | | 285 | | |
| Lys | Asn | Asp | Lys | Thr | Leu | Leu | Lys | Asn | Ala | Leu | Ala | Tyr | Val | Ile | Leu |
| | | 290 | | | | | 295 | | | | | 300 | | | |
| Ala | Arg | Gly | Ile | Pro | Ile | Val | Tyr | Tyr | Gly | Thr | Glu | Gln | Gly | Tyr | Ala |
| 305 | | | | | 310 | | | | | 315 | | | | | 320 |
| Gly | Gly | Asn | Asp | Pro | Ala | Asn | Arg | Glu | Asp | Leu | Trp | Arg | Ser | Ser | Phe |
| | | | | 325 | | | | | 330 | | | | | 335 | |
| Ser | Thr | Asp | Ala | Glu | Leu | Tyr | Gln | Ala | Ile | Lys | Arg | Leu | Ser | Ala | Ala |
| | | | 340 | | | | | 345 | | | | | 350 | | |
| Arg | Ser | Ala | Val | Gly | Gly | Leu | Ala | Ala | Asp | His | Gln | His | Val | Leu |
| | | | 355 | | | | | 360 | | | | | 365 | | |
| Val | Ser | Asp | Gly | Val | Tyr | Ala | Trp | Lys | Arg | Ala | Gly | Gly | Asp | Leu | Val |
| | | 370 | | | | | 375 | | | | | 380 | | | |

```
Val Leu Thr Thr Asn Ser Gly Ser Gly Gly Glu Arg Cys Leu
385                 390                 395                 400

Gln Thr Gly Arg Ala Asn Gln Lys Tyr Asp Asp Ala Phe Gly Asp Gly
                405                 410                 415

Ser Tyr Thr Ala Asp Gly Asn Gly Gln Val Cys Val Thr Ile Ser Gly
            420                 425                 430

Gly Asn Pro Val Val Leu Val Ala Ser Gly
        435                 440

<210> SEQ ID NO 116
<211> LENGTH: 1323
<212> TYPE: DNA
<213> ORGANISM: Fusarium sp.
<220> FEATURE:
<221> NAME/KEY: CDS
<222> LOCATION: (1)..(1323)

<400> SEQUENCE: 116 gcg gac gca aac gct tgg aag tcg cga aac atc tat ttc gca ctt act    48
Ala Asp Ala Asn Ala Trp Lys Ser Arg Asn Ile Tyr Phe Ala Leu Thr
1               5                   10                  15 gat cgt gtt gcg cga agc gct gac gat aat ggc ggt agt gca tgc gga    96
Asp Arg Val Ala Arg Ser Ala Asp Asp Asn Gly Gly Ser Ala Cys Gly
            20                  25                  30 aac ctc gga aat tat tgt ggt gga act ttc aag ggt ctc gag tcg aag   144
Asn Leu Gly Asn Tyr Cys Gly Gly Thr Phe Lys Gly Leu Glu Ser Lys
        35                  40                  45 ctt gat tat atc aag ggc atg gga ttt gat gct atc tgg att act ccc   192
Leu Asp Tyr Ile Lys Gly Met Gly Phe Asp Ala Ile Trp Ile Thr Pro
    50                  55                  60 gtt gtt gac aat act gat gga gga tac cac gga tac tgg gcc aag gat   240
Val Val Asp Asn Thr Asp Gly Gly Tyr His Gly Tyr Trp Ala Lys Asp
65                  70                  75                  80 ctt tat gcg gtc aac ccc aag tat ggt act gca gat gac ttg aag agt   288
Leu Tyr Ala Val Asn Pro Lys Tyr Gly Thr Ala Asp Asp Leu Lys Ser
                85                  90                  95 ctt gtc aag tct gct cat gac aag aac atg tac gtc atg tgc gac gtg   336
Leu Val Lys Ser Ala His Asp Lys Asn Met Tyr Val Met Cys Asp Val
            100                 105                 110 gtc gca aac cac atg ggc aaa gga atc tca gac cac aaa ccc tcg ccc   384
Val Ala Asn His Met Gly Lys Gly Ile Ser Asp His Lys Pro Ser Pro
        115                 120                 125 ctc aac gaa caa agc tca tac cac act cct tgc gac atc gac tac agc   432
Leu Asn Glu Gln Ser Ser Tyr His Thr Pro Cys Asp Ile Asp Tyr Ser
    130                 135                 140 aac cag aac agc att gaa cag tgc gaa atc gcc ggt ctt cca gat ctc   480
Asn Gln Asn Ser Ile Glu Gln Cys Glu Ile Ala Gly Leu Pro Asp Leu
145                 150                 155                 160 aac acc ggc agc gac act gtc aag aag gtc ctc tac gac tgg atc aaa   528
Asn Thr Gly Ser Asp Thr Val Lys Lys Val Leu Tyr Asp Trp Ile Lys
                165                 170                 175 tgg ctc gtc tct gag tac agc ttc gac ggt atc cgc atc gac act gtc   576
Trp Leu Val Ser Glu Tyr Ser Phe Asp Gly Ile Arg Ile Asp Thr Val
            180                 185                 190 aag cat gtt gaa aag ccc ttc tgg cct ggt ttc caa gac gcc gct ggt   624
Lys His Val Glu Lys Pro Phe Trp Pro Gly Phe Gln Asp Ala Ala Gly
        195                 200                 205 gtt tac gcc atc ggt gaa gtc tgg gac gga ggt cct gat tat ctc gct   672
Val Tyr Ala Ile Gly Glu Val Trp Asp Gly Gly Pro Asp Tyr Leu Ala
    210                 215                 220 ggt tat gcc cag gtc atg cct ggt ctt ttg aac tac gct atg tac tac   720
```

```
                Gly Tyr Ala Gln Val Met Pro Gly Leu Leu Asn Tyr Ala Met Tyr Tyr
                225                 230                 235                 240 ccc atg aac cgc ttt tac cag caa aag gga gat cct tca gat gtt gtc        768
Pro Met Asn Arg Phe Tyr Gln Gln Lys Gly Asp Pro Ser Asp Val Val
                245                 250                 255 gcc atg cac gat gag att agc aac aaa ttc cct gat ccc act atc ctc        816
Ala Met His Asp Glu Ile Ser Asn Lys Phe Pro Asp Pro Thr Ile Leu
                260                 265                 270 gga aca ttc atc gac aac cac gat aac cct cgt tgg ctc agc cag aag        864
Gly Thr Phe Ile Asp Asn His Asp Asn Pro Arg Trp Leu Ser Gln Lys
                275                 280                 285 aat gac aaa gct ctt ctg aag aac gcc ctc gca tac gtt atc ctt gct        912
Asn Asp Lys Ala Leu Leu Lys Asn Ala Leu Ala Tyr Val Ile Leu Ala
                290                 295                 300 cga gga att ccc atc gtc tac tac gga aca gag caa ggt tac gct ggc        960
Arg Gly Ile Pro Ile Val Tyr Tyr Gly Thr Glu Gln Gly Tyr Ala Gly
305                 310                 315                 320 ggc aat gac ccc gcc aac cgg gaa gat ctc tgg cga agc agt ttc agc       1008
Gly Asn Asp Pro Ala Asn Arg Glu Asp Leu Trp Arg Ser Ser Phe Ser
                325                 330                 335 acc aac gca gat ctc tac caa cac atc tcg cgt ctc tct aag gct cgg       1056
Thr Asn Ala Asp Leu Tyr Gln His Ile Ser Arg Leu Ser Lys Ala Arg
                340                 345                 350 tcg gca gtc ggt ggc ctc ggt gga aat gac cac aag cat ctt tac tct       1104
Ser Ala Val Gly Gly Leu Gly Gly Asn Asp His Lys His Leu Tyr Ser
                355                 360                 365 cag aac agc gcc tac gcc tgg agt cgt gcg gac ggc gat ctt atc gtg       1152
Gln Asn Ser Ala Tyr Ala Trp Ser Arg Ala Asp Gly Asp Leu Ile Val
                370                 375                 380 ctt acg ttg aac cgc ggt cag gga tac tca gga cag tac tgc ttc aac       1200
Leu Thr Leu Asn Arg Gly Gln Gly Tyr Ser Gly Gln Tyr Cys Phe Asn
385                 390                 395                 400 act gga aag aac aac aag act tgg gac aag gta ttt gga agt ggc act       1248
Thr Gly Lys Asn Asn Lys Thr Trp Asp Lys Val Phe Gly Ser Gly Thr
                405                 410                 415 gtt acc tct gat ggc aat gga cag gtt tgc gtt agc tac act aac ggt       1296
Val Thr Ser Asp Gly Asn Gly Gln Val Cys Val Ser Tyr Thr Asn Gly
                420                 425                 430 gag cct gag gtc ttg gtt gcc tct agc                                   1323
Glu Pro Glu Val Leu Val Ala Ser Ser
                435                 440

<210> SEQ ID NO 117
<211> LENGTH: 441
<212> TYPE: PRT
<213> ORGANISM: Fusarium sp.

<400> SEQUENCE: 117

Ala Asp Ala Asn Ala Trp Lys Ser Arg Asn Ile Tyr Phe Ala Leu Thr
1               5                   10                  15

Asp Arg Val Ala Arg Ser Ala Asp Asp Asn Gly Gly Ser Ala Cys Gly
                20                  25                  30

Asn Leu Gly Asn Tyr Cys Gly Gly Thr Phe Lys Gly Leu Glu Ser Lys
            35                  40                  45

Leu Asp Tyr Ile Lys Gly Met Gly Phe Asp Ala Ile Trp Ile Thr Pro
    50                  55                  60

Val Val Asp Asn Thr Asp Gly Gly Tyr His Gly Tyr Trp Ala Lys Asp
65                  70                  75                  80

Leu Tyr Ala Val Asn Pro Lys Tyr Gly Thr Ala Asp Asp Leu Lys Ser
                85                  90                  95
```

```
Leu Val Lys Ser Ala His Asp Lys Asn Met Tyr Val Met Cys Asp Val
            100                 105                 110

Val Ala Asn His Met Gly Lys Gly Ile Ser Asp His Lys Pro Ser Pro
        115                 120                 125

Leu Asn Glu Gln Ser Ser Tyr His Thr Pro Cys Asp Ile Asp Tyr Ser
    130                 135                 140

Asn Gln Asn Ser Ile Glu Gln Cys Glu Ile Ala Gly Leu Pro Asp Leu
145                 150                 155                 160

Asn Thr Gly Ser Asp Thr Val Lys Lys Val Leu Tyr Asp Trp Ile Lys
                165                 170                 175

Trp Leu Val Ser Glu Tyr Ser Phe Asp Gly Ile Arg Ile Asp Thr Val
            180                 185                 190

Lys His Val Glu Lys Pro Phe Trp Pro Gly Phe Gln Asp Ala Ala Gly
        195                 200                 205

Val Tyr Ala Ile Gly Glu Val Trp Asp Gly Gly Pro Asp Tyr Leu Ala
    210                 215                 220

Gly Tyr Ala Gln Val Met Pro Gly Leu Leu Asn Tyr Ala Met Tyr Tyr
225                 230                 235                 240

Pro Met Asn Arg Phe Tyr Gln Gln Lys Gly Asp Pro Ser Asp Val Val
                245                 250                 255

Ala Met His Asp Glu Ile Ser Asn Lys Phe Pro Asp Pro Thr Ile Leu
            260                 265                 270

Gly Thr Phe Ile Asp Asn His Asp Asn Pro Arg Trp Leu Ser Gln Lys
        275                 280                 285

Asn Asp Lys Ala Leu Leu Lys Asn Ala Leu Ala Tyr Val Ile Leu Ala
    290                 295                 300

Arg Gly Ile Pro Ile Val Tyr Tyr Gly Thr Glu Gln Gly Tyr Ala Gly
305                 310                 315                 320

Gly Asn Asp Pro Ala Asn Arg Glu Asp Leu Trp Arg Ser Ser Phe Ser
                325                 330                 335

Thr Asn Ala Asp Leu Tyr Gln His Ile Ser Arg Leu Ser Lys Ala Arg
            340                 345                 350

Ser Ala Val Gly Gly Leu Gly Gly Asn Asp His Lys His Leu Tyr Ser
        355                 360                 365

Gln Asn Ser Ala Tyr Ala Trp Ser Arg Ala Asp Gly Asp Leu Ile Val
    370                 375                 380

Leu Thr Leu Asn Arg Gly Gln Gly Tyr Ser Gly Gln Tyr Cys Phe Asn
385                 390                 395                 400

Thr Gly Lys Asn Asn Lys Thr Trp Asp Lys Val Phe Gly Ser Gly Thr
                405                 410                 415

Val Thr Ser Asp Gly Asn Gly Gln Val Cys Val Ser Tyr Thr Asn Gly
            420                 425                 430

Glu Pro Glu Val Leu Val Ala Ser Ser
        435                 440

<210> SEQ ID NO 118
<211> LENGTH: 1371
<212> TYPE: DNA
<213> ORGANISM: Trametes currogata
<220> FEATURE:
<221> NAME/KEY: CDS
<222> LOCATION: (1)..(1371)

<400> SEQUENCE: 118 gcg gat acg agt gca tgg aag tcc cgc agc atc tac ttc gtt ctg acc     48
Ala Asp Thr Ser Ala Trp Lys Ser Arg Ser Ile Tyr Phe Val Leu Thr
```

-continued

```
1               5                   10                  15
gat cgt gtt gct cga agc agc agc gac acc ggc ggt tcc tct tgc agc          96
Asp Arg Val Ala Arg Ser Ser Ser Asp Thr Gly Gly Ser Ser Cys Ser
             20                  25                  30 aac ctg ggc aat tac tgt gga gga act ttc aaa ggt ctc gaa tct aag         144
Asn Leu Gly Asn Tyr Cys Gly Gly Thr Phe Lys Gly Leu Glu Ser Lys
         35                  40                  45 ctg gat tac atc caa ggc ttg ggc ttt gac gct atc tgg atc acg cct         192
Leu Asp Tyr Ile Gln Gly Leu Gly Phe Asp Ala Ile Trp Ile Thr Pro
     50                  55                  60 gtc gtt gct aac agt gct ggt ggc tac cat ggc tat tgg gca caa gac         240
Val Val Ala Asn Ser Ala Gly Gly Tyr His Gly Tyr Trp Ala Gln Asp
 65                  70                  75                  80 ttg tat tct gtc aac tcg aat tat ggt act gca gac gac cta aag agc         288
Leu Tyr Ser Val Asn Ser Asn Tyr Gly Thr Ala Asp Asp Leu Lys Ser
                 85                  90                  95 ctg gtc agc tct gct cat gcg aag ggc ata tat gtg atg gtc gat gtc         336
Leu Val Ser Ser Ala His Ala Lys Gly Ile Tyr Val Met Val Asp Val
             100                 105                 110 gta gcc aat cat atg ggt aac ggt gca att gcc gat aac cgc cct gag         384
Val Ala Asn His Met Gly Asn Gly Ala Ile Ala Asp Asn Arg Pro Glu
         115                 120                 125 cct ttg aac cag gct tca tcc tac cac cca gcc tgc gac atc aac tac         432
Pro Leu Asn Gln Ala Ser Ser Tyr His Pro Ala Cys Asp Ile Asn Tyr
     130                 135                 140 gat aac cag acc agc atc gag cag tgc agc atc ggc ggt ctt gct gat         480
Asp Asn Gln Thr Ser Ile Glu Gln Cys Ser Ile Gly Gly Leu Ala Asp
145                 150                 155                 160 ctt aac act gag agt acc gag gtt cgc act gtt ctc aac acc tgg gtt         528
Leu Asn Thr Glu Ser Thr Glu Val Arg Thr Val Leu Asn Thr Trp Val
                 165                 170                 175 tca tgg ctc gtc gac gag tac agc ttc gac gga gta cgt atc gac aca         576
Ser Trp Leu Val Asp Glu Tyr Ser Phe Asp Gly Val Arg Ile Asp Thr
             180                 185                 190 gtc aag cac gtt caa aag gac ttc tgg cca gac ttc gtg tct tcc ata         624
Val Lys His Val Gln Lys Asp Phe Trp Pro Asp Phe Val Ser Ser Ile
         195                 200                 205 ggc gaa tac agc atc ggt gag gtg ttt gac ggc aac cct cca tac ctc         672
Gly Glu Tyr Ser Ile Gly Glu Val Phe Asp Gly Asn Pro Pro Tyr Leu
     210                 215                 220 gct gag tat gcc aag ctc atg cct ggg gtt cta aac tat gca gtc tac         720
Ala Glu Tyr Ala Lys Leu Met Pro Gly Val Leu Asn Tyr Ala Val Tyr
225                 230                 235                 240 tac ccc atg aat gcc ttc tac cag caa acg ggc tca tct cag gca ctg         768
Tyr Pro Met Asn Ala Phe Tyr Gln Gln Thr Gly Ser Ser Gln Ala Leu
                 245                 250                 255 gtc gac atg atg aac acg att agc agc aca ttc cca gac ccc tca gca         816
Val Asp Met Met Asn Thr Ile Ser Ser Thr Phe Pro Asp Pro Ser Ala
             260                 265                 270 ctc ggc acg ttc ctc gac aac cac gac aac ccg cgc tgg cta aac gtg         864
Leu Gly Thr Phe Leu Asp Asn His Asp Asn Pro Arg Trp Leu Asn Val
         275                 280                 285 aag aac gac cag aca ctc ctg aag aac gca cta gcc tac gtc att cta         912
Lys Asn Asp Gln Thr Leu Leu Lys Asn Ala Leu Ala Tyr Val Ile Leu
     290                 295                 300 gcc cga ggc att ccc atc cta tac tac ggc acc gag caa ggt tac tcc         960
Ala Arg Gly Ile Pro Ile Leu Tyr Tyr Gly Thr Glu Gln Gly Tyr Ser
305                 310                 315                 320 gga ggc gcc gac cca gca aac cgc gaa gat ctt tgg cgc agc agc ttc        1008
Gly Gly Ala Asp Pro Ala Asn Arg Glu Asp Leu Trp Arg Ser Ser Phe
```

```
                325                 330                 335
aat aca aac gcg gac ctc tac caa tcc atc aaa aag ctc acc gca gcc    1056
Asn Thr Asn Ala Asp Leu Tyr Gln Ser Ile Lys Lys Leu Thr Ala Ala
            340                 345                 350 cga aaa gcc gcc ggc ggc ctc gcc ggc aac gac cac acg cat ctc tac    1104
Arg Lys Ala Ala Gly Gly Leu Ala Gly Asn Asp His Thr His Leu Tyr
        355                 360                 365 gtc gcc gac acg gca tat gcc tgg agc cgg gca aac ggc gcc ctc atc    1152
Val Ala Asp Thr Ala Tyr Ala Trp Ser Arg Ala Asn Gly Ala Leu Ile
    370                 375                 380 gtg ctc acc acc aac gcc ggc agc agc tcc aac gcg caa cac tgc ttc    1200
Val Leu Thr Thr Asn Ala Gly Ser Ser Ser Asn Ala Gln His Cys Phe
385                 390                 395                 400 aac acg cag atg gca aac ggg aaa tgg acg aac acg tat ggt gat ggc    1248
Asn Thr Gln Met Ala Asn Gly Lys Trp Thr Asn Thr Tyr Gly Asp Gly
                405                 410                 415 gca acg gtg acc gcg gat tcc agc ggt aat atc tgc gtc acc gtt agc    1296
Ala Thr Val Thr Ala Asp Ser Ser Gly Asn Ile Cys Val Thr Val Ser
            420                 425                 430 aac ggc gag cct gtt gtc ctc gtc gcc agc gca tca aca acg ggg gtt    1344
Asn Gly Glu Pro Val Val Leu Val Ala Ser Ala Ser Thr Thr Gly Val
        435                 440                 445 acg ccc act aca gct aca acg ctg cgc                                1371
Thr Pro Thr Thr Ala Thr Thr Leu Arg
    450                 455

<210> SEQ ID NO 119
<211> LENGTH: 457
<212> TYPE: PRT
<213> ORGANISM: Trametes currogata

<400> SEQUENCE: 119

Ala Asp Thr Ser Ala Trp Lys Ser Arg Ser Ile Tyr Phe Val Leu Thr
1               5                   10                  15

Asp Arg Val Ala Arg Ser Ser Asp Thr Gly Gly Ser Ser Cys Ser
            20                  25                  30

Asn Leu Gly Asn Tyr Cys Gly Gly Thr Phe Lys Gly Leu Glu Ser Lys
        35                  40                  45

Leu Asp Tyr Ile Gln Gly Leu Gly Phe Asp Ala Ile Trp Ile Thr Pro
    50                  55                  60

Val Val Ala Asn Ser Ala Gly Gly Tyr His Gly Tyr Trp Ala Gln Asp
65                  70                  75                  80

Leu Tyr Ser Val Asn Ser Asn Tyr Gly Thr Ala Asp Asp Leu Lys Ser
                85                  90                  95

Leu Val Ser Ala His Ala Lys Gly Ile Tyr Val Met Val Asp Val
            100                 105                 110

Val Ala Asn His Met Gly Asn Gly Ala Ile Ala Asp Asn Arg Pro Glu
        115                 120                 125

Pro Leu Asn Gln Ala Ser Ser Tyr His Pro Ala Cys Asp Ile Asn Tyr
    130                 135                 140

Asp Asn Gln Thr Ser Ile Glu Gln Cys Ser Ile Gly Gly Leu Ala Asp
145                 150                 155                 160

Leu Asn Thr Glu Ser Thr Glu Val Arg Thr Val Leu Asn Thr Trp Val
                165                 170                 175

Ser Trp Leu Val Asp Glu Tyr Ser Phe Asp Gly Val Arg Ile Asp Thr
            180                 185                 190

Val Lys His Val Gln Lys Asp Phe Trp Pro Asp Phe Val Ser Ser Ile
        195                 200                 205
```

```
Gly Glu Tyr Ser Ile Gly Glu Val Phe Asp Gly Asn Pro Pro Tyr Leu
    210                 215                 220

Ala Glu Tyr Ala Lys Leu Met Pro Gly Val Leu Asn Tyr Ala Val Tyr
225                 230                 235                 240

Tyr Pro Met Asn Ala Phe Tyr Gln Gln Thr Gly Ser Ser Gln Ala Leu
                245                 250                 255

Val Asp Met Met Asn Thr Ile Ser Ser Thr Phe Pro Asp Pro Ser Ala
            260                 265                 270

Leu Gly Thr Phe Leu Asp Asn His Asp Asn Pro Arg Trp Leu Asn Val
        275                 280                 285

Lys Asn Asp Gln Thr Leu Leu Lys Asn Ala Leu Ala Tyr Val Ile Leu
    290                 295                 300

Ala Arg Gly Ile Pro Ile Leu Tyr Tyr Gly Thr Glu Gln Gly Tyr Ser
305                 310                 315                 320

Gly Gly Ala Asp Pro Ala Asn Arg Glu Asp Leu Trp Arg Ser Ser Phe
                325                 330                 335

Asn Thr Asn Ala Asp Leu Tyr Gln Ser Ile Lys Lys Leu Thr Ala Ala
            340                 345                 350

Arg Lys Ala Ala Gly Gly Leu Ala Gly Asn Asp His Thr His Leu Tyr
        355                 360                 365

Val Ala Asp Thr Ala Tyr Ala Trp Ser Arg Ala Asn Gly Ala Leu Ile
    370                 375                 380

Val Leu Thr Thr Asn Ala Gly Ser Ser Ser Asn Ala Gln His Cys Phe
385                 390                 395                 400

Asn Thr Gln Met Ala Asn Gly Lys Trp Thr Asn Thr Tyr Gly Asp Gly
                405                 410                 415

Ala Thr Val Thr Ala Asp Ser Ser Gly Asn Ile Cys Val Thr Val Ser
            420                 425                 430

Asn Gly Glu Pro Val Val Leu Val Ala Ser Ala Ser Thr Thr Gly Val
        435                 440                 445

Thr Pro Thr Thr Ala Thr Thr Leu Arg
    450                 455

<210> SEQ ID NO 120
<211> LENGTH: 1428
<212> TYPE: DNA
<213> ORGANISM: Penicillium sp.
<220> FEATURE:
<221> NAME/KEY: CDS
<222> LOCATION: (1)..(1428)

<400> SEQUENCE: 120 gca gaa tgg cgc agt cag tcg atc tac ttt ctt cta act gat cgc ttt    48
Ala Glu Trp Arg Ser Gln Ser Ile Tyr Phe Leu Leu Thr Asp Arg Phe
1               5                   10                  15 ggc cga acg gac aat tcc acc acg gca gca tgc aat gtc agc gat cgg    96
Gly Arg Thr Asp Asn Ser Thr Thr Ala Ala Cys Asn Val Ser Asp Arg
            20                  25                  30 gtc tac tgt ggt ggc agc tgg caa gga atc atc aat cac ttg gat tac   144
Val Tyr Cys Gly Gly Ser Trp Gln Gly Ile Ile Asn His Leu Asp Tyr
        35                  40                  45 att cag ggc atg gga ttc acc gcg att tgg att acc cct gtc aca gaa   192
Ile Gln Gly Met Gly Phe Thr Ala Ile Trp Ile Thr Pro Val Thr Glu
    50                  55                  60 cag ctc tct caa gac act gga gat ggc gag gca tac cac gga tac tgg   240
Gln Leu Ser Gln Asp Thr Gly Asp Gly Glu Ala Tyr His Gly Tyr Trp
65                  70                  75                  80
```

-continued

```
caa caa gag ata tac aac gtc aac aca aac tat ggc act gct gct gac        288
Gln Gln Glu Ile Tyr Asn Val Asn Thr Asn Tyr Gly Thr Ala Ala Asp
            85              90                  95 ctt ttg gca ctt tct aaa gcc ctg cac agt cgt ggc atg tac ctc atg        336
Leu Leu Ala Leu Ser Lys Ala Leu His Ser Arg Gly Met Tyr Leu Met
        100             105                 110 gta gac gtg gtt gca aac cac atg ggc tat gat gga gct gga aat act        384
Val Asp Val Val Ala Asn His Met Gly Tyr Asp Gly Ala Gly Asn Thr
            115             120                 125 gtt gac tac agt gtc ttt aat cca ttc gac tct tcg tct tac ttc cac        432
Val Asp Tyr Ser Val Phe Asn Pro Phe Asp Ser Ser Ser Tyr Phe His
    130             135                 140 tcg tat tgt gag atc agc gat tac tct gat cag aca aac gtg gag gac        480
Ser Tyr Cys Glu Ile Ser Asp Tyr Ser Asp Gln Thr Asn Val Glu Asp
145             150                 155                 160 tgt tgg ctt gga gac act aca gtt tct ctt cca gat ctc gac acg acc        528
Cys Trp Leu Gly Asp Thr Thr Val Ser Leu Pro Asp Leu Asp Thr Thr
                165                 170                 175 ctt act tct gtt cag acg atc tgg tat aac tgg gtc act gaa ttg gtg        576
Leu Thr Ser Val Gln Thr Ile Trp Tyr Asn Trp Val Thr Glu Leu Val
            180                 185                 190 tcc aac tac tcc att gat ggt ttg cga att gat aca gtc aaa cac gtg        624
Ser Asn Tyr Ser Ile Asp Gly Leu Arg Ile Asp Thr Val Lys His Val
        195                 200                 205 cag aag tcg ttc tgg ccg ggc tac aac agt gct gca ggt gtc tac tgt        672
Gln Lys Ser Phe Trp Pro Gly Tyr Asn Ser Ala Ala Gly Val Tyr Cys
    210                 215                 220 gtg gga gag gtg ttt gat ggg gac cca gca tac act tgc ccc tac cag        720
Val Gly Glu Val Phe Asp Gly Asp Pro Ala Tyr Thr Cys Pro Tyr Gln
225                 230                 235                 240 agc tac ctc gat ggt gtt ctg aac tat ccg att tat tac caa ctg ctg        768
Ser Tyr Leu Asp Gly Val Leu Asn Tyr Pro Ile Tyr Tyr Gln Leu Leu
                245                 250                 255 tac gca ttc gag tcg aca agt ggc agt atc agc ggt cta tat aat atg        816
Tyr Ala Phe Glu Ser Thr Ser Gly Ser Ile Ser Gly Leu Tyr Asn Met
            260                 265                 270 atc aac tcc gtt gca tct gac tgt tcc gat cca acc ttg ctc gga aac        864
Ile Asn Ser Val Ala Ser Asp Cys Ser Asp Pro Thr Leu Leu Gly Asn
        275                 280                 285 ttc atc gag aat cat gac aac cca cgc ttt gct tcc tac acg agc gat        912
Phe Ile Glu Asn His Asp Asn Pro Arg Phe Ala Ser Tyr Thr Ser Asp
    290                 295                 300 tat tct caa gcg aag aat gtg att tct ttc atc ttc ttc tcg gat ggt        960
Tyr Ser Gln Ala Lys Asn Val Ile Ser Phe Ile Phe Phe Ser Asp Gly
305                 310                 315                 320 att cca atc gtc tat gct ggc cag gaa caa cac tat agc ggt ggc agt       1008
Ile Pro Ile Val Tyr Ala Gly Gln Glu Gln His Tyr Ser Gly Gly Ser
                325                 330                 335 gac cct gcc aat cgt gaa gca act tgg cta tcc gga tac gac aag aca       1056
Asp Pro Ala Asn Arg Glu Ala Thr Trp Leu Ser Gly Tyr Asp Lys Thr
            340                 345                 350 gct cag ctt tac acc tac atc acc acc aca aac aag atc cgt gcc cta       1104
Ala Gln Leu Tyr Thr Tyr Ile Thr Thr Thr Asn Lys Ile Arg Ala Leu
        355                 360                 365 gcc att tca aag gac agc gcc tac ata agt tcc aag aat aat gct ttc       1152
Ala Ile Ser Lys Asp Ser Ala Tyr Ile Ser Ser Lys Asn Asn Ala Phe
    370                 375                 380 tac act gat agc aat act att gcc atg aag aaa gga tct agc ggc tcg       1200
Tyr Thr Asp Ser Asn Thr Ile Ala Met Lys Lys Gly Ser Ser Gly Ser
385                 390                 395                 400
```

```
caa gtt ata act gtt ctt tca aac cgt ggc tca tcg ggt agc tcg tat    1248
Gln Val Ile Thr Val Leu Ser Asn Arg Gly Ser Ser Gly Ser Ser Tyr
            405                 410                 415 acc ttg act ctt agc gga agc ggt tac tcg tct ggc acg aag ctc atg    1296
Thr Leu Thr Leu Ser Gly Ser Gly Tyr Ser Ser Gly Thr Lys Leu Met
            420                 425                 430 gag atg tac acc tgc aca gcc gtg act gtg gac tct agt ggc aac atc    1344
Glu Met Tyr Thr Cys Thr Ala Val Thr Val Asp Ser Ser Gly Asn Ile
            435                 440                 445 gcc gtg ccg atg gct tcc gga ctc cct cga gtc tac atg ctt gct tcc    1392
Ala Val Pro Met Ala Ser Gly Leu Pro Arg Val Tyr Met Leu Ala Ser
    450                 455                 460 tcg gct tgc tct att tgc agt tct gcc tgt tca gca                    1428
Ser Ala Cys Ser Ile Cys Ser Ser Ala Cys Ser Ala
465                 470                 475

<210> SEQ ID NO 121
<211> LENGTH: 476
<212> TYPE: PRT
<213> ORGANISM: Penicillium sp.

<400> SEQUENCE: 121

Ala Glu Trp Arg Ser Gln Ser Ile Tyr Phe Leu Leu Thr Asp Arg Phe
1               5                   10                  15

Gly Arg Thr Asp Asn Ser Thr Thr Ala Ala Cys Asn Val Ser Asp Arg
            20                  25                  30

Val Tyr Cys Gly Gly Ser Trp Gln Gly Ile Ile Asn His Leu Asp Tyr
        35                  40                  45

Ile Gln Gly Met Gly Phe Thr Ala Ile Trp Ile Thr Pro Val Thr Glu
    50                  55                  60

Gln Leu Ser Gln Asp Thr Gly Asp Gly Glu Ala Tyr His Gly Tyr Trp
65                  70                  75                  80

Gln Gln Glu Ile Tyr Asn Val Asn Thr Asn Tyr Gly Thr Ala Ala Asp
                85                  90                  95

Leu Leu Ala Leu Ser Lys Ala Leu His Ser Arg Gly Met Tyr Leu Met
            100                 105                 110

Val Asp Val Val Ala Asn His Met Gly Tyr Asp Gly Ala Gly Asn Thr
        115                 120                 125

Val Asp Tyr Ser Val Phe Asn Pro Phe Asp Ser Ser Tyr Phe His
    130                 135                 140

Ser Tyr Cys Glu Ile Ser Asp Tyr Ser Asp Gln Thr Asn Val Glu Asp
145                 150                 155                 160

Cys Trp Leu Gly Asp Thr Thr Val Ser Leu Pro Asp Leu Asp Thr Thr
                165                 170                 175

Leu Thr Ser Val Gln Thr Ile Trp Tyr Asn Trp Val Thr Glu Leu Val
            180                 185                 190

Ser Asn Tyr Ser Ile Asp Gly Leu Arg Ile Asp Thr Val Lys His Val
        195                 200                 205

Gln Lys Ser Phe Trp Pro Gly Tyr Asn Ser Ala Ala Gly Val Tyr Cys
    210                 215                 220

Val Gly Glu Val Phe Asp Gly Asp Pro Ala Tyr Thr Cys Pro Tyr Gln
225                 230                 235                 240

Ser Tyr Leu Asp Gly Val Leu Asn Tyr Pro Ile Tyr Tyr Gln Leu Leu
                245                 250                 255

Tyr Ala Phe Glu Ser Thr Ser Gly Ser Ile Ser Gly Leu Tyr Asn Met
            260                 265                 270

Ile Asn Ser Val Ala Ser Asp Cys Ser Asp Pro Thr Leu Leu Gly Asn
```

```
                    275                 280                 285
Phe Ile Glu Asn His Asp Asn Pro Arg Phe Ala Ser Tyr Thr Ser Asp
290                 295                 300

Tyr Ser Gln Ala Lys Asn Val Ile Ser Phe Ile Phe Phe Ser Asp Gly
305                 310                 315                 320

Ile Pro Ile Val Tyr Ala Gly Gln Glu Gln His Tyr Ser Gly Gly Ser
                    325                 330                 335

Asp Pro Ala Asn Arg Glu Ala Thr Trp Leu Ser Gly Tyr Asp Lys Thr
                340                 345                 350

Ala Gln Leu Tyr Thr Tyr Ile Thr Thr Thr Asn Lys Ile Arg Ala Leu
            355                 360                 365

Ala Ile Ser Lys Asp Ser Ala Tyr Ile Ser Ser Lys Asn Asn Ala Phe
370                 375                 380

Tyr Thr Asp Ser Asn Thr Ile Ala Met Lys Lys Gly Ser Ser Gly Ser
385                 390                 395                 400

Gln Val Ile Thr Val Leu Ser Asn Arg Gly Ser Ser Gly Ser Ser Tyr
                    405                 410                 415

Thr Leu Thr Leu Ser Gly Ser Gly Tyr Ser Ser Gly Thr Lys Leu Met
                420                 425                 430

Glu Met Tyr Thr Cys Thr Ala Val Thr Val Asp Ser Ser Gly Asn Ile
            435                 440                 445

Ala Val Pro Met Ala Ser Gly Leu Pro Arg Val Tyr Met Leu Ala Ser
450                 455                 460

Ser Ala Cys Ser Ile Cys Ser Ser Ala Cys Ser Ala
465                 470                 475

<210> SEQ ID NO 122
<211> LENGTH: 1353
<212> TYPE: DNA
<213> ORGANISM: Valsaria spartii
<220> FEATURE:
<221> NAME/KEY: CDS
<222> LOCATION: (1)..(1353)

<400> SEQUENCE: 122 gcc agc aac gcg gat tgg aaa tcg cgc aac atc tac ttt gcc ttg acg      48
Ala Ser Asn Ala Asp Trp Lys Ser Arg Asn Ile Tyr Phe Ala Leu Thr
1               5                   10                  15 gac cgc gtc gct ggt cct acc ggg gga tca tgc ggc aac ctg gga aac      96
Asp Arg Val Ala Gly Pro Thr Gly Gly Ser Cys Gly Asn Leu Gly Asn
            20                  25                  30 tac tgc ggc ggt acc tgg aac gga ttg acg gat aag ttg gac tac atc     144
Tyr Cys Gly Gly Thr Trp Asn Gly Leu Thr Asp Lys Leu Asp Tyr Ile
        35                  40                  45 cag ggc atg gga ttc gat gcc atc tgg atc acc ccg gtc atc aag aac     192
Gln Gly Met Gly Phe Asp Ala Ile Trp Ile Thr Pro Val Ile Lys Asn
    50                  55                  60 agc ccc ggc ggt tat cac gga tat tgg gct caa gat ctc tac agc gtg     240
Ser Pro Gly Gly Tyr His Gly Tyr Trp Ala Gln Asp Leu Tyr Ser Val
65                  70                  75                  80 aac gag aac tat ggc act gcg caa gat ctg aag gat ttc gta aat gcg     288
Asn Glu Asn Tyr Gly Thr Ala Gln Asp Leu Lys Asp Phe Val Asn Ala
                85                  90                  95 gcg cac gca aag ggg atc tac gtc atg gtc gac gtg gtc gca aac cac     336
Ala His Ala Lys Gly Ile Tyr Val Met Val Asp Val Val Ala Asn His
            100                 105                 110 atg ggc aac ggt gga atc tca act ctc tcc cca cct ccc ttg aac cag     384
Met Gly Asn Gly Gly Ile Ser Thr Leu Ser Pro Pro Pro Leu Asn Gln
        115                 120                 125
```

```
gag agt tcc tat cac tcc aaa tgc aac atc gac tac agc agc caa aac      432
Glu Ser Ser Tyr His Ser Lys Cys Asn Ile Asp Tyr Ser Ser Gln Asn
    130             135                 140 agc atc gag aat tgc tgg atc gct gac ctg ccc gac ctc gtc acc acc      480
Ser Ile Glu Asn Cys Trp Ile Ala Asp Leu Pro Asp Leu Val Thr Thr
145                 150                 155                 160 gac aac acc atc cgc gat gtc ttc aag gac tgg atc gcc aac ctc acc      528
Asp Asn Thr Ile Arg Asp Val Phe Lys Asp Trp Ile Ala Asn Leu Thr
                165                 170                 175 acc acc tac tcc ttc gac ggc ctc cgc gtc gac acc gtc aag cat gta      576
Thr Thr Tyr Ser Phe Asp Gly Leu Arg Val Asp Thr Val Lys His Val
            180                 185                 190 gag aag gac ttt tgg ccg ggc ttc gtc gag gct gcc ggc atg tat gcc      624
Glu Lys Asp Phe Trp Pro Gly Phe Val Glu Ala Ala Gly Met Tyr Ala
        195                 200                 205 atc ggc gag gtt ctc gat ggc ggc acc tcc tac gtt gcc ggc tac cag      672
Ile Gly Glu Val Leu Asp Gly Gly Thr Ser Tyr Val Ala Gly Tyr Gln
    210                 215                 220 agc gtg atg cca ggc ctt ctc aac tat ccc atg tac tat cct ctc atc      720
Ser Val Met Pro Gly Leu Leu Asn Tyr Pro Met Tyr Tyr Pro Leu Ile
225                 230                 235                 240 cgc acc ttt acc cag ggc gcc tcc ttc aac gac ttc gtc aac agt cac      768
Arg Thr Phe Thr Gln Gly Ala Ser Phe Asn Asp Phe Val Asn Ser His
                245                 250                 255 aac gag gtt ggt tcc gga ttc tcc gat ccc acc ctc ctc ggc acc ttc      816
Asn Glu Val Gly Ser Gly Phe Ser Asp Pro Thr Leu Leu Gly Thr Phe
            260                 265                 270 atc gac aac cac gac cag cag cgc ttc ctc tac aag aac agc gac cac      864
Ile Asp Asn His Asp Gln Gln Arg Phe Leu Tyr Lys Asn Ser Asp His
        275                 280                 285 gcc ctc ttg aag aac gct ctg gcc tac gtg atc ctt ggc cga ggt atc      912
Ala Leu Leu Lys Asn Ala Leu Ala Tyr Val Ile Leu Gly Arg Gly Ile
    290                 295                 300 cca atc gtg tac tac ggc acc gag caa gcc tac ggc ggt ggt gac gac      960
Pro Ile Val Tyr Tyr Gly Thr Glu Gln Ala Tyr Gly Gly Gly Asp Asp
305                 310                 315                 320 ccg gcg aac cgc gag gac ctc tgg cga agc ggc tac tcc acc acc tcc     1008
Pro Ala Asn Arg Glu Asp Leu Trp Arg Ser Gly Tyr Ser Thr Thr Ser
                325                 330                 335 gag ata tac acc acc atc tcg ggc cta tcc tcc gct cgc aaa tcc gcc     1056
Glu Ile Tyr Thr Thr Ile Ser Gly Leu Ser Ser Ala Arg Lys Ser Ala
            340                 345                 350 ggc ggc ctc cca ggc aac gac cac tcc cac ctc tac acc acc aac aac     1104
Gly Gly Leu Pro Gly Asn Asp His Ser His Leu Tyr Thr Thr Asn Asn
        355                 360                 365 gcg tac gcc tgg tcc cgc gcg gac ggg aag gtg atc gcg ttg gtg acc     1152
Ala Tyr Ala Trp Ser Arg Ala Asp Gly Lys Val Ile Ala Leu Val Thr
    370                 375                 380 aac gcc ggc ggc tcc gac acc agc acc cac tgc ttc aac acc aag aaa     1200
Asn Ala Gly Gly Ser Asp Thr Ser Thr His Cys Phe Asn Thr Lys Lys
385                 390                 395                 400 ccg agc ggc acg cgc tgg acc agc gtc ctc cgc agc ggc gga acc agc     1248
Pro Ser Gly Thr Arg Trp Thr Ser Val Leu Arg Ser Gly Gly Thr Ser
                405                 410                 415 tac acc gcc gac ggc aac ggc caa atc tgc atc cag atc caa aac ggc     1296
Tyr Thr Ala Asp Gly Asn Gly Gln Ile Cys Ile Gln Ile Gln Asn Gly
            420                 425                 430 ggg ccc gag gca atc gtc ctc tcc acc ggc acc ggc acc gaa acc aca     1344
Gly Pro Glu Ala Ile Val Leu Ser Thr Gly Thr Gly Thr Glu Thr Thr
        435                 440                 445
```

```
tcc agc gcc                                                        1353
Ser Ser Ala
    450
```

<210> SEQ ID NO 123
<211> LENGTH: 451
<212> TYPE: PRT
<213> ORGANISM: Valsaria spartii

<400> SEQUENCE: 123

```
Ala Ser Asn Ala Asp Trp Lys Ser Arg Asn Ile Tyr Phe Ala Leu Thr
1               5                   10                  15

Asp Arg Val Ala Gly Pro Thr Gly Gly Ser Cys Gly Asn Leu Gly Asn
            20                  25                  30

Tyr Cys Gly Gly Thr Trp Asn Gly Leu Thr Asp Lys Leu Asp Tyr Ile
        35                  40                  45

Gln Gly Met Gly Phe Asp Ala Ile Trp Ile Thr Pro Val Ile Lys Asn
    50                  55                  60

Ser Pro Gly Gly Tyr His Gly Tyr Trp Ala Gln Asp Leu Tyr Ser Val
65                  70                  75                  80

Asn Glu Asn Tyr Gly Thr Ala Gln Asp Leu Lys Asp Phe Val Asn Ala
                85                  90                  95

Ala His Ala Lys Gly Ile Tyr Val Met Val Asp Val Ala Asn His
            100                 105                 110

Met Gly Asn Gly Gly Ile Ser Thr Leu Ser Pro Pro Leu Asn Gln
        115                 120                 125

Glu Ser Ser Tyr His Ser Lys Cys Asn Ile Asp Tyr Ser Ser Gln Asn
    130                 135                 140

Ser Ile Glu Asn Cys Trp Ile Ala Asp Leu Pro Asp Leu Val Thr Thr
145                 150                 155                 160

Asp Asn Thr Ile Arg Asp Val Phe Lys Asp Trp Ile Ala Asn Leu Thr
                165                 170                 175

Thr Thr Tyr Ser Phe Asp Gly Leu Arg Val Asp Thr Val Lys His Val
            180                 185                 190

Glu Lys Asp Phe Trp Pro Gly Phe Val Glu Ala Ala Gly Met Tyr Ala
        195                 200                 205

Ile Gly Glu Val Leu Asp Gly Gly Thr Ser Tyr Val Ala Gly Tyr Gln
    210                 215                 220

Ser Val Met Pro Gly Leu Leu Asn Tyr Pro Met Tyr Tyr Pro Leu Ile
225                 230                 235                 240

Arg Thr Phe Thr Gln Gly Ala Ser Phe Asn Asp Phe Val Asn Ser His
                245                 250                 255

Asn Glu Val Gly Ser Gly Phe Ser Asp Pro Thr Leu Leu Gly Thr Phe
            260                 265                 270

Ile Asp Asn His Asp Gln Gln Arg Phe Leu Tyr Lys Asn Ser Asp His
        275                 280                 285

Ala Leu Leu Lys Asn Ala Leu Ala Tyr Val Ile Leu Gly Arg Gly Ile
    290                 295                 300

Pro Ile Val Tyr Tyr Gly Thr Glu Gln Ala Tyr Gly Gly Asp Asp
305                 310                 315                 320

Pro Ala Asn Arg Glu Asp Leu Trp Arg Ser Gly Tyr Ser Thr Thr Ser
                325                 330                 335

Glu Ile Tyr Thr Thr Ile Ser Gly Leu Ser Ser Ala Arg Lys Ser Ala
            340                 345                 350

Gly Gly Leu Pro Gly Asn Asp His Ser His Leu Tyr Thr Thr Asn Asn
```

```
                355                 360                 365
Ala Tyr Ala Trp Ser Arg Ala Asp Gly Lys Val Ile Ala Leu Val Thr
370                 375                 380

Asn Ala Gly Gly Ser Asp Thr Ser Thr His Cys Phe Asn Thr Lys Lys
385                 390                 395                 400

Pro Ser Gly Thr Arg Trp Thr Ser Val Leu Arg Ser Gly Gly Thr Ser
                405                 410                 415

Tyr Thr Ala Asp Gly Asn Gly Gln Ile Cys Ile Gln Ile Gln Asn Gly
                420                 425                 430

Gly Pro Glu Ala Ile Val Leu Ser Thr Gly Thr Gly Thr Glu Thr Thr
                435                 440                 445

Ser Ser Ala
    450

<210> SEQ ID NO 124
<211> LENGTH: 1431
<212> TYPE: DNA
<213> ORGANISM: Thermoascus auranticus
<220> FEATURE:
<221> NAME/KEY: CDS
<222> LOCATION: (1)..(1431)

<400> SEQUENCE: 124
```

| | | | | | | | | | | | | | | | | |
|---|---|---|---|---|---|---|---|---|---|---|---|---|---|---|---|---|
| gcc | acg | cca | gcc | caa | tgg | cgc | tct | cga | tca | gta | tac | ttc | ctt | ctg | acg | 48 |
| Ala | Thr | Pro | Ala | Gln | Trp | Arg | Ser | Arg | Ser | Val | Tyr | Phe | Leu | Leu | Thr | |
| 1 | | | | 5 | | | | | 10 | | | | | 15 | | |
| gac | agg | ttt | gca | agg | agt | gat | ggg | tca | acc | acc | gct | gcc | tgt | gac | acc | 96 |
| Asp | Arg | Phe | Ala | Arg | Ser | Asp | Gly | Ser | Thr | Thr | Ala | Ala | Cys | Asp | Thr | |
| | | | | 20 | | | | | 25 | | | | | 30 | | |
| agt | gca | agg | caa | tac | tgc | ggc | gga | act | tgg | cag | ggg | ata | atc | gac | cat | 144 |
| Ser | Ala | Arg | Gln | Tyr | Cys | Gly | Gly | Thr | Trp | Gln | Gly | Ile | Ile | Asp | His | |
| | | 35 | | | | | 40 | | | | | 45 | | | | |
| ctc | gac | tat | atc | caa | gga | atg | gga | ttc | act | gct | att | tgg | att | tcc | ccc | 192 |
| Leu | Asp | Tyr | Ile | Gln | Gly | Met | Gly | Phe | Thr | Ala | Ile | Trp | Ile | Ser | Pro | |
| 50 | | | | | 55 | | | | | 60 | | | | | | |
| gtc | acc | gaa | cag | ctg | cct | cag | gat | acg | gga | gat | ggg | aca | gcg | tat | cat | 240 |
| Val | Thr | Glu | Gln | Leu | Pro | Gln | Asp | Thr | Gly | Asp | Gly | Thr | Ala | Tyr | His | |
| 65 | | | | | 70 | | | | | 75 | | | | | 80 | |
| ggc | tac | tgg | cag | caa | gat | att | tac | tcc | ctg | aat | ccc | aac | ttt | ggc | aca | 288 |
| Gly | Tyr | Trp | Gln | Gln | Asp | Ile | Tyr | Ser | Leu | Asn | Pro | Asn | Phe | Gly | Thr | |
| | | | | 85 | | | | | 90 | | | | | 95 | | |
| gcc | gac | gac | ctc | cgc | gcg | ctc | gca | gac | gct | ctc | cat | gca | cgc | gga | atg | 336 |
| Ala | Asp | Asp | Leu | Arg | Ala | Leu | Ala | Asp | Ala | Leu | His | Ala | Arg | Gly | Met | |
| | | | 100 | | | | | 105 | | | | | 110 | | | |
| tac | ctc | atg | gtc | gac | gtc | gta | gcc | aac | cat | atg | gga | tac | gcc | ggc | ccg | 384 |
| Tyr | Leu | Met | Val | Asp | Val | Val | Ala | Asn | His | Met | Gly | Tyr | Ala | Gly | Pro | |
| | | 115 | | | | | 120 | | | | | 125 | | | | |
| ggg | aac | tct | gtc | gac | tac | agc | gtc | ttc | aac | ccc | ttc | aac | aaa | cag | gaa | 432 |
| Gly | Asn | Ser | Val | Asp | Tyr | Ser | Val | Phe | Asn | Pro | Phe | Asn | Lys | Gln | Glu | |
| | 130 | | | | | 135 | | | | | 140 | | | | | |
| tac | ttc | cac | ccc | tac | tgc | gag | ata | acc | aac | tac | gac | gac | caa | tcc | aac | 480 |
| Tyr | Phe | His | Pro | Tyr | Cys | Glu | Ile | Thr | Asn | Tyr | Asp | Asp | Gln | Ser | Asn | |
| 145 | | | | | 150 | | | | | 155 | | | | | 160 | |
| gtc | gag | aat | tgc | tgg | ctc | gga | gac | aca | ata | gtc | tca | ctg | ccc | gat | ctg | 528 |
| Val | Glu | Asn | Cys | Trp | Leu | Gly | Asp | Thr | Ile | Val | Ser | Leu | Pro | Asp | Leu | |
| | | | | 165 | | | | | 170 | | | | | 175 | | |
| aat | acg | gcc | agg | tcg | gat | gta | gag | gat | ata | tgg | tac | agt | tgg | gtg | agg | 576 |
| Asn | Thr | Ala | Arg | Ser | Asp | Val | Glu | Asp | Ile | Trp | Tyr | Ser | Trp | Val | Arg | |
| | | | 180 | | | | | 185 | | | | | 190 | | | |
| gct | ctg | gtg | tcg | aac | tac | tcg | gtc | gac | ggc | ctc | cgc | atc | gac | acc | gtc | 624 |

```
Ala Leu Val Ser Asn Tyr Ser Val Asp Gly Leu Arg Ile Asp Thr Val
        195                 200                 205 aaa cac gtc cag aag gac ttc tgg ccc ggc tac aac gac gcc gcg ggc     672
Lys His Val Gln Lys Asp Phe Trp Pro Gly Tyr Asn Asp Ala Ala Gly
    210                 215                 220 gtc tac tgc gtg ggc gag gtg ttc gac ggt gac ccc agc tac acc tgc     720
Val Tyr Cys Val Gly Glu Val Phe Asp Gly Asp Pro Ser Tyr Thr Cys
225                 230                 235                 240 gac tac cag aac tat ctg gat ggg gtg ctg aac tat ccg atg tac tac     768
Asp Tyr Gln Asn Tyr Leu Asp Gly Val Leu Asn Tyr Pro Met Tyr Tyr
                245                 250                 255 ccc ctc ctc aga gcg ttc tcc tcc acg agc ggc agc atc agc gac ctg     816
Pro Leu Leu Arg Ala Phe Ser Ser Thr Ser Gly Ser Ile Ser Asp Leu
            260                 265                 270 tac aac atg atc aac acg gtg aaa tcg cag tgc gcg gat tcg acc ctc     864
Tyr Asn Met Ile Asn Thr Val Lys Ser Gln Cys Ala Asp Ser Thr Leu
        275                 280                 285 ctg ggt acc ttt gtc gag aac cat gac gtg ccg agg ttt gct tca tac     912
Leu Gly Thr Phe Val Glu Asn His Asp Val Pro Arg Phe Ala Ser Tyr
    290                 295                 300 acg agc gac atc gcc ctc gcc aag aac gcg atc gcg ttc acc atc ctc     960
Thr Ser Asp Ile Ala Leu Ala Lys Asn Ala Ile Ala Phe Thr Ile Leu
305                 310                 315                 320 tcg gac ggc atc cct att atc tat gcc ggc cag gag cag cac tac agc    1008
Ser Asp Gly Ile Pro Ile Ile Tyr Ala Gly Gln Glu Gln His Tyr Ser
                325                 330                 335 ggc ggc aac gac ccc gcg aac cgc gag gcg gtc tgg ctg tcc ggc tac    1056
Gly Gly Asn Asp Pro Ala Asn Arg Glu Ala Val Trp Leu Ser Gly Tyr
            340                 345                 350 tcg acg acc agc gag ctc tac cag ttc atc gcg gtc tcg aac cag atc    1104
Ser Thr Thr Ser Glu Leu Tyr Gln Phe Ile Ala Val Ser Asn Gln Ile
        355                 360                 365 cgc aat tac gcc atc tat gtg gac gag ggg tat ttg acg tac aag gcc    1152
Arg Asn Tyr Ala Ile Tyr Val Asp Glu Gly Tyr Leu Thr Tyr Lys Ala
    370                 375                 380 tgg ccc atc tat caa gac agc cac acg ctc gca atc cgc aaa gga ttc    1200
Trp Pro Ile Tyr Gln Asp Ser His Thr Leu Ala Ile Arg Lys Gly Phe
385                 390                 395                 400 gac ggc aat cag gtc atc acc gtg ctc tcg aac ctg ggt tcc tcc ggc    1248
Asp Gly Asn Gln Val Ile Thr Val Leu Ser Asn Leu Gly Ser Ser Gly
                405                 410                 415 agc tcg tac acg ctc tcg ctg agc ggg acg ggc tat gct gcc ggc cag    1296
Ser Ser Tyr Thr Leu Ser Leu Ser Gly Thr Gly Tyr Ala Ala Gly Gln
            420                 425                 430 cag gtg acc gag atc tac tcc tgc acg gat gtc acg gcc gac tcg aac    1344
Gln Val Thr Glu Ile Tyr Ser Cys Thr Asp Val Thr Ala Asp Ser Asn
        435                 440                 445 ggg aat atc gcg gtc tcc atg ggt ggt ggg ctt ccg aag gcg ttt ttc    1392
Gly Asn Ile Ala Val Ser Met Gly Gly Gly Leu Pro Lys Ala Phe Phe
    450                 455                 460 ccg aca gca aag ctg gct ggg agt gga atc tgt tgg aaa                1431
Pro Thr Ala Lys Leu Ala Gly Ser Gly Ile Cys Trp Lys
465                 470                 475

<210> SEQ ID NO 125
<211> LENGTH: 477
<212> TYPE: PRT
<213> ORGANISM: Thermoascus auranticus

<400> SEQUENCE: 125

Ala Thr Pro Ala Gln Trp Arg Ser Arg Ser Val Tyr Phe Leu Leu Thr
```

```
              1               5                  10                 15
Asp Arg Phe Ala Arg Ser Asp Gly Ser Thr Ala Ala Cys Asp Thr
                20                  25                  30

Ser Ala Arg Gln Tyr Cys Gly Gly Thr Trp Gln Gly Ile Ile Asp His
                35                  40                  45

Leu Asp Tyr Ile Gln Gly Met Gly Phe Thr Ala Ile Trp Ile Ser Pro
    50                  55                  60

Val Thr Glu Gln Leu Pro Gln Asp Thr Gly Asp Gly Thr Ala Tyr His
65                  70                  75                  80

Gly Tyr Trp Gln Gln Asp Ile Tyr Ser Leu Asn Pro Asn Phe Gly Thr
                85                  90                  95

Ala Asp Asp Leu Arg Ala Leu Ala Asp Ala Leu His Ala Arg Gly Met
                100                 105                 110

Tyr Leu Met Val Asp Val Val Ala Asn His Met Gly Tyr Ala Gly Pro
            115                 120                 125

Gly Asn Ser Val Asp Tyr Ser Val Phe Asn Pro Phe Asn Lys Gln Glu
    130                 135                 140

Tyr Phe His Pro Tyr Cys Glu Ile Thr Asn Tyr Asp Asp Gln Ser Asn
145                 150                 155                 160

Val Glu Asn Cys Trp Leu Gly Asp Thr Ile Val Ser Leu Pro Asp Leu
                165                 170                 175

Asn Thr Ala Arg Ser Asp Val Glu Asp Ile Trp Tyr Ser Trp Val Arg
                180                 185                 190

Ala Leu Val Ser Asn Tyr Ser Val Asp Gly Leu Arg Ile Asp Thr Val
            195                 200                 205

Lys His Val Gln Lys Asp Phe Trp Pro Gly Tyr Asn Asp Ala Ala Gly
    210                 215                 220

Val Tyr Cys Val Gly Glu Val Phe Asp Gly Asp Pro Ser Tyr Thr Cys
225                 230                 235                 240

Asp Tyr Gln Asn Tyr Leu Asp Gly Val Leu Asn Tyr Pro Met Tyr Tyr
                245                 250                 255

Pro Leu Leu Arg Ala Phe Ser Ser Thr Ser Gly Ser Ile Ser Asp Leu
                260                 265                 270

Tyr Asn Met Ile Asn Thr Val Lys Ser Gln Cys Ala Asp Ser Thr Leu
            275                 280                 285

Leu Gly Thr Phe Val Glu Asn His Asp Val Pro Arg Phe Ala Ser Tyr
    290                 295                 300

Thr Ser Asp Ile Ala Leu Ala Lys Asn Ala Ile Ala Phe Thr Ile Leu
305                 310                 315                 320

Ser Asp Gly Ile Pro Ile Ile Tyr Ala Gly Gln Glu Gln His Tyr Ser
                325                 330                 335

Gly Gly Asn Asp Pro Ala Asn Arg Glu Ala Val Trp Leu Ser Gly Tyr
                340                 345                 350

Ser Thr Thr Ser Glu Leu Tyr Gln Phe Ile Ala Val Ser Asn Gln Ile
            355                 360                 365

Arg Asn Tyr Ala Ile Tyr Val Asp Glu Gly Tyr Leu Thr Tyr Lys Ala
    370                 375                 380

Trp Pro Ile Tyr Gln Asp Ser His Thr Leu Ala Ile Arg Lys Gly Phe
385                 390                 395                 400

Asp Gly Asn Gln Val Ile Thr Val Leu Ser Asn Leu Gly Ser Ser Gly
                405                 410                 415

Ser Ser Tyr Thr Leu Ser Leu Ser Gly Thr Gly Tyr Ala Ala Gly Gln
                420                 425                 430
```

```
Gln Val Thr Glu Ile Tyr Ser Cys Thr Asp Val Thr Ala Asp Ser Asn
        435                 440                 445

Gly Asn Ile Ala Val Ser Met Gly Gly Gly Leu Pro Lys Ala Phe Phe
        450                 455                 460

Pro Thr Ala Lys Leu Ala Gly Ser Gly Ile Cys Trp Lys
465                 470                 475

<210> SEQ ID NO 126
<211> LENGTH: 1347
<212> TYPE: DNA
<213> ORGANISM: Phanerochaete chryosporium
<220> FEATURE:
<221> NAME/KEY: CDS
<222> LOCATION: (1)..(1347)

<400> SEQUENCE: 126 gcg ccc gcg cac cat gcc gtg cgc gcg ccc tcg cag gcc aag acc gtc      48
Ala Pro Ala His His Ala Val Arg Ala Pro Ser Gln Ala Lys Thr Val
1               5                  10                  15 atc gcg cag atg ttc gag tgg acg tgg gac agc gtc gcc gcc gag tgc      96
Ile Ala Gln Met Phe Glu Trp Thr Trp Asp Ser Val Ala Ala Glu Cys
            20                  25                  30 acc gcg ttc ctc ggc ccc gcc ggc tac ggc ttc gtg cag gtc agc ccc     144
Thr Ala Phe Leu Gly Pro Ala Gly Tyr Gly Phe Val Gln Val Ser Pro
        35                  40                  45 gcg cag gag cac gtc cag ggc ccg cag tgg tgg acg gac tac cag ccc     192
Ala Gln Glu His Val Gln Gly Pro Gln Trp Trp Thr Asp Tyr Gln Pro
    50                  55                  60 gtg tcg tac acc ctc acc tcc aag cgc ggc acg cgc gcg cag cac cag     240
Val Ser Tyr Thr Leu Thr Ser Lys Arg Gly Thr Arg Ala Gln His Gln
65                  70                  75                  80 aac atg gtc aat acg tgc caa gcc gcc ggc gtg gga gtc att gcg gac     288
Asn Met Val Asn Thr Cys Gln Ala Ala Gly Val Gly Val Ile Ala Asp
                85                  90                  95 acg atc ttc aat cac atg agc ggc cag gac aat ggc ggc gtc ggc gtc     336
Thr Ile Phe Asn His Met Ser Gly Gln Asp Asn Gly Gly Val Gly Val
            100                 105                 110 gcg ggg tcg tcc ttc cag cac tat gta tac ccc ggc atc tac cag aac     384
Ala Gly Ser Ser Phe Gln His Tyr Val Tyr Pro Gly Ile Tyr Gln Asn
        115                 120                 125 cag gac ttc cac cac tgc ggc ctc gag ccc ggc gac gac atc gtg aac     432
Gln Asp Phe His His Cys Gly Leu Glu Pro Gly Asp Asp Ile Val Asn
    130                 135                 140 tac gac aat gcc gtc gag gtg cag acc tgc gag ctc gtg aac ctc gcc     480
Tyr Asp Asn Ala Val Glu Val Gln Thr Cys Glu Leu Val Asn Leu Ala
145                 150                 155                 160 gac ctt gct aca gag acc gag tat gtt cgc agc cgg ctc gca gag tac     528
Asp Leu Ala Thr Glu Thr Glu Tyr Val Arg Ser Arg Leu Ala Glu Tyr
                165                 170                 175 gcc aac gat ttg ctg tcg ttg ggc gtc gac ggg ctg cgg ctc gac gca     576
Ala Asn Asp Leu Leu Ser Leu Gly Val Asp Gly Leu Arg Leu Asp Ala
            180                 185                 190 gcg aag cac atc aat gcg aat gac att gcc aac atc acg tct cgc ttc     624
Ala Lys His Ile Asn Ala Asn Asp Ile Ala Asn Ile Thr Ser Arg Phe
        195                 200                 205 acg cgg aag ccc tac cta aca cag gag gtc atc tac ggg gcc ggg gag     672
Thr Arg Lys Pro Tyr Leu Thr Gln Glu Val Ile Tyr Gly Ala Gly Glu
    210                 215                 220 ccc atc acg ccc aat caa tac gtc ttc att ggt gat gtg caa gac gcc     720
Pro Ile Thr Pro Asn Gln Tyr Val Phe Ile Gly Asp Val Gln Asp Ala
225                 230                 235                 240
```

| | | |
|---|---|---|
| ttc tct ggc ggc ggg atc tcg agc ctg cag aac ctc gac aac caa ggc<br>Phe Ser Gly Gly Gly Ile Ser Ser Leu Gln Asn Leu Asp Asn Gln Gly<br>245 250 255 | 768 | |
| tgg gtc ccg ggc acc tct gcg aac gtc ttc gtc acg atc cac gac acg<br>Trp Val Pro Gly Thr Ser Ala Asn Val Phe Val Thr Ile His Asp Thr<br>260 265 270 | 816 | |
| gag agg aac gga gcc tcg ctg aac gca aac tcg cca tcg aac aca tac<br>Glu Arg Asn Gly Ala Ser Leu Asn Ala Asn Ser Pro Ser Asn Thr Tyr<br>275 280 285 | 864 | |
| acg ctc gcg atg gtc ttc tcg ctc gca cac ccg tac ggc acg ccg acg<br>Thr Leu Ala Met Val Phe Ser Leu Ala His Pro Tyr Gly Thr Pro Thr<br>290 295 300 | 912 | |
| atc ctc tcg agc tac agc ggc ttc acg gac acg gac gcc ggt gca ccc<br>Ile Leu Ser Ser Tyr Ser Gly Phe Thr Asp Thr Asp Ala Gly Ala Pro<br>305 310 315 320 | 960 | |
| aac ggc ggc aca ggc acc tgc acg gcc ggc ggc gcg gac ggc tgg<br>Asn Gly Gly Thr Gly Thr Cys Thr Ala Gly Gly Ala Asp Gly Trp<br>325 330 335 | 1008 | |
| ctg tgc cag cac cgc tgg acg gcc gtc gcg ggc atg gtc ggc ttc cgg<br>Leu Cys Gln His Arg Trp Thr Ala Val Ala Gly Met Val Gly Phe Arg<br>340 345 350 | 1056 | |
| aac acc gtc ggc ggc gcg ccg ctc acg aac tgg gcc gcg ccg agc gct<br>Asn Thr Val Gly Gly Ala Pro Leu Thr Asn Trp Ala Ala Pro Ser Ala<br>355 360 365 | 1104 | |
| gag caa att gcg ttc ggg cgc ggc gcg ctc ggg ttc gtc gcg ctc aac<br>Glu Gln Ile Ala Phe Gly Arg Gly Ala Leu Gly Phe Val Ala Leu Asn<br>370 375 380 | 1152 | |
| aac gcg gac gcg gtg tgg agc gcg gcg ttc agc acg gcg ctc ccc gac<br>Asn Ala Asp Ala Val Trp Ser Ala Ala Phe Ser Thr Ala Leu Pro Asp<br>385 390 395 400 | 1200 | |
| ggc acg tac tgc gat gtc gtc ggc ggc gcg agc cag ggt ggg aag tgc<br>Gly Thr Tyr Cys Asp Val Val Gly Gly Ala Ser Gln Gly Gly Lys Cys<br>405 410 415 | 1248 | |
| acg ggc agc gcg ttt acg gtc aag ggc ggg gcg ttc acc gcg aac gta<br>Thr Gly Ser Ala Phe Thr Val Lys Gly Gly Ala Phe Thr Ala Asn Val<br>420 425 430 | 1296 | |
| cag gcg cgc aac gcg att gcg ata cac gtc ggc gcg aag ggc acc gcg<br>Gln Ala Arg Asn Ala Ile Ala Ile His Val Gly Ala Lys Gly Thr Ala<br>435 440 445 | 1344 | |
| ggc<br>Gly | 1347 | |

<210> SEQ ID NO 127
<211> LENGTH: 449
<212> TYPE: PRT
<213> ORGANISM: Phanerochaete chryosporium

<400> SEQUENCE: 127

Ala Pro Ala His His Ala Val Arg Ala Pro Ser Gln Ala Lys Thr Val
1               5                   10                  15

Ile Ala Gln Met Phe Glu Trp Thr Trp Asp Ser Val Ala Ala Glu Cys
                20                  25                  30

Thr Ala Phe Leu Gly Pro Ala Gly Tyr Gly Phe Val Gln Val Ser Pro
            35                  40                  45

Ala Gln Glu His Val Gln Gly Pro Gln Trp Trp Thr Asp Tyr Gln Pro
        50                  55                  60

Val Ser Tyr Thr Leu Thr Ser Lys Arg Gly Thr Arg Ala Gln His Gln
65                  70                  75                  80

Asn Met Val Asn Thr Cys Gln Ala Ala Gly Val Gly Val Ile Ala Asp
                85                  90                  95

```
Thr Ile Phe Asn His Met Ser Gly Gln Asp Asn Gly Gly Val Gly Val
            100                 105                 110

Ala Gly Ser Ser Phe Gln His Tyr Val Tyr Pro Gly Ile Tyr Gln Asn
        115                 120                 125

Gln Asp Phe His His Cys Gly Leu Glu Pro Gly Asp Asp Ile Val Asn
    130                 135                 140

Tyr Asp Asn Ala Val Glu Val Gln Thr Cys Glu Leu Val Asn Leu Ala
145                 150                 155                 160

Asp Leu Ala Thr Glu Thr Glu Tyr Val Arg Ser Arg Leu Ala Glu Tyr
                165                 170                 175

Ala Asn Asp Leu Leu Ser Leu Gly Val Asp Gly Leu Arg Leu Asp Ala
            180                 185                 190

Ala Lys His Ile Asn Ala Asn Asp Ile Ala Asn Ile Thr Ser Arg Phe
        195                 200                 205

Thr Arg Lys Pro Tyr Leu Thr Gln Glu Val Ile Tyr Gly Ala Gly Glu
    210                 215                 220

Pro Ile Thr Pro Asn Gln Tyr Val Phe Ile Gly Asp Val Gln Asp Ala
225                 230                 235                 240

Phe Ser Gly Gly Gly Ile Ser Ser Leu Gln Asn Leu Asp Asn Gln Gly
                245                 250                 255

Trp Val Pro Gly Thr Ser Ala Asn Val Phe Val Thr Ile His Asp Thr
            260                 265                 270

Glu Arg Asn Gly Ala Ser Leu Asn Ala Asn Ser Pro Ser Asn Thr Tyr
        275                 280                 285

Thr Leu Ala Met Val Phe Ser Leu Ala His Pro Tyr Gly Thr Pro Thr
    290                 295                 300

Ile Leu Ser Ser Tyr Ser Gly Phe Thr Asp Thr Asp Ala Gly Ala Pro
305                 310                 315                 320

Asn Gly Gly Thr Gly Thr Cys Thr Ala Gly Gly Ala Asp Gly Trp
                325                 330                 335

Leu Cys Gln His Arg Trp Thr Ala Val Ala Gly Met Val Gly Phe Arg
            340                 345                 350

Asn Thr Val Gly Gly Ala Pro Leu Thr Asn Trp Ala Ala Pro Ser Ala
        355                 360                 365

Glu Gln Ile Ala Phe Gly Arg Gly Ala Leu Gly Phe Val Ala Leu Asn
    370                 375                 380

Asn Ala Asp Ala Val Trp Ser Ala Ala Phe Ser Thr Ala Leu Pro Asp
385                 390                 395                 400

Gly Thr Tyr Cys Asp Val Val Gly Ala Ser Gln Gly Gly Lys Cys
                405                 410                 415

Thr Gly Ser Ala Phe Thr Val Lys Gly Gly Ala Phe Thr Ala Asn Val
            420                 425                 430

Gln Ala Arg Asn Ala Ile Ala Ile His Val Gly Ala Lys Gly Thr Ala
        435                 440                 445

Gly
```

<210> SEQ ID NO 128
<211> LENGTH: 1308
<212> TYPE: DNA
<213> ORGANISM: Rhizopus oryzae
<220> FEATURE:
<221> NAME/KEY: CDS
<222> LOCATION: (1)..(1308)

<400> SEQUENCE: 128

```
gcc tca gcc agc gac tgg gag aac cga gtc atc tac caa ttg tta act      48
Ala Ser Ala Ser Asp Trp Glu Asn Arg Val Ile Tyr Gln Leu Leu Thr
 1               5                  10                  15 gat cga ttt gca aaa tcg acc gat gat acc aat ggc tgc aat aac ctg      96
Asp Arg Phe Ala Lys Ser Thr Asp Asp Thr Asn Gly Cys Asn Asn Leu
             20                  25                  30 agt gac tac tgt ggc gga aca ttt caa gga atc att aat cac ttg gat     144
Ser Asp Tyr Cys Gly Gly Thr Phe Gln Gly Ile Ile Asn His Leu Asp
         35                  40                  45 tac att gcc gga atg gga ttt gat gct atc tgg ata tca cct atc ccc     192
Tyr Ile Ala Gly Met Gly Phe Asp Ala Ile Trp Ile Ser Pro Ile Pro
     50                  55                  60 aaa aat gcg aat gga ggt tac cat ggc tat tgg gct act gac ttt tct     240
Lys Asn Ala Asn Gly Gly Tyr His Gly Tyr Trp Ala Thr Asp Phe Ser
 65                  70                  75                  80 caa ata aat gag cat ttt gga act gct gat gac ttg aaa aag ttg gtt     288
Gln Ile Asn Glu His Phe Gly Thr Ala Asp Asp Leu Lys Lys Leu Val
             85                  90                  95 gca gct gct cat gca aag aac atg tac gtt atg ctg gac gtt gtt gcc     336
Ala Ala Ala His Ala Lys Asn Met Tyr Val Met Leu Asp Val Val Ala
            100                 105                 110 aat cat gct ggc att cct tca tca ggt ggc gac tac tct ggc tac acg     384
Asn His Ala Gly Ile Pro Ser Ser Gly Gly Asp Tyr Ser Gly Tyr Thr
        115                 120                 125 ttc ggt caa agc tct gaa tac cac aca gcc tgt gat atc aat tac aac     432
Phe Gly Gln Ser Ser Glu Tyr His Thr Ala Cys Asp Ile Asn Tyr Asn
    130                 135                 140 agc cag acc tct att gag cag tgc tgg att tct ggt ttg cct gat atc     480
Ser Gln Thr Ser Ile Glu Gln Cys Trp Ile Ser Gly Leu Pro Asp Ile
145                 150                 155                 160 aac act gaa gac tcg gcc att gtt agc aaa ttg aat tcg att gtt tct     528
Asn Thr Glu Asp Ser Ala Ile Val Ser Lys Leu Asn Ser Ile Val Ser
                165                 170                 175 ggt tgg gta tct gat tat ggc ttt gac ggt ctt cga atc gac act gtg     576
Gly Trp Val Ser Asp Tyr Gly Phe Asp Gly Leu Arg Ile Asp Thr Val
            180                 185                 190 aag cac att cgt aaa gat ttc tgg gac ggc tat gtc tct gct gct ggt     624
Lys His Ile Arg Lys Asp Phe Trp Asp Gly Tyr Val Ser Ala Ala Gly
        195                 200                 205 gta ttt gct acc gga gaa gtg ctt agc ggc gat gtt tct tat gtc tca     672
Val Phe Ala Thr Gly Glu Val Leu Ser Gly Asp Val Ser Tyr Val Ser
    210                 215                 220 ccc tat cag cag cat gtt cct tct tta ctc aac tac cca ttg tat tat     720
Pro Tyr Gln Gln His Val Pro Ser Leu Leu Asn Tyr Pro Leu Tyr Tyr
225                 230                 235                 240 cca gtc tat gat gta ttc acc aaa tcc cgt acc atg agc cgt tta agc     768
Pro Val Tyr Asp Val Phe Thr Lys Ser Arg Thr Met Ser Arg Leu Ser
                245                 250                 255 tct ggc ttt tct gat att aaa aat gga aac ttt aaa gac att gat gtc     816
Ser Gly Phe Ser Asp Ile Lys Asn Gly Asn Phe Lys Asp Ile Asp Val
            260                 265                 270 ttg gtc aac ttt att gac aat cac gat cag cct cgt ttg tta tcc aaa     864
Leu Val Asn Phe Ile Asp Asn His Asp Gln Pro Arg Leu Leu Ser Lys
        275                 280                 285 gct gat caa agt ctc gtc aag aat gct ctt gct tat tct ttc atg gtc     912
Ala Asp Gln Ser Leu Val Lys Asn Ala Leu Ala Tyr Ser Phe Met Val
    290                 295                 300 caa ggt atc cct gtc ttg tac tat ggt aca gaa caa tcc ttc aag ggt     960
Gln Gly Ile Pro Val Leu Tyr Tyr Gly Thr Glu Gln Ser Phe Lys Gly
305                 310                 315                 320
```

```
ggt aac gat cct aac aac aga gag gtc tta tgg acc act ggt tac tcg    1008
Gly Asn Asp Pro Asn Asn Arg Glu Val Leu Trp Thr Thr Gly Tyr Ser
            325                 330                 335 acc aca tct gat atg tac aag ttt gtc act act ctt gtc aag gca cgc    1056
Thr Thr Ser Asp Met Tyr Lys Phe Val Thr Thr Leu Val Lys Ala Arg
        340                 345                 350 aag ggc tca aac tcc aca gta aat atg gga att gct caa acc gat aac    1104
Lys Gly Ser Asn Ser Thr Val Asn Met Gly Ile Ala Gln Thr Asp Asn
    355                 360                 365 gtc tat gtg ttc caa aga ggt ggc tct ctg gtt gtt gtc aat aac tat    1152
Val Tyr Val Phe Gln Arg Gly Gly Ser Leu Val Val Val Asn Asn Tyr
370                 375                 380 ggt caa gga tca aca aac aca att act gta aag gct ggc tcg ttc tct    1200
Gly Gln Gly Ser Thr Asn Thr Ile Thr Val Lys Ala Gly Ser Phe Ser
385                 390                 395                 400 aat gga gat act ttg act gat gtg ttc tcc aac aaa tct gtt act gtt    1248
Asn Gly Asp Thr Leu Thr Asp Val Phe Ser Asn Lys Ser Val Thr Val
            405                 410                 415 caa aat aac cag atc aca ttc caa ttg cag aat gga aac cct gcc ata    1296
Gln Asn Asn Gln Ile Thr Phe Gln Leu Gln Asn Gly Asn Pro Ala Ile
        420                 425                 430 ttc caa aag aaa                                                    1308
Phe Gln Lys Lys
    435

<210> SEQ ID NO 129
<211> LENGTH: 436
<212> TYPE: PRT
<213> ORGANISM: Rhizopus oryzae

<400> SEQUENCE: 129

Ala Ser Ala Ser Asp Trp Glu Asn Arg Val Ile Tyr Gln Leu Leu Thr
1               5                   10                  15

Asp Arg Phe Ala Lys Ser Thr Asp Asp Thr Asn Gly Cys Asn Asn Leu
            20                  25                  30

Ser Asp Tyr Cys Gly Gly Thr Phe Gln Gly Ile Ile Asn His Leu Asp
        35                  40                  45

Tyr Ile Ala Gly Met Gly Phe Asp Ala Ile Trp Ile Ser Pro Ile Pro
    50                  55                  60

Lys Asn Ala Asn Gly Gly Tyr His Gly Tyr Trp Ala Thr Asp Phe Ser
65                  70                  75                  80

Gln Ile Asn Glu His Phe Gly Thr Ala Asp Asp Leu Lys Lys Leu Val
                85                  90                  95

Ala Ala Ala His Ala Lys Asn Met Tyr Val Met Leu Asp Val Val Ala
            100                 105                 110

Asn His Ala Gly Ile Pro Ser Ser Gly Gly Asp Tyr Ser Gly Tyr Thr
        115                 120                 125

Phe Gly Gln Ser Ser Glu Tyr His Thr Ala Cys Asp Ile Asn Tyr Asn
    130                 135                 140

Ser Gln Thr Ser Ile Glu Gln Cys Trp Ile Ser Gly Leu Pro Asp Ile
145                 150                 155                 160

Asn Thr Glu Asp Ser Ala Ile Val Ser Lys Leu Asn Ser Ile Val Ser
                165                 170                 175

Gly Trp Val Ser Asp Tyr Gly Phe Asp Gly Leu Arg Ile Asp Thr Val
            180                 185                 190

Lys His Ile Arg Lys Asp Phe Trp Asp Gly Tyr Val Ser Ala Ala Gly
        195                 200                 205

Val Phe Ala Thr Gly Glu Val Leu Ser Gly Asp Val Ser Tyr Val Ser
```

```
                    210                  215                  220
Pro Tyr Gln Gln His Val Pro Ser Leu Leu Asn Tyr Pro Leu Tyr Tyr
225                 230                 235                 240

Pro Val Tyr Asp Val Phe Thr Lys Ser Arg Thr Met Ser Arg Leu Ser
                    245                 250                 255

Ser Gly Phe Ser Asp Ile Lys Asn Gly Asn Phe Lys Asp Ile Asp Val
                260                 265                 270

Leu Val Asn Phe Ile Asp Asn His Asp Gln Pro Arg Leu Leu Ser Lys
            275                 280                 285

Ala Asp Gln Ser Leu Val Lys Asn Ala Leu Ala Tyr Ser Phe Met Val
290                 295                 300

Gln Gly Ile Pro Val Leu Tyr Tyr Gly Thr Glu Gln Ser Phe Lys Gly
305                 310                 315                 320

Gly Asn Asp Pro Asn Asn Arg Glu Val Leu Trp Thr Thr Gly Tyr Ser
                325                 330                 335

Thr Thr Ser Asp Met Tyr Lys Phe Val Thr Thr Leu Val Lys Ala Arg
                340                 345                 350

Lys Gly Ser Asn Ser Thr Val Asn Met Gly Ile Ala Gln Thr Asp Asn
                355                 360                 365

Val Tyr Val Phe Gln Arg Gly Gly Ser Leu Val Val Val Asn Asn Tyr
370                 375                 380

Gly Gln Gly Ser Thr Asn Thr Ile Thr Val Lys Ala Gly Ser Phe Ser
385                 390                 395                 400

Asn Gly Asp Thr Leu Thr Asp Val Phe Ser Asn Lys Ser Val Thr Val
                405                 410                 415

Gln Asn Asn Gln Ile Thr Phe Gln Leu Gln Asn Gly Asn Pro Ala Ile
                420                 425                 430

Phe Gln Lys Lys
            435

<210> SEQ ID NO 130
<211> LENGTH: 1338
<212> TYPE: DNA
<213> ORGANISM: Thaminidium elegans
<220> FEATURE:
<221> NAME/KEY: CDS
<222> LOCATION: (1)..(1338)

<400> SEQUENCE: 130 aac ggt gtc acg act ttg agc aag cgt gca gct gct gat gac tgg aaa       48
Asn Gly Val Thr Thr Leu Ser Lys Arg Ala Ala Ala Asp Asp Trp Lys
1               5                   10                  15 tcc cgg tcc att tac caa gtt gtg acg gat cgt ttc ggt cgc tcg gat       96
Ser Arg Ser Ile Tyr Gln Val Val Thr Asp Arg Phe Gly Arg Ser Asp
                20                  25                  30 ggc tcg acc tct gct tgc ggt gac ctg tcc aac tac tgc ggt ggt gac      144
Gly Ser Thr Ser Ala Cys Gly Asp Leu Ser Asn Tyr Cys Gly Gly Asp
            35                  40                  45 tac aag ggc att cag aat cag ctc gac tac att gct ggc atg ggc ttc      192
Tyr Lys Gly Ile Gln Asn Gln Leu Asp Tyr Ile Ala Gly Met Gly Phe
    50                  55                  60 gac gcc att tgg atc tcg cct att cct gag aac aca gac ggc ggc tac      240
Asp Ala Ile Trp Ile Ser Pro Ile Pro Glu Asn Thr Asp Gly Gly Tyr
65                  70                  75                  80 cat ggt tac tgg gca aag gac ttt gaa aag ctc aac acc aat ttt ggc      288
His Gly Tyr Trp Ala Lys Asp Phe Glu Lys Leu Asn Thr Asn Phe Gly
                85                  90                  95 agt gcg gat gat ctc aag gct ctc gtg aca gct gcg cac ggc aag ggc      336
```

-continued

```
                Ser Ala Asp Asp Leu Lys Ala Leu Val Thr Ala Ala His Gly Lys Gly
                            100                 105                 110 atg tat gtc atg ctg gat gtc gtc aca aac cac gca ggt ccc gcc agc        384
Met Tyr Val Met Leu Asp Val Val Thr Asn His Ala Gly Pro Ala Ser
            115                 120                 125 ggc gac tac agc ggc ttc acc ttc agc tcc gcc agt aat tat cat ccg        432
Gly Asp Tyr Ser Gly Phe Thr Phe Ser Ser Ala Ser Asn Tyr His Pro
        130                 135                 140 cag tgc acg atc gac tgc gac aac cag act tcc gtc gag cag tgc tgg        480
Gln Cys Thr Ile Asp Cys Asp Asn Gln Thr Ser Val Glu Gln Cys Trp
145                 150                 155                 160 gtg gcg gac aac ctg ccc gac att aac acc gag gat gat acc att gtt        528
Val Ala Asp Asn Leu Pro Asp Ile Asn Thr Glu Asp Asp Thr Ile Val
                165                 170                 175 tcc aag ctg cac agc att gtc tct gat tgg gtc acc acc tac gat ttt        576
Ser Lys Leu His Ser Ile Val Ser Asp Trp Val Thr Thr Tyr Asp Phe
            180                 185                 190 gat ggc att cgt atc gat act gtc aag cat atc cgt aaa gac ttc tgg        624
Asp Gly Ile Arg Ile Asp Thr Val Lys His Ile Arg Lys Asp Phe Trp
        195                 200                 205 tct ggc tac gaa gag gct gct gga gtc ttt gct act ggc gaa gtc ttt        672
Ser Gly Tyr Glu Glu Ala Ala Gly Val Phe Ala Thr Gly Glu Val Phe
    210                 215                 220 gac ggc gac gcg gct tat gtc ggt cct tac cag gac cag ttg agc tcg        720
Asp Gly Asp Ala Ala Tyr Val Gly Pro Tyr Gln Asp Gln Leu Ser Ser
225                 230                 235                 240 ctc atc aac tac cca ctt tac tat gct atc cgc gat gtc ttc acc gcc        768
Leu Ile Asn Tyr Pro Leu Tyr Tyr Ala Ile Arg Asp Val Phe Thr Ala
                245                 250                 255 ggc tcg ggc ttt agc cgc atc agc gac atg ctt tcc agc atc aac tcg        816
Gly Ser Gly Phe Ser Arg Ile Ser Asp Met Leu Ser Ser Ile Asn Ser
            260                 265                 270 aac ttc aag gac ccc tcc gcg ctc acg acc ttt gtg gat aac caa gac        864
Asn Phe Lys Asp Pro Ser Ala Leu Thr Thr Phe Val Asp Asn Gln Asp
        275                 280                 285 aac gcc cgc ttc ctc agt gtg aag agt gac atg tct ctg tac aag aat        912
Asn Ala Arg Phe Leu Ser Val Lys Ser Asp Met Ser Leu Tyr Lys Asn
    290                 295                 300 gct ctt gcg ttc acg att ctg acc gag ggt atc cct gtt gtg tac tac        960
Ala Leu Ala Phe Thr Ile Leu Thr Glu Gly Ile Pro Val Val Tyr Tyr
305                 310                 315                 320 ggc acc gag caa ggc ttc aaa ggt ggt gat gac ccc aag aac cgt gag       1008
Gly Thr Glu Gln Gly Phe Lys Gly Gly Asp Asp Pro Lys Asn Arg Glu
                325                 330                 335 gtc ctc tgg acc tcc aac tat gat acc tcc tcg gat ctc tac aag ttt       1056
Val Leu Trp Thr Ser Asn Tyr Asp Thr Ser Ser Asp Leu Tyr Lys Phe
            340                 345                 350 atc aag att gtg aac aat gat gtt cgc cag aaa tca aac aag tct gtg       1104
Ile Lys Ile Val Asn Asn Asp Val Arg Gln Lys Ser Asn Lys Ser Val
        355                 360                 365 act ctg aac gta gac gtg gga acc aac acc tac gcg ttc aca cac ggc       1152
Thr Leu Asn Val Asp Val Gly Thr Asn Thr Tyr Ala Phe Thr His Gly
    370                 375                 380 aag aat ctc atc gtt gtc aac aac tat ggc agt ggt tcc act gcg tct       1200
Lys Asn Leu Ile Val Val Asn Asn Tyr Gly Ser Gly Ser Thr Ala Ser
385                 390                 395                 400 gtc act gtc aag gct ggt gac att gca gac ggc aca aaa ctg gtg gat       1248
Val Thr Val Lys Ala Gly Asp Ile Ala Asp Gly Thr Lys Leu Val Asp
                405                 410                 415 gct gtc agt aac att acg gct acc gtc tcg gga ggc agc atc aca ttc       1296
```

| | | | | | | | | | | | | | |
|---|---|---|---|---|---|---|---|---|---|---|---|---|---|
| Ala | Val | Ser | Asn | Ile | Thr | Ala | Thr | Val | Ser | Gly | Gly | Ser | Ile | Thr | Phe |
| | | | 420 | | | | | 425 | | | | | 430 | | |

```
tcc ttg aag gac ggt ctt ccg gct ctt ttc gtg ccc agc tcg            1338
Ser Leu Lys Asp Gly Leu Pro Ala Leu Phe Val Pro Ser Ser
    435                 440                 445
```

<210> SEQ ID NO 131
<211> LENGTH: 446
<212> TYPE: PRT
<213> ORGANISM: Thaminidium elegans

<400> SEQUENCE: 131

```
Asn Gly Val Thr Thr Leu Ser Lys Arg Ala Ala Asp Asp Trp Lys
1               5                   10                  15

Ser Arg Ser Ile Tyr Gln Val Val Thr Asp Arg Phe Gly Arg Ser Asp
                20                  25                  30

Gly Ser Thr Ser Ala Cys Gly Asp Leu Ser Asn Tyr Cys Gly Gly Asp
            35                  40                  45

Tyr Lys Gly Ile Gln Asn Gln Leu Asp Tyr Ile Ala Gly Met Gly Phe
        50                  55                  60

Asp Ala Ile Trp Ile Ser Pro Ile Pro Glu Asn Thr Asp Gly Gly Tyr
65                  70                  75                  80

His Gly Tyr Trp Ala Lys Asp Phe Glu Lys Leu Asn Thr Asn Phe Gly
                85                  90                  95

Ser Ala Asp Asp Leu Lys Ala Leu Val Thr Ala Ala His Gly Lys Gly
            100                 105                 110

Met Tyr Val Met Leu Asp Val Val Thr Asn His Ala Gly Pro Ala Ser
        115                 120                 125

Gly Asp Tyr Ser Gly Phe Thr Phe Ser Ser Ala Ser Asn Tyr His Pro
    130                 135                 140

Gln Cys Thr Ile Asp Cys Asp Asn Gln Thr Ser Val Glu Gln Cys Trp
145                 150                 155                 160

Val Ala Asp Asn Leu Pro Asp Ile Asn Thr Glu Asp Thr Ile Val
                165                 170                 175

Ser Lys Leu His Ser Ile Val Ser Asp Trp Val Thr Thr Tyr Asp Phe
            180                 185                 190

Asp Gly Ile Arg Ile Asp Thr Val Lys His Ile Arg Lys Asp Phe Trp
        195                 200                 205

Ser Gly Tyr Glu Glu Ala Ala Gly Val Phe Ala Thr Gly Glu Val Phe
    210                 215                 220

Asp Gly Asp Ala Ala Tyr Val Gly Pro Tyr Gln Asp Gln Leu Ser Ser
225                 230                 235                 240

Leu Ile Asn Tyr Pro Leu Tyr Tyr Ala Ile Arg Asp Val Phe Thr Ala
                245                 250                 255

Gly Ser Gly Phe Ser Arg Ile Ser Asp Met Leu Ser Ser Ile Asn Ser
            260                 265                 270

Asn Phe Lys Asp Pro Ser Ala Leu Thr Thr Phe Val Asp Asn Gln Asp
        275                 280                 285

Asn Ala Arg Phe Leu Ser Val Lys Ser Asp Met Ser Leu Tyr Lys Asn
    290                 295                 300

Ala Leu Ala Phe Thr Ile Leu Thr Glu Gly Ile Pro Val Val Tyr Tyr
305                 310                 315                 320

Gly Thr Glu Gln Gly Phe Lys Gly Gly Asp Pro Lys Asn Arg Glu
                325                 330                 335

Val Leu Trp Thr Ser Asn Tyr Asp Thr Ser Ser Asp Leu Tyr Lys Phe
            340                 345                 350
```

```
Ile Lys Ile Val Asn Asn Asp Val Arg Gln Lys Ser Asn Lys Ser Val
        355                 360                 365

Thr Leu Asn Val Asp Val Gly Thr Asn Thr Tyr Ala Phe Thr His Gly
        370                 375                 380

Lys Asn Leu Ile Val Val Asn Asn Tyr Gly Ser Gly Ser Thr Ala Ser
385                 390                 395                 400

Val Thr Val Lys Ala Gly Asp Ile Ala Asp Gly Thr Lys Leu Val Asp
            405                 410                 415

Ala Val Ser Asn Ile Thr Ala Thr Val Ser Gly Gly Ser Ile Thr Phe
                420                 425                 430

Ser Leu Lys Asp Gly Leu Pro Ala Leu Phe Val Pro Ser Ser
        435                 440                 445

<210> SEQ ID NO 132
<211> LENGTH: 1305
<212> TYPE: DNA
<213> ORGANISM: Absidia crista
<220> FEATURE:
<221> NAME/KEY: CDS
<222> LOCATION: (1)..(1305)

<400> SEQUENCE: 132
```

| | | | | | | | | | | | | | | | | |
|---|---|---|---|---|---|---|---|---|---|---|---|---|---|---|---|---|
| gca | ggc | gcc | gat | gat | tgg | aga | tca | cgt | tcc | atc | tat | caa | tta | ttg | act | 48 |
| Ala | Gly | Ala | Asp | Asp | Trp | Arg | Ser | Arg | Ser | Ile | Tyr | Gln | Leu | Leu | Thr | |
| 1 | | | 5 | | | | | 10 | | | | | 15 | | | |
| gat | cgc | ttt | gct | ggt | ggc | ggt | gat | tgt | tct | gat | tta | tcc | gat | tat | tgt | 96 |
| Asp | Arg | Phe | Ala | Gly | Gly | Gly | Asp | Cys | Ser | Asp | Leu | Ser | Asp | Tyr | Cys | |
| | | | 20 | | | | | 25 | | | | | 30 | | | |
| ggt | ggt | aat | tat | aaa | ggc | atg | att | gaa | cac | ctg | gat | tat | atc | caa | gga | 144 |
| Gly | Gly | Asn | Tyr | Lys | Gly | Met | Ile | Glu | His | Leu | Asp | Tyr | Ile | Gln | Gly | |
| | | 35 | | | | | 40 | | | | | 45 | | | | |
| atg | gga | ttc | gat | gcc | atc | tgg | att | tcc | ccc | atc | cct | acc | aac | tca | ccc | 192 |
| Met | Gly | Phe | Asp | Ala | Ile | Trp | Ile | Ser | Pro | Ile | Pro | Thr | Asn | Ser | Pro | |
| | 50 | | | | | 55 | | | | | 60 | | | | | |
| ggc | ggt | tac | cat | ggc | tac | tgg | gca | act | gac | ttc | aat | ggt | tta | aat | gaa | 240 |
| Gly | Gly | Tyr | His | Gly | Tyr | Trp | Ala | Thr | Asp | Phe | Asn | Gly | Leu | Asn | Glu | |
| 65 | | | | | 70 | | | | | 75 | | | | | 80 | |
| aac | ttt | gga | acc | aag | gac | gat | ctc | aag | gct | ttg | gtg | gat | gca | gca | cat | 288 |
| Asn | Phe | Gly | Thr | Lys | Asp | Asp | Leu | Lys | Ala | Leu | Val | Asp | Ala | Ala | His | |
| | | | | 85 | | | | | 90 | | | | | 95 | | |
| aag | ctc | gac | atg | tat | gtc | atg | ttg | gat | gtc | gtt | gcc | aat | cat | gct | gga | 336 |
| Lys | Leu | Asp | Met | Tyr | Val | Met | Leu | Asp | Val | Val | Ala | Asn | His | Ala | Gly | |
| | | | 100 | | | | | 105 | | | | | 110 | | | |
| caa | ccc | agt | acg | gca | ggt | gac | tat | tct | ggc | tac | aca | ttc | gat | tct | aaa | 384 |
| Gln | Pro | Ser | Thr | Ala | Gly | Asp | Tyr | Ser | Gly | Tyr | Thr | Phe | Asp | Ser | Lys | |
| | | 115 | | | | | 120 | | | | | 125 | | | | |
| gac | caa | tac | cat | tcc | caa | tgc | aaa | atc | gat | tat | gat | gat | caa | aac | tct | 432 |
| Asp | Gln | Tyr | His | Ser | Gln | Cys | Lys | Ile | Asp | Tyr | Asp | Asp | Gln | Asn | Ser | |
| | 130 | | | | | 135 | | | | | 140 | | | | | |
| att | gag | cag | tgt | tgg | gtg | gct | gat | gtg | ttg | cct | gac | atc | aac | act | gag | 480 |
| Ile | Glu | Gln | Cys | Trp | Val | Ala | Asp | Val | Leu | Pro | Asp | Ile | Asn | Thr | Glu | |
| 145 | | | | | 150 | | | | | 155 | | | | | 160 | |
| gat | gat | aac | gtg | gtc | aag | acg | ctc | aat | gat | att | gtc | agc | aac | tgg | gta | 528 |
| Asp | Asp | Asn | Val | Val | Lys | Thr | Leu | Asn | Asp | Ile | Val | Ser | Asn | Trp | Val | |
| | | | | 165 | | | | | 170 | | | | | 175 | | |
| act | aca | tat | ggc | ttt | gat | ggt | att | cgc | att | gac | act | gtc | aag | cat | gta | 576 |
| Thr | Thr | Tyr | Gly | Phe | Asp | Gly | Ile | Arg | Ile | Asp | Thr | Val | Lys | His | Val | |
| | | | 180 | | | | | 185 | | | | | 190 | | | |
| cgt | caa | gac | ttt | tgg | gat | gga | tac | aat | gaa | gca | gct | ggt | gta | ttt | gct | 624 |
| Arg | Gln | Asp | Phe | Trp | Asp | Gly | Tyr | Asn | Glu | Ala | Ala | Gly | Val | Phe | Ala | |

```
                195                 200                 205
aca gga gaa gtc ttt gat ggt gat tca tcc tat gtt ggt gga tat caa      672
Thr Gly Glu Val Phe Asp Gly Asp Ser Ser Tyr Val Gly Gly Tyr Gln
    210                 215                 220 aag cat ttg gac tcg ctt ctc aat tac cca atg tat tac gca ctc aat      720
Lys His Leu Asp Ser Leu Leu Asn Tyr Pro Met Tyr Tyr Ala Leu Asn
225                 230                 235                 240 gat gta ttt ggt tct gga aag ggt ttt agt cgt atc agc gag atg att      768
Asp Val Phe Gly Ser Gly Lys Gly Phe Ser Arg Ile Ser Glu Met Ile
                245                 250                 255 gca acc aat gca gat gca ttt gct gat acc agt gtt ctg acc aac ttt      816
Ala Thr Asn Ala Asp Ala Phe Ala Asp Thr Ser Val Leu Thr Asn Phe
        260                 265                 270 att gac aac cat gat aac cca cgt ttc ctt aat acc aac aag gat act      864
Ile Asp Asn His Asp Asn Pro Arg Phe Leu Asn Thr Asn Lys Asp Thr
    275                 280                 285 act ctc ttc aag aac gct ttg acc tac gtg ttg ctc gct gat ggt att      912
Thr Leu Phe Lys Asn Ala Leu Thr Tyr Val Leu Leu Ala Asp Gly Ile
290                 295                 300 cca gtg gtg tat tat gga tca gaa caa ggc ttt tca ggt ggt gct gat      960
Pro Val Val Tyr Tyr Gly Ser Glu Gln Gly Phe Ser Gly Gly Ala Asp
305                 310                 315                 320 cct gcc aat cgt gaa gca tta tgg tca act gac ttt gac acc tcg tcc      1008
Pro Ala Asn Arg Glu Ala Leu Trp Ser Thr Asp Phe Asp Thr Ser Ser
                325                 330                 335 gat ttg tac aag ttt atg gct act gtc aac aag gat gtt cgt caa aag      1056
Asp Leu Tyr Lys Phe Met Ala Thr Val Asn Lys Asp Val Arg Gln Lys
        340                 345                 350 gaa aac aaa aag gtg gtg atg gat gtt gat gtg caa gac aac gtg tat      1104
Glu Asn Lys Lys Val Val Met Asp Val Asp Val Gln Asp Asn Val Tyr
    355                 360                 365 gca ttc atg cac ggc gat gct ctt gtg gta ttg aac aac tac ggc agt      1152
Ala Phe Met His Gly Asp Ala Leu Val Val Leu Asn Asn Tyr Gly Ser
370                 375                 380 gga gcc agc aac gag gtt act gtc aag gtc gga tca cat gtt gat gat      1200
Gly Ala Ser Asn Glu Val Thr Val Lys Val Gly Ser His Val Asp Asp
385                 390                 395                 400 gga gcc aag atg aac gac gtc ttt acc aat agc aca gtc tcg gta tct      1248
Gly Ala Lys Met Asn Asp Val Phe Thr Asn Ser Thr Val Ser Val Ser
                405                 410                 415 ggt ggt tca ttc act ttc aaa ctt gac aat gga aat cct gcc atc ttt      1296
Gly Gly Ser Phe Thr Phe Lys Leu Asp Asn Gly Asn Pro Ala Ile Phe
        420                 425                 430 acc act gct                                                          1305
Thr Thr Ala
    435

<210> SEQ ID NO 133
<211> LENGTH: 435
<212> TYPE: PRT
<213> ORGANISM: Absidia crista

<400> SEQUENCE: 133

Ala Gly Ala Asp Asp Trp Arg Ser Arg Ser Ile Tyr Gln Leu Leu Thr
1               5                   10                  15

Asp Arg Phe Ala Gly Gly Asp Cys Ser Asp Leu Ser Asp Tyr Cys
            20                  25                  30

Gly Gly Asn Tyr Lys Gly Met Ile Glu His Leu Asp Tyr Ile Gln Gly
        35                  40                  45

Met Gly Phe Asp Ala Ile Trp Ile Ser Pro Ile Pro Thr Asn Ser Pro
```

```
              50                  55                  60
Gly Gly Tyr His Gly Tyr Trp Ala Thr Asp Phe Asn Gly Leu Asn Glu
 65                  70                  75                  80

Asn Phe Gly Thr Lys Asp Asp Leu Lys Ala Leu Val Asp Ala Ala His
                 85                  90                  95

Lys Leu Asp Met Tyr Val Met Leu Asp Val Val Ala Asn His Ala Gly
                100                 105                 110

Gln Pro Ser Thr Ala Gly Asp Tyr Ser Gly Tyr Thr Phe Asp Ser Lys
                115                 120                 125

Asp Gln Tyr His Ser Gln Cys Lys Ile Asp Tyr Asp Gln Asn Ser
            130                 135                 140

Ile Glu Gln Cys Trp Val Ala Asp Val Leu Pro Asp Ile Asn Thr Glu
145                 150                 155                 160

Asp Asp Asn Val Val Lys Thr Leu Asn Asp Ile Val Ser Asn Trp Val
                165                 170                 175

Thr Thr Tyr Gly Phe Asp Gly Ile Arg Ile Asp Thr Val Lys His Val
                180                 185                 190

Arg Gln Asp Phe Trp Asp Gly Tyr Asn Glu Ala Ala Gly Val Phe Ala
                195                 200                 205

Thr Gly Glu Val Phe Asp Gly Asp Ser Ser Tyr Val Gly Gly Tyr Gln
210                 215                 220

Lys His Leu Asp Ser Leu Leu Asn Tyr Pro Met Tyr Tyr Ala Leu Asn
225                 230                 235                 240

Asp Val Phe Gly Ser Gly Lys Gly Phe Ser Arg Ile Ser Glu Met Ile
                245                 250                 255

Ala Thr Asn Ala Asp Ala Phe Ala Asp Thr Ser Val Leu Thr Asn Phe
                260                 265                 270

Ile Asp Asn His Asp Asn Pro Arg Phe Leu Asn Thr Asn Lys Asp Thr
                275                 280                 285

Thr Leu Phe Lys Asn Ala Leu Thr Tyr Val Leu Ala Asp Gly Ile
290                 295                 300

Pro Val Val Tyr Tyr Gly Ser Glu Gln Gly Phe Ser Gly Gly Ala Asp
305                 310                 315                 320

Pro Ala Asn Arg Glu Ala Leu Trp Ser Thr Asp Phe Asp Thr Ser Ser
                325                 330                 335

Asp Leu Tyr Lys Phe Met Ala Thr Val Asn Lys Asp Val Arg Gln Lys
                340                 345                 350

Glu Asn Lys Lys Val Val Met Asp Val Asp Val Gln Asp Asn Val Tyr
                355                 360                 365

Ala Phe Met His Gly Asp Ala Leu Val Val Leu Asn Asn Tyr Gly Ser
370                 375                 380

Gly Ala Ser Asn Glu Val Thr Val Lys Val Gly Ser His Val Asp Asp
385                 390                 395                 400

Gly Ala Lys Met Asn Asp Val Phe Thr Asn Ser Thr Val Ser Val Ser
                405                 410                 415

Gly Gly Ser Phe Thr Phe Lys Leu Asp Asn Gly Asn Pro Ala Ile Phe
                420                 425                 430

Thr Thr Ala
        435

<210> SEQ ID NO 134
<211> LENGTH: 1308
<212> TYPE: DNA
<213> ORGANISM: Syncephalastrum racemosum
<220> FEATURE:
```

```
<221> NAME/KEY: CDS
<222> LOCATION: (1)..(1308)

<400> SEQUENCE: 134 gcg act gct agt gac tgg gaa aat cga gtt atc tac caa ttg ttg aca      48
Ala Thr Ala Ser Asp Trp Glu Asn Arg Val Ile Tyr Gln Leu Leu Thr
1               5                   10                  15 gat cga ttt gct aaa agc tct gac gac aca aac ggt tgc tcc aac cta      96
Asp Arg Phe Ala Lys Ser Ser Asp Asp Thr Asn Gly Cys Ser Asn Leu
            20                  25                  30 ggc aat tat tgt ggc ggg acg ttt caa ggg att atc aat cat cta gac     144
Gly Asn Tyr Cys Gly Gly Thr Phe Gln Gly Ile Ile Asn His Leu Asp
        35                  40                  45 tat att gcc ggt atg gga ttc gat gcg atc tgg ata tcg cca att cct     192
Tyr Ile Ala Gly Met Gly Phe Asp Ala Ile Trp Ile Ser Pro Ile Pro
    50                  55                  60 gaa aac tcg gat ggg ggg tat cac ggt tac tgg gct acc aac ttt tct     240
Glu Asn Ser Asp Gly Gly Tyr His Gly Tyr Trp Ala Thr Asn Phe Ser
65                  70                  75                  80 gcc atc aac tca cat ttt ggg tcg tct aat gat ttg aag aaa ttg gtg     288
Ala Ile Asn Ser His Phe Gly Ser Ser Asn Asp Leu Lys Lys Leu Val
                85                  90                  95 tca gca gct cat gac aag ggc atg tat gtt atg ctt gac gtg gtt gct     336
Ser Ala Ala His Asp Lys Gly Met Tyr Val Met Leu Asp Val Val Ala
            100                 105                 110 aac cac gtt ggc ata cct tcc tcc agt ggc caa tac tcg gga tac acg     384
Asn His Val Gly Ile Pro Ser Ser Ser Gly Gln Tyr Ser Gly Tyr Thr
        115                 120                 125 ttt gat caa agc tct cag tat cat agt tct tgt gat att aac tat gac     432
Phe Asp Gln Ser Ser Gln Tyr His Ser Ser Cys Asp Ile Asn Tyr Asp
    130                 135                 140 aac caa aac tct att gaa caa tgc tgg atc tct ggc tta cct gat ctt     480
Asn Gln Asn Ser Ile Glu Gln Cys Trp Ile Ser Gly Leu Pro Asp Leu
145                 150                 155                 160 aac acc gaa gat tca gcg gta gtc agc aag cta aac tcg att gtg tca     528
Asn Thr Glu Asp Ser Ala Val Val Ser Lys Leu Asn Ser Ile Val Ser
                165                 170                 175 aac tgg gta tcc gaa tat gac ttt gat ggg ctt cgt att gat act gtc     576
Asn Trp Val Ser Glu Tyr Asp Phe Asp Gly Leu Arg Ile Asp Thr Val
            180                 185                 190 aag cac att cgc aag gat ttt tgg gat ggc tat gta tct gct gca ggt     624
Lys His Ile Arg Lys Asp Phe Trp Asp Gly Tyr Val Ser Ala Ala Gly
        195                 200                 205 gta ttt gcc act ggg gaa gtc ttg aac ggt gct gtt tct tat gtt gct     672
Val Phe Ala Thr Gly Glu Val Leu Asn Gly Ala Val Ser Tyr Val Ala
    210                 215                 220 cca tac caa caa cat gtt ccc tct tta ctc aac tac cca ctg tat ttc     720
Pro Tyr Gln Gln His Val Pro Ser Leu Leu Asn Tyr Pro Leu Tyr Phe
225                 230                 235                 240 ccc gtc aat gat gtg ttc acg aag gct tct acc atg agt cgt ttg gga     768
Pro Val Asn Asp Val Phe Thr Lys Ala Ser Thr Met Ser Arg Leu Gly
                245                 250                 255 tca ggc tat gct gat atc cag tct ggc agc ttt aca aac aga aac cat     816
Ser Gly Tyr Ala Asp Ile Gln Ser Gly Ser Phe Thr Asn Arg Asn His
            260                 265                 270 ctg gtt aac ttt atc gac aac cat gac aat cct cgt ttg tta tcc aag     864
Leu Val Asn Phe Ile Asp Asn His Asp Asn Pro Arg Leu Leu Ser Lys
        275                 280                 285 tct gat cag gtc ttg gtg aag aat gct ctt aca tac acc atg atg att     912
Ser Asp Gln Val Leu Val Lys Asn Ala Leu Thr Tyr Thr Met Met Ile
    290                 295                 300
```

-continued

```
gaa gga atc cca gcc atg tac tat ggt acc gag caa tca ttc aat gga      960
Glu Gly Ile Pro Ala Met Tyr Tyr Gly Thr Glu Gln Ser Phe Asn Gly
305                 310                 315                 320 ggc tct gac cct gcc aac aga gag gtc tta tgg acc acg aat tat tcg     1008
Gly Ser Asp Pro Ala Asn Arg Glu Val Leu Trp Thr Thr Asn Tyr Ser
                325                 330                 335 acc aca tcc gac atg tac aag ttt gtc act tta ctc gtc aaa aca cgc     1056
Thr Thr Ser Asp Met Tyr Lys Phe Val Thr Leu Leu Val Lys Thr Arg
            340                 345                 350 aag agc tcg gga aac acg gtt act aca ggc att gac cag acc aac aat     1104
Lys Ser Ser Gly Asn Thr Val Thr Thr Gly Ile Asp Gln Thr Asn Asn
        355                 360                 365 gtt tat gtg ttt caa aga gac aag tat ctg gtt gtt gtg aac aat tac     1152
Val Tyr Val Phe Gln Arg Asp Lys Tyr Leu Val Val Val Asn Asn Tyr
    370                 375                 380 ggc tca gga tcc acc aat tcg atc act gta aag gct ggt tca ttc tcc     1200
Gly Ser Gly Ser Thr Asn Ser Ile Thr Val Lys Ala Gly Ser Phe Ser
385                 390                 395                 400 aat ggt gtt acc ctt gtg gat ata ttc tcg aat aaa aca gtg act gtg     1248
Asn Gly Val Thr Leu Val Asp Ile Phe Ser Asn Lys Thr Val Thr Val
                405                 410                 415 tca aac gga tcg atc acc ttc cag ctt caa aat ggt aat cct gct gta     1296
Ser Asn Gly Ser Ile Thr Phe Gln Leu Gln Asn Gly Asn Pro Ala Val
            420                 425                 430 ttc caa agc aaa                                                     1308
Phe Gln Ser Lys
        435
```

<210> SEQ ID NO 135
<211> LENGTH: 436
<212> TYPE: PRT
<213> ORGANISM: Syncephalastrum racemosum

<400> SEQUENCE: 135

```
Ala Thr Ala Ser Asp Trp Glu Asn Arg Val Ile Tyr Gln Leu Leu Thr
1               5                   10                  15

Asp Arg Phe Ala Lys Ser Ser Asp Thr Asn Gly Cys Ser Asn Leu
                20                  25                  30

Gly Asn Tyr Cys Gly Gly Thr Phe Gln Gly Ile Ile Asn His Leu Asp
            35                  40                  45

Tyr Ile Ala Gly Met Gly Phe Asp Ala Ile Trp Ile Ser Pro Ile Pro
    50                  55                  60

Glu Asn Ser Asp Gly Tyr His Gly Tyr Trp Ala Thr Asn Phe Ser
65                  70                  75                  80

Ala Ile Asn Ser His Phe Gly Ser Ser Asn Asp Leu Lys Lys Leu Val
                85                  90                  95

Ser Ala Ala His Asp Lys Gly Met Tyr Val Met Leu Asp Val Val Ala
            100                 105                 110

Asn His Val Gly Ile Pro Ser Ser Gly Gln Tyr Ser Gly Tyr Thr
    115                 120                 125

Phe Asp Gln Ser Ser Gln Tyr His Ser Ser Cys Asp Ile Asn Tyr Asp
    130                 135                 140

Asn Gln Asn Ser Ile Glu Gln Cys Trp Ile Ser Gly Leu Pro Asp Leu
145                 150                 155                 160

Asn Thr Glu Asp Ser Ala Val Val Ser Lys Leu Asn Ser Ile Val Ser
                165                 170                 175

Asn Trp Val Ser Glu Tyr Asp Phe Asp Gly Leu Arg Ile Asp Thr Val
            180                 185                 190
```

```
Lys His Ile Arg Lys Asp Phe Trp Asp Gly Tyr Val Ser Ala Ala Gly
            195                 200                 205

Val Phe Ala Thr Gly Glu Val Leu Asn Gly Ala Val Ser Tyr Val Ala
        210                 215                 220

Pro Tyr Gln Gln His Val Pro Ser Leu Leu Asn Tyr Pro Leu Tyr Phe
225                 230                 235                 240

Pro Val Asn Asp Val Phe Thr Lys Ala Ser Thr Met Ser Arg Leu Gly
                245                 250                 255

Ser Gly Tyr Ala Asp Ile Gln Ser Gly Ser Phe Thr Asn Arg Asn His
            260                 265                 270

Leu Val Asn Phe Ile Asp Asn His Asp Asn Pro Arg Leu Leu Ser Lys
        275                 280                 285

Ser Asp Gln Val Leu Val Lys Asn Ala Leu Thr Tyr Thr Met Met Ile
290                 295                 300

Glu Gly Ile Pro Ala Met Tyr Tyr Gly Thr Glu Gln Ser Phe Asn Gly
305                 310                 315                 320

Gly Ser Asp Pro Ala Asn Arg Glu Val Leu Trp Thr Thr Asn Tyr Ser
                325                 330                 335

Thr Thr Ser Asp Met Tyr Lys Phe Val Thr Leu Leu Val Lys Thr Arg
            340                 345                 350

Lys Ser Ser Gly Asn Thr Val Thr Thr Gly Ile Asp Gln Thr Asn Asn
        355                 360                 365

Val Tyr Val Phe Gln Arg Asp Lys Tyr Leu Val Val Val Asn Asn Tyr
370                 375                 380

Gly Ser Gly Ser Thr Asn Ser Ile Thr Val Lys Ala Gly Ser Phe Ser
385                 390                 395                 400

Asn Gly Val Thr Leu Val Asp Ile Phe Ser Asn Lys Thr Val Thr Val
                405                 410                 415

Ser Asn Gly Ser Ile Thr Phe Gln Leu Gln Asn Gly Asn Pro Ala Val
            420                 425                 430

Phe Gln Ser Lys
        435

<210> SEQ ID NO 136
<211> LENGTH: 297
<212> TYPE: DNA
<213> ORGANISM: Coniochaeta sp.
<220> FEATURE:
<221> NAME/KEY: CDS
<222> LOCATION: (1)..(297)

<400> SEQUENCE: 136 gta gcc atc acg ttc aac gag ctc gtg tcc aca gcc tac ggc gat acg      48
Val Ala Ile Thr Phe Asn Glu Leu Val Ser Thr Ala Tyr Gly Asp Thr
1               5                   10                  15 atc aag ctc tcc ggc aac ata acc gcc cta ggc agc tgg aac gcg gcc      96
Ile Lys Leu Ser Gly Asn Ile Thr Ala Leu Gly Ser Trp Asn Ala Ala
            20                  25                  30 aac gcc gtc agc ctg agc gcg tcg ggg tac acg gcc gcc aac ccg ctg     144
Asn Ala Val Ser Leu Ser Ala Ser Gly Tyr Thr Ala Ala Asn Pro Leu
        35                  40                  45 tgg tcg ggc acg gtg aac ctc gcg ccg ggg acc ggg gtg cag tac aag     192
Trp Ser Gly Thr Val Asn Leu Ala Pro Gly Thr Gly Val Gln Tyr Lys
    50                  55                  60 ttc gtg aag gtc ggc agc tcg gga agc gtc acc tgg gag gcg gac ccg     240
Phe Val Lys Val Gly Ser Ser Gly Ser Val Thr Trp Glu Ala Asp Pro
65                  70                  75                  80
```

```
aat cac acg tac gcc gtg ccg tgc gcg ggg gct act gtt agt ggg agc      288
Asn His Thr Tyr Ala Val Pro Cys Ala Gly Ala Thr Val Ser Gly Ser
                85                  90                  95 tgg cag agc                                                          297
Trp Gln Ser <210> SEQ ID NO 137
<211> LENGTH: 99
<212> TYPE: PRT
<213> ORGANISM: Coniochaeta sp.

<400> SEQUENCE: 137

Val Ala Ile Thr Phe Asn Glu Leu Val Ser Thr Ala Tyr Gly Asp Thr
1               5                   10                  15

Ile Lys Leu Ser Gly Asn Ile Thr Ala Leu Gly Ser Trp Asn Ala Ala
            20                  25                  30

Asn Ala Val Ser Leu Ser Ala Ser Gly Tyr Thr Ala Ala Asn Pro Leu
        35                  40                  45

Trp Ser Gly Thr Val Asn Leu Ala Pro Gly Thr Gly Val Gln Tyr Lys
    50                  55                  60

Phe Val Lys Val Gly Ser Ser Gly Ser Val Thr Trp Glu Ala Asp Pro
65                  70                  75                  80

Asn His Thr Tyr Ala Val Pro Cys Ala Gly Ala Thr Val Ser Gly Ser
                85                  90                  95

Trp Gln Ser

<210> SEQ ID NO 138
<211> LENGTH: 300
<212> TYPE: DNA
<213> ORGANISM: Trametes corrugata
<220> FEATURE:
<221> NAME/KEY: CDS
<222> LOCATION: (1)..(300)

<400> SEQUENCE: 138 gtt gca gta tcg ttc acg cac agc atc acc act gtg ccc ggc gac act      48
Val Ala Val Ser Phe Thr His Ser Ile Thr Thr Val Pro Gly Asp Thr
1               5                   10                  15 atc aag atc gcg ggt aac acg acg caa ctc ggt agc tgg act gta gct      96
Ile Lys Ile Ala Gly Asn Thr Thr Gln Leu Gly Ser Trp Thr Val Ala
            20                  25                  30 tcc gca ccc gcg ctc tca gcg tca tcg tac acg tcg agt aac cct gta      144
Ser Ala Pro Ala Leu Ser Ala Ser Ser Tyr Thr Ser Ser Asn Pro Val
        35                  40                  45 tgg acg att acg ctg agc atg ccg gcg aag cag gcg gtg cag tat aag      192
Trp Thr Ile Thr Leu Ser Met Pro Ala Lys Gln Ala Val Gln Tyr Lys
    50                  55                  60 ttt gtt aag gtg gcg agt ggg ggc gcg gtg acg tgg gag agc gat ccg      240
Phe Val Lys Val Ala Ser Gly Gly Ala Val Thr Trp Glu Ser Asp Pro
65                  70                  75                  80 aat cgt agt tat agc gtc ccg gcg tgt cag gcg agt gcg gcg gtg agt      288
Asn Arg Ser Tyr Ser Val Pro Ala Cys Gln Ala Ser Ala Ala Val Ser
                85                  90                  95 agt agt tgg cag                                                      300
Ser Ser Trp Gln
                100

<210> SEQ ID NO 139
<211> LENGTH: 100
<212> TYPE: PRT
<213> ORGANISM: Trametes corrugata
```

<400> SEQUENCE: 139

Val Ala Val Ser Phe Thr His Ser Ile Thr Val Pro Gly Asp Thr
1               5                   10                  15

Ile Lys Ile Ala Gly Asn Thr Thr Gln Leu Gly Ser Trp Thr Val Ala
            20                  25                  30

Ser Ala Pro Ala Leu Ser Ala Ser Ser Tyr Thr Ser Ser Asn Pro Val
        35                  40                  45

Trp Thr Ile Thr Leu Ser Met Pro Ala Lys Gln Ala Val Gln Tyr Lys
    50                  55                  60

Phe Val Lys Val Ala Ser Gly Gly Ala Val Thr Trp Glu Ser Asp Pro
65                  70                  75                  80

Asn Arg Ser Tyr Ser Val Pro Ala Cys Gln Ala Ser Ala Ala Val Ser
                85                  90                  95

Ser Ser Trp Gln
            100

<210> SEQ ID NO 140
<211> LENGTH: 306
<212> TYPE: DNA
<213> ORGANISM: Valsario spartii
<220> FEATURE:
<221> NAME/KEY: CDS
<222> LOCATION: (1)..(306)

<400> SEQUENCE: 140 gtc tcc gtc aca ttc acc aac ctc gtc aca acc cag gtc ggc gac acc      48
Val Ser Val Thr Phe Thr Asn Leu Val Thr Thr Gln Val Gly Asp Thr
1               5                   10                  15 atc aaa gtc acc ggc aac gtc tcg cag ctg ggc aac tgg aac cct tcc      96
Ile Lys Val Thr Gly Asn Val Ser Gln Leu Gly Asn Trp Asn Pro Ser
            20                  25                  30 tcc gcc ccc gcc tta tcc gca acc gga tac acg gcc agc aac ccc aaa    144
Ser Ala Pro Ala Leu Ser Ala Thr Gly Tyr Thr Ala Ser Asn Pro Lys
        35                  40                  45 tgg agc gga acc gtc aag ttg ccc gcc ggc tcg acg gtg cag tat aag    192
Trp Ser Gly Thr Val Lys Leu Pro Ala Gly Ser Thr Val Gln Tyr Lys
    50                  55                  60 ttt gtg aag gtc gct agc ggg ggt ggc gcc gtg act tgg gag agc gat    240
Phe Val Lys Val Ala Ser Gly Gly Ala Val Thr Trp Glu Ser Asp
65                  70                  75                  80 ccc aac agg agt tat agc gtt cct agt tgt cag gct agc gcg act gtt    288
Pro Asn Arg Ser Tyr Ser Val Pro Ser Cys Gln Ala Ser Ala Thr Val
                85                  90                  95 gat tcg agc tgg aag taa                                            306
Asp Ser Ser Trp Lys
            100

<210> SEQ ID NO 141
<211> LENGTH: 101
<212> TYPE: PRT
<213> ORGANISM: Valsario spartii

<400> SEQUENCE: 141

```
Val Ser Val Thr Phe Thr Asn Leu Val Thr Thr Gln Val Gly Asp Thr
1               5                   10                  15

Ile Lys Val Thr Gly Asn Val Ser Gln Leu Gly Asn Trp Asn Pro Ser
            20                  25                  30

Ser Ala Pro Ala Leu Ser Ala Thr Gly Tyr Thr Ala Ser Asn Pro Lys
        35                  40                  45

Trp Ser Gly Thr Val Lys Leu Pro Ala Gly Ser Thr Val Gln Tyr Lys
```

```
                50                   55                   60
Phe Val Lys Val Ala Ser Gly Gly Ala Val Thr Trp Glu Ser Asp
 65                  70                  75                  80

Pro Asn Arg Ser Tyr Ser Val Pro Ser Cys Gln Ala Ser Ala Thr Val
                 85                  90                  95

Asp Ser Ser Trp Lys
            100

<210> SEQ ID NO 142
<211> LENGTH: 312
<212> TYPE: DNA
<213> ORGANISM: Penicillium sp.
<220> FEATURE:
<221> NAME/KEY: CDS
<222> LOCATION: (1)..(312)

<400> SEQUENCE: 142 ttg cca gtt ttg ttc aaa gag att gtc acc act tca tac ggg cag agt      48
Leu Pro Val Leu Phe Lys Glu Ile Val Thr Thr Ser Tyr Gly Gln Ser
  1               5                  10                  15 atc tat atc tca ggc tct ata agt caa ctc gga agc tgg gac acg tct      96
Ile Tyr Ile Ser Gly Ser Ile Ser Gln Leu Gly Ser Trp Asp Thr Ser
             20                  25                  30 agc gcc gtt gcc ctc tct gct gat cag tac aca tca tcc agc cat ctg     144
Ser Ala Val Ala Leu Ser Ala Asp Gln Tyr Thr Ser Ser Ser His Leu
         35                  40                  45 tgg tat gtt gtc gtg aca att cca gtg ggc acc tcg ttc cag tac aag     192
Trp Tyr Val Val Val Thr Ile Pro Val Gly Thr Ser Phe Gln Tyr Lys
     50                  55                  60 ttc atc gag gag acg agc ggg tct agt act att act tgg gag agt gat     240
Phe Ile Glu Glu Thr Ser Gly Ser Ser Thr Ile Thr Trp Glu Ser Asp
 65                  70                  75                  80 ccg aac cgc tct tat acg gtg cca acg ggc tgt gca ggc tca acg gct     288
Pro Asn Arg Ser Tyr Thr Val Pro Thr Gly Cys Ala Gly Ser Thr Ala
                 85                  90                  95 acc gtc aca gcg acc tgg aga tag                                     312
Thr Val Thr Ala Thr Trp Arg
            100

<210> SEQ ID NO 143
<211> LENGTH: 103
<212> TYPE: PRT
<213> ORGANISM: Penicillium sp.

<400> SEQUENCE: 143

Leu Pro Val Leu Phe Lys Glu Ile Val Thr Thr Ser Tyr Gly Gln Ser
  1               5                  10                  15

Ile Tyr Ile Ser Gly Ser Ile Ser Gln Leu Gly Ser Trp Asp Thr Ser
             20                  25                  30

Ser Ala Val Ala Leu Ser Ala Asp Gln Tyr Thr Ser Ser Ser His Leu
         35                  40                  45

Trp Tyr Val Val Val Thr Ile Pro Val Gly Thr Ser Phe Gln Tyr Lys
     50                  55                  60

Phe Ile Glu Glu Thr Ser Gly Ser Ser Thr Ile Thr Trp Glu Ser Asp
 65                  70                  75                  80

Pro Asn Arg Ser Tyr Thr Val Pro Thr Gly Cys Ala Gly Ser Thr Ala
                 85                  90                  95

Thr Val Thr Ala Thr Trp Arg
            100
```

```
<210> SEQ ID NO 144
<211> LENGTH: 123
<212> TYPE: DNA
<213> ORGANISM: Coniochaeta sp.
<220> FEATURE:
<221> NAME/KEY: CDS
<222> LOCATION: (1)..(123)

<400> SEQUENCE: 144 acg acg tcg acg agt acg ggg acg agc tcg acc acg agg acg ggg acg    48
Thr Thr Ser Thr Ser Thr Gly Thr Ser Ser Thr Thr Arg Thr Gly Thr
1               5                   10                  15 acg ctg acg acg tcc acg aag act acg gcg tcg acg acg acg aag        96
Thr Leu Thr Thr Ser Thr Lys Thr Thr Ala Ser Thr Thr Thr Thr Lys
            20                  25                  30 agc agc agt tcc tgc acc gcc aca gca                                123
Ser Ser Ser Ser Cys Thr Ala Thr Ala
        35                  40

<210> SEQ ID NO 145
<211> LENGTH: 41
<212> TYPE: PRT
<213> ORGANISM: Coniochaeta sp.

<400> SEQUENCE: 145

Thr Thr Ser Thr Ser Thr Gly Thr Ser Ser Thr Thr Arg Thr Gly Thr
1               5                   10                  15

Thr Leu Thr Thr Ser Thr Lys Thr Thr Ala Ser Thr Thr Thr Thr Lys
            20                  25                  30

Ser Ser Ser Ser Cys Thr Ala Thr Ala
        35                  40

<210> SEQ ID NO 146
<211> LENGTH: 30
<212> TYPE: DNA
<213> ORGANISM: Trametes corrugata
<220> FEATURE:
<221> NAME/KEY: CDS
<222> LOCATION: (1)..(30)

<400> SEQUENCE: 146 act acc aca gcc tcc gcg tgt ccg act tcc                            30
Thr Thr Thr Ala Ser Ala Cys Pro Thr Ser
1               5                   10

<210> SEQ ID NO 147
<211> LENGTH: 10
<212> TYPE: PRT
<213> ORGANISM: Trametes corrugata

<400> SEQUENCE: 147

Thr Thr Thr Ala Ser Ala Cys Pro Thr Ser
1               5                   10

<210> SEQ ID NO 148
<211> LENGTH: 33
<212> TYPE: DNA
<213> ORGANISM: Valsario spartii
<220> FEATURE:
<221> NAME/KEY: CDS
<222> LOCATION: (1)..(33)

<400> SEQUENCE: 148 acc acc tcc cca acc gcc ggc tgc ccc tcc acc                        33
Thr Thr Ser Pro Thr Ala Gly Cys Pro Ser Thr
1               5                   10
```

<210> SEQ ID NO 149
<211> LENGTH: 11
<212> TYPE: PRT
<213> ORGANISM: Valsario spartii

<400> SEQUENCE: 149

Thr Thr Ser Pro Thr Ala Gly Cys Pro Ser Thr
1               5                   10

<210> SEQ ID NO 150
<211> LENGTH: 132
<212> TYPE: DNA
<213> ORGANISM: Penicillium sp.
<220> FEATURE:
<221> NAME/KEY: CDS
<222> LOCATION: (1)..(132)

<400> SEQUENCE: 150 act acc aca acc tcg tcg acg gct tct act tca acg aca acg tca acc      48
Thr Thr Thr Thr Ser Ser Thr Ala Ser Thr Ser Thr Thr Thr Ser Thr
1               5                   10                  15 aca ctg aag act acc acg aca acg tca act act tcg aaa act act acg      96
Thr Leu Lys Thr Thr Thr Thr Thr Ser Thr Thr Ser Lys Thr Thr Thr
            20                  25                  30 tcc act aca tcc acg agc tgc aca cag gct act gca                      132
Ser Thr Thr Ser Thr Ser Cys Thr Gln Ala Thr Ala
        35                  40

<210> SEQ ID NO 151
<211> LENGTH: 44
<212> TYPE: PRT
<213> ORGANISM: Penicillium sp.

<400> SEQUENCE: 151

Thr Thr Thr Thr Ser Ser Thr Ala Ser Thr Ser Thr Thr Thr Ser Thr
1               5                   10                  15

Thr Leu Lys Thr Thr Thr Thr Thr Ser Thr Thr Ser Lys Thr Thr Thr
            20                  25                  30

Ser Thr Thr Ser Thr Ser Cys Thr Gln Ala Thr Ala
        35                  40

<210> SEQ ID NO 152

<400> SEQUENCE: 152

000

<210> SEQ ID NO 153

<400> SEQUENCE: 153

000

<210> SEQ ID NO 154
<211> LENGTH: 1221
<212> TYPE: DNA
<213> ORGANISM: Streptomyces limosus
<220> FEATURE:
<221> NAME/KEY: CDS
<222> LOCATION: (1)..(1221)

<400> SEQUENCE: 154 gcc ccg ccc ggg gcg aag gac gtc acc gcc gtc ctc ttc gag tgg aag      48
Ala Pro Pro Gly Ala Lys Asp Val Thr Ala Val Leu Phe Glu Trp Lys
1               5                   10                  15

```
ttc gcc tcc gta gcc cgc gcc tgc acc gac agc ctc ggc ccg gcc ggc     96
Phe Ala Ser Val Ala Arg Ala Cys Thr Asp Ser Leu Gly Pro Ala Gly
             20                  25                  30 tac gga tac gtc cag gtc tcg ccg ccc cag gag cac atc cag ggc agc     144
Tyr Gly Tyr Val Gln Val Ser Pro Pro Gln Glu His Ile Gln Gly Ser
         35                  40                  45 cag tgg tgg acc tcc tac cag ccc gtc agc tac aag atc gcc gga cgg     192
Gln Trp Trp Thr Ser Tyr Gln Pro Val Ser Tyr Lys Ile Ala Gly Arg
     50                  55                  60 ctc ggc gac cgc gcc gcc ttc aag tcc atg gtc gac acc tgc cac gcg     240
Leu Gly Asp Arg Ala Ala Phe Lys Ser Met Val Asp Thr Cys His Ala
65                  70                  75                  80 gcc ggc gtc aag gtc gtc gcc gac tcg gtc atc aac cac atg gcc gcg     288
Ala Gly Val Lys Val Val Ala Asp Ser Val Ile Asn His Met Ala Ala
                 85                  90                  95 ggt tcc ggc acc ggc acc ggc ggc agc gcg tac cag aag tac gac tac     336
Gly Ser Gly Thr Gly Thr Gly Gly Ser Ala Tyr Gln Lys Tyr Asp Tyr
            100                 105                 110 ccg ggc atc tgg tcc ggc gcc gac atg gac gac tgc cgc agc gag atc     384
Pro Gly Ile Trp Ser Gly Ala Asp Met Asp Asp Cys Arg Ser Glu Ile
        115                 120                 125 aac gac tac ggc aac cgc gcc aac gtc cag aac tgc gaa ctg gtc ggc     432
Asn Asp Tyr Gly Asn Arg Ala Asn Val Gln Asn Cys Glu Leu Val Gly
    130                 135                 140 ctc gcc gac ctc gac acc ggt gag tcg tac gtc cgc gac cgc atc gcc     480
Leu Ala Asp Leu Asp Thr Gly Glu Ser Tyr Val Arg Asp Arg Ile Ala
145                 150                 155                 160 gcc tac ctc aac gac ctg ctc tcg ctc ggt gtg gac ggc ttc cgc atc     528
Ala Tyr Leu Asn Asp Leu Leu Ser Leu Gly Val Asp Gly Phe Arg Ile
                165                 170                 175 gac gcc gcc aag cac atg ccc gcc gcc gac ctc acc gcc atc aag gcc     576
Asp Ala Ala Lys His Met Pro Ala Ala Asp Leu Thr Ala Ile Lys Ala
            180                 185                 190 aag gtc ggc aac ggg agc acg tac tgg aag cag gag gcc atc cac ggc     624
Lys Val Gly Asn Gly Ser Thr Tyr Trp Lys Gln Glu Ala Ile His Gly
        195                 200                 205 gcg ggc gag gcc gtc cag ccc agc gag tac ctc ggc acc ggc gac gtc     672
Ala Gly Glu Ala Val Gln Pro Ser Glu Tyr Leu Gly Thr Gly Asp Val
    210                 215                 220 cag gag ttc cgc tac gcc cgc gac ctc aag cgg gtc ttc cag aac gag     720
Gln Glu Phe Arg Tyr Ala Arg Asp Leu Lys Arg Val Phe Gln Asn Glu
225                 230                 235                 240 aac ctc gcc cac ctg aag aac ttc ggc gag gac tgg ggc tac atg gcg     768
Asn Leu Ala His Leu Lys Asn Phe Gly Glu Asp Trp Gly Tyr Met Ala
                245                 250                 255 agc ggc aag tcc gcc gtc ttc gtc gac aac cac gac acc gag cgg ggc     816
Ser Gly Lys Ser Ala Val Phe Val Asp Asn His Asp Thr Glu Arg Gly
            260                 265                 270 ggc gac acc ctc aac tac aag aac ggc tcc gcc tac acc ctc gcc ggc     864
Gly Asp Thr Leu Asn Tyr Lys Asn Gly Ser Ala Tyr Thr Leu Ala Gly
        275                 280                 285 gtc ttc atg ctg gcc tgg ccc tac ggc tcc ccg gac gtc cac tcc ggc     912
Val Phe Met Leu Ala Trp Pro Tyr Gly Ser Pro Asp Val His Ser Gly
    290                 295                 300 tac gag ttc acc gac cac gac gcc ggc ccg ccc aac ggc ggc acc gtc     960
Tyr Glu Phe Thr Asp His Asp Ala Gly Pro Pro Asn Gly Gly Thr Val
305                 310                 315                 320 aac gcc tgc tac agc gac ggc tgg aag tgc cag cac gcc tgg ccc gag    1008
Asn Ala Cys Tyr Ser Asp Gly Trp Lys Cys Gln His Ala Trp Pro Glu
                325                 330                 335
```

```
ctc tcc tcc atg gtc ggc ctg cgc aac acc gcc tcc ggg cag ccc gtc      1056
Leu Ser Ser Met Val Gly Leu Arg Asn Thr Ala Ser Gly Gln Pro Val
            340                 345                 350 acc aac tgg tgg gac aac ggc ggc gac cag atc gcc ttc ggc cgc ggc      1104
Thr Asn Trp Trp Asp Asn Gly Gly Asp Gln Ile Ala Phe Gly Arg Gly
        355                 360                 365 gac aag gcg tac gtc gcc atc aac cac gag ggc tcc gcg ctg aac cgc      1152
Asp Lys Ala Tyr Val Ala Ile Asn His Glu Gly Ser Ala Leu Asn Arg
    370                 375                 380 acc ttc cag agc ggc ctg ccc ggc ggc gcc tac tgc gac gtc cag agc      1200
Thr Phe Gln Ser Gly Leu Pro Gly Gly Ala Tyr Cys Asp Val Gln Ser
385                 390                 395                 400 ggc agg tcc gtc acg gtc ggc                                          1221
Gly Arg Ser Val Thr Val Gly
                405

<210> SEQ ID NO 155
<211> LENGTH: 407
<212> TYPE: PRT
<213> ORGANISM: Streptomyces limosus

<400> SEQUENCE: 155

Ala Pro Pro Gly Ala Lys Asp Val Thr Ala Val Leu Phe Glu Trp Lys
1               5                   10                  15

Phe Ala Ser Val Ala Arg Ala Cys Thr Asp Ser Leu Gly Pro Ala Gly
            20                  25                  30

Tyr Gly Tyr Val Gln Val Ser Pro Pro Gln Glu His Ile Gln Gly Ser
        35                  40                  45

Gln Trp Trp Thr Ser Tyr Gln Pro Val Ser Tyr Lys Ile Ala Gly Arg
    50                  55                  60

Leu Gly Asp Arg Ala Ala Phe Lys Ser Met Val Asp Thr Cys His Ala
65                  70                  75                  80

Ala Gly Val Lys Val Ala Asp Ser Val Ile Asn His Met Ala Ala
                85                  90                  95

Gly Ser Gly Thr Gly Thr Gly Gly Ser Ala Tyr Gln Lys Tyr Asp Tyr
            100                 105                 110

Pro Gly Ile Trp Ser Gly Ala Asp Met Asp Asp Cys Arg Ser Glu Ile
        115                 120                 125

Asn Asp Tyr Gly Asn Arg Ala Asn Val Gln Asn Cys Glu Leu Val Gly
    130                 135                 140

Leu Ala Asp Leu Asp Thr Gly Glu Ser Tyr Val Arg Asp Arg Ile Ala
145                 150                 155                 160

Ala Tyr Leu Asn Asp Leu Leu Ser Leu Gly Val Asp Gly Phe Arg Ile
                165                 170                 175

Asp Ala Ala Lys His Met Pro Ala Asp Leu Thr Ala Ile Lys Ala
            180                 185                 190

Lys Val Gly Asn Gly Ser Thr Tyr Trp Lys Gln Glu Ala Ile His Gly
        195                 200                 205

Ala Gly Glu Ala Val Gln Pro Ser Glu Tyr Leu Gly Thr Gly Asp Val
    210                 215                 220

Gln Glu Phe Arg Tyr Ala Arg Asp Leu Lys Arg Val Phe Gln Asn Glu
225                 230                 235                 240

Asn Leu Ala His Leu Lys Asn Phe Gly Glu Asp Trp Gly Tyr Met Ala
                245                 250                 255

Ser Gly Lys Ser Ala Val Phe Val Asp Asn His Asp Thr Glu Arg Gly
            260                 265                 270

Gly Asp Thr Leu Asn Tyr Lys Asn Gly Ser Ala Tyr Thr Leu Ala Gly
```

```
                275                 280                 285
Val Phe Met Leu Ala Trp Pro Tyr Gly Ser Pro Asp Val His Ser Gly
            290                 295                 300

Tyr Glu Phe Thr Asp His Asp Ala Gly Pro Pro Asn Gly Gly Thr Val
305                 310                 315                 320

Asn Ala Cys Tyr Ser Asp Gly Trp Lys Cys Gln His Ala Trp Pro Glu
                325                 330                 335

Leu Ser Ser Met Val Gly Leu Arg Asn Thr Ala Ser Gly Gln Pro Val
            340                 345                 350

Thr Asn Trp Trp Asp Asn Gly Asp Gln Ile Ala Phe Gly Arg Gly
                355                 360                 365

Asp Lys Ala Tyr Val Ala Ile Asn His Glu Gly Ser Ala Leu Asn Arg
        370                 375                 380

Thr Phe Gln Ser Gly Leu Pro Gly Gly Ala Tyr Cys Asp Val Gln Ser
385                 390                 395                 400

Gly Arg Ser Val Thr Val Gly
                405

<210> SEQ ID NO 156
<211> LENGTH: 1443
<212> TYPE: DNA
<213> ORGANISM: Absidia cristata
<220> FEATURE:
<221> NAME/KEY: CDS
<222> LOCATION: (1)..(1443)
<220> FEATURE:
<221> NAME/KEY: sig_peptide
<222> LOCATION: (1)..(120)
<220> FEATURE:
<221> NAME/KEY: misc_feature
<222> LOCATION: (121)..(1443)
<223> OTHER INFORMATION: Catalytic domain

<400> SEQUENCE: 156 atg cat cca acg cgt tgg gag ctc tcc cat atg gtc gac ctg cag gcg      48
Met His Pro Thr Arg Trp Glu Leu Ser His Met Val Asp Leu Gln Ala
1               5                   10                  15 gcc gca cta gtg att atg aag ctt tcc att ctt aca tta tcc aca ctc      96
Ala Ala Leu Val Ile Met Lys Leu Ser Ile Leu Thr Leu Ser Thr Leu
                20                  25                  30 ctt tgt gct act gct gtt ctt ggt cgt ccc att gtg aag cgt gca ggc     144
Leu Cys Ala Thr Ala Val Leu Gly Arg Pro Ile Val Lys Arg Ala Gly
            35                  40                  45 gcc gat gat tgg aga tca cgt tcc atc tat caa tta ttg act gat cgc     192
Ala Asp Asp Trp Arg Ser Arg Ser Ile Tyr Gln Leu Leu Thr Asp Arg
50                  55                  60 ttt gct ggt ggc ggt gat tgt tct gat tta tcc gat tat tgt ggt ggt     240
Phe Ala Gly Gly Gly Asp Cys Ser Asp Leu Ser Asp Tyr Cys Gly Gly
65                  70                  75                  80 aat tat aaa ggc atg att gaa cac ctg gat tat atc caa gga atg gga     288
Asn Tyr Lys Gly Met Ile Glu His Leu Asp Tyr Ile Gln Gly Met Gly
                85                  90                  95 ttc gat gcc atc tgg att tcc ccc atc cct acc aac tca ccc ggc ggt     336
Phe Asp Ala Ile Trp Ile Ser Pro Ile Pro Thr Asn Ser Pro Gly Gly
            100                 105                 110 tac cat ggc tac tgg gca act gac ttc aat ggt tta aat gaa aac ttt     384
Tyr His Gly Tyr Trp Ala Thr Asp Phe Asn Gly Leu Asn Glu Asn Phe
        115                 120                 125 gga acc aag gac gat ctc aag gct ttg gtg gat gca gca cat aag ctc     432
Gly Thr Lys Asp Asp Leu Lys Ala Leu Val Asp Ala Ala His Lys Leu
130                 135                 140
```

```
gac atg tat gtc atg ttg gat gtc gtt gcc aat cat gct gga caa ccc      480
Asp Met Tyr Val Met Leu Asp Val Val Ala Asn His Ala Gly Gln Pro
145                 150                 155                 160 agt acg gca ggt gac tat tct ggc tac aca ttc gat tct aaa gac caa      528
Ser Thr Ala Gly Asp Tyr Ser Gly Tyr Thr Phe Asp Ser Lys Asp Gln
                165                 170                 175 tac cat tcc caa tgc aaa atc gat tat gat gat caa aac tct att gag      576
Tyr His Ser Gln Cys Lys Ile Asp Tyr Asp Asp Gln Asn Ser Ile Glu
            180                 185                 190 cag tgt tgg gtg gct gat gtg ttg cct gac atc aac act gag gat gat      624
Gln Cys Trp Val Ala Asp Val Leu Pro Asp Ile Asn Thr Glu Asp Asp
        195                 200                 205 aac gtg gtc aag acg ctc aat gat att gtc agc aac tgg gta act aca      672
Asn Val Val Lys Thr Leu Asn Asp Ile Val Ser Asn Trp Val Thr Thr
210                 215                 220 tat ggc ttt gat ggt att cgc att gac act gtc aag cat gta cgt caa      720
Tyr Gly Phe Asp Gly Ile Arg Ile Asp Thr Val Lys His Val Arg Gln
225                 230                 235                 240 gac ttt tgg gat gga tac aat gaa gca gct ggt gta ttt gct aca gga      768
Asp Phe Trp Asp Gly Tyr Asn Glu Ala Ala Gly Val Phe Ala Thr Gly
                245                 250                 255 gaa gtc ttt gat ggt gat tca tcc tat gtt ggt gga tat caa aag cat      816
Glu Val Phe Asp Gly Asp Ser Ser Tyr Val Gly Gly Tyr Gln Lys His
            260                 265                 270 ttg gac tcg ctt ctc aat tac cca atg tat tac gca ctc aat gat gta      864
Leu Asp Ser Leu Leu Asn Tyr Pro Met Tyr Tyr Ala Leu Asn Asp Val
        275                 280                 285 ttt ggt tct gga aag ggt ttt agt cgt atc agc gag atg att gca acc      912
Phe Gly Ser Gly Lys Gly Phe Ser Arg Ile Ser Glu Met Ile Ala Thr
290                 295                 300 aat gca gat gca ttt gct gat acc agt gtt ctg acc aac ttt att gac      960
Asn Ala Asp Ala Phe Ala Asp Thr Ser Val Leu Thr Asn Phe Ile Asp
305                 310                 315                 320 aac cat gat aac cca cgt ttc ctt aat acc aac aag gat act act ctc     1008
Asn His Asp Asn Pro Arg Phe Leu Asn Thr Asn Lys Asp Thr Thr Leu
                325                 330                 335 ttc aag aac gct ttg acc tac gtg ttg ctc gct gat ggt att cca gtg     1056
Phe Lys Asn Ala Leu Thr Tyr Val Leu Leu Ala Asp Gly Ile Pro Val
            340                 345                 350 gtg tat tat gga tca gaa caa ggc ttt tca ggt ggt gct gat cct gcc     1104
Val Tyr Tyr Gly Ser Glu Gln Gly Phe Ser Gly Gly Ala Asp Pro Ala
        355                 360                 365 aat cgt gaa gca tta tgg tca act gac ttt gac acc tcg tcc gat ttg     1152
Asn Arg Glu Ala Leu Trp Ser Thr Asp Phe Asp Thr Ser Ser Asp Leu
370                 375                 380 tac aag ttt atg gct act gtc aac aag gat gtt cgt caa aag gaa aac     1200
Tyr Lys Phe Met Ala Thr Val Asn Lys Asp Val Arg Gln Lys Glu Asn
385                 390                 395                 400 aaa aag gtg gtg atg gat gtt gat gtg caa gac aac gtg tat gca ttc     1248
Lys Lys Val Val Met Asp Val Asp Val Gln Asp Asn Val Tyr Ala Phe
                405                 410                 415 atg cac ggc gat gct ctt gtg gta ttg aac aac tac ggc agt gga gcc     1296
Met His Gly Asp Ala Leu Val Val Leu Asn Asn Tyr Gly Ser Gly Ala
            420                 425                 430 agc aac gag gtt act gtc aag gtc gga tca cat gtt gat gat gga gcc     1344
Ser Asn Glu Val Thr Val Lys Val Gly Ser His Val Asp Asp Gly Ala
        435                 440                 445 aag atg aac gac gtc ttt acc aat agc aca gtc tcg gta tct ggt ggt     1392
Lys Met Asn Asp Val Phe Thr Asn Ser Thr Val Ser Val Ser Gly Gly
450                 455                 460
```

```
tca ttc act ttc aaa ctt gac aat gga aat cct gcc atc ttt acc act    1440
Ser Phe Thr Phe Lys Leu Asp Asn Gly Asn Pro Ala Ile Phe Thr Thr
465             470                 475                 480 gct                                                                1443
Ala
```

<210> SEQ ID NO 157
<211> LENGTH: 481
<212> TYPE: PRT
<213> ORGANISM: Absidia cristata

<400> SEQUENCE: 157

```
Met His Pro Thr Arg Trp Glu Leu Ser His Met Val Asp Leu Gln Ala
1               5                   10                  15

Ala Ala Leu Val Ile Met Lys Leu Ser Ile Leu Thr Leu Ser Thr Leu
            20                  25                  30

Leu Cys Ala Thr Ala Val Leu Gly Arg Pro Ile Val Lys Arg Ala Gly
        35                  40                  45

Ala Asp Asp Trp Arg Ser Arg Ser Ile Tyr Gln Leu Leu Thr Asp Arg
    50                  55                  60

Phe Ala Gly Gly Asp Cys Ser Asp Leu Ser Asp Tyr Cys Gly Gly
65                  70                  75                  80

Asn Tyr Lys Gly Met Ile Glu His Leu Asp Tyr Ile Gln Gly Met Gly
                85                  90                  95

Phe Asp Ala Ile Trp Ile Ser Pro Ile Pro Thr Asn Ser Pro Gly Gly
            100                 105                 110

Tyr His Gly Tyr Trp Ala Thr Asp Phe Asn Gly Leu Asn Glu Asn Phe
        115                 120                 125

Gly Thr Lys Asp Asp Leu Lys Ala Leu Val Asp Ala Ala His Lys Leu
    130                 135                 140

Asp Met Tyr Val Met Leu Asp Val Val Ala Asn His Ala Gly Gln Pro
145                 150                 155                 160

Ser Thr Ala Gly Asp Tyr Ser Gly Tyr Thr Phe Asp Ser Lys Asp Gln
                165                 170                 175

Tyr His Ser Gln Cys Lys Ile Tyr Asp Asp Gln Asn Ser Ile Glu
            180                 185                 190

Gln Cys Trp Val Ala Asp Val Leu Pro Asp Ile Asn Thr Glu Asp Asp
        195                 200                 205

Asn Val Val Lys Thr Leu Asn Asp Ile Val Ser Asn Trp Val Thr Thr
    210                 215                 220

Tyr Gly Phe Asp Gly Ile Arg Ile Asp Thr Val Lys His Val Arg Gln
225                 230                 235                 240

Asp Phe Trp Asp Gly Tyr Asn Glu Ala Ala Gly Val Phe Ala Thr Gly
                245                 250                 255

Glu Val Phe Asp Gly Asp Ser Ser Tyr Val Gly Gly Tyr Gln Lys His
            260                 265                 270

Leu Asp Ser Leu Leu Asn Tyr Pro Met Tyr Tyr Ala Leu Asn Asp Val
        275                 280                 285

Phe Gly Ser Gly Lys Gly Phe Ser Arg Ile Ser Glu Met Ile Ala Thr
    290                 295                 300

Asn Ala Asp Ala Phe Ala Asp Thr Ser Val Leu Thr Asn Phe Ile Asp
305                 310                 315                 320

Asn His Asp Asn Pro Arg Phe Leu Asn Thr Asn Lys Asp Thr Thr Leu
                325                 330                 335

Phe Lys Asn Ala Leu Thr Tyr Val Leu Leu Ala Asp Gly Ile Pro Val
            340                 345                 350
```

```
Val Tyr Tyr Gly Ser Glu Gln Gly Phe Ser Gly Gly Ala Asp Pro Ala
        355                 360                 365

Asn Arg Glu Ala Leu Trp Ser Thr Asp Phe Asp Thr Ser Ser Asp Leu
370                 375                 380

Tyr Lys Phe Met Ala Thr Val Asn Lys Asp Val Arg Gln Lys Glu Asn
385                 390                 395                 400

Lys Lys Val Val Met Asp Val Asp Val Gln Asp Asn Val Tyr Ala Phe
                405                 410                 415

Met His Gly Asp Ala Leu Val Val Leu Asn Asn Tyr Gly Ser Gly Ala
                420                 425                 430

Ser Asn Glu Val Thr Val Lys Val Gly Ser His Val Asp Asp Gly Ala
            435                 440                 445

Lys Met Asn Asp Val Phe Thr Asn Ser Thr Val Ser Val Ser Gly Gly
        450                 455                 460

Ser Phe Thr Phe Lys Leu Asp Asn Gly Asn Pro Ala Ile Phe Thr Thr
465                 470                 475                 480

Ala
```

<210> SEQ ID NO 158
<211> LENGTH: 1878
<212> TYPE: DNA
<213> ORGANISM: Acremonium sp.
<220> FEATURE:
<221> NAME/KEY: CDS
<222> LOCATION: (1)..(1878)
<220> FEATURE:
<221> NAME/KEY: sig_peptide
<222> LOCATION: (1)..(63)
<220> FEATURE:
<221> NAME/KEY: misc_feature
<222> LOCATION: (64)..(1506)
<223> OTHER INFORMATION: Catalytic domain
<220> FEATURE:
<221> NAME/KEY: misc_feature
<222> LOCATION: (1507)..(1584)
<223> OTHER INFORMATION: Linker
<220> FEATURE:
<221> NAME/KEY: misc_feature
<222> LOCATION: (1585)..(1878)
<223> OTHER INFORMATION: CBM

<400> SEQUENCE: 158

```
atg cgc act ctc cac caa gcc ctt ctt gtc ctg gcc gga gca gtc ctg    48
Met Arg Thr Leu His Gln Ala Leu Leu Val Leu Ala Gly Ala Val Leu
1               5                   10                  15 gaa gct tcg caa ggt gct gcc ggg ctc tcg gct gcc gag tgg cgg agc    96
Glu Ala Ser Gln Gly Ala Ala Gly Leu Ser Ala Ala Glu Trp Arg Ser
                20                  25                  30 cag tcc atc tac cag gtt gtc acc gac agg ttc gcc cgg acc gac ctg   144
Gln Ser Ile Tyr Gln Val Val Thr Asp Arg Phe Ala Arg Thr Asp Leu
            35                  40                  45 tcg acc acg gcg tcg tgc aac acg gca gac caa gtc tac tgc gga ggg   192
Ser Thr Thr Ala Ser Cys Asn Thr Ala Asp Gln Val Tyr Cys Gly Gly
        50                  55                  60 aca tgg cag ggg ctc atc tcc aag ctg gac tac atc cag ggc atg ggt   240
Thr Trp Gln Gly Leu Ile Ser Lys Leu Asp Tyr Ile Gln Gly Met Gly
65                  70                  75                  80 ttc acc gcc gta tgg atc tca cca gtg gtc aag cag gtg gaa ggc aat   288
Phe Thr Ala Val Trp Ile Ser Pro Val Val Lys Gln Val Glu Gly Asn
                85                  90                  95 tcc cag gac ggg tcg gcc tat cac gga tac tgg gcg cag gat atc tgg   336
Ser Gln Asp Gly Ser Ala Tyr His Gly Tyr Trp Ala Gln Asp Ile Trp
            100                 105                 110
```

-continued

| | | | | | | | | | | | | | | | | |
|---|---|---|---|---|---|---|---|---|---|---|---|---|---|---|---|---|
| gcc | ttg | aat | ccg | gct | ttt | ggg | acc | gag | gag | gat | ctc | gct | gcg | ctt | gcc | 384 |
| Ala | Leu | Asn | Pro | Ala | Phe | Gly | Thr | Glu | Glu | Asp | Leu | Ala | Ala | Leu | Ala | |
| | | 115 | | | | | 120 | | | | | 125 | | | | |

| gcg | gcg | ctg | cat | gcc | cga | ggc | atg | tac | ctc | atg | gtt | gac | att | gtc | acc | 432 |
|---|---|---|---|---|---|---|---|---|---|---|---|---|---|---|---|---|
| Ala | Ala | Leu | His | Ala | Arg | Gly | Met | Tyr | Leu | Met | Val | Asp | Ile | Val | Thr | |
| 130 | | | | | 135 | | | | | 140 | | | | | | |

| aac | cac | atg | gca | tac | atg | ggc | tgc | ggc | acc | tgt | gta | gac | tac | agc | ctg | 480 |
|---|---|---|---|---|---|---|---|---|---|---|---|---|---|---|---|---|
| Asn | His | Met | Ala | Tyr | Met | Gly | Cys | Gly | Thr | Cys | Val | Asp | Tyr | Ser | Leu | |
| 145 | | | | | 150 | | | | | 155 | | | | | 160 | |

| ttc | aac | ccc | ttc | tca | tcg | tca | tcg | tac | ttc | cac | cca | tat | tgc | gcc | atc | 528 |
|---|---|---|---|---|---|---|---|---|---|---|---|---|---|---|---|---|
| Phe | Asn | Pro | Phe | Ser | Ser | Ser | Ser | Tyr | Phe | His | Pro | Tyr | Cys | Ala | Ile | |
| | | | | 165 | | | | | 170 | | | | | 175 | | |

| gac | tac | agc | aac | cag | acg | tcg | gtc | gag | gtt | tgc | tgg | caa | ggg | gat | aac | 576 |
|---|---|---|---|---|---|---|---|---|---|---|---|---|---|---|---|---|
| Asp | Tyr | Ser | Asn | Gln | Thr | Ser | Val | Glu | Val | Cys | Trp | Gln | Gly | Asp | Asn | |
| | | 180 | | | | | 185 | | | | | 190 | | | | |

| att | gtc | agt | ctg | cct | gac | ctg | cgc | acc | gag | gat | gac | acg | gtg | cgc | agc | 624 |
|---|---|---|---|---|---|---|---|---|---|---|---|---|---|---|---|---|
| Ile | Val | Ser | Leu | Pro | Asp | Leu | Arg | Thr | Glu | Asp | Asp | Thr | Val | Arg | Ser | |
| | | | 195 | | | | | 200 | | | | | 205 | | | |

| atc | tgg | aac | cgc | tgg | gtt | agc | cag | ctc | gtg | tcc | aac | tac | tcc | atc | gac | 672 |
|---|---|---|---|---|---|---|---|---|---|---|---|---|---|---|---|---|
| Ile | Trp | Asn | Arg | Trp | Val | Ser | Gln | Leu | Val | Ser | Asn | Tyr | Ser | Ile | Asp | |
| 210 | | | | | 215 | | | | | 220 | | | | | | |

| ggc | ttc | cga | gtc | gac | agc | gca | aaa | cac | gtc | gag | acg | tcc | ttt | tgg | caa | 720 |
|---|---|---|---|---|---|---|---|---|---|---|---|---|---|---|---|---|
| Gly | Phe | Arg | Val | Asp | Ser | Ala | Lys | His | Val | Glu | Thr | Ser | Phe | Trp | Gln | |
| 225 | | | | | 230 | | | | | 235 | | | | | 240 | |

| gac | ttc | tcg | aca | gcg | gcg | ggc | gtg | tac | ctg | ctg | ggc | gag | gtc | ttt | gac | 768 |
|---|---|---|---|---|---|---|---|---|---|---|---|---|---|---|---|---|
| Asp | Phe | Ser | Thr | Ala | Ala | Gly | Val | Tyr | Leu | Leu | Gly | Glu | Val | Phe | Asp | |
| | | | | 245 | | | | | 250 | | | | | 255 | | |

| ggg | gac | ccg | tcg | tac | gtg | gcg | cct | tac | cag | aac | tac | ctc | aac | ggg | gtt | 816 |
|---|---|---|---|---|---|---|---|---|---|---|---|---|---|---|---|---|
| Gly | Asp | Pro | Ser | Tyr | Val | Ala | Pro | Tyr | Gln | Asn | Tyr | Leu | Asn | Gly | Val | |
| | | 260 | | | | | 265 | | | | | 270 | | | | |

| ctg | gat | tat | ccc | agc | tac | tac | tgg | atc | ctc | cgg | gct | ttc | cag | tca | tcc | 864 |
|---|---|---|---|---|---|---|---|---|---|---|---|---|---|---|---|---|
| Leu | Asp | Tyr | Pro | Ser | Tyr | Tyr | Trp | Ile | Leu | Arg | Ala | Phe | Gln | Ser | Ser | |
| | | | 275 | | | | | 280 | | | | | 285 | | | |

| agc | ggc | agc | atc | agc | gac | ctc | gtc | tcc | ggg | ctc | aac | acg | ctc | cat | ggc | 912 |
|---|---|---|---|---|---|---|---|---|---|---|---|---|---|---|---|---|
| Ser | Gly | Ser | Ile | Ser | Asp | Leu | Val | Ser | Gly | Leu | Asn | Thr | Leu | His | Gly | |
| | | 290 | | | | | 295 | | | | | 300 | | | | |

| gtt | gct | ctg | gac | ctg | agt | cta | tat | ggg | tcc | ttc | ctc | gag | aac | cac | gat | 960 |
|---|---|---|---|---|---|---|---|---|---|---|---|---|---|---|---|---|
| Val | Ala | Leu | Asp | Leu | Ser | Leu | Tyr | Gly | Ser | Phe | Leu | Glu | Asn | His | Asp | |
| 305 | | | | | 310 | | | | | 315 | | | | | 320 | |

| gtg | gcg | cgg | ttt | gcg | tcc | ttc | acg | cag | gac | atg | tcc | cta | gcg | aag | aat | 1008 |
|---|---|---|---|---|---|---|---|---|---|---|---|---|---|---|---|---|
| Val | Ala | Arg | Phe | Ala | Ser | Phe | Thr | Gln | Asp | Met | Ser | Leu | Ala | Lys | Asn | |
| | | | | 325 | | | | | 330 | | | | | 335 | | |

| gcc | atc | gca | ttc | aca | atg | ctg | aaa | gac | ggc | atc | ccc | atc | ata | tac | cag | 1056 |
|---|---|---|---|---|---|---|---|---|---|---|---|---|---|---|---|---|
| Ala | Ile | Ala | Phe | Thr | Met | Leu | Lys | Asp | Gly | Ile | Pro | Ile | Ile | Tyr | Gln | |
| | | | 340 | | | | | 345 | | | | | 350 | | | |

| gga | caa | gag | caa | cat | tac | gct | ggc | gga | acg | acg | ccc | aac | aac | cgc | gag | 1104 |
|---|---|---|---|---|---|---|---|---|---|---|---|---|---|---|---|---|
| Gly | Gln | Glu | Gln | His | Tyr | Ala | Gly | Gly | Thr | Thr | Pro | Asn | Asn | Arg | Glu | |
| | | 355 | | | | | 360 | | | | | 365 | | | | |

| gcg | ctc | tgg | ctc | tcg | ggc | tac | tcg | act | agc | tcc | gag | ctc | tac | aag | tgg | 1152 |
|---|---|---|---|---|---|---|---|---|---|---|---|---|---|---|---|---|
| Ala | Leu | Trp | Leu | Ser | Gly | Tyr | Ser | Thr | Ser | Ser | Glu | Leu | Tyr | Lys | Trp | |
| | | 370 | | | | | 375 | | | | | 380 | | | | |

| att | gcc | gcc | ttg | aac | cag | atc | cgg | gcc | cga | gct | att | gct | caa | gat | agc | 1200 |
|---|---|---|---|---|---|---|---|---|---|---|---|---|---|---|---|---|
| Ile | Ala | Ala | Leu | Asn | Gln | Ile | Arg | Ala | Arg | Ala | Ile | Ala | Gln | Asp | Ser | |
| 385 | | | | | 390 | | | | | 395 | | | | | 400 | |

| ggc | tac | ctc | tcc | tac | agc | agc | caa | gcc | atc | tac | tcg | gac | agc | cat | acc | 1248 |
|---|---|---|---|---|---|---|---|---|---|---|---|---|---|---|---|---|
| Gly | Tyr | Leu | Ser | Tyr | Ser | Ser | Gln | Ala | Ile | Tyr | Ser | Asp | Ser | His | Thr | |
| | | | | 405 | | | | | 410 | | | | | 415 | | |

| att | gcc | atg | cgc | aaa | ggt | acc | tcg | gga | tac | cag | atc | gtg | ggc | gtg | ttc | 1296 |
|---|---|---|---|---|---|---|---|---|---|---|---|---|---|---|---|---|
| Ile | Ala | Met | Arg | Lys | Gly | Thr | Ser | Gly | Tyr | Gln | Ile | Val | Gly | Val | Phe | |
| | | | 420 | | | | | 425 | | | | | 430 | | | |

```
acc aat gtc ggg gcc tcg tcg tcg gct acg gtc acc cta acc tct tcc      1344
Thr Asn Val Gly Ala Ser Ser Ser Ala Thr Val Thr Leu Thr Ser Ser
        435                 440                 445 gca acg ggc ttc ggg gcg aac caa gca ctc gtc gac gtg atg agc tgc      1392
Ala Thr Gly Phe Gly Ala Asn Gln Ala Leu Val Asp Val Met Ser Cys
    450                 455                 460 acc gct tac acc aca gat tcg acg gga gcc ctc acg gta acc ctg aac      1440
Thr Ala Tyr Thr Thr Asp Ser Thr Gly Ala Leu Thr Val Thr Leu Asn
465                 470                 475                 480 gac ggc ctg ccc aag gtg ctt tat ccg att gcg cgg ctc tcg ggc agc      1488
Asp Gly Leu Pro Lys Val Leu Tyr Pro Ile Ala Arg Leu Ser Gly Ser
                485                 490                 495 ggt atc tgc cca ggg cag acc agc aca gcg ctg ccg acg tca agc ttg      1536
Gly Ile Cys Pro Gly Gln Thr Ser Thr Ala Leu Pro Thr Ser Ser Leu
            500                 505                 510 act gca gca tca gcc acg acg act gcc tca gcc tgc tcc ttg tcg gcg      1584
Thr Ala Ala Ser Ala Thr Thr Ala Ser Ala Cys Ser Leu Ser Ala
            515                 520                 525 gtg aac atc acc ttc aac gag ctc gtc acc acg gtg tgg ggg gac acg      1632
Val Asn Ile Thr Phe Asn Glu Leu Val Thr Thr Val Trp Gly Asp Thr
    530                 535                 540 atc aag ctg gcc ggc aac ata tcc gct ctc ggc agc tgg agc cca agc      1680
Ile Lys Leu Ala Gly Asn Ile Ser Ala Leu Gly Ser Trp Ser Pro Ser
545                 550                 555                 560 agc gcc ttg aca ctg agc gca tcg cag tat tca caa agc aat ccg ctc      1728
Ser Ala Leu Thr Leu Ser Ala Ser Gln Tyr Ser Gln Ser Asn Pro Leu
                565                 570                 575 tgg tcg gtc tca acc ctg ctc ggt cca gga acg gtg atc gag tac aag      1776
Trp Ser Val Ser Thr Leu Leu Gly Pro Gly Thr Val Ile Glu Tyr Lys
            580                 585                 590 ttt atc aag gtc agc gcc tcc ggg act gta acg tgg gag tca gac ccg      1824
Phe Ile Lys Val Ser Ala Ser Gly Thr Val Thr Trp Glu Ser Asp Pro
        595                 600                 605 aac cgc gtc tac act gtg ccc tgc gca act gcg acg gtc agt agc act      1872
Asn Arg Val Tyr Thr Val Pro Cys Ala Thr Ala Thr Val Ser Ser Thr
    610                 615                 620 tgg cga                                                              1878
Trp Arg
625

<210> SEQ ID NO 159
<211> LENGTH: 626
<212> TYPE: PRT
<213> ORGANISM: Acremonium sp.

<400> SEQUENCE: 159

Met Arg Thr Leu His Gln Ala Leu Leu Val Leu Ala Gly Ala Val Leu
1               5                   10                  15

Glu Ala Ser Gln Gly Ala Ala Gly Leu Ser Ala Ala Glu Trp Arg Ser
            20                  25                  30

Gln Ser Ile Tyr Gln Val Val Thr Asp Arg Phe Ala Arg Thr Asp Leu
        35                  40                  45

Ser Thr Thr Ala Ser Cys Asn Thr Ala Asp Gln Val Tyr Cys Gly Gly
    50                  55                  60

Thr Trp Gln Gly Leu Ile Ser Lys Leu Asp Tyr Ile Gln Gly Met Gly
65                  70                  75                  80

Phe Thr Ala Val Trp Ile Ser Pro Val Val Lys Gln Val Glu Gly Asn
                85                  90                  95

Ser Gln Asp Gly Ser Ala Tyr His Gly Tyr Trp Ala Gln Asp Ile Trp
```

```
                    100                 105                 110
Ala Leu Asn Pro Ala Phe Gly Thr Glu Glu Asp Leu Ala Ala Leu Ala
                115                 120                 125
Ala Ala Leu His Ala Arg Gly Met Tyr Leu Met Val Asp Ile Val Thr
            130                 135                 140
Asn His Met Ala Tyr Met Gly Cys Gly Thr Cys Val Asp Tyr Ser Leu
145                 150                 155                 160
Phe Asn Pro Phe Ser Ser Ser Tyr Phe His Pro Tyr Cys Ala Ile
                165                 170                 175
Asp Tyr Ser Asn Gln Thr Ser Val Glu Val Cys Trp Gln Gly Asp Asn
                180                 185                 190
Ile Val Ser Leu Pro Asp Leu Arg Thr Glu Asp Thr Val Arg Ser
                195                 200                 205
Ile Trp Asn Arg Trp Val Ser Gln Leu Val Ser Asn Tyr Ser Ile Asp
            210                 215                 220
Gly Phe Arg Val Asp Ser Ala Lys His Val Glu Thr Ser Phe Trp Gln
225                 230                 235                 240
Asp Phe Ser Thr Ala Ala Gly Val Tyr Leu Leu Gly Glu Val Phe Asp
                245                 250                 255
Gly Asp Pro Ser Tyr Val Ala Pro Tyr Gln Asn Tyr Leu Asn Gly Val
                260                 265                 270
Leu Asp Tyr Pro Ser Tyr Tyr Trp Ile Leu Arg Ala Phe Gln Ser Ser
                275                 280                 285
Ser Gly Ser Ile Ser Asp Leu Val Ser Gly Leu Asn Thr Leu His Gly
            290                 295                 300
Val Ala Leu Asp Leu Ser Leu Tyr Gly Ser Phe Leu Glu Asn His Asp
305                 310                 315                 320
Val Ala Arg Phe Ala Ser Phe Thr Gln Asp Met Ser Leu Ala Lys Asn
                325                 330                 335
Ala Ile Ala Phe Thr Met Leu Lys Asp Gly Ile Pro Ile Ile Tyr Gln
                340                 345                 350
Gly Gln Glu Gln His Tyr Ala Gly Gly Thr Thr Pro Asn Asn Arg Glu
            355                 360                 365
Ala Leu Trp Leu Ser Gly Tyr Ser Thr Ser Ser Glu Leu Tyr Lys Trp
            370                 375                 380
Ile Ala Ala Leu Asn Gln Ile Arg Ala Arg Ala Ile Ala Gln Asp Ser
385                 390                 395                 400
Gly Tyr Leu Ser Tyr Ser Ser Gln Ala Ile Tyr Ser Asp Ser His Thr
                405                 410                 415
Ile Ala Met Arg Lys Gly Thr Ser Gly Tyr Gln Ile Val Gly Val Phe
            420                 425                 430
Thr Asn Val Gly Ala Ser Ser Ala Thr Val Thr Leu Thr Ser Ser
            435                 440                 445
Ala Thr Gly Phe Gly Ala Asn Gln Ala Leu Val Asp Val Met Ser Cys
            450                 455                 460
Thr Ala Tyr Thr Thr Asp Ser Thr Gly Ala Leu Thr Val Thr Leu Asn
465                 470                 475                 480
Asp Gly Leu Pro Lys Val Leu Tyr Pro Ile Ala Arg Leu Ser Gly Ser
                485                 490                 495
Gly Ile Cys Pro Gly Gln Thr Ser Thr Ala Leu Pro Thr Ser Ser Leu
            500                 505                 510
Thr Ala Ala Ser Ala Thr Thr Thr Ala Ser Ala Cys Ser Leu Ser Ala
            515                 520                 525
```

```
Val Asn Ile Thr Phe Asn Glu Leu Val Thr Thr Val Trp Gly Asp Thr
    530                 535                 540

Ile Lys Leu Ala Gly Asn Ile Ser Ala Leu Gly Ser Trp Ser Pro Ser
545                 550                 555                 560

Ser Ala Leu Thr Leu Ser Ala Ser Gln Tyr Ser Gln Ser Asn Pro Leu
                565                 570                 575

Trp Ser Val Ser Thr Leu Leu Gly Pro Gly Thr Val Ile Glu Tyr Lys
                580                 585                 590

Phe Ile Lys Val Ser Ala Ser Gly Thr Val Thr Trp Glu Ser Asp Pro
        595                 600                 605

Asn Arg Val Tyr Thr Val Pro Cys Ala Thr Ala Thr Val Ser Ser Thr
    610                 615                 620

Trp Arg
625

<210> SEQ ID NO 160
<211> LENGTH: 1890
<212> TYPE: DNA
<213> ORGANISM: Coniochaeta sp.
<220> FEATURE:
<221> NAME/KEY: CDS
<222> LOCATION: (1)..(1890)
<220> FEATURE:
<221> NAME/KEY: sig_peptide
<222> LOCATION: (1)..(69)
<220> FEATURE:
<221> NAME/KEY: misc_feature
<222> LOCATION: (70)..(1497)
<223> OTHER INFORMATION: Catalytic domain
<220> FEATURE:
<221> NAME/KEY: misc_feature
<222> LOCATION: (1498)..(1596)
<223> OTHER INFORMATION: Linker
<220> FEATURE:
<221> NAME/KEY: misc_feature
<222> LOCATION: (1597)..(1890)
<223> OTHER INFORMATION: CBM

<400> SEQUENCE: 160 atg cgg cct atc cta agc tgc ctc ttt ctc gcg tcc gtc gtg gcc cag      48
Met Arg Pro Ile Leu Ser Cys Leu Phe Leu Ala Ser Val Val Ala Gln
1               5                   10                  15 gtg gcg tgg ggc ctc agc gca gca gac tgg cgt gag cag tcc atc tac      96
Val Ala Trp Gly Leu Ser Ala Ala Asp Trp Arg Glu Gln Ser Ile Tyr
            20                  25                  30 cag gtc gtg acg gac cgc ttc gcg cgg acg gac ctg tcc acc acg gcc     144
Gln Val Val Thr Asp Arg Phe Ala Arg Thr Asp Leu Ser Thr Thr Ala
        35                  40                  45 acg tgc gac acc tcg gcg cag gtg tat tgc ggc ggc acg tac aag ggt     192
Thr Cys Asp Thr Ser Ala Gln Val Tyr Cys Gly Gly Thr Tyr Lys Gly
    50                  55                  60 ctg atc tcc aag ctg gat tac att cag ggc atg ggc ttc act gcc atc     240
Leu Ile Ser Lys Leu Asp Tyr Ile Gln Gly Met Gly Phe Thr Ala Ile
65                  70                  75                  80 tgg ata tcg ccc atc gtc gag cag atg gac ggt aat act gcc gac ggc     288
Trp Ile Ser Pro Ile Val Glu Gln Met Asp Gly Asn Thr Ala Asp Gly
                85                  90                  95 tcc tcg tat cac ggt tac tgg gcg cag gat att tgg agt ctg aac ccg     336
Ser Ser Tyr His Gly Tyr Trp Ala Gln Asp Ile Trp Ser Leu Asn Pro
            100                 105                 110 tcg ttc gga tcg gct ggc gac ctg atc gcg ctc tcc aac gcg ctg cac     384
Ser Phe Gly Ser Ala Gly Asp Leu Ile Ala Leu Ser Asn Ala Leu His
        115                 120                 125 gcc cgg ggc atg tac ctc atg ctg gac gtg gtg acc aac cac ttt gct     432
```

| | | | | | | | | | | | | | | | | |
|---|---|---|---|---|---|---|---|---|---|---|---|---|---|---|---|---|
| Ala | Arg | Gly | Met | Tyr | Leu | Met | Leu | Asp | Val | Val | Thr | Asn | His | Phe | Ala | |
| | 130 | | | | 135 | | | | | 140 | | | | | | |
| tac | aac | ggc | tgc | ggc | aac | tgc | gtc | gac | tac | agc | atc | ttc | acc | ccg | ttc | 480 |
| Tyr | Asn | Gly | Cys | Gly | Asn | Cys | Val | Asp | Tyr | Ser | Ile | Phe | Thr | Pro | Phe | |
| 145 | | | | | 150 | | | | | 155 | | | | | 160 | |
| aac | tcg | tcg | tcg | tac | ttc | cac | ccc | ttc | tgc | ttg | atc | gac | tac | aac | aac | 528 |
| Asn | Ser | Ser | Ser | Tyr | Phe | His | Pro | Phe | Cys | Leu | Ile | Asp | Tyr | Asn | Asn | |
| | | | | 165 | | | | | 170 | | | | | 175 | | |
| cag | acg | tcg | atc | gag | cag | tgc | tgg | gag | gga | gac | aac | acc | gtc | agc | ctg | 576 |
| Gln | Thr | Ser | Ile | Glu | Gln | Cys | Trp | Glu | Gly | Asp | Asn | Thr | Val | Ser | Leu | |
| | | | 180 | | | | | 185 | | | | | 190 | | | |
| ccg | gac | ctg | cgg | acg | gag | aac | tcc | aac | gta | cgc | gcg | ata | tgg | aac | gac | 624 |
| Pro | Asp | Leu | Arg | Thr | Glu | Asn | Ser | Asn | Val | Arg | Ala | Ile | Trp | Asn | Asp | |
| | | 195 | | | | | 200 | | | | | 205 | | | | |
| tgg | atc | acg | cag | att | gtg | gcg | gcg | tac | ggc | atc | gac | ggt | ctg | cgc | atc | 672 |
| Trp | Ile | Thr | Gln | Ile | Val | Ala | Ala | Tyr | Gly | Ile | Asp | Gly | Leu | Arg | Ile | |
| | 210 | | | | | 215 | | | | | 220 | | | | | |
| gac | agc | gtc | aag | cac | cag | gag | acg | tcg | ttc | tgg | tcc | ggt | ttc | ggg | tcg | 720 |
| Asp | Ser | Val | Lys | His | Gln | Glu | Thr | Ser | Phe | Trp | Ser | Gly | Phe | Gly | Ser | |
| 225 | | | | | 230 | | | | | 235 | | | | | 240 | |
| gcc | gcc | ggc | gtg | ttc | atg | ctg | ggc | gag | gtg | tac | aac | ggc | gat | ccg | acg | 768 |
| Ala | Ala | Gly | Val | Phe | Met | Leu | Gly | Glu | Val | Tyr | Asn | Gly | Asp | Pro | Thr | |
| | | | | 245 | | | | | 250 | | | | | 255 | | |
| cag | ctg | gcg | ccg | tac | cag | gat | tac | atg | ccc | gga | ctg | ctg | gac | tac | gcg | 816 |
| Gln | Leu | Ala | Pro | Tyr | Gln | Asp | Tyr | Met | Pro | Gly | Leu | Leu | Asp | Tyr | Ala | |
| | | | 260 | | | | | 265 | | | | | 270 | | | |
| agc | tac | tac | tgg | atc | acg | agg | gcg | ttc | cag | tcg | agc | agc | ggg | agt | atg | 864 |
| Ser | Tyr | Tyr | Trp | Ile | Thr | Arg | Ala | Phe | Gln | Ser | Ser | Ser | Gly | Ser | Met | |
| | | 275 | | | | | 280 | | | | | 285 | | | | |
| agc | gat | ctg | gcg | tct | ggt | gtc | aac | aca | ctc | aag | agc | att | gcc | agg | aac | 912 |
| Ser | Asp | Leu | Ala | Ser | Gly | Val | Asn | Thr | Leu | Lys | Ser | Ile | Ala | Arg | Asn | |
| | 290 | | | | | 295 | | | | | 300 | | | | | |
| aca | agc | ctg | tac | gga | tct | ttc | ctg | gag | aac | cac | gac | cag | ccg | cgg | ttc | 960 |
| Thr | Ser | Leu | Tyr | Gly | Ser | Phe | Leu | Glu | Asn | His | Asp | Gln | Pro | Arg | Phe | |
| 305 | | | | | 310 | | | | | 315 | | | | | 320 | |
| gcg | tcg | ctt | acc | tcg | gac | gtc | gcc | ttg | gcg | aag | aat | gcg | ata | gcg | ttt | 1008 |
| Ala | Ser | Leu | Thr | Ser | Asp | Val | Ala | Leu | Ala | Lys | Asn | Ala | Ile | Ala | Phe | |
| | | | | 325 | | | | | 330 | | | | | 335 | | |
| act | atg | ctg | aag | gac | ggt | atc | ccg | gtc | gtt | tac | cag | ggc | caa | gag | cag | 1056 |
| Thr | Met | Leu | Lys | Asp | Gly | Ile | Pro | Val | Val | Tyr | Gln | Gly | Gln | Glu | Gln | |
| | | | 340 | | | | | 345 | | | | | 350 | | | |
| cac | tat | gcg | ggc | gga | aat | gtc | cca | gct | gac | cgc | gaa | gcg | atc | tgg | ttg | 1104 |
| His | Tyr | Ala | Gly | Gly | Asn | Val | Pro | Ala | Asp | Arg | Glu | Ala | Ile | Trp | Leu | |
| | | 355 | | | | | 360 | | | | | 365 | | | | |
| tcg | ggg | tac | tcc | acg | tct | gcg | acg | ctg | tac | acc | tgg | atc | gcc | gcg | ctg | 1152 |
| Ser | Gly | Tyr | Ser | Thr | Ser | Ala | Thr | Leu | Tyr | Thr | Trp | Ile | Ala | Ala | Leu | |
| | 370 | | | | | 375 | | | | | 380 | | | | | |
| aac | aag | gtc | cgt | tcg | agg | gct | atc | gcg | caa | gac | agc | agc | tac | ctg | agc | 1200 |
| Asn | Lys | Val | Arg | Ser | Arg | Ala | Ile | Ala | Gln | Asp | Ser | Ser | Tyr | Leu | Ser | |
| 385 | | | | | 390 | | | | | 395 | | | | | 400 | |
| tat | cag | gcg | tat | cct | gtc | tat | acg | gac | agc | aac | acc | att | gcc | atg | cgc | 1248 |
| Tyr | Gln | Ala | Tyr | Pro | Val | Tyr | Thr | Asp | Ser | Asn | Thr | Ile | Ala | Met | Arg | |
| | | | 405 | | | | | 410 | | | | | 415 | | | |
| aag | gga | cgg | gac | gga | tac | cag | gtc | atc | ggg | gtg | ttc | acc | aac | aag | gga | 1296 |
| Lys | Gly | Arg | Asp | Gly | Tyr | Gln | Val | Ile | Gly | Val | Phe | Thr | Asn | Lys | Gly | |
| | | | 420 | | | | | 425 | | | | | 430 | | | |
| tcg | agc | ggg | ttg | tcc | agt | ctc | acc | ctc | acg | acg | tcg | atg | acc | gga | ttc | 1344 |
| Ser | Ser | Gly | Leu | Ser | Ser | Leu | Thr | Leu | Thr | Thr | Ser | Met | Thr | Gly | Phe | |
| | | 435 | | | | | 440 | | | | | 445 | | | | |
| acg | gcg | ggc | cag | gcg | gtc | gtg | gat | gtc | atg | agc | tgc | acc | act | ttc | acg | 1392 |

-continued

```
              Thr Ala Gly Gln Ala Val Val Asp Val Met Ser Cys Thr Thr Phe Thr
                  450                 455                 460 acg gac tac agc ggt agc ctc gct gtc acc ctt tcg gga ggc att ccg         1440
Thr Asp Tyr Ser Gly Ser Leu Ala Val Thr Leu Ser Gly Gly Ile Pro
465                 470                 475                 480 cgg gtg ttc tat cca agc gcg agg ttg agt ggc tca gga ata tgt ggc         1488
Arg Val Phe Tyr Pro Ser Ala Arg Leu Ser Gly Ser Gly Ile Cys Gly
                485                 490                 495 tcc aat ggg acc acg aca aca gct acg acg aag acg agc acg acg ctg         1536
Ser Asn Gly Thr Thr Thr Thr Ala Thr Thr Lys Thr Ser Thr Thr Leu
        500                 505                 510 acc acg tcg acg aca aca acc tcc aca aag aca agt agt tct tgc acc         1584
Thr Thr Ser Thr Thr Thr Thr Ser Thr Lys Thr Ser Ser Ser Cys Thr
    515                 520                 525 gcc acc gcg gta gca atc acc ttc aac gag ctc gtg tcg acc tcc tac         1632
Ala Thr Ala Val Ala Ile Thr Phe Asn Glu Leu Val Ser Thr Ser Tyr
530                 535                 540 ggc gac aca gtc aag ctc acg ggc aac ata aca gcc ctg ggc agc tgg         1680
Gly Asp Thr Val Lys Leu Thr Gly Asn Ile Thr Ala Leu Gly Ser Trp
545                 550                 555                 560 aac acg gcc aac gcc gtc agc ctc agc gca tcg cag tac aca tct ggt         1728
Asn Thr Ala Asn Ala Val Ser Leu Ser Ala Ser Gln Tyr Thr Ser Gly
                565                 570                 575 agc ccg ctc tgg tcg ggc acc gtg tct ctg cct ccg ggc gtc ggg gta         1776
Ser Pro Leu Trp Ser Gly Thr Val Ser Leu Pro Pro Gly Val Gly Val
            580                 585                 590 cag tac aag ttc gtc agg gtc ggc agc tcg ggg agc gtg acg tgg gag         1824
Gln Tyr Lys Phe Val Arg Val Gly Ser Ser Gly Ser Val Thr Trp Glu
        595                 600                 605 gcg gac ccg aac cac act tat tct gtg ccg tgc gcg gct gct act gtc         1872
Ala Asp Pro Asn His Thr Tyr Ser Val Pro Cys Ala Ala Ala Thr Val
    610                 615                 620 ggt ggg agt tgg cag agc                                                 1890
Gly Gly Ser Trp Gln Ser
625                 630

<210> SEQ ID NO 161
<211> LENGTH: 630
<212> TYPE: PRT
<213> ORGANISM: Coniochaeta sp.

<400> SEQUENCE: 161

Met Arg Pro Ile Leu Ser Cys Leu Phe Leu Ala Ser Val Val Ala Gln
1               5                   10                  15

Val Ala Trp Gly Leu Ser Ala Ala Asp Trp Arg Glu Gln Ser Ile Tyr
            20                  25                  30

Gln Val Thr Asp Arg Phe Ala Arg Thr Asp Leu Ser Thr Thr Ala
        35                  40                  45

Thr Cys Asp Thr Ser Ala Gln Val Tyr Cys Gly Gly Thr Tyr Lys Gly
    50                  55                  60

Leu Ile Ser Lys Leu Asp Tyr Ile Gln Gly Met Gly Phe Thr Ala Ile
65                  70                  75                  80

Trp Ile Ser Pro Ile Val Glu Gln Met Asp Gly Asn Thr Ala Asp Gly
                85                  90                  95

Ser Ser Tyr His Gly Tyr Trp Ala Gln Asp Ile Trp Ser Leu Asn Pro
            100                 105                 110

Ser Phe Gly Ser Ala Gly Asp Leu Ile Ala Leu Ser Asn Ala Leu His
        115                 120                 125

Ala Arg Gly Met Tyr Leu Met Leu Asp Val Val Thr Asn His Phe Ala
```

-continued

```
                130                 135                 140
Tyr Asn Gly Cys Gly Asn Cys Val Asp Tyr Ser Ile Phe Thr Pro Phe
145                 150                 155                 160

Asn Ser Ser Ser Tyr Phe His Pro Phe Cys Leu Ile Asp Tyr Asn Asn
                165                 170                 175

Gln Thr Ser Ile Glu Gln Cys Trp Glu Gly Asp Asn Thr Val Ser Leu
                180                 185                 190

Pro Asp Leu Arg Thr Glu Asn Ser Asn Val Arg Ala Ile Trp Asn Asp
                195                 200                 205

Trp Ile Thr Gln Ile Val Ala Ala Tyr Gly Ile Asp Gly Leu Arg Ile
210                 215                 220

Asp Ser Val Lys His Gln Glu Thr Ser Phe Trp Ser Gly Phe Gly Ser
225                 230                 235                 240

Ala Ala Gly Val Phe Met Leu Gly Glu Val Tyr Asn Gly Asp Pro Thr
                245                 250                 255

Gln Leu Ala Pro Tyr Gln Asp Tyr Met Pro Gly Leu Leu Asp Tyr Ala
                260                 265                 270

Ser Tyr Tyr Trp Ile Thr Arg Ala Phe Gln Ser Ser Gly Ser Met
                275                 280                 285

Ser Asp Leu Ala Ser Gly Val Asn Thr Leu Lys Ser Ile Ala Arg Asn
290                 295                 300

Thr Ser Leu Tyr Gly Ser Phe Leu Glu Asn His Asp Gln Pro Arg Phe
305                 310                 315                 320

Ala Ser Leu Thr Ser Asp Val Ala Leu Ala Lys Asn Ala Ile Ala Phe
                325                 330                 335

Thr Met Leu Lys Asp Gly Ile Pro Val Val Tyr Gln Gly Gln Glu Gln
                340                 345                 350

His Tyr Ala Gly Gly Asn Val Pro Ala Asp Arg Glu Ala Ile Trp Leu
                355                 360                 365

Ser Gly Tyr Ser Thr Ser Ala Thr Leu Tyr Thr Trp Ile Ala Ala Leu
                370                 375                 380

Asn Lys Val Arg Ser Arg Ala Ile Ala Gln Asp Ser Ser Tyr Leu Ser
385                 390                 395                 400

Tyr Gln Ala Tyr Pro Val Tyr Thr Asp Ser Asn Thr Ile Ala Met Arg
                405                 410                 415

Lys Gly Arg Asp Gly Tyr Gln Val Ile Gly Val Phe Thr Asn Lys Gly
                420                 425                 430

Ser Ser Gly Leu Ser Ser Leu Thr Leu Thr Thr Ser Met Thr Gly Phe
                435                 440                 445

Thr Ala Gly Gln Ala Val Val Asp Val Met Ser Cys Thr Thr Phe Thr
450                 455                 460

Thr Asp Tyr Ser Gly Ser Leu Ala Val Thr Leu Ser Gly Gly Ile Pro
465                 470                 475                 480

Arg Val Phe Tyr Pro Ser Ala Arg Leu Ser Gly Ser Gly Ile Cys Gly
                485                 490                 495

Ser Asn Gly Thr Thr Thr Thr Ala Thr Thr Lys Thr Ser Thr Thr Leu
                500                 505                 510

Thr Thr Ser Thr Thr Thr Thr Ser Thr Lys Thr Ser Ser Ser Cys Thr
                515                 520                 525

Ala Thr Ala Val Ala Ile Thr Phe Asn Glu Leu Val Ser Thr Ser Tyr
                530                 535                 540

Gly Asp Thr Val Lys Leu Thr Gly Asn Ile Thr Ala Leu Gly Ser Trp
545                 550                 555                 560
```

-continued

```
Asn Thr Ala Asn Ala Val Ser Leu Ser Ala Ser Gln Tyr Thr Ser Gly
                565                 570                 575

Ser Pro Leu Trp Ser Gly Thr Val Ser Leu Pro Pro Gly Val Gly Val
            580                 585                 590

Gln Tyr Lys Phe Val Arg Val Gly Ser Ser Gly Ser Val Thr Trp Glu
        595                 600                 605

Ala Asp Pro Asn His Thr Tyr Ser Val Pro Cys Ala Ala Ala Thr Val
    610                 615                 620

Gly Gly Ser Trp Gln Ser
625                 630

<210> SEQ ID NO 162
<211> LENGTH: 1806
<212> TYPE: DNA
<213> ORGANISM: Meripilus giganteus
<220> FEATURE:
<221> NAME/KEY: CDS
<222> LOCATION: (1)..(1806)
<220> FEATURE:
<221> NAME/KEY: sig_peptide
<222> LOCATION: (1)..(78)
<220> FEATURE:
<221> NAME/KEY: misc_feature
<222> LOCATION: (79)..(1476)
<223> OTHER INFORMATION: Catalytic domain
<220> FEATURE:
<221> NAME/KEY: misc_feature
<222> LOCATION: (1477)..(1521)
<223> OTHER INFORMATION: Linker
<220> FEATURE:
<221> NAME/KEY: misc_feature
<222> LOCATION: (1522)..(1806)
<223> OTHER INFORMATION: CBM

<400> SEQUENCE: 162 atg tca aac tgg gtc aag ctc gcc gca ctc gcc gca ctc gcc gcc ctc    48
Met Ser Asn Trp Val Lys Leu Ala Ala Leu Ala Ala Leu Ala Ala Leu
1               5                   10                  15 gga gtg ttc tgc acc gcc gcc gtc gac gcc cgc cct act gtc ttt gac    96
Gly Val Phe Cys Thr Ala Ala Val Asp Ala Arg Pro Thr Val Phe Asp
            20                  25                  30 gcc ggc gcg gac gca cac tcg ctg cat gcc cgg gcc ccc tcc ggc agc   144
Ala Gly Ala Asp Ala His Ser Leu His Ala Arg Ala Pro Ser Gly Ser
        35                  40                  45 aag gat gtc atc atc cag atg ttt gag tgg aac tgg gac agc gtc gct   192
Lys Asp Val Ile Ile Gln Met Phe Glu Trp Asn Trp Asp Ser Val Ala
    50                  55                  60 gcc gag tgc act aac ttc atc ggc ccc gcc ggg tac ggc ttc gtg caa   240
Ala Glu Cys Thr Asn Phe Ile Gly Pro Ala Gly Tyr Gly Phe Val Gln
65                  70                  75                  80 gtg agc ccg ccc cag gag acc atc cag ggc gcg cag tgg tgg acc gac   288
Val Ser Pro Pro Gln Glu Thr Ile Gln Gly Ala Gln Trp Trp Thr Asp
                85                  90                  95 tac cag ccg gtg tcg tac acg ctc act ggg aag cgg ggc gac cgc tcc   336
Tyr Gln Pro Val Ser Tyr Thr Leu Thr Gly Lys Arg Gly Asp Arg Ser
            100                 105                 110 cag ttt gcg aac atg att act acg tgc cac gcc gcg ggc gtc ggc gtg   384
Gln Phe Ala Asn Met Ile Thr Thr Cys His Ala Ala Gly Val Gly Val
        115                 120                 125 atc gtt gac acc atc tgg aac cac atg gcg ggc gtc gac tcc ggc acg   432
Ile Val Asp Thr Ile Trp Asn His Met Ala Gly Val Asp Ser Gly Thr
    130                 135                 140 ggt acc gcc ggc tcg tcc ttc acg cac tac aac tac ccc ggc atc tac   480
Gly Thr Ala Gly Ser Ser Phe Thr His Tyr Asn Tyr Pro Gly Ile Tyr
145                 150                 155                 160
```

```
caa aac cag gac ttt cac cac tgc ggc ctc gag ccg ggc gat gac atc    528
Gln Asn Gln Asp Phe His His Cys Gly Leu Glu Pro Gly Asp Asp Ile
                165                 170                 175 gtc aac tac gac aac gcg gtt gag gtc cag acc tgc gag ctt gtc aac    576
Val Asn Tyr Asp Asn Ala Val Glu Val Gln Thr Cys Glu Leu Val Asn
            180                 185                 190 ctc gct gac ctc gcc acc gac acg gag tat gtg cgc ggt cgc ctt gcc    624
Leu Ala Asp Leu Ala Thr Asp Thr Glu Tyr Val Arg Gly Arg Leu Ala
        195                 200                 205 cag tac gga aac gac ctg ctc tcg ctc ggt gcc gat ggc ctg cgt ctt    672
Gln Tyr Gly Asn Asp Leu Leu Ser Leu Gly Ala Asp Gly Leu Arg Leu
    210                 215                 220 gac gct tcc aaa cac att cct gtg ggc gac atc gcg aac atc ctg tct    720
Asp Ala Ser Lys His Ile Pro Val Gly Asp Ile Ala Asn Ile Leu Ser
225                 230                 235                 240 cgc ctc agt cgc tct gtc tac atc acc cag gaa gtc atc ttt ggg gcc    768
Arg Leu Ser Arg Ser Val Tyr Ile Thr Gln Glu Val Ile Phe Gly Ala
                245                 250                 255 ggc gag ccc atc acg ccg aac cag tac acc ggg aac ggc gac gtt cag    816
Gly Glu Pro Ile Thr Pro Asn Gln Tyr Thr Gly Asn Gly Asp Val Gln
            260                 265                 270 gag ttc cgc tac acc tct gcg cta aag gac gcc ttg ttg agc tcg ggc    864
Glu Phe Arg Tyr Thr Ser Ala Leu Lys Asp Ala Phe Leu Ser Ser Gly
        275                 280                 285 ata tcc aac ctg cag gac ttc gaa aac cgt gga tgg gta cct ggc tcg    912
Ile Ser Asn Leu Gln Asp Phe Glu Asn Arg Gly Trp Val Pro Gly Ser
    290                 295                 300 ggc gcc aac gtg ttc gtc gtc aac cat gac acc gag cgg aac ggc gcg    960
Gly Ala Asn Val Phe Val Val Asn His Asp Thr Glu Arg Asn Gly Ala
305                 310                 315                 320 tcg ctg aac aac aac tcg cct tcg aac acc tac gtc acc gcg acg atc   1008
Ser Leu Asn Asn Asn Ser Pro Ser Asn Thr Tyr Val Thr Ala Thr Ile
                325                 330                 335 ttc tcg ctc gca cac ccg tac ggc acg ccc acg atc ctc tcc tcg tat   1056
Phe Ser Leu Ala His Pro Tyr Gly Thr Pro Thr Ile Leu Ser Ser Tyr
            340                 345                 350 gat ggc ttc acg aac acc gac gcc ggt gcg ccg aac aac aac gtc ggc   1104
Asp Gly Phe Thr Asn Thr Asp Ala Gly Ala Pro Asn Asn Asn Val Gly
        355                 360                 365 aca tgc tcg acc agc ggt ggt gcg aac ggg tgg ctc tgc cag cac cgc   1152
Thr Cys Ser Thr Ser Gly Gly Ala Asn Gly Trp Leu Cys Gln His Arg
    370                 375                 380 tgg acc gcg atc gcc ggc atg gtc ggc ttc cgc aac aac gtc ggc agc   1200
Trp Thr Ala Ile Ala Gly Met Val Gly Phe Arg Asn Asn Val Gly Ser
385                 390                 395                 400 gct gca ctc aac aac tgg cag gcc ccg cag tcg cag cag att gcg ttc   1248
Ala Ala Leu Asn Asn Trp Gln Ala Pro Gln Ser Gln Gln Ile Ala Phe
                405                 410                 415 ggt cgc ggc gca ctt ggc ttc gtc gcg atc aac aac gcc gac tcg gcc   1296
Gly Arg Gly Ala Leu Gly Phe Val Ala Ile Asn Asn Ala Asp Ser Ala
            420                 425                 430 tgg tct acg acg ttc acc act tcc ctc ccc gat ggt tcc tac tgc gat   1344
Trp Ser Thr Thr Phe Thr Thr Ser Leu Pro Asp Gly Ser Tyr Cys Asp
        435                 440                 445 gtc atc agc ggc aag gcc tcc ggc agt agc tgc acc ggt tct tcg ttc   1392
Val Ile Ser Gly Lys Ala Ser Gly Ser Ser Cys Thr Gly Ser Ser Phe
    450                 455                 460 acc gtc tcc ggc ggg aag ctg acc gcc acg gtg ccg gcg cgt agc gcc   1440
Thr Val Ser Gly Gly Lys Leu Thr Ala Thr Val Pro Ala Arg Ser Ala
465                 470                 475                 480
```

```
atc gcc gtg cac acc ggt cag aaa ggt tct ggt ggt gcc acg ccc acc      1488
Ile Ala Val His Thr Gly Gln Lys Gly Ser Gly Gly Ala Thr Pro Thr
                485                 490                 495 tcc gcc cct agt act aca cca acc agc ggc act gtc agc atg acc ttc      1536
Ser Ala Pro Ser Thr Thr Pro Thr Ser Gly Thr Val Ser Met Thr Phe
            500                 505                 510 gct gag cag gcg acg acc acc ttc ggc gag aac atc ttc ctc gtc ggc      1584
Ala Glu Gln Ala Thr Thr Thr Phe Gly Glu Asn Ile Phe Leu Val Gly
        515                 520                 525 agt att tcg cag ctc ggg aac tgg aac cca gcc agc gcg atc gcc ctg      1632
Ser Ile Ser Gln Leu Gly Asn Trp Asn Pro Ala Ser Ala Ile Ala Leu
    530                 535                 540 tcc tct gcg gcg tac cct acg tgg tct gtg tct gtg aac att ccc gct      1680
Ser Ser Ala Ala Tyr Pro Thr Trp Ser Val Ser Val Asn Ile Pro Ala
545                 550                 555                 560 gga acg acc ttc cag tac aag ttc atc cgc aag gag acg gac ggt agc      1728
Gly Thr Thr Phe Gln Tyr Lys Phe Ile Arg Lys Glu Thr Asp Gly Ser
                565                 570                 575 gtc gtc tgg gag tcg gac ccc aac cgc cag gct acc gcg ccc gcg tcc      1776
Val Val Trp Glu Ser Asp Pro Asn Arg Gln Ala Thr Ala Pro Ala Ser
            580                 585                 590 ggt acc acc acg ctc acg tcc agc tgg cgg                              1806
Gly Thr Thr Thr Leu Thr Ser Ser Trp Arg
        595                 600

<210> SEQ ID NO 163
<211> LENGTH: 602
<212> TYPE: PRT
<213> ORGANISM: Meripilus giganteus

<400> SEQUENCE: 163

Met Ser Asn Trp Val Lys Leu Ala Ala Leu Ala Ala Leu Ala Ala Leu
1               5                   10                  15

Gly Val Phe Cys Thr Ala Ala Val Asp Ala Arg Pro Thr Val Phe Asp
            20                  25                  30

Ala Gly Ala Asp Ala His Ser Leu His Ala Arg Ala Pro Ser Gly Ser
        35                  40                  45

Lys Asp Val Ile Ile Gln Met Phe Glu Trp Asn Trp Asp Ser Val Ala
    50                  55                  60

Ala Glu Cys Thr Asn Phe Ile Gly Pro Ala Gly Tyr Gly Phe Val Gln
65                  70                  75                  80

Val Ser Pro Pro Gln Glu Thr Ile Gln Gly Ala Gln Trp Trp Thr Asp
                85                  90                  95

Tyr Gln Pro Val Ser Tyr Thr Leu Thr Gly Lys Arg Gly Asp Arg Ser
            100                 105                 110

Gln Phe Ala Asn Met Ile Thr Thr Cys His Ala Ala Gly Val Gly Val
        115                 120                 125

Ile Val Asp Thr Ile Trp Asn His Met Ala Gly Val Asp Ser Gly Thr
    130                 135                 140

Gly Thr Ala Gly Ser Ser Phe Thr His Tyr Asn Tyr Pro Gly Ile Tyr
145                 150                 155                 160

Gln Asn Gln Asp Phe His His Cys Gly Leu Glu Pro Gly Asp Ile
                165                 170                 175

Val Asn Tyr Asp Asn Ala Val Glu Val Gln Thr Cys Glu Leu Val Asn
            180                 185                 190

Leu Ala Asp Leu Ala Thr Asp Thr Glu Tyr Val Arg Gly Arg Leu Ala
        195                 200                 205
```

```
Gln Tyr Gly Asn Asp Leu Leu Ser Leu Gly Ala Asp Gly Leu Arg Leu
    210                 215                 220

Asp Ala Ser Lys His Ile Pro Val Gly Asp Ile Ala Asn Ile Leu Ser
225                 230                 235                 240

Arg Leu Ser Arg Ser Val Tyr Ile Thr Gln Glu Val Ile Phe Gly Ala
                245                 250                 255

Gly Glu Pro Ile Thr Pro Asn Gln Tyr Thr Gly Asn Gly Asp Val Gln
            260                 265                 270

Glu Phe Arg Tyr Thr Ser Ala Leu Lys Asp Ala Phe Leu Ser Ser Gly
        275                 280                 285

Ile Ser Asn Leu Gln Asp Phe Glu Asn Arg Gly Trp Val Pro Gly Ser
    290                 295                 300

Gly Ala Asn Val Phe Val Val Asn His Asp Thr Glu Arg Asn Gly Ala
305                 310                 315                 320

Ser Leu Asn Asn Asn Ser Pro Ser Asn Thr Tyr Val Thr Ala Thr Ile
                325                 330                 335

Phe Ser Leu Ala His Pro Tyr Gly Thr Pro Thr Ile Leu Ser Ser Tyr
            340                 345                 350

Asp Gly Phe Thr Asn Thr Asp Ala Gly Ala Pro Asn Asn Val Gly
        355                 360                 365

Thr Cys Ser Thr Ser Gly Gly Ala Asn Gly Trp Leu Cys Gln His Arg
    370                 375                 380

Trp Thr Ala Ile Ala Gly Met Val Gly Phe Arg Asn Asn Val Gly Ser
385                 390                 395                 400

Ala Ala Leu Asn Asn Trp Gln Ala Pro Gln Ser Gln Ile Ala Phe
                405                 410                 415

Gly Arg Gly Ala Leu Gly Phe Val Ala Ile Asn Asn Ala Asp Ser Ala
            420                 425                 430

Trp Ser Thr Thr Phe Thr Thr Ser Leu Pro Asp Gly Ser Tyr Cys Asp
    435                 440                 445

Val Ile Ser Gly Lys Ala Ser Gly Ser Ser Cys Thr Gly Ser Ser Phe
450                 455                 460

Thr Val Ser Gly Gly Lys Leu Thr Ala Thr Val Pro Ala Arg Ser Ala
465                 470                 475                 480

Ile Ala Val His Thr Gly Gln Lys Gly Ser Gly Ala Thr Pro Thr
                485                 490                 495

Ser Ala Pro Ser Thr Pro Thr Ser Gly Thr Val Ser Met Thr Phe
            500                 505                 510

Ala Glu Gln Ala Thr Thr Thr Phe Gly Glu Asn Ile Phe Leu Val Gly
        515                 520                 525

Ser Ile Ser Gln Leu Gly Asn Trp Asn Pro Ala Ser Ala Ile Ala Leu
    530                 535                 540

Ser Ser Ala Ala Tyr Pro Thr Trp Ser Val Ser Val Asn Ile Pro Ala
545                 550                 555                 560

Gly Thr Thr Phe Gln Tyr Lys Phe Ile Arg Lys Glu Thr Asp Gly Ser
                565                 570                 575

Val Val Trp Glu Ser Asp Pro Asn Arg Gln Ala Thr Ala Pro Ala Ser
            580                 585                 590

Gly Thr Thr Thr Leu Thr Ser Ser Trp Arg
        595                 600

<210> SEQ ID NO 164
<211> LENGTH: 1929
<212> TYPE: DNA
<213> ORGANISM: Penicillium sp.
```

```
<220> FEATURE:
<221> NAME/KEY: CDS
<222> LOCATION: (1)..(1929)
<220> FEATURE:
<221> NAME/KEY: sig_peptide
<222> LOCATION: (1)..(60)
<220> FEATURE:
<221> NAME/KEY: misc_feature
<222> LOCATION: (61)..(1488)
<223> OTHER INFORMATION: Catalytic domain
<220> FEATURE:
<221> NAME/KEY: misc_feature
<222> LOCATION: (1489)..(1617)
<223> OTHER INFORMATION: Linker
<220> FEATURE:
<221> NAME/KEY: misc_feature
<222> LOCATION: (1618)..(1929)
<223> OTHER INFORMATION: CBM

<400> SEQUENCE: 164 atg aag gca ctt gcg ttg gcc gca cta tgc ctc gcg aag gct gtt gcc      48
Met Lys Ala Leu Ala Leu Ala Ala Leu Cys Leu Ala Lys Ala Val Ala
1               5                   10                  15 ggt ctg acg gct gca gaa tgg cgc agt cag tcg atc tac ttt ctt cta      96
Gly Leu Thr Ala Ala Glu Trp Arg Ser Gln Ser Ile Tyr Phe Leu Leu
            20                  25                  30 act gat cgc ttt ggc cga acg gac aat tcc acc acg gca gca tgc aat     144
Thr Asp Arg Phe Gly Arg Thr Asp Asn Ser Thr Thr Ala Ala Cys Asn
        35                  40                  45 gtc agc gat cgg gtc tac tgt ggt ggc agc tgg caa gga atc atc aat     192
Val Ser Asp Arg Val Tyr Cys Gly Gly Ser Trp Gln Gly Ile Ile Asn
    50                  55                  60 cac ttg gat tac att cag ggc atg gga ttc acc gcg att tgg att acc     240
His Leu Asp Tyr Ile Gln Gly Met Gly Phe Thr Ala Ile Trp Ile Thr
65                  70                  75                  80 cct gtc aca gaa cag ctc tct caa gac act gga gat ggc gag gca tac     288
Pro Val Thr Glu Gln Leu Ser Gln Asp Thr Gly Asp Gly Glu Ala Tyr
                85                  90                  95 cac gga tac tgg caa caa gag ata tac aac gtc aac aca aac tat ggc     336
His Gly Tyr Trp Gln Gln Glu Ile Tyr Asn Val Asn Thr Asn Tyr Gly
            100                 105                 110 act gct gct gac ctt ttg gca ctt tct aaa gcc ctg cac agt cgt ggc     384
Thr Ala Ala Asp Leu Leu Ala Leu Ser Lys Ala Leu His Ser Arg Gly
        115                 120                 125 atg tac ctc atg gta gac gtg gtt gca aac cac atg ggc tat gat gga     432
Met Tyr Leu Met Val Asp Val Val Ala Asn His Met Gly Tyr Asp Gly
    130                 135                 140 gct gga aat act gtt gac tac agt gtc ttt aat cca ttc gac tct tcg     480
Ala Gly Asn Thr Val Asp Tyr Ser Val Phe Asn Pro Phe Asp Ser Ser
145                 150                 155                 160 tct tac ttc cac tcg tat tgt gag atc agc gat tac tct gat cag aca     528
Ser Tyr Phe His Ser Tyr Cys Glu Ile Ser Asp Tyr Ser Asp Gln Thr
                165                 170                 175 aac gtg gag gac tgt tgg ctt gga gac act aca gtt tct ctt cca gat     576
Asn Val Glu Asp Cys Trp Leu Gly Asp Thr Thr Val Ser Leu Pro Asp
            180                 185                 190 ctc gac acg acc ctt act tct gtt cag acg atc tgg tat aac tgg gtc     624
Leu Asp Thr Thr Leu Thr Ser Val Gln Thr Ile Trp Tyr Asn Trp Val
        195                 200                 205 act gaa ttg gtg tcc aac tac tcc att gat ggt ttg cga att gat aca     672
Thr Glu Leu Val Ser Asn Tyr Ser Ile Asp Gly Leu Arg Ile Asp Thr
    210                 215                 220 gtc aaa cac gtg cag aag tcg ttc tgg ccg ggc tac aac agt gct gca     720
Val Lys His Val Gln Lys Ser Phe Trp Pro Gly Tyr Asn Ser Ala Ala
225                 230                 235                 240
```

-continued

| | | |
|---|---|---|
| ggt gtc tac tgt gtg gga gag gtg ttt gat ggg gac cca gca tac act<br>Gly Val Tyr Cys Val Gly Glu Val Phe Asp Gly Asp Pro Ala Tyr Thr<br>              245                      250                    255 | 768 | |
| tgc ccc tac cag agc tac ctc gat ggt gtt ctg aac tat ccg att tat<br>Cys Pro Tyr Gln Ser Tyr Leu Asp Gly Val Leu Asn Tyr Pro Ile Tyr<br>        260                      265                      270 | 816 | |
| tac caa ctg ctg tac gca ttc gag tcg aca agt ggc agt atc agc ggt<br>Tyr Gln Leu Leu Tyr Ala Phe Glu Ser Thr Ser Gly Ser Ile Ser Gly<br>            275                      280                    285 | 864 | |
| cta tat aat atg atc aac tcc gtt gca tct gac tgt tcc gat cca acc<br>Leu Tyr Asn Met Ile Asn Ser Val Ala Ser Asp Cys Ser Asp Pro Thr<br>    290                      295                      300 | 912 | |
| ttg ctc gga aac ttc atc gag aat cat gac aac cca cgc ttt gct tcc<br>Leu Leu Gly Asn Phe Ile Glu Asn His Asp Asn Pro Arg Phe Ala Ser<br>305                      310                      315                  320 | 960 | |
| tac acg agc gat tat tct caa gcg aag aat gtg att tct ttc atc ttc<br>Tyr Thr Ser Asp Tyr Ser Gln Ala Lys Asn Val Ile Ser Phe Ile Phe<br>                325                      330                    335 | 1008 | |
| ttc tcg gat ggt att cca atc gtc tat gct ggc cag gaa caa cac tat<br>Phe Ser Asp Gly Ile Pro Ile Val Tyr Ala Gly Gln Glu Gln His Tyr<br>        340                      345                      350 | 1056 | |
| agc ggt ggc agt gac cct gcc aat cgt gaa gca act tgg cta tcc gga<br>Ser Gly Gly Ser Asp Pro Ala Asn Arg Glu Ala Thr Trp Leu Ser Gly<br>            355                      360                    365 | 1104 | |
| tac gac aag aca gct cag ctt tac acc tac atc acc acc aca aac aag<br>Tyr Asp Lys Thr Ala Gln Leu Tyr Thr Tyr Ile Thr Thr Thr Asn Lys<br>    370                      375                      380 | 1152 | |
| atc cgt gcc cta gcc att tca aag gac agc gcc tac ata agt tcc aag<br>Ile Arg Ala Leu Ala Ile Ser Lys Asp Ser Ala Tyr Ile Ser Ser Lys<br>385                      390                      395                  400 | 1200 | |
| aat aat gct ttc tac act gat agc aat act att gcc atg aag aaa gga<br>Asn Asn Ala Phe Tyr Thr Asp Ser Asn Thr Ile Ala Met Lys Lys Gly<br>                405                      410                    415 | 1248 | |
| tct agc ggc tcg caa gtt ata act gtt ctt tca aac cgt ggc tca tcg<br>Ser Ser Gly Ser Gln Val Ile Thr Val Leu Ser Asn Arg Gly Ser Ser<br>                420                      425                    430 | 1296 | |
| ggt agc tcg tat acc ttg act ctt agc gga agc ggt tac tcg tct ggc<br>Gly Ser Ser Tyr Thr Leu Thr Leu Ser Gly Ser Gly Tyr Ser Ser Gly<br>            435                      440                    445 | 1344 | |
| acg aag ctc atg gag atg tac acc tgc aca gcc gtg act gtg gac tct<br>Thr Lys Leu Met Glu Met Tyr Thr Cys Thr Ala Val Thr Val Asp Ser<br>    450                      455                      460 | 1392 | |
| agt ggc aac atc gcc gtg ccg atg gct tcc gga ctc cct cga gtc tac<br>Ser Gly Asn Ile Ala Val Pro Met Ala Ser Gly Leu Pro Arg Val Tyr<br>465                      470                      475                  480 | 1440 | |
| atg ctt gct tcc tcg gct tgc tct att tgc agt tct gcc tgt tca gca<br>Met Leu Ala Ser Ser Ala Cys Ser Ile Cys Ser Ser Ala Cys Ser Ala<br>                485                      490                    495 | 1488 | |
| act acc aca acc tcg tcg acg gct tct act tca acg aca acg tca acc<br>Thr Thr Thr Thr Ser Ser Thr Ala Ser Thr Ser Thr Thr Thr Ser Thr<br>        500                      505                      510 | 1536 | |
| aca ctg aag act acc acg aca acg tca act act tcg aaa act act acg<br>Thr Leu Lys Thr Thr Thr Thr Ser Thr Thr Ser Lys Thr Thr Thr<br>            515                      520                    525 | 1584 | |
| tcc act aca tcc acg agc tgc aca cag gct act gca ttg cca gtt ttg<br>Ser Thr Thr Ser Thr Ser Cys Thr Gln Ala Thr Ala Leu Pro Val Leu<br>    530                      535                      540 | 1632 | |
| ttc aaa gag att gtc acc act tca tac ggg cag agt atc tat atc tca<br>Phe Lys Glu Ile Val Thr Thr Ser Tyr Gly Gln Ser Ile Tyr Ile Ser<br>545                      550                      555                  560 | 1680 | |

-continued

```
ggc tct ata agt caa ctc gga agc tgg gac acg tct agc gcc gtt gcc    1728
Gly Ser Ile Ser Gln Leu Gly Ser Trp Asp Thr Ser Ser Ala Val Ala
            565                 570                 575 ctc tct gct gat cag tac aca tca tcc agc cat ctg tgg tat gtt gtc    1776
Leu Ser Ala Asp Gln Tyr Thr Ser Ser Ser His Leu Trp Tyr Val Val
        580                 585                 590 gtg aca att cca gtg ggc acc tcg ttc cag tac aag ttc atc gag gag    1824
Val Thr Ile Pro Val Gly Thr Ser Phe Gln Tyr Lys Phe Ile Glu Glu
    595                 600                 605 acg agc ggg tct agt act att act tgg gag agt gat ccg aac cgc tct    1872
Thr Ser Gly Ser Ser Thr Ile Thr Trp Glu Ser Asp Pro Asn Arg Ser
610                 615                 620 tat acg gtg cca acg ggc tgt gca ggc tca acg gct acc gtc aca gcg    1920
Tyr Thr Val Pro Thr Gly Cys Ala Gly Ser Thr Ala Thr Val Thr Ala
625                 630                 635                 640 acc tgg aga                                                        1929
Thr Trp Arg <210> SEQ ID NO 165
<211> LENGTH: 643
<212> TYPE: PRT
<213> ORGANISM: Penicillium sp.

<400> SEQUENCE: 165

Met Lys Ala Leu Ala Leu Ala Ala Leu Cys Leu Ala Lys Ala Val Ala
1               5                   10                  15

Gly Leu Thr Ala Ala Glu Trp Arg Ser Gln Ser Ile Tyr Phe Leu Leu
            20                  25                  30

Thr Asp Arg Phe Gly Arg Thr Asp Asn Ser Thr Thr Ala Ala Cys Asn
        35                  40                  45

Val Ser Asp Arg Val Tyr Cys Gly Gly Ser Trp Gln Gly Ile Ile Asn
    50                  55                  60

His Leu Asp Tyr Ile Gln Gly Met Gly Phe Thr Ala Ile Trp Ile Thr
65                  70                  75                  80

Pro Val Thr Glu Gln Leu Ser Gln Asp Thr Gly Asp Gly Glu Ala Tyr
                85                  90                  95

His Gly Tyr Trp Gln Gln Glu Ile Tyr Asn Val Asn Thr Asn Tyr Gly
            100                 105                 110

Thr Ala Ala Asp Leu Leu Ala Leu Ser Lys Ala Leu His Ser Arg Gly
        115                 120                 125

Met Tyr Leu Met Val Asp Val Val Ala Asn His Met Gly Tyr Asp Gly
    130                 135                 140

Ala Gly Asn Thr Val Asp Tyr Ser Val Phe Asn Pro Phe Asp Ser Ser
145                 150                 155                 160

Ser Tyr Phe His Ser Tyr Cys Glu Ile Ser Asp Tyr Ser Asp Gln Thr
                165                 170                 175

Asn Val Glu Asp Cys Trp Leu Gly Asp Thr Thr Val Ser Leu Pro Asp
            180                 185                 190

Leu Asp Thr Thr Leu Thr Ser Val Gln Thr Ile Trp Tyr Asn Trp Val
        195                 200                 205

Thr Glu Leu Val Ser Asn Tyr Ser Ile Asp Gly Leu Arg Ile Asp Thr
    210                 215                 220

Val Lys His Val Gln Lys Ser Phe Trp Pro Gly Tyr Asn Ser Ala Ala
225                 230                 235                 240

Gly Val Tyr Cys Val Gly Glu Val Phe Asp Gly Asp Pro Ala Tyr Thr
                245                 250                 255
```

Cys Pro Tyr Gln Ser Tyr Leu Asp Gly Val Leu Asn Tyr Pro Ile Tyr
            260                 265                 270

Tyr Gln Leu Leu Tyr Ala Phe Glu Ser Thr Ser Gly Ser Ile Ser Gly
        275                 280                 285

Leu Tyr Asn Met Ile Asn Ser Val Ala Ser Asp Cys Ser Asp Pro Thr
290                 295                 300

Leu Leu Gly Asn Phe Ile Glu Asn His Asp Asn Pro Arg Phe Ala Ser
305                 310                 315                 320

Tyr Thr Ser Asp Tyr Ser Gln Ala Lys Asn Val Ile Ser Phe Ile Phe
                325                 330                 335

Phe Ser Asp Gly Ile Pro Ile Val Tyr Ala Gly Gln Glu Gln His Tyr
            340                 345                 350

Ser Gly Gly Ser Asp Pro Ala Asn Arg Glu Ala Thr Trp Leu Ser Gly
        355                 360                 365

Tyr Asp Lys Thr Ala Gln Leu Tyr Thr Tyr Ile Thr Thr Asn Lys
    370                 375                 380

Ile Arg Ala Leu Ala Ile Ser Lys Asp Ser Ala Tyr Ile Ser Ser Lys
385                 390                 395                 400

Asn Asn Ala Phe Tyr Thr Asp Ser Asn Thr Ile Ala Met Lys Lys Gly
                405                 410                 415

Ser Ser Gly Ser Gln Val Ile Thr Val Leu Ser Asn Arg Gly Ser Ser
            420                 425                 430

Gly Ser Ser Tyr Thr Leu Thr Leu Ser Gly Ser Gly Tyr Ser Ser Gly
        435                 440                 445

Thr Lys Leu Met Glu Met Tyr Thr Cys Thr Ala Val Thr Val Asp Ser
450                 455                 460

Ser Gly Asn Ile Ala Val Pro Met Ala Ser Gly Leu Pro Arg Val Tyr
465                 470                 475                 480

Met Leu Ala Ser Ser Ala Cys Ser Ile Cys Ser Ser Ala Cys Ser Ala
                485                 490                 495

Thr Thr Thr Thr Ser Ser Thr Ala Ser Thr Ser Thr Thr Ser Thr
            500                 505                 510

Thr Leu Lys Thr Thr Thr Thr Ser Thr Thr Ser Lys Thr Thr Thr
        515                 520                 525

Ser Thr Thr Ser Thr Ser Cys Thr Gln Ala Thr Ala Leu Pro Val Leu
530                 535                 540

Phe Lys Glu Ile Val Thr Thr Ser Tyr Gly Gln Ser Ile Tyr Ile Ser
545                 550                 555                 560

Gly Ser Ile Ser Gln Leu Gly Ser Trp Asp Thr Ser Ser Ala Val Ala
                565                 570                 575

Leu Ser Ala Asp Gln Tyr Thr Ser Ser Ser His Leu Trp Tyr Val Val
            580                 585                 590

Val Thr Ile Pro Val Gly Thr Ser Phe Gln Tyr Lys Phe Ile Glu Glu
        595                 600                 605

Thr Ser Gly Ser Ser Thr Ile Thr Trp Glu Ser Asp Pro Asn Arg Ser
    610                 615                 620

Tyr Thr Val Pro Thr Gly Cys Ala Gly Ser Thr Ala Val Thr Ala
625                 630                 635                 640

Thr Trp Arg

<210> SEQ ID NO 166
<211> LENGTH: 1698
<212> TYPE: DNA
<213> ORGANISM: Streptomyces limosus
<220> FEATURE:

```
<221> NAME/KEY: CDS
<222> LOCATION: (1)..(1698)
<220> FEATURE:
<221> NAME/KEY: sig_peptide
<222> LOCATION: (1)..(84)
<220> FEATURE:
<221> NAME/KEY: misc_feature
<222> LOCATION: (85)..(1503)
<223> OTHER INFORMATION: Catalytic domain
<220> FEATURE:
<221> NAME/KEY: misc_feature
<222> LOCATION: (1504)..(1701)
<223> OTHER INFORMATION: Linker+CBM

<400> SEQUENCE: 166
```

| | | | | | | | | | | | | | | | | |
|---|---|---|---|---|---|---|---|---|---|---|---|---|---|---|---|---|
| atg | gcc | cgc | aga | ctc | gcc | acc | gcg | tcc | cta | gcc | gtg | ctg | gcg | gcg | gcc | 48 |
| Met | Ala | Arg | Arg | Leu | Ala | Thr | Ala | Ser | Leu | Ala | Val | Leu | Ala | Ala | Ala | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gcc | acc | gcc | ctc | acc | gcg | ccc | aca | ccc | gcc | gct | gcc | ccg | ccc | ggg | | 96 |
| Ala | Thr | Ala | Leu | Thr | Ala | Pro | Thr | Pro | Ala | Ala | Ala | Pro | Pro | Gly | | |
| | | | 20 | | | | | 25 | | | | | 30 | | | |

| | | | | | | | | | | | | | | | | |
|---|---|---|---|---|---|---|---|---|---|---|---|---|---|---|---|---|
| gcg | aag | gac | gtc | acc | gcc | gtc | ctc | ttc | gag | tgg | aag | ttc | gcc | tcc | gta | 144 |
| Ala | Lys | Asp | Val | Thr | Ala | Val | Leu | Phe | Glu | Trp | Lys | Phe | Ala | Ser | Val | |
| | | 35 | | | | | 40 | | | | | 45 | | | | |

| | | | | | | | | | | | | | | | | |
|---|---|---|---|---|---|---|---|---|---|---|---|---|---|---|---|---|
| gcc | cgc | gcc | tgc | acc | gac | agc | ctc | ggc | ccg | gcc | ggc | tac | gga | tac | gtc | 192 |
| Ala | Arg | Ala | Cys | Thr | Asp | Ser | Leu | Gly | Pro | Ala | Gly | Tyr | Gly | Tyr | Val | |
| 50 | | | | | 55 | | | | | 60 | | | | | | |

| | | | | | | | | | | | | | | | | |
|---|---|---|---|---|---|---|---|---|---|---|---|---|---|---|---|---|
| cag | gtc | tcg | ccg | ccc | cag | gag | cac | atc | cag | ggc | agc | cag | tgg | tgg | acc | 240 |
| Gln | Val | Ser | Pro | Pro | Gln | Glu | His | Ile | Gln | Gly | Ser | Gln | Trp | Trp | Thr | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| tcc | tac | cag | ccc | gtc | agc | tac | aag | atc | gcc | gga | cgg | ctc | ggc | gac | cgc | 288 |
| Ser | Tyr | Gln | Pro | Val | Ser | Tyr | Lys | Ile | Ala | Gly | Arg | Leu | Gly | Asp | Arg | |
| | | | | 85 | | | | | 90 | | | | | 95 | | |

| | | | | | | | | | | | | | | | | |
|---|---|---|---|---|---|---|---|---|---|---|---|---|---|---|---|---|
| gcc | gcc | ttc | aag | tcc | atg | gtc | gac | acc | tgc | cac | gcg | gcc | ggc | gtc | aag | 336 |
| Ala | Ala | Phe | Lys | Ser | Met | Val | Asp | Thr | Cys | His | Ala | Ala | Gly | Val | Lys | |
| | | | 100 | | | | | 105 | | | | | 110 | | | |

| | | | | | | | | | | | | | | | | |
|---|---|---|---|---|---|---|---|---|---|---|---|---|---|---|---|---|
| gtc | gtc | gcc | gac | tcg | gtc | atc | aac | cac | atg | gcc | gcg | ggt | tcc | ggc | acc | 384 |
| Val | Val | Ala | Asp | Ser | Val | Ile | Asn | His | Met | Ala | Ala | Gly | Ser | Gly | Thr | |
| | | 115 | | | | | 120 | | | | | 125 | | | | |

| | | | | | | | | | | | | | | | | |
|---|---|---|---|---|---|---|---|---|---|---|---|---|---|---|---|---|
| ggc | acc | ggc | ggc | agc | gcg | tac | cag | aag | tac | gac | tac | ccg | ggc | atc | tgg | 432 |
| Gly | Thr | Gly | Gly | Ser | Ala | Tyr | Gln | Lys | Tyr | Asp | Tyr | Pro | Gly | Ile | Trp | |
| | 130 | | | | | 135 | | | | | 140 | | | | | |

| | | | | | | | | | | | | | | | | |
|---|---|---|---|---|---|---|---|---|---|---|---|---|---|---|---|---|
| tcc | ggc | gcc | gac | atg | gac | gac | tgc | cgc | agc | gag | atc | aac | gac | tac | ggc | 480 |
| Ser | Gly | Ala | Asp | Met | Asp | Asp | Cys | Arg | Ser | Glu | Ile | Asn | Asp | Tyr | Gly | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| aac | cgc | gcc | aac | gtc | cag | aac | tgc | gaa | ctg | gtc | ggc | ctc | gcc | gac | ctc | 528 |
| Asn | Arg | Ala | Asn | Val | Gln | Asn | Cys | Glu | Leu | Val | Gly | Leu | Ala | Asp | Leu | |
| | | | | 165 | | | | | 170 | | | | | 175 | | |

| | | | | | | | | | | | | | | | | |
|---|---|---|---|---|---|---|---|---|---|---|---|---|---|---|---|---|
| gac | acc | ggt | gag | tcg | tac | gtc | cgc | gac | cgc | atc | gcc | gcc | tac | ctc | aac | 576 |
| Asp | Thr | Gly | Glu | Ser | Tyr | Val | Arg | Asp | Arg | Ile | Ala | Ala | Tyr | Leu | Asn | |
| | | | 180 | | | | | 185 | | | | | 190 | | | |

| | | | | | | | | | | | | | | | | |
|---|---|---|---|---|---|---|---|---|---|---|---|---|---|---|---|---|
| gac | ctg | ctc | tcg | ctc | ggt | gtg | gac | ggc | ttc | cgc | atc | gac | gcc | gcc | aag | 624 |
| Asp | Leu | Leu | Ser | Leu | Gly | Val | Asp | Gly | Phe | Arg | Ile | Asp | Ala | Ala | Lys | |
| | | 195 | | | | | 200 | | | | | 205 | | | | |

| | | | | | | | | | | | | | | | | |
|---|---|---|---|---|---|---|---|---|---|---|---|---|---|---|---|---|
| cac | atg | ccc | gcc | gcc | gac | ctc | acc | gcc | atc | aag | gcc | aag | gtc | ggc | aac | 672 |
| His | Met | Pro | Ala | Ala | Asp | Leu | Thr | Ala | Ile | Lys | Ala | Lys | Val | Gly | Asn | |
| | 210 | | | | | 215 | | | | | 220 | | | | | |

| | | | | | | | | | | | | | | | | |
|---|---|---|---|---|---|---|---|---|---|---|---|---|---|---|---|---|
| ggg | agc | acg | tac | tgg | aag | cag | gag | gcc | atc | cac | ggc | gcg | ggc | gag | gcc | 720 |
| Gly | Ser | Thr | Tyr | Trp | Lys | Gln | Glu | Ala | Ile | His | Gly | Ala | Gly | Glu | Ala | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gtc | cag | ccc | agc | gag | tac | ctc | ggc | acc | ggc | gac | gtc | cag | gag | ttc | cgc | 768 |
| Val | Gln | Pro | Ser | Glu | Tyr | Leu | Gly | Thr | Gly | Asp | Val | Gln | Glu | Phe | Arg | |
| | | | | 245 | | | | | 250 | | | | | 255 | | |

-continued

| | | |
|---|---|---|
| tac gcc cgc gac ctc aag cgg gtc ttc cag aac gag aac ctc gcc cac<br>Tyr Ala Arg Asp Leu Lys Arg Val Phe Gln Asn Glu Asn Leu Ala His<br>          260                  265                270 | | 816 |
| ctg aag aac ttc ggc gag gac tgg ggc tac atg gcg agc ggc aag tcc<br>Leu Lys Asn Phe Gly Glu Asp Trp Gly Tyr Met Ala Ser Gly Lys Ser<br>275                  280                  285 | | 864 |
| gcc gtc ttc gtc gac aac cac gac acc gag cgg ggc ggc gac acc ctc<br>Ala Val Phe Val Asp Asn His Asp Thr Glu Arg Gly Gly Asp Thr Leu<br>          290                  295                300 | | 912 |
| aac tac aag aac ggc tcc gcc tac acc ctc gcc ggc gtc ttc atg ctg<br>Asn Tyr Lys Asn Gly Ser Ala Tyr Thr Leu Ala Gly Val Phe Met Leu<br>305                  310                  315                320 | | 960 |
| gcc tgg ccc tac ggc tcc ccg gac gtc cac tcc ggc tac gag ttc acc<br>Ala Trp Pro Tyr Gly Ser Pro Asp Val His Ser Gly Tyr Glu Phe Thr<br>                        325                  330                335 | | 1008 |
| gac cac gac gcc ggc ccg ccc aac ggc ggc acc gtc aac gcc tgc tac<br>Asp His Asp Ala Gly Pro Pro Asn Gly Gly Thr Val Asn Ala Cys Tyr<br>          340                  345                350 | | 1056 |
| agc gac ggc tgg aag tgc cag cac gcc tgg ccc gag ctc tcc tcc atg<br>Ser Asp Gly Trp Lys Cys Gln His Ala Trp Pro Glu Leu Ser Ser Met<br>355                  360                  365 | | 1104 |
| gtc ggc ctg cgc aac acc gcc tcc ggg cag ccc gtc acc aac tgg tgg<br>Val Gly Leu Arg Asn Thr Ala Ser Gly Gln Pro Val Thr Asn Trp Trp<br>          370                  375                380 | | 1152 |
| gac aac ggc ggc gac cag atc gcc ttc ggc cgc ggc gac aag gcg tac<br>Asp Asn Gly Gly Asp Gln Ile Ala Phe Gly Arg Gly Asp Lys Ala Tyr<br>385                  390                  395                400 | | 1200 |
| gtc gcc atc aac cac gag ggc tcc gcg ctg aac cgc acc ttc cag agc<br>Val Ala Ile Asn His Glu Gly Ser Ala Leu Asn Arg Thr Phe Gln Ser<br>                        405                  410                415 | | 1248 |
| ggc ctg ccc ggc ggc gcc tac tgc gac gtc cag agc ggc agg tcc gtc<br>Gly Leu Pro Gly Gly Ala Tyr Cys Asp Val Gln Ser Gly Arg Ser Val<br>          420                  425                430 | | 1296 |
| acg gtc ggc tcc gac ggc acc ttc acc gcc acc gtc gcc gcc ggc acc<br>Thr Val Gly Ser Asp Gly Thr Phe Thr Ala Thr Val Ala Ala Gly Thr<br>435                  440                  445 | | 1344 |
| gcc ctg gcc ctg cac acc ggg gcc cgt acc tgc tcc ggc ggc gga acc<br>Ala Leu Ala Leu His Thr Gly Ala Arg Thr Cys Ser Gly Gly Gly Thr<br>          450                  455                460 | | 1392 |
| ggc ccc ggc acc ggg cag acc tcc gcc tcc ttc cac gtc aac gcc acc<br>Gly Pro Gly Thr Gly Gln Thr Ser Ala Ser Phe His Val Asn Ala Thr<br>465                  470                  475                480 | | 1440 |
| acc gcc tgg ggc gag aac atc tac gtc acc ggt gac cag gcc gcc ctc<br>Thr Ala Trp Gly Glu Asn Ile Tyr Val Thr Gly Asp Gln Ala Ala Leu<br>                        485                  490                495 | | 1488 |
| ggc aac tgg gac ccg gcc cgc gcc ctc aag ctc gac ccg gcc gcc tac<br>Gly Asn Trp Asp Pro Ala Arg Ala Leu Lys Leu Asp Pro Ala Ala Tyr<br>          500                  505                510 | | 1536 |
| ccg gtg tgg aag ctc gac gtg ccg ctg gcc gcc gga acc ccc ttc cag<br>Pro Val Trp Lys Leu Asp Val Pro Leu Ala Ala Gly Thr Pro Phe Gln<br>515                  520                  525 | | 1584 |
| tac aag tac ctg cgc aag gac gcc gcg ggg aag gcc gtc tgg gag tcc<br>Tyr Lys Tyr Leu Arg Lys Asp Ala Ala Gly Lys Ala Val Trp Glu Ser<br>          530                  535                540 | | 1632 |
| ggc gcc aac cgc acg gcg acc gtc ggc acc acc ggc gcc ctc acc ctc<br>Gly Ala Asn Arg Thr Ala Thr Val Gly Thr Thr Gly Ala Leu Thr Leu<br>545                  550                  555                560 | | 1680 |
| aac gac acc tgg cgc ggc<br>Asn Asp Thr Trp Arg Gly<br>          565 | | 1698 |

<210> SEQ ID NO 167
<211> LENGTH: 566
<212> TYPE: PRT
<213> ORGANISM: Streptomyces limosus

<400> SEQUENCE: 167

```
Met Ala Arg Arg Leu Ala Thr Ala Ser Leu Ala Val Leu Ala Ala
1               5                   10                  15

Ala Thr Ala Leu Thr Ala Pro Thr Pro Ala Ala Ala Pro Pro Gly
                20                  25                  30

Ala Lys Asp Val Thr Ala Val Leu Phe Glu Trp Lys Phe Ala Ser Val
                35                  40                  45

Ala Arg Ala Cys Thr Asp Ser Leu Gly Pro Ala Gly Tyr Gly Tyr Val
50                  55                  60

Gln Val Ser Pro Pro Gln Glu His Ile Gln Gly Ser Gln Trp Trp Thr
65                  70                  75                  80

Ser Tyr Gln Pro Val Ser Tyr Lys Ile Ala Gly Arg Leu Gly Asp Arg
                85                  90                  95

Ala Ala Phe Lys Ser Met Val Asp Thr Cys His Ala Ala Gly Val Lys
                100                 105                 110

Val Val Ala Asp Ser Val Ile Asn His Met Ala Gly Ser Gly Thr
                115                 120                 125

Gly Thr Gly Gly Ser Ala Tyr Gln Lys Tyr Asp Tyr Pro Gly Ile Trp
                130                 135                 140

Ser Gly Ala Asp Met Asp Asp Cys Arg Ser Glu Ile Asn Asp Tyr Gly
145                 150                 155                 160

Asn Arg Ala Asn Val Gln Asn Cys Glu Leu Val Gly Leu Ala Asp Leu
                165                 170                 175

Asp Thr Gly Glu Ser Tyr Val Arg Asp Arg Ile Ala Ala Tyr Leu Asn
                180                 185                 190

Asp Leu Leu Ser Leu Gly Val Asp Gly Phe Arg Ile Asp Ala Ala Lys
                195                 200                 205

His Met Pro Ala Ala Asp Leu Thr Ala Ile Lys Ala Lys Val Gly Asn
                210                 215                 220

Gly Ser Thr Tyr Trp Lys Gln Glu Ala Ile His Gly Ala Gly Glu Ala
225                 230                 235                 240

Val Gln Pro Ser Glu Tyr Leu Gly Thr Gly Asp Val Gln Glu Phe Arg
                245                 250                 255

Tyr Ala Arg Asp Leu Lys Arg Val Phe Gln Asn Glu Asn Leu Ala His
                260                 265                 270

Leu Lys Asn Phe Gly Glu Asp Trp Gly Tyr Met Ala Ser Gly Lys Ser
                275                 280                 285

Ala Val Phe Val Asp Asn His Asp Thr Glu Arg Gly Gly Asp Thr Leu
                290                 295                 300

Asn Tyr Lys Asn Gly Ser Ala Tyr Thr Leu Ala Gly Val Phe Met Leu
305                 310                 315                 320

Ala Trp Pro Tyr Gly Ser Pro Asp Val His Ser Gly Tyr Glu Phe Thr
                325                 330                 335

Asp His Asp Ala Gly Pro Pro Asn Gly Gly Thr Val Asn Ala Cys Tyr
                340                 345                 350

Ser Asp Gly Trp Lys Cys Gln His Ala Trp Pro Glu Leu Ser Ser Met
                355                 360                 365

Val Gly Leu Arg Asn Thr Ala Ser Gly Gln Pro Val Thr Asn Trp Trp
                370                 375                 380
```

```
Asp Asn Gly Gly Asp Gln Ile Ala Phe Gly Arg Gly Asp Lys Ala Tyr
385                 390                 395                 400

Val Ala Ile Asn His Glu Gly Ser Ala Leu Asn Arg Thr Phe Gln Ser
                405                 410                 415

Gly Leu Pro Gly Gly Ala Tyr Cys Asp Val Gln Ser Gly Arg Ser Val
            420                 425                 430

Thr Val Gly Ser Asp Gly Thr Phe Thr Ala Thr Val Ala Ala Gly Thr
        435                 440                 445

Ala Leu Ala Leu His Thr Gly Ala Arg Thr Cys Ser Gly Gly Gly Thr
    450                 455                 460

Gly Pro Gly Thr Gly Gln Thr Ser Ala Ser Phe His Val Asn Ala Thr
465                 470                 475                 480

Thr Ala Trp Gly Glu Asn Ile Tyr Val Thr Gly Asp Gln Ala Ala Leu
                485                 490                 495

Gly Asn Trp Asp Pro Ala Arg Ala Leu Lys Leu Asp Pro Ala Ala Tyr
            500                 505                 510

Pro Val Trp Lys Leu Asp Val Pro Leu Ala Ala Gly Thr Pro Phe Gln
        515                 520                 525

Tyr Lys Tyr Leu Arg Lys Asp Ala Ala Gly Lys Ala Val Trp Glu Ser
    530                 535                 540

Gly Ala Asn Arg Thr Ala Thr Val Gly Thr Thr Gly Ala Leu Thr Leu
545                 550                 555                 560

Asn Asp Thr Trp Arg Gly
                565

<210> SEQ ID NO 168
<211> LENGTH: 1842
<212> TYPE: DNA
<213> ORGANISM: Subulispora provurta
<220> FEATURE:
<221> NAME/KEY: CDS
<222> LOCATION: (1)..(1842)
<220> FEATURE:
<221> NAME/KEY: sig_peptide
<222> LOCATION: (1)..(63)
<220> FEATURE:
<221> NAME/KEY: misc_feature
<222> LOCATION: (64)..(1461)
<223> OTHER INFORMATION: Catalytic domain
<220> FEATURE:
<221> NAME/KEY: misc_feature
<222> LOCATION: (1462)..(1536)
<223> OTHER INFORMATION: Linker
<220> FEATURE:
<221> NAME/KEY: misc_feature
<222> LOCATION: (1537)..(1842)
<223> OTHER INFORMATION: CBM

<400> SEQUENCE: 168 atg aag acg aac gcg ctg ttg ctg ccc ggc ctc tgg gct gcc act gcc    48
Met Lys Thr Asn Ala Leu Leu Leu Pro Gly Leu Trp Ala Ala Thr Ala
1               5                   10                  15 caa gcc ttg tct gcc acc gaa tgg ggg agt cag tcc atc tac cag gta    96
Gln Ala Leu Ser Ala Thr Glu Trp Gly Ser Gln Ser Ile Tyr Gln Val
            20                  25                  30 ttg acg gat cgc ttt gcc cgc act gat ggg tct act acc gcc tcc tgt   144
Leu Thr Asp Arg Phe Ala Arg Thr Asp Gly Ser Thr Thr Ala Ser Cys
        35                  40                  45 gat gtg aac aag tac tgc ggc ggc acc tgg cag ggc ata atc gac aag   192
Asp Val Asn Lys Tyr Cys Gly Gly Thr Trp Gln Gly Ile Ile Asp Lys
    50                  55                  60 ctg gac tac atc cag ggc atg ggt ttc act gcg atc tgg att tcg cct   240
Leu Asp Tyr Ile Gln Gly Met Gly Phe Thr Ala Ile Trp Ile Ser Pro
```

```
                65                  70                  75                  80
atc gtc gac aac atc gac gcc gat act gtt gat ggc acc tct tat cac      288
Ile Val Asp Asn Ile Asp Ala Asp Thr Val Asp Gly Thr Ser Tyr His
                    85                  90                  95 ggt tac tgg gcc cag gac atc acc tca gtg aac tcg gcg ttc ggc acg      336
Gly Tyr Trp Ala Gln Asp Ile Thr Ser Val Asn Ser Ala Phe Gly Thr
                    100                 105                 110 gag cag gac ctc atc aac ctc tca gca gct ctg cac gac agg ggc atg      384
Glu Gln Asp Leu Ile Asn Leu Ser Ala Ala Leu His Asp Arg Gly Met
                    115                 120                 125 tat ctg atg gta gac gtg gta aac aac cac atg gga tac aac ggc tgc      432
Tyr Leu Met Val Asp Val Val Asn Asn His Met Gly Tyr Asn Gly Cys
                    130                 135                 140 ggc gat tgt gtt gac tac agc ata tac acg cca ttc aac cag cag tcc      480
Gly Asp Cys Val Asp Tyr Ser Ile Tyr Thr Pro Phe Asn Gln Gln Ser
145                 150                 155                 160 tac tac cac ccg tac tgc gcc act gat tac agc aac ctg acc tcc atc      528
Tyr Tyr His Pro Tyr Cys Ala Thr Asp Tyr Ser Asn Leu Thr Ser Ile
                    165                 170                 175 cag gtg tgc tgg gag ggt gac aac att gtc agt ctc ccc gac ctg agg      576
Gln Val Cys Trp Glu Gly Asp Asn Ile Val Ser Leu Pro Asp Leu Arg
                    180                 185                 190 aca gag gat gac gat gtc cgc acc atg tgg tac gac tgg atc acg ccg      624
Thr Glu Asp Asp Asp Val Arg Thr Met Trp Tyr Asp Trp Ile Thr Pro
                    195                 200                 205 ttg gta acc aag tac tcg atc gat gga ctg cgc atg gac agc gcc gag      672
Leu Val Thr Lys Tyr Ser Ile Asp Gly Leu Arg Met Asp Ser Ala Glu
                    210                 215                 220 cat gtc gag aag agc ttc tgg cct ggt tgg gta tcc gcc tcg gga gta      720
His Val Glu Lys Ser Phe Trp Pro Gly Trp Val Ser Ala Ser Gly Val
225                 230                 235                 240 tac aac ata gga gag gtt gat gag ggc gac ccc acc atc ttc cca gac      768
Tyr Asn Ile Gly Glu Val Asp Glu Gly Asp Pro Thr Ile Phe Pro Asp
                    245                 250                 255 tgg ctg aac tac atc gac gga acc ttg aac tat cca gct tac tac tgg      816
Trp Leu Asn Tyr Ile Asp Gly Thr Leu Asn Tyr Pro Ala Tyr Tyr Trp
                    260                 265                 270 atc act caa gct ttc cag tca act tct ggt tct atc agc aac ctg gtt      864
Ile Thr Gln Ala Phe Gln Ser Thr Ser Gly Ser Ile Ser Asn Leu Val
                    275                 280                 285 aat gga atc aac caa atg aag ggc tca atg aaa acc agc acc ctc ggg      912
Asn Gly Ile Asn Gln Met Lys Gly Ser Met Lys Thr Ser Thr Leu Gly
                    290                 295                 300 tcg ttc ctt gag aat cac gac cag cca cga ttc cct tct ctg act agt      960
Ser Phe Leu Glu Asn His Asp Gln Pro Arg Phe Pro Ser Leu Thr Ser
305                 310                 315                 320 gat gcg gat ttg gcg aag aac gct atc gct ttt gct atg ctt gct gat      1008
Asp Ala Asp Leu Ala Lys Asn Ala Ile Ala Phe Ala Met Leu Ala Asp
                    325                 330                 335 ggc gtc cca atc gtc tac tat ggt caa gag cag gcc tac tcg ggt ggt      1056
Gly Val Pro Ile Val Tyr Tyr Gly Gln Glu Gln Ala Tyr Ser Gly Gly
                    340                 345                 350 ggc gtg cct aat gac cgt gag cca ctg tgg aca tcg gga tac agc acc      1104
Gly Val Pro Asn Asp Arg Glu Pro Leu Trp Thr Ser Gly Tyr Ser Thr
                    355                 360                 365 aca tcg gca ggt tac acg ttc atc acg acc atc aac aaa atc cgc cgc      1152
Thr Ser Ala Gly Tyr Thr Phe Ile Thr Thr Ile Asn Lys Ile Arg Arg
                    370                 375                 380 ctg gct ctc acc cag gac agt gcc tac gta gca tac cag acc tac ccg      1200
Leu Ala Leu Thr Gln Asp Ser Ala Tyr Val Ala Tyr Gln Thr Tyr Pro
```

```
                385          390          395          400
atc tat tcg gat tct cac gtc atc gcc atg aag aag agc agc gtc gtc      1248
Ile Tyr Ser Asp Ser His Val Ile Ala Met Lys Lys Ser Ser Val Val
            405                  410                  415 tcc gtc tat agc aac att ggc tcc agc ggc agc acc tat tcg atc acc      1296
Ser Val Tyr Ser Asn Ile Gly Ser Ser Gly Ser Thr Tyr Ser Ile Thr
            420                  425                  430 cta cct gcc ggc aca ttc act ggg agt gta gcg ctc aca gac gtg gtg      1344
Leu Pro Ala Gly Thr Phe Thr Gly Ser Val Ala Leu Thr Asp Val Val
            435                  440                  445 agc tgc cag acg tac acg gcg agc tct act ggc agc ctc acc ttc acc      1392
Ser Cys Gln Thr Tyr Thr Ala Ser Ser Thr Gly Ser Leu Thr Phe Thr
            450                  455                  460 ttc gga caa gtt ccc tcc gtc ttc tac ccg acg gca agc ctg tcc ggc      1440
Phe Gly Gln Val Pro Ser Val Phe Tyr Pro Thr Ala Ser Leu Ser Gly
465                  470                  475                  480 agc ggg ctc tgc tct agc tcc gga ggc agc ggt acc act acc acg acc      1488
Ser Gly Leu Cys Ser Ser Ser Gly Gly Ser Gly Thr Thr Thr Thr Thr
                485                  490                  495 act acc agc act gca ggc aca tcg cca act tcg aca gcg tgc tcc tcg      1536
Thr Thr Ser Thr Ala Gly Thr Ser Pro Thr Ser Thr Ala Cys Ser Ser
            500                  505                  510 gtc ccc gta acg ttc cgc gaa acg gtc aca act acg gta gga cag aca      1584
Val Pro Val Thr Phe Arg Glu Thr Val Thr Thr Thr Val Gly Gln Thr
            515                  520                  525 atc aag ata tct ggc gac gtc tcc gcc ctt gga aac tgg gat acg gac      1632
Ile Lys Ile Ser Gly Asp Val Ser Ala Leu Gly Asn Trp Asp Thr Asp
530                  535                  540 gac gcg gtg gcc ctg agc gcc gcg agc tac acg tcc agc aac ccc gtg      1680
Asp Ala Val Ala Leu Ser Ala Ala Ser Tyr Thr Ser Ser Asn Pro Val
545                  550                  555                  560 tgg gac gtg acc gtc agc ttc gcc ccc ggc acc gtc atc gag tac aag      1728
Trp Asp Val Thr Val Ser Phe Ala Pro Gly Thr Val Ile Glu Tyr Lys
                565                  570                  575 tac atc aac gtg gcg agc ggc ggc gcc gtg acc tgg gag gcc gac ccg      1776
Tyr Ile Asn Val Ala Ser Gly Gly Ala Val Thr Trp Glu Ala Asp Pro
            580                  585                  590 aac cac acc tac acg gtg cct tcg tcc tgc gcc acc gcc gtg gtc tcc      1824
Asn His Thr Tyr Thr Val Pro Ser Ser Cys Ala Thr Ala Val Val Ser
            595                  600                  605 aac acc tgg cag acg tga                                              1842
Asn Thr Trp Gln Thr
        610

<210> SEQ ID NO 169
<211> LENGTH: 613
<212> TYPE: PRT
<213> ORGANISM: Subulispora provurta

<400> SEQUENCE: 169

Met Lys Thr Asn Ala Leu Leu Leu Pro Gly Leu Trp Ala Ala Thr Ala
1               5                   10                  15

Gln Ala Leu Ser Ala Thr Glu Trp Gly Ser Gln Ser Ile Tyr Gln Val
            20                  25                  30

Leu Thr Asp Arg Phe Ala Arg Thr Asp Gly Ser Thr Thr Ala Ser Cys
        35                  40                  45

Asp Val Asn Lys Tyr Cys Gly Gly Thr Trp Gln Gly Ile Ile Asp Lys
    50                  55                  60

Leu Asp Tyr Ile Gln Gly Met Gly Phe Thr Ala Ile Trp Ile Ser Pro
65                  70                  75                  80
```

```
Ile Val Asp Asn Ile Asp Ala Asp Thr Val Asp Gly Thr Ser Tyr His
                85                  90                  95

Gly Tyr Trp Ala Gln Asp Ile Thr Ser Val Asn Ser Ala Phe Gly Thr
            100                 105                 110

Glu Gln Asp Leu Ile Asn Leu Ser Ala Ala Leu His Asp Arg Gly Met
            115                 120                 125

Tyr Leu Met Val Asp Val Val Asn Asn His Met Gly Tyr Asn Gly Cys
        130                 135                 140

Gly Asp Cys Val Asp Tyr Ser Ile Tyr Thr Pro Phe Asn Gln Gln Ser
145                 150                 155                 160

Tyr Tyr His Pro Tyr Cys Ala Thr Asp Tyr Ser Asn Leu Thr Ser Ile
                165                 170                 175

Gln Val Cys Trp Glu Gly Asp Asn Ile Val Ser Leu Pro Asp Leu Arg
            180                 185                 190

Thr Glu Asp Asp Asp Val Arg Thr Met Trp Tyr Asp Trp Ile Thr Pro
            195                 200                 205

Leu Val Thr Lys Tyr Ser Ile Asp Gly Leu Arg Met Asp Ser Ala Glu
        210                 215                 220

His Val Glu Lys Ser Phe Trp Pro Gly Trp Val Ser Ala Ser Gly Val
225                 230                 235                 240

Tyr Asn Ile Gly Glu Val Asp Glu Gly Asp Pro Thr Ile Phe Pro Asp
                245                 250                 255

Trp Leu Asn Tyr Ile Asp Gly Thr Leu Asn Tyr Pro Ala Tyr Tyr Trp
            260                 265                 270

Ile Thr Gln Ala Phe Gln Ser Thr Ser Gly Ser Ile Ser Asn Leu Val
        275                 280                 285

Asn Gly Ile Asn Gln Met Lys Gly Ser Met Lys Thr Ser Thr Leu Gly
        290                 295                 300

Ser Phe Leu Glu Asn His Asp Gln Pro Arg Phe Pro Ser Leu Thr Ser
305                 310                 315                 320

Asp Ala Asp Leu Ala Lys Asn Ala Ile Ala Phe Ala Met Leu Ala Asp
                325                 330                 335

Gly Val Pro Ile Val Tyr Tyr Gly Gln Glu Gln Ala Tyr Ser Gly Gly
            340                 345                 350

Gly Val Pro Asn Asp Arg Glu Pro Leu Trp Thr Ser Gly Tyr Ser Thr
        355                 360                 365

Thr Ser Ala Gly Tyr Thr Phe Ile Thr Thr Ile Asn Lys Ile Arg Arg
        370                 375                 380

Leu Ala Leu Thr Gln Asp Ser Ala Tyr Val Ala Tyr Gln Thr Tyr Pro
385                 390                 395                 400

Ile Tyr Ser Asp Ser His Val Ile Ala Met Lys Lys Ser Ser Val Val
                405                 410                 415

Ser Val Tyr Ser Asn Ile Gly Ser Ser Gly Ser Thr Tyr Ser Ile Thr
            420                 425                 430

Leu Pro Ala Gly Thr Phe Thr Gly Ser Val Ala Leu Thr Asp Val Val
        435                 440                 445

Ser Cys Gln Thr Tyr Thr Ala Ser Ser Thr Gly Ser Leu Thr Phe Thr
        450                 455                 460

Phe Gly Gln Val Pro Ser Val Phe Tyr Pro Thr Ala Ser Leu Ser Gly
465                 470                 475                 480

Ser Gly Leu Cys Ser Ser Ser Gly Gly Ser Gly Thr Thr Thr Thr Thr
                485                 490                 495

Thr Thr Ser Thr Ala Gly Thr Ser Pro Thr Ser Thr Ala Cys Ser Ser
```

|  |  |  | 500 |  |  |  |  | 505 |  |  |  |  | 510 |  |  |
|---|---|---|---|---|---|---|---|---|---|---|---|---|---|---|---|

Val Pro Val Thr Phe Arg Glu Thr Val Thr Thr Val Gly Gln Thr
    515               520              525

Ile Lys Ile Ser Gly Asp Val Ser Ala Leu Gly Asn Trp Asp Thr Asp
530                 535              540

Asp Ala Val Ala Leu Ser Ala Ala Ser Tyr Thr Ser Ser Asn Pro Val
545                550             555              560

Trp Asp Val Thr Val Ser Phe Ala Pro Gly Thr Val Ile Glu Tyr Lys
               565              570              575

Tyr Ile Asn Val Ala Ser Gly Gly Ala Val Thr Trp Glu Ala Asp Pro
        580                585              590

Asn His Thr Tyr Thr Val Pro Ser Ser Cys Ala Thr Ala Val Val Ser
        595                600              605

Asn Thr Trp Gln Thr
    610

```
<210> SEQ ID NO 170
<211> LENGTH: 1389
<212> TYPE: DNA
<213> ORGANISM: Syncephalastrum racemosum
<220> FEATURE:
<221> NAME/KEY: CDS
<222> LOCATION: (1)..(1389)
<220> FEATURE:
<221> NAME/KEY: sig_peptide
<222> LOCATION: (1)..(60)
<220> FEATURE:
<221> NAME/KEY: misc_feature
<222> LOCATION: (61)..(1389)
<223> OTHER INFORMATION: Catalytic domain

<400> SEQUENCE: 170
```

| atg aag gtc ttt atg aac gtt ctc tgt ggg gtc ctt ttc ctg tct ctt | 48 |
|---|---|
| Met Lys Val Phe Met Asn Val Leu Cys Gly Val Leu Phe Leu Ser Leu | |
| 1                5                    10              15 | |
| ttg act gaa tcc aaa cct att gtg aaa aaa cgt gcg act gct agt gac | 96 |
| Leu Thr Glu Ser Lys Pro Ile Val Lys Lys Arg Ala Thr Ala Ser Asp | |
|           20                   25                   30 | |
| tgg gaa aat cga gtt atc tac caa ttg ttg aca gat cga ttt gct aaa | 144 |
| Trp Glu Asn Arg Val Ile Tyr Gln Leu Leu Thr Asp Arg Phe Ala Lys | |
|                35                   40              45 | |
| agc tct gac gac aca aac ggt tgc tcc aac cta ggc aat tat tgt ggc | 192 |
| Ser Ser Asp Asp Thr Asn Gly Cys Ser Asn Leu Gly Asn Tyr Cys Gly | |
|  50                    55                   60 | |
| ggg acg ttt caa ggg att atc aat cat cta gac tat att gcc ggt atg | 240 |
| Gly Thr Phe Gln Gly Ile Ile Asn His Leu Asp Tyr Ile Ala Gly Met | |
| 65                70                    75                    80 | |
| gga ttc gat gcg atc tgg ata tcg cca att cct gaa aac tcg gat ggg | 288 |
| Gly Phe Asp Ala Ile Trp Ile Ser Pro Ile Pro Glu Asn Ser Asp Gly | |
|                85                   90              95 | |
| ggg tat cac ggt tac tgg gct acc aac ttt tct gcc atc aac tca cat | 336 |
| Gly Tyr His Gly Tyr Trp Ala Thr Asn Phe Ser Ala Ile Asn Ser His | |
|               100               105              110 | |
| ttt ggg tcg tct aat gat ttg aag aaa ttg gtg tca gca gct cat gac | 384 |
| Phe Gly Ser Ser Asn Asp Leu Lys Lys Leu Val Ser Ala Ala His Asp | |
|          115                120              125 | |
| aag ggc atg tat gtt atg ctt gac gtg gtt gct aac cac gtt ggc ata | 432 |
| Lys Gly Met Tyr Val Met Leu Asp Val Val Ala Asn His Val Gly Ile | |
| 130                135              140 | |
| cct tcc tcc agt ggc caa tac tcg gga tac acg ttt gat caa agc tct | 480 |
| Pro Ser Ser Ser Gly Gln Tyr Ser Gly Tyr Thr Phe Asp Gln Ser Ser | |
| 145                150              155              160 | |

```
cag tat cat agt tct tgt gat att aac tat gac aac caa aac tct att      528
Gln Tyr His Ser Ser Cys Asp Ile Asn Tyr Asp Asn Gln Asn Ser Ile
            165                 170                 175 gaa caa tgc tgg atc tct ggc tta cct gat ctt aac acc gaa gat tca      576
Glu Gln Cys Trp Ile Ser Gly Leu Pro Asp Leu Asn Thr Glu Asp Ser
        180                 185                 190 gcg gta gtc agc aag cta aac tcg att gtg tca aac tgg gta tcc gaa      624
Ala Val Val Ser Lys Leu Asn Ser Ile Val Ser Asn Trp Val Ser Glu
    195                 200                 205 tat gac ttt gat ggg ctt cgt att gat act gtc aag cac att cgc aag      672
Tyr Asp Phe Asp Gly Leu Arg Ile Asp Thr Val Lys His Ile Arg Lys
210                 215                 220 gat ttt tgg gat ggc tat gta tct gct gca ggt gta ttt gcc act ggg      720
Asp Phe Trp Asp Gly Tyr Val Ser Ala Ala Gly Val Phe Ala Thr Gly
225                 230                 235                 240 gaa gtc ttg aac ggt gct gtt tct tat gtt gct cca tac caa caa cat      768
Glu Val Leu Asn Gly Ala Val Ser Tyr Val Ala Pro Tyr Gln Gln His
                245                 250                 255 gtt ccc tct tta ctc aac tac cca ctg tat ttc ccc gtc aat gat gtg      816
Val Pro Ser Leu Leu Asn Tyr Pro Leu Tyr Phe Pro Val Asn Asp Val
            260                 265                 270 ttc acg aag gct tct acc atg agt cgt ttg gga tca ggc tat gct gat      864
Phe Thr Lys Ala Ser Thr Met Ser Arg Leu Gly Ser Gly Tyr Ala Asp
        275                 280                 285 atc cag tct ggc agc ttt aca aac aga aac cat ctg gtt aac ttt atc      912
Ile Gln Ser Gly Ser Phe Thr Asn Arg Asn His Leu Val Asn Phe Ile
    290                 295                 300 gac aac cat gac aat cct cgt ttg tta tcc aag tct gat cag gtc ttg      960
Asp Asn His Asp Asn Pro Arg Leu Leu Ser Lys Ser Asp Gln Val Leu
305                 310                 315                 320 gtg aag aat gct ctt aca tac acc atg atg att gaa gga atc cca gcc     1008
Val Lys Asn Ala Leu Thr Tyr Thr Met Met Ile Glu Gly Ile Pro Ala
                325                 330                 335 atg tac tat ggt acc gag caa tca ttc aat gga ggc tct gac cct gcc     1056
Met Tyr Tyr Gly Thr Glu Gln Ser Phe Asn Gly Gly Ser Asp Pro Ala
            340                 345                 350 aac aga gag gtc tta tgg acc acg aat tat tcg acc aca tcc gac atg     1104
Asn Arg Glu Val Leu Trp Thr Thr Asn Tyr Ser Thr Thr Ser Asp Met
        355                 360                 365 tac aag ttt gtc act tta ctc gtc aaa aca cgc aag agc tcg gga aac     1152
Tyr Lys Phe Val Thr Leu Leu Val Lys Thr Arg Lys Ser Ser Gly Asn
    370                 375                 380 acg gtt act aca ggc att gac cag acc aac aat gtt tat gtg ttt caa     1200
Thr Val Thr Thr Gly Ile Asp Gln Thr Asn Asn Val Tyr Val Phe Gln
385                 390                 395                 400 aga gac aag tat ctg gtt gtt gtg aac aat tac ggc tca gga tcc acc     1248
Arg Asp Lys Tyr Leu Val Val Val Asn Asn Tyr Gly Ser Gly Ser Thr
                405                 410                 415 aat tcg atc act gta aag gct ggt tca ttc tcc aat ggt gtt acc ctt     1296
Asn Ser Ile Thr Val Lys Ala Gly Ser Phe Ser Asn Gly Val Thr Leu
            420                 425                 430 gtg gat ata ttc tcg aat aaa aca gtg act gtg tca aac gga tcg atc     1344
Val Asp Ile Phe Ser Asn Lys Thr Val Thr Val Ser Asn Gly Ser Ile
        435                 440                 445 acc ttc cag ctt caa aat ggt aat cct gct gta ttc caa agc aaa         1389
Thr Phe Gln Leu Gln Asn Gly Asn Pro Ala Val Phe Gln Ser Lys
    450                 455                 460

<210> SEQ ID NO 171
<211> LENGTH: 463
```

<212> TYPE: PRT
<213> ORGANISM: Syncephalastrum racemosum

<400> SEQUENCE: 171

```
Met Lys Val Phe Met Asn Val Leu Cys Gly Val Leu Phe Leu Ser Leu
1               5                   10                  15

Leu Thr Glu Ser Lys Pro Ile Val Lys Lys Arg Ala Thr Ala Ser Asp
            20                  25                  30

Trp Glu Asn Arg Val Ile Tyr Gln Leu Leu Thr Asp Arg Phe Ala Lys
        35                  40                  45

Ser Ser Asp Asp Thr Asn Gly Cys Ser Asn Leu Gly Asn Tyr Cys Gly
    50                  55                  60

Gly Thr Phe Gln Gly Ile Ile Asn His Leu Asp Tyr Ile Ala Gly Met
65                  70                  75                  80

Gly Phe Asp Ala Ile Trp Ile Ser Pro Ile Pro Glu Asn Ser Asp Gly
                85                  90                  95

Gly Tyr His Gly Tyr Trp Ala Thr Asn Phe Ser Ala Ile Asn Ser His
            100                 105                 110

Phe Gly Ser Ser Asn Asp Leu Lys Lys Leu Val Ser Ala Ala His Asp
        115                 120                 125

Lys Gly Met Tyr Val Met Leu Asp Val Val Ala Asn His Val Gly Ile
    130                 135                 140

Pro Ser Ser Ser Gly Gln Tyr Ser Gly Tyr Thr Phe Asp Gln Ser Ser
145                 150                 155                 160

Gln Tyr His Ser Ser Cys Asp Ile Asn Tyr Asp Asn Gln Asn Ser Ile
                165                 170                 175

Glu Gln Cys Trp Ile Ser Gly Leu Pro Asp Leu Asn Thr Glu Asp Ser
            180                 185                 190

Ala Val Val Ser Lys Leu Asn Ser Ile Val Ser Asn Trp Val Ser Glu
        195                 200                 205

Tyr Asp Phe Asp Gly Leu Arg Ile Asp Thr Val Lys His Ile Arg Lys
    210                 215                 220

Asp Phe Trp Asp Gly Tyr Val Ser Ala Ala Gly Val Phe Ala Thr Gly
225                 230                 235                 240

Glu Val Leu Asn Gly Ala Val Ser Tyr Val Ala Pro Tyr Gln Gln His
                245                 250                 255

Val Pro Ser Leu Leu Asn Tyr Pro Leu Tyr Phe Pro Val Asn Asp Val
            260                 265                 270

Phe Thr Lys Ala Ser Thr Met Ser Arg Leu Gly Ser Gly Tyr Ala Asp
        275                 280                 285

Ile Gln Ser Gly Ser Phe Thr Asn Arg Asn His Leu Val Asn Phe Ile
    290                 295                 300

Asp Asn His Asp Asn Pro Arg Leu Leu Ser Lys Ser Asp Gln Val Leu
305                 310                 315                 320

Val Lys Asn Ala Leu Thr Tyr Thr Met Met Ile Glu Gly Ile Pro Ala
                325                 330                 335

Met Tyr Tyr Gly Thr Glu Gln Ser Phe Asn Gly Gly Ser Asp Pro Ala
            340                 345                 350

Asn Arg Glu Val Leu Trp Thr Thr Asn Tyr Ser Thr Thr Ser Asp Met
        355                 360                 365

Tyr Lys Phe Val Thr Leu Leu Val Lys Thr Arg Lys Ser Ser Gly Asn
    370                 375                 380

Thr Val Thr Thr Gly Ile Asp Gln Thr Asn Asn Val Tyr Val Phe Gln
385                 390                 395                 400
```

-continued

```
Arg Asp Lys Tyr Leu Val Val Asn Asn Tyr Gly Ser Gly Ser Thr
                405                 410                 415
Asn Ser Ile Thr Val Lys Ala Gly Ser Phe Ser Asn Gly Val Thr Leu
            420                 425                 430
Val Asp Ile Phe Ser Asn Lys Thr Val Thr Val Ser Asn Gly Ser Ile
            435                 440                 445
Thr Phe Gln Leu Gln Asn Gly Asn Pro Ala Val Phe Gln Ser Lys
450                 455                 460

<210> SEQ ID NO 172
<211> LENGTH: 1764
<212> TYPE: DNA
<213> ORGANISM: Trametes corrugata
<220> FEATURE:
<221> NAME/KEY: CDS
<222> LOCATION: (1)..(1764)
<220> FEATURE:
<221> NAME/KEY: sig_peptide
<222> LOCATION: (1)..(60)
<220> FEATURE:
<221> NAME/KEY: misc_feature
<222> LOCATION: (61)..(1431)
<223> OTHER INFORMATION: Catalytic domain
<220> FEATURE:
<221> NAME/KEY: misc_feature
<222> LOCATION: (1432)..(1473)
<223> OTHER INFORMATION: Linker
<220> FEATURE:
<221> NAME/KEY: misc_feature
<222> LOCATION: (1474)..(1764)
<223> OTHER INFORMATION: CBM

<400> SEQUENCE: 172 atg ttg ttc ctt tct acg ctc ctc tcg ttc ttc ttt tac ttc agc tcc     48
Met Leu Phe Leu Ser Thr Leu Leu Ser Phe Phe Phe Tyr Phe Ser Ser
1               5                   10                  15 att gtg aca gcg gcg gat acg agt gca tgg aag tcc cgc agc atc tac     96
Ile Val Thr Ala Ala Asp Thr Ser Ala Trp Lys Ser Arg Ser Ile Tyr
                20                  25                  30 ttc gtt ctg acc gat cgt gtt gct cga agc agc agc gac acc ggc ggt    144
Phe Val Leu Thr Asp Arg Val Ala Arg Ser Ser Ser Asp Thr Gly Gly
            35                  40                  45 tcc tct tgc agc aac ctg ggc aat tac tgt gga gga act ttc aaa ggt    192
Ser Ser Cys Ser Asn Leu Gly Asn Tyr Cys Gly Gly Thr Phe Lys Gly
        50                  55                  60 ctc gaa tct aag ctg gat tac atc caa ggc ttg ggc ttt gac gct atc    240
Leu Glu Ser Lys Leu Asp Tyr Ile Gln Gly Leu Gly Phe Asp Ala Ile
65                  70                  75                  80 tgg atc acg cct gtc gtt gct aac agt gct ggt ggc tac cat ggc tat    288
Trp Ile Thr Pro Val Val Ala Asn Ser Ala Gly Gly Tyr His Gly Tyr
                85                  90                  95 tgg gca caa gac ttg tat tct gtc aac tcg aat tat ggt act gca gac    336
Trp Ala Gln Asp Leu Tyr Ser Val Asn Ser Asn Tyr Gly Thr Ala Asp
            100                 105                 110 gac cta aag agc ctg gtc agc tct gct cat gcg aag ggc ata tat gtg    384
Asp Leu Lys Ser Leu Val Ser Ser Ala His Ala Lys Gly Ile Tyr Val
        115                 120                 125 atg gtc gat gtc gta gcc aat cat atg ggt aac ggt gca att gcc gat    432
Met Val Asp Val Val Ala Asn His Met Gly Asn Gly Ala Ile Ala Asp
130                 135                 140 aac cgc cct gag cct ttg aac cag gct tca tcc tac cac cca gcc tgc    480
Asn Arg Pro Glu Pro Leu Asn Gln Ala Ser Ser Tyr His Pro Ala Cys
145                 150                 155                 160 gac atc aac tac gat aac cag acc agc atc gag cag tgc agc atc ggc    528
Asp Ile Asn Tyr Asp Asn Gln Thr Ser Ile Glu Gln Cys Ser Ile Gly
```

-continued

|  | 165 | 170 | 175 |  |
|---|---|---|---|---|

```
ggt ctt gct gat ctt aac act gag agt acc gag gtt cgc act gtt ctc    576
Gly Leu Ala Asp Leu Asn Thr Glu Ser Thr Glu Val Arg Thr Val Leu
            180             185             190 aac acc tgg gtt tca tgg ctc gtc gac gag tac agc ttc gac gga gta    624
Asn Thr Trp Val Ser Trp Leu Val Asp Glu Tyr Ser Phe Asp Gly Val
        195             200             205 cgt atc gac aca gtc aag cac gtt caa aag gac ttc tgg cca gac ttc    672
Arg Ile Asp Thr Val Lys His Val Gln Lys Asp Phe Trp Pro Asp Phe
    210             215             220 gtg tct tcc ata ggc gaa tac agc atc ggt gag gtg ttt gac ggc aac    720
Val Ser Ser Ile Gly Glu Tyr Ser Ile Gly Glu Val Phe Asp Gly Asn
225             230             235             240 cct cca tac ctc gct gag tat gcc aag ctc atg cct ggg gtt cta aac    768
Pro Pro Tyr Leu Ala Glu Tyr Ala Lys Leu Met Pro Gly Val Leu Asn
            245             250             255 tat gca gtc tac tac ccc atg aat gcc ttc tac cag caa acg ggc tca    816
Tyr Ala Val Tyr Tyr Pro Met Asn Ala Phe Tyr Gln Gln Thr Gly Ser
        260             265             270 tct cag gca ctg gtc gac atg atg aac acg att agc agc aca ttc cca    864
Ser Gln Ala Leu Val Asp Met Met Asn Thr Ile Ser Ser Thr Phe Pro
    275             280             285 gac ccc tca gca ctc ggc acg ttc ctc gac aac cac gac aac ccg cgc    912
Asp Pro Ser Ala Leu Gly Thr Phe Leu Asp Asn His Asp Asn Pro Arg
290             295             300 tgg cta aac gtg aag aac gac cag aca ctc ctg aag aac gca cta gcc    960
Trp Leu Asn Val Lys Asn Asp Gln Thr Leu Leu Lys Asn Ala Leu Ala
305             310             315             320 tac gtc att cta gcc cga ggc att ccc atc cta tac tac ggc acc gag   1008
Tyr Val Ile Leu Ala Arg Gly Ile Pro Ile Leu Tyr Tyr Gly Thr Glu
            325             330             335 caa ggt tac tcc gga ggc gcc gac cca gca aac cgc gaa gat ctt tgg   1056
Gln Gly Tyr Ser Gly Gly Ala Asp Pro Ala Asn Arg Glu Asp Leu Trp
        340             345             350 cgc agc agc ttc aat aca aac gcg gac ctc tac caa tcc atc aaa aag   1104
Arg Ser Ser Phe Asn Thr Asn Ala Asp Leu Tyr Gln Ser Ile Lys Lys
    355             360             365 ctc acc gca gcc cga aaa gcc gcc ggc ggc ctc gcc ggc aac gac cac   1152
Leu Thr Ala Ala Arg Lys Ala Ala Gly Gly Leu Ala Gly Asn Asp His
370             375             380 acg cat ctc tac gtc gcc gac acg gca tat gcc tgg agc cgg gca aac   1200
Thr His Leu Tyr Val Ala Asp Thr Ala Tyr Ala Trp Ser Arg Ala Asn
385             390             395             400 ggc gcc ctc atc gtg ctc acc acc aac gcc ggc agc agc tcc aac gcg   1248
Gly Ala Leu Ile Val Leu Thr Thr Asn Ala Gly Ser Ser Ser Asn Ala
            405             410             415 caa cac tgc ttc aac acg cag atg gca aac ggg aaa tgg acg aac acg   1296
Gln His Cys Phe Asn Thr Gln Met Ala Asn Gly Lys Trp Thr Asn Thr
        420             425             430 tat ggt gat ggc gca acg gtg acc gcg gat tcc agc ggt aat atc tgc   1344
Tyr Gly Asp Gly Ala Thr Val Thr Ala Asp Ser Ser Gly Asn Ile Cys
    435             440             445 gtc acc gtt agc aac ggc gag cct gtt gtc ctc gtc gcc agc gca tca   1392
Val Thr Val Ser Asn Gly Glu Pro Val Val Leu Val Ala Ser Ala Ser
450             455             460 aca acg ggg gtt acg ccc act aca gct aca acg ctg cgc act acc aca   1440
Thr Thr Gly Val Thr Pro Thr Thr Ala Thr Thr Leu Arg Thr Thr Thr
465             470             475             480 gcc tcc gcg tgt ccg act tcc gtt gca gta tcg ttc acg cac agc atc   1488
Ala Ser Ala Cys Pro Thr Ser Val Ala Val Ser Phe Thr His Ser Ile
```

```
                      485                 490                 495
acc act gtg ccc ggc gac act atc aag atc gcg ggt aac acg acg caa       1536
Thr Thr Val Pro Gly Asp Thr Ile Lys Ile Ala Gly Asn Thr Thr Gln
            500                 505                 510 ctc ggt agc tgg act gta gct tcc gca ccc gcg ctc tca gcg tca tcg       1584
Leu Gly Ser Trp Thr Val Ala Ser Ala Pro Ala Leu Ser Ala Ser Ser
            515                 520                 525 tac acg tcg agt aac cct gta tgg acg att acg ctg agc atg ccg gcg       1632
Tyr Thr Ser Ser Asn Pro Val Trp Thr Ile Thr Leu Ser Met Pro Ala
        530                 535                 540 aag cag gcg gtg cag tat aag ttt gtt aag gtg gcg agt ggg ggc gcg       1680
Lys Gln Ala Val Gln Tyr Lys Phe Val Lys Val Ala Ser Gly Gly Ala
545                 550                 555                 560 gtg acg tgg gag agc gat ccg aat cgt agt tat agc gtc ccg gcg tgt       1728
Val Thr Trp Glu Ser Asp Pro Asn Arg Ser Tyr Ser Val Pro Ala Cys
                565                 570                 575 cag gcg agt gcg gcg gtg agt agt agt tgg cag tga                       1764
Gln Ala Ser Ala Ala Val Ser Ser Ser Trp Gln
            580                 585

<210> SEQ ID NO 173
<211> LENGTH: 587
<212> TYPE: PRT
<213> ORGANISM: Trametes corrugata

<400> SEQUENCE: 173

Met Leu Phe Leu Ser Thr Leu Leu Ser Phe Phe Tyr Phe Ser Ser
1               5                   10                  15

Ile Val Thr Ala Ala Asp Thr Ser Ala Trp Lys Ser Arg Ser Ile Tyr
            20                  25                  30

Phe Val Leu Thr Asp Arg Val Ala Arg Ser Ser Ser Asp Thr Gly Gly
        35                  40                  45

Ser Ser Cys Ser Asn Leu Gly Asn Tyr Cys Gly Gly Thr Phe Lys Gly
    50                  55                  60

Leu Glu Ser Lys Leu Asp Tyr Ile Gln Gly Leu Gly Phe Asp Ala Ile
65                  70                  75                  80

Trp Ile Thr Pro Val Ala Asn Ser Ala Gly Gly Tyr His Gly Tyr
                85                  90                  95

Trp Ala Gln Asp Leu Tyr Ser Val Asn Ser Asn Tyr Gly Thr Ala Asp
            100                 105                 110

Asp Leu Lys Ser Leu Val Ser Ala His Ala Lys Gly Ile Tyr Val
        115                 120                 125

Met Val Asp Val Val Ala Asn His Met Gly Asn Gly Ala Ile Ala Asp
130                 135                 140

Asn Arg Pro Glu Pro Leu Asn Gln Ala Ser Ser Tyr His Pro Ala Cys
145                 150                 155                 160

Asp Ile Asn Tyr Asp Asn Gln Thr Ser Ile Glu Gln Cys Ser Ile Gly
                165                 170                 175

Gly Leu Ala Asp Leu Asn Thr Glu Ser Thr Glu Val Arg Thr Val Leu
            180                 185                 190

Asn Thr Trp Val Ser Trp Leu Val Asp Glu Tyr Ser Phe Asp Gly Val
        195                 200                 205

Arg Ile Asp Thr Val Lys His Val Gln Lys Asp Phe Trp Pro Asp Phe
    210                 215                 220

Val Ser Ser Ile Gly Glu Tyr Ser Ile Gly Glu Val Phe Asp Gly Asn
225                 230                 235                 240

Pro Pro Tyr Leu Ala Glu Tyr Ala Lys Leu Met Pro Gly Val Leu Asn
```

245                 250                 255
Tyr Ala Val Tyr Tyr Pro Met Asn Ala Phe Tyr Gln Gln Thr Gly Ser
                260                 265                 270

Ser Gln Ala Leu Val Asp Met Met Asn Thr Ile Ser Ser Thr Phe Pro
            275                 280                 285

Asp Pro Ser Ala Leu Gly Thr Phe Leu Asp Asn His Asp Asn Pro Arg
        290                 295                 300

Trp Leu Asn Val Lys Asn Asp Gln Thr Leu Leu Lys Asn Ala Leu Ala
305                 310                 315                 320

Tyr Val Ile Leu Ala Arg Gly Ile Pro Ile Leu Tyr Tyr Gly Thr Glu
                325                 330                 335

Gln Gly Tyr Ser Gly Gly Ala Asp Pro Ala Asn Arg Glu Asp Leu Trp
            340                 345                 350

Arg Ser Ser Phe Asn Thr Asn Ala Asp Leu Tyr Gln Ser Ile Lys Lys
        355                 360                 365

Leu Thr Ala Ala Arg Lys Ala Ala Gly Gly Leu Ala Gly Asn Asp His
    370                 375                 380

Thr His Leu Tyr Val Ala Asp Thr Ala Tyr Ala Trp Ser Arg Ala Asn
385                 390                 395                 400

Gly Ala Leu Ile Val Leu Thr Thr Asn Ala Gly Ser Ser Asn Ala
                405                 410                 415

Gln His Cys Phe Asn Thr Gln Met Ala Asn Gly Lys Trp Thr Asn Thr
            420                 425                 430

Tyr Gly Asp Gly Ala Thr Val Thr Ala Asp Ser Ser Gly Asn Ile Cys
        435                 440                 445

Val Thr Val Ser Asn Gly Glu Pro Val Val Leu Val Ala Ser Ala Ser
    450                 455                 460

Thr Thr Gly Val Thr Pro Thr Thr Ala Thr Thr Leu Arg Thr Thr Thr
465                 470                 475                 480

Ala Ser Ala Cys Pro Thr Ser Val Ala Val Ser Phe Thr His Ser Ile
                485                 490                 495

Thr Thr Val Pro Gly Asp Thr Ile Lys Ile Ala Gly Asn Thr Thr Gln
            500                 505                 510

Leu Gly Ser Trp Thr Val Ala Ser Ala Pro Ala Leu Ser Ala Ser Ser
        515                 520                 525

Tyr Thr Ser Ser Asn Pro Val Trp Thr Ile Thr Leu Ser Met Pro Ala
    530                 535                 540

Lys Gln Ala Val Gln Tyr Lys Phe Val Lys Val Ala Ser Gly Gly Ala
545                 550                 555                 560

Val Thr Trp Glu Ser Asp Pro Asn Arg Ser Tyr Ser Val Pro Ala Cys
                565                 570                 575

Gln Ala Ser Ala Ala Val Ser Ser Ser Trp Gln
            580                 585

<210> SEQ ID NO 174
<211> LENGTH: 2322
<212> TYPE: DNA
<213> ORGANISM: Trichopheraea saccata
<220> FEATURE:
<221> NAME/KEY: CDS
<222> LOCATION: (1)..(2322)
<220> FEATURE:
<221> NAME/KEY: sig_peptide
<222> LOCATION: (1)..(60)
<220> FEATURE:
<221> NAME/KEY: misc_feature
<222> LOCATION: (61)..(861)
<223> OTHER INFORMATION: Linker + CBM (N-term)

```
<220> FEATURE:
<221> NAME/KEY: misc_feature
<222> LOCATION: (862)..(2322)
<223> OTHER INFORMATION: Catalytic domain

<400> SEQUENCE: 174 atg tgt tcg ctg cgt tac ttc gcc ctt ttt ctg ttt cca ttt ctc ctt     48
Met Cys Ser Leu Arg Tyr Phe Ala Leu Phe Leu Phe Pro Phe Leu Leu
1               5                   10                  15 ttg gtc agt gca tcg cca gtt cat cag aac acc aaa cga tct acc caa     96
Leu Val Ser Ala Ser Pro Val His Gln Asn Thr Lys Arg Ser Thr Gln
            20                  25                  30 gtg tcg ttg atc agc tat acg ttt tct aac aat att ctc tct gga tcc    144
Val Ser Leu Ile Ser Tyr Thr Phe Ser Asn Asn Ile Leu Ser Gly Ser
        35                  40                  45 atc agc att caa aac att gct tac gcc aaa acg gtc agc gtt acc tat    192
Ile Ser Ile Gln Asn Ile Ala Tyr Ala Lys Thr Val Ser Val Thr Tyr
    50                  55                  60 gcc att ggg agc tct tgg agc tcc tct cag gtg ata agc gct gcc tac    240
Ala Ile Gly Ser Ser Trp Ser Ser Ser Gln Val Ile Ser Ala Ala Tyr
65              70                  75                  80 tcc aca ggt cct gat agc acc ggt tat gaa gtc tgg acg ttt agc ggc    288
Ser Thr Gly Pro Asp Ser Thr Gly Tyr Glu Val Trp Thr Phe Ser Gly
                85                  90                  95 aca gca acg ggg gca act cag ttc tac att gcg tat act gtc tca ggg    336
Thr Ala Thr Gly Ala Thr Gln Phe Tyr Ile Ala Tyr Thr Val Ser Gly
            100                 105                 110 acc acc tac tac gat cct gga aat ggc atc aat tac acg atc ggc acg    384
Thr Thr Tyr Tyr Asp Pro Gly Asn Gly Ile Asn Tyr Thr Ile Gly Thr
        115                 120                 125 ggt tcg tcc act act tcc agc aca tct gcc act tcg aca acc aaa agt    432
Gly Ser Ser Thr Thr Ser Ser Thr Ser Ala Thr Ser Thr Thr Lys Ser
    130                 135                 140 tcc acc act tcc acg agc act gcg act agc aca agc gtg gcg acc agc    480
Ser Thr Thr Ser Thr Ser Thr Ala Thr Ser Thr Ser Val Ala Thr Ser
145                 150                 155                 160 agt ctc cct gct atc att tca tcc agt att cct tct gag gcg gca gcc    528
Ser Leu Pro Ala Ile Ile Ser Ser Ser Ile Pro Ser Glu Ala Ala Ala
                165                 170                 175 acc gcg ctt tct gga tgc aat act tgg gat ggt ttt gac aac tgc caa    576
Thr Ala Leu Ser Gly Cys Asn Thr Trp Asp Gly Phe Asp Asn Cys Gln
            180                 185                 190 act agt ggc gtg tac gac ttt gtg gcc agt gcc gaa aac cgc aga tgg    624
Thr Ser Gly Val Tyr Asp Phe Val Ala Ser Ala Glu Asn Arg Arg Trp
        195                 200                 205 cag acg ccc ccg gac ggc gat cct gcc tat gtc aat acg ttc caa gac    672
Gln Thr Pro Pro Asp Gly Asp Pro Ala Tyr Val Asn Thr Phe Gln Asp
    210                 215                 220 tac cga gat ctc att ggc tac gcc gat atc cag tac agc cct tca cga    720
Tyr Arg Asp Leu Ile Gly Tyr Ala Asp Ile Gln Tyr Ser Pro Ser Arg
225                 230                 235                 240 acc tcc gcc gtt gtg act gtc aat gct gct tcg cgg acc ggc gag act    768
Thr Ser Ala Val Val Thr Val Asn Ala Ala Ser Arg Thr Gly Glu Thr
                245                 250                 255 ttg acc tac aaa ttt ggg gga att act cag acg tct aac gcg tac acc    816
Leu Thr Tyr Lys Phe Gly Gly Ile Thr Gln Thr Ser Asn Ala Tyr Thr
            260                 265                 270 gtg agc agc tcg ttt atc gga acc ctg gca atc aca gtc acc agt tca    864
Val Ser Ser Ser Phe Ile Gly Thr Leu Ala Ile Thr Val Thr Ser Ser
        275                 280                 285 tcc ggc aag aaa tta gag ctg gag gcc ctc aac ttt gtt tgg cag aat    912
```

-continued

| | | |
|---|---|---|
| Ser Gly Lys Lys Leu Glu Leu Glu Ala Leu Asn Phe Val Trp Gln Asn<br>290                    295                    300 | | |
| gca gtt ctt act ggc gct cag agc act ttc aac aat ggg cag aag ggc<br>Ala Val Leu Thr Gly Ala Gln Ser Thr Phe Asn Asn Gly Gln Lys Gly<br>305                    310                    315                    320 | 960 | |
| gct att gtg gag ctt ttt ggg tgg ccg tat gca gat att gca aag gag<br>Ala Ile Val Glu Leu Phe Gly Trp Pro Tyr Ala Asp Ile Ala Lys Glu<br>325                    330                    335 | 1008 | |
| tgc gct ttc ctt gga aaa gcc gga tac atg gga gtc aag gtt tgg cct<br>Cys Ala Phe Leu Gly Lys Ala Gly Tyr Met Gly Val Lys Val Trp Pro<br>340                    345                    350 | 1056 | |
| cca aac gag cac atc tgg gga tcg gac tac tac gaa acc gac aat atg<br>Pro Asn Glu His Ile Trp Gly Ser Asp Tyr Tyr Glu Thr Asp Asn Met<br>355                    360                    365 | 1104 | |
| ttc cgt ccg tgg tat ctg gtg tac cag ccg gtc agt tac aag ctt gtg<br>Phe Arg Pro Trp Tyr Leu Val Tyr Gln Pro Val Ser Tyr Lys Leu Val<br>370                    375                    380 | 1152 | |
| agc cgt caa gga acc cgt gag gag ctt cga gct atg ata act gct tgc<br>Ser Arg Gln Gly Thr Arg Glu Glu Leu Arg Ala Met Ile Thr Ala Cys<br>385                    390                    395                    400 | 1200 | |
| cgg agt gct gga gtg cgc gtc tat gcc gac gcc gtc att aat cac atg<br>Arg Ser Ala Gly Val Arg Val Tyr Ala Asp Ala Val Ile Asn His Met<br>                    405                    410                    415 | 1248 | |
| tct gga aac gga aac gat atc caa aac cat cgt aat acc gcc tgc gcc<br>Ser Gly Asn Gly Asn Asp Ile Gln Asn His Arg Asn Thr Ala Cys Ala<br>          420                    425                    430 | 1296 | |
| tac tgg aca ggc cac aac gca acc gcg aat tcg cct tac ttc acc tcc<br>Tyr Trp Thr Gly His Asn Ala Thr Ala Asn Ser Pro Tyr Phe Thr Ser<br>                    435                    440                    445 | 1344 | |
| ggt tac acc tat ctt att aat ccc ttc acg aac aca cgc ccc acc ttc<br>Gly Tyr Thr Tyr Leu Ile Asn Pro Phe Thr Asn Thr Arg Pro Thr Phe<br>450                    455                    460 | 1392 | |
| gag tac cca gcg gta cca tgg ggc cca act gat ttc cat tgc gtt tcc<br>Glu Tyr Pro Ala Val Pro Trp Gly Pro Thr Asp Phe His Cys Val Ser<br>465                    470                    475                    480 | 1440 | |
| tct atc aca gat tgg acc aac ggc caa atc gtc aca aag ggc tat ctc<br>Ser Ile Thr Asp Trp Thr Asn Gly Gln Ile Val Thr Lys Gly Tyr Leu<br>                    485                    490                    495 | 1488 | |
| gtg gga ctc tcc gat ctc aac aca gag aag gat tac gtc cag gac cgc<br>Val Gly Leu Ser Asp Leu Asn Thr Glu Lys Asp Tyr Val Gln Asp Arg<br>500                    505                    510 | 1536 | |
| atc gcc act tat ctt gtg gat ctc ttg tca atc ggc ttc tcc ggc ttc<br>Ile Ala Thr Tyr Leu Val Asp Leu Leu Ser Ile Gly Phe Ser Gly Phe<br>515                    520                    525 | 1584 | |
| cgt gtt gat gcg gca aaa cat att ggc ccc acc tcc atg gca cag atc<br>Arg Val Asp Ala Ala Lys His Ile Gly Pro Thr Ser Met Ala Gln Ile<br>530                    535                    540 | 1632 | |
| ttc gga agg gtt gca aag aag atg ggc gga agt ctt cca gat gat ttt<br>Phe Gly Arg Val Ala Lys Lys Met Gly Gly Ser Leu Pro Asp Asp Phe<br>545                    550                    555                    560 | 1680 | |
| atc act tgg ctt gaa gtg ttg atg ggt ggt gag aag gag cag tat gct<br>Ile Thr Trp Leu Glu Val Leu Met Gly Gly Glu Lys Glu Gln Tyr Ala<br>                    565                    570                    575 | 1728 | |
| tgc ggc ggc ggt gaa tgg agt tgg tac acc aac ttc aat acc cag ctt<br>Cys Gly Gly Gly Glu Trp Ser Trp Tyr Thr Asn Phe Asn Thr Gln Leu<br>                    580                    585                    590 | 1776 | |
| tcc aat gcg gga att agt gac act gat atc aat aag atc aag att tgg<br>Ser Asn Ala Gly Ile Ser Asp Thr Asp Ile Asn Lys Ile Lys Ile Trp<br>                    595                    600                    605 | 1824 | |
| agc tcc gac tat ccc aag gag ttc ccg atc tgc ggt tct tgg atc atc | 1872 | |

-continued

| | | | | | | | | | | | | | | |
|---|---|---|---|---|---|---|---|---|---|---|---|---|---|---|
| Ser | Ser | Asp | Tyr | Pro | Lys | Glu | Phe | Pro | Ile | Cys | Gly | Ser | Trp | Ile Ile |
| | 610 | | | | 615 | | | | 620 | | | | | |

```
cca tcc act cgc ttt gtc atc caa aat gac gac cat gac cag cag aac    1920
Pro Ser Thr Arg Phe Val Ile Gln Asn Asp Asp His Asp Gln Gln Asn
625                 630                 635                 640 ccg ggc tct tcc tcc aga gat atg ggt gac caa ggc tcc gta ctc atc    1968
Pro Gly Ser Ser Ser Arg Asp Met Gly Asp Gln Gly Ser Val Leu Ile
            645                 650                 655 aaa gat caa gat gta gcc aag cac cgg gca ttt gag gtc aag ctc ttc    2016
Lys Asp Gln Asp Val Ala Lys His Arg Ala Phe Glu Val Lys Leu Phe
        660                 665                 670 acc cgt acc gac ggt gac tgg caa atc agg aat atc ctc tcc tct tat    2064
Thr Arg Thr Asp Gly Asp Trp Gln Ile Arg Asn Ile Leu Ser Ser Tyr
    675                 680                 685 atg ttt gcc tcc aac gga gca aat ggc ttc ccc gat ggt ctt tcg gat    2112
Met Phe Ala Ser Asn Gly Ala Asn Gly Phe Pro Asp Gly Leu Ser Asp
690                 695                 700 tgt tcc ctt tat act ggc tca cag agt gcg agt ggt tgt ttg ggt atc    2160
Cys Ser Leu Tyr Thr Gly Ser Gln Ser Ala Ser Gly Cys Leu Gly Ile
705                 710                 715                 720 gcg aag gat acc gct tat gta gaa ggt atc tgt ggg tat act atg gtt    2208
Ala Lys Asp Thr Ala Tyr Val Glu Gly Ile Cys Gly Tyr Thr Met Val
            725                 730                 735 gct gga agg tac acc agg ccg cat agg gat ctg agc atc att aat gct    2256
Ala Gly Arg Tyr Thr Arg Pro His Arg Asp Leu Ser Ile Ile Asn Ala
        740                 745                 750 atg agg agt tgg gtc ggg ttg tcg agt acc aca gcg gat gct ctt gga    2304
Met Arg Ser Trp Val Gly Leu Ser Ser Thr Thr Ala Asp Ala Leu Gly
    755                 760                 765 atc ccc ggt tgt agc tga                                            2322
Ile Pro Gly Cys Ser
    770
```

<210> SEQ ID NO 175
<211> LENGTH: 773
<212> TYPE: PRT
<213> ORGANISM: Trichopheraea saccata

<400> SEQUENCE: 175

| | | | | | | | | | | | | | | |
|---|---|---|---|---|---|---|---|---|---|---|---|---|---|---|
| Met | Cys | Ser | Leu | Arg | Tyr | Phe | Ala | Leu | Phe | Leu | Phe | Pro | Phe | Leu Leu |
| 1 | | | | 5 | | | | | 10 | | | | | 15 |
| Leu | Val | Ser | Ala | Ser | Pro | Val | His | Gln | Asn | Thr | Lys | Arg | Ser | Thr Gln |
| | | | 20 | | | | | 25 | | | | | 30 | |
| Val | Ser | Leu | Ile | Ser | Tyr | Thr | Phe | Ser | Asn | Asn | Ile | Leu | Ser | Gly Ser |
| | | | 35 | | | | 40 | | | | | 45 | | |
| Ile | Ser | Ile | Gln | Asn | Ile | Ala | Tyr | Ala | Lys | Thr | Val | Ser | Val | Thr Tyr |
| | 50 | | | | | 55 | | | | | 60 | | | |
| Ala | Ile | Gly | Ser | Ser | Trp | Ser | Ser | Ser | Gln | Val | Ile | Ser | Ala | Ala Tyr |
| 65 | | | | | 70 | | | | | 75 | | | | | 80 |
| Ser | Thr | Gly | Pro | Asp | Ser | Thr | Gly | Tyr | Glu | Val | Trp | Thr | Phe | Ser Gly |
| | | | | 85 | | | | | 90 | | | | | 95 |
| Thr | Ala | Thr | Gly | Ala | Thr | Gln | Phe | Tyr | Ile | Ala | Tyr | Val | Ser | Gly |
| | | | | 100 | | | | | 105 | | | | | 110 |
| Thr | Thr | Tyr | Tyr | Asp | Pro | Gly | Asn | Gly | Ile | Asn | Tyr | Thr | Ile | Gly Thr |
| | | | | 115 | | | | | 120 | | | | | 125 |
| Gly | Ser | Ser | Thr | Thr | Ser | Ser | Thr | Ser | Ala | Thr | Ser | Thr | Thr | Lys Ser |
| | | 130 | | | | | 135 | | | | | 140 | | |
| Ser | Thr | Thr | Ser | Thr | Ser | Thr | Ala | Thr | Ser | Thr | Ser | Val | Ala | Thr Ser |
| 145 | | | | | 150 | | | | | 155 | | | | | 160 |

```
Ser Leu Pro Ala Ile Ile Ser Ser Ile Pro Ser Glu Ala Ala
            165                 170                 175

Thr Ala Leu Ser Gly Cys Asn Thr Trp Asp Gly Phe Asp Asn Cys Gln
            180                 185                 190

Thr Ser Gly Val Tyr Asp Phe Val Ala Ser Ala Glu Asn Arg Arg Trp
            195                 200                 205

Gln Thr Pro Pro Asp Gly Asp Pro Ala Tyr Val Asn Thr Phe Gln Asp
    210                 215                 220

Tyr Arg Asp Leu Ile Gly Tyr Ala Asp Ile Gln Tyr Ser Pro Ser Arg
225                 230                 235                 240

Thr Ser Ala Val Val Thr Val Asn Ala Ala Ser Arg Thr Gly Glu Thr
                245                 250                 255

Leu Thr Tyr Lys Phe Gly Gly Ile Thr Gln Thr Ser Asn Ala Tyr Thr
            260                 265                 270

Val Ser Ser Ser Phe Ile Gly Thr Leu Ala Ile Thr Val Thr Ser Ser
            275                 280                 285

Ser Gly Lys Lys Leu Glu Leu Glu Ala Leu Asn Phe Val Trp Gln Asn
    290                 295                 300

Ala Val Leu Thr Gly Ala Gln Ser Thr Phe Asn Asn Gly Gln Lys Gly
305                 310                 315                 320

Ala Ile Val Glu Leu Phe Gly Trp Pro Tyr Ala Asp Ile Ala Lys Glu
                325                 330                 335

Cys Ala Phe Leu Gly Lys Ala Gly Tyr Met Gly Val Lys Val Trp Pro
            340                 345                 350

Pro Asn Glu His Ile Trp Gly Ser Asp Tyr Tyr Glu Thr Asp Asn Met
    355                 360                 365

Phe Arg Pro Trp Tyr Leu Val Tyr Gln Pro Val Ser Tyr Lys Leu Val
    370                 375                 380

Ser Arg Gln Gly Thr Arg Glu Glu Leu Arg Ala Met Ile Thr Ala Cys
385                 390                 395                 400

Arg Ser Ala Gly Val Arg Val Tyr Ala Asp Ala Val Ile Asn His Met
                405                 410                 415

Ser Gly Asn Gly Asn Asp Ile Gln Asn His Arg Asn Thr Ala Cys Ala
            420                 425                 430

Tyr Trp Thr Gly His Asn Ala Thr Ala Asn Ser Pro Tyr Phe Thr Ser
            435                 440                 445

Gly Tyr Thr Tyr Leu Ile Asn Pro Phe Thr Asn Thr Arg Pro Thr Phe
    450                 455                 460

Glu Tyr Pro Ala Val Pro Trp Gly Pro Thr Asp Phe His Cys Val Ser
465                 470                 475                 480

Ser Ile Thr Asp Trp Thr Asn Gly Gln Ile Val Thr Lys Gly Tyr Leu
                485                 490                 495

Val Gly Leu Ser Asp Leu Asn Thr Glu Lys Asp Tyr Val Gln Asp Arg
            500                 505                 510

Ile Ala Thr Tyr Leu Val Asp Leu Leu Ser Ile Gly Phe Ser Gly Phe
            515                 520                 525

Arg Val Asp Ala Ala Lys His Ile Gly Pro Thr Ser Met Ala Gln Ile
    530                 535                 540

Phe Gly Arg Val Ala Lys Lys Met Gly Ser Leu Pro Asp Asp Phe
545                 550                 555                 560

Ile Thr Trp Leu Glu Val Leu Met Gly Gly Glu Lys Glu Gln Tyr Ala
                565                 570                 575

Cys Gly Gly Gly Glu Trp Ser Trp Tyr Thr Asn Phe Asn Thr Gln Leu
```

-continued

```
                      580                 585                 590
Ser Asn Ala Gly Ile Ser Asp Thr Asp Ile Asn Lys Ile Lys Ile Trp
                595                 600                 605

Ser Ser Asp Tyr Pro Lys Glu Phe Pro Ile Cys Gly Ser Trp Ile Ile
            610                 615                 620

Pro Ser Thr Arg Phe Val Ile Gln Asn Asp His Asp Gln Asn
625                 630                 635                 640

Pro Gly Ser Ser Ser Arg Asp Met Gly Asp Gln Gly Ser Val Leu Ile
                645                 650                 655

Lys Asp Gln Asp Val Ala Lys His Arg Ala Phe Glu Val Lys Leu Phe
            660                 665                 670

Thr Arg Thr Asp Gly Asp Trp Gln Ile Arg Asn Ile Leu Ser Ser Tyr
                675                 680                 685

Met Phe Ala Ser Asn Gly Ala Asn Gly Phe Pro Asp Gly Leu Ser Asp
            690                 695                 700

Cys Ser Leu Tyr Thr Gly Ser Gln Ser Ala Ser Gly Cys Leu Gly Ile
705                 710                 715                 720

Ala Lys Asp Thr Ala Tyr Val Glu Gly Ile Cys Gly Tyr Thr Met Val
                725                 730                 735

Ala Gly Arg Tyr Thr Arg Pro His Arg Asp Leu Ser Ile Ile Asn Ala
            740                 745                 750

Met Arg Ser Trp Val Gly Leu Ser Ser Thr Thr Ala Asp Ala Leu Gly
                755                 760                 765

Ile Pro Gly Cys Ser
    770
```

```
<210> SEQ ID NO 176
<211> LENGTH: 1761
<212> TYPE: DNA
<213> ORGANISM: Valsaria rubricosa
<220> FEATURE:
<221> NAME/KEY: CDS
<222> LOCATION: (1)..(1761)
<220> FEATURE:
<221> NAME/KEY: sig_peptide
<222> LOCATION: (1)..(63)
<220> FEATURE:
<221> NAME/KEY: misc_feature
<222> LOCATION: (64)..(1413)
<223> OTHER INFORMATION: Catalytic domain
<220> FEATURE:
<221> NAME/KEY: misc_feature
<222> LOCATION: (1414)..(1458)
<223> OTHER INFORMATION: Linker
<220> FEATURE:
<221> NAME/KEY: misc_feature
<222> LOCATION: (1459)..(1761)
<223> OTHER INFORMATION: CBM

<400> SEQUENCE: 176
```

```
atg cga tcc ttc ctc gcc ctc tca gcc ttg ctg ctg tac ccg ctg          48
Met Arg Ser Phe Leu Ala Leu Ser Ala Leu Leu Leu Tyr Pro Leu
1               5                   10                  15 cag ctg ctc gcc gcc agc aac tcc gac tgg agg tcc gcc aat atc tac     96
Gln Leu Leu Ala Ala Ser Asn Ser Asp Trp Arg Ser Arg Asn Ile Tyr
            20                  25                  30 ttt gcc ttg acc gac cgc gtc gcc aat ccg tcc acc acg acc gca tgt    144
Phe Ala Leu Thr Asp Arg Val Ala Asn Pro Ser Thr Thr Thr Ala Cys
        35                  40                  45 agt gac ctg agc aac tac tgc ggc ggc acg tgg agc ggc ctg tcg agc    192
Ser Asp Leu Ser Asn Tyr Cys Gly Gly Thr Trp Ser Gly Leu Ser Ser
    50                  55                  60
```

```
aag ctg gac tac atc caa ggg atg ggc ttc gat tcc atc tgg att acc        240
Lys Leu Asp Tyr Ile Gln Gly Met Gly Phe Asp Ser Ile Trp Ile Thr
 65              70                  75                  80 ccc gtg gtc gag aac tgc gac ggt ggc tac cac ggc tac tgg gcc aag        288
Pro Val Val Glu Asn Cys Asp Gly Gly Tyr His Gly Tyr Trp Ala Lys
                 85                  90                  95 gcg ctc tac aac gtc aac acg aac tac ggc agt gcg gat gat ctg aag        336
Ala Leu Tyr Asn Val Asn Thr Asn Tyr Gly Ser Ala Asp Asp Leu Lys
            100                 105                 110 aac ttc gtt gcg gcc gcc cat gcg aag ggc atg tac gtg atg gtg gac        384
Asn Phe Val Ala Ala Ala His Ala Lys Gly Met Tyr Val Met Val Asp
        115                 120                 125 gtc gtc gcg aat cac atg ggt tcc tgc ggc atc gcc aac ctc tcc cca        432
Val Val Ala Asn His Met Gly Ser Cys Gly Ile Ala Asn Leu Ser Pro
    130                 135                 140 cct ccc ctg aac gag cag agc tct tat cac acc cag tgc gac att gac        480
Pro Pro Leu Asn Glu Gln Ser Ser Tyr His Thr Gln Cys Asp Ile Asp
145                 150                 155                 160 tac agc agt cag tcc agc att gag acg tgc tgg ata tcc ggc ctc cct        528
Tyr Ser Ser Gln Ser Ser Ile Glu Thr Cys Trp Ile Ser Gly Leu Pro
                165                 170                 175 gac ctg gac acc acc gat agc act atc cga tcc ctc ttc cag acc tgg        576
Asp Leu Asp Thr Thr Asp Ser Thr Ile Arg Ser Leu Phe Gln Thr Trp
            180                 185                 190 gtc cac ggc ctg gtc agc aac tac agc ttc gac ggt ctc cgc gtc gac        624
Val His Gly Leu Val Ser Asn Tyr Ser Phe Asp Gly Leu Arg Val Asp
        195                 200                 205 acc gtc aag cac gtg gag aag gat tac tgg ccc ggc ttc gtg tcg gcg        672
Thr Val Lys His Val Glu Lys Asp Tyr Trp Pro Gly Phe Val Ser Ala
    210                 215                 220 gcg ggc acc tac gcc atc ggc gaa gtc ttc tcc ggc gac acc tcc tac        720
Ala Gly Thr Tyr Ala Ile Gly Glu Val Phe Ser Gly Asp Thr Ser Tyr
225                 230                 235                 240 gtg gcc ggc tat caa tcg gtg atg ccg ggc ttg ctc aac tat ccc atc        768
Val Ala Gly Tyr Gln Ser Val Met Pro Gly Leu Leu Asn Tyr Pro Ile
                245                 250                 255 tac tat ccg ctc atc cgc gtc ttc gcg cag ggt gcg tcc ttc acc gat        816
Tyr Tyr Pro Leu Ile Arg Val Phe Ala Gln Gly Ala Ser Phe Thr Asp
            260                 265                 270 ctc gtc aac aac cac gat acc gtc ggc tcg acc ttc tcc gac ccg acg        864
Leu Val Asn Asn His Asp Thr Val Gly Ser Thr Phe Ser Asp Pro Thr
        275                 280                 285 ctg ctg ggt aac ttt atc gac aac cac gac aac cca cgt ttc ctg agc        912
Leu Leu Gly Asn Phe Ile Asp Asn His Asp Asn Pro Arg Phe Leu Ser
    290                 295                 300 tac acc agc gac cac gcc ctc ctc aag aac gct ctg gcc tac gtc atc        960
Tyr Thr Ser Asp His Ala Leu Leu Lys Asn Ala Leu Ala Tyr Val Ile
305                 310                 315                 320 ctg gcc aga ggc atc ccc atc gtc tac tac ggc acc gag caa ggc tac       1008
Leu Ala Arg Gly Ile Pro Ile Val Tyr Tyr Gly Thr Glu Gln Gly Tyr
                325                 330                 335 tcg ggt tcg tcc gac ccg gcg aac cgc gag gat ctc tgg cgt agc gga       1056
Ser Gly Ser Ser Asp Pro Ala Asn Arg Glu Asp Leu Trp Arg Ser Gly
            340                 345                 350 tac agc act acg gga gac atc tac acc acc atc gcc gcg ctc tcc gcc       1104
Tyr Ser Thr Thr Gly Asp Ile Tyr Thr Thr Ile Ala Ala Leu Ser Ala
        355                 360                 365 gcg cgc acc gcg gcc ggt ggc ctc gcc ggt aac gac cac gtc cac ctg       1152
Ala Arg Thr Ala Ala Gly Gly Leu Ala Gly Asn Asp His Val His Leu
    370                 375                 380
```

```
tac acg acc gac aac gcg tac gcc tgg tcc cgg gcg agc ggc aag ctc      1200
Tyr Thr Thr Asp Asn Ala Tyr Ala Trp Ser Arg Ala Ser Gly Lys Leu
385                 390                 395                 400 atc gtc gtc acg tcc aac cgc ggc agc tcc gac agc agc acc atc tgc      1248
Ile Val Val Thr Ser Asn Arg Gly Ser Ser Asp Ser Ser Thr Ile Cys
                405                 410                 415 ttc agc acc cag cag gcc agc ggc acc acc tgg acc agc acg atc acc      1296
Phe Ser Thr Gln Gln Ala Ser Gly Thr Thr Trp Thr Ser Thr Ile Thr
            420                 425                 430 ggc aac tcg tac acc gcc gac agc aac ggc cag atc tgc gtg cag ctg      1344
Gly Asn Ser Tyr Thr Ala Asp Ser Asn Gly Gln Ile Cys Val Gln Leu
        435                 440                 445 tcc agc ggc gga ccc gag gcg ctc gtc gtc tcc acc gcg acc ggc acc      1392
Ser Ser Gly Gly Pro Glu Ala Leu Val Val Ser Thr Ala Thr Gly Thr
    450                 455                 460 gcc acc gcg acg act ctg tcc acg acc acc aag acg tcc acc tcg acc      1440
Ala Thr Ala Thr Thr Leu Ser Thr Thr Thr Lys Thr Ser Thr Ser Thr
465                 470                 475                 480 gcc tcc tgc gcc gcc acc gtc gcc gtc acc ttc aac gag ctc gtc acc      1488
Ala Ser Cys Ala Ala Thr Val Ala Val Thr Phe Asn Glu Leu Val Thr
                485                 490                 495 acg aac tac ggc gac acc atc cgc ctg acg ggc tcc atc tcc cag ctc      1536
Thr Asn Tyr Gly Asp Thr Ile Arg Leu Thr Gly Ser Ile Ser Gln Leu
            500                 505                 510 agc agc tgg agc gca acc tcg ggg ctg gcc ctg agc gcg tcc gcg tac      1584
Ser Ser Trp Ser Ala Thr Ser Gly Leu Ala Leu Ser Ala Ser Ala Tyr
        515                 520                 525 acg tcc agc aac ccg ctc tgg agc gtg acg gtc agc ctg ccg gcc ggc      1632
Thr Ser Ser Asn Pro Leu Trp Ser Val Thr Val Ser Leu Pro Ala Gly
    530                 535                 540 acg tcg ttc gag tac aag ttc gtc cgc atc acg agc gac ggc acc gtg      1680
Thr Ser Phe Glu Tyr Lys Phe Val Arg Ile Thr Ser Asp Gly Thr Val
545                 550                 555                 560 acc tgg gaa tcg gac ccg aac cgc agc tac acc gtc ccg acg tgc gcg      1728
Thr Trp Glu Ser Asp Pro Asn Arg Ser Tyr Thr Val Pro Thr Cys Ala
                565                 570                 575 agc acc gcg acg atc agc aat acc tgg cgg tga                          1761
Ser Thr Ala Thr Ile Ser Asn Thr Trp Arg
            580                 585
```

<210> SEQ ID NO 177
<211> LENGTH: 586
<212> TYPE: PRT
<213> ORGANISM: Valsaria rubricosa

<400> SEQUENCE: 177

```
Met Arg Ser Phe Leu Ala Leu Ser Ala Leu Leu Leu Tyr Pro Leu
1               5                   10                  15

Gln Leu Leu Ala Ala Ser Asn Ser Asp Trp Arg Ser Arg Asn Ile Tyr
            20                  25                  30

Phe Ala Leu Thr Asp Arg Val Ala Asn Pro Ser Thr Thr Ala Cys
        35                  40                  45

Ser Asp Leu Ser Asn Tyr Cys Gly Gly Thr Trp Ser Gly Leu Ser Ser
    50                  55                  60

Lys Leu Asp Tyr Ile Gln Gly Met Gly Phe Asp Ser Ile Trp Ile Thr
65                  70                  75                  80

Pro Val Val Glu Asn Cys Asp Gly Gly Tyr His Gly Tyr Trp Ala Lys
                85                  90                  95

Ala Leu Tyr Asn Val Asn Thr Asn Tyr Gly Ser Ala Asp Asp Leu Lys
            100                 105                 110
```

```
Asn Phe Val Ala Ala His Ala Lys Gly Met Tyr Val Met Val Asp
        115                 120                 125

Val Val Ala Asn His Met Gly Ser Cys Gly Ile Ala Asn Leu Ser Pro
130                 135                 140

Pro Pro Leu Asn Glu Gln Ser Ser Tyr His Thr Gln Cys Asp Ile Asp
145                 150                 155                 160

Tyr Ser Ser Gln Ser Ser Ile Glu Thr Cys Trp Ile Ser Gly Leu Pro
                165                 170                 175

Asp Leu Asp Thr Thr Asp Ser Thr Ile Arg Ser Leu Phe Gln Thr Trp
            180                 185                 190

Val His Gly Leu Val Ser Asn Tyr Ser Phe Asp Gly Leu Arg Val Asp
        195                 200                 205

Thr Val Lys His Val Glu Lys Asp Tyr Trp Pro Gly Phe Val Ser Ala
    210                 215                 220

Ala Gly Thr Tyr Ala Ile Gly Glu Val Phe Ser Gly Asp Thr Ser Tyr
225                 230                 235                 240

Val Ala Gly Tyr Gln Ser Val Met Pro Gly Leu Leu Asn Tyr Pro Ile
                245                 250                 255

Tyr Tyr Pro Leu Ile Arg Val Phe Ala Gln Gly Ala Ser Phe Thr Asp
            260                 265                 270

Leu Val Asn Asn His Asp Thr Val Gly Ser Thr Phe Ser Asp Pro Thr
        275                 280                 285

Leu Leu Gly Asn Phe Ile Asp Asn His Asp Asn Pro Arg Phe Leu Ser
    290                 295                 300

Tyr Thr Ser Asp His Ala Leu Leu Lys Asn Ala Leu Ala Tyr Val Ile
305                 310                 315                 320

Leu Ala Arg Gly Ile Pro Ile Val Tyr Tyr Gly Thr Glu Gln Gly Tyr
                325                 330                 335

Ser Gly Ser Ser Asp Pro Ala Asn Arg Glu Asp Leu Trp Arg Ser Gly
            340                 345                 350

Tyr Ser Thr Thr Gly Asp Ile Tyr Thr Thr Ile Ala Ala Leu Ser Ala
        355                 360                 365

Ala Arg Thr Ala Ala Gly Gly Leu Ala Gly Asn Asp His Val His Leu
    370                 375                 380

Tyr Thr Thr Asp Asn Ala Tyr Ala Trp Ser Arg Ala Ser Gly Lys Leu
385                 390                 395                 400

Ile Val Val Thr Ser Asn Arg Gly Ser Ser Asp Ser Ser Thr Ile Cys
                405                 410                 415

Phe Ser Thr Gln Gln Ala Ser Gly Thr Thr Trp Thr Ser Thr Ile Thr
            420                 425                 430

Gly Asn Ser Tyr Thr Ala Asp Ser Asn Gly Gln Ile Cys Val Gln Leu
        435                 440                 445

Ser Ser Gly Gly Pro Glu Ala Leu Val Val Ser Thr Ala Thr Gly Thr
    450                 455                 460

Ala Thr Ala Thr Thr Leu Ser Thr Thr Thr Lys Thr Ser Thr Ser Thr
465                 470                 475                 480

Ala Ser Cys Ala Ala Thr Val Ala Val Thr Phe Asn Glu Leu Val Thr
                485                 490                 495

Thr Asn Tyr Gly Asp Thr Ile Arg Leu Thr Gly Ser Ile Ser Gln Leu
            500                 505                 510

Ser Ser Trp Ser Ala Thr Ser Gly Leu Ala Leu Ser Ala Ser Ala Tyr
        515                 520                 525

Thr Ser Ser Asn Pro Leu Trp Ser Val Thr Val Ser Leu Pro Ala Gly
```

-continued

```
                     530                 535                 540
Thr Ser Phe Glu Tyr Lys Phe Val Arg Ile Thr Ser Asp Gly Thr Val
545                 550                 555                 560

Thr Trp Glu Ser Asp Pro Asn Arg Ser Tyr Thr Val Pro Thr Cys Ala
                565                 570                 575

Ser Thr Ala Thr Ile Ser Asn Thr Trp Arg
                580                 585

<210> SEQ ID NO 178
<211> LENGTH: 1749
<212> TYPE: DNA
<213> ORGANISM: Valsaria spartii
<220> FEATURE:
<221> NAME/KEY: CDS
<222> LOCATION: (1)..(1749)
<220> FEATURE:
<221> NAME/KEY: sig_peptide
<222> LOCATION: (1)..(57)
<220> FEATURE:
<221> NAME/KEY: misc_feature
<222> LOCATION: (58)..(1410)
<223> OTHER INFORMATION: Catalytic domain
<220> FEATURE:
<221> NAME/KEY: misc_feature
<222> LOCATION: (1411)..(1443)
<223> OTHER INFORMATION: Linker
<220> FEATURE:
<221> NAME/KEY: misc_feature
<222> LOCATION: (1444)..(1749)
<223> OTHER INFORMATION: CBM

<400> SEQUENCE: 178 atg cag ttc ctt tgc gcc ctt gca gca ctc ctg tgc ttc cca tcg cag      48
Met Gln Phe Leu Cys Ala Leu Ala Ala Leu Leu Cys Phe Pro Ser Gln
1               5                   10                  15 ctt ctc gcc gcc agc aac gcg gat tgg aaa tcg cgc aac atc tac ttt      96
Leu Leu Ala Ala Ser Asn Ala Asp Trp Lys Ser Arg Asn Ile Tyr Phe
            20                  25                  30 gcc ttg acg gac cgc gtc gct ggt cct acc ggg gga tca tgc ggc aac     144
Ala Leu Thr Asp Arg Val Ala Gly Pro Thr Gly Gly Ser Cys Gly Asn
        35                  40                  45 ctg gga aac tac tgc ggc ggt acc tgg aac gga ttg acg gat aag ttg     192
Leu Gly Asn Tyr Cys Gly Gly Thr Trp Asn Gly Leu Thr Asp Lys Leu
    50                  55                  60 gac tac atc cag ggc atg gga ttc gat gcc atc tgg atc acc ccg gtc     240
Asp Tyr Ile Gln Gly Met Gly Phe Asp Ala Ile Trp Ile Thr Pro Val
65                  70                  75                  80 atc aag aac agc ccc ggc ggt tat cac gga tat tgg gct caa gat ctc     288
Ile Lys Asn Ser Pro Gly Gly Tyr His Gly Tyr Trp Ala Gln Asp Leu
                85                  90                  95 tac agc gtg aac gag aac tat ggc act gcg caa gat ctg aag gat ttc     336
Tyr Ser Val Asn Glu Asn Tyr Gly Thr Ala Gln Asp Leu Lys Asp Phe
            100                 105                 110 gta aat gcg gcg cac gca aag ggg atc tac gtc atg gtc gac gtg gtc     384
Val Asn Ala Ala His Ala Lys Gly Ile Tyr Val Met Val Asp Val Val
        115                 120                 125 gca aac cac atg ggc aac ggt gga atc tca act ctc tcc cca cct ccc     432
Ala Asn His Met Gly Asn Gly Gly Ile Ser Thr Leu Ser Pro Pro Pro
    130                 135                 140 ttg aac cag gag agt tcc tat cac tcc aaa tgc aac atc gac tac agc     480
Leu Asn Gln Glu Ser Ser Tyr His Ser Lys Cys Asn Ile Asp Tyr Ser
145                 150                 155                 160 agc caa aac agc atc gag aat tgc tgg atc gct gac ctg ccc gac ctc     528
Ser Gln Asn Ser Ile Glu Asn Cys Trp Ile Ala Asp Leu Pro Asp Leu
                165                 170                 175
```

```
gtc acc acc gac aac acc atc cgc gat gtc ttc aag gac tgg atc gcc      576
Val Thr Thr Asp Asn Thr Ile Arg Asp Val Phe Lys Asp Trp Ile Ala
        180                 185                 190 aac ctc acc acc acc tac tcc ttc gac ggc ctc cgc gtc gac acc gtc      624
Asn Leu Thr Thr Thr Tyr Ser Phe Asp Gly Leu Arg Val Asp Thr Val
            195                 200                 205 aag cat gta gag aag gac ttt tgg ccg ggc ttc gtc gag gct gcc ggc      672
Lys His Val Glu Lys Asp Phe Trp Pro Gly Phe Val Glu Ala Ala Gly
    210                 215                 220 atg tat gcc atc ggc gag gtt ctc gat ggc ggc acc tcc tac gtt gcc      720
Met Tyr Ala Ile Gly Glu Val Leu Asp Gly Gly Thr Ser Tyr Val Ala
225                 230                 235                 240 ggc tac cag agc gtg atg cca ggc ctt ctc aac tat ccc atg tac tat      768
Gly Tyr Gln Ser Val Met Pro Gly Leu Leu Asn Tyr Pro Met Tyr Tyr
                245                 250                 255 cct ctc atc cgc acc ttt acc cag ggc gcc tcc ttc aac gac ttc gtc      816
Pro Leu Ile Arg Thr Phe Thr Gln Gly Ala Ser Phe Asn Asp Phe Val
            260                 265                 270 aac agt cac aac gag gtt ggt tcc gga ttc tcc gat ccc acc ctc ctc      864
Asn Ser His Asn Glu Val Gly Ser Gly Phe Ser Asp Pro Thr Leu Leu
    275                 280                 285 ggc acc ttc atc gac aac cac gac cag cag cgc ttc ctc tac aag aac      912
Gly Thr Phe Ile Asp Asn His Asp Gln Gln Arg Phe Leu Tyr Lys Asn
290                 295                 300 agc gac cac gcc ctc ttg aag aac gct ctg gcc tac gtg atc ctt ggc      960
Ser Asp His Ala Leu Leu Lys Asn Ala Leu Ala Tyr Val Ile Leu Gly
305                 310                 315                 320 cga ggt atc cca atc gtg tac tac ggc acc gag caa gcc tac ggc ggt     1008
Arg Gly Ile Pro Ile Val Tyr Tyr Gly Thr Glu Gln Ala Tyr Gly Gly
                325                 330                 335 ggt gac gac ccg gcg aac cgc gag gac ctc tgg cga agc ggc tac tcc     1056
Gly Asp Asp Pro Ala Asn Arg Glu Asp Leu Trp Arg Ser Gly Tyr Ser
            340                 345                 350 acc acc tcc gag ata tac acc acc atc tcg ggc cta tcc tcc gct cgc     1104
Thr Thr Ser Glu Ile Tyr Thr Thr Ile Ser Gly Leu Ser Ser Ala Arg
    355                 360                 365 aaa tcc gcc ggc ggc ctc cca ggc aac gac cac tcc cac ctc tac acc     1152
Lys Ser Ala Gly Gly Leu Pro Gly Asn Asp His Ser His Leu Tyr Thr
370                 375                 380 acc aac aac gcg tac gcc tgg tcc cgc gcg gac ggg aag gtg atc gcg     1200
Thr Asn Asn Ala Tyr Ala Trp Ser Arg Ala Asp Gly Lys Val Ile Ala
385                 390                 395                 400 ttg gtg acc aac gcc ggc ggc tcc gac acc agc acc cac tgc ttc aac     1248
Leu Val Thr Asn Ala Gly Gly Ser Asp Thr Ser Thr His Cys Phe Asn
                405                 410                 415 acc aag aaa ccg agc ggc acg cgc tgg acc agc gtc ctc cgc agc ggc     1296
Thr Lys Lys Pro Ser Gly Thr Arg Trp Thr Ser Val Leu Arg Ser Gly
            420                 425                 430 gga acc agc tac acc gcc gac ggc aac ggc caa atc tgc atc cag atc     1344
Gly Thr Ser Tyr Thr Ala Asp Gly Asn Gly Gln Ile Cys Ile Gln Ile
    435                 440                 445 caa aac ggc ggg ccc gag gca atc gtc ctc tcc acc ggc acc ggc acc     1392
Gln Asn Gly Gly Pro Glu Ala Ile Val Leu Ser Thr Gly Thr Gly Thr
450                 455                 460 gaa acc aca tcc agc gcc acc acc tcc cca acc gcc ggc tgc ccc tcc     1440
Glu Thr Thr Ser Ser Ala Thr Thr Ser Pro Thr Ala Gly Cys Pro Ser
465                 470                 475                 480 acc gtc tcc gtc aca ttc acc aac ctc gtc aca acc cag gtc ggc gac     1488
Thr Val Ser Val Thr Phe Thr Asn Leu Val Thr Thr Gln Val Gly Asp
                485                 490                 495
```

```
acc atc aaa gtc acc ggc aac gtc tcg cag ctg ggc aac tgg aac cct    1536
Thr Ile Lys Val Thr Gly Asn Val Ser Gln Leu Gly Asn Trp Asn Pro
            500                 505                 510 tcc tcc gcc ccc gcc tta tcc gca acc gga tac acg gcc agc aac ccc    1584
Ser Ser Ala Pro Ala Leu Ser Ala Thr Gly Tyr Thr Ala Ser Asn Pro
        515                 520                 525 aaa tgg agc gga acc gtc aag ttg ccc gcc ggc tcg acg gtg cag tat    1632
Lys Trp Ser Gly Thr Val Lys Leu Pro Ala Gly Ser Thr Val Gln Tyr
530                 535                 540 aag ttt gtg aag gtc gct agc ggg ggt ggc gcc gtg act tgg gag agc    1680
Lys Phe Val Lys Val Ala Ser Gly Gly Gly Ala Val Thr Trp Glu Ser
545                 550                 555                 560 gat ccc aac agg agt tat agc gtt cct agt tgt cag gct agc gcg act    1728
Asp Pro Asn Arg Ser Tyr Ser Val Pro Ser Cys Gln Ala Ser Ala Thr
            565                 570                 575 gtt gat tcg agc tgg aag taa                                        1749
Val Asp Ser Ser Trp Lys
            580

<210> SEQ ID NO 179
<211> LENGTH: 582
<212> TYPE: PRT
<213> ORGANISM: Valsaria spartii

<400> SEQUENCE: 179

Met Gln Phe Leu Cys Ala Leu Ala Ala Leu Leu Cys Phe Pro Ser Gln
1               5                   10                  15

Leu Leu Ala Ala Ser Asn Ala Asp Trp Lys Ser Arg Asn Ile Tyr Phe
            20                  25                  30

Ala Leu Thr Asp Arg Val Ala Gly Pro Thr Gly Gly Ser Cys Gly Asn
        35                  40                  45

Leu Gly Asn Tyr Cys Gly Gly Thr Trp Asn Gly Leu Thr Asp Lys Leu
    50                  55                  60

Asp Tyr Ile Gln Gly Met Gly Phe Asp Ala Ile Trp Ile Thr Pro Val
65                  70                  75                  80

Ile Lys Asn Ser Pro Gly Gly Tyr His Gly Tyr Trp Ala Gln Asp Leu
                85                  90                  95

Tyr Ser Val Asn Glu Asn Tyr Gly Thr Ala Gln Asp Leu Lys Asp Phe
            100                 105                 110

Val Asn Ala Ala His Ala Lys Gly Ile Tyr Val Met Val Asp Val Val
        115                 120                 125

Ala Asn His Met Gly Asn Gly Gly Ile Ser Thr Leu Ser Pro Pro Pro
    130                 135                 140

Leu Asn Gln Glu Ser Ser Tyr His Ser Lys Cys Asn Ile Asp Tyr Ser
145                 150                 155                 160

Ser Gln Asn Ser Ile Glu Asn Cys Trp Ile Ala Asp Leu Pro Asp Leu
                165                 170                 175

Val Thr Thr Asp Asn Thr Ile Arg Asp Val Phe Lys Asp Trp Ile Ala
            180                 185                 190

Asn Leu Thr Thr Thr Tyr Ser Phe Asp Gly Leu Arg Val Asp Thr Val
        195                 200                 205

Lys His Val Glu Lys Asp Phe Trp Pro Gly Phe Val Glu Ala Ala Gly
    210                 215                 220

Met Tyr Ala Ile Gly Glu Val Leu Asp Gly Thr Ser Tyr Val Ala
225                 230                 235                 240

Gly Tyr Gln Ser Val Met Pro Gly Leu Leu Asn Tyr Pro Met Tyr Tyr
                245                 250                 255
```

-continued

```
Pro Leu Ile Arg Thr Phe Thr Gln Gly Ala Ser Phe Asn Asp Phe Val
            260                 265                 270
Asn Ser His Asn Glu Val Gly Ser Gly Phe Ser Asp Pro Thr Leu Leu
        275                 280                 285
Gly Thr Phe Ile Asp Asn His Asp Gln Gln Arg Phe Leu Tyr Lys Asn
        290                 295                 300
Ser Asp His Ala Leu Leu Lys Asn Ala Leu Ala Tyr Val Ile Leu Gly
305                 310                 315                 320
Arg Gly Ile Pro Ile Val Tyr Tyr Gly Thr Glu Gln Ala Tyr Gly Gly
                325                 330                 335
Gly Asp Asp Pro Ala Asn Arg Glu Asp Leu Trp Arg Ser Gly Tyr Ser
                340                 345                 350
Thr Thr Ser Glu Ile Tyr Thr Thr Ile Ser Gly Leu Ser Ser Ala Arg
            355                 360                 365
Lys Ser Ala Gly Gly Leu Pro Gly Asn Asp His Ser His Leu Tyr Thr
        370                 375                 380
Thr Asn Asn Ala Tyr Ala Trp Ser Arg Ala Asp Gly Lys Val Ile Ala
385                 390                 395                 400
Leu Val Thr Asn Ala Gly Gly Ser Asp Thr Ser Thr His Cys Phe Asn
                405                 410                 415
Thr Lys Lys Pro Ser Gly Thr Arg Trp Thr Ser Val Leu Arg Ser Gly
                420                 425                 430
Gly Thr Ser Tyr Thr Ala Asp Gly Asn Gly Gln Ile Cys Ile Gln Ile
            435                 440                 445
Gln Asn Gly Gly Pro Glu Ala Ile Val Leu Ser Thr Gly Thr Gly Thr
        450                 455                 460
Glu Thr Thr Ser Ser Ala Thr Thr Ser Pro Thr Ala Gly Cys Pro Ser
465                 470                 475                 480
Thr Val Ser Val Thr Phe Thr Asn Leu Val Thr Thr Gln Val Gly Asp
                485                 490                 495
Thr Ile Lys Val Thr Gly Asn Val Ser Gln Leu Gly Asn Trp Asn Pro
                500                 505                 510
Ser Ser Ala Pro Ala Leu Ser Ala Thr Gly Tyr Thr Ala Ser Asn Pro
            515                 520                 525
Lys Trp Ser Gly Thr Val Lys Leu Pro Ala Gly Ser Thr Val Gln Tyr
        530                 535                 540
Lys Phe Val Lys Val Ala Ser Gly Gly Gly Ala Val Thr Trp Glu Ser
545                 550                 555                 560
Asp Pro Asn Arg Ser Tyr Ser Val Pro Ser Cys Gln Ala Ser Ala Thr
                565                 570                 575
Val Asp Ser Ser Trp Lys
            580
```

ENZYMES FOR STARCH PROCESSING

CROSS-REFERENCE TO RELATED APPLICATIONS

This application is a continuation of U.S. application Ser. No. 11/316,535 filed on Dec. 22, 2005, now abandoned, which claims the benefit under 35 U.S.C. 119 of U.S. provisional application Nos. 60/638,614 and 60/650,612 filed Dec. 22, 2004 and Feb. 7, 2005, respectively, the contents of which are fully incorporated herein by reference.

CROSS-REFERENCE TO SEQUENCE LISTING

This application contains a Sequence Listing in computer readable form, which is incorporated herein by reference.

CROSS-REFERENCE TO DEPOSITED MICROORGANISMS

The present application refers to deposited microorganisms, which are fully incorporated herein by reference.

FIELD OF THE INVENTION

The present invention relates to polypeptides comprising a carbohydrate-binding module ("CBM") and an alpha-amylase catalytic domain. Furthermore, the invention relates to wild type alpha-amylases polypeptides comprising useful alpha-amylase catalytic domains and/or CBMs as well as to the catalytic domain sequences and/or CBM sequences. The invention also relates to the use of such polypeptides in a starch liquefaction process in which starch is degraded to smaller oligo- and/or polysaccharide fragments.

BACKGROUND OF THE INVENTION

A large number of enzymes and processes have been described for converting starch to starch hydrolysates, such as maltose, glucose or specialty syrups, either for use as sweeteners or as precursors for other saccharides such as fructose. Glucose may also be fermented to ethanol or other fermentation products, such as citric acid, monosodium glutamate, gluconic acid, sodium gluconate, calcium gluconate, potassium gluconate, glucono delta lactone, or sodium erythorbate, itaconic acid, lactic acid, gluconic acid; ketones; amino acids, glutamic acid (sodium monoglutaminate), penicillin, tetracyclin; enzymes; vitamins, such as riboflavin, B12, beta-carotene or hormones.

Starch is a high molecular-weight polymer consisting of chains of glucose units. It usually consists of about 80% amylopectin and 20% amylose. Amylopectin is a branched polysaccharide in which linear chains of alpha-1,4 D-glucose residues are joined by alpha-1,6 glucosidic linkages.

Amylose is a linear polysaccharide built up of D-glucopyranose units linked together by alpha-1,4 glucosidic linkages. In the case of converting starch into a soluble starch hydrolysate, the starch is depolymerized. The conventional depolymerization process consists of a gelatinization step and two consecutive process steps, namely a liquefaction process and a saccharification process.

Granular starch consists of microscopic granules, which are insoluble in water at room temperature. When an aqueous starch slurry is heated, the granules swell and eventually burst, dispersing the starch molecules into the solution. During this "gelatinization" process there is a dramatic increase in viscosity. As the solids level is 30-40% in a typical industrial process, the starch has to be thinned or "liquefied" so that it can be handled. This reduction in viscosity is today mostly obtained by enzymatic degradation. During the liquefaction step, the long-chained starch is degraded into smaller branched and linear units (maltodextrins) by an alpha-amylase. The liquefaction process is typically carried out at about 105-110° C. for about 5 to 10 minutes followed by about 1-2 hours at about 95° C. The temperature is then lowered to 60° C., a glucoamylase (also known as GA or AMG) or a beta-amylase and optionally a debranching enzyme, such as an isoamylase or a pullulanase are added, and the saccharification process proceeds for about 24 to 72 hours.

It will be apparent from the above discussion that the conventional starch conversion process is very energy consuming due to the different requirements in terms of temperature during the various steps. It is thus desirable to be able to select and/or design the enzymes used in the process so that the overall process can be performed without having to gelatinize the starch. Such "raw starch" processes are U.S. Pat. Nos. 4,591,560, 4,727,026, and 4,009,074, EP Patent No. 0171218 and Danish patent application PA 2003 00949. The present invention discloses polypeptides designed for, inter alia, such processes and comprising an amino acid sequence of a CBM and an amino acid sequence of a starch degrading enzyme. Hybrid enzymes are the subject of WO 9814601, WO0077165, and PCT/US2004/020499

SUMMARY OF THE INVENTION

The present inventor have surprisingly discovered that by adding a carbohydrate-binding module (CBM) to certain alpha-amylases the activity and specificity can be altered thereby increasing the efficacy of various starch degrading processes, e.g., comprising degradation of raw, e.g., ungelatinized starch and/or gelatinized starch. Also by exchanging one CBM by another the activity and specificity can be altered.

Such hybrids consisting of a polypeptide having alpha-amylase activity and a carbohydrate binding module, primarily having affinity for starch, have the advantage over existing alpha-amylases that by selecting a catalytic domain with desire properties eg. the pH profile, the temperature profile, the oxidation resistance, the calcium stability, the substrate affinity or the product profile can be combined with a carbohydrate binding module with stronger or weaker binding affinities, e.g., specific affinities for amylose, specific affinities for amylopectin or affinities for specific structure in the carbohydrate. Thus the invention relates to hybrids having altered properties relative to the alpha-amylase without the CBM and/or relative to prior art amylases, such as having increased stability and/or activity at low pH, e.g., at pH below 4, such as at 3.5, increased activity towards granular starch, and/or increased degradation of granular starch at low pH even in the absence of glucoamylase or at low glucoamylase levels, and/or with altered product profile.

Due to the superior hydrolysis activity of these polypeptide the overall starch conversion process can be performed without having to gelatinize the starch, i.e., the polypeptides hydrolyses granular starch in a raw starch process as well as fully or partially gelatinized starch in a traditional starch process.

Accordingly the invention provides in a first aspect a polypeptide comprising a first amino acid sequence comprising a catalytic module having alpha-amylase activity and a second amino acid sequence comprising a carbohydrate-binding module, wherein said second amino acid sequence has at least 60% homology to any amino acid sequence selected from the group consisting of SEQ ID NO: 52, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 109, SEQ ID NO: 137, SEQ ID NO: 139, SEQ ID NO: 141 and SEQ ID NO: 143.

In a second aspect the invention provides a polypeptide having alpha-amylase activity, selected from the group consisting of: (a) a polypeptide having an amino acid sequence which has at least 75% homology with amino acids for the mature polypeptide selected from the group consisting of amino acids 1-441 in SEQ ID NO: 14, as amino acids 1-471 in SEQ ID NO: 18, as amino acids 1-450 in SEQ ID NO: 20, as amino acids 1-445 in SEQ ID NO: 22, as amino acids 1-498 in SEQ ID NO: 26, as amino acids 18-513 in SEQ ID NO: 28, as amino acids 1-507 in SEQ ID NO: 30, as amino acids 1-481 in SEQ ID NO: 32, as amino acids 1-495 in SEQ ID NO: 34, as amino acids 1-477 in SEQ ID NO: 38, as amino acids 1-449 in SEQ ID NO: 42, as amino acids 1-442 in SEQ ID NO: 115, as amino acids 1-441 in SEQ ID NO: 117, as amino acids 1-477 in SEQ ID NO: 125, as amino acids 1-446 in SEQ ID NO: 131, as amino acids 41-481 in SEQ ID NO: 157, as amino acids 22-626 in SEQ ID NO: 159, as amino acids 24-630 in SEQ ID NO: 161, as amino acids 27-602 in SEQ ID NO: 163, as amino acids 21-643 in SEQ ID NO: 165, as amino acids 29-566 in SEQ ID NO: 167, as amino acids 22-613 in SEQ ID NO: 169, as amino acids 21-463 in SEQ ID NO: 171, as amino acids 21-587 in SEQ ID NO: 173, as amino acids 30-773 in SEQ ID NO: 175, as amino acids 22-586 in SEQ ID NO: 177, as amino acids 20-582 in SEQ ID NO: 179, (b) a polypeptide which is encoded by a nucleotide sequence (i) which hybridizes under at least low stringency conditions with nucleotides 1-1326 in SEQ ID NO: 13, nucleotides 1-1413 in SEQ ID NO: 17, nucleotides 1-1350 in SEQ ID NO: 19, nucleotides 1-1338 in SEQ ID NO: 21, nucleotides 1-1494 in SEQ ID NO: 25, nucleotides 52-1539 in SEQ ID NO: 27, nucleotides 1-1521 in SEQ ID NO: 29, nucleotides 1-1443 in SEQ ID NO: 31, nucleotides 1-1485 in SEQ ID NO: 33, nucleotides 1-1431 in SEQ ID NO: 37, nucleotides 1-1347 in SEQ ID NO: 41, nucleotides 1-1326 in SEQ ID NO: 114, nucleotides 1-1323 in SEQ ID NO: 116, nucleotides 1-1431 in SEQ ID NO: 124, nucleotides 1-1338 in SEQ ID NO: 130, nucleotides 121-1443 in SEQ ID NO: 156, nucleotides 64-1878 in SEQ ID NO: 158, nucleotides 70-1890 in SEQ ID NO: 160, nucleotides 79-1806 in SEQ ID NO: 162, nucleotides 61-1929 in SEQ ID NO: 164, nucleotides 85-1701 in SEQ ID NO: 166, nucleotides 64-1842 in SEQ ID NO: 168, nucleotides 61-1389 in SEQ ID NO: 170, nucleotides 61-1764 in SEQ ID NO: 172, nucleotides 61-2322 in SEQ ID NO: 174, nucleotides 64-1761 in SEQ ID NO: 176, nucleotides 58-1749 in SEQ ID NO: 178, or (ii) which hybridizes under at least medium stringency conditions with the cDNA sequence contained in the polynucleotides shown as nucleotides 1-1326 in SEQ ID NO: 13, as nucleotides 1-1413 in SEQ ID NO: 17, as nucleotides 1-1350 in SEQ ID NO: 19, as nucleotides 1-1338 in SEQ ID NO: 21, as nucleotides 1-1494 in SEQ ID NO: 25, as nucleotides 52-1539 in SEQ ID NO: 27, as nucleotides 1-1521 in SEQ ID NO: 29, as nucleotides 1-1443 in SEQ ID NO: 31, as nucleotides 1-1485 in SEQ ID NO: 33, as nucleotides 1-1431 in SEQ ID NO: 37, as nucleotides 1-1347 in SEQ ID NO: 41, as nucleotides 1-1326 in SEQ ID NO: 114, as nucleotides 1-1323 in SEQ ID NO: 116, as nucleotides 1-1431 in SEQ ID NO: 124, as nucleotides 1-1338 in SEQ ID NO: 130, as nucleotides 121-1443 in SEQ ID NO: 156, as nucleotides 64-1878 in SEQ ID NO: 158, as nucleotides 70-1890 in SEQ ID NO: 160, as nucleotides 79-1806 in SEQ ID NO: 162, as nucleotides 61-1929 in SEQ ID NO: 164, as nucleotides 85-1701 in SEQ ID NO: 166, as nucleotides 64-1842 in SEQ ID NO: 168, as nucleotides 61-1389 in SEQ ID NO: 170, as nucleotides 61-1764 in SEQ ID NO: 172, as nucleotides 61-2322 in SEQ ID NO: 174, as nucleotides 64-1761 in SEQ ID NO: 176, as nucleotides 58-1749 in SEQ ID NO: 178, or (iii) a complementary strand of (i) or (ii); and (c) a variant comprising a conservative substitution, deletion, and/or insertion of one or more amino acids in an acid amino sequence selected from the group consisting of amino acids 1-441 in SEQ ID NO: 14, amino acids 1-471 in SEQ ID NO: 18, amino acids 1-450 in SEQ ID NO: 20, amino acids 1-445 in SEQ ID NO: 22, amino acids 1-498 in SEQ ID NO: 26, amino acids 18-513 in SEQ ID NO: 28, amino acids 1-507 in SEQ ID NO: 30, amino acids 1-481 in SEQ ID NO: 32, amino acids 1-495 in SEQ ID NO: 34, amino acids 1-477 in SEQ ID NO: 38, amino acids 1-449 in SEQ ID NO: 42, amino acids 1-442 in SEQ ID NO: 115, amino acids 1-441 in SEQ ID NO: 117, amino acids 1-477 in SEQ ID NO: 125, amino acids 1-446 in SEQ ID NO: 131, amino acids 41-481 in SEQ ID NO: 157, amino acids 22-626 in SEQ ID NO: 159, amino acids 24-630 in SEQ ID NO: 161, amino acids 27-602 in SEQ ID NO: 163, amino acids 21-643 in SEQ ID NO: 165, amino acids 29-566 in SEQ ID NO: 167, amino acids 22-613 in SEQ ID NO: 169, amino acids 21-463 in SEQ ID NO: 171, amino acids 21-587 in SEQ ID NO: 173, amino acids 30-773 in SEQ ID NO: 175, amino acids 22-586 in SEQ ID NO: 177 and amino acids 20-582 in SEQ ID NO: 179.

In a second aspect the invention provides a polypeptide having carbohydrate-binding affinity, selected from the group consisting of: (a) i) a polypeptide comprising an amino acid sequence which has at least 60% homology with a sequence selected from the group consisting of amino acids 529-626 of SEQ ID NO: 159, amino acids 533-630 of SEQ ID NO: 161, amino acids 508-602 of SEQ ID NO: 163, amino acids 540-643 of SEQ ID NO: 165, amino acids 502-566 of SEQ ID NO: 167, amino acids 513-613 of SEQ ID NO: 169, 492-587 of SEQ ID NO: 173, amino acids 30-287 of SEQ ID NO: 175, amino acids 487-586 of SEQ ID NO: 177 and amino acids 482-582 of SEQ ID NO: 179; (b) a polypeptide which is encoded by a nucleotide sequence which hybridizes under low stringency conditions with a polynucleotide probe selected from the group consisting of (i) the complementary strand of a sequence selected from the group consisting of nucleotides 1585-1878 in SEQ ID NO: 158, nucleotides 1597-1890 in SEQ ID NO: 160, nucleotides 1522-1806 in SEQ ID NO: 162, nucleotides 1618-1929 in SEQ ID NO: 164, nucleotides 1504-1701 in SEQ ID NO: 166, nucleotides 1537-1842 in SEQ ID NO: 168, nucleotides 1474-1764 in SEQ ID NO: 172, nucleotides 61-861 in SEQ ID NO: 174, nucleotides 1459-1761 in SEQ ID NO: 176 and nucleotides 1444-1749 in SEQ ID NO: 178, (c) a fragment of (a) or (b) that has carbohydrate binding affinity.

In other aspects the invention provides uses of the polypeptide of the first, second and/or third aspect for saccharification, in a process comprising fermentation, in a starch conversion process, in a process for producing oligosaccharides, e.g., a process for producing maltodextrins or glucose and/or fructose syrups, in a process for producing fuel or drinking ethanol, for producing a beverage, and/or in a fermentation process for producing organic compounds, such as citric acid, ascorbic acid, lysine, glutamic acid.

In a further aspect the invention provides a composition comprising the polypeptide of the first, second and/or third aspect.

In a further aspect the invention provides a process for saccharifying starch, wherein a starch is treated with the polypeptide of the first, second and/or third aspect.

In a further aspect the invention provides a process comprising; a) contacting a starch with a polypeptide comprising a catalytic module having alpha-amylase activity and a carbohydrate-binding module, e.g., the polypeptide of the first, second and/or third aspect; b) incubating said starch with said polypeptide; c) fermenting to produce a fermentation product, d) optionally recovering the fermentation product, wherein an enzyme having glucoamylase activity is either absent or present in an amount of less than 0.5 AGU/g DS of starch substrate and wherein step a, b, c, and/or d may be performed separately or simultaneously.

In a further aspect the invention provides a process comprising; a) contacting a starch substrate with a yeast cell transformed to express a polypeptide comprising a catalytic module having alpha-amylase activity and a carbohydrate-binding module, e.g., the polypeptide of the first and/or second aspect; b) holding said starch substrate with said yeast; c) fermenting to produce ethanol; d) optionally recovering ethanol, wherein steps a), b), and c) are performed separately or simultaneously. In a preferred embodiment comprise holding the substrate with said yeast for a time and at a temperature sufficient to achieve conversion of at least 90% w/w of said starch substrate into fermentable sugars.

In a further aspect the invention provides a process of producing ethanol from starch-containing material by fermentation, said process comprises: (i) liquefying said starch-containing material with a polypeptide comprising a catalytic module having alpha-amylase activity and a carbohydrate-binding module, e.g., the polypeptide of the first and/or second aspect; (ii) saccharifying the liquefied mash obtained; (iii) fermenting the material obtained in step (ii) in the presence of a fermenting organism and optionally comprising recovery of the ethanol.

In further aspects the invention provides a DNA sequence encoding a polypeptide according to the first, second and/or third aspect, a DNA construct comprising said DNA sequence, a recombinant expression vector which carries said DNA construct, a host cell which is transformed with said DNA construct or said vector, said host cell, which is a microorganism, in particular a bacterium or a fungal cell, a yeast or a plant cell.

DETAILED DESCRIPTION OF THE INVENTION

The term "granular starch" is understood as raw uncooked starch, i.e., starch that has not been subjected to a gelatinization. Starch is formed in plants as tiny granules insoluble in water. These granules are preserved in starches at temperatures below the initial gelatinization temperature. When put in cold water, the grains may absorb a small amount of the liquid. Up to 50° C. to 70° C. the swelling is reversible, the degree of reversibility being dependent upon the particular starch. With higher temperatures an irreversible swelling called gelatinization begins.

The term "initial gelatinization temperature" is understood as the lowest temperature at which gelatinization of the starch commences. Starch heated in water begins to gelatinize between 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. In the context of this invention the initial gelatinization temperature of a given starch is the temperature at which birefringence is lost in 5% of the starch granules using the method described by Gorinstein. S. and Lii. C., Starch/Stärke, Vol. 44 (12) pp. 461-466 (1992).

The term "soluble starch hydrolysate" is understood as the soluble products of the processes of the invention and may comprise mono-, di-, and oligosaccharides, such as glucose, maltose, maltodextrins, cyclodextrins and any mixture of these. Preferably at least 90%, at least 91%, at least 92%, at least 93%, at least 94%, at least 95%, at least 96%, at least 97% or at least 98% of the dry solids of the granular starch is converted into a soluble starch hydrolysate.

The term polypeptide "homology" is understood as the degree of identity between two sequences indicating a derivation of the first sequence from the second. The homology may suitably be determined by means of computer programs known in the art such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-453. The following settings for amino acid sequence comparison are used: GAP creation penalty of 3.0 and GAP extension penalty of 0.1. The relevant part of the amino acid sequence for the homology determination is the mature polypeptide, i.e., without the signal peptide.

Suitable experimental conditions for determining hybridization at low, medium, or high stringency between a nucleotide probe and a homologous DNA or RNA sequence involves presoaking of the filter containing the DNA fragments or RNA to hybridize in 5×SSC (Sodium chloride/Sodium citrate, Sambrook et al. 1989) for 10 min, and pre-hybridization of the filter in a solution of 5×SSC, 5×Denhardt's solution (Sambrook et al. 1989), 0.5% SDS and 100 micrograms/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) Anal. Biochem. 132:6-13), 32P-dCTP-labeled (specific activity>1×109 cpm/microgram) probe for 12 hours at about 45° C. The filter is then washed twice for 30 minutes in 2×SSC, 0.5% SDS at about 55° C. (low stringency), more preferably at about 60° C. (medium stringency), still more preferably at about 65° C. (medium/high stringency), even more preferably at about 70° C. (high stringency), and even more preferably at about 75° C. (very high stringency).

Molecules to which the oligonucleotide probe hybridizes under these conditions are detected using an x-ray film.
Polypeptides The polypeptide of the invention may be a hybrid enzyme or the polypeptide may be a wild type enzyme which already comprises a catalytic module having alpha-amylase activity and a carbohydrate-binding module. The polypeptide of the invention may also be a variant of such a wild type enzyme. The hybrid may be produced by fusion of a first DNA sequence encoding a first amino acid sequences and a second DNA sequence encoding a second amino acid sequences, or the hybrid may be produced as a completely synthetic gene based on knowledge of the amino acid sequences of suitable CBMs, linkers and catalytic domains.

The terms "hybrid enzyme" or "hybrid polypeptide" is used herein to characterize those of the polypeptides of the invention that comprises a first amino acid sequence comprising at least one catalytic module having alpha-amylase activity and a second amino acid sequence comprising at least one carbohydrate-binding module wherein the first and the second are derived from different sources. The term "source" being understood as, e.g., but not limited to a parent enzyme, e.g., an amylase or glucoamylase, or other catalytic activity comprising a suitable catalytic module and/or a suitable CBM and/or a suitable linker.

The Enzyme classification numbers (EC numbers) are in accordance with the *Recommendations* (1992) *of the Nomenclature Committee of the International Union of Biochemistry and Molecular Biology*, Academic Press Inc, 1992.

Polypeptides as referred to herein include species comprising an amino acid sequence of an alpha-amylase enzyme (EC 3.2.1.1) linked (i.e., covalently bound) to an amino acid sequence comprising a carbohydrate-binding module (CBM).

CBM-containing hybrid enzymes, as well as detailed descriptions of the preparation and purification thereof, are known in the art [see, e.g., WO 90/00609, WO 94/24158 and WO 95/16782, as well as Greenwood et al. *Biotechnology and Bioengineering* 44 (1994) pp. 1295-1305]. They may, e.g., be prepared by transforming into a host cell a DNA construct comprising at least a fragment of DNA encoding the carbohydrate-binding module ligated, with or without a linker, to a DNA sequence encoding the polypeptide of interest, and growing the transformed host cell to express the fused gene. The CBM in a polypeptide of the invention may be positioned C-terminally, N-terminally or internally in polypeptide. In an embodiment a polypeptide may comprise more than one CBM, e.g., two CBMs; one positioned C-terminally, the other N-terminally or the two CBMs in tandem positioned C-terminally, N-terminally or internally. However, polypeptides with more than two CBMs are equally contemplated.

Alpha-Amylases of the Invention

The invention relates to alpha-amylase polypeptides useful as donors (parent amylases) of CBMs, linkers and/or catalytic modules. The polypeptide of the invention may be a wild type alpha-amylase enzyme (EC 3.2.1.1) or the polypeptide may also be a variant of such a wild type enzyme. Furthermore the polypeptide of the invention may be a fragment of such an enzyme, e.g., such as a catalytic domain, i.e., a fragment having alpha-amylase activity but which is separated from a CBM if such is present in the wild-type enzyme, or such as a CBM, i.e., a fragment having a carbohydrate binding module. It may also be a hybrid enzyme comprising a fragment of such an alpha-amylase enzyme, e.g., comprising a catalytic domain, a linker and/or a CBM derived from an alpha-amylase enzyme of the invention.

Furthermore, the polypeptide of the invention may be a fragment of such an enzyme, e.g., a fragment which still comprises a functional catalytic domain as well as a CBM if such is present in the wild type enzyme, or, e.g., a fragment of a wild-type enzyme, which wild-type enzyme does not comprise a CBM, and wherein said fragment comprises a functional catalytic domain.

Alpha-Amylase Enzymes:

The invention relates to novel polypeptides comprising a carbohydrate-binding module ("CBM") and having alpha-amylase activity. Such polypeptides may be derived from any organism, preferred are those of fungal or bacterial origin.

The alpha-amylases of the invention include alpha-amylases obtainable from a species within a genus selected from the list consisting of *Absidia, Acremonium, Coniochaeta, Coriolus, Cryptosporiopsis, Dichotomocladium, Dinemasporium, Diplodia, Fusarium, Gliocladium, Malbranchea, Meripilus, Necteria, Penicillium, Rhizomucor, Stereum, Streptomyces, Subulispora, Syncephalastrum, Thamindium, Thermoascus, Thermomyces, Trametes, Trichophaea* and *Valsaria*. The alpha-amylase may be derived from any genus, species or sequence listed in table 1.

Preferably the alpha-amylase is derived from any species selected from the group consisting of *Thermomyces lanuginosus*; in particular a polypeptide having the amino acids 1-441 in SEQ ID NO: 14, *Malbranchea* sp.; in particular a polypeptide having the amino acids 1-471 in SEQ ID NO: 18, *Rhizomucor pusillus*; in particular a polypeptide having the amino acids 1-450 in SEQ ID NO: 20, *Dichotomocladium hesseltinei*; in particular a polypeptide having the amino acids 1-445 in SEQ ID NO: 22, *Stereum* sp.; in particular a polypeptide having the amino acids 1-498 in SEQ ID NO: 26, *Trametes* sp.; in particular a polypeptide having the amino acids 18-513 in SEQ ID NO: 28, *Coriolus consors*; in particular a polypeptide having the amino acids 1-507 in SEQ ID NO: 30, *Dinemasporium* sp.; in particular a polypeptide having the amino acids 1-481 in SEQ ID NO: 32, *Cryptosporiopsis* sp.; in particular a polypeptide having the amino acids 1-495 in SEQ ID NO: 34, *Diplodia* sp.; in particular a polypeptide having the amino acids 1-477 in SEQ ID NO: 38, *Gliocladium* sp.; in particular a polypeptide having the amino acids 1-449 in SEQ ID NO: 42, *Nectria* sp.; in particular a polypeptide having the amino acids 1-442 in SEQ ID NO: 115, *Fusarium* sp.; in particular a polypeptide having the amino acids 1-441 in SEQ ID NO: 117, *Thermoascus auranticus*; in particular a polypeptide having the amino acids 1-477 in SEQ ID NO: 125, *Thamindium elegans*; in particular a polypeptide having the amino acids 1-446 in SEQ ID NO: 131, *Absidia cristata*; in particular a polypeptide having the amino acids 41-481 in SEQ ID NO: 157, *Acremonium* sp.; in particular a polypeptide having the amino acids 22-626 in SEQ ID NO: 159, *Coniochaeta* sp.; in particular a polypeptide having the amino acids 24-630 in SEQ ID NO: 161, *Meripilus giganteus*; in particular a polypeptide having the amino acids 27-602 in SEQ ID NO: 163, *Penicillium* sp.; in particular a polypeptide having the amino acids 21-643 in SEQ ID NO: 165, *Streptomyces limosus*; in particular a polypeptide having the amino acids 29-566 in SEQ ID NO: 167, *Subulispora procurvata*; in particular a polypeptide having the amino acids 22-613 in SEQ ID NO: 169, *Syncephalastrum racemosum*; in particular a polypeptide having the amino acids 21-463 in SEQ ID NO: 171, *Trametes currugata*; in particular a polypeptide having the amino acids 21-587 in SEQ ID NO: 173, *Trichophaea saccata*; in particular a polypeptide having the amino acids 30-773 in SEQ ID NO: 175, *Valsaria rubricosa*; in particular a polypeptide having the amino acids 22-586 in SEQ ID NO: 177 and *Valsaria spartii*; in particular a polypeptide having the amino acids 20-582 in SEQ ID NO: 179.

Also preferred are alpha-amylase amino acid sequences having at least 60%, at least 65%, at least 70%, at least 75%, at least 80%, at least 85%, at least 90%, at least 95%, or even at least 98% homology to the mature peptide of any of the aforementioned polypeptides. In another preferred embodiment the alpha-amylase amino acid sequence have an amino acid sequence which differs from any of the aforementioned amino acid sequences in no more than 10 positions, no more than 9 positions, no more than 8 positions, no more than 7 positions, no more than 6 positions, no more than 5 positions, no more than 4 positions, no more than 3 positions, no more than 2 positions, or even no more than 1 position.

Also preferred are alpha-amylase amino acid sequence encoded by a DNA sequence having at least 50%, at least 60%, at least 65%, at least 70%, at least 75%, at least 80%, at least 85%, at least 90%, at least 95%, or even at least 98% homology to any sequence selected from the group consisting of the polynucleotides shown as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 154 and SEQ ID NO: 156. SEQ ID NO: 13, SEQ ID NO: 17, SEQ ID NO: 19, SEQ ID NO: 21, SEQ ID NO: 25, SEQ ID NO: 27, SEQ ID NO: 29, SEQ ID NO: 31, SEQ ID NO: 33, SEQ ID NO: 37, SEQ ID NO: 41, SEQ ID NO: 114, SEQ ID NO: 116, SEQ ID NO: 124, SEQ ID NO: 130, SEQ ID NO: 156, SEQ ID NO: 158, SEQ ID NO: 160, SEQ ID NO: 162, SEQ ID NO: 164, SEQ ID NO: 166, SEQ ID NO: 168, SEQ ID NO: 170, SEQ ID NO: 172, SEQ ID NO: 174, SEQ ID NO: 176 and SEQ ID NO: 178. Further preferred is any alpha-amylase amino acid sequence encoded by a DNA sequence which hybridizes under low, medium, medium/high, high and/or very high stringency to any of the aforementioned alpha-amylase DNA sequences. Also preferred are DNA sequences encoding an alpha-amylase amino acid sequence and having at least 50%, at least 60%, at least 65%, at least 70%, at least 75%, at least 80%, at least 85%, at least 90%, at least 95%, at least 99%, or even 100% homology any of the aforementioned alpha-amylase DNA sequences.

Alpha-Amylase Catalytic Domains:

In one embodiment the invention relates to catalytic domains derived from polypeptides comprising a carbohydrate-binding module ("CBM") and an having alpha-amylase activity, such as catalytic domains derived from a polypeptide selected from the alpha-amylases shown in SEQ ID NO: 14, SEQ ID NO: 18, SEQ ID NO: 20, SEQ ID NO: 22, SEQ ID NO: 26, SEQ ID NO: 28, SEQ ID NO: 30, SEQ ID NO: 32, SEQ ID NO: 34, SEQ ID NO: 38, SEQ ID NO: 42, SEQ ID NO: 115, SEQ ID NO: 117, SEQ ID NO: 125, SEQ ID NO: 131, SEQ ID NO: 157, SEQ ID NO: 159, SEQ ID NO: 161, SEQ ID NO: 163, SEQ ID NO: 165, SEQ ID NO: 167, SEQ ID NO: 169, SEQ ID NO: 171, SEQ ID NO: 173, SEQ ID NO: 175, SEQ ID NO: 177 and SEQ ID NO: 179. Preferred are the catalytic domains shown in the amino acids 1-441 in SEQ ID NO: 14, the amino acids 1-471 in SEQ ID NO: 18, the amino acids 1-450 in SEQ ID NO: 20, the amino acids 1-445 in SEQ ID NO: 22, the amino acids 1-498 in SEQ ID NO: 26, the amino acids 18-513 in SEQ ID NO: 28, the amino acids 1-507 in SEQ ID NO: 30, the amino acids 1-481 in SEQ ID NO: 32, the amino acids 1-495 in SEQ ID NO: 34, the amino acids 1-477 in SEQ ID NO: 38, the amino acids 1-449 in SEQ ID NO: 42, the amino acids 1-442 in SEQ ID NO: 115, the amino acids 1-441 in SEQ ID NO: 117, the amino acids 1-477 in SEQ ID NO: 125, the amino acids 1-446 in SEQ ID NO: 131, the amino acids 41-481 in SEQ ID NO: 157, the amino acids 22-502 in SEQ ID NO: 159, the amino acids 24-499 in SEQ ID NO: 161, the amino acids 27-492 in SEQ ID NO: 163, the amino acids 21-496 in SEQ ID NO: 165, the amino acids 29-501 in SEQ ID NO: 167, the amino acids 22-487 in SEQ ID NO: 169, the amino acids 21-463 in SEQ ID NO: 171, the amino acids 21-477 in SEQ ID NO: 173, the amino acids 288-773 in SEQ ID NO: 175, the amino acids 22-471 in SEQ ID NO: 177 and the amino acids 20-470 in SEQ ID NO: 179. Also preferred are catalytic domain sequences having at least 60%, at least 65%, at least 70%, at least 75%, at least 80%, at least 85%, at least 90% or even at least 95% homology to any of the aforementioned catalytic domain sequences. In another preferred embodiment the catalytic domain sequence have an amino acid sequence which differs from any of the aforementioned catalytic domain sequences in no more than 10 positions, no more than 9 positions, no more than 8 positions, no more than 7 positions, no more than 6 positions, no more than 5 positions, no more than 4 positions, no more than 3 positions, no more than 2 positions, or even no more than 1 position.

Also preferred are catalytic domain amino acid sequence encoded by a DNA sequence having at least 50%, at least 60%, at least 65%, at least 70%, at least 75%, at least 80%, at least 85%, at least 90% or even at least 95% homology to any sequence selected from the group consisting of the polynucleotides shown as the nucleotides 1-1326 in SEQ ID NO: 13, nucleotides 1-1413 in SEQ ID NO: 17, nucleotides 1-1350 in SEQ ID NO: 19, nucleotides 1-1338 in SEQ ID NO: 21, nucleotides 1-1494 in SEQ ID NO: 25, nucleotides 52-1539 in SEQ ID NO: 27, nucleotides 1-1521 in SEQ ID NO: 29, nucleotides 1-1443 in SEQ ID NO: 31, nucleotides 1-1485 in SEQ ID NO: 33, nucleotides 1-1431 in SEQ ID NO: 37, nucleotides 1-1347 in SEQ ID NO: 41, nucleotides 1-1326 in SEQ ID NO: 114, nucleotides 1-1323 in SEQ ID NO: 116, nucleotides 1-1431 in SEQ ID NO: 124, nucleotides 1-1338 in SEQ ID NO: 130, nucleotides 121-1443 in SEQ ID NO: 156, nucleotides 64-1506 in SEQ ID NO: 158, nucleotides 70-1497 in SEQ ID NO: 160, nucleotides 79-1476 in SEQ ID NO: 162, nucleotides 61-1488 in SEQ ID NO: 164, nucleotides 85-1503 in SEQ ID NO: 166, nucleotides 64-1461 in SEQ ID NO: 168, nucleotides 61-1389 in SEQ ID NO: 170, nucleotides 61-1431 in SEQ ID NO: 172, nucleotides 862-2322 in SEQ ID NO: 174, nucleotides 64-1413 in SEQ ID NO: 176 and nucleotides 58-1410 in SEQ ID NO: 178. Further preferred is any catalytic domain amino acid sequence encoded by a DNA sequence hybridizing under low, medium, medium/high, high and/or very high stringency to any of the aforementioned DNA sequences. Also preferred are DNA sequences encoding a catalytic domain amino acid sequence and having at least 50%, at least 60%, at least 65%, at least 70%, at least 75%, at least 80%, at least 85%, at least 90%, at least 95%, at least 99%, or even 100% homology any of the aforementioned catalytic domain DNA sequences.

Linker Sequences:

In one embodiment the invention relates to linker sequences derived from polypeptides comprising a carbohydrate-binding module ("CBM") and an having alpha-amylase activity. Preferred are a linker amino acid sequences selected from the group consisting of the shown as amino acids 503-528 in SEQ ID NO: 159, amino acids 500-532 in SEQ ID NO: 161, amino acids 493-507 in SEQ ID NO: 163, amino acids 497-539 in SEQ ID NO: 165, amino acids 488-512 in SEQ ID NO: 169 in 478-491 in SEQ ID NO: 173, amino acids 472-486 in SEQ ID NO: 177 and amino acids 471-481 in SEQ ID NO: 179. Also preferred are linker amino acid sequences having at least 60%, at least 65%, at least 70%, at least 75%, at least 80%, at least 85%, at least 90% or even at least 95% homology to any of the aforementioned linker sequences. In another preferred embodiment the linker sequence have an amino acid sequence which differs from any of the aforementioned linker sequences in no more than 10 positions, no more than 9 positions, no more than 8 positions, no more than 7 positions, no more than 6 positions, no more than 5 positions, no more than 4 positions, no more than 3 positions, no more than 2 positions, or even no more than 1 position.

Carbohydrate-Binding Modules:

In one embodiment the invention relates to CBMs derived from polypeptides comprising a carbohydrate-binding module ("CBM") and an having alpha-amylase activity, said CBM derived from a polypeptide selected from the alpha-amylases shown in SEQ ID NO: 14, SEQ ID NO: 18, SEQ ID NO: 20, SEQ ID NO: 22, SEQ ID NO: 26, SEQ ID NO: 28, SEQ ID NO: 30, SEQ ID NO: 32, SEQ ID NO: 34, SEQ ID NO: 38, SEQ ID NO: 42, SEQ ID NO: 115, SEQ ID NO: 117, SEQ ID NO: 125, SEQ ID NO: 131, SEQ ID NO: 157, SEQ ID NO: 159, SEQ ID NO: 161, SEQ ID NO: 163, SEQ ID NO: 165, SEQ ID NO: 167, SEQ ID NO: 169, SEQ ID NO: 171, SEQ ID NO: 173, SEQ ID NO: 175, SEQ ID NO: 177 and SEQ ID NO: 179. Preferred are a CBM amino acid sequence selected from the group consisting of the sequence having the amino acids 529-626 in SEQ ID NO: 159, the amino acids 533-630 in SEQ ID NO: 161, the amino acids 508-602 in SEQ ID NO: 163, the amino acids 540-643 in SEQ ID NO: 165, the amino acids 502-566 in SEQ ID NO: 167, the amino acids 513-613 in SEQ ID NO: 169, the amino acids 492-587 in SEQ ID NO: 173, the amino acids 30-287 in SEQ ID NO: 175, the amino acids 487-586 in SEQ ID NO: 177 and the amino acids 482-582 in SEQ ID NO: 179. Also preferred are CBM amino acid sequences having at least 60%, at least 65%, at least 70%, at least 75%, at least 80%, at least 85%, at least 90% or even at least 95% homology to any of the aforementioned CBM amino acid sequences. In another preferred embodiment the CBM sequence have an amino acid sequence which differs from any of the aforementioned CBM sequences in no more than 10 positions, no more than 9 positions, no more than 8 positions, no more than 7 positions, no more than 6 positions, no more than 5 positions, no more than 4 positions, no more than 3 positions, no more than 2 positions, or even no more than 1 position.

Also preferred are a CBM amino acid sequence encoded by a DNA sequence having at least 50%, at least 60%, at least 65%, at least 70%, at least 75%, at least 80%, at least 85%, at least 90% or even at least 95% homology to any sequence selected from the group consisting of the polynucleotides shown as nucleotides 1585-1878 in SEQ ID NO: 158, nucleotides 1597-1890 in SEQ ID NO: 160, nucleotides 1522-1806 in SEQ ID NO: 162, nucleotides 1618-1929 in SEQ ID NO: 164, nucleotides 1504-1701 in SEQ ID NO: 166, nucleotides 1537-1842 in SEQ ID NO: 168, nucleotides 1474-1764 in SEQ ID NO: 172, nucleotides 61-861 in SEQ ID NO: 174, nucleotides 1459-1761 in SEQ ID NO: 176 and nucleotides 1444-1749 in SEQ ID NO: 178. SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 154 and SEQ ID NO: 156. Further preferred is any CBM amino acid sequence encoded by a DNA sequence hybridizing under low, medium, medium/high, high and/or very high stringency to the complementary DNA sequence of any of the aforementioned CBM DNA sequences. Also preferred are DNA sequences encoding a CBM amino acid sequence and having at least 50%, at least 60%, at least 65%, at least 70%, at least 75%, at least 80%, at least 85%, at least 90%, at least 95%, at least 99%, or even 100% homology any of the aforementioned CBM DNA sequences.

The DNA sequences shown as nucleotides 1504-1701 in SEQ ID NO: 166 and nucleotides 61-861 in SEQ ID NO: 174 and the encoded amino acid sequences comprise in addition to the CBD also a linker sequence.

TABLE 1

Alpha-amylases used as catalytic doman and CBM donors. Positions for catalytic domain, linker and CBM sequences.

| Species | Strain No | SEQ ID NO | Mature peptide | Catalytic domain | Linker | CBM | Type |
|---|---|---|---|---|---|---|---|
| *Absidia cristata* | NN047841 | SEQ ID NO: 156 | 121-1443 | 121-1443 | | | Dna |
| *Absidia cristata* | NN047841 | SEQ ID NO: 157 | 41-481 | 41-481 | | | Aa |
| *Acremonium* sp. | NN045509 | SEQ ID NO: 158 | 64-1878 | 64-1506 | 1507-1584 | 1585-1878 | Dna |
| *Acremonium* sp. | NN045509 | SEQ ID NO: 159 | 22-626 | 22-502 | 503-528 | 529-626 | Aa |
| *Coniochaeta* sp. | NN047603 | SEQ ID NO: 160 | 70-1890 | 70-1497 | 1498-1596 | 1597-1890 | Dna |
| *Coniochaeta* sp. | NN047603 | SEQ ID NO: 161 | 24-630 | 24-499 | 500-532 | 533-630 | Aa |
| *Coriolus consors* | NN048884 | SEQ ID NO: 29 | 1-1521 | 1-1521 | | | Dna |
| *Coriolus consors* | NN048884 | SEQ ID NO: 30 | 1-507 | 1-507 | | | Aa |
| *Cryptosporiopsis* sp. | NN047117 | SEQ ID NO: 33 | 1-1485 | 1-1485 | | | Dna |
| *Cryptosporiopsis* sp. | NN047117 | SEQ ID NO: 34 | 1-495 | 1-495 | | | Aa |
| *Dichotomocladium hesseltinei* | NN103100 | SEQ ID NO: 21 | 1-1338 | 1-1338 | | | Dna |
| *Dichotomocladium hesseltinei* | NN103100 | SEQ ID NO: 22 | 1-445 | 1-445 | | | Aa |
| *Dinemasporium* sp. | NN043050 | SEQ ID NO: 31 | 1-1443 | 1-1443 | | | Dna |
| *Dinemasporium* sp. | NN043050 | SEQ ID NO: 32 | 1-481 | 1-481 | | | Aa |
| *Diplodia* sp. | NN047649 | SEQ ID NO: 37 | 1-1431 | 1-1431 | | | Dna |
| *Diplodia* sp. | NN047649 | SEQ ID NO: 38 | 1-477 | 1-477 | | | Aa |
| *Fusarium* sp. | NN046318 | SEQ ID NO: 116 | 1-1323 | 1-1323 | | | Dna |
| *Fusarium* sp. | NN046318 | SEQ ID NO: 117 | 1-441 | 1-441 | | | Aa |
| *Gliocladium* sp. | NN047683 | SEQ ID NO: 41 | 1-1347 | 1-1347 | | | Dna |
| *Gliocladium* sp. | NN047683 | SEQ ID NO: 42 | 1-449 | 1-449 | | | Aa |
| *Malbranchea* sp. | NN046840 | SEQ ID NO: 17 | 1-1413 | 1-1413 | | | Dna |
| *Malbranchea* sp. | NN046840 | SEQ ID NO: 18 | 1-471 | 1-471 | | | Aa |
| *Meripilus giganteus* | NN006040 | SEQ ID NO: 162 | 79-1806 | 79-1476 | 1477-1521 | 1522-1806 | Dna |
| *Meripilus giganteus* | NN006040 | SEQ ID NO: 163 | 27-602 | 27-492 | 493-507 | 508-602 | Aa |
| *Nectria* sp. | NN047728 | SEQ ID NO: 114 | 1-1326 | 1-1326 | | | Dna |
| *Nectria* sp. | NN047728 | SEQ ID NO: 115 | 1-442 | 1-442 | | | Aa |
| *Penicillium* sp. | NN050730 | SEQ ID NO: 164 | 61-1929 | 61-1488 | 1489-1617 | 1618-1929 | Dna |
| *Penicillium* sp. | NN050730 | SEQ ID NO: 165 | 21-643 | 21-496 | 497-539 | 540-643 | Aa |
| *Rhizomucor pusillus* | NN101459 | SEQ ID NO: 19 | 1-1350 | 1-1350 | | | Dna |
| *Rhizomucor pusillus* | NN101459 | SEQ ID NO: 20 | 1-450 | 1-450 | | | Aa |
| *Stereum* sp. | NN048875 | SEQ ID NO: 25 | 1-1494 | 1-1494 | | | Dna |
| *Stereum* sp. | NN048875 | SEQ ID NO: 26 | 1-498 | 1-498 | | | Aa |
| *Streptomyces limosus* | ATCC19778 | SEQ ID NO: 166 | 85-1701 | 85-1503 | | [1)]1504-1701 | Dna |
| *Streptomyces limosus* | ATCC19778 | SEQ ID NO: 167 | 29-566 | 29-501 | | [1)]502-566 | Aa |

TABLE 1-continued

Alpha-amylases used as catalytic doman and CBM donors. Positions for catalytic domain, linker and CBM sequences.

| Species | Strain No | SEQ ID NO | Mature peptide | Catalytic domain | Linker | CBM | Type |
|---|---|---|---|---|---|---|---|
| Subulispora procurvata | NN042875 | SEQ ID NO: 169 | 22-613 | 22-487 | 488-512 | 513-613 | Aa |
| Subulispora provurvata | NN042875 | SEQ ID NO: 168 | 64-1842 | 64-1461 | 1462-1536 | 1537-1842 | Dna |
| Syncephalastrum racemosum | NN047920 | SEQ ID NO: 170 | 61-1389 | 61-1389 | | | Dna |
| Syncephalastrum racemosum | NN047920 | SEQ ID NO: 171 | 21-463 | 21-463 | | | Aa |
| Thamindium elegans | NN050372 | SEQ ID NO: 130 | 1-1338 | 1-1338 | | | Dna |
| Thamindium elegans | NN050372 | SEQ ID NO: 131 | 1-446 | 1-446 | | | Aa |
| Thermoascus auranticus | NN047354 | SEQ ID NO: 124 | 1-1431 | 1-1431 | | | Dna |
| Thermoascus auranticus | NN047354 | SEQ ID NO: 125 | 1-477 | 1-477 | | | Aa |
| Thermomyces lanuginosus | NN044958 | SEQ ID NO: 13 | 1-1326 | 1-1326 | | | Dna |
| Thermomyces lanuginosus | NN044958 | SEQ ID NO: 14 | 1-441 | 1-441 | | | Aa |
| Trametes currugata | CGMCC5.61 | SEQ ID NO: 172 | 61-1764 | 61-1431 | 1432-1473 | 1474-1764 | Dna |
| Trametes currugata | CGMCC5.61 | SEQ ID NO: 173 | 21-587 | 21-477 | 478-491 | 492-587 | Aa |
| Trametes sp. | NN048968 | SEQ ID NO: 27 | 52-1539 | 52-1539 | | | Dna |
| Trametes sp. | NN048968 | SEQ ID NO: 28 | 18-513 | 18-513 | | | aa |
| Trichophaea saccata | NN102806 | SEQ ID NO: 174 | 61-2322 | 862-2322 | | [1]61-861 | Dna |
| Trichophaea saccata | NN102806 | SEQ ID NO: 175 | 30-773 | 288-773 | | [1]30-287 | Aa |
| Valsaria rubricosa | NN046835 | SEQ ID NO: 176 | 64-1761 | 64-1413 | 1414-1458 | 1459-1761 | Dna |
| Valsaria rubricosa | NN046835 | SEQ ID NO: 177 | 22-586 | 22-471 | 472-486 | 487-586 | Aa |
| Valsaria spartii | NN050508 | SEQ ID NO: 178 | 58-1749 | 58-1410 | 1411-1443 | 1444-1749 | Dna |
| Valsaria spartii | NN050508 | SEQ ID NO: 179 | 20-582 | 20-470 | 471-481 | 482-582 | Aa |

[1]The sequence comprises both CBM and linker

The alpha-amylase polypeptides may be applied in starch degradation processes and/or used as donors of catalytic domain and/or CBM for a hybrid polypeptide. A preferred polypeptide of the invention, e.g., a hybrid polypeptide, comprises a first amino acid sequence comprising a catalytic module having alpha-amylase activity and a second amino acid sequence comprising a carbohydrate-binding module, wherein said second amino acid sequence has at least 60%, at least 70%, at least 80%, at least 85%, at least 90%, such as at least 95% homology to any amino acid sequence selected from the group consisting of amino acids 529-626 in SEQ ID NO: 159, the amino acids 533-630 in SEQ ID NO: 161, the amino acids 508-602 in SEQ ID NO: 163, the amino acids 540-643 in SEQ ID NO: 165, the amino acids 502-566 in SEQ ID NO: 167, the amino acids 513-613 in SEQ ID NO: 169, the amino acids 492-587 in SEQ ID NO: 173, the amino acids 30-287 in SEQ ID NO: 175, the amino acids 487-586 in SEQ ID NO: 177 and the amino acids 482-582 in SEQ ID NO: 179. Further preferred are polypeptides, e.g., hybrid polypeptides, wherein said first amino acid sequence has at least 60%, at least 70%, at least 80%, at least 85%, at least 90%, such as at least 95% homology to any amino acid sequence selected from the group consisting of amino acids 1-441 in SEQ ID NO: 14, the amino acids 1-471 in SEQ ID NO: 18, the amino acids 1-450 in SEQ ID NO: 20, the amino acids 1-445 in SEQ ID NO: 22, the amino acids 1-498 in SEQ ID NO: 26, the amino acids 18-513 in SEQ ID NO: 28, the amino acids 1-507 in SEQ ID NO: 30, the amino acids 1-481 in SEQ ID NO: 32, the amino acids 1-495 in SEQ ID NO: 34, the amino acids 1-477 in SEQ ID NO: 38, the amino acids 1-449 in SEQ ID NO: 42, the amino acids 1-442 in SEQ ID NO: 115, the amino acids 1-441 in SEQ ID NO: 117, the amino acids 1-477 in SEQ ID NO: 125, the amino acids 1-446 in SEQ ID NO: 131, the amino acids 41-481 in SEQ ID NO: 157, the amino acids 22-502 in SEQ ID NO: 159, the amino acids 24-499 in SEQ ID NO: 161, the amino acids 27-492 in SEQ ID NO: 163, the amino acids 21-496 in SEQ ID NO: 165, the amino acids 29-501 in SEQ ID NO: 167, the amino acids 22-487 in SEQ ID NO: 169, the amino acids 21-463 in SEQ ID NO: 171, the amino acids 21-477 in SEQ ID NO: 173, the amino acids 288-773 in SEQ ID NO: 175, the amino acids 22-471 in SEQ ID NO: 177 and the amino acids 20-470 in SEQ ID NO: 179.

Also preferred are polypeptides, e.g., hybrid polypeptides, wherein a linker sequence is present in a position between said first and said second amino acid sequence, said linker sequence having at least 60%, at least 70%, at least 80%, at least 85%, at least 90%, such as at least 95% homology to any amino acid sequence selected from the group consisting of as amino acids 503-528 in SEQ ID NO: 159, amino acids 500-532 in SEQ ID NO: 161, amino acids 493-507 in SEQ ID NO: 163, amino acids 497-539 in SEQ ID NO: 165, amino acids 488-512 in SEQ ID NO: 169 in 478-491 in SEQ ID NO: 173, amino acids 472-486 in SEQ ID NO: 177 and amino acids 471-481 in SEQ ID NO: 179.

Alpha-Amylase Sequence

Catalytic domains, i.e., alpha-amylase catalytic domains (in particular acid stable alpha-amylases), which are appropriate for construction of polypeptides of the types of the present invention may be derived from any organism, preferred are those of fungal or bacterial origin.

Preferably the alpha-amylase is a wild type enzyme. More preferably the alpha-amylase is a variant alpha-amylases comprising amino acid modifications leading to increased activity, increased protein stability at low pH, and/or at high pH, increased stability towards calcium depletion, and/or increased stability at elevated temperature.

Relevant alpha-amylases for use in a hybrid of the invention include alpha-amylases obtainable from a species selected from the list consisting of *Absidia, Acremonium, Aspergillus, Coniochaeta, Coniochaeta, Cryptosporiopsis, Dichotomocladium, Dinemasporium* sp., *Diplodia, Fusarium, Gliocladium, Malbranchea, Meripilus Trametes, Nectria, Nectria, Penicillium, Phanerochaete, Rhizomucor, Rhizopus, Streptomyces, Subulispora, Syncephalastrum, Thaminidium, Thermoascus, Thermomyces, Trametes, Trichophaea* and *Valsaria*. The alpha-amylases catalytic domain may also be derived from a bacteria, e.g., *Bacillus*.

Preferably the alpha-amylases amino acid sequence selected is derived from any species selected from the group consisting of *Absidia cristata, Acremonium* sp., *Aspergillus niger, Aspergillus kawachii, Aspergillus oryzae, Coniochaeta* sp., *Coniochaeta* sp., *Cryptosporiopsis* sp., *Dichotomocladium hesseltinei, Dinemasporium* sp., *Diplodia* sp., *Fusarium* sp., *Gliocladium* sp., *Malbranchea* sp., *Meripilus*

*giganteus, Nectria* sp., *Nectria* sp., *Penicillium* sp., *Phanerochaete chrysosporium, Rhizomucor pusillus, Rhizopus oryzae, Stereum* sp. *Streptomyces thermocyaneoviolaceus, Streptomyces limosus, Subulispora procurvata, Syncephalastrum racemosum, Thaminidium elegans, Thermoascus aurantiacus, Thermoascus* sp., *Thermomyces lanuginosus, Trametes corrugata, Trametes* sp., *Trichophaea saccata, Valsaria rubricosa, Valsaria spartii* and *Bacillus flavothermus* (Syn. *Anoxybacillus contaminans*).

Preferably the hybrid comprises an alpha-amylase amino acid sequence selected from the group consisting of the alpha-amylase catalytic modules listed in table 1 or 2.

Most preferably the hybrid comprises an alpha-amylase amino acid sequence selected from the group consisting of the alpha-amylases from *Aspergillus niger* (SEQ ID NO: 2), *Aspergillus oryzae* (SEQ ID NO: 4 and SEQ ID NO: 6), *Trichophaea saccata* (SEQ ID NO: 8), *Subulispora procurvata* (SEQ ID NO: 10), *Valsaria rubricosa* (SEQ ID NO: 12), *Thermomyces lanuginosus* (SEQ ID NO: 14), *Acremonium* sp. (SEQ ID NO: 16), *Malbranchea* sp. (SEQ ID NO: 18), *Rhizomucor pusillus* (SEQ ID NO: 20), *Dichotomocladium hesseltinei* (SEQ ID NO: 22), *Meripilus giganteus* (SEQ ID NO: 24), *Stereum* sp. AMY1179 (SEQ ID NO: 26), *Trametes* sp. (SEQ ID NO: 28), *Coriolus censors* (SEQ ID NO: 30), *Dinemasporium* sp. (SEQ ID NO: 32), *Cryptosporiopsis* sp. (SEQ ID NO: 34), *Coniochaeta* sp. (SEQ ID NO: 36), *Diplodia* sp. (SEQ ID NO: 38), *Nectria* sp. (SEQ ID NO: 40), *Gliocladium* sp. (SEQ ID NO: 42), *Streptomyces thermocyaneoviolaceus* (SEQ ID NO: 44), *Thermoascus* sp. II (SEQ ID NO: 111), *Coniochaeta* sp. (SEQ ID NO: 113), *Nectria* sp. (SEQ ID NO: 115), *Fusarium* sp. (SEQ ID NO: 117), *Trametes corrugata* (SEQ ID NO: 119), *Penicillium* sp. (SEQ ID NO: 121), *Valsaria spartii* (SEQ ID NO: 123), *Thermoascus aurantiacus* (SEQ ID NO: 125), *Phanerochaete chrysosporium* (SEQ ID NO: 127), *Rhizopus oryzae* (SEQ ID NO: 129), *Thaminidium elegans* (SEQ ID NO: 131), *Absidia cristata* (SEQ ID NO: 133), *Syncephalastrum racemosum* (SEQ ID NO: 135) and *Streptomyces limosus* (SEQ ID NO: 155).

Also preferred for the invention are hybrids comprising a alpha-amylase amino acid sequence having at least 60%, at least 65%, at least 70%, at least 75%, at least 80%, at least 85%, at least 90% or even at least 95% homology to any sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135 and SEQ ID NO: 155.

In another preferred embodiment the hybrid enzyme has a alpha-amylase sequence which differs from an amino acid sequences selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135 and SEQ ID NO: 155 in no more than 10 positions, no more than 9 positions, no more than 8 positions, no more than 7 positions, no more than 6 positions, no more than 5 positions, no more than 4 positions, no more than 3 positions, no more than 2 positions, or even no more than 1 position.

Also preferred are hybrids comprising a alpha-amylases amino acid sequence encoded by a DNA sequence having at least 50%, at least 60%, at least 65%, at least 70%, at least 75%, at least 80%, at least 85%, at least 90% or even at least 95% homology to any sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134 and SEQ ID NO: 154.

Further preferred are hybrids comprising a alpha-amylase encoded by a DNA sequence hybridizing under low, medium, medium/high, high and/or very high stringency to any DNA sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134 and SEQ ID NO: 154.

Linker Sequence

The linker sequence may be any suitable linker sequence, e.g., a linker sequence derived from an alpha-amylase or a glucoamylase. The linker may be a bond, or a short linking group comprising from about 2 to about 100 carbon atoms, in particular of from 2 to 40 carbon atoms. However, the linker is preferably a sequence of from about 2 to about 100 amino acid residues, more preferably of from 4 to 40 amino acid residues, such as from 6 to 15 amino acid residues.

Preferably the hybrids comprising a linker sequence derived from any species selected from the group consisting of *Acremonium, Coniochaeta, Coniochaeta, Meripilus, Pachykytospora, Penicillium, Sublispora, Trametes, Trichophaea, Valsaria, Athelia, Aspergillus, Trametes* and *Leucopaxillus*. The linker may also be derived from a bacterium, e.g., from a strain within *Bacillus* sp. More the preferably linker is derived from a species selected from the group consisting of *Acremonium* sp., *Coniochaeta* sp., *Coniochaeta* sp., *Meripilus giganteus, Penicillium* sp., *Sublispora provurvata, Trametes corrugata, Trichophaea saccata, Valsaria rubricosa, Valsario spartii, Aspergillus kawachii, Aspergillus niger, Athelia rolfsii, Leucopaxillus gigantus, Pachykytospora papayracea, Trametes cingulata* and *Bacillus flavothermus*.

Preferably the hybrid comprises a linker amino acid sequence selected from the group consisting of the linkers listed in table 1 or 2.

More preferably the linker is a linker from a glucoamylase selected from the group consisting of *Pachykytospora papayracea* (SEQ ID NO: 46), *Trametes cingulata* (SEQ ID NO: 48), *Leucopaxillus gigantus* (SEQ ID NO: 50), *Athelia rolfsii*

(SEQ ID NO: 68), *Aspergillus kawachii* (SEQ ID NO: 70), *Aspergillus niger* (SEQ ID NO: 72) or a linker from an alpha-amylase selected from the group consisting of *Sublispora provurvata* (SEQ ID NO: 54), *Valsaria rubricosa* (SEQ ID NO: 56), *Acremonium* sp. (SEQ ID NO: 58), *Meripilus giganteus* (SEQ ID NO: 60), *Bacillus flavothermus* (SEQ ID NO: 62, SEQ ID NO: 64 or SEQ ID NO: 66), *Coniochaeta* sp. AM603 (SEQ ID NO: 74), *Coniochaeta* sp. (SEQ ID NO: 145), *Trametes corrugata* (SEQ ID NO: 147), *Valsario spartii* (SEQ ID NO: 149), *Penicillium* sp. (SEQ ID NO: 151), *Trichophaea saccata* (SEQ ID NO: 52).

Also preferred for the invention is any linker amino acid sequence having at least 60%, at least 65%, at least 70%, at least 75%, at least 80%, at least 85%, at least 90% or even at least 95% homology to any sequence selected from the group consisting of SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 145, SEQ ID NO: 147, SEQ ID NO: 149 and SEQ ID NO: 151.

In another preferred embodiment the hybrid enzyme has a linker sequence which differs from an amino acid sequences selected from the group consisting of SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 145, SEQ ID NO: 147, SEQ ID NO: 149 and SEQ ID NO: 151 in no more than 10 positions, no more than 9 positions, no more than 8 positions, no more than 7 positions, no more than 6 positions, no more than 5 positions, no more than 4 positions, no more than 3 positions, no more than 2 positions, or even no more than 1 position.

Also preferred are the hybrids comprising a linker sequence encoded by a DNA sequence having at least 60%, at least 65%, at least 70%, at least 75%, at least 80%, at least 85%, at least 90% or even at least 95% homology to any sequence selected from the group consisting of SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 144, SEQ ID NO: 146, SEQ ID NO: 148, and SEQ ID NO: 150.

Further preferred are the hybrids comprising a linker sequence encoded by a DNA sequence hybridizing under high, medium or low stringency to any DNA sequence selected from the group consisting SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 144, SEQ ID NO: 146, SEQ ID NO: 148, and SEQ ID NO: 150.

In preferred embodiments the linker originating from the CBM source is used, e.g., when using the CBM from *A. rolfsii* glucoamylase the linker sequence from the *A. rolfsii* glucoamylase is used in the hybrid as well.

Carbohydrate-Binding Modules

A carbohydrate-binding module (CBM), or as often referred to, a carbohydrate-binding domain (CBM), is a polypeptide amino acid sequence which binds preferentially to a poly- or oligosaccharide (carbohydrate), frequently—but not necessarily exclusively—to a water-insoluble (including crystalline) form thereof.

CBMs derived from starch degrading enzymes are often referred to as starch-binding modules or SBMs (CBMs which may occur in certain amylolytic enzymes, such as certain glucoamylases (GA), or in enzymes such as cyclodextrin glucanotransferases, or in alpha-amylases). Likewise, other sub-classes of CBMs would embrace, e.g., cellulose-binding modules (CBMs from cellulolytic enzymes), chitin-binding modules (CBMs which typically occur in chitinases), xylan-binding modules (CBMs which typically occur in xylanases), mannan-binding modules (CBMs which typically occur in mannanases). SBMs are often referred to as SBDs (Starch Binding Domains).

CBMs are found as integral parts of large polypeptides or proteins consisting of two or more polypeptide amino acid sequence regions, especially in hydrolytic enzymes (hydrolases) which typically comprise a catalytic module containing the active site for substrate hydrolysis and a carbohydrate-binding module (CBM) for binding to the carbohydrate substrate in question. Such enzymes can comprise more than one catalytic module and one, two or three CBMs and optionally further comprise one or more polypeptide amino acid sequence regions linking the CBM(s) with the catalytic module(s), a region of the latter type usually being denoted a "linker". Examples of hydrolytic enzymes comprising a CBM—some of which have already been mentioned above—are cellulases, xylanases, mannanases, arabinofuranosidases, acetylesterases and chitinases. CBMs have also been found in algae, e.g., in the red alga *Porphyra purpurea* in the form of a non-hydrolytic polysaccharide-binding protein.

In proteins/polypeptides in which CBMs occur (e.g., enzymes, typically hydrolytic enzymes), a CBM may be located at the N or C terminus or at an internal position.

That part of a polypeptide or protein (e.g., hydrolytic enzyme) which constitutes a CBM per se typically consists of more than about 30 and less than about 250 amino acid residues.

The "Carbohydrate-Binding Module of Family 20" or a CBM-20 module is in the context of this invention defined as a sequence of approximately 100 amino acids having at least 45% homology to the Carbohydrate-Binding Module (CBM) of the polypeptide disclosed in FIG. 1 by Joergensen et al. (1997) in Biotechnol. Lett. 19:1027-1031. The CBM comprises the last 102 amino acids of the polypeptide, i.e., the subsequence from amino acid 582 to amino acid 683. The numbering of Glycoside Hydrolase Families applied in this disclosure follows the concept of Coutinho, P. M. & Henrissat, B. (1999) CAZy—Carbohydrate-Active Enzymes server at URL: afmb.cnrs-mrs.fr/~cazy/CAZY/index.html or alternatively Coutinho, P. M. & Henrissat, B. 1999; The modular structure of cellulases and other carbohydrate-active enzymes: an integrated database approach. In "*Genetics, Biochemistry and Ecology of Cellulose Degradation*", K. Ohmiya, K. Hayashi, K. Sakka, Y. Kobayashi, S. Karita and T. Kimura eds., Uni Publishers Co., Tokyo, pp. 15-23 and Bourne, Y. & Henrissat, B. 2001; Glycoside hydrolases and glycosyltransferases: families and functional modules, *Current Opinion in Structural Biology* 11:593-600.

Examples of enzymes which comprise a CBM suitable for use in the context of the invention are alpha-amylases, maltogenic alpha-amylases, cellulases, xylanases, mannanases, arabinofuranosidases, acetylesterases and chitinases. Further CBMs of interest in relation to the present invention include CBMs deriving from glucoamylases (EC 3.2.1.3) or from CGTases (EC 2.4.1.19).

CBMs deriving from fungal, bacterial or plant sources will generally be suitable for use in the hybrid of the invention.

Preferred are CBMs of fungal origin. In this connection, techniques suitable for isolating the relevant genes are well known in the art.

Preferred are hybrids comprising a CBM of Carbohydrate-Binding Module Family 20, 21 or 25. CBMs of Carbohydrate-Binding Module Family 20 suitable for the invention may be derived from glucoamylases of *Aspergillus awamori* (SWISSPROT Q12537), *Aspergillus kawachii* (SWISSPROT P23176), *Aspergillus niger* (SWISSPROT P04064), *Aspergillus oryzae* (SWISSPROT P36914), from alpha-amylases of *Aspergillus kawachii* (EMBL:#AB008370), *Aspergillus nidulans* (NCBI AAF17100.1), from beta-amylases of *Bacillus cereus* (SWISSPROT P36924), or from CGTases of *Bacillus circulans* (SWISSPROT P43379). Preferred is a CBM from the alpha-amylase of *Aspergillus kawachii* (EMBL:#AB008370) as well as CBMs having at least 60%, at least 65%, at least 70%, at least 75%, at least 80%, at least 85%, at least 90% or even at least 95% homology to the CBM of the alpha-amylase of *Aspergillus kawachii* (EMBL:#AB008370). Further preferred CBMs include the CBMs of the glucoamylase from *Hormoconis* sp. such as from *Hormoconis resinae* (Syn. Creosote fungus or *Amorphotheca resinae*) such as the CBM of SWISSPROT: Q03045, from *Lentinula* sp. such as from *Lentinula edodes* (shiitake mushroom) such as the CBM of SPTREMBL: Q9P4C5, from *Neurospora* sp. such as from *Neurospora crassa* such as the CBM of SWISSPROT:P14804, from *Talaromyces* sp. such as from *Talaromyces byssochlamydioides*, from *Geosmithia* sp. such as from *Geosmithia cylindrospora*, from *Scorias* sp. such as from *Scorias spongiosa*, from *Eupenicillium* sp. such as from *Eupenicillium ludwigii*, from *Aspergillus* sp. such as from *Aspergillus japonicus*, from *Penicillium* sp. such as from *Penicillium* cf. *miczynskii*, from *Thysanophora* sp., and from *Humicola* sp. such as from *Humicola grisea* var. *thermoidea* such as the CBM of SPTREMBL:Q12623.

Preferably the hybrid comprises a CBM which is derived from any family or species selected from the group consisting of *Acremonium*, *Aspergillus*, *Athelia*, *Coniochaeta*, *Cryptosporiopsis*, *Dichotomocladium*, *Dinemasporium*, *Diplodia*, *Gliocladium*, *Leucopaxillus*, *Malbranchea*, *Meripilus*, *Nectria*, *Pachykytospora*, *Penicillium*, *Rhizomucor*, *Rhizomucor pusillus*, *Streptomyces*, *Subulispora*, *Thermomyces*, *Trametes*, *Trichophaea saccata* and *Valsaria*. The CBM may also be derived from a plant, e.g., from corn (e.g., *Zea mays*) or a bacterial, e.g., *Bacillus*. More preferably the hybrid comprises a CBM derived from any species selected from the group consisting of *Acremonium* sp., *Aspergillus kawachii*, *Aspergillus niger*, *Aspergillus oryzae*, *Athelia rolfsii*, *Bacillus flavothermus*, *Coniochaeta* sp., *Cryptosporiopsis* sp., *Dichotomocladium hesseltinei*, *Dinemasporium* sp., *Diplodia* sp., *Gliocladium* sp., *Leucopaxillus gigantus*, *Malbranchea* sp, *Meripilus giganteus*, *Nectria* sp., *Pachykytospora papayracea*, *Penicillium* sp., *Rhizomucor pusillus*, *Streptomyces thermocyaneoviolaceus*, *Streptomyces limosus*, *Subulispora provurvata*, *Thermomyces lanuginosus*, *Trametes cingulata*, *Trametes corrugata*, *Trichophaea saccata*, *Valsaria rubricosa*, *Valsario spartii* and *Zea mays*.

Preferably the hybrid comprises a CBM amino acid sequence selected from the group consisting of the CBMs listed in table 1 or 2.

Most preferably the hybrid comprises a CBM from a glucoamylase selected from the group consisting of the *Pachykytospora papayracea* (SEQ ID NO: 76), *Trametes cingulata* (SEQ ID NO: 78), *Leucopaxillus gigantus* (SEQ ID NO: 80), *Athelia rolfsii* (SEQ ID NO: 92), *Aspergillus kawachii* (SEQ ID NO: 94), *Aspergillus niger* (SEQ ID NO: 96) or from a alpha-amylase selected from the group consisting of *Trichopheraea saccata* (SEQ ID NO: 52), *Subulispora provurvata* (SEQ ID NO: 82), *Valsaria rubricosa* (SEQ ID NO: 84), *Acremonium* sp. (SEQ ID NO: 86), *Meripilus giganteus* (SEQ ID NO: 88), *Bacillus flavothermus* (SEQ ID NO: 90), *Coniochaeta* sp. (SEQ ID NO: 98), *Zea mays* (SEQ ID NO: 109), *Coniochaeta* sp. (SEQ ID NO: 137), *Trametes corrugata* (SEQ ID NO: 139), *Valsario spartii* (SEQ ID NO: 141) and *Penicillium* sp. (SEQ ID NO: 143).

In another preferred embodiment the hybrid enzyme has a CBM sequence which differs from an amino acid sequences selected from the group consisting of SEQ ID NO: 52, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 109, SEQ ID NO: 137, SEQ ID NO: 139, SEQ ID NO: 141 and SEQ ID NO: 143 in no more than 10 positions, no more than 9 positions, no more than 8 positions, no more than 7 positions, no more than 6 positions, no more than 5 positions, no more than 4 positions, no more than 3 positions, no more than 2 positions, or even no more than 1 position.

Also preferred are any CBM encoded by a DNA sequence having at least 60%, at least 65%, at least 70%, at least 75%, at least 80%, at least 85%, at least 90% or even at least 95% homology to any sequence selected from the group consisting of SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 108, SEQ ID NO: 136, SEQ ID NO: 138, SEQ ID NO: 140 and SEQ ID NO: 142. Further preferred are any CBM encoded by a DNA sequence hybridizing under high, medium or low stringency to any DNA sequence selected from the group consisting of SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 108, SEQ ID NO: 136, SEQ ID NO: 138, SEQ ID NO: 140 and SEQ ID NO: 142.

Further suitable CBMs of Carbohydrate-Binding Module Family 20, 21 or 25 may be found at URL: afmb.cnrs-mrs.fr/~cazy/CAZY/index.html.

Once a nucleotide sequence encoding the substrate-binding (carbohydrate-binding) region has been identified, either as cDNA or chromosomal DNA, it may then be manipulated in a variety of ways to fuse it to a DNA sequence encoding the polypeptide of interest. The DNA fragment encoding the carbohydrate-binding amino acid sequence and the DNA encoding the polypeptide of interest are then ligated with or without a linker. The resulting ligated DNA may then be manipulated in a variety of ways to achieve expression.

Particular Embodiments

In a preferred embodiment the polypeptide comprises a CDM derived from *Athelia rolfsii*, *Pachykytospora papayracea*, *Valsaria rubricosa* or *Meripilus giganteus*. Preferred are any polypeptide comprising a CBM amino acid sequence selected from the group consisting of *Athelia rolfsii* glucoamylase (SEQ ID NO: 92), the *Pachykytospora papayracea* glucoamylase (SEQ ID NO: 76), the *Valsaria rubricosa* alpha-amylase (SEQ ID NO: 84) and the *Meripilus giganteus* alpha-amylase (SEQ ID NO: 88).

In yet a preferred embodiment the polypeptide comprises an alpha-amylase sequence derived from the *A. oryzae* acid alpha-amylase (SEQ ID NO: 4), Preferably the wherein said *A. oryzae* amino acid sequence comprises one or more amino acid substitutions selected from the group consisting of A128P, K138V, S141N, Q143A, D144S, Y155W, E156D, D157N, N244E, M246L, G446D, D448S and N450D. Most preferably the polypeptide comprises an catalytic domain having the amino acid sequence shown in SEQ ID NO: 6. In a preferred embodiment the polypeptide further comprises a CBM derived from *A. rolfsii*, Preferably the polypeptide further comprises a CBM having the amino acid sequence shown in SEQ ID NO: 92. Most preferably the polypeptide has the amino acid sequence shown in SEQ ID NO: 100 or the polypeptide has an amino acid sequence having at least 60%, at least 65%, at least 70%, at least 75%, at least 80%, at least 85%, at least 90% or even at least 95% homology to the afore mentioned amino acid sequence.

Also preferred is any polypeptide encoded by a DNA sequence having at least 60%, at least 65%, at least 70%, at least 75%, at least 80%, at least 85%, at least 90% or even at least 95% homology to the DNA sequence shown in SEQ ID NO: 99.

In another preferred embodiment the polypeptide comprises a catalytic module derived from the *Rhizomucor pusillus* alpha-amylase and/or a CBM derived from *A. rolfsii*. In a particular preferred embodiment the polypeptide has the amino acid sequence shown in SEQ ID NO: 101 or the polypeptide has an amino acid sequence having at least 60%, at least 65%, at least 70%, at least 75%, at least 80%, at least 85%, at least 90% or even at least 95% homology to any of the afore mentioned amino acid sequence.

In yet a preferred embodiment the polypeptide comprises a catalytic module derived from the *Meripilus giganteus* alpha-amylase and/or a CBM derived from *A. rolfsii*. In a particular preferred embodiment the polypeptide has the amino acid sequence shown in SEQ ID NO: 102 or the polypeptide has an amino acid sequence having at least 60%, at least 65%, at least 70%, at least 75%, at least 80%, at least 85%, at least 90% or even at least 95% homology to the afore mentioned amino acid sequence.

In yet another preferred embodiment the polypeptide has an amino acid sequence which differs from any the amino acid sequence amino acid sequences shown in SEQ ID NO: 100, SEQ ID NO: 101 and SEQ ID NO: 102 in no more than 10 positions, no more than 9 positions, no more than 8 positions, no more than 7 positions, no more than 6 positions, no more than 5 positions, no more than 4 positions, no more than 3 positions, no more than 2 positions, or even no more than 1 position.

Also preferred are any polypeptide encoded by a DNA sequence having at least 60%, at least 65%, at least 70%, at least 75%, at least 80%, at least 85%, at least 90% or even at least 95% homology to any sequence DNA sequence encoding any the amino acid sequence amino acid sequences shown in SEQ ID NO: 100, SEQ ID NO: 101 and SEQ ID NO: 102.

Further preferred are any CBM encoded by a DNA sequence which hybridizing under high, medium or low stringency to any DNA sequence encoding any of the amino acid sequence amino acid sequences shown in SEQ ID NO: 100, SEQ ID NO: 101 and SEQ ID NO: 102.

Other preferred embodiments of the polypeptides of the invention are shown in table 3, 4, 5 and 6 in the examples section. Also preferred is any polypeptide having at least 70%, more preferred at least 80% and even more preferred at least 90% homology to any of the amino acid sequences of the polypeptides shown in tables 1 to 7. Further preferred is any polypeptide encoded by a DNA sequence which hybridizes at low, medium, or high stringency with DNA sequence encoding any of the amino acid sequences of the polypeptides shown in tables 1 to 7.

In a preferred embodiment the polypeptide comprises a catalytic domain having at least 75% homology to the *A. oryzae* catalytic domain (SEQ ID NO: 6) and a CBM having at least 75% homology to a CBM selected from the group consisting of SEQ ID NO: 82, SEQ ID NO: 84, SEQ ID NO: 86, SEQ ID NO: 76, SEQ ID NO: 78, SEQ ID NO: 80, SEQ ID NO: 88, SEQ ID NO: 52, SEQ ID NO: 92, SEQ ID NO: 52, and SEQ ID NO: 90. In a more preferred embodiment the polypeptide comprises the *A. oryzae* catalytic domain (SEQ ID NO: 6) and a CBM selected from the group consisting of SEQ ID NO: 82, SEQ ID NO: 84, SEQ ID NO: 86, SEQ ID NO: 76, SEQ ID NO: 78, SEQ ID NO: 80, SEQ ID NO: 88, SEQ ID NO: 52, SEQ ID NO: 92, SEQ ID NO: 52, SEQ ID NO: 90, SEQ ID NO: 90 and SEQ ID NO: 90.

In a preferred embodiment the polypeptide comprises a CBM having at least 75% homology to the *A. rolfsii* glucoamylase CBM (SEQ ID NO: 92) and a catalytic domain having at least 75% homology to a catalytic domain selected from the group consisting of SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 155, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 111, SEQ ID NO: 113, SEQ ID NO: 115, SEQ ID NO: 117, SEQ ID NO: 119, SEQ ID NO: 123, SEQ ID NO: 125, SEQ ID NO: 121, SEQ ID NO: 127, SEQ ID NO: 129, SEQ ID NO: 131, SEQ ID NO: 133 and SEQ ID NO: 135. In a more preferred embodiment the polypeptide comprises the *A. rolfsii* glucoamylase CBM (SEQ ID NO: 92) and a catalytic domain selected from the group consisting of SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 155, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 111, SEQ ID NO: 113, SEQ ID NO: 115, SEQ ID NO: 117, SEQ ID NO: 119, SEQ ID NO: 123, SEQ ID NO: 125, SEQ ID NO: 121, SEQ ID NO: 127, SEQ ID NO: 129, SEQ ID NO: 131, SEQ ID NO: 133 and SEQ ID NO: 135.

In a preferred embodiment the polypeptide comprises a CBM having at least 75% homology the *Pachykytospora papayracea* glucoamylase CBM in SEQ ID NO: 145 and a catalytic domain having at least 75% homology to a CBM selected from the group consisting of the *Acremonium* sp. alpha-amylase CBM in SEQ ID NO: 16, the *Rhizomucor pusiflus* alpha-amylase CBM in SEQ ID NO: 20 and the *Meripilus giganteus* alpha-amylase CBM in SEQ ID NO: 24. In a more preferred embodiment the polypeptide comprises the *Pachykytospora papayracea* glucoamylase CBM in SEQ ID NO: 145 and a CBM selected from the group consisting of the *Acremonium* sp. alpha-amylase CBM in SEQ ID NO: 16, the *Rhizomucor pusiflus* alpha-amylase CBM in SEQ ID NO: 20 and the *Meripilus giganteus* alpha-amylase CBM in SEQ ID NO: 24.

In a preferred embodiment the polypeptide comprises a catalytic domain having at least 75% homology to the *Rhizomucor pusiflus* alpha-amylase catalytic domain (SEQ ID NO: 20) and a CBM having at least 75% homology to a CBM selected from the group consisting of *Aspergillus kawachii* glucoamylase CBM SEQ ID NO: 94 and the *Aspergillus niger* glucoamylase CBM in SEQ ID NO: 96. In a more preferred embodiment the polypeptide comprises the *Rhizomucor pusiflus* alpha-amylase catalytic domain (SEQ ID NO: 20) and a CBM selected from the group consisting of *Aspergillus kawachii* glucoamylase CBM SEQ ID NO: 94 and the *Aspergillus niger* glucoamylase CBM in SEQ ID NO: 96.

In a preferred embodiment the polypeptide comprises a catalytic domain having at least 75% homology to the *Meripilus giganteus* alpha-amylase catalytic domain (SEQ ID NO: 24) and a CBM having at least 75% homology to a CBM selected from the group consisting of *Pachykytospora papayracea* glucoamylase CBM in SEQ ID NO: 145, the *Valsaria rubricosa* alpha-amylase CBM SEQ ID NO: 84 in and the *Zea mays* CBM in SEQ ID NO: 109. In a more preferred embodiment the polypeptide comprises the *Meripilus giganteus* alpha-amylase catalytic domain (SEQ ID NO: 24) and a CBM selected from the group consisting of *Pachykytospora papayracea* glucoamylase CBM in SEQ ID NO: 145, the *Valsaria rubricosa* alpha-amylase CBM SEQ ID NO: 84 in and the *Zea mays* CBM in SEQ ID NO: 109.

In a preferred embodiment the polypeptide comprises a catalytic domain having at least 75% homology to the *Rhizomucor pusiflus* alpha-amylase catalytic domain (SEQ ID NO: 20) and a CBM having at least 75% homology to a CBM selected from the group consisting of the *A. rolfsii* glucoamylase CBM in SEQ ID NO: 92 and the *Zea mays* CBM in SEQ ID NO: 109, the *Coniochaeta* sp. alpha-amylase CBM in SEQ ID NO: 113, the *Trametes corrugata* alpha-amylase CBM in SEQ ID NO: 119, the *Valsaria spartii* alpha-amylase CBM in SEQ ID NO: 123, the *Penicillium* sp. alpha-amylase CBM in SEQ ID NO: 121 and the *Meripulus giganteus* alpha-amylase CBM in SEQ ID NO: 88. In a more preferred embodiment the polypeptide comprises the *Rhizomucor pusillus* alpha-amylase catalytic domain (SEQ ID NO: 20) and a CBM selected from the group consisting of the *A. rolfsii* glucoamylase CBM in SEQ ID NO: 92 and the *Zea mays* CBM in SEQ ID NO: 109, the *Coniochaeta* sp. alpha-amylase CBM in SEQ ID NO: 113, the *Trametes corrugata* alpha-amylase CBM in SEQ ID NO: 119, the *Valsaria spartii* alpha-amylase CBM in SEQ ID NO: 123, the *Penicillium* sp. alpha-amylase CBM in SEQ ID NO: 121 and the *Meripulus giganteus* alpha-amylase CBM in SEQ ID NO: 88.

In a particularly preferred embodiment the polypeptide is selected from the group consisting of V001, V002, V003, V004, V005, V006, V007, V008, V009, V010, V011, V012, V013, V014, V015, V016, V017, V018, V019, V021, V022, V023, V024, V025, V026, V027, V028, V029, V030, V031, V032, V033, V034, V035, V036, V037, V038, V039, V040, V041, V042, V043, V047, V048, V049, V050, V051, V052, V054, V055, V057, V059, V060, V061, V063, V064, V065, V066, V067, V068 and V069.

Expression Vectors

The present invention also relates to recombinant expression vectors which may comprise a DNA sequence encoding the polypeptide, a promoter, a signal peptide sequence and transcriptional and translational stop signals. The various DNA and control sequences described above may be joined together to produce a recombinant expression vector which may include one or more convenient restriction sites to allow for insertion or substitution of the DNA sequence encoding the polypeptide at such sites. Alternatively, the DNA sequence of the present invention may be expressed by inserting the DNA sequence or a DNA construct comprising the sequence into an appropriate vector for expression. In creating the expression vector, the coding sequence is located in the vector so that the coding sequence is operably linked with the appropriate control sequences for expression and possibly secretion.

The recombinant expression vector may be any vector (e.g., a plasmid or virus), which can be conveniently subjected to recombinant DNA procedures and can bring about the expression of the DNA sequence. The choice of the vector will typically depend on the compatibility of the vector with the host cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, a cosmid or an artificial chromosome. The vector may contain any means for assuring self-replication. Alternatively, the vector may be one which, when introduced into the host cell, is integrated into the genome and replicated together with the chromosome(s) into which it has been integrated. The vector system may be a single vector or plasmid or two or more vectors or plasmids which together contain the total DNA to be introduced into the genome of the host cell, or a transposon.

Markers

The vectors of the present invention preferably contain one or more selectable markers, which permit easy selection of transformed cells. A selectable marker is a gene the product of which provides for biocide or viral resistance, resistance to heavy metals, prototrophy to auxotrophs and the like.

Examples of selectable markers for use in a filamentous fungus host cell may be selected from the group including, but not limited to, amdS (acetamidase), argB (ornithine carbamoyltransferase), bar (phosphinothricin acetyltransferase), hygB (hygromycin phosphor-transferase), niaD (nitrate reductase), pyrG (orotidine-5'-phosphate decarboxylase), sC (sulfate adenyltransferase), trpC (anthranilate synthase), and glufosinate resistance markers, as well as equivalents from other species. Preferred for use in an *Aspergillus* cell are the amdS and pyrG markers of *Aspergillus nidulans* or *Aspergillus oryzae* and the bar marker of *Streptomyces hygroscopicus*. Furthermore, selection may be accomplished by co-transformation, e.g., as described in WO 91/17243, where the selectable marker is on a separate vector.

The vectors of the present invention preferably contain an element(s) that permits stable integration of the vector into the host cell genome or autonomous replication of the vector in the cell independent of the genome of the cell.

The vectors of the present invention may be integrated into the host cell genome when introduced into a host cell. For integration, the vector may rely on the DNA sequence encoding the polypeptide of interest or any other element of the vector for stable integration of the vector into the genome by homologous or none homologous recombination. Alternatively, the vector may contain additional DNA sequences for directing integration by homologous recombination into the genome of the host cell. The additional DNA sequences enable the vector to be integrated into the host cell genome at a precise location(s) in the chromosome(s). To increase the likelihood of integration at a precise location, the integrational elements should preferably contain a sufficient number of DNAs, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding DNA sequences. On the other hand, the vector may be integrated into the genome of the host cell by non-homologous recombination. These DNA sequences may be any sequence that is homologous with a target sequence in the genome of the host cell, and, furthermore, may be non-encoding or encoding sequences.

For autonomous replication, the vector may further comprise an origin of replication enabling the vector to replicate autonomously in the host cell in question.

The episomal replicating the AMA1 plasmid vector disclosed in WO 00/24883 may be used.

More than one copy of a DNA sequence encoding a polypeptide of interest may be inserted into the host cell to amplify expression of the DNA sequence. Stable amplification of the DNA sequence can be obtained by integrating at least one additional copy of the sequence into the host cell genome using methods well known in the art and selecting for transformants.

The procedures used to ligate the elements described above to construct the recombinant expression vectors of the present invention are well known to one skilled in the art (see, e.g., Sambrook et al, 1989, Molecular Cloning, A Laboratory Manual, 2$^{nd}$ edition, Cold Spring Harbor, N.Y.).

Host Cells

The host cell of the invention, either comprising a DNA construct or an expression vector comprising the DNA sequence encoding the polypeptide, is advantageously used as a host cell in the recombinant production of the polypeptide, e.g., a hybrid enzyme, a wild-type enzyme or a genetically modified wild-type enzyme. The cell may be transformed with an expression vector. Alternatively, the cell may be transformed with the DNA construct of the invention encoding the polypeptide, e.g., a hybrid enzyme, a wild type enzyme or a genetically modified wild type enzyme, conveniently by integrating the DNA construct (in one or more copies) in the host chromosome. Integration of the DNA construct into the host chromosome may be performed according to conventional methods, e.g., by homologous or heterologous recombination.

The host cell may be any appropriate prokaryotic or eukaryotic cell, e.g., a bacterial cell, a filamentous fungus cell, a yeast, a plant cell or a mammalian cell.

In a preferred embodiment, the host cell is a filamentous fungus represented by the following groups of *Ascomycota*, include, e.g., *Neurospora, Eupenicillium* (=*Penicillium*), *Emericella* (=*Aspergillus*), *Eurotium* (=*Aspergillus*).

In a more preferred embodiment, the filamentous fungus includes all filamentous forms of the subdivision *Eumycota* and *Oomycota* (as defined by Hawksworth et al. In, *Ainsworth and Bisby's Dictionary of The Fungi*, 8$^{th}$ edition, 1995, CAB International, University Press, Cambridge, UK. The filamentous fungi are characterized by a vegetative mycelium composed of chitin, cellulose, glucan, chitosan, mannan, and other complex polysaccharides. Vegetative growth is by hyphal elongation and carbon catabolism is obligately aerobic.

In an even more preferred embodiment, the filamentous fungus host cell is a cell of a species of, but not limited to a cell selected from the group consisting of a strain belonging to a species of *Aspergillus*, preferably *Aspergillus oryzae, Aspergillus niger, Aspergillus awamori, Aspergillus kawachii*, or a strain of *Bacillus*, or a strain of *Fusarium*, such as a strain of *Fusarium oxysporium, Fusarium graminearum* (in the perfect state named *Gribberella zeae*, previously *Sphaeria zeae*, synonym with *Gibberella roseum* and *Gibberella roseum* f. sp. *cerealis*), or *Fusarium sulphureum* (in the prefect state named *Gibberella puricaris*, synonym with *Fusarium trichothecioides, Fusarium bactridioides, Fusarium sambucium, Fusarium roseum*, and *Fusarium roseum* var. *graminearum*), *Fusarium cerealis* (synonym with *Fusarium crookwellense*), or *Fusarium venenatum*.

In a most preferred embodiment, the filamentous fungus host cell is a cell of a strain belonging to a species of *Aspergillus*, preferably *Aspergillus oryzae* or *Aspergillus niger*.

The filamentous fungus host cell may be a wild type filamentous fungus host cell or a variant, a mutant or a genetically modified filamentous fungus host cell. In a preferred embodiment of the invention the host cell is a protease deficient or protease minus strain. Also specifically contemplated is *Aspergillus* strains, such as *Aspergillus niger* strains, genetically modified to disrupt or reduce expression of glucoamylase, acid-stable alpha-amylase, alpha-1,6 transglucosidase, and protease activities.

Transformation of Filamentous Fungus Host Cells

Filamentous fungus host cells may be transformed by a process involving protoplast formation, transformation of the protoplasts, and regeneration of the cell wall in a manner known in the art. Suitable procedures for transformation of *Aspergillus* host cells are described in EP 238 023, EP 184 438, and Yelton et al. 1984, *Proceedings of the National Academy of Sciences USA* 81:1470-1474. A suitable method of transforming *Fusarium* species is described by Malardier et al. 1989, *Gene* 78:147-156 or U.S. Pat. No. 6,060,305.

Isolating and Cloning a DNA Sequence Encoding a Parent Alpha-Amylase

The techniques used to isolate or clone a DNA sequence encoding a polypeptide of interest are known in the art and include isolation from genomic DNA, preparation from cDNA, or a combination thereof. The cloning of the DNA sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other DNA amplification procedures such as ligase chain reaction (LCR), ligated activated transcription (LAT) and DNA sequence-based amplification (NASBA) may be used.

The DNA sequence encoding a parent alpha-amylase may be isolated from any cell or microorganism producing the alpha-amylase in question, using various methods well known in the art. First, a genomic DNA and/or cDNA library should be constructed using chromosomal DNA or messenger RNA from the organism that produces the alpha-amylase to be studied. Then, if the amino acid sequence of the alpha-amylase is known, labeled oligonucleotide probes may be synthesized and used to identify alpha-amylase-encoding clones from a genomic library prepared from the organism in question. Alternatively, a labelled oligonucleotide probe containing sequences homologous to another known alpha-amylase gene could be used as a probe to identify alpha-amylase-encoding clones, using hybridization and washing conditions of very low to very high stringency.

Yet another method for identifying alpha-amylase-encoding clones would involve inserting fragments of genomic DNA into an expression vector, such as a plasmid, transforming alpha-amylase-negative bacteria with the resulting genomic DNA library, and then plating the transformed bacteria onto agar containing a substrate for alpha-amylase (i.e., maltose), thereby allowing clones expressing the alpha-amylase to be identified.

Alternatively, the DNA sequence encoding the polypeptide may be prepared synthetically by established standard methods, e.g., the phosphoroamidite method described S. L. Beaucage and M. H. Caruthers, (1981), Tetrahedron Letters 22, p. 1859-1869, or the method described by Matthes et al. (1984), EMBO J. 3, p. 801-805. In the phosphoroamidite method, oligonucleotides are synthesized, e.g., in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al. (1988), Science 239, 1988, pp. 487-491.

Isolated DNA Sequence

The present invention relates, inter alia, to an isolated DNA sequence comprising a DNA sequence encoding a polypeptide, e.g., a hybrid enzyme, a wild type enzyme or a genetically modified wild type enzyme comprising an amino acid sequence of a catalytic module having alpha-amylase activity and an amino acid sequence of a carbohydrate-binding module, wherein the catalytic module is of fungal origin.

The term "isolated DNA sequence" as used herein refers to a DNA sequence, which is essentially free of other DNA sequences, e.g., at least about 20% pure, preferably at least about 40% pure, more preferably at least about 60% pure, even more preferably at least about 80% pure, and most preferably at least about 90% pure as determined by agarose electrophoresis.

For example, an isolated DNA sequence can be obtained by standard cloning procedures used in genetic engineering to relocate the DNA sequence from its natural location to a different site where it will be reproduced. The cloning procedures may involve excision and isolation of a desired DNA fragment comprising the DNA sequence encoding the polypeptide of interest, insertion of the fragment into a vector molecule, and incorporation of the recombinant vector into a host cell where multiple copies or clones of the DNA sequence will be replicated. An isolated DNA sequence may be manipulated in a variety of ways to provide for expression of the polypeptide of interest. Manipulation of the DNA sequence prior to its insertion into a vector may be desirable or necessary depending on the expression vector. The techniques for modifying DNA sequences utilizing recombinant DNA methods are well known in the art.

DNA Construct

The present invention relates, inter alia, to a DNA construct comprising a DNA sequence encoding a polypeptide, e.g., a hybrid enzyme comprising a first amino acid sequence comprising a catalytic module having alpha-amylase activity and a second amino acid sequence comprising a carbohydrate-binding module or a wild type enzyme comprising a first amino acid sequence comprising a catalytic module having alpha-amylase activity and a second amino acid sequence comprising a carbohydrate-binding module. "DNA construct" is defined herein as a DNA molecule, either single- or double-stranded, which is isolated from a naturally occurring gene or which has been modified to contain segments of DNA, which are combined and juxtaposed in a manner, which would not otherwise exist in nature. The term DNA construct is synonymous with the term expression cassette when the DNA construct contains all the control sequences required for expression of a coding sequence of the present invention.

Site-Directed Mutagenesis

Once a parent alpha-amylase-encoding DNA sequence has been isolated, and desirable sites for mutation identified, mutations may be introduced using synthetic oligonucleotides. These oligonucleotides contain nucleotide sequences flanking the desired mutation sites. In a specific method, a single-stranded gap of DNA, the alpha-amylase-encoding sequence, is created in a vector carrying the alpha-amylase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al. (1984), Biotechnology 2, p. 646-639. U.S. Pat. No. 4,760,025 disclose the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method for introducing mutations into alpha-amylase-encoding DNA sequences is described in Nelson and Long, (1989), Analytical Biochemistry 180, p. 147-151. It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Localized Random Mutagenesis

The random mutagenesis may be advantageously localized to a part of the parent alpha-amylase in question. This may, e.g., be advantageous when certain regions of the enzyme have been identified to be of particular importance for a given property of the enzyme, and when modified are expected to result in a variant having improved properties. Such regions may normally be identified when the tertiary structure of the parent enzyme has been elucidated and related to the function of the enzyme.

The localized or region-specific, random mutagenesis is conveniently performed by use of PCR generated mutagenesis techniques as described above or any other suitable technique known in the art. Alternatively, the DNA sequence encoding the part of the DNA sequence to be modified may be isolated, e.g., by insertion into a suitable vector, and said part may be subsequently subjected to mutagenesis by use of any of the mutagenesis methods discussed above.

Variants of Hybrid or Wild-Type Enzymes

The performance in a starch degradation process of a wild type or hybrid enzyme comprising a carbohydrate-binding module ("CBM") and an alpha-amylase catalytic module may be improved through protein engineering, such as by site directed mutagenesis, by localized random mutagenesis, by synthetically preparing a new variant of the parent wild type enzyme or parent hybrid enzyme, or by any other suitable protein engineering techniques.

The variants may be produced using conventional protein engineering techniques.

Expression of the Polypeptides in a Host Cell

The nucleotide sequence to be introduced into the DNA of the host cell may be integrated in nucleic acid constructs comprising the nucleotide sequence operably linked to one or more control sequences that direct the expression of the coding sequence in a suitable host cell under conditions compatible with the control sequences.

A nucleotide sequence encoding a polypeptide may be manipulated in a variety of ways to provide for expression of the polypeptide. Manipulation of the nucleotide sequence prior to its insertion into a vector may be desirable or necessary depending on the expression vector. The techniques for modifying nucleotide sequences utilizing recombinant DNA methods are well known in the art.

The control sequence may be an appropriate promoter sequence, a nucleotide sequence which is recognized by a host cell for expression of the nucleotide sequence. The promoter sequence contains transcriptional control sequences, which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American,* 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

The various nucleotide and control sequences described above may be joined together to produce a recombinant expression vector which may include one or more convenient restriction sites to allow for insertion or substitution of the nucleotide sequence encoding the polypeptide at such sites. Alternatively, the nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome.

The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyl-transferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof.

Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell's genome or autonomous replication of the vector in the cell independent of the genome.

For integration into the host cell genome, the vector may rely on the nucleotide sequence encoding the polypeptide or any other element of the vector for stable integration of the vector into the genome by homologous or nonhomologous recombination. Alternatively, the vector may contain additional nucleotide sequences for directing integration by homologous recombination into the genome of the host cell. The additional nucleotide sequences enable the vector to be integrated into the host cell genome at a precise location(s) in the chromosome(s). To increase the likelihood of integration at a precise location, the integrational elements should preferably contain a sufficient number of nucleotides, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleotide sequence of the present invention may be inserted into the host cell to increase production of the gene product. An increase in the copy number of the nucleotide sequence can be obtained by integrating at least one additional copy of the sequence into the host cell genome or by including an amplifiable selectable marker gene with the nucleotide sequence where cells containing amplified copies of the selectable marker gene, and thereby additional copies of the nucleotide sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells:

The present invention also relates to recombinant fermenting fungus, or a host cell comprising the nucleic acid construct of the invention, which are advantageously used in the recombinant production of the polypeptides on site. A vector comprising a nucleotide sequence of the present invention is introduced into a host cell so that the vector is maintained as a chromosomal integrant or as a self-replicating extra-chromosomal vector as described earlier.

The host cell is a fungal cell. "Fungi" as used herein includes the phyla *Ascomycota, Basidiomycota, Chytridiomycota,* and *Zygomycota* (as defined by Hawksworth et al., In, *Ainsworth and Bisby's Dictionary of The Fungi,* 8th edition, 1995, CAB International, University Press, Cambridge, UK) as well as the *Oomycota* (as cited in Hawksworth et al., 1995, supra, page 171) and all mitosporic fungi (Hawksworth et al., 1995, supra).

In a more preferred embodiment, the fungal host cell is a filamentous fungal cell. "Filamentous fungi" include all filamentous forms of the subdivision *Eumycota* and *Oomycota* (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic.

In a preferred embodiment, the filamentous fungal host cell is a cell of a thermophilic or thermo tolerant fungi such as a species within *Ascomycotina, Basidiomycotina, Zygomycota* or *Chytridiomycota,* in particular a species within the group consisting of *Chaetomium, Thermoascus, Malbranchea,* or *Thielavia,* such as *Thielavia terrestris,* or *Trichophaea.* Even more preferably the host cell is a strain of *Trichophaea saccata* or *Humicola,* such as *H. insolens.*

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Expression of the Enzymes in Plants

A DNA sequence encoding a polypeptide of interest, such as a hybrid enzyme or a variant of a wild type enzyme or a hybrid of the present invention, may be transformed and expressed in transgenic plants as described below.

The transgenic plant can be dicotyledonous or monocotyledonous, for short a dicot or a monocot. Examples of monocot plants are grasses, such as meadow grass (blue grass, Poa), forage grass such as *Festuca, Lolium,* temperate grass, such as *Agrostis,* and cereals, e.g., wheat, oats, rye, barley, rice, sorghum and maize (corn).

Examples of dicot plants are tobacco, legumes, such as lupins, potato, sugar beet, pea, bean and soybean, and cruciferous plants (family *Brassicaceae*), such as cauliflower, oil seed rape and the closely related model organism *Arabidopsis thaliana.*

Examples of plant parts are stem, callus, leaves, root, fruits, seeds, and tubers as well as the individual tissues comprising these parts, e.g., epidermis, mesophyll, parenchyme, vascular tissues, meristems. In the present context, also specific plant cell compartments, such as chloroplast, apoplast, mitochondria, vacuole, peroxisomes and cytoplasm are considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the invention are the progeny of such plants, plant parts and plant cells.

The transgenic plant or plant cell expressing the polypeptide of interest may be constructed in accordance with methods known in the art. In short the plant or plant cell is constructed by incorporating one or more expression constructs encoding the polypeptide of interest into the plant host genome and propagating the resulting modified plant or plant cell into a transgenic plant or plant cell.

Conveniently, the expression construct is a DNA construct which comprises a gene encoding the polypeptide of interest in operable association with appropriate regulatory sequences required for expression of the gene in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, e.g., on the basis of when, where and how the enzyme is desired to be expressed. For instance, the expression of the gene encoding the enzyme of the invention may be constitutive or inducible, or may be developmental, stage or tissue specific, and the gene product may be targeted to a specific cell compartment, tissue or plant part such as seeds or leaves. Regulatory sequences are, e.g., described by Tague et al, Plant Phys., 86, 506, 1988.

For constitutive expression the 35S-CaMV, the maize ubiquitin 1 and the rice actin 1 promoter may be used (Franck et al., 1980, *Cell* 21: 285-294, Christensen A H, Sharrock R A and Quail 1992. Maize polyubiquitin genes: structure, thermal perturbation of expression and transcript splicing, and promoter activity following transfer to protoplasts by electroporation. *Plant Mol. Biol.* 18, 675-689.; Zhang W, McElroy D. and Wu R 1991, Analysis of rice Act1 5' region activity in transgenic rice plants. *Plant Cell* 3, 1155-1165). Organ-specific promoters may, e.g., be a promoter from storage sink tissues such as seeds, potato tubers, and fruits (Edwards & Coruzzi, 1990, *Annu. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin or albumin promoter from rice (Wu et al., 1998, *Plant and Cell Physiology* 39(8): 885-889), a *Vicia faba* promoter from the legumin B4 and the unknown seed protein gene from *Vicia faba* described by Conrad et al, 1998, *Journal of Plant Physiology* 152(6): 708-711, a promoter from a seed oil body protein (Chen et al., 1998, *Plant and Cell Physiology* 39(9): 935-941, the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102(3): 991-1000, the chlorella virus adenine methyltransferase gene promoter (Mitra et al., 1994, *Plant Molecular Biology* 26(1): 85-93, or the aldP gene promoter from rice (Kagaya et al., 1995, *Molecular and General Genetics* 248(6): 668-674, or a wound inducible promoter such as the potato pin2 promoter (Xu et al, 1993, *Plant Molecular Biology* 22(4) 573-588. Likewise, the promoter may inducible by abiotic treatments such as temperature, drought or alterations in salinity or induced by exogenously applied substances that activate the promoter, e.g., ethanol, oestrogens, plant hormones like ethylene, abscisic acid and gibberellic acid and heavy metals.

A promoter enhancer element may be used to achieve higher expression of the enzyme in the plant. For instance, the promoter enhancer element may be an intron which is placed between the promoter and the nucleotide sequence encoding the enzyme. For instance, Xu et al. op cit disclose the use of the first intron of the rice actin 1 gene to enhance expression.

The selectable marker gene and any other parts of the expression construct may be chosen from those available in the art.

The DNA construct is incorporated into the plant genome according to conventional techniques known in the art, including *Agrobacterium*-mediated transformation, virus-mediated transformation, micro injection, particle bombardment, biolistic transformation, and electroporation (Gasser et al, *Science* 244: 1293; Potrykus, 1990, *Bio/Techn.* 8: 535; Shimamoto et al., 1989, *Nature* 338: 274).

Presently, *Agrobacterium tumefaciens* mediated gene transfer is the method of choice for generating transgenic dicots (for review Hooykas & Schilperoort, 1992, *Plant Mol. Biol.* 19: 15-38), and can also be used for transforming monocots, although other transformation methods often are used for these plants. Presently, the method of choice for generating transgenic monocots supplementing the *Agrobacterium* approach is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21(3): 415-428.

Following transformation, the transformants having incorporated the expression construct are selected and regenerated into whole plants according to methods well-known in the art. Often the transformation procedure is designed for the selective elimination of selection genes either during regeneration or in the following generations by using, e.g., co-transformation with two separate T-DNA constructs or site specific excision of the selection gene by a specific recombinase.

Starch Processing

The polypeptide of the first, second and/or third aspect may be used in a process for liquefying starch, wherein a gelatinized or granular starch substrate is treated in aqueous medium with the hybrid enzyme. The polypeptide of the first, second and/or third aspect may also be used in a process for saccharification of a liquefied starch substrate. A preferred use is in a fermentation process wherein a starch substrate is liquefied and/or saccharified in the presence of the polypeptide of the first, second and/or third aspect to produce glucose and/or maltose suitable for conversion into a fermentation product by a fermenting organism, preferably a yeast. Such fermentation processes include a process for producing ethanol for fuel or drinking ethanol (portable alcohol), a process for producing a beverage, a process for producing desired organic compounds, such as citric acid, itaconic acid, lactic acid, gluconic acid, sodium gluconate, calcium gluconate, potassium gluconate, glucono delta lactone, or sodium erythorbate; ketones; amino acids, such as glutamic acid (sodium monoglutaminate), but also more complex compounds such as antibiotics, such as penicillin, tetracyclin; enzymes; vitamins, such as riboflavin, B12, beta-carotene; hormones, which are difficult to produce synthetically.

The starch to be processed may be a highly refined starch quality, preferably at least 90%, at least 95%, at least 97% or at least 99.5% pure or it may be a more crude starch containing material comprising milled whole grain including non-starch fractions such as germ residues and fibres. The raw material, such as whole grain, is milled in order to open up the structure and allowing for further processing. Two milling processes are preferred according to the invention: wet and dry milling. Also corn grits, and preferably milled corn grits may be applied.

Dry milled grain will in addition to starch comprise significant amounts of non-starch carbohydrate compounds. When such a heterogeneous material is processed by jet cooking often only a partial gelatinization of the starch is achieved. As the polypeptides of the invention have a high activity towards ungelatinized starch the polypeptides are advantageously applied in a process comprising liquefaction and/or saccharification jet cooked dry milled starch.

Furthermore, due to the superior hydrolysis activity of the polypeptide of the first aspect the need for glucoamylase during the saccharification step is greatly reduced. This allows saccharification to be performed at very low levels of glucoamylase activity and preferably glucoamylase activity is either absent or if present, then present in an amount of no more than or even less than 0.5 AGU/g DS, more preferably no more than or even less than 0.4 AGU/g DS, even more preferably no more than or even less than 0.3 AGU/g DS, and most preferably less than 0.1 AGU, such as no more than or even less than 0.05 AGU/g DS of starch substrate. Expressed in mg enzyme protein the enzyme having glucoamylase activity is either absent or present in an in an amount of no more than or even less than 0.5 mg EP/g DS, more preferably no more than or even less than 0.4 mg EP/g DS, even more preferably no more than or even less than 0.3 mg EP/g DS, and most preferably no more than or even less than 0.1 mg EP/g DS, such as no more than or even less than 0.05 mg EP/g DS or no more than or even less than 0.02 mg EP/g DS of starch substrate. The glucoamylase may preferably be derived from a strain within *Aspergillus* sp., *Talaromyces* sp., *Pachykytospora* sp. or *Trametes* sp., more preferably from *Aspergillus niger, Talaromyces emersonii, Trametes cingulata* or *Pachykytospora papyracea*.

Again due to the superior hydrolysis activity of the polypeptide of the first aspect the need for alpha-amylase in the liquefaction and/or saccharification step is greatly reduced. Expressed in mg enzyme protein the polypeptide of the first aspect may be dosed in amounts of no more than or even less than 0.5 mg EP/g DS, more preferably no more than or even less than 0.4 mg EP/g DS, even more preferably no more than or even less than 0.3 mg EP/g DS, and most preferably no more than or even less than 0.1 mg EP/g DS, such as no more than or even less than 0.05 mg EP/g DS or no more than or even less than 0.02 mg EP/g DS of starch substrate. The polypeptide of the first aspect may be dosed in amounts of 0.05 to 10.0 AFAU/g DS, preferably 0.1 to 5.0 AFAU/g DS, more preferably from 0.25 to 2.5 AFAU/g DS starch. The process may comprise; a) contacting a starch substrate with a polypeptide comprising a catalytic module having alpha-amylase activity and a carbohydrate-binding module, e.g, the polypeptide of the first aspect; b) incubating said starch substrate with said polypeptide for a time and at a temperature sufficient to achieve conversion of at least 90%, or at least 92%, at least 94%, at least 95%, at least 96%, at least 97%, at least 98%, at least 99%, at least 99.5% w/w of said starch substrate into fermentable sugars; c) fermenting to produce a fermentation product, d) optionally recovering the fermentation product. During the process steps b) and/or c) an enzyme having glucoamylase activity is either absent or present in an amount from 0.001 to 2.0 AGU/g DS, from 0.01 to 1.5 AGU/g DS, from 0.05 to 1.0 AGU/g DS, from 0.01 to 0.5 AGU/g DS. Preferably the enzyme having glucoamylase activity is either absent or present in an in an amount of no more than or even less than 0.5 AGU/g DS, more preferably no more than or even less than 0.4 AGU/g DS, even more preferably no more than or even less than 0.3 AGU/g DS, and most preferably no more than or even less than 0.1 AGU, such as no more than or even less than 0.05 AGU/g DS of starch substrate. Expressed in mg enzyme protein the enzyme having glucoamylase activity is either absent or present in an in an amount of no more than or even less than 0.5 mg EP/g DS, more preferably no more than or even less than 0.4 mg EP/g DS, even more preferably no more than or even less than 0.3 mg EP/g DS, and most preferably no more than or even less than 0.1 mg EP/g DS, such as no more than or even less than 0.05 mg EP/g DS or no more than or even less than 0.02 mg EP/g DS of starch substrate. In the process step a, b, c, and/or d may be performed separately or simultaneously.

In another aspect the process may comprise; a) contacting a starch substrate with a yeast cell transformed to express a polypeptide comprising a catalytic module having alpha-amylase activity and a carbohydrate-binding module, e.g, the polypeptide of the first and/or second aspect; b) incubating said starch substrate with said yeast for a time and at a temperature sufficient to achieve conversion of at least 90% w/w of said starch substrate into fermentable sugars; c) fermenting to produce ethanol; d) optionally recovering ethanol. The steps a, b, and c may performed separately or simultaneously.

In yet another aspect the process comprising hydrolysis of a slurry of gelatinized or granular starch, in particular hydrolysis of granular starch into a soluble starch hydrolysate at a temperature below the initial gelatinization temperature of said granular starch. In addition to being contacted with a polypeptide comprising a catalytic module having alpha-amylase activity and a carbohydrate-binding module, e.g., the polypeptide of the first aspect, the starch may be contacted with an enzyme selected from the group consisting of; a fungal alpha-amylase (EC 3.2.1.1), a beta-amylase (E.C. 3.2.1.2), and a glucoamylase (E.C. 3.2.1.3). In an embodiment further a bacterial alpha-amylase or a debranching enzyme, such as an isoamylase (E.C. 3.2.1.68) or a pullulanases (E.C. 3.2.1.41) may be added. In the context of the present invention a bacterial alpha-amylase is an alpha-amylase as defined in WO 99/19467 on page 3, line 18 to page 6, line 27.

In an embodiment the process is conducted at a temperature below the initial gelatinization temperature. Preferably the temperature at which the processes are conducted is at least 30° C., at least 31° C., at least 32° C., at least 33° C., at least 34° C., at least 35° C., at least 36° C., at least 37° C., at least 38° C., at least 39° C., at least 40° C., at least 41° C., at least 42° C., at least 43° C., at least 44° C., at least 45° C., at least 46° C., at least 47° C., at least 48° C., at least 49° C., at least 50° C., at least 51° C., at least 52° C., at least 53° C., at least 54° C., at least 55° C., at least 56° C., at least 57° C., at least 58° C., at least 59° C., or preferably at least 60° C. The pH at which the process is conducted may in be in the range of 3.0 to 7.0, preferably from 3.5 to 6.0, or more preferably from 4.0-5.0. In a preferred embodiment the process comprises fermentation, e.g with a yeast to produce ethanol, e.g., at a temperature around 32° C., such as from 30 to 35° C.

In another preferred embodiment the process comprises simultaneous saccharification and fermentation, e.g with a yeast to produce ethanol, or another suitable fermentation organism to produce a desired organic compound, such as at a temperature from 30 to 35° C., e.g., at around 32° C.

In the above fermentation processes the ethanol content reaches at least 7%, at least 8%, at least 9%, at least 10%, at least 11%, at least 12%, at least 13%, at least 14%, at least 15% such as at least 16% ethanol.

The starch slurry to be used in any of the above aspects may have 20-55% dry solids granular starch, preferably 25-40% dry solids granular starch, more preferably 30-35% dry solids granular starch. After being contacted with the polypeptide comprising a catalytic module having alpha-amylase activity and a carbohydrate-binding module, e.g, the polypeptide of the first aspect at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids of the granular starch is converted into a soluble starch hydrolysate.

In another preferred embodiment the polypeptide comprising a catalytic module having alpha-amylase activity and a carbohydrate-binding module, e.g, the polypeptide of the first aspect, is used in a process for liquefaction, saccharification of a gelatinized starch, e.g., but not limited to gelatinization by jet cooking. The process may comprise fermentation to produce a fermentation product, e.g., ethanol. Such a process for producing ethanol from starch-containing material by fermentation comprises: (i) liquefying said starch-containing material with a polypeptide comprising a catalytic module having alpha-amylase activity and a carbohydrate-binding module, e.g, the polypeptide of the first aspect; (ii) saccharifying the liquefied mash obtained; (iii) fermenting the material obtained in step (ii) in the presence of a fermenting organism. Optionally the process further comprises recovery of the ethanol. The saccharification and fermentation may be carried out as a simultaneous saccharification and fermentation process (SSF process). During the fermentation the ethanol content reaches at least 7%, at least 8%, at least 9%, at least 10% such as at least 11%, at least 12%, at least 13%, at least 14%, at least 15% such as at least 16% ethanol.

The starch to be processed in the processes of the above aspects may in particular be obtained from tubers, roots, stems, legumes, cereals or whole grain. More specifically the granular starch may be obtained from corns, cobs, wheat, barley, rye, milo, sago, cassava, tapioca, sorghum, rice, peas, bean, banana or potatoes. Specially contemplated are both waxy and non-waxy types of corn and barley.

The invention also relates to a composition comprising the polypeptide of the first and/or second aspect. In a particularly preferred embodiment the composition comprises a polypeptide of the first aspect which polypeptide is selected from the group consisting of V001, V002, V003, V004, V005, V006, V007, V008, V009, V010, V011, V012, V013, V014, V015, V016, V017, V018, V019, V021, V022, V023, V024, V025, V026, V027, V028, V029, V030, V031, V032, V033, V034, V035, V036, V037, V038, V039, V040, V041, V042, V043, V047, V048, V049, V050, V051, V052, V054, V055, V057, V059, V060, V061, V063, V064, V065, V066, V067, V068 and V069. The composition may further comprise an enzyme selected from the group comprising of; a fungal alpha-amylase (EC 3.2.1.1), a beta-amylase (E.C. 3.2.1.2), a glucoamylase (E.C. 3.2.1.3) and a pullulanases (E.C. 3.2.1.41). The glucoamylase may preferably be derived from a strain of *Aspergillus* sp., such as *Aspergillus niger*, or from a strain of *Talaromyces* sp. and in particular derived from *Talaromyces leycettanus* such as the glucoamylase disclosed in U.S. Pat. No. Re. 32,153, *Talaromyces duponti* and/or *Talaromyces thermopiles* such as the glucoamylases disclosed in U.S. Pat. No. 4,587,215 and more preferably derived from *Talaromyces emersonii*. Most preferably the glucoamylase is derived from *Talaromyces emersonii* strain CBS 793.97 and/or having the sequence disclosed as SEQ ID NO: 7 in WO 99/28448. Further preferred is a glucoamylase which has an amino acid sequence having at least 50%, at least 60%, at least 70%, at least 80%, at least 90% or even at least 95% homology to the aforementioned amino acid sequence. A commercial *Talaromyces glucoamylase* preparation is supplied by Novozymes A/S as Spirizyme Fuel.

Also preferred for a composition comprising the polypeptide of the first and/or second aspect and a glucoamylase are polypeptides having glucoamylase activity which are derived from a strain of the genus *Trametes*, preferably *Trametes cingulata*. Further preferred is polypeptides having glucoamylase activity and havering at least 50%, at least 60%, at least 70%, at least 80%, at least 90% or even at least 95% homology with amino acids for mature polypeptide amino acids 1 to 575 of SEQ ID NO: 5 in U.S. Patent Application No. 60/650,612.

Also preferred for a composition comprising the polypeptide of the first and/or second aspect and a glucoamylase are polypeptides having glucoamylase activity which are derived from a strain of the genus *Pachykytospora*, preferably *Pachykytospora papyracea* or the *E. coli* strain deposited at DSMZ and given the no. DSM 17105. Further preferred are polypeptides having glucoamylase activity and having at least 50%, at least 60%, at least 70%, at least 80%, at least 90% or even at least 95% homology with amino acids for mature polypeptide amino acids 1 to 556 of SEQ ID NO: 2 in U.S. Patent Application No. 60/650,612.

The composition described above may be used for liquefying and/or saccharifying a gelatinized or a granular starch, as well as a partly gelatinized starch. A partly gelatinized starch is a starch which to some extent is gelatinized, i.e., wherein part of the starch has irreversibly swelled and gelatinized and part of the starch is still present in a granular state.

The composition described above may preferably comprise acid alpha-amylase present in an amount of 0.01 to 10 AFAU/g DS, preferably 0.1 to 5 AFAU/g DS, more preferably 0.5 to 3 AFAU/AGU, and most preferably 0.3 to 2 AFAU/g DS. The composition may be applied in any of the starch processes described above.

Materials and Methods
Determination of Acid Alpha-Amylase Activity

When used according to the present invention the activity of any acid alpha-amylase may be measured in AFAU (Acid Fungal Alpha-amylase Units), which are determined relative to an enzyme standard. 1 AFAU is defined as the amount of enzyme which degrades 5.260 mg starch dry matter per hour under the below mentioned standard conditions.

Acid alpha-amylase, i.e., acid stable alpha-amylase, an endo-alpha-amylase (1,4-alpha-D-glucan-glucano-hydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

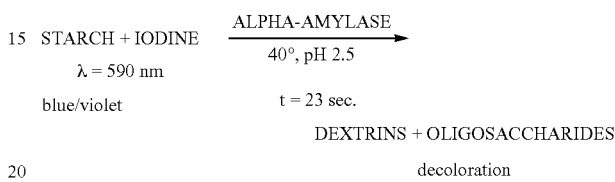

Standard Conditions/Reaction Conditions:
Substrate: Soluble starch, approx. 0.17 g/L
Buffer: Citrate, approx. 0.03 M
Iodine (I2): 0.03 g/L
CaCl2: 1.85 mM
pH: 2.50±0.05
Incubation temperature: 40° C.
Reaction time: 23 seconds
Wavelength: 590 nm
Enzyme concentration: 0.025 AFAU/mL
Enzyme working range: 0.01-0.04 AFAU/mL A folder EB-SM-0259.02/01 describing this analytical method in more detail is available upon request to Novozymes A/S, Denmark, which folder is hereby included by reference.

Glucoamylase Activity

Glucoamylase activity may be measured in AmyloGlucosidase Units (AGU). The AGU is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

AMG Incubation:
Substrate: maltose 23.2 mM
Buffer: acetate 0.1 M
Ph: 4.30±0.05
Incubation 37° C.±1
temperature:
Reaction time: 5 minutes
Enzyme working range: 0.5-4.0 AGU/mL
Color Reaction:
GlucDH: 430 U/L
Mutarotase: 9 U/L
NAD: 0.21 mM
Buffer: phosphate 0.12 M; 0.15 M NaCl
pH: 7.60±0.05
Incubation temperature: 37° C.±1
Reaction time: 5 minutes
Wavelength: 340 nm A folder (EB-SM-0131.02/01) describing this analytical method in more detail is available on request from Novozymes A/S, Denmark, which folder is hereby included by reference.

Strains and Plasmids

E. coli DH12S (available from Gibco BRL) was used for yeast plasmid rescue.

pLA1 is a S. cerevisiae and E. coli shuttle vector under the control of TPI promoter, constructed from pJC039 described in WO 01/92502. The acid Aspergillus niger alpha-amylase signal sequence, the acid Aspergillus niger alpha-amylase gene (SEQ ID NO: 1) and the partial Athelia rolfsii glucoamylase gene sequence comprising the linker (SEQ ID NO: 67) and the CBM (SEQ ID NO: 91) has been inserted. The full sequence of the plasmid is given in SEQ ID NO: 103. The alpha-amylase gene is the sequence from 5029 to 6468, the linker is the sequence from 6469 to 6501 and the CBM is the sequence from 6502 to 6795. The vector was used for alpha-amylase CBM hybrid construction.

Saccharomyces cerevisiae YNG318: MATa Dpep4[cir+] ura3-52, leu2-D2, his 4-539 was used for alpha-amylase variants expression. It is described in J. Biol. Chem. 272 (15), pp 9720-9727, 1997.

Media and Substrates

10× Basal solution: Yeast nitrogen base w/o amino acids (DIFCO) 66.8 g/l, succinate 100 g/l, NaOH 60 g/l.

SC-qlucose: 20% glucose (i.e., a final concentration of 2%=2 g/100 ml)) 100 ml/l, 5% threonine 4 ml/l, 1% tryptophan 10 ml/l, 20% casamino acids 25 ml/l, 10× basal solution 100 ml/l. The solution is sterilized using a filter of a pore size of 0.20 micrometer. Agar and $H_2O$ (approx. 761 ml) is autoclaved together, and the separately sterilized SC-glucose solution added to the agar solution.

YPD: Bacto peptone 20 g/l, yeast extract 10 g/l, 20% glucose 100 ml/l.

PEG/LiAc solution: 40% PEG4000 50 ml, 5 M Lithium Acetate 1 ml

DNA Manipulations

Unless otherwise stated, DNA manipulations and transformations were performed using standard methods of molecular biology as described in Sambrook et al. (1989) Molecular Cloning: A Laboratory Manual, Cold Spring Harbor Lab., Cold Spring Harbor, N.Y.; Ausubel, F. M. et al. (eds.) "Current Protocols in Molecular Biology", John Wiley and Sons, 1995; Harwood, C. R. and Cutting, S. M. (eds.).

Yeast Transformation

Yeast transformation was carried out by lithium acetate method. Mix 0.5 microL of vector (digested by restriction endnucleases) and 1 microL of PCR fragments. Thaw YNG318 competent cells on ice. Mix 100 microL of the cells, the DNA mixture and 10 microL of carrier DNA (Clontech) in 12 ml polypropylene tubes (Falcon 2059). Add 0.6 ml PEG/LiAc solution and mix gently. Incubate for 30 min at 30° C., and 200 rpm. Incubate for 30 min at 42° C. (heat shock). Transfer to an eppendorf tube and centrifuge for 5 sec. Remove the supernatant and resolve in 3 ml of YPD. Incubate the cell suspension for 45 min at 200 rpm at 30° C. Pour the suspension to SC-glucose plates and incubate 30° C. for 3 days to make colonies. Yeast total DNA was extracted by the Robzyk and Kassir's method described in Nucleic Acids Research 20(14): 3790 (1992).

DNA Sequencing

E. coli transformation for DNA sequencing was carried out by electroporation (BIO-RAD Gene Pulser). DNA Plasmids were prepared by alkaline method (Molecular Cloning, Cold Spring Harbor) or with the Qiagen® Plasmid Kit. DNA fragments were recovered from agarose gel by the Qiagen gel extraction Kit. PCR was performed using a PTC-200 DNA Engine. The ABI PRISM™ 310 Genetic Analyzer was used for determination of all DNA sequences.

TABLE 2

Amino acid (AA) and DNA sequences numbers of catalytic domains (CD), linkers, carbohydrate binding modules (CBM), plasmids, and primers applied. AA is alpha-amylase, GA is glucoamylase.

| Type | CODE | Sequence origin | SEQ ID | |
|------|------|-----------------|--------|---|
| CD | C001 | Aspergillus niger AA | SEQ ID NO: 1 | dna |
| CD | C001 | Aspergillus niger AA | SEQ ID NO: 2 | aa |
| CD | C002 | Aspergillus oryzae AA Fungamyl | SEQ ID NO: 3 | dna |
| CD | C002 | Aspergillus oryzae AA Fungamyl | SEQ ID NO: 4 | Aa |
| CD | C003 | Aspergillus oryzae AA Fungamyl variant | SEQ ID NO: 5 | Dna |
| CD | C003 | Aspergillus oryzae AA Fungamyl variant | SEQ ID NO: 6 | Aa |
| CD | C004 | Trichophaea saccata AA | SEQ ID NO: 7 | Dna |
| CD | C004 | Trichophaea saccata AA | SEQ ID NO: 8 | Aa |
| CD | C005 | Subulispora provurvata AA | SEQ ID NO: 9 | Dna |
| CD | C005 | Subulispora procurvata AA | SEQ ID NO: 10 | Aa |
| CD | C006 | Valsaria rubricosa AA | SEQ ID NO: 11 | Dna |
| CD | C006 | Valsaria rubricosa AA | SEQ ID NO: 12 | Aa |
| CD | C007 | Thermomyces lanuginosus AA | SEQ ID NO: 13 | Dna |
| CD | C007 | Thermomyces lanuginosus AA | SEQ ID NO: 14 | Aa |
| CD | C008 | Acremonium sp. AA | SEQ ID NO: 15 | Dna |
| CD | C008 | Acremonium sp. AA | SEQ ID NO: 16 | Aa |
| CD | C009 | Malbranchea sp. AA | SEQ ID NO: 17 | dna |
| CD | C009 | Malbranchea sp. AA | SEQ ID NO: 18 | Aa |
| CD | C010 | Rhizomucor pusillus AA | SEQ ID NO: 19 | Dna |
| CD | C010 | Rhizomucor pusillus AA | SEQ ID NO: 20 | Aa |
| CD | C011 | Dichotomocladium hesseltinei AA | SEQ ID NO: 21 | dna |
| CD | C011 | Dichotomocladium hesseltinei AA | SEQ ID NO: 22 | Aa |
| CD | C012 | Meripilus giganteus AA | SEQ ID NO: 23 | dna |
| CD | C012 | Meripilus giganteus AA | SEQ ID NO: 24 | Aa |
| CD | C013 | Stereum sp. AA | SEQ ID NO: 25 | dna |
| CD | C013 | Stereum sp. AA | SEQ ID NO: 26 | aa |
| CD | C014 | Trametes sp. | SEQ ID NO: 27 | dna |
| CD | C014 | Trametes sp. | SEQ ID NO: 28 | aa |
| CD | C015 | Coriolus censors AA | SEQ ID NO: 29 | dna |
| CD | C015 | Coriolus censors AA | SEQ ID NO: 30 | aa |
| CD | C016 | Dinemasporium sp. AA | SEQ ID NO: 31 | dna |

TABLE 2-continued

Amino acid (AA) and DNA sequences numbers of catalytic domains (CD),
linkers, carbohydrate binding modules (CBM), plasmids, and primers applied.
AA is alpha-amylase, GA is glucoamylase.

| Type | CODE | Sequence origin | SEQ ID | |
|---|---|---|---|---|
| CD | C016 | *Dinemasporium* sp. AA | SEQ ID NO: 32 | aa |
| CD | C017 | *Cryptosporiopsis* sp. AA | SEQ ID NO: 33 | dna |
| CD | C017 | *Cryptosporiopsis* sp. AA | SEQ ID NO: 34 | aa |
| CD | C018 | *Coniochaeta* sp. AA | SEQ ID NO: 35 | dna |
| CD | C018 | *Coniochaeta* sp. AA | SEQ ID NO: 36 | aa |
| CD | C020 | *Diplodia* sp. AA | SEQ ID NO: 37 | Dna |
| CD | C020 | *Diplodia* sp. AA | SEQ ID NO: 38 | Aa |
| CD | C021 | *Nectria* sp. AA | SEQ ID NO: 39 | Dna |
| CD | C021 | *Nectria* sp. AA | SEQ ID NO: 40 | Aa |
| CD | C022 | *Gliocladium* sp. AA | SEQ ID NO: 41 | Dna |
| CD | C022 | *Gliocladium* sp. AA | SEQ ID NO: 42 | Aa |
| CD | C023 | *Streptomyces thermocyaneoviolaceus* AA | SEQ ID NO: 43 | Dna |
| CD | C023 | *Streptomyces thermocyaneoviolaceus* AA | SEQ ID NO: 44 | Aa |
| Linker | C024 | *Pachykytospora papayracea* GA | SEQ ID NO: 45 | Dna |
| Linker | C024 | *Pachykytospora papayracea* GA | SEQ ID NO: 46 | Aa |
| Linker | C025 | *Trametes cingulata* GA | SEQ ID NO: 47 | Dna |
| Linker | C025 | *Trametes cingulata* GA | SEQ ID NO: 48 | Aa |
| Linker | C026 | *Leucopaxillus gigantus* GA | SEQ ID NO: 49 | Dna |
| Linker | C026 | *Leucopaxillus gigantus* GA | SEQ ID NO: 50 | Aa |
| Linker + CBM | C027 | *Trichophaea saccata* AA | SEQ ID NO: 51 | Dna |
| Linker + CBM | C027 | *Trichophaea saccata* AA | SEQ ID NO: 52 | Aa |
| Linker | C028 | *Sublispora provurvata* AA | SEQ ID NO: 53 | dna |
| Linker | C028 | *Sublispora provurvata* AA | SEQ ID NO: 54 | aa |
| Linker | C029 | *Valsaria rubricosa* AA | SEQ ID NO: 55 | dna |
| Linker | C029 | *Valsaria rubricosa* AA | SEQ ID NO: 56 | aa |
| Linker | C030 | *Acremonium* sp. AA | SEQ ID NO: 57 | dna |
| Linker | C030 | *Acremonium* sp. AA | SEQ ID NO: 58 | aa |
| Linker | C031 | *Meripilus giganteus* AA | SEQ ID NO: 59 | dna |
| Linker | C031 | *Meripilus giganteus* AA | SEQ ID NO: 60 | aa |
| Linker | C032 | *Bacillus flavothermus* AA short linker | SEQ ID NO: 61 | dna |
| Linker | C032 | *Bacillus flavothermus* AA short linker | SEQ ID NO: 62 | aa |
| Linker | C033 | *Bacillus flavothermus* AA long linker | SEQ ID NO: 63 | dna |
| Linker | C033 | *Bacillus flavothermus* AA long linker | SEQ ID NO: 64 | aa |
| Linker | C034 | *Bacillus flavothermus* AA | SEQ ID NO: 65 | dna |
| Linker | C034 | *Bacillus flavothermus* AA | SEQ ID NO: 66 | aa |
| Linker | C035 | *Athelia rolfsii* GA | SEQ ID NO: 67 | dna |
| Linker | C035 | *Athelia rolfsii* GA | SEQ ID NO: 68 | aa |
| Linker | C036 | *Aspergillus kawachii* GA | SEQ ID NO: 69 | Dna |
| Linker | C036 | *Aspergillus kawachii* GA | SEQ ID NO: 70 | Aa |
| Linker | C037 | *Aspergillus niger* GA | SEQ ID NO: 71 | dna |
| Linker | C037 | *Aspergillus niger* GA | SEQ ID NO: 72 | aa |
| Linker | C038 | *Coniochaeta* sp. AA | SEQ ID NO: 73 | dna |
| Linker | C038 | *Coniochaeta* sp. AA | SEQ ID NO: 74 | aa |
| CBM | C039 | *Pachykytospora papayracea* GA | SEQ ID NO: 75 | dna |
| CBM | C039 | *Pachykytospora papayracea* GA | SEQ ID NO: 76 | aa |
| CBM | C040 | *Trametes cingulata* GA | SEQ ID NO: 77 | dna |
| CBM | C040 | *Trametes cingulata* GA | SEQ ID NO: 78 | aa |
| CBM | C041 | *Leucopaxillus gigantus* GA | SEQ ID NO: 79 | dna |
| CBM | C041 | *Leucopaxillus gigantus* GA | SEQ ID NO: 80 | aa |
| CBM | C042 | *Subulispora provurvata* AA | SEQ ID NO: 81 | dna |
| CBM | C042 | *Subulispora provurvata* AA | SEQ ID NO: 82 | aa |
| CBM | C043 | *Valsaria rubricosa* AA | SEQ ID NO: 83 | dna |
| CBM | C043 | *Valsaria rubricosa* AA | SEQ ID NO: 84 | aa |
| CBM | C044 | *Acremonium* sp. AA | SEQ ID NO: 85 | dna |
| CBM | C044 | *Acremonium* sp. AA | SEQ ID NO: 86 | aa |
| CBM | C045 | *Meripilus giganteus* AA | SEQ ID NO: 87 | dna |
| CBM | C045 | *Meripilus giganteus* AA | SEQ ID NO: 88 | aa |
| CBM | C046 | *Bacillus flavothermus* AA | SEQ ID NO: 89 | dna |
| CBM | C046 | *Bacillus flavothermus* AA | SEQ ID NO: 90 | aa |
| CBM | C047 | *Athelia rolfsii* GA | SEQ ID NO: 91 | dna |
| CBM | C047 | *Athelia rolfsii* GA | SEQ ID NO: 92 | aa |
| CBM | C048 | *Aspergillus kawachii* GA | SEQ ID NO: 93 | dna |
| CBM | C048 | *Aspergillus kawachii* GA | SEQ ID NO: 94 | aa |
| CBM | C049 | *Aspergillus niger* GA | SEQ ID NO: 95 | dna |
| CBM | C049 | *Aspergillus niger* GA | SEQ ID NO: 96 | aa |
| CBM | C050 | *Coniochaeta* sp. | SEQ ID NO: 97 | dna |
| CBM | C050 | *Coniochaeta* sp. | SEQ ID NO: 98 | aa |
| Hybrid | V051 | Hybrid of Fungamyl variant CD and *A. rolfsii* GA CBM | SEQ ID NO: 99 | dna |
| Hybrid | V051 | Hybrid of Fungamyl variant CD and *A. rolfsii* GA CBM | SEQ ID NO: 100 | aa |
| Hybrid | V019 | Hybrid of *R. pusillus* AA CD and *A. rolfsii* GA CBM | SEQ ID NO: 101 | aa |
| Hybrid | V022 | Hybrid of *M. giganteus* AA and *A. rolfsii* GA CBM | SEQ ID NO: 102 | aa |
| Plasmid | pLA1 | Plasmid | SEQ ID NO: 103 | dna |
| Primer | P001 | Primer | SEQ ID NO: 104 | dna |
| Primer | P002 | Primer | SEQ ID NO: 105 | dna |

TABLE 2-continued

Amino acid (AA) and DNA sequences numbers of catalytic domains (CD),
linkers, carbohydrate binding modules (CBM), plasmids, and primers applied.
AA is alpha-amylase, GA is glucoamylase.

| Type | CODE | Sequence origin | SEQ ID | |
|---|---|---|---|---|
| Primer | P003 | Primer | SEQ ID NO: 106 | dna |
| Primer | P004 | Primer | SEQ ID NO: 107 | dna |
| CBM | | Zea mays | SEQ ID NO: 108 | dna |
| CBM | | Zea mays | SEQ ID NO: 109 | aa |
| CD | C051 | Thermoascus sp. II | SEQ ID NO: 110 | dna |
| CD | C051 | Thermoascus sp. II AA | SEQ ID NO: 111 | aa |
| CD | C055 | Coniochaeta sp.II AA | SEQ ID NO: 112 | dna |
| CD | C055 | Coniochaeta sp.II AA | SEQ ID NO: 113 | aa |
| CD | C052 | Nectria sp. AA | SEQ ID NO: 114 | dna |
| CD | C052 | Nectria sp. AA | SEQ ID NO: 115 | aa |
| CD | C054 | Fusarium sp. AA | SEQ ID NO: 116 | dna |
| CD | C054 | Fusarium sp. AA | SEQ ID NO: 117 | aa |
| CD | C057 | Trametes corrugata AA | SEQ ID NO: 118 | dna |
| CD | C057 | Trametes corrugata AA | SEQ ID NO: 119 | aa |
| CD | C059 | Penicillium sp. AA | SEQ ID NO: 120 | dna |
| CD | C059 | Penicillium sp. AA | SEQ ID NO: 121 | aa |
| CD | C060 | Valsaria spartii AA | SEQ ID NO: 122 | dna |
| CD | C060 | Valsaria spartii AA | SEQ ID NO: 123 | aa |
| CD | C061 | Thermoascus aurantiacus AA | SEQ ID NO: 124 | dna |
| CD | C061 | Thermoascus aurantiacus AA | SEQ ID NO: 125 | aa |
| CD | C062 | Phanerochaete chrysosporium AA | SEQ ID NO: 126 | dna |
| CD | C062 | Phanerochaete chrysosporium AA | SEQ ID NO: 127 | aa |
| CD | C063 | Rhizopus oryzae AA | SEQ ID NO: 128 | dna |
| CD | C063 | Rhizopus oryzae AA | SEQ ID NO: 129 | aa |
| CD | C064 | Thaminidium elegans AA | SEQ ID NO: 130 | dna |
| CD | C064 | Thaminidium elegans AA | SEQ ID NO: 131 | aa |
| CD | C065 | Absidia cristata AA | SEQ ID NO: 132 | dna |
| CD | C065 | Absidia cristata AA | SEQ ID NO: 133 | aa |
| CD | C066 | Syncephalastrum racemosum AA | SEQ ID NO: 134 | dna |
| CD | C066 | Syncephalastrum racemosum AA | SEQ ID NO: 135 | aa |
| CBM | C067 | Coniochaeta sp. AA | SEQ ID NO: 136 | dna |
| CBM | C067 | Coniochaeta sp. AA | SEQ ID NO: 137 | aa |
| CBM | C068 | Trametes corrugata AA | SEQ ID NO: 138 | dna |
| CBM | C068 | Trametes corrugata AA | SEQ ID NO: 139 | aa |
| CBM | C069 | Valsario spartii AA | SEQ ID NO: 140 | dna |
| CBM | C069 | Valsario spartii AA | SEQ ID NO: 141 | aa |
| CBM | C070 | Penicillium sp. AA | SEQ ID NO: 142 | dna |
| CBM | C070 | Penicillium sp. AA | SEQ ID NO: 143 | aa |
| Linker | C072 | Coniochaeta sp. AA | SEQ ID NO: 144 | dna |
| Linker | C072 | Coniochaeta sp. AA | SEQ ID NO: 145 | aa |
| Linker | C073 | Trametes corrugata AA | SEQ ID NO: 146 | dna |
| Linker | C073 | Trametes corrugata AA | SEQ ID NO: 147 | aa |
| Linker | C074 | Valsario spartii AA | SEQ ID NO: 148 | dna |
| Linker | C074 | Valsario spartii AA | SEQ ID NO: 149 | aa |
| Linker | C075 | Penicillium sp. AA | SEQ ID NO: 150 | dna |
| Linker | C075 | Penicillium sp. AA | SEQ ID NO: 151 | aa |
| CD | C077 | Streptomyces limosus AA | SEQ ID NO: 154 | dna |
| CD | C077 | Streptomyces limosus AA | SEQ ID NO: 155 | aa |

Example 1

Construction of the Nucleic Acid Sequence V019, Encoding *Rhizomucor Pusillus* Alpha Amylases and *Athelia Rolfsii* Glucoamylase CBM Vector pLA1 was digested with the appropriate restriction endonuclease to cut out the region encoding *A. niger* alpha-amylase catalytic domain. The *Rhizomucor pusillus* alpha-amylase gene was amplified by PCR using the primers P001 (SEQ ID NO: 104) and P002 (SEQ ID NO: 105), the amplified fragment is shown as SEQ ID NO: 19.

| PCR reaction system: | | Conditions: | |
|---|---|---|---|
| 38.9 micro L | H₂O | 1 | 98° C. 10 sec |
| 5 micro L | 10X reaction buffer | 2 | 68° C. 90 sec |

-continued

| PCR reaction system: | | Conditions: | |
|---|---|---|---|
| 1 micro L | Klen Taq LA (CLONTECH) | 1-2 | 30 cycles |
| 4 micro L | 10 mM dNTPs | 3 | 68° C. 10 min |
| 0.3 micro L × 2 | 100 pmole/micro L Primers | | |
| 0.5 micro L | Template DNA | | |

DNA fragments were recovered from agarose gel by the Qiagen gel extraction Kit. The resulting purified fragments were mixed with the vector digest. The mixed solution was introduced into *Saccharomyces cerevisiae* to construct the expression plasmid pLAV019 by in vivo recombination.

Example 2

Construction of the Nucleic Acid Sequence V022, Encoding *Meripilus Giganteus* Alpha Amylase and *Athelia Rolfsii* Glucoamylase CBM The *Meripilus giganteus* alpha-amylase gene was amplified by PCR using the primers P003 (SEQ ID NO: 106) and P004 (SEQ ID NO: 107).

DNA fragments were recovered from agarose gel by the Qiagen gel extraction Kit. The resulting purified fragments and the appropriate restriction endonuclease digested vector pLA1 to cut out the region encoding *A. niger* alpha-amylase catalytic domain were mixed. The mixed solution was introduced into *Saccharomyces cerevisiae* to construct the expression plasmid pLAV022 by in vivo recombination.

Example 3

Expression of Amylases with CBM in *Aspergillus Oryzae*

The constructs comprising the alpha amylase genes with CBM described in examples 1 and 2 were used to construct expression vectors, pAspV019 and pAspV022, respectively. The two plasmids, pAspV019 and pAspV022, consist of an expression cassette based on the *Aspergillus niger* neutral amylase II promoter fused to the *Aspergillus nidulans* triose phosphate isomerase non translated leader sequence (Pna2/tpi) and the *Aspergillus niger* amyloglycosidase terminator (Tamg). Also present on the plasmid was the *Aspergillus* selective marker amdS from *Aspergillus nidulans* enabling growth on acetamide as sole nitrogen source. The expression plasmids pAspV019 and pAspV022 were transformed into *Aspergillus* as described in Lassen et al., 2001, *Applied and Environmental Microbiology* 67: 4701-4707. Transformants expressing V019 and V022, were isolated, purified and cultivated in shake flasks. The culture broths from fermentations of *Aspergillus oryzae* expressing amylase with CBM were purified by affinity purification (*Biochem. J.* 372: 905-910 (2003)).

Example 4

Amylases with CBM

Polypeptides of the invention were produced; a selection of catalytic domains were fused to the linker-CBM region of *Athelia rolfsii* glucoamylase, and a selection of CBM regions were attached to the C003 *Aspergillus oryzae* catalytic domain (a Fungamyl PE variant).

Because the CBM+linker from *Trichophaea saccata* alpha-amylase is located at N-terminal, it was inserted between SP288 signal and the *Aspergillus oryzae* catalytic domain. The other CBMs were all C-terminally placed.

The variant V008 comprised both a C-terminally placed linker and CBM region of *Athelia rolfsii* glucoamylase and an N-terminally placed linker+CBM from *Trichophaea saccata* alpha-amylase.

CBM variants of the *Aspergillus oryzae* alpha-amylase and catalytic domain variants of the *Athelia rolfsii* glucoamylase CBM are listed in tables 3 and 4 respectively. Other produced polypeptides of the invention are listed in tables 5 and 6.

The variants have improved activity on starch, especially on granular starch.

TABLE 3

Polypeptides with the *A. oryzae* AA Fungamyl variant catalytic domain (SEQ ID NO: 6)

| Code | Linker and CBM from | CBM | Linker |
|---|---|---|---|
| V001 | *Sublispora provurvata* AA | SEQ ID NO: 82 | SEQ ID NO: 54 |
| V002 | *Valsaria rubricosa* | SEQ ID NO: 84 | SEQ ID NO: 56 |
| V003 | *Acremonium* sp. AA | SEQ ID NO: 86 | SEQ ID NO: 58 |
| V004 | *Pachykytospora papayracea* GA | SEQ ID NO: 76 | SEQ ID NO: 46 |
| V005 | *Trametes cingulata* GA | SEQ ID NO: 78 | SEQ ID NO: 48 |
| V006 | *Leucopaxillus gigantus* GA | SEQ ID NO: 80 | SEQ ID NO: 50 |
| V007 | *Meripilus giganteus* AA | SEQ ID NO: 88 | SEQ ID NO: 60 |
| V008 | *Trichophaea saccata* AA (CBM21-Nterm incl. linker) | SEQ ID NO: 52 | |
| | +*A. rolfsii* GA (C-term) | SEQ ID NO: 92 | SEQ ID NO: 68 |
| V009 | *Trichophaea saccata* AA (CBM21-Nterm incl. linker) | SEQ ID NO: 52 | |
| V010 | *Bacillus flavothermus* AA with short linker | SEQ ID NO: 90 | SEQ ID NO: 62 |
| V011 | *Bacillus flavothermus* AA with long linker | SEQ ID NO: 90 | SEQ ID NO: 64 |
| V012 | *Bacillus flavothermus* AA | SEQ ID NO: 90 | SEQ ID NO: 66 |

TABLE 4

Polypeptides with the *A. rolfsii* GA linker (SEQ ID NO: 68) and CBM (SEQ ID NO: 92)

| Code | Catalytic module from: | Catalytic domain SEQ ID |
|---|---|---|
| V013 | *Trichophaea saccata* AA | SEQ ID NO: 8 |
| V014 | *Subulispora provurvata* AA | SEQ ID NO: 10 |
| V015 | *Valsaria rubricosa* AA | SEQ ID NO: 12 |
| V016 | *Thermomyces lanuginosus* AA | SEQ ID NO: 14 |
| V017 | *Acremonium* sp. AA | SEQ ID NO: 16 |
| V018 | *Malbranchea* sp. AA | SEQ ID NO: 18 |
| V019 | *Rhizomucor pusillus* AA | SEQ ID NO: 20 |
| V021 | *Dichotomocladium hesseltinei* AA | SEQ ID NO: 22 |
| V022 | *Meripilus giganteus* AA | SEQ ID NO: 24 |
| V023 | *Stereum* sp. | SEQ ID NO: 26 |
| V024 | *Streptomyces limosus* AA | SEQ ID NO: 155 |
| V025 | *Coriolus censors* | SEQ ID NO: 30 |
| V026 | *Dinemasporium* sp. AA | SEQ ID NO: 32 |
| V027 | *Cryptosporiopsis* sp. AA | SEQ ID NO: 34 |
| V028 | *Coniochaeta* sp. AA | SEQ ID NO: 36 |
| V029 | *Diplodia* sp. AA | SEQ ID NO: 38 |
| V030 | *Nectria* sp. AA | SEQ ID NO: 40 |
| V031 | *Gliocladium* sp. AA | SEQ ID NO: 42 |
| V032 | *Streptomyces thermocyaneoviolaceus* AA | SEQ ID NO: 44 |
| V047 | *Thermoascus* sp. II | SEQ ID NO: 111 |
| V048 | *Coniochaeta* sp.2 | SEQ ID NO: 113 |
| V049 | *Nectria* sp. AA | SEQ ID NO: 115 |

TABLE 4-continued

Polypeptides with the *A. rolfsii* GA linker (SEQ ID NO: 68) and CBM (SEQ ID NO: 92)

| Code | Catalytic module from: | Catalytic domain SEQ ID |
|---|---|---|
| V050 | *Fusarium* sp. | SEQ ID NO: 117 |
| V051 | *Trametes corrugata* | SEQ ID NO: 119 |
| V052 | *Valsaria spartii* | SEQ ID NO: 123 |
| V054 | *Thermoascus aurantiacus* | SEQ ID NO: 125 |
| V055 | *Penicillium* sp. | SEQ ID NO: 121 |
| V057 | *Phanerochaete chrysosporium* | SEQ ID NO: 127 |
| V059 | *Rhizopus oryzae* | SEQ ID NO: 129 |
| V060 | *Thaminidium elegans* | SEQ ID NO: 131 |
| V061 | *Absidia cristata* | SEQ ID NO: 133 |
| V063 | *Syncephalastrum racemosum* | SEQ ID NO: 135 |

TABLE 5

Polypeptides with other catalytic domains/CBMs with linker. In V069 CBM and linker are of different origin.

| Code | Catalytic domain from: | CD SEQ ID NO | CBM and linker from: | Linker SEQ ID NO | CBM SEQ ID NO |
|---|---|---|---|---|---|
| V033 | *Acremonium* sp. AA | SEQ ID NO: 16 | *Pachykytospora papayracea* GA | SEQ ID NO: 46 | SEQ ID NO: 145 |
| V034 | *Rhizomucor pusillus* AA | SEQ ID NO: 20 | *Pachykytospora papayracea* GA | SEQ ID NO: 46 | SEQ ID NO: 145 |
| V035 | *Meripilus giganteus* AA | SEQ ID NO: 24 | *Pachykytospora papayracea* GA | SEQ ID NO: 46 | SEQ ID NO: 145 |
| V036 | *Meripilus giganteus* AA | SEQ ID NO: 24 | *Valsaria rubricosa* | SEQ ID NO: 56 | SEQ ID NO: 84 |
| V037 | *Meripilus giganteus* AA | SEQ ID NO: 24 | *Meripilus giganteus* AA | SEQ ID NO: 60 | SEQ ID NO: 88 |
| V038 | *Rhizomucor pusillus* AA | SEQ ID NO: 20 | *Aspergillus kawachii* GA | SEQ ID NO: 70 | SEQ ID NO: 94 |
| V039 | *Rhizomucor pusillus* AA | SEQ ID NO: 20 | *Aspergillus niger* GA | SEQ ID NO: 72 | SEQ ID NO: 96 |
| V040 | *A. oryzae* Fungamyl variant | SEQ ID NO: 06 | *Coniochaeta* sp. AM603 | SEQ ID NO: 74 | SEQ ID NO: 98 |
| V069 | *Meripilus giganteus* AA | SEQ ID NO: 24 | *Zea mays* CBM *A. rolf* GA linker | SEQ ID NO: 68 | SEQ ID NO: 109 |

TABLE 6

Polypeptides with *Rhizomucor pusillus* AA catalytic domain (SEQ ID NO: 20) and CBM and linker from:

| Code | CBM from | CBM SEQ ID NO | Linker from | Linker SEQ ID NO |
|---|---|---|---|---|
| V041 | *A. rolfsii* GA | SEQ ID NO: 92 | *A. kawachii* AA | SEQ ID NO: 70 |
| V042 | *A. rolfsii* GA | SEQ ID NO: 92 | *A. niger* GA | SEQ ID NO: 72 |
| V043 | *Zea mays* | SEQ ID NO: 109 | *A. rolf* GA | SEQ ID NO: 68 |
| V064 | *Coniochaeta* sp. | SEQ ID NO: 113 | *Coniochaeta* sp. | SEQ ID NO: 145 |
| V065 | *Trametes corrugata* | SEQ ID NO: 119 | *Trametes corrugata* | SEQ ID NO: 147 |
| V066 | *Valsaria spartii* | SEQ ID NO: 123 | *Valsaria spartii* | SEQ ID NO: 149 |
| V067 | *Penicillium* sp. | SEQ ID NO: 121 | *Penicillium* sp. | SEQ ID NO: 151 |
| V068 | *Meripulus giganteus* | SEQ ID NO: 88 | *Meripilus giganteus* | SEQ ID NO: 60 |

Example 5

The performance of the polypeptide V019 was evaluated in mini-scale fermentations with different dosages of *Talaromyces emersonii* glucoamylase. Starch substrate, 583.3 g of ground corn was added to 912.2 g tap water. This mixture was supplemented with 4.5 ml of a 1 g/L penicillin solution. The pH of this slurry was adjusted to 5.0 with 40% $H_2SO_4$. DS level was determined in duplicate to be 34.2±0.8%. Approximately 5 g of this slurry was added to 20 ml vials. Each vial was dosed with the appropriate amount of enzyme followed by addition of 200 microL yeast propagate/5 g slurry. Actual dosages were based on the exact weight of corn slurry in each vial. Vials were incubated at 32° C. Fermentations were followed by measuring weight loss over time. At 70 hours the fermentations were stopped and prepared for HPLC analysis. The HPLC preparation consisted of stopping the reaction by addition of 50 microL of 40% $H_2SO_4$, centrifuging, and filtering through a 0.45 micrometer filter. Samples awaiting HPLC analysis were stored at 4° C.

TABLE 7

Performance of polypeptide V019 in mini-scale fermentations.
70 hr Ethanol relative to 0.14 AGU/DS and no alpha-amylase.

| Amylase Dose (mg Protein/g DS) | T. emersonii GA Dose (AGU/g DS) | 70 hr Ethanol |
|---|---|---|
| 0 | 0.14 | 1.00 |
| 0 | 0.50 | 1.35 |
| 0 | 0.86 | 1.73 |
| 0.05 | None | 3.69 |
| 0.05 | 0.14 | 3.69 |
| 0.05 | 0.50 | 3.73 |
| 0.05 | 0.86 | 3.73 |

Example 6

Substrates for saccharification were prepared by dissolving a DE 11 maltodextrin prepared from corn starch liquefied with thermostable bacterial alpha-amylase (LIQUOZYME X™, Novozymes A/S) in Milli-Q™ water, and adjusting the dry solid matter content (DS) to 30%. The saccharification experiments were carried out in sealed 2 ml glass vials at 60° C. and initial pH of 4.3 under continuous stirring. Two different dosages of CBM alpha-amylase V019 or V022 were applied on top of a standard treatment with *Talaromyces emersonii* glucoamylase 0.35 AGU/g DS and *A. niger* acid alpha-amylase 0.04 AFAU/g DS.

Samples were taken at set intervals and heated in boiling water for 15 minutes to inactivate the enzymes. After cooling, the samples were diluted to 5% DS and filtered (Sartorius MINISART™ NML 0.2 micro-m), before being analysed by HPLC. The glucose levels as a % of total soluble carbohydrate are given in table 8 below.

TABLE 8

All treatments with *Talaromyces emersonii* glucoamylase 0.35 AGU/g DS and *A. niger* acid alpha-amylase 0.04 AFAU/g DS. Acid alpha-amylase variants V019 and V022 were dosed on top according to the table.

| Additional Enzyme | Acid alpha-amylase variant AFAU/g DS | DP1 24 h | DP1 48 h | DP1 70 h |
|---|---|---|---|---|
| Control | 0 | 81.5 | 90.2 | 93.1 |
| V019 | 0.0875 | 95.7 | 96.2 | 95.6 |
|  | 0.1750 | 92.1 | 96.2 | 96.2 |
| V022 | 0.0875 | 93.8 | 95.6 | 95.5 |
|  | 0.1750 | 92.9 | 95.9 | 96.0 |

Example 6

Raw starch SSF treatments were evaluated in mini-scale fermentations. A 35% DS granular starch slurry was obtained from mixing 410 g finely ground corn, 590 ml tap water, 3.0 mls 1 g/L penicillin and 1 g of urea. The slurry was adjusted to pH 4.5 using 5 N NaOH and samples of 5 g were distributed to 20 ml vials. The appropriate amount of enzymes was dosed and the vials were inoculated with yeast. Vials were incubated at 32° C. 9 replicate fermentations of each treatment were run. Three replicates were selected for 24 hours, 48 hours and 70 hours time point analysis. Vials were vortexed at 24, 48 and 70 hours. The time point analysis consisted of weighing the vials and prepping the sample for HPLC. For HPLC the reaction was stopped by addition of 50 microL of 40% $H_2SO_4$, centrifuging, and filtering through a 0.45 um filter. Samples awaiting HPLC analysis were stored at 4° C.

Example 6a

Enzymes and amounts used are shown in the table below. A-AMG is an *Aspergillus niger* glucoamylase composition.

TABLE 9

Raw starch SSF with *Aspergillus niger* glucoamylase and V019, enzyme dosage

| trial | % dose | | mg/gDS | | AGU/gDS | AFAU/gDS |
|---|---|---|---|---|---|---|
| No | A-AMG | V019 | A-AMG | V019 | A-AMG | V019 |
| 2 | 100% | 0% | 0.5 | 0 | 0.95 | 0 |
| 3 | 90% | 10% | 0.45 | 0.01 | 0.855 | 0.01 |
| 4 | 80% | 20% | 0.4 | 0.02 | 0.76 | 0.02 |
| 5 | 70% | 30% | 0.35 | 0.03 | 0.665 | 0.03 |
| 6 | 60% | 40% | 0.3 | 0.04 | 0.57 | 0.04 |
| 7 | 45% | 55% | 0.225 | 0.055 | 0.4275 | 0.055 |
| 8 | 30% | 70% | 0.15 | 0.07 | 0.285 | 0.07 |
| 9 | 15% | 85% | 0.075 | 0.085 | 0.1425 | 0.085 |
| 10 | 0% | 100% | 0 | 0.1 | 0 | 0.1 |

Good ethanol yield after 70 hours fermentation was observed in the range of 1.7-85.5 AGU/AFAU ratio of *A. niger* AMG to V019, indicating robust performance in a broad activity ratio range for the mixtures of *A. niger* AMG to V019.

TABLE 10

Raw starch SSF with *Aspergillus niger* glucoamylase and V019, results

| Trial | AGU/gDS | AFAU/gDS | Ethanol Yield (g/l) | | | AGU/AFAU |
|---|---|---|---|---|---|---|
| No | A-AMG | V019 | 24 hr | 48 hr | 70 hr | Ratio |
| 2 | 0.950 | 0.000 | 77.73 | 119.46 | 139.27 | N/A |
| 3 | 0.855 | 0.010 | 92.93 | 134.65 | 144.39 | 85.5 |
| 4 | 0.760 | 0.020 | 93.13 | 133.74 | 145.42 | 38.0 |
| 5 | 0.665 | 0.030 | 92.66 | 134.32 | 147.56 | 22.2 |
| 6 | 0.570 | 0.040 | 91.68 | 132.86 | 145.77 | 14.3 |
| 7 | 0.428 | 0.055 | 90.17 | 130.87 | 146.26 | 7.8 |
| 8 | 0.285 | 0.070 | 87.11 | 127.74 | 144.82 | 4.1 |
| 9 | 0.143 | 0.085 | 84.32 | 120.95 | 143.40 | 1.7 |
| 10 | 0.000 | 0.100 | 80.80 | 114.55 | 134.08 | 0.0 |

Example 6b

Enzymes and amounts used are shown in the table below. A-AMG is a *Talaromyces emersonii* glucoamylase composition.

TABLE 11

Raw starch SSF with *Talaromyces emersonii* glucoamylase and V019, enzyme dosages

| trial | % dose | | mg/gDS | | AGU/gDS | AFAU/gDS |
|---|---|---|---|---|---|---|
| No | T-AMG | V019 | T-AMG | V019 | T-AMG | V019 |
| 2 | 100% | 0% | 0.3 | 0 | 2.4 | 0 |
| 3 | 90% | 10% | 0.27 | 0.01 | 2.16 | 0.01 |
| 4 | 80% | 20% | 0.24 | 0.02 | 1.92 | 0.02 |
| 5 | 70% | 30% | 0.21 | 0.03 | 1.68 | 0.03 |
| 6 | 60% | 40% | 0.18 | 0.04 | 1.44 | 0.04 |
| 7 | 45% | 55% | 0.135 | 0.055 | 1.08 | 0.055 |
| 8 | 30% | 70% | 0.09 | 0.07 | 0.72 | 0.07 |

TABLE 11-continued

Raw starch SSF with *Talaromyces emersonii* glucoamylase and V019, enzyme dosages

| trial | % dose | | mg/gDS | | AGU/gDS | AFAU/gDS |
|---|---|---|---|---|---|---|
| No | T-AMG | V019 | T-AMG | V019 | T-AMG | V019 |
| 9 | 15% | 85% | 0.045 | 0.085 | 0.36 | 0.085 |
| 10 | 0% | 100% | 0 | 0.1 | 0 | 0.1 |

Good ethanol yield after 70 hours fermentation was observed in the range of 10-216 AGU/AFAU ratio of *T. emersonii* AMG to V019, indicating a broad activity ratio range for the mixtures of *T. emersonii* AMG to V019.

TABLE 12

Raw starch SSF with *Talaromyces emersonii* glucoamylase and V019, results

| trial | AGU/gDS | AFAU/gDS | Ethanol Yield (g/l) | | | AGU/AFAU |
|---|---|---|---|---|---|---|
| No | Sp Fuel | V019 | 24 hrs | 48 hrs | 70 hrs | Ratio |
| 2 | 2.4 | 0 | 60.07 | 91.77 | 113.17 | N/A |
| 3 | 2.16 | 0.01 | 89.00 | 129.36 | 142.91 | 216.0 |
| 4 | 1.92 | 0.02 | 91.02 | 132.07 | 147.18 | 96.0 |
| 5 | 1.68 | 0.03 | 93.31 | 133.75 | 148.19 | 56.0 |
| 6 | 1.44 | 0.04 | 93.71 | 134.16 | 146.84 | 36.0 |
| 7 | 1.08 | 0.055 | 92.83 | 131.53 | 141.80 | 19.6 |
| 8 | 0.72 | 0.07 | 91.25 | 125.48 | 139.25 | 10.3 |
| 9 | 0.36 | 0.085 | 86.14 | 124.22 | 137.38 | 4.2 |
| 10 | 0 | 0.1 | 80.63 | 115.00 | 132.08 | 0.0 |

DEPOSIT OF BIOLOGICAL MATERIAL

The following biological material has been deposited under the terms of the Budapest Treaty at Deutshe Sammmlung von Microorganismen and Zellkulturen GmbH (DSMZ), Mascheroder Weg 1 b, D-38124 Braunschweig DE, and given the following accession number:

| Deposit | Accession Number | Date of Deposit |
|---|---|---|
| *Escherichia coli* NN049798 | DSM 17106 | 2 Feb. 2005 |
| *Escherichia coli* NN049797 | DSM 17105 | 2 Feb. 2005 |

The strains have been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposits represent a substantially pure culture of the deposited strain. The deposits are available as required by foreign patent laws in countries wherein counterparts of the subject application, or its progeny are filed. However, it should be understood that the availability of a deposit does not constitute a license to practice the subject invention in derogation of patent rights granted by governmental action.

The invention claimed is:

1. An isolated polypeptide comprising a first amino acid sequence comprising a catalytic module having alpha-amylase activity and a second amino acid sequence comprising a carbohydrate-binding module, wherein
the first amino acid sequence has at least 90% homology to the amino acid sequence of SEQ ID NO: 20 and
the second amino acid sequence has at least 90% homology to any amino acid sequence selected from the group consisting of SEQ ID NO: 92, SEQ ID NO: 94, and SEQ ID NO: 96.

2. The polypeptide of claim 1, wherein the first amino acid sequence has at least 95% homology to the amino acid sequence of SEQ ID NO: 20.

3. The polypeptide of claim 1, wherein the second amino acid sequence has at least 90% homology to the amino acid sequence of SEQ ID NO: 92.

4. The polypeptide of claim 1, wherein the second amino acid sequence has at least 95% homology to the amino acid sequence of SEQ ID NO:92.

5. The polypeptide of claim 2, wherein the second amino acid sequence has at least 90% homology to the amino acid sequence of SEQ ID NO: 92.

6. The polypeptide of claim 2, wherein the second amino acid sequence has at least 95% homology to the amino acid sequence of SEQ ID NO: 92.

7. The polypeptide of claim 1, wherein the second amino acid sequence has at least 90% homology to the amino acid sequence of SEQ ID NO: 94.

8. The polypeptide of claim 1, wherein the second amino acid sequence has at least 95% homology to the amino acid sequence of SEQ ID NO: 94.

9. The polypeptide of claim 2, wherein the second amino acid sequence has at least 90% homology to the amino acid sequence of SEQ ID NO: 94.

10. The polypeptide of claim 2, wherein the second amino acid sequence has at least 95% homology to the amino acid sequence of SEQ ID NO: 94.

11. The polypeptide of claim 1, wherein the second amino acid sequence has at least 90% homology to the amino acid sequence of SEQ ID NO: 96.

12. The polypeptide of claim 1, wherein the second amino acid sequence has at least 95% homology to the amino acid sequence of SEQ ID NO: 96.

13. The polypeptide of claim 2, wherein the second amino acid sequence has at least 90% homology to the amino acid sequence of SEQ ID NO: 96.

14. The polypeptide of claim 2, wherein the second amino acid sequence has at least 95% homology to the amino acid sequence of SEQ ID NO: 96.

15. The polypeptide of claim 1, further comprising a linker sequence between the first and second amino acid sequences.

16. A composition comprising a polypeptide of claim 1 and a glucoamylase.

17. A process for saccharifying starch, comprising treating a starch with the polypeptide of claim 1.

18. The process of claim 17, comprising converting starch into a syrup containing dextrose and/or maltose.

19. The process of claim 17, wherein the starch is gelatinized or granular starch.

20. The process of claim 17, further comprising contacting the saccharified starch with a fermenting organism to produce a fermentation product.

* * * * *